US010266544B2

(12) United States Patent
Lee et al.

(10) Patent No.: US 10,266,544 B2
(45) Date of Patent: Apr. 23, 2019

(54) ARYL SUBSTITUTED AMINOMETHYL SPECTINOMYCIN ANALOGS AS ANTIBACTERIAL AGENTS

(71) Applicant: ST. JUDE CHILDREN'S RESEARCH HOSPITAL, INC., Memphis, TN (US)

(72) Inventors: Richard E. Lee, Cordova, TN (US); Samanthi L. Waidyarachchi, Southaven, MS (US); David F. Bruhn, Memphis, TN (US); Jiuyu Liu, Bartlett, TN (US); Zhong Zheng, Irvine, CA (US); Jason W. Rosch, Memphis, TN (US)

(73) Assignee: St. Jude Children's Research Hospital, Inc., Memphis, TN (US)

( * ) Notice: Subject to any disclaimer, the term of this patent is extended or adjusted under 35 U.S.C. 154(b) by 0 days.

(21) Appl. No.: 15/024,549

(22) PCT Filed: Sep. 29, 2014

(86) PCT No.: PCT/US2014/058137
§ 371 (c)(1),
(2) Date: Mar. 24, 2016

(87) PCT Pub. No.: WO2015/048692
PCT Pub. Date: Apr. 2, 2015

(65) Prior Publication Data
US 2016/0347762 A1     Dec. 1, 2016

Related U.S. Application Data

(60) Provisional application No. 61/884,085, filed on Sep. 29, 2013.

(51) Int. Cl.
| | |
|---|---|
| C07D 493/04 | (2006.01) |
| A61K 9/00 | (2006.01) |
| A61K 31/357 | (2006.01) |
| A61K 31/381 | (2006.01) |
| A61K 31/4025 | (2006.01) |
| A61K 31/4045 | (2006.01) |
| A61K 31/4178 | (2006.01) |
| A61K 31/427 | (2006.01) |
| A61K 31/428 | (2006.01) |
| A61K 31/4433 | (2006.01) |
| A61K 31/497 | (2006.01) |
| A61K 31/5377 | (2006.01) |
| A61K 45/06 | (2006.01) |

(52) U.S. Cl.
CPC .......... *C07D 493/04* (2013.01); *A61K 9/0019* (2013.01); *A61K 31/357* (2013.01); *A61K 31/381* (2013.01); *A61K 31/4025* (2013.01); *A61K 31/4045* (2013.01); *A61K 31/4178* (2013.01); *A61K 31/427* (2013.01); *A61K 31/428* (2013.01); *A61K 31/4433* (2013.01); *A61K 31/497* (2013.01); *A61K 31/5377* (2013.01); *A61K 45/06* (2013.01)

(58) Field of Classification Search
CPC ... C07D 311/82; A61K 9/0019; A61K 31/436
USPC .......................................... 549/223; 514/232
See application file for complete search history.

(56) References Cited

U.S. PATENT DOCUMENTS

| | | | |
|---|---|---|---|
| 4,173,647 A | 11/1979 | Maier et al. | |
| 4,465,848 A | 8/1984 | Thomas et al. | |
| 5,543,158 A | 8/1996 | Gref et al. | |
| 8,685,978 B2 * | 4/2014 | Lee ..................... | C07D 493/04 |
| | | | 514/252.01 |
| 2006/0002852 A1 | 1/2006 | Saltzmann et al. | |
| 2006/0222652 A1 | 10/2006 | Sebbel et al. | |
| 2006/0251677 A1 | 11/2006 | Bachmann et al. | |
| 2008/0145441 A1 | 6/2008 | Penades et al. | |
| 2009/0028910 A1 | 1/2009 | DeSimone et al. | |
| 2009/0226525 A1 | 9/2009 | de los Rios | |
| 2011/0118272 A1 | 5/2011 | Lee et al. | |
| 2012/0178915 A1 | 7/2012 | Xu | |

FOREIGN PATENT DOCUMENTS

| | | |
|---|---|---|
| EP | 0 079 125 A1 | 5/1983 |
| WO | WO 2009/051837 A2 | 4/2009 |
| WO | WO 2009/106999 A2 | 9/2009 |
| WO | WO 2010/047839 A1 | 4/2010 |

OTHER PUBLICATIONS

Barry et al., "Antibacterial Activity of Trospectomycin (U-63366F) and Initial Evaluations of Disk Diffusion Susceptibility Tests", Antimicrob. Agent. Chemother., 33(4): 569-572 (1989).
Borovinskaya et al., "A Steric Block in Translation Caused by the Antibiotic Spectinomycin", ACS Chem. Biol., 2(8): 545-552 (2007).
Carter et al., "Dissecting the Catalytic Triad of a Serine Protease", Nature, 332: 564-568 (1988).
Carter et al., "Functional Insights from the Structure of the 30S Ribosomal Subunit and its Interactions with Antibiotics", Nature, 407(6802): 340-348 (2000).
CAS Registry No. 686704-56-3.
Ejiri et al., "Negishi Alkyl-Aryl Cross-Coupling Catalyzed by Rh: Efficiency of Novel Tripodal 3-Diphenylphosphino-2-(diphenylphosphino) methyl-2-methylpropyl Acetate Ligand", Org. Lett., 12(8): 1692-1695 (2010).
Fattori et al., "Fragment-Based Approach to Drug Lead Discovery", Drugs R.D., 9(4): 217-227 (2008).
Fischbach et al., "Antibiotics for Emerging Pathogens", Science, 325(5944): 1089-1093 (2009).

(Continued)

*Primary Examiner* — Rita J Desai
(74) *Attorney, Agent, or Firm* — Leon R. Yankwich; David G. O'Brien; Yankwich & Associates, P.C.

(57) ABSTRACT

The invention relates to aryl substituted aminomethyl spectinomycin analogs, derivatives thereof, and related compounds, which are useful as anti-bacterial agents; methods for making the compounds; pharmaceutical compositions comprising the compounds; and methods of treating antibacterial infections using the compounds and compositions.

31 Claims, 3 Drawing Sheets

(56) References Cited

OTHER PUBLICATIONS

Goldston et al., "The Garrett Lee Smith Memorial Suicide Prevention Program", Suicide Life Threat. Behave., 40(3): 245-256 (2010).
Lange et al., "The Targets of Currently Used Antibacterial Agents: Lessons for Drug Discovery", Curr. Phar. Design, 13: 3140-3154 (2007).
Lebensberger et al., "Hydroxyurea therapy of a murine model of sickle cell anemia inhibits the progression of pneumococcal disease by down-modulating E-selectin", Blood, 119(8): 1915-1921 (2012).
Mani et al., "In Vitro Characterization of the Antibacterial Spectrum of Novel Bacterial Type II Topoisomerase Inhibitors of the Aminobenzimidazole Class", Antimicrob. Agents Chemother., 50(4): 1228-1237 (2006).
McCormack et al., "Drugs Five Years Later: Spectinomycin", Annals of internal medicine, 84(6): 712-716 (1976).
Mills, "When Will the Genomic Investment Pay Off for Antibacterial Discovery?", Biochem. Pharmacol., 71: 1096-1102 (2006).
Montiel et al., "In Vitro Antibacterial Activity of Trospectomycin (U-63,366F) Against Anaerobic Bacteria and Aerobic Gram-Positive Cocci in Chile", Diagn. Microbial. Infect. Dis., 14(3); 259-264 (1991).
Nakasako et al., "The ph-dependent Structural Variation of Complementarity-determining Region H3 in the Crystal Structures of the Fv Fragment from an Anti-dansyl Monoclonal Antibody", J. Mol. Biol., 291(1): 117-134 (1999).
Nicasio et al., "The Current State of Multidrug-resistant Gram-negative Bacilli in North America", Pharmacotherapy, 28 (2): 235-249 (2008).
Payne et al., "Drugs for Bad Bugs: Confronting the Challenges of Antibacterial Discovery", Nat. Rev. Drug Disc., 6:29-40 (2007).
Reyn et al., "Spectinomycin Hydrochloride (Trobicin) in the treatment of Gonorrhoea, Observation of Resistant Strains of Neisseria Gonorrhoeae", Br. J. Vener. Dis., 49(1): 54-59 (1973).
Salian et al, "Structure-Activity Relationships Among the Kanamycin Aminoglycosides: Role of Ring I Hydroxyl and Amino Groups", Antimicrob. Agents Chemother., 56(12): 6104-6108 (2011).
Sykes et al., "Monocyclic β-lactam Antibiotics Produced by Bacteria", Nature, 291(5815): 489-491 (1981).
Wilcox et al., "Spectinomycin Dihydrochloride in the Treatment of Gonorrhoea in Males", Br. J. Clin. Pract., 29(2): 34-36 (1975).
Wirmer et al., "Molecular Contacts between Antibiotics and the 30S Ribosomal Particle", Meth. Enzmol., 415: 180-202 (2006).
Wright et al., "New Strategies for Combating Multidrug-Resistant Bacteria", Trends Mol. Med., 13(6): 260-270 (2007).
Zenilman et al., "Spectinomycin-Resistant Gonococcal Infections in the United States", J. Infect. Dis., 156(6): 1002-1004 (1987).
Zurenko et al., "Trospectomycin, a Novel Spectinomycin Analogue: Antibacterial Activity and Preliminary Human Pharmacokinetics", Drugs Exp. Clin. Res., 14(6): 403-409 (1988).

* cited by examiner

ARYL SUBSTITUTED AMINOMETHYL SPECTINOMYCIN ANALOGS AS ANTIBACTERIAL AGENTS

CROSS-REFERENCE TO PRIORITY APPLICATIONS

This application is a United States national stage filing under 35 U.S.C. § 371 of international (PCT) application no. PCT/US2014/058137, filed Sep. 29, 2014, and designating the U.S., which claims priority to U.S. Provisional Appln. No. 61/884,085 filed Sep. 29, 2013.

STATEMENT OF FEDERALLY SPONSORED RESEARCH

This invention was made with government support under grant AI090810 awarded by the National Institutes of Health (NIH). The government has certain rights in the invention.

BACKGROUND OF THE INVENTION

The dramatic rise in the prevalence of antibiotic resistance among bacteria requires the discovery and development of new antimicrobials to treat infections caused by these organisms. Of major health concern are drug resistant infections caused by Methicillin-resistant *Staphylococcus aureus* (MRSA), vancomycin-resistant *Enterococcus*, multidrug resistant *Streptococci pneumoniae, Neisseria gonorrhoeae*, and *Mycobacterium tuberculosis*, pan-resistant *Klebsiella pneumoniae, Pseudomonas aeruginosa* and *Acinetobacter baumannii* (Fischbach et al. *Science* 2009, 325 (5944), 1089-1093; Goldston et al. *Suicide Life Threat. Behav.* 2010, 40(3), 245-256; Nicasio et al. *Pharmacotherapy* 2008, 28 (2), 235-249). There is also a need for new therapeutic agents to treat biodefense pathogens.

The rise of these organisms comes at a time when the pipeline for the development of new antibiotics has become sparse (Fattori et al. *Drugs R. D.* 2008, 9 (4), 217-227; Ejiri et al. *Org. Lett.* 2010, 12 (8), 1692-1695). Moreover, the application of bacterial genomics coupled with high throughput screening technologies has been met with limited success (Lange, et al. *Curr. Pharm. Design* 2007 13, 3140-3154; Mills, *Biochem. Pharmacol.* 2006 71, 1096-1102; and Payne, et al. *Nat. Rev. Drug Disc.* 2007 6, 29-40). In this context, it is prudent to consider what has been the most successful strategy in antibacterial drug discovery, namely the synthetic modification of natural products to produce new semisynthetic antibiotics (Fischbach et al. *Science* 2009, 325 (5944), 1089-1093; Wright et al. *Trends Mol. Med.* 2007, 13 (6), 260-270; Nakasako et al. *J. Mol. Biol.* 1999, 291 (1), 117-134).

Spectinomycin is an aminocyclitol antibiotic that specifically inhibits bacterial protein synthesis by binding to 30S ribosome at a unique site that is highly conserved across bacterial pathogens (Carter et al. *Nature* 2000, 407(6802), 340-348; Borovinskaya et al. *ACS Chem. Biol.* 2007, 2 (8), 545-552; Wirmer et al. *Meth. Enzmol.* 2006, 415, 180-202). Although spectinomycin is potent in cell free assays its clinical use is restricted to second line treatment for *Neisseria gonorrhoeae* infections (McCormack et al. *Annals of internal medicine* 1976, 84 (6), 712-716; Reyn et al. *Br. J. Vener. Dis.* 1973, 49 (1), 54-59; Zenilman et al. *J. Infect. Dis.* 1987, 156 (6), 1002-1004. Over 25 years ago, attempts to develop spectinomycin analogs led to the discovery of trospectinomycin, which progressed into late stage clinical trials before being abandoned by Upjohn.

Despite advances in antimicrobial research directed to semisynthetic analogs of natural products, there remains a significant need for antibiotic compounds that are potent, efficacious, and effective in the treatment of infectious disease associated with infection by gram positive and gram negative bacteria, particularly for broad spectrum antibiotics and for use against resistant bacterial strains. These needs and other needs are satisfied by the present invention.

SUMMARY OF THE INVENTION

In accordance with the purpose(s) of the invention, as embodied and broadly described herein, the invention, in one aspect, relates to aryl substituted aminomethyl spectinomycin analogs useful as antibacterial agents, methods of making same, pharmaceutical compositions comprising same, and methods of treating bacterial infections using same.

Disclosed are compounds having a structure represented by Formula I:

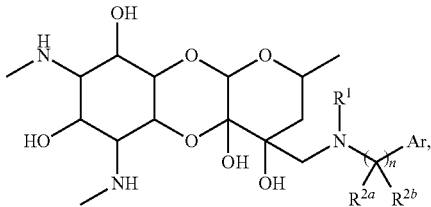

wherein n is an integer selected from 0, 1, 2, and 3; wherein $R^1$ is selected from hydrogen and C1-C4 alkyl; wherein each occurrence of $R^{2a}$ and $R^{2b}$, when present, is independently selected from hydrogen and C1-C3 alkyl; and wherein Ar is aryl or heteroaryl substituted with 0 to 3 groups independently selected from halo, cyano, hydroxyl, —$NH_2$, C1-C3 alkyl, C1-C3 monohaloalkyl, C1-C3 polyhaloalkyl, C1-C3 alkoxy, C1-C3 monohaloalkoxy, C1-C3 polyhaloalkoxy, —(C=O)$OR^9$, —(C=O)$NR^{10a}R^{10b}$, —$SO_2NR^{10a}R^{10b}$, —$SR^9$, and —$SO_2R^9$; wherein each occurrence of $R^9$, when present, is selected from hydrogen and C1-C3 alkyl; wherein each occurrence of $R^{10a}$ and $R^{10b}$, when present, is independently selected from hydrogen and C1-C3 alkyl; or a pharmaceutically acceptable salt, solvate, or polymorph thereof.

Also disclosed are compositions comprising one or more compounds of Formula I, or a pharmaceutically acceptable salt, solvate, or polymorph thereof, and a pharmaceutically acceptable carrier. Also disclosed are pharmaceutical compositions comprising an effective amount of at least one compound according to Formula I or a pharmaceutically acceptable salt, solvate, or polymorph thereof, and a pharmaceutically acceptable carrier. In a preferred embodiment, the pharmaceutical compositions of the present invention comprise a therapeutically effective amount of at least one compound of Formula I or a pharmaceutically acceptable salt, solvate, or polymorph thereof, and a pharmaceutically acceptable carrier.

Also disclosed are methods for treating an infectious disease, in particular a bacterial infection, in a human subject comprising the step of administering to the human subject a therapeutically effective amount of at least one compound according to Formula I, or a pharmaceutically acceptable salt, solvate, or polymorph thereof.

Also disclosed are methods for treating an infectious disease, particularly a bacterial infection, in a vertebrate animal comprising the step of administering to the vertebrate animal a therapeutically effective amount of at least one compound of Formula I, or a pharmaceutically acceptable salt, solvate, or polymorph thereof.

Also disclosed are methods for treating a human subject for a disorder associated with exposure to a biodefense pathogen comprising the step of administering to the human subject an effective amount of at least one compound according to Formula I, or a pharmaceutically acceptable salt, solvate, or polymorph thereof.

Also disclosed are methods for inhibiting protein synthesis in at least one bacterial cell, comprising the step of contacting the bacterial cell with an effective amount of at least one compound according to Formula I, or a pharmaceutically acceptable salt, solvate, or polymorph thereof.

Also disclosed are kits comprising at least one compound according to Formula I, or a pharmaceutically acceptable salt, solvate, or polymorph thereof; and one or more of: (a) at least one agent known to inhibit microbial ribosomal activity; (b) at least one agent known to have antimicrobial activity; (c) at least one agent known to treat an infectious disease; (d) instructions for treating an infectious disease; (e) instructions for administering the compound in connection with treating a microbial infection; or (f) instructions for administering the compound with at least one agent known to treat an infectious disease.

While aspects of the present invention can be described and claimed in a particular statutory class, such as the system statutory class, this is for convenience only and one of skill in the art will understand that each aspect of the present invention can be described and claimed in any statutory class. Unless otherwise expressly stated, it is in no way intended that any method or aspect set forth herein be construed as requiring that its steps be performed in a specific order. Accordingly, where a method claim does not specifically state in the claims or descriptions that the steps are to be limited to a specific order, it is no way intended that an order be inferred, in any respect. This holds for any possible non-express basis for interpretation, including matters of logic with respect to arrangement of steps or operational flow, plain meaning derived from grammatical organization or punctuation, or the number or type of aspects described in the specification.

BRIEF DESCRIPTION OF THE FIGURES

The accompanying figures, which are incorporated in and constitute a part of this specification, illustrate several aspects and together with the description serve to explain the principles of the invention.

Figure 1:
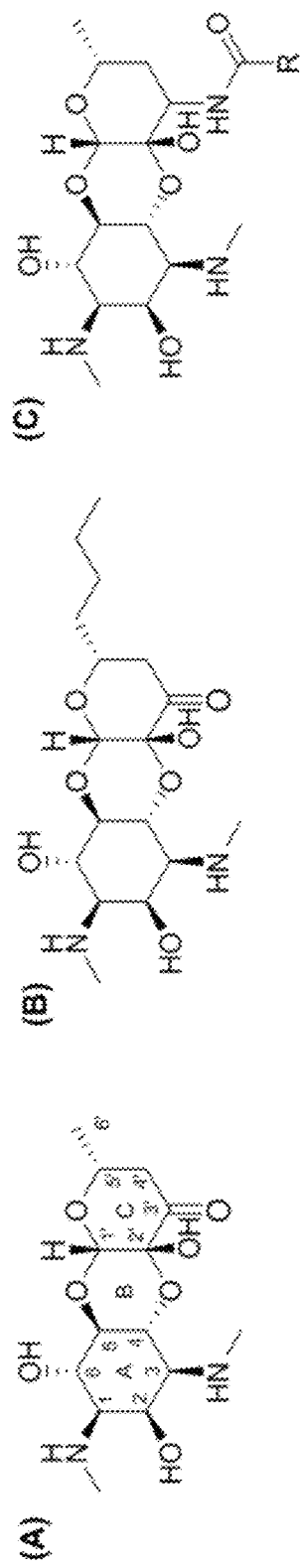
FIG. 1 shows the chemical structure of spectinomycin and spectinomycin analogs, specifically, (A) spectinomycin, which also shows the generally accepted ring numbering and nomenclature system; (B) trospectomycin; and (C) spectinamides as disclosed in US 2011/0118272.

Additional advantages of the invention will be set forth in part in the description which follows, and in part will be obvious from the description, or can be learned by practice of the invention. The advantages of the invention will be realized and attained by means of the elements and combinations particularly pointed out in the appended claims. It is to be understood that both the foregoing general description and the following detailed description are exemplary and explanatory only and are not restrictive of the invention, as claimed.

DETAILED DESCRIPTION

The present invention can be understood more readily by reference to the following detailed description of the invention and the Examples included therein.

Before the present compounds, compositions, articles, systems, devices, and/or methods are disclosed and described, it is to be understood that they are not limited to specific synthetic methods unless otherwise specified, or to particular reagents unless otherwise specified, as such may, of course, vary. It is also to be understood that the terminology used herein is for the purpose of describing particular aspects only and is not intended to be limiting. Although any methods and materials similar or equivalent to those described herein can be used in the practice or testing of the present invention, example methods and materials are now described.

Unless defined otherwise, all technical and scientific terms used herein have the same meaning as commonly understood by one of ordinary skill in the art to which this invention belongs. In this specification and in the claims which follow, reference will be made to a number of terms which shall be defined herein.

A. Definitions

As used in the specification and the appended claims, the singular forms "a," "an" and "the" include plural referents unless the context clearly dictates otherwise. Thus, for example, reference to "a functional group," "an alkyl," or "a residue" includes mixtures of two or more such functional groups, alkyls, or residues, and the like.

As used in the specification and in the claims, the term "comprising" can include the aspects "consisting of" and "consisting essentially of."

Ranges can be expressed herein as from "about" one particular value, and/or to "about" another particular value. When such a range is expressed, another aspect includes from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. It is also understood that each unit between two particular units are also disclosed. For example, if 10 and 15 are disclosed, then 11, 12, 13, and 14 are also disclosed.

As used herein, the terms "about" and "at or about" mean that the amount or value in question can be the value designated some other value approximately or about the same. It is generally understood, as used herein, that it is the nominal value indicated ±10% variation unless otherwise indicated or inferred. The term is intended to convey that similar values promote equivalent results or effects recited in the claims. That is, it is understood that amounts, sizes, formulations, parameters, and other quantities and characteristics are not and need not be exact, but can be approximate and/or larger or smaller, as desired, reflecting tolerances, conversion factors, rounding off, measurement error and the like, and other factors known to those of skill in the art. In general, an amount, size, formulation, parameter or other quantity or characteristic is "about" or "approximate" whether or not expressly stated to be such. It is understood that where "about" is used before a quantitative value, the parameter also includes the specific quantitative value itself, unless specifically stated otherwise.

References in the specification and concluding claims to parts by weight of a particular element or component in a composition denotes the weight relationship between the element or component and any other elements or components in the composition or article for which a part by weight is expressed. Thus, in a compound containing 2 parts by weight of component X and 5 parts by weight component Y, X and Y are present at a weight ratio of 2:5, and are present in such ratio regardless of whether additional components are contained in the compound.

A weight percent (wt. %) of a component, unless specifically stated to the contrary, is based on the total weight of the formulation or composition in which the component is included.

As used herein, the terms "optional" or "optionally" means that the subsequently described event or circumstance can or cannot occur, and that the description includes instances where said event or circumstance occurs and instances where it does not.

As used herein, the term "subject" can be a vertebrate, such as a mammal, a fish, a bird, a reptile, or an amphibian. Thus, the subject of the herein disclosed methods can be a human, non-human primate, horse, pig, rabbit, dog, sheep, goat, cow, cat, guinea pig or rodent. The term does not denote a particular age or sex. Thus, adult and juvenile subjects, whether male or female, are intended to be covered. In one aspect, the subject is a mammal. A patient refers to a subject afflicted with a disease or disorder. The term "patient" includes human and veterinary subjects.

The terms "antimicrobial activity," "microbicidal," and "microbistatic" refer to the ability of a spectinomycin analog or derivative described herein to modify a function or metabolic process of a target microorganism, for example so as to at least partially affect replication, vegetative growth, toxin production, survival, viability in a quiescent state, or other attribute. Bacteria to be inhibited or killed using the compositions and method described herein can include gram-negative and gram-positive bacteria, in addition to organisms classified in orders of the class Mollicutes and the like, such as species of the *Mycoplasma* and *Acholeplasma* genera. Examples of gram-positive bacteria include, but are not limited to, *Staphylococcus aureus*, *Staphylococcus epidermis*, *Streptococcus agalactiae*, Group A *streptococcus*, *Streptococcus pyogenes*, *Enterococcus faecalis*, Group B gram-positive *streptococcus*, *Corynebacterium xerosis*, and *Listeria monocytogenes*. Specific examples of gram-negative bacteria include, but are not limited to, *Escherichia coli*, *Acinetobacter baumannii*, *Pseudomonas aeruginosa*, *Klebsiella pneumoniae*, *Salmonella*, *Hemophilus influenza*, *Neisseria gonorrhoeae*, *Chlamydia trachomatis*, *Vibrio cholerae*, *Vibrio parahemolyticus* and *Helicobacter pylori*. Examples of fungi can include yeasts, such as *Candida albicans*. Examples of viruses can include measles virus, herpes simplex virus (HSV-1 and -2), herpes family members (HIV, hepatitis C, vesicular, stomatitis virus (VSV), visna virus, and cytomegalovirus (CMV). Examples of protozoa can include Giardia.

As used herein, the terms "multidrug-resistant tuberculosis," "multidrug-resistant TB," and "MDR TB," which can be used interchangeably, refer to a form of tuberculosis that is resistant to two or more of the primary drugs (isoniazid and rifampin) used for the treatment of tuberculosis. These terms refer not only to this particular type of the tuberculosis disease, but also to the *Mycobacterium tuberculosis* that are associated with the disease.

As used herein, the terms "extensively drug-resistant tuberculosis," "extensively drug-resistant TB," and "XDR TB," which can be used interchangeably, refer to a form of tuberculosis that is resistant to at least isoniazid and rifampin among the first-line anti-TB drugs and is resistant to any fluoroquinolone and at least one of the three second-line injectable drugs. These terms refer not only to this particular type of the tuberculosis disease, but also to the *Mycobacterium tuberculosis* that are associated with the disease.

As used herein, the term "treatment" refers to the medical management of a patient with the intent to cure, ameliorate, stabilize, or prevent a disease, pathological condition, or disorder. This term includes active treatment, that is, treatment directed specifically toward the improvement of a disease, pathological condition, or disorder, and also includes causal treatment, that is, treatment directed toward removal of the cause of the associated disease, pathological condition, or disorder. In addition, this term includes palliative treatment, that is, treatment designed for the relief of symptoms rather than the curing of the disease, pathological condition, or disorder; preventative treatment, that is, treatment directed to minimizing or partially or completely inhibiting the development of the associated disease, pathological condition, or disorder; and supportive treatment, that is, treatment employed to supplement another specific therapy directed toward the improvement of the associated disease, pathological condition, or disorder. In various aspects, the term covers any treatment of a subject, including a mammal (e.g., a human), and includes: (i) preventing the disease from occurring in a subject that can be predisposed to the disease but has not yet been diagnosed as having it; (ii) inhibiting the disease, i.e., arresting its development; or (iii) relieving the disease, i.e., causing regression of the disease. In one aspect, the subject is a mammal such as a primate, and, in a further aspect, the subject is a human. The term "subject" also includes domesticated animals (e.g., cats, dogs, etc.), livestock (e.g., cattle, horses, pigs, sheep, goats, chickens, turkeys, etc.), and laboratory animals (e.g., mouse, rabbit, rat, guinea pig, fruit fly, etc.).

As used herein, the phrase "treating or inhibiting a microbial infection" means to inhibit the replication of the particular microorganism causing the infection, to inhibit transmission of the microorganism, or to prevent the microorganism from establishing itself in its host, and to ameliorate or alleviate the symptoms of the disease caused by the infection. The treatment is considered therapeutic if there is a reduction in microorganism load, microorganism replication, microorganism counts or cell numbers, decrease in mortality, decrease in symptoms of the infection, such as a fever, and/or morbidity of a subject.

As used herein, the term "prevent" or "preventing" refers to precluding, averting, obviating, forestalling, stopping, or hindering something from happening, especially by advance action. It is understood that where reduce, inhibit or prevent are used herein, unless specifically indicated otherwise, the use of the other two words is also expressly disclosed.

As used herein, the term "diagnosed" means having been subjected to a physical examination by a person of skill, for example, a physician, and found to have a condition that can be diagnosed or treated by the compounds, compositions, or methods disclosed herein.

As used herein, the terms "administering" and "administration" refer to any method of providing a pharmaceutical preparation to a subject. Such methods are well known to those skilled in the art and include, but are not limited to, oral administration, transdermal administration, administration by inhalation, nasal administration, topical administration, intravaginal administration, ophthalmic administration, intraaural administration, intracerebral administration, rectal administration, sublingual administration, buccal administration, and parenteral administration, including injectable such as intravenous administration, intra-arterial administration, intramuscular administration, and subcutaneous administration. Administration can be continuous or intermittent. In various aspects, a preparation can be administered therapeutically; that is, administered to treat an existing disease or condition. In further various aspects, a preparation can be administered prophylactically; that is, administered for prevention of a disease or condition.

As used herein, the terms "effective amount" and "amount effective" refer to an amount that is sufficient to achieve the desired result or to have an effect on an undesired condition. For example, a "therapeutically effective amount" refers to an amount that is sufficient to achieve the desired therapeutic result or to have an effect on undesired symptoms, but is generally insufficient to cause adverse side effects. The specific therapeutically effective dose level for any particular patient will depend upon a variety of factors including the disorder being treated and the severity of the disorder; the specific composition employed; the age, body weight, general health, sex and diet of the patient; the time of administration; the route of administration; the rate of excretion of the specific compound employed; the duration of the treatment; drugs used in combination or coincidental with the specific compound employed and like factors well known in the medical arts. For example, it is well within the skill of the art to start doses of a compound at levels lower than those required to achieve the desired therapeutic effect and to gradually increase the dosage until the desired effect is achieved. If desired, the effective daily dose can be divided into multiple doses for purposes of administration. Consequently, single dose compositions can contain such amounts or submultiples thereof to make up the daily dose. The dosage can be adjusted by the individual physician in the event of any contraindications. Dosage can vary, and can be administered in one or more dose administrations daily, for one or several days. Guidance can be found in the literature for appropriate dosages for given classes of pharmaceutical products. In further various aspects, a preparation can be administered in a "prophylactically effective amount"; that is, an amount effective for prevention of a disease or condition.

As used herein, "dosage form" means a pharmacologically active material in a medium, carrier, vehicle, or device suitable for administration to a subject. A suitable dosage form can comprise a compound according to Formula I, a product of a disclosed method of making, or a salt, solvate, or polymorph thereof, in combination with a pharmaceutically acceptable excipient, such as a preservative, buffer, saline, or phosphate buffered saline. Dosage forms can be made using conventional pharmaceutical manufacturing and compounding techniques. Dosage forms can comprise inorganic or organic buffers (e.g., sodium or potassium salts of phosphate, carbonate, acetate, or citrate) and pH adjustment agents (e.g., hydrochloric acid, sodium or potassium hydroxide, salts of citrate or acetate, amino acids and their salts) antioxidants (e.g., ascorbic acid, alpha-tocopherol), surfactants (e.g., polysorbate 20, polysorbate 80, polyoxyethylene9-10 nonyl phenol, sodium desoxycholate), solution and/or cryo/lyo stabilizers (e.g., sucrose, lactose, mannitol, trehalose), osmotic adjustment agents (e.g., salts or sugars), antibacterial agents (e.g., benzoic acid, phenol, gentamicin), antifoaming agents (e.g., polydimethylsilozone), preservatives (e.g., thimerosal, 2-phenoxyethanol, EDTA), polymeric stabilizers and viscosity-adjustment agents (e.g., polyvinylpyrrolidone, poloxamer 488, carboxymethylcellulose) and co-solvents (e.g., glycerol, polyethylene glycol, ethanol). A dosage form formulated for injectable use can have a disclosed compound according to Formula I, a product of a disclosed method of making, or a salt, solvate, or polymorph thereof, suspended in sterile saline solution for injection together with a preservative.

As used herein, "encapsulate in a nanocarrier" or "encapsulate in a synthetic nanocarrier" both refer to enclosing at least a portion of a substance within a synthetic nanocarrier. For example, the substance can be enclosed completely within a synthetic nanocarrier. Alternatively, most or all of a substance that is encapsulated is not exposed to the local environment external to the synthetic nanocarrier. In the context where some of a substance is not exposed to the local environment external to the synthetic nanocarrier, this can mean that no more than 50%, 40%, 30%, 20%, 10% or 5% is exposed to the local environment. Encapsulation is distinct from adsorption, which places most or all of a substance on a surface of a synthetic nanocarrier, and leaves the substance exposed to the local environment external to the synthetic nanocarrier.

As used herein, "synthetic nanocarrier" refers to a discrete object that is not found in nature, and that possesses at least one dimension that is less than or equal to 5 microns in size. A synthetic nanocarrier can be, but is not limited to, one or a plurality of lipid-based nanoparticles, polymeric nanoparticles, metallic nanoparticles, surfactant-based emulsions, dendrimers, buckyballs, nanowires, peptide or protein-based particles (such as albumin nanoparticles) and/or nanoparticles that are developed using a combination of nanomaterials such as lipid-polymer nanoparticles. Synthetic nanocarriers may be a variety of different shapes, including but not limited to spheroidal, cuboidal, pyramidal, oblong, cylindrical, toroidal, and the like. Synthetic nanocarriers according to the invention comprise one or more surfaces. Exemplary synthetic nanocarriers include: (1) the biodegradable nanoparticles disclosed in U.S. Pat. No. 5,543,158 to Gref et al., (2) the polymeric nanoparticles of Published US Patent Application 20060002852 to Saltzman et al., (3) the lithographically constructed nanoparticles of Published US Patent Application 20090028910 to DeSimone et al., (4) the disclosure of WO 2009/051837 to von Andrian et al., or (5) the nanoparticles disclosed in Published US Patent Application 2008/0145441 to Penades et al., (6) the protein nanoparticles disclosed in Published US Patent Application 20090226525 to de los Rios et al., (7) the virus-like particles disclosed in published US Patent Application 20060222652 to Sebbel et al., (8) the nucleic acid coupled virus-like particles disclosed in published US Patent Application 20060251677 to Bachmann et al., (9) the virus-like particles disclosed in WO2010047839A1 or WO2009106999A2, or (10) the nanoprecipitated nanoparticles disclosed in P. Paolicelli et al., "Surface-modified PLGA-based Nanoparticles that can Efficiently Associate and Deliver Virus-like Particles" Nanomedicine. 5(6):843-853 (2010). In embodiments, synthetic nanocarriers may possess an aspect ratio greater than 1:1, 1:1.2, 1:1.5, 1:2, 1:3, 1:5, 1:7, or greater than 1:10.

As used herein, "kit" means a collection of at least two components constituting the kit. Together, the components constitute a functional unit for a given purpose. Individual member components may be physically packaged together or separately. For example, a kit comprising an instruction for using the kit may or may not physically include the instruction with other individual member components. Instead, the instruction can be supplied as a separate member component, either in a paper form or an electronic form which may be supplied on computer readable memory device or downloaded from an internet website, or as recorded presentation.

As used herein, "instruction(s)" means documents describing relevant materials or methodologies pertaining to a kit. These materials may include any combination of the following: background information, list of components and their availability information (purchase information, etc.), brief or detailed protocols for using the kit, trouble-shooting, references, technical support, and any other related documents. Instructions can be supplied with the kit or as a separate member component, either as a paper form or an electronic form which may be supplied on computer readable memory device or downloaded from an internet website, or as recorded presentation. Instructions can comprise one or multiple documents, and are meant to include future updates.

As used herein, the term "therapeutic agent" include any synthetic or naturally occurring biologically active compound or composition of matter which, when administered to an organism (human or nonhuman animal), induces a desired pharmacologic, immunogenic, and/or physiologic effect by local and/or systemic action. The term therefore encompasses those compounds or chemicals traditionally regarded as drugs, vaccines, and biopharmaceuticals including molecules such as proteins, peptides, hormones, nucleic acids, gene constructs and the like. Examples of therapeutic agents are described in well-known literature references such as the Merck Index (14$^{th}$ edition), the Physicians' Desk Reference (64$^{th}$ edition), and The Pharmacological Basis of Therapeutics (12$^{th}$ edition), and they include, without limitation, medicaments; vitamins; mineral supplements; substances used for the treatment, prevention, diagnosis, cure or mitigation of a disease or illness; substances that affect the structure or function of the body, or pro-drugs, which become biologically active or more active after they have been placed in a physiological environment. For example, the term "therapeutic agent" includes compounds or compositions for use in all of the major therapeutic areas including, but not limited to, adjuvants; anti-infectives such as antibiotics and antiviral agents; analgesics and analgesic combinations, anorexics, anti-inflammatory agents, anti-epileptics, local and general anesthetics, hypnotics, sedatives, antipsychotic agents, neuroleptic agents, antidepressants, anxiolytics, antagonists, neuron blocking agents, anticholinergic and cholinomimetic agents, antimuscarinic and muscarinic agents, antiadrenergics, antiarrhythmics, antihypertensive agents, hormones, and nutrients, antiarthritics, antiasthmatic agents, anticonvulsants, antihistamines, antinauseants, antineoplastics, antipruritics, antipyretics; antispasmodics, cardiovascular preparations (including calcium channel blockers, beta-blockers, beta-agonists and antiarrythmics), antihypertensives, diuretics, vasodilators; central nervous system stimulants; cough and cold preparations; decongestants; diagnostics; hormones; bone growth stimulants and bone resorption inhibitors; immunosuppressives; muscle relaxants; psychostimulants; sedatives; tranquilizers; proteins, peptides, and fragments thereof (whether naturally occurring, chemically synthesized or recombinantly produced); and nucleic acid molecules (polymeric forms of two or more nucleotides, either ribonucleotides (RNA) or deoxyribonucleotides (DNA) including both double- and single-stranded molecules, gene constructs, expression vectors, antisense molecules and the like), small molecules (e.g., doxorubicin) and other biologically active macromolecules such as, for example, proteins and enzymes. The agent may be a biologically active agent used in medical, including veterinary, applications and in agriculture, such as with plants, as well as other areas. The term therapeutic agent also includes without limitation, medicaments; vitamins; mineral supplements; substances used for the treatment, prevention, diagnosis, cure or mitigation of disease or illness; or substances which affect the structure or function of the body; or pro-drugs, which become biologically active or more active after they have been placed in a predetermined physiological environment.

The term "pharmaceutically acceptable" describes a material that is not biologically or otherwise undesirable, i.e., without causing an unacceptable level of undesirable biological effects or interacting in a deleterious manner.

As used herein, the term "derivative" refers to a compound having a structure derived from the structure of a parent compound (e.g., a compound disclosed herein) and whose structure is sufficiently similar to those disclosed herein and based upon that similarity, would be expected by one skilled in the art to exhibit the same or similar activities and utilities as the claimed compounds, or to induce, as a precursor, the same or similar activities and utilities as the claimed compounds. Exemplary derivatives include salts, esters, amides, salts of esters or amides, and N-oxides of a parent compound.

As used herein, the term "pharmaceutically acceptable carrier" refers to aqueous or nonaqueous solutions, dispersions, suspensions or emulsions, as well as powders for reconstitution into injectable solutions or dispersions just prior to use. Preferably, a pharmaceutically acceptable carrier will be sterile or sterilizable, e.g., where the pharmaceutical composition is intended for injection. The pharmaceutically acceptable carrier is advantageously selected so as not to significantly decrease or neutralize the active ingredient. Examples of suitable aqueous and nonaqueous carriers, diluents, solvents or vehicles include water, ethanol, polyols (such as glycerol, propylene glycol, polyethylene glycol and the like), carboxymethylcellulose and suitable mixtures thereof, vegetable oils (such as olive oil) and injectable organic esters such as ethyl oleate. Proper fluidity can be maintained, for example, by the use of coating materials such as lecithin, by the maintenance of the required particle size in the case of dispersions and by the use of surfactants. These compositions can also contain adjuvants such as preservatives, wetting agents, emulsifying agents and dispersing agents. Prevention of the action of microorganisms can be ensured by the inclusion of various antibacterial and antifungal agents such as paraben, chlorobutanol, phenol, sorbic acid and the like. It can also be desirable to include isotonic agents such as sugars, sodium chloride and the like. Prolonged absorption of the injectable pharmaceutical form can be brought about by the inclusion of agents, such as aluminum monostearate and gelatin, which delay absorption. Injectable depot forms are made by forming microencapsule matrices of the drug in biodegradable polymers such as polylactide-polyglycolide, poly(orthoesters) and poly(anhydrides). Depending upon the ratio of drug to polymer and the nature of the particular polymer employed, the rate of drug release can be controlled. Depot injectable formulations are also prepared by entrapping the drug in liposomes or microemulsions which are compatible with body tissues. The injectable formulations can be sterilized, for example, by filtration through a bacterial-retaining filter or by incorporating sterilizing agents in the form of sterile solid compositions which can be dissolved or dispersed in sterile water or other sterile injectable media just prior to use. Suitable inert carriers can include sugars such as lactose. Desirably, at least 95% by weight of the particles of the active ingredient have an effective particle size in the range of 0.01 to 10 micrometers.

The term "bacteria" as used herein is intended to encompass all variants of bacteria, for example, prokaryotic organisms and cyanobacteria. Accordingly, bacterial infections to be treated using the compositions and methods described herein include, but are not limited to, infections caused by gram-positive bacteria such as, but not limited to, *Bacillus cereus, Bacillus anthracis, Bacillus cereus, Bacillus anthracis, Clostridium botulinum, Clostridium difficle, Clostridium tetani, Clostridium perfringens, Corynebacteria diptheriae, Enterococcus* (*Streptococcus D*), *Listeria monocytogenes*, Pneumococcal infections (*Streptococcus pneumoniae*), Staphylococcal infections and Streptococcal infections; infections caused by gram-negative bacteria such as, but not limited to, *Bacteroides* sp., *Bordetella pertussis, Brucella* sp., *Chlamydia trachomatis, Chlamydia* sp., *Campylobacter* infections, enterohaemorrhagic *Escherichia coli* (EHEC/*E. coli* O157:17), enteroinvasive *Escherichia coli* (EIEC), enterotoxigenic *Escherichia coli* (ETEC), *Haemophilus influenzae, Helicobacter pylori, Klebsiella pneumoniae, Legionella* sp., *Moraxella catarrhalis, Neisseria gonnorrhoeae, Neisseria meningitidis, Proteus* sp., *Pseudomonas aeruginosa, Salmonella* sp., *Shigella* sp., *Vibrio cholera* and *Yersinia*; infections caused by acid fast bacteria including, but not limited to, *Mycobacterium tuberculosis, Mycobacterium avium-intracellulare, Mycobacterium johnei, Mycobacterium leprae*, atypical bacteria, *Mycoplasma, Rickettsia, Spirochetes, Treponema pallidum, Borrelia recurrentis, Borrelia burgdorfii* and *Leptospira icterohemorrhagiae* and other miscellaneous bacteria, including *Actinomyces* sp. and *Nocardia* sp.

Examples of bacterial infections and situations in which such bacterial infections can occur that are not necessarily specific to a particular bacterial species, but encompassed by the term "bacterial infection," as used herein, include bacterial wound infections, such as in burn wound patients; mucosal infections, enteric infections, bacteremia and septic conditions, pneumonia, trachoma, onithosis, trichomoniasis and salmonellosis, especially in veterinary practice; urinary tract infections; post-surgery infections on or caused by invasive devises; endocarditis by intravenous administration of contaminated drug solutions; bacterial infections in patients with acquired immunodeficiency syndrome, cancer chemotherapy, steroid therapy, hematological malignancies, organ transplantation, renal replacement therapy, and other situations with severe neutropenia; community-acquired respiratory tract infections; meningitis; folliculitis and infections of the ear canal caused by contaminated waters; malignant otitis externa in the elderly and diabetics; osteomyelitis of the caleaneus in children; eye infections commonly associated with contaminated contact lens; Skin infections such as nail infections in people whose hands are frequently exposed to water; gastrointestinal tract infections; and musculoskeletal system infections.

The term "biological sample" as used herein refers to a cell or population of cells or a quantity of tissue or fluid from a subject or source, such as an environmental source or a food source, for example. In some embodiments the sample is isolated from or removed from a subject, but, in some embodiments, the term "biological sample" can also refer to cells or tissue analyzed in vivo, i.e. without removal from the subject. Often, a "biological sample" will contain cells from the animal, but the term can also refer to non-cellular biological material. The term biological sample encompasses cellular, tissue or fluid extracts, including, but not limited to, skin, plasma, serum, spinal fluid, lymph fluid, synovial fluid, urine, tears, blood cells, organs, tumors, and also to samples of in vitro cell culture constituents (including, but not limited to, conditioned medium resulting from the growth of cells (including prokaryotic and eukaryotic cells) in cell culture medium, recombinant cells, and cell components). Samples can comprise cellular or tissue explants obtained from an individual or organism during a medical procedure or intervention, such as a surgical procedure or biopsy. Samples from environmental sources are also included among "samples" to which the compositions and methods described herein can be applied.

As used herein, "spectinomycin" and "SPC" can be used interchangeably, and refer to a compound having a structure represented by a formula:

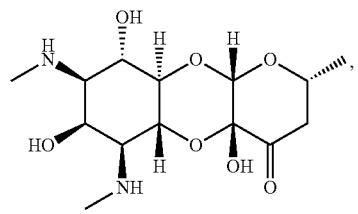

and is an antibiotic produced by *Streptomyces spectabilis*. Alternatively, spectinomycin can also be referred to as (2R,4aR,5aR,6S,7S,8R,9S,9aR,10aS)-4a,7,9-trihydroxy-2-methyl-6,8-bis(methylamino)decahydro-4H-benzo[b]pyrano[2,3-e][1,4]dioxin-4-one, Actinospectacin, Trobicin, Togamycin, Spectam, espectinomicina, spectinomycine, spectinomicina, and actinospectacina. It is understood that the core spectinomycin tricyclic ring structure has the following numbering convention:

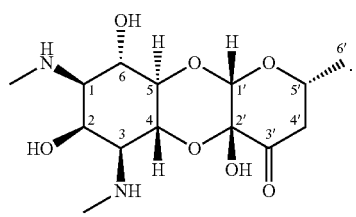

As used herein, "3'-aminomethyl-3'-hydroxy spectinomycin," "3'-aminomethyl-3'-hydroxy spectinomycin," and "mSPC" can be used interchangeably, and refer to a compound having a structure represented by a formula:

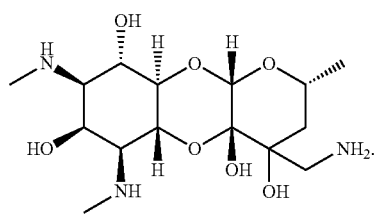 [SMILES: CN[C@@H]1[C@H](O)[C@H](NC)[C@H]2O[C@]3(O)[C@H](O[C@@H]2[C@H]1O)O[C@H](C)CC3(O)CN]

As used herein, "di-benzyloxy carbonyl-3'-(R)-methylene mSPC" refers to a compound having a structure represented by a formula:

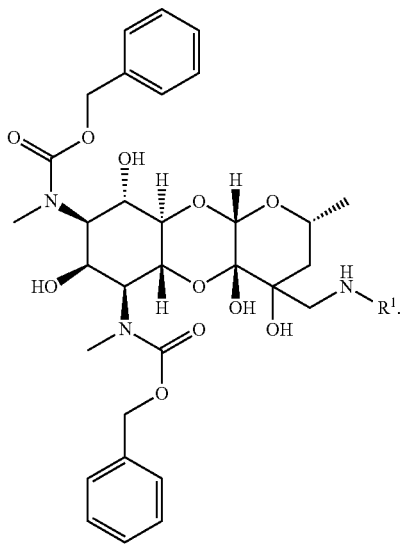

It is understood that "di-benzyloxy carbonyl-3'-(R)-methylene mSPC" includes specific examples of the above compound, e.g. such a specific example of a di-benzyloxy carbonyl-3'-(R)-methylene mSPC is a compound having a structure represented by a formula:

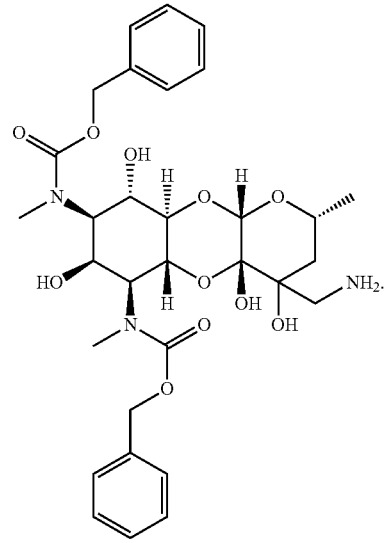 [SMILES: C[C@@H]1CC(O)(CN)[C@]2(O)O[C@H]3[C@H](O[C@@H]2O1)[C@@H](O)[C@H](N(C)C(=O)OCc1ccccc1)[C@H](O)[C@@H]3N(C)C(=O)OCc1ccccc1]

As used herein, "di-benzyloxy carbonyl-3'-deoxo-3'-(R)-mSPC oxide" refers a compound having a structure represented by a formula:

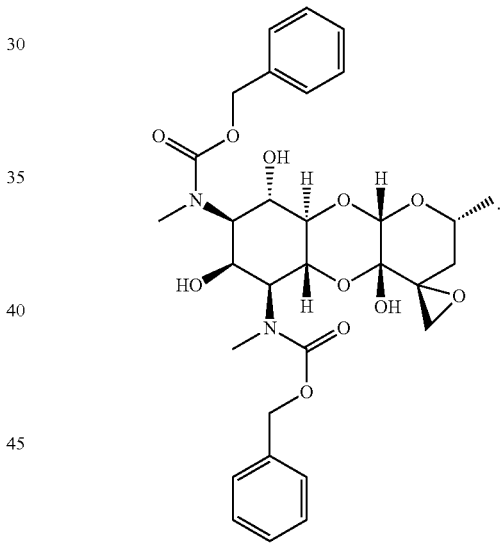

A residue of a chemical species, as used in the specification and concluding claims, refers to the moiety that is the resulting product of the chemical species in a particular reaction scheme or subsequent formulation or chemical product, regardless of whether the moiety is actually obtained from the chemical species. Thus, an ethylene glycol residue in a polyester refers to one or more —OCH$_2$CH$_2$O— units in the polyester, regardless of whether ethylene glycol was used to prepare the polyester. Similarly, a sebacic acid residue in a polyester refers to one or more —OCO(CH$_2$)$_8$OCO— moieties in the polyester, regardless of whether the residue is obtained by reacting sebacic acid or an ester thereof to obtain the polyester.

As used herein, the term "substituted" is contemplated to include all permissible substituents of organic compounds. In a broad aspect, the permissible substituents include acyclic and cyclic, branched and unbranched, carbocyclic and heterocyclic, and aromatic and nonaromatic substituents of organic compounds. Illustrative substituents include, for example, those described below. The permissible substituents can be one or more and the same or different for appropriate organic compounds. For purposes of this disclosure, the heteroatoms, such as nitrogen, can have hydrogen substituents and/or any permissible substituents of organic compounds described herein which satisfy the valences of the heteroatoms. This disclosure is not intended to be limited in any manner by the permissible substituents of organic compounds. Also, the terms "substitution" or "substituted with" include the implicit proviso that such substitution is in accordance with permitted valence of the substituted atom and the substituent, and that the substitution results in a stable compound, e.g., a compound that does not spontaneously undergo transformation such as by rearrangement, cyclization, elimination, etc. It is also contemplated that, in certain aspects, unless expressly indicated to the contrary, individual substituents can be further optionally substituted (i.e., further substituted or unsubstituted).

In defining various terms, "$A^1$," "$A^2$," "$A^3$," and "$A^4$" are used herein as generic symbols to represent various specific substituents. These symbols can be any substituent, not limited to those disclosed herein, and when they are defined to be certain substituents in one instance, they can, in another instance, be defined as some other substituents.

The term "aliphatic" or "aliphatic group," as used herein, denotes a hydrocarbon moiety that may be straight-chain (i.e., unbranched), branched, or cyclic (including fused, bridging, and spirofused polycyclic) and may be completely saturated or may contain one or more units of unsaturation, but which is not aromatic. Unless otherwise specified, aliphatic groups contain 1-20 carbon atoms. Aliphatic groups include, but are not limited to, linear or branched, alkyl, alkenyl, and alkynyl groups, and hybrids thereof such as (cycloalkyl)alkyl, (cycloalkenyl)alkyl or (cycloalkyl)alkenyl.

The term "alkyl" as used herein is a branched or unbranched saturated hydrocarbon group of 1 to 24 carbon atoms, such as methyl, ethyl, n-propyl, isopropyl, n-butyl, isobutyl, s-butyl, t-butyl, n-pentyl, isopentyl, s-pentyl, neopentyl, hexyl, heptyl, octyl, nonyl, decyl, dodecyl, tetradecyl, hexadecyl, eicosyl, tetracosyl, and the like. The alkyl group can be cyclic or acyclic. The alkyl group can be branched or unbranched. The alkyl group can also be substituted or unsubstituted. For example, the alkyl group can be substituted with one or more groups including, but not limited to, alkyl, cycloalkyl, alkoxy, amino, ether, halide, hydroxy, nitro, silyl, sulfo-oxo, or thiol, as described herein. A "lower alkyl" group is an alkyl group containing from one to four carbon atoms, e.g., methyl, ethyl, propyl, butyl. The term alkyl group can also be a C1 alkyl, C1-C2 alkyl, C1-C3 alkyl, C1-C4 alkyl, C1-C5 alkyl, C1-C6 alkyl, C1-C7 alkyl, C1-C8 alkyl, C1-C9 alkyl, C1-C10 alkyl, and the like up to and including a C1-C24 alkyl.

Throughout the specification "alkyl" is generally used to refer to both unsubstituted alkyl groups and substituted alkyl groups; however, substituted alkyl groups are also specifically referred to herein by identifying the specific substituent(s) on the alkyl group. For example, the term "halogenated alkyl" or "haloalkyl" specifically refers to an alkyl group that is substituted with one or more halide, e.g., fluorine, chlorine, bromine, or iodine. Alternatively, the term "monohaloalkyl" specifically refers to an alkyl group that is substituted with a single halide, e.g. fluorine, chlorine, bromine, or iodine. The term "polyhaloalkyl" specifically refers to an alkyl group that is independently substituted with two or more halides, i.e., each halide substituent need not be the same halide as another halide substituent, nor do the multiple instances of a halide substituent need to be on the same carbon. The term "alkoxyalkyl" specifically refers to an alkyl group that is substituted with one or more alkoxy groups, as described below. The term "aminoalkyl" specifically refers to an alkyl group that is substituted with one or more amino groups. The term "hydroxyalkyl" specifically refers to an alkyl group that is substituted with one or more hydroxy groups. When "alkyl" is used in one instance and a specific term such as "hydroxyalkyl" is used in another, it is not meant to imply that the term "alkyl" does not also refer to specific terms such as "hydroxyalkyl" and the like.

This practice is also used for other groups described herein. That is, while a term such as "cycloalkyl" refers to both unsubstituted and substituted cycloalkyl moieties, the substituted moieties can, in addition, be specifically identified herein; for example, a particular substituted cycloalkyl can be referred to as, e.g., an "alkylcycloalkyl." Similarly, a substituted alkoxy can be specifically referred to as, e.g., a "halogenated alkoxy," a particular substituted alkenyl can be, e.g., an "alkenylalcohol," and the like. Again, the practice of using a general term, such as "cycloalkyl," and a specific term, such as "alkylcycloalkyl," is not meant to imply that the general term does not also include the specific term.

The term "cycloalkyl" as used herein is a non-aromatic carbon-based ring composed of at least three carbon atoms. Examples of cycloalkyl groups include, but are not limited to, cyclopropyl, cyclobutyl, cyclopentyl, cyclohexyl, norbornyl, and the like. The term "heterocycloalkyl" is a type of cycloalkyl group as defined above, and is included within the meaning of the term "cycloalkyl," where at least one of the carbon atoms of the ring is replaced with a heteroatom such as, but not limited to, nitrogen, oxygen, sulfur, or phosphorus. The cycloalkyl group and heterocycloalkyl group can be substituted or unsubstituted. The cycloalkyl group and heterocycloalkyl group can be substituted with one or more groups including, but not limited to, alkyl, cycloalkyl, alkoxy, amino, ether, halide, hydroxy, nitro, silyl, sulfo-oxo, or thiol as described herein.

The term "polyalkylene group" as used herein is a group having two or more $CH_2$ groups linked to one another. The polyalkylene group can be represented by the formula —$(CH_2)_a$—, where "a" is an integer of from 2 to 500.

The terms "alkoxy" and "alkoxyl" as used herein to refer to an alkyl or cycloalkyl group bonded through an ether linkage; that is, an "alkoxy" group can be defined as —$OA^1$ where $A^1$ is alkyl or cycloalkyl as defined above. "Alkoxy" also includes polymers of alkoxy groups as just described; that is, an alkoxy can be a polyether such as —$OA^1$-$OA^2$ or —$OA^1$-$(OA^2)_a$-OA, where "a" is an integer of from 1 to 200 and $A^1$, $A^2$, and $A^3$ are alkyl and/or cycloalkyl groups.

The term "alkenyl" as used herein is a hydrocarbon group of from 2 to 24 carbon atoms with a structural formula containing at least one carbon-carbon double bond. Asymmetric structures such as $(A^1A^2)C=C(A^3A^4)$ are intended to include both the E and Z isomers. This can be presumed in structural formulae herein wherein an asymmetric alkene is present, or it can be explicitly indicated by the bond symbol C=C. The alkenyl group can be substituted with one or more groups including, but not limited to, alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol, as described herein.

The term "cycloalkenyl" as used herein is a non-aromatic carbon-based ring composed of at least three carbon atoms and containing at least one carbon-carbon double bound, i.e., C═C. Examples of cycloalkenyl groups include, but are not limited to, cyclopropenyl, cyclobutenyl, cyclopentenyl, cyclopentadienyl, cyclohexenyl, cyclohexadienyl, norbornenyl, and the like. The term "heterocycloalkenyl" is a type of cycloalkenyl group as defined above, and is included within the meaning of the term "cycloalkenyl," where at least one of the carbon atoms of the ring is replaced with a heteroatom such as, but not limited to, nitrogen, oxygen, sulfur, or phosphorus. The cycloalkenyl group and heterocycloalkenyl group can be substituted or unsubstituted. The cycloalkenyl group and heterocycloalkenyl group can be substituted with one or more groups including, but not limited to, alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol as described herein.

The term "alkynyl" as used herein is a hydrocarbon group of 2 to 24 carbon atoms with a structural formula containing at least one carbon-carbon triple bond. The alkynyl group can be unsubstituted or substituted with one or more groups including, but not limited to, alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol, as described herein.

The term "cycloalkynyl" as used herein is a non-aromatic carbon-based ring composed of at least seven carbon atoms and containing at least one carbon-carbon triple bound. Examples of cycloalkynyl groups include, but are not limited to, cycloheptynyl, cyclooctynyl, cyclononynyl, and the like. The term "heterocycloalkynyl" is a type of cycloalkenyl group as defined above, and is included within the meaning of the term "cycloalkynyl," where at least one of the carbon atoms of the ring is replaced with a heteroatom such as, but not limited to, nitrogen, oxygen, sulfur, or phosphorus. The cycloalkynyl group and heterocycloalkynyl group can be substituted or unsubstituted. The cycloalkynyl group and heterocycloalkynyl group can be substituted with one or more groups including, but not limited to, alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol as described herein.

The term "aromatic group" as used herein refers to a ring structure having cyclic clouds of delocalized π electrons above and below the plane of the molecule, where the it clouds contain (4n+2) π electrons. A further discussion of aromaticity is found in Morrison and Boyd, Organic Chemistry, (5th Ed., 1987), Chapter 13, entitled "Aromaticity," pages 477-497, incorporated herein by reference. The term "aromatic group" is inclusive of both aryl and heteroaryl groups.

The term "aryl" as used herein is a group that contains any carbon-based aromatic group including, but not limited to, benzene, naphthalene, phenyl, biphenyl, anthracene, and the like. The aryl group can be substituted or unsubstituted. The aryl group can be substituted with one or more groups including, but not limited to, alkyl, cycloalkyl, alkoxy, alkenyl, cycloalkenyl, alkynyl, cycloalkynyl, aryl, heteroaryl, aldehyde, —$NH_2$, carboxylic acid, ester, ether, halide, hydroxy, ketone, azide, nitro, silyl, sulfo-oxo, or thiol as described herein. The term "biaryl" is a specific type of aryl group and is included in the definition of "aryl." In addition, the aryl group can be a single ring structure or comprise multiple ring structures that are either fused ring structures or attached via one or more bridging groups such as a carbon-carbon bond. For example, biaryl can be two aryl groups that are bound together via a fused ring structure, as in naphthalene, or are attached via one or more carbon-carbon bonds, as in biphenyl.

The term "aldehyde" as used herein is represented by the formula —C(O)H. Throughout this specification "C(O)" is a short hand notation for a carbonyl group, i.e., C═O.

The terms "amine" or "amino" as used herein are represented by the formula —$NA^1A^2$, where $A^1$ and $A^2$ can be, independently, hydrogen or alkyl, cycloalkyl, alkenyl, cycloalkenyl, alkynyl, cycloalkynyl, aryl, or heteroaryl group as described herein. A specific example of amino is —$NH_2$.

The term "alkylamino" as used herein is represented by the formula —NH(-alkyl) where alkyl is a described herein. Representative examples include, but are not limited to, methylamino group, ethylamino group, propylamino group, isopropylamino group, butylamino group, isobutylamino group, (sec-butyl)amino group, (tert-butyl)amino group, pentylamino group, isopentylamino group, (tert-pentyl) amino group, hexylamino group, and the like.

The term "dialkylamino" as used herein is represented by the formula —$N(-alkyl)_2$ where alkyl is a described herein. Representative examples include, but are not limited to, dimethylamino group, diethylamino group, dipropylamino group, diisopropylamino group, dibutylamino group, diisobutylamino group, di(sec-butyl)amino group, di(tert-butyl)amino group, dipentylamino group, diisopentylamino group, di(tert-pentyl)amino group, dihexylamino group, N-ethyl-N-methylamino group, N-methyl-N-propylamino group, N-ethyl-N-propylamino group and the like.

The term "carboxylic acid" as used herein is represented by the formula —C(O)OH.

The term "ester" as used herein is represented by the formula —OC(O)$A^1$ or —C(O)O$A^1$, where $A^1$ can be alkyl, cycloalkyl, alkenyl, cycloalkenyl, alkynyl, cycloalkynyl, aryl, or heteroaryl group as described herein. The term "polyester" as used herein is represented by the formula -($A^1$O(O)C-$A^2$-C(O)O)$_a$— or -($A^1$O(O)C-$A^2$-OC(O))$_a$—, where $A^1$ and $A^2$ can be, independently, an alkyl, cycloalkyl, alkenyl, cycloalkenyl, alkynyl, cycloalkynyl, aryl, or heteroaryl group described herein and "a" is an integer from 1 to 500. "Polyester" is as the term used to describe a group that is produced by the reaction between a compound having at least two carboxylic acid groups with a compound having at least two hydroxyl groups.

The term "ether" as used herein is represented by the formula $A^1$O$A^2$, where $A^1$ and $A^2$ can be, independently, an alkyl, cycloalkyl, alkenyl, cycloalkenyl, alkynyl, cycloalkynyl, aryl, or heteroaryl group described herein. The term "polyether" as used herein is represented by the formula -($A^1$O-$A^2$O)$_a$—, where $A^1$ and $A^2$ can be, independently, an alkyl, cycloalkyl, alkenyl, cycloalkenyl, alkynyl, cycloalkynyl, aryl, or heteroaryl group described herein and "a" is an integer of from 1 to 500. Examples of polyether groups include polyethylene oxide, polypropylene oxide, and polybutylene oxide.

The terms "halo," "halogen," or "halide," as used herein can be used interchangeably and refer to F, Cl, Br, or I.

The terms "pseudohalide," "pseudohalogen," or "pseudohalo," as used herein can be used interchangeably and refer to functional groups that behave substantially similar to halides. Such functional groups include, by way of example, cyano, thiocyanato, azido, trifluoromethyl, trifluoromethoxy, perfluoroalkyl, and perfluoroalkoxy groups.

The term "heteroalkyl," as used herein refers to an alkyl group containing at least one heteroatom. Suitable heteroatoms include, but are not limited to, O, N, Si, P and S, wherein the nitrogen, phosphorous and sulfur atoms are optionally oxidized, and the nitrogen heteroatom is optionally quaternized. Heteroalkyls can be substituted as defined above for alkyl groups.

The term "heteroaryl," as used herein refers to an aromatic group that has at least one heteroatom incorporated within the ring of the aromatic group. Examples of heteroatoms include, but are not limited to, nitrogen, oxygen, sulfur, and phosphorus, where N-oxides, sulfur oxides, and dioxides are permissible heteroatom substitutions. The heteroaryl group can be substituted or unsubstituted. The heteroaryl group can be substituted with one or more groups including, but not limited to, alkyl, cycloalkyl, alkoxy, amino, ether, halide, hydroxy, nitro, silyl, sulfo-oxo, or thiol as described herein. Heteroaryl groups can be monocyclic, or alternatively fused ring systems. Heteroaryl groups include, but are not limited to, furyl, imidazolyl, pyrimidinyl, tetrazolyl, thienyl, pyridinyl, pyrrolyl, N-methylpyrrolyl, quinolinyl, isoquinolinyl, pyrazolyl, triazolyl, thiazolyl, oxazolyl, isoxazolyl, oxadiazolyl, thiadiazolyl, isothiazolyl, pyridazinyl, pyrazinyl, benzofuranyl, benzodioxolyl, benzothiophenyl, indolyl, indazolyl, benzimidazolyl, imidazopyridinyl, pyrazolopyridinyl, and pyrazolopyrimidinyl. Further not limiting examples of heteroaryl groups include, but are not limited to, pyridinyl, pyridazinyl, pyrimidinyl, pyrazinyl, thiophenyl, pyrazolyl, imidazolyl, benzo[d]oxazolyl, benzo[d]thiazolyl, quinolinyl, quinazolinyl, indazolyl, imidazo[1,2-b]pyridazinyl, imidazo[1,2-a]pyrazinyl, benzo[c][1,2,5]thiadiazolyl, benzo[c][1,2,5]oxadiazolyl, and pyrido[2,3-b]pyrazinyl.

The terms "heterocycle" or "heterocyclyl," as used herein can be used interchangeably and refer to single and multi-cyclic aromatic or non-aromatic ring systems in which at least one of the ring members is other than carbon. Thus, the term is inclusive of, but not limited to, "heterocycloalkyl", "heteroaryl", "bicyclic heterocycle" and "polycyclic heterocycle." Heterocycle includes pyridine, pyrimidine, furan, thiophene, pyrrole, isoxazole, isothiazole, pyrazole, oxazole, thiazole, imidazole, oxazole, including, 1,2,3-oxadiazole, 1,2,5-oxadiazole and 1,3,4-oxadiazole, thiadiazole, including, 1,2,3-thiadiazole, 1,2,5-thiadiazole, and 1,3,4-thiadiazole, triazole, including, 1,2,3-triazole, 1,3,4-triazole, tetrazole, including 1,2,3,4-tetrazole and 1,2,4,5-tetrazole, pyridazine, pyrazine, triazine, including 1,2,4-triazine and 1,3,5-triazine, tetrazine, including 1,2,4,5-tetrazine, pyrrolidine, piperidine, piperazine, morpholine, azetidine, tetrahydropyran, tetrahydrofuran, dioxane, and the like. The term heterocyclyl group can also be a C2 heterocyclyl, C2-C3 heterocyclyl, C2-C4 heterocyclyl, C2-C5 heterocyclyl, C2-C6 heterocyclyl, C2-C7 heterocyclyl, C2-C8 heterocyclyl, C2-C9 heterocyclyl, C2-C10 heterocyclyl, C2-C11 heterocyclyl, and the like up to and including a C2-C18 heterocyclyl. For example, a C2 heterocyclyl comprises a group which has two carbon atoms and at least one heteroatom, including, but not limited to, aziridinyl, diazetidinyl, dihydrodiazetyl, oxiranyl, thiiranyl, and the like. Alternatively, for example, a C5 heterocyclyl comprises a group which has five carbon atoms and at least one heteroatom, including, but not limited to, piperidinyl, tetrahydropyranyl, tetrahydrothiopyranyl, diazepanyl, pyridinyl, and the like. It is understood that a heterocyclyl group may be bound either through a heteroatom in the ring, where chemically possible, or one of carbons comprising the heterocyclyl ring.

The term "bicyclic heterocycle" or "bicyclic heterocyclyl," as used herein refers to a ring system in which at least one of the ring members is other than carbon. Bicyclic heterocyclyl encompasses ring systems wherein an aromatic ring is fused with another aromatic ring, or wherein an aromatic ring is fused with a non-aromatic ring. Bicyclic heterocyclyl encompasses ring systems wherein a benzene ring is fused to a 5- or a 6-membered ring containing 1, 2 or 3 ring heteroatoms or wherein a pyridine ring is fused to a 5- or a 6-membered ring containing 1, 2 or 3 ring heteroatoms. Bicyclic heterocyclic groups include, but are not limited to, indolyl, indazolyl, pyrazolo[1,5-a]pyridinyl, benzofuranyl, quinolinyl, quinoxalinyl, 1,3-benzodioxolyl, 2,3-dihydro-1,4-benzodioxinyl, 3,4-dihydro-2H-chromenyl, 1H-pyrazolo[4,3-c]pyridin-3-yl; 1H-pyrrolo[3,2-b]pyridin-3-yl; and 1H-pyrazolo[3,2-b]pyridin-3-yl.

The term "heterocycloalkyl" as used herein refers to an aliphatic, partially unsaturated or fully saturated, 3- to 14-membered ring system, including single rings of 3 to 8 atoms and bi- and tricyclic ring systems. The heterocycloalkyl ring-systems include one to four heteroatoms independently selected from oxygen, nitrogen, and sulfur, wherein a nitrogen and sulfur heteroatom optionally can be oxidized and a nitrogen heteroatom optionally can be substituted. Representative heterocycloalkyl groups include, but are not limited to, pyrrolidinyl, pyrazolinyl, pyrazolidinyl, imidazolinyl, imidazolidinyl, piperidinyl, piperazinyl, oxazolidinyl, isoxazolidinyl, morpholinyl, thiazolidinyl, isothiazolidinyl, and tetrahydrofuryl.

The term "hydroxyl" or "hydroxy" as used herein is represented by the formula —OH.

The term "ketone" as used herein is represented by the formula $A^1C(O)A^2$, where $A^1$ and $A^2$ can be, independently, an alkyl, cycloalkyl, alkenyl, cycloalkenyl, alkynyl, cycloalkynyl, aryl, or heteroaryl group as described herein.

The term "azide" or "azido" as used herein is represented by the formula —$N_3$.

The term "nitro" as used herein is represented by the formula —$NO_2$.

The term "nitrile" or "cyano" as used herein is represented by the formula —CN.

The term "silyl" as used herein is represented by the formula —$SiA^1A^2A^3$, where $A^1$, $A^2$, and $A^3$ can be, independently, hydrogen or an alkyl, cycloalkyl, alkoxy, alkenyl, cycloalkenyl, alkynyl, cycloalkynyl, aryl, or heteroaryl group as described herein.

The term "sulfo-oxo" as used herein is represented by the formulas —$S(O)A^1$, —$S(O)_2A^1$, —$OS(O)_2A^1$, or —$OS(O)_2OA^1$, where $A^1$ can be hydrogen or an alkyl, cycloalkyl, alkenyl, cycloalkenyl, alkynyl, cycloalkynyl, aryl, or heteroaryl group as described herein. Throughout this specification "S(O)" is a short hand notation for S=O. The term "sulfonyl" is used herein to refer to the sulfo-oxo group represented by the formula —$S(O)_2A^1$, where $A^1$ can be hydrogen or an alkyl, cycloalkyl, alkenyl, cycloalkenyl, alkynyl, cycloalkynyl, aryl, or heteroaryl group as described herein. The term "sulfone" is represented by the formula $A^1S(O)_2A^2$, where $A^1$ and $A^2$ can be, independently, an alkyl, cycloalkyl, alkenyl, cycloalkenyl, alkynyl, cycloalkynyl, aryl, or heteroaryl group as described herein. The term "sulfoxide" as used herein is represented by the formula $A^1S(O)A^2$, where $A^1$ and $A^2$ can be, independently, an alkyl, cycloalkyl, alkenyl, cycloalkenyl, alkynyl, cycloalkynyl, aryl, or heteroaryl group as described herein.

The term "thiol" as used herein is represented by the formula —SH.

"$R^1$," "$R^2$," "$R^3$," "$R^n$," where n is an integer, as used herein can, independently, possess one or more of the groups listed above. For example, if $R^1$ is a straight chain alkyl group, one of the hydrogen atoms of the alkyl group can optionally be substituted with a hydroxyl group, an alkoxy group, an alkyl group, a halide, and the like. Depending upon the groups that are selected, a first group can be incorporated within second group or, alternatively, the first group can be pendant (i.e., attached) to the second group. For example, with the phrase "an alkyl group comprising an amino group," the amino group can be incorporated within the backbone of the alkyl group. Alternatively, the amino group can be attached to the backbone of the alkyl group. The nature of the group(s) that is (are) selected will determine if the first group is embedded or attached to the second group.

As described herein, compounds of the invention may contain "optionally substituted" moieties. In general, the term "substituted," whether preceded by the term "optionally" or not, means that one or more hydrogen of the designated moiety are replaced with a suitable substituent. Unless otherwise indicated, an "optionally substituted" group may have a suitable substituent at each substitutable position of the group, and when more than one position in any given structure may be substituted with more than one substituent selected from a specified group, the substituent may be either the same or different at every position. Combinations of substituents envisioned by this invention are preferably those that result in the formation of stable or chemically feasible compounds. In is also contemplated that, in certain aspects, unless expressly indicated to the contrary, individual substituents can be further optionally substituted (i.e., further substituted or unsubstituted).

The term "stable," as used herein, refers to compounds that are not substantially altered when subjected to conditions to allow for their production, detection, and, in certain aspects, their recovery, purification, and use for one or more of the purposes disclosed herein.

Suitable monovalent substituents on a substitutable carbon atom of an "optionally substituted" group are independently halogen; $-(CH_2)_{0-4}R^°$; $-(CH_2)_{0-4}OR^°$; $-O(CH_2)_{0-4}R^°$, $-O-(CH_2)_{0-4}C(O)OR^°$; $-(CH_2)_{0-4}CH(OR^°)_2$; $-(CH_2)_{0-4}SR^°$; $-(CH_2)_{0-4}Ph$, which may be substituted with $R^°$; $-(CH_2)_{0-4}O(CH_2)_{0-1}Ph$ which may be substituted with $R^°$; $-CH=CHPh$, which may be substituted with $R^°$; $-(CH_2)_{0-4}O(CH_2)_{0-1}$-pyridyl which may be substituted with $R^°$; $-NO_2$; $-CN$; $-N_3$; $-(CH_2)_{0-4}N(R^°)_2$; $-(CH_2)_{0-4}N(R^°)C(O)R^°$; $-N(R^°)C(S)R^°$; $-(CH_2)_{0-4}N(R^°)C(O)NR^°_2$; $-N(R^°)C(S)NR^°_2$; $-(CH_2)_{0-4}N(R^°)C(O)OR^°$; $-N(R^°)N(R^°)C(O)R^°$; $-N(R^°)N(R^°)C(O)NR^°_2$; $-N(R^°)N(R^°)C(O)OR^°$; $-(CH_2)_{0-4}C(O)R^°$; $-C(S)R^°$; $-(CH_2)_{0-4}C(O)OR^°$; $-(CH_2)_{0-4}C(O)SR^°$; $-(CH_2)_{0-4}C(O)OSiR^°_3$; $-(CH_2)_{0-4}OC(O)R^°$; $-OC(O)(CH_2)_{0-4}SR-$, $SC(S)SR^°$; $-(CH_2)_{0-4}SC(O)R^°$; $-(CH_2)_{0-4}C(O)NR^°_2$; $-C(S)NR^°_2$; $-C(S)SR^°$; $-(CH_2)_{0-4}OC(O)NR^°_2$; $-C(O)N(OR^°)R^°$; $-C(O)C(O)R^°$; $-C(O)CH_2C(O)R^°$; $-C(NOR^°)R^°$; $-(CH_2)_{0-4}SSR^°$; $-(CH_2)_{0-4}S(O)_2R^°$; $-(CH_2)_{0-4}S(O)_2OR^°$; $-(CH_2)_{0-4}OS(O)_2R^°$; $-S(O)_2NR^°_2$; $-(CH_2)_{0-4}S(O)R^°$; $-N(R^°)S(O)_2NR^°_2$; $-N(R^°)S(O)_2R$; $-N(OR^°)R^°$; $-C(NH)NR^°_2$; $-P(O)_2R^°$; $-P(O)R^°_2$; $-OP(O)R^°_2$; $-OP(O)(OR^°)_2$; $SiR^°_3$; $-(C_{1-4}$ straight or branched alkylene)$O-N(R^°)_2$; or $-(C_{1-4}$ straight or branched alkylene)$C(O)O-N(R^°)_2$, wherein each $R^°$ may be substituted as defined below and is independently hydrogen, $C_{1-6}$ aliphatic, $-CH_2Ph$, $-O(CH_2)_{0-1}Ph$, $-CH_2$-(5-6 membered heteroaryl ring), or a 5-6-membered saturated, partially unsaturated, or aryl ring having 0-4 heteroatoms independently selected from nitrogen, oxygen, or sulfur, or, notwithstanding the definition above, two independent occurrences of $R^°$, taken together with their intervening atom(s), form a 3-12-membered saturated, partially unsaturated, or aryl mono- or bicyclic ring having 0-4 heteroatoms independently selected from nitrogen, oxygen, or sulfur, which may be substituted as defined below.

Suitable monovalent substituents on $R^°$ (or the ring formed by taking two independent occurrences of $R^°$ together with their intervening atoms), are independently halogen, $-(CH_2)_{0-2}R^●$, $-(haloR^●)$, $-(CH_2)_{0-2}OH$, $-(CH_2)_{0-2}OR^●$, $-(CH_2)_{0-2}CH(OR^●)_2$; $-O(haloR^●)$, $-CN$, $-N_3$, $-(CH_2)_{0-2}C(O)R^●$, $-(CH_2)_{0-2}C(O)OH$, $-(CH_2)_{0-2}C(O)OR^●$, $-(CH_2)_{0-2}SR^●$, $-(CH_2)_{0-2}SH$, $-(CH_2)_{0-2}NH_2$, $-(CH_2)_{0-2}NHR^●$, $-(CH_2)_{0-2}NR^●_2$, $-NO_2$, $-SiR^●_3$, $-OSiR^°_3$, $-C(O)SR^●$, $-(C_{1-4}$ straight or branched alkylene)$C(O)OR^●$, or $-SSR^●$ wherein each $R^●$ is unsubstituted or where preceded by "halo" is substituted only with one or more halogens, and is independently selected from $C_{1-4}$ aliphatic, $-CH_2Ph$, $-O(CH_2)_{0-1}Ph$, or a 5-6-membered saturated, partially unsaturated, or aryl ring having 0-4 heteroatoms independently selected from nitrogen, oxygen, or sulfur. Suitable divalent substituents on a saturated carbon atom of $R^°$ include $=O$ and $=S$.

Suitable divalent substituents on a saturated carbon atom of an "optionally substituted" group include the following: $=O$, $=S$, $=NNR^*_2$, $=NNHC(O)R^*$, $=NNHC(O)OR^*$, $=NNHS(O)_2R^*$, $=NR^*$, $=NOR^*$, $-O(C(R^*_2))_{2-3}O-$, or $-S(C(R^*_2))_{2-3}S-$, wherein each independent occurrence of $R^*$ is selected from hydrogen, $C_{1-6}$ aliphatic which may be substituted as defined below, or an unsubstituted 5-6-membered saturated, partially unsaturated, or aryl ring having 0-4 heteroatoms independently selected from nitrogen, oxygen, or sulfur. Suitable divalent substituents that are bound to vicinal substitutable carbons of an "optionally substituted" group include: $-O(CR^*_2)_{2-3}O-$, wherein each independent occurrence of $R^*$ is selected from hydrogen, $C_{1-6}$ aliphatic which may be substituted as defined below, or an unsubstituted 5-6-membered saturated, partially unsaturated, or aryl ring having 0-4 heteroatoms independently selected from nitrogen, oxygen, or sulfur.

Suitable substituents on the aliphatic group of $R^*$ include halogen, $-R^●$, $-(haloR^●)$, $-OH$, $-OR^●$, $-O(haloR^●)$, $-CN$, $-C(O)OH$, $-C(O)OR^●$, $-NH_2$, $-NHR^●$, $-NR^●_2$, or $-NO_2$, wherein each $R^●$ is unsubstituted or where preceded by "halo" is substituted only with one or more halogens, and is independently $C_{1-4}$ aliphatic, $-CH_2Ph$, $-O(CH_2)_{0-1}Ph$, or a 5-6-membered saturated, partially unsaturated, or aryl ring having 0-4 heteroatoms independently selected from nitrogen, oxygen, or sulfur.

Suitable substituents on a substitutable nitrogen of an "optionally substituted" group include $-R^†$, $-NR^†_2$, $-C(O)R^†$, $-C(O)OR^†$, $-C(O)C(O)R^†$, $-C(O)CH_2C(O)R^†$, $-S(O)_2R^†$, $-S(O)_2NR^†_2$, $-C(S)NR^†_2$, $-C(NH)NR^†_2$, or $-N(R^†)S(O)_2R^†$; wherein each $R^†$ is independently hydrogen, $C_{1-6}$ aliphatic which may be substituted as defined below, unsubstituted $-OPh$, or an unsubstituted 5-6-membered saturated, partially unsaturated, or aryl ring having 0-4 heteroatoms independently selected from nitrogen, oxygen, or sulfur, or, notwithstanding the definition above, two independent occurrences of $R^†$, taken together with their intervening atom(s) form an unsubstituted 3-12-membered saturated, partially unsaturated, or aryl mono- or bicyclic ring having 0-4 heteroatoms independently selected from nitrogen, oxygen, or sulfur.

Suitable substituents on the aliphatic group of $R^†$ are independently halogen, $-R^●$, $-(haloR^●)$, $-OH$, $-OR^●$, —O(haloR●), —CN, —C(O)OH, —C(O)OR●, —NH₂, —NHR●, —NR●₂, or —NO₂, wherein each R● is unsubstituted or where preceded by "halo" is substituted only with one or more halogens, and is independently C₁₋₄ aliphatic, —CH₂Ph, —O(CH₂)₀₋₁Ph, or a 5-6-membered saturated, partially unsaturated, or aryl ring having 0-4 heteroatoms independently selected from nitrogen, oxygen, or sulfur.

The term "leaving group" refers to an atom (or a group of atoms) with electron withdrawing ability that can be displaced as a stable species, taking with it the bonding electrons. Examples of suitable leaving groups include halides and sulfonate esters, including, but not limited to, triflate, mesylate, tosylate, and brosylate.

The terms "hydrolysable group" and "hydrolysable moiety" refer to a functional group capable of undergoing hydrolysis, e.g., under basic or acidic conditions. Examples of hydrolysable residues include, without limitation, acid halides, activated carboxylic acids, and various protecting groups known in the art (see, for example, "Protective Groups in Organic Synthesis," T. W. Greene, P. G. M. Wuts, Wiley-Interscience, 1999).

The term "organic residue" defines a carbon containing residue, i.e., a residue comprising at least one carbon atom, and includes but is not limited to the carbon-containing groups, residues, or radicals defined hereinabove. Organic residues can contain various heteroatoms, or be bonded to another molecule through a heteroatom, including oxygen, nitrogen, sulfur, phosphorus, or the like. Examples of organic residues include but are not limited alkyl or substituted alkyls, alkoxy or substituted alkoxy, mono or di-substituted amino, amide groups, etc. Organic residues can preferably comprise 1 to 18 carbon atoms, 1 to 15, carbon atoms, 1 to 12 carbon atoms, 1 to 8 carbon atoms, 1 to 6 carbon atoms, or 1 to 4 carbon atoms. In a further aspect, an organic residue can comprise 2 to 18 carbon atoms, 2 to 15, carbon atoms, 2 to 12 carbon atoms, 2 to 8 carbon atoms, 2 to 4 carbon atoms, or 2 to 4 carbon atoms.

A very close synonym of the term "residue" is the term "radical," which as used in the specification and concluding claims, refers to a fragment, group, or substructure of a molecule described herein, regardless of how the molecule is prepared. For example, a 2,4-thiazolidinedione radical in a particular compound has the structure:

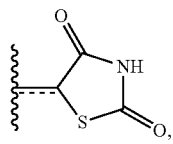

regardless of whether thiazolidinedione is used to prepare the compound. In some embodiments the radical (for example an alkyl) can be further modified (i.e., substituted alkyl) by having bonded thereto one or more "substituent radicals." The number of atoms in a given radical is not critical to the present invention unless it is indicated to the contrary elsewhere herein.

"Organic radicals," as the term is defined and used herein, contain one or more carbon atoms. An organic radical can have, for example, 1-26 carbon atoms, 1-18 carbon atoms, 1-12 carbon atoms, 1-8 carbon atoms, 1-6 carbon atoms, or 1-4 carbon atoms. In a further aspect, an organic radical can have 2-26 carbon atoms, 2-18 carbon atoms, 2-12 carbon atoms, 2-8 carbon atoms, 2-6 carbon atoms, or 2-4 carbon atoms. Organic radicals often have hydrogen bound to at least some of the carbon atoms of the organic radical. One example, of an organic radical that comprises no inorganic atoms is a 5, 6, 7, 8-tetrahydro-2-naphthyl radical. In some embodiments, an organic radical can contain 1-10 inorganic heteroatoms bound thereto or therein, including halogens, oxygen, sulfur, nitrogen, phosphorus, and the like. Examples of organic radicals include but are not limited to an alkyl, substituted alkyl, cycloalkyl, substituted cycloalkyl, mono-substituted amino, di-substituted amino, acyloxy, cyano, carboxy, carboalkoxy, alkylcarboxamide, substituted alkylcarboxamide, dialkylcarboxamide, substituted dialkylcarboxamide, alkylsulfonyl, alkylsulfinyl, thioalkyl, thiohaloalkyl, alkoxy, substituted alkoxy, haloalkyl, haloalkoxy, aryl, substituted aryl, heteroaryl, heterocyclic, or substituted heterocyclic radicals, wherein the terms are defined elsewhere herein. A few non-limiting examples of organic radicals that include heteroatoms include alkoxy radicals, trifluoromethoxy radicals, acetoxy radicals, dimethylamino radicals and the like.

"Inorganic radicals," as the term is defined and used herein, contain no carbon atoms and therefore comprise only atoms other than carbon. Inorganic radicals comprise bonded combinations of atoms selected from hydrogen, nitrogen, oxygen, silicon, phosphorus, sulfur, selenium, and halogens such as fluorine, chlorine, bromine, and iodine, which can be present individually or bonded together in their chemically stable combinations. Inorganic radicals have 10 or fewer, or preferably one to six or one to four inorganic atoms as listed above bonded together. Examples of inorganic radicals include, but are not limited to, amino, hydroxy, halogens, nitro, thiol, sulfate, phosphate, and like commonly known inorganic radicals. The inorganic radicals do not have bonded therein the metallic elements of the periodic table (such as the alkali metals, alkaline earth metals, transition metals, lanthanide metals, or actinide metals), although such metal ions can sometimes serve as a pharmaceutically acceptable cation for anionic inorganic radicals such as a sulfate, phosphate, or like anionic inorganic radical. Inorganic radicals do not comprise metalloids elements such as boron, aluminum, gallium, germanium, arsenic, tin, lead, or tellurium, or the noble gas elements, unless otherwise specifically indicated elsewhere herein.

Compounds described herein can contain one or more double bonds and, thus, potentially give rise to cis/trans (E/Z) isomers, as well as other conformational isomers. Unless stated to the contrary, the invention includes all such possible isomers, as well as mixtures of such isomers.

Unless stated to the contrary, a formula with chemical bonds shown only as solid lines and not as wedges or dashed lines contemplates each possible isomer, e.g., each enantiomer and diastereomer, and a mixture of isomers, such as a racemic or scalemic mixture. Compounds described herein can contain one or more asymmetric centers and, thus, potentially give rise to diastereomers and optical isomers. Unless stated to the contrary, the present invention includes all such possible diastereomers as well as their racemic mixtures, their substantially pure resolved enantiomers, all possible geometric isomers, and pharmaceutically acceptable salts thereof. Mixtures of stereoisomers, as well as isolated specific stereoisomers, are also included. During the course of the synthetic procedures used to prepare such compounds, or in using racemization or epimerization procedures known to those skilled in the art, the products of such procedures can be a mixture of stereoisomers.

Many organic compounds exist in optically active forms having the ability to rotate the plane of plane-polarized light.

In describing an optically active compound, the prefixes D and L or R and S are used to denote the absolute configuration of the molecule about its chiral center(s). The prefixes d and l or (+) and (−) are employed to designate the sign of rotation of plane-polarized light by the compound, with (−) or meaning that the compound is levorotatory. A compound prefixed with (+) or d is dextrorotatory. For a given chemical structure, these compounds, called stereoisomers, are identical except that they are non-superimposable mirror images of one another. A specific stereoisomer can also be referred to as an enantiomer, and a mixture of such isomers is often called an enantiomeric mixture. A 50:50 mixture of enantiomers is referred to as a racemic mixture. Many of the compounds described herein can have one or more chiral centers and therefore can exist in different enantiomeric forms. If desired, a chiral carbon can be designated with an asterisk (*). When bonds to the chiral carbon are depicted as straight lines in the disclosed formulas, it is understood that both the (R) and (S) configurations of the chiral carbon, and hence both enantiomers and mixtures thereof, are embraced within the formula. As is used in the art, when it is desired to specify the absolute configuration about a chiral carbon, one of the bonds to the chiral carbon can be depicted as a wedge (bonds to atoms above the plane) and the other can be depicted as a series or wedge of short parallel lines is (bonds to atoms below the plane). The Cahn-Inglod-Prelog system can be used to assign the (R) or (S) configuration to a chiral carbon.

Compounds described herein comprise atoms in both their natural isotopic abundance and in non-natural abundance. The disclosed compounds of the present invention can be isotopically-labeled or isotopically-substituted compounds identical to those described, but for the fact that one or more atoms are replaced by an atom having an atomic mass or mass number different from the atomic mass or mass number typically found in nature. Examples of isotopes that can be incorporated into compounds of the invention include isotopes of hydrogen, carbon, nitrogen, oxygen, phosphorous, fluorine and chlorine, such as $^2H$, $^3H$, $^{13}C$, $^{14}C$, $^{15}N$, $^{18}O$, $^{17}O$, $^{35}S$, $^{18}F$ and $^{36}Cl$, respectively. Compounds further comprise prodrugs thereof, and pharmaceutically acceptable salts of said compounds or of said prodrugs which contain the aforementioned isotopes and/or other isotopes of other atoms are within the scope of this invention. Certain isotopically-labeled compounds of the present invention, for example those into which radioactive isotopes such as $^3H$ and $^{14}C$ are incorporated, are useful in drug and/or substrate tissue distribution assays. Tritiated, i.e., $^3H$, and carbon-14, i.e., $^{14}C$, isotopes are particularly preferred for their ease of preparation and detectability. Further, substitution with heavier isotopes such as deuterium, i.e., $^2H$, can afford certain therapeutic advantages resulting from greater metabolic stability, for example increased in vivo half-life or reduced dosage requirements and, hence, may be preferred in some circumstances. Isotopically labeled compounds of the present invention and prodrugs thereof can generally be prepared by carrying out the procedures below, by substituting a readily available isotopically labeled reagent for a non-isotopically labeled reagent.

The compounds described in the invention can be present as a solvate. In some cases, the solvent used to prepare the solvate is an aqueous solution, and the solvate is then often referred to as a hydrate. The compounds can be present as a hydrate, which can be obtained, for example, by crystallization from a solvent or from aqueous solution. In this connection, one, two, three or any arbitrary number of solvent or water molecules can combine with the compounds according to the invention to form solvates and hydrates. Unless stated to the contrary, the invention includes all such possible solvates.

The term "co-crystal" means a physical association of two or more molecules which owe their stability through non-covalent interaction. One or more components of this molecular complex provide a stable framework in the crystalline lattice. In certain instances, the guest molecules are incorporated in the crystalline lattice as anhydrates or solvates, see e.g. "Crystal Engineering of the Composition of Pharmaceutical Phases. Do Pharmaceutical Co-crystals Represent a New Path to Improved Medicines?" Almarasson, O., et. al., The Royal Society of Chemistry, 1889-1896, 2004. Examples of co-crystals include p-toluenesulfonic acid and benzenesulfonic acid.

It is also appreciated that certain compounds described herein can be present as an equilibrium of tautomers. For example, ketones with an α-hydrogen can exist in an equilibrium of the keto form and the enol form.

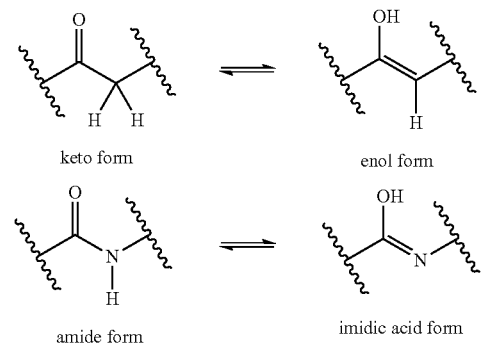

keto form          enol form amide form          imidic acid form

Likewise, amides with an N-hydrogen can exist in an equilibrium of the amide form and the imidic acid form. As another example, pyrazoles can exist in two tautomeric forms, $N^1$-unsubstituted, 3-$A^3$ and $N^1$-unsubstituted, 5-$A^3$ as shown below.

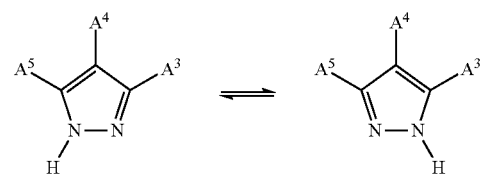

Unless stated to the contrary, the invention includes all such possible tautomers.

It is known that chemical substances form solids which are present in different states of order which are termed polymorphic forms or modifications. The different modifications of a polymorphic substance can differ greatly in their physical properties. The compounds according to the invention can be present in different polymorphic forms, with it being possible for particular modifications to be metastable. Unless stated to the contrary, the invention includes all such possible polymorphic forms.

In some aspects, a structure of a compound can be represented by a formula:

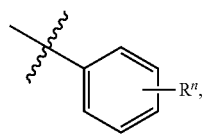

which is understood to be equivalent to a formula:

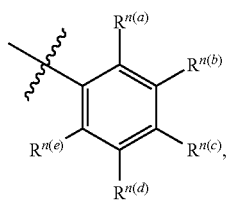

wherein n is typically an integer. That is, $R^n$ is understood to represent five independent substituents, $R^{n(a)}$, $R^{n(b)}$, $R^{n(c)}$, $R^{n(d)}$, $R^{n(e)}$. By "independent substituents," it is meant that each R substituent can be independently defined. For example, if in one instance $R^{n(a)}$ is halogen, then $R^{n(b)}$ is not necessarily halogen in that instance.

Certain materials, compounds, compositions, and components disclosed herein can be obtained commercially or readily synthesized using techniques generally known to those of skill in the art. For example, the starting materials and reagents used in preparing the disclosed compounds of the present invention and compositions are either available from commercial suppliers such as Aldrich Chemical Co., (Milwaukee, Wis.), Acros Organics (Morris Plains, N.J.), Fisher Scientific (Pittsburgh, Pa.), or Sigma (St. Louis, Mo.) or are prepared by methods known to those skilled in the art following procedures set forth in references such as Fieser and Fieser's Reagents for Organic Synthesis, Volumes 1-17 (John Wiley and Sons, 1991); Rodd's Chemistry of Carbon Compounds, Volumes 1-5 and supplemental volumes (Elsevier Science Publishers, 1989); Organic Reactions, Volumes 1-40 (John Wiley and Sons, 1991); March's Advanced Organic Chemistry, (John Wiley and Sons, 4th Edition); and Larock's Comprehensive Organic Transformations (VCH Publishers Inc., 1989).

Unless otherwise expressly stated, it is in no way intended that any method set forth herein be construed as requiring that its steps be performed in a specific order. Accordingly, where a method claim does not actually recite an order to be followed by its steps or it is not otherwise specifically stated in the claims or descriptions that the steps are to be limited to a specific order, it is no way intended that an order be inferred, in any respect. This holds for any possible non-express basis for interpretation, including: matters of logic with respect to arrangement of steps or operational flow; plain meaning derived from grammatical organization or punctuation; and the number or type of embodiments described in the specification.

Disclosed are the components to be used to prepare the compositions of the invention as well as the compositions themselves to be used within the methods disclosed herein. These and other materials are disclosed herein, and it is understood that when combinations, subsets, interactions, groups, etc. of these materials are disclosed that while specific reference of each various individual and collective combinations and permutation of these compounds cannot be explicitly disclosed, each is specifically contemplated and described herein. For example, if a particular compound is disclosed and discussed and a number of modifications that can be made to a number of molecules including the compounds are discussed, specifically contemplated is each and every combination and permutation of the compound and the modifications that are possible unless specifically indicated to the contrary. Thus, if a class of molecules A, B, and C are disclosed as well as a class of molecules D, E, and F and an example of a combination molecule, A-D is disclosed, then even if each is not individually recited each is individually and collectively contemplated meaning combinations, A-E, A-F, B-D, B-E, B-F, C-D, C-E, and C-F are considered disclosed. Likewise, any subset or combination of these is also disclosed. Thus, for example, the sub-group of A-E, B-F, and C-E would be considered disclosed. This concept applies to all aspects of this application including, but not limited to, steps in methods of making and using the compositions of the invention. Thus, if there are a variety of additional steps that can be performed it is understood that each of these additional steps can be performed with any specific embodiment or combination of embodiments of the methods of the invention.

It is understood that the compositions disclosed herein have certain functions. Disclosed herein are certain structural requirements for performing the disclosed functions, and it is understood that there are a variety of structures that can perform the same function that are related to the disclosed structures, and that these structures will typically achieve the same result.

B. Compounds

In one aspect, the invention relates to compounds according to Formula I useful as antibacterial agents. More specifically, in one aspect, the present invention relates to compounds that are aryl substituted aminomethyl spectinomycin analogs using for treating bacterial infections.

It is contemplated that each disclosed derivative can be optionally further substituted. It is also contemplated that any one or more derivative can be optionally omitted from the invention. It is understood that a disclosed compound of the present invention can be provided by the disclosed methods. It is also understood that the disclosed compounds of the present invention can be employed in the disclosed methods of using.

1. Structure

In one aspect, the invention relates to a compound having a structure represented by Formula I:

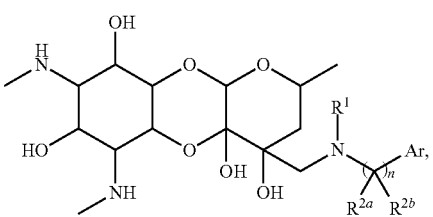

wherein n is an integer selected from 0, 1, 2, and 3; wherein $R^1$ is selected from hydrogen and C1-C4 alkyl; wherein each occurrence of $R^{2a}$ and $R^{2b}$, when present, is independently selected from hydrogen and C1-C3 alkyl; and wherein Ar is aryl or heteroaryl substituted with 0 to 3 groups independently selected from halo, cyano, hydroxyl, —$NH_2$, C1-C3 alkyl, C1-C3 monoalkyl, C1-C3 polyhaloalkoxy, —(C=O)$OR^9$, —(C=O)$NR^{10a}R^{10b}$, —$SO_2NR^{10a}R^{10b}$, —$SR^9$, and —SO$_2$R$^9$; wherein each occurrence of R$^9$, when present, is selected from hydrogen and C1-C3 alkyl; wherein each occurrence of R$^{10a}$ and R$^{10b}$, when present, is independently selected from hydrogen and C1-C3 alkyl; or a pharmaceutically acceptable salt, solvate, or polymorph thereof.

In various aspects, n is an integer selected from 0, 1, and 3. In a further aspect, n is an integer selected from 0, 1, and 2. In a still further aspect, n is an integer selected from 0, 2, and 3. In yet further aspect, n is an integer selected from 1, 2, and 3. In an even further aspect, n is an integer selected from 0 and 1. In a still further aspect, n is an integer selected from 0 and 2. In a yet further aspect, n is an integer selected from 0 and 3. In an even further aspect, n is an integer selected from 1 and 2. In a still further aspect, n is an integer selected from 1 and 3. In a yet further aspect, n is an integer selected from 2 and 3. In an even further aspect, n is 0. In a still further aspect, n is 1. In a yet further aspect, n is 2. In an even further aspect, n is 3.

In one aspect, the invention relates to a compound having a structure represented by a formula:

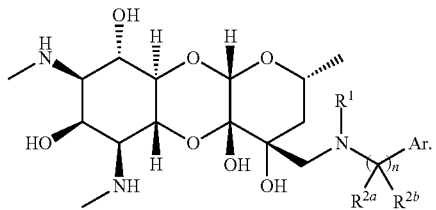

In various aspects, a compound can have a structure represented by a formula:

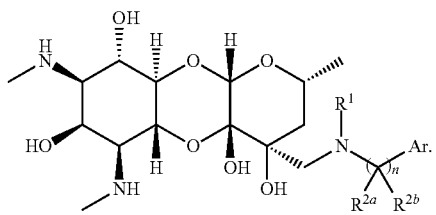

In various aspects, a compound can have a structure represented by a formula:

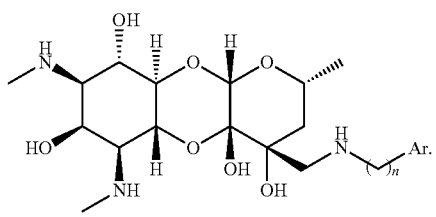

In various aspects, a compound can have a structure represented by a formula:

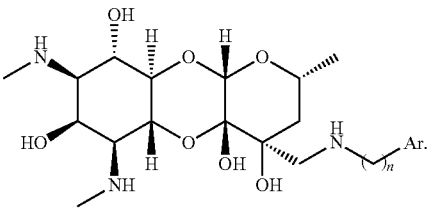

In various aspects, a compound can have a structure represented by a formula:

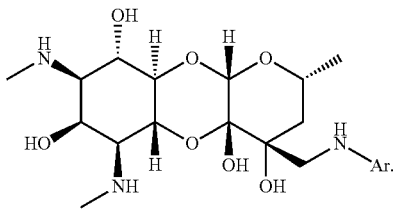

In various aspects, a compound can have a structure represented by a formula:

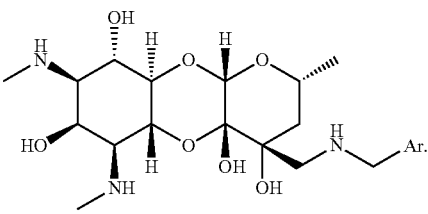

In various aspects, a compound can have a structure represented by a formula:

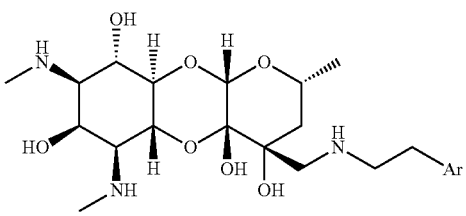

In various aspects, a compound can have a structure represented by a formula:

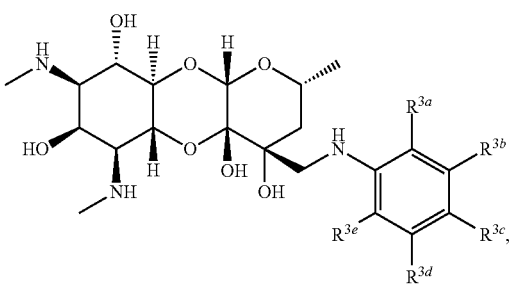

wherein each of R$^{3a}$, R$^{3b}$, R$^{3c}$, R$^{3d}$, and R$^{3e}$ are independently selected from hydrogen, halo, cyano, hydroxyl, —NH$_2$, C1-C3 alkyl, C1-C3 monoalkyl, C1-C3 polyhaloalkyl, C1-C3 alkoxy, C1-C3 monohaloalkoxy, C1-C3 polyhaloalkyl, C1-C3 alkoxy, C1-C3 monohaloalkoxy, C1-C3 polyhaloalkoxy, —(C=O)OR$^9$, —(C=O)NR$^{10a}$R$^{10b}$, —SO$_2$NR$^{10a}$R$^{10b}$, —SR$^9$, and —SO$_2$R$^9$, provided that at least two of R$^{3a}$, R$^{3b}$, R$^{3c}$, R$^{3d}$, and R$^{3e}$ are hydrogen.

In various aspects, a compound an have a structure represented by a formula:

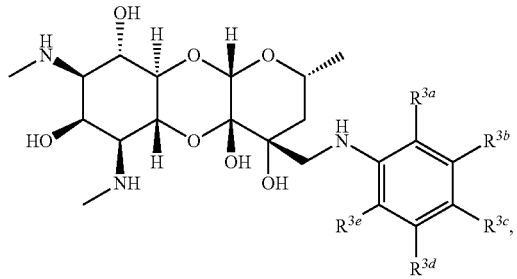

wherein each of R$^{3a}$, R$^{3b}$, R$^{3c}$, R$^{3d}$, and R$^{3e}$ is independently selected from hydrogen, —F, —Cl, —Br, cyano, hydroxyl, —NH$_2$, methyl, ethyl, propyl, isopropyl, —CH$_2$F, —CHF$_2$, —CF$_3$, —CH$_2$Cl, —CHCl$_2$, —CCl$_3$, —CH$_2$CH$_2$F, —CH$_2$CHF$_2$, —CH$_2$CF$_3$, —CH$_2$CH$_2$Cl, —CH$_2$CHCl$_2$, —CH$_2$CCl$_3$, —OCH$_3$, —OCH$_2$CH$_3$, —OCH$_2$F, —OCHF$_2$, —OCF$_3$, —OCH$_2$Cl, —OCHCl$_2$, —OCCl$_3$, —OCH$_2$CH$_2$F, —OCH$_2$CHF$_2$, —OCH$_2$CF$_3$, —OCH$_2$CH$_2$Cl, —OCH$_2$CHCl$_2$, —(C=O)OCH$_2$CH$_3$, —(C=O)OCH$_2$CH$_3$, —(C=O)OCH$_3$, —(C=O)OH, —(C=O)NHCH$_2$CH$_3$, —(C=O)NHCH$_3$, —(C=O)NH$_2$, —SO$_2$N(CH$_3$)$_2$, —SO$_2$NHCH$_2$CH$_3$, —SO$_2$NHCH$_3$, and —SO$_2$NH$_2$, provided that at least two of R$^{3a}$, R$^{3b}$, R$^{3c}$, R$^{3d}$, and R$^{3e}$ are hydrogen.

In various aspects, a compound can have a structure represented by a formula:

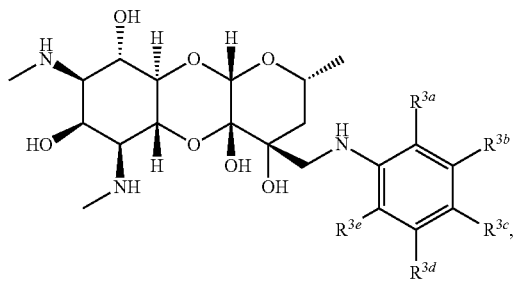

wherein each of R$^{3a}$, R$^{3b}$, R$^{3c}$, R$^{3d}$, and R$^{3e}$ are independently selected from hydrogen, —F, —Cl, —Br, methyl, ethyl, isopropyl, —CH$_2$F, —CHF$_2$, —CF$_3$, —CH$_2$CF$_3$, —OCH$_3$, —OCF$_3$, —OCH$_2$CF$_3$, —(C=O)OH, —(C=O)NH$_2$, —SO$_2$NHCH$_3$, and —SO$_2$NH$_2$, provided that at least two of R$^{3a}$, R$^{3b}$, R$^{3c}$, R$^{3d}$, and R$^{3e}$ are hydrogen.

In various aspects, a compound can have a structure represented by a formula:

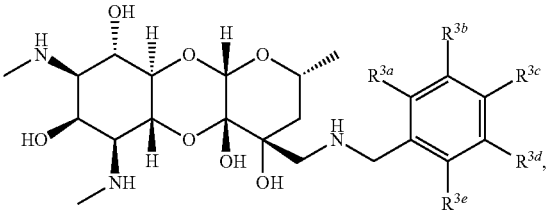

wherein each of R$^{3a}$, R$^{3b}$, R$^{3c}$, R$^{3d}$, and R$^{3e}$ are independently selected from hydrogen, halo, cyano, hydroxyl, —NH$_2$, C1-C3 alkyl, C1-C3 monoalkyl, C1-C3 polyhaloalkyl, C1-C3 alkoxy, C1-C3 monohaloalkoxy, C1-C3 polyhaloalkyl, C1-C3 alkoxy, C1-C3 monohaloalkoxy, C1-C3 polyhaloalkoxy, —(C=O)OR$^9$, —(C=O)NR$^{10a}$R$^{10b}$, —SO$_2$NR$^{10a}$R$^{10b}$, —SR$^9$, and —SO$_2$R$^9$, provided that at least two of R$^{3a}$, R$^{3b}$, R$^{3c}$, R$^{3d}$, and R$^{3e}$ are hydrogen.

In various aspects, a compound can have a structure represented by a formula:

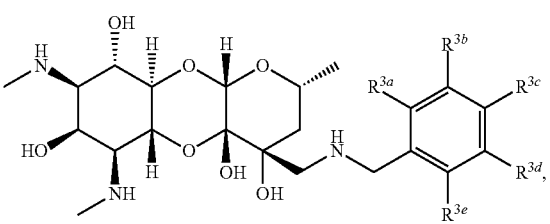

wherein each of R$^{3a}$, R$^{3b}$, R$^{3c}$, R$^{3d}$, and R$^{3e}$ are independently selected from hydrogen, —F, —Cl, —Br, cyano, hydroxyl, —NH$_2$, methyl, ethyl, propyl, isopropyl, —CH$_2$F, —CHF$_2$, —CF$_3$, —CH$_2$Cl, —CHCl$_2$, —CCl$_3$, —CH$_2$CH$_2$F, —CH$_2$CHF$_2$, —CH$_2$CF$_3$, —CH$_2$CH$_2$Cl, —CH$_2$CHCl$_2$, —CH$_2$CCl$_3$, —OCH$_3$, —OCH$_2$CH$_3$, —OCH$_2$F, —OCHF$_2$, —OCF$_3$, —OCH$_2$Cl, —OCHCl$_2$, —OCCl$_3$, —OCH$_2$CH$_2$F, —OCH$_2$CHF$_2$, —OCH$_2$CF$_3$, —OCH$_2$CH$_2$Cl, —OCH$_2$CHCl$_2$, —(C=O)OCH$_2$CH$_3$, —(C=O)OCH$_2$CH$_3$, —(C=O)OCH$_3$, —(C=O)OH, —(C=O)NHCH$_2$CH$_3$, —(C=O)NHCH$_3$, —(C=O)NH$_2$, —SO$_2$N(CH$_3$)$_2$, —SO$_2$NHCH$_2$CH$_3$, —SO$_2$NHCH$_3$, and —SO$_2$NH$_2$, provided that at least two of R$^{3a}$, R$^{3b}$, R$^{3c}$, R$^{3d}$, and R$^{3e}$ are hydrogen.

In various aspects, a compound can have a structure represented by a formula:

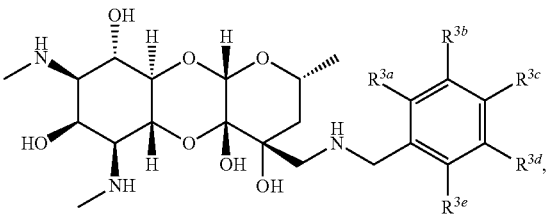

wherein each of R$^{3a}$, R$^{3b}$, R$^{3c}$, R$^{3d}$, and R$^{3e}$ are independently selected from hydrogen, —F, —Cl, —Br, methyl, ethyl, isopropyl, —CH$_2$F, —CHF$_2$, —CF$_3$, —CH$_2$CF$_3$, —OCH$_3$, —OCF$_3$, —OCH$_2$CF$_3$, —(C=O)OH, —(C=O)NH$_2$, —SO$_2$NHCH$_3$, and —SO$_2$NH$_2$, provided that at least two of R$^{3a}$, R$^{3b}$, R$^{3c}$, R$^{3d}$, and R$^{3e}$ are hydrogens.

In various aspects, a compound can have a structure represented by a formula:

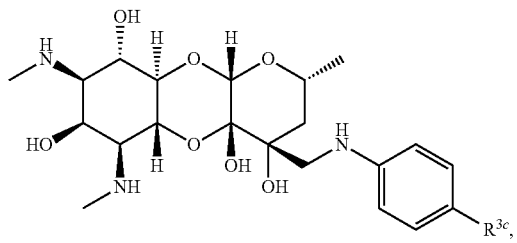

wherein $R^{3c}$ is selected from halo, cyano, hydroxyl, —NH$_2$, C1-C3 alkyl, C1-C3 monoalkyl, C1-C3 polyhaloalkyl, C1-C3 alkoxy, C1-C3 monohaloalkoxy, C1-C3 polyhaloalkyl, C1-C3 alkoxy, C1-C3 monohaloalkoxy, C1-C3 polyhaloalkoxy, —(C=O)OR$^9$, —(C=O)NR$^{10a}$R$^{10b}$, —SO$_2$NR$^{10a}$R$^{10b}$, —SR$^9$, and —SO$_2$R$^9$.

In various aspects a compound can have a structure represented by a formula:

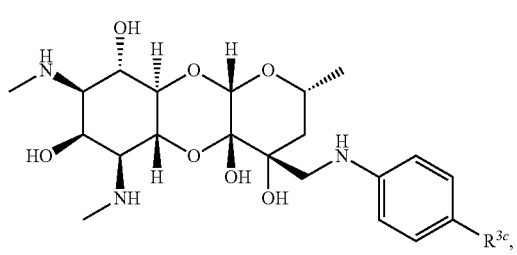

wherein $R^{3c}$ is selected from —F, —Cl, —Br, cyano, hydroxyl, —NH$_2$, methyl, ethyl, propyl, isopropyl, —CH$_2$F, —CHF$_2$, —CF$_3$, —CH$_2$Cl, —CHCl$_2$, —CCl$_3$, —CH$_2$CH$_2$F, —CH$_2$CHF$_2$, —CH$_2$CF$_3$, —CH$_2$CH$_2$Cl, —CH$_2$CHCl$_2$, —CH$_2$CCl$_3$, —OCH$_3$, —OCH$_2$CH$_3$, —OCH$_2$F, —OCHF$_2$, —OCF$_3$, —OCH$_2$Cl, —OCHCl$_2$, —OCCl$_3$, —OCH$_2$CH$_2$F, —OCH$_2$CHF$_2$, —OCH$_2$CF$_3$, —OCH$_2$CH$_2$Cl, —OCH$_2$CHCl$_2$, —(C=O)OCH$_2$CH$_3$, —(C=O)OCH$_2$CH$_3$, —(C=O)OCH$_3$, —(C=O)OH, —(C=O)NHCH$_2$CH$_3$, —(C=O)NHCH$_3$, —(C=O)NH$_2$, —SO$_2$N(CH$_3$)$_2$, —SO$_2$NHCH$_2$CH$_3$, —SO$_2$NHCH$_3$, and —SO$_2$NH$_2$.

In various aspects, a compound can have a structure represented by a formula:

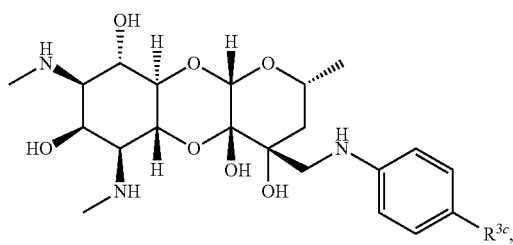

wherein $R^{3c}$ is selected from —F, —Cl, —Br, methyl, ethyl, isopropyl, —CH$_2$F, —CHF$_2$, —CF$_3$, —CH$_2$CF$_3$, —OCH$_3$, —OCF$_3$, —OCH$_2$CF$_3$, —(C=O)OH, —(C=O)NH$_2$, —SO$_2$NHCH$_3$, and —SO$_2$NH$_2$.

In various aspects, a compound can have a structure represented by a formula:

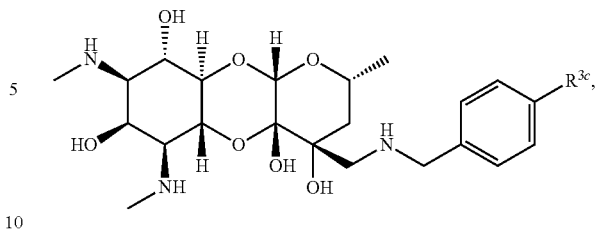

wherein $R^{3c}$ is selected from halo, cyano, hydroxyl, —NH$_2$, C1-C3 alkyl, C1-C3 monoalkyl, C1-C3 polyhaloalkyl, C1-C3 alkoxy, C1-C3 monohaloalkoxy, C1-C3 polyhaloalkyl, C1-C3 alkoxy, C1-C3 monohaloalkoxy, C1-C3 polyhaloalkoxy, —(C=O)OR$^9$, —(C=O)NR$^{10a}$R$^{10b}$, —SO$_2$NR$^{10a}$R$^{10b}$, —SR$^9$, and —SO$_2$R$^9$.

In various aspects, a compound can have a structure represented by a formula:

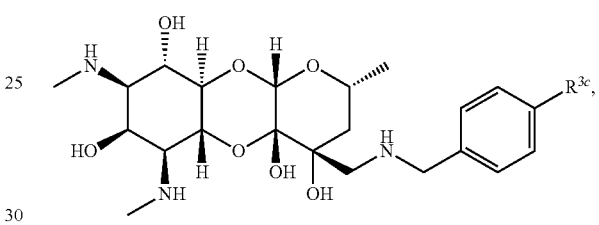

wherein $R^{3c}$ is selected from —F, —Cl, —Br, cyano, hydroxyl, —NH$_2$, methyl, ethyl, propyl, isopropyl, —CH$_2$F, —CHF$_2$, —CF$_3$, —CH$_2$Cl, —CHCl$_2$, —CCl$_3$, —CH$_2$CH$_2$F, —CH$_2$CHF$_2$, —CH$_2$CF$_3$, —CH$_2$CH$_2$Cl, —CH$_2$CHCl$_2$, —CH$_2$CCl$_3$, —OCH$_3$, —OCH$_2$CH$_3$, —OCH$_2$F, —OCHF$_2$, —OCF$_3$, —OCH$_2$Cl, —OCHCl$_2$, —OCCl$_3$, —OCH$_2$CH$_2$F, —OCH$_2$CHF$_2$, —OCH$_2$CF$_3$, —OCH$_2$CH$_2$Cl, —OCH$_2$CHCl$_2$, —(C=O)OCH$_2$CH$_3$, —(C=O)OCH$_2$CH$_3$, —(C=O)OCH$_3$, —(C=O)OH, —(C=O)NHCH$_2$CH$_3$, —(C=O)NHCH$_3$, —(C=O)NH$_2$, —SO$_2$N(CH$_3$)$_2$, —SO$_2$NHCH$_2$CH$_3$, —SO$_2$NHCH$_3$, and —SO$_2$NH$_2$.

In various aspects, a compound can have a structure represented by a formula:

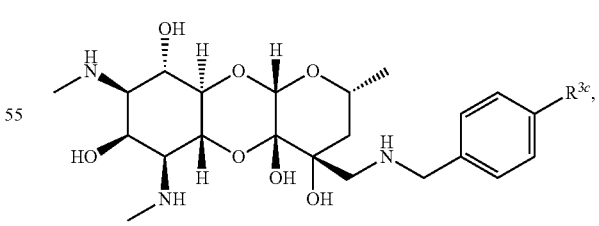

wherein $R^{3c}$ is selected from —F, —Cl, —Br, methyl, ethyl, isopropyl, —CH$_2$F, —CHF$_2$, —CF$_3$, —CH$_2$CF$_3$, —OCH$_3$, —OCF$_3$, —OCH$_2$CF$_3$, —(C=O)OH, —(C=O)NH$_2$, —SO$_2$NHCH$_3$, and —SO$_2$NH$_2$.

In various aspects, a compound can have a structure represented by a formula:

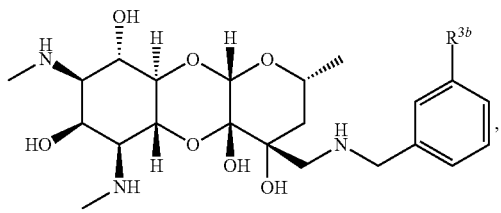,

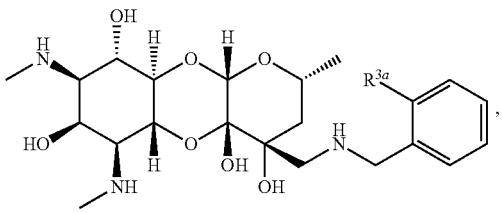, wherein $R^{3b}$ is selected from halo, cyano, hydroxyl, —NH$_2$, C1-C3 alkyl, C1-C3 monoalkyl, C1-C3 polyhaloalkyl, C1-C3 alkoxy, C1-C3 monohaloalkoxy, C1-C3 polyhaloalkyl, C1-C3 alkoxy, C1-C3 monohaloalkoxy, C1-C3 polyhaloalkoxy, —(C=O)OR$^9$, —(C=O)NR$^{10a}$R$^{10b}$, —SO$_2$NR$^{10a}$R$^{10b}$, —SR$^9$, and —SO$_2$R$^9$.

In various aspects a compound can have a structure represented by a formula:

wherein $R^{3a}$ is selected from halo, cyano, hydroxyl, —NH$_2$, C1-C3 alkyl, C1-C3 monoalkyl, C1-C3 polyhaloalkyl, C1-C3 alkoxy, C1-C3 monohaloalkoxy, C1-C3 polyhaloalkyl, C1-C3 alkoxy, C1-C3 monohaloalkoxy, C1-C3 polyhaloalkoxy, —(C=O)OR$^9$, —(C=O)NR$^{10a}$R$^{10b}$, —SO$_2$NR$^{10a}$R$^{10b}$, —SR$^9$, and —SO$_2$R$^9$.

In various aspects, a compound can have a structure represented by a formula:

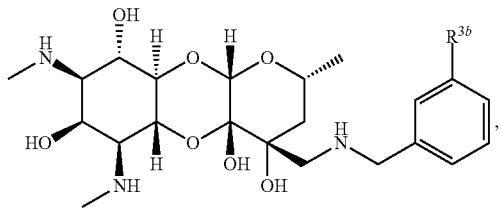,

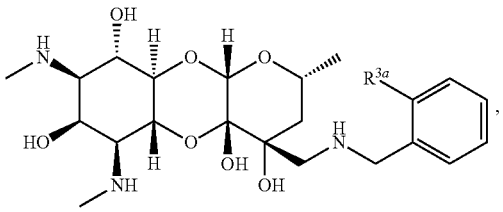, wherein $R^{3b}$ is selected from —F, —Cl, —Br, cyano, hydroxyl, —NH$_2$, methyl, ethyl, propyl, isopropyl, —CH$_2$F, —CHF$_2$, —CF$_3$, —CH$_2$Cl, —CHCl$_2$, —CCl$_3$, —CH$_2$CH$_2$F, —CH$_2$CHF$_2$, —CH$_2$CF$_3$, —CH$_2$CH$_2$Cl, —CH$_2$CHCl$_2$, —CH$_2$CCl$_3$, —OCH$_3$, —OCH$_2$CH$_3$, —OCH$_2$F, —OCHF$_2$, —OCF$_3$, —OCH$_2$Cl, —OCHCl$_2$, —OCCl$_3$, —OCH$_2$CH$_2$F, —OCH$_2$CHF$_2$, —OCH$_2$CF$_3$, —OCH$_2$CH$_2$Cl, —OCH$_2$CHCl$_2$, —(C=O)OCH$_2$CH$_3$, —(C=O)OCH$_2$CH$_3$, —(C=O)OCH$_3$, —(C=O)OH, —(C=O)NHCH$_2$CH$_3$, —(C=O)NHCH$_3$, —(C=O)NH$_2$, —SO$_2$N(CH$_3$)$_2$, —SO$_2$NHCH$_2$CH$_3$, —SO$_2$NHCH$_3$, and —SO$_2$NH$_2$.

In various aspects, a compound can have a structure represented by a formula:

wherein $R^{3a}$ is selected from —F, —Cl, —Br, cyano, hydroxyl, —NH$_2$, methyl, ethyl, propyl, isopropyl, —CH$_2$F, —CHF$_2$, —CF$_3$, —CH$_2$Cl, —CHCl$_2$, —CCl$_3$, —CH$_2$CH$_2$F, —CH$_2$CHF$_2$, —CH$_2$CF$_3$, —CH$_2$CH$_2$Cl, —CH$_2$CHCl$_2$, —CH$_2$CCl$_3$, —OCH$_3$, —OCH$_2$CH$_3$, —OCH$_2$F, —OCHF$_2$, —OCF$_3$, —OCH$_2$Cl, —OCHCl$_2$, —OCCl$_3$, —OCH$_2$CH$_2$F, —OCH$_2$CHF$_2$, —OCH$_2$CF$_3$, —OCH$_2$CH$_2$Cl, —OCH$_2$CHCl$_2$, —(C=O)OCH$_2$CH$_3$, —(C=O)OCH$_2$CH$_3$, —(C=O)OCH$_3$, —(C=O)OH, —(C=O)NHCH$_2$CH$_3$, —(C=O)NHCH$_3$, —(C=O)NH$_2$, —SO$_2$N(CH$_3$)$_2$, —SO$_2$NHCH$_2$CH$_3$, —SO$_2$NHCH$_3$, and —SO$_2$NH$_2$.

In various aspects, a compound can have a structure represented by a formula:

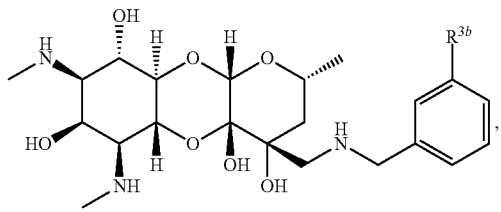,

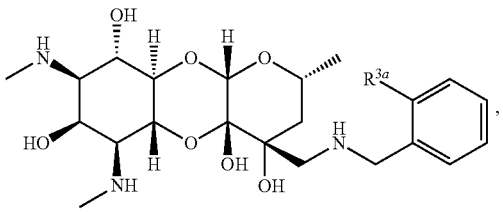, wherein $R^{3b}$ is selected from —F, —Cl, —Br, methyl, ethyl, isopropyl, —CH$_2$F, —CHF$_2$, —CF$_3$, —CH$_2$CF$_3$, —OCH$_3$, —OCF$_3$, —OCH$_2$CF$_3$, —(C=O)OH, —(C=O)NH$_2$, —SO$_2$NHCH$_3$, and —SO$_2$NH$_2$.

In various aspects, a compound can have a structure represented by a formula:

wherein $R^{3a}$ is selected from —F, —Cl, —Br, methyl, ethyl, isopropyl, —CH$_2$F, —CHF$_2$, —CF$_3$, —CH$_2$CF$_3$, —OCH$_3$, —OCF$_3$, —OCH$_2$CF$_3$, —(C=O)OH, —(C=O)NH$_2$, —SO$_2$NHCH$_3$, and —SO$_2$NH$_2$.

In various aspects, a compound can have a structure represented by a formula:

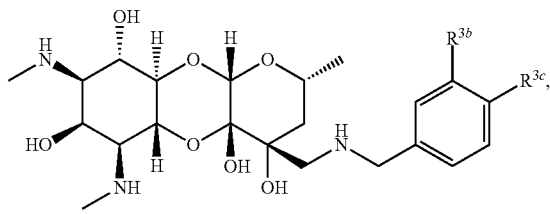

wherein each of $R^{3b}$ and $R^{3c}$ is selected from halo, cyano, hydroxyl, —$NH_2$, C1-C3 alkyl, C1-C3 monoalkyl, C1-C3 polyhaloalkyl, C1-C3 alkoxy, C1-C3 monohaloalkoxy, C1-C3 polyhaloalkyl, C1-C3 alkoxy, C1-C3 monohaloalkoxy, C1-C3 polyhaloalkoxy, —(C=O)$OR^9$, —(C=O)$NR^{10a}R^{10b}$, —$SO_2NR^{10a}R^{10b}$, —$SR^9$, and —$SO_2R^9$.

In various aspects, a compound can have a structure represented by a formula:

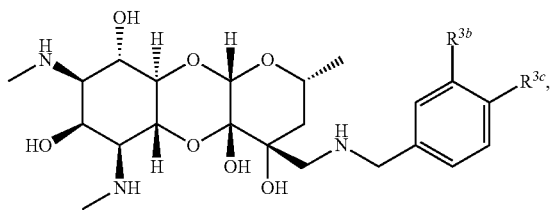

wherein each of $R^{3b}$ and $R^{3c}$ is selected from —F, —Cl, —Br, cyano, hydroxyl, —$NH_2$, methyl, ethyl, propyl, isopropyl, —$CH_2F$, —$CHF_2$, —$CF_3$, —$CH_2Cl$, —$CHCl_2$, —$CCl_3$, —$CH_2CH_2F$, —$CH_2CHF_2$, —$CH_2CF_3$, —$CH_2CH_2Cl$, —$CH_2CHCl_2$, —$CH_2CCl_3$, —$OCH_3$, —$OCH_2CH_3$, —$OCH_2F$, —$OCHF_2$, —$OCF_3$, —$OCH_2Cl$, —$OCHCl_2$, —$OCCl_3$, —$OCH_2CH_2F$, —$OCH_2CHF_2$, —$OCH_2CF_3$, —$OCH_2CH_2Cl$, —$OCH_2CHCl_2$, —(C=O)$OCH_2CH_3$, —(C=O)$OCH_2CH_3$, —(C=O)$OCH_3$, —(C=O)OH, —(C=O)$NHCH_2CH_3$, —(C=O)$NHCH_3$, —(C=O)$NH_2$, —$SO_2N(CH_3)_2$, —$SO_2NHCH_2CH_3$, —$SO_2NHCH_3$, and —$SO_2NH_2$.

In various aspects, a compound can have a structure represented by a formula:

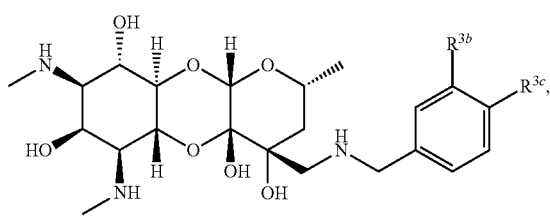

wherein each of $R^{3b}$ and $R^{3c}$ is selected from —F, —Cl, —Br, methyl, ethyl, isopropyl, —$CH_2F$, —$CHF_2$, —$CF_3$, —$CH_2CF_3$, —$OCH_3$, —$OCF_3$, —$OCH_2CF_3$, —(C=O)OH, —(C=O)$NH_2$, —$SO_2NHCH_3$, and —$SO_2NH_2$.

In various aspects, a compound can have a structure represented by a formula:

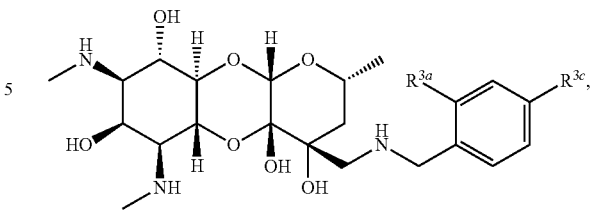

wherein each of $R^{3a}$ and $R^{3c}$ is selected from halo, cyano, hydroxyl, —$NH_2$, C1-C3 alkyl, C1-C3 monoalkyl, C1-C3 polyhaloalkyl, C1-C3 alkoxy, C1-C3 monohaloalkoxy, C1-C3 polyhaloalkyl, C1-C3 alkoxy, C1-C3 monohaloalkoxy, C1-C3 polyhaloalkoxy, —(C=O)$OR^9$, —(C=O)$NR^{10a}R^{10b}$, —$SO_2NR^{10a}R^{10b}$, —$SR^9$, and —$SO_2R^9$.

In various aspects, a compound can have a structure represented by a formula:

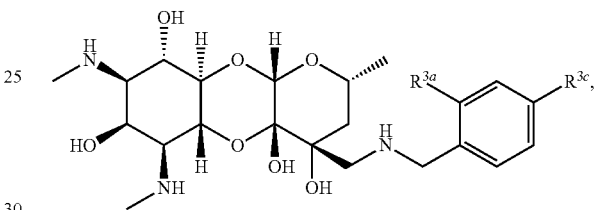

wherein each of $R^{3a}$ and $R^{3c}$ is selected from —F, —Cl, —Br, cyano, hydroxyl, —$NH_2$, methyl, ethyl, propyl, isopropyl, —$CH_2F$, —$CHF_2$, —$CF_3$, —$CH_2Cl$, —$CHCl_2$, —$CCl_3$, —$CH_2CH_2F$, —$CH_2CHF_2$, —$CH_2CF_3$, —$CH_2CH_2Cl$, —$CH_2CHCl_2$, —$CH_2CCl_3$, —$OCH_3$, —$OCH_2CH_3$, —$OCH_2F$, —$OCHF_2$, —$OCF_3$, —$OCH_2Cl$, —$OCHCl_2$, —$OCCl_3$, —$OCH_2CH_2F$, —$OCH_2CHF_2$, —$OCH_2CF_3$, —$OCH_2CH_2Cl$, —$OCH_2CHCl_2$, —(C=O)$OCH_2CH_3$, —(C=O)$OCH_2CH_3$, —(C=O)$OCH_3$, —(C=O)OH, —(C=O)$NHCH_2CH_3$, —(C=O)$NHCH_3$, —(C=O)$NH_2$, —$SO_2N(CH_3)_2$, —$SO_2NHCH_2CH_3$, —$SO_2NHCH_3$, and —$SO_2NH_2$.

In various aspects, a compound can have a structure represented by a formula:

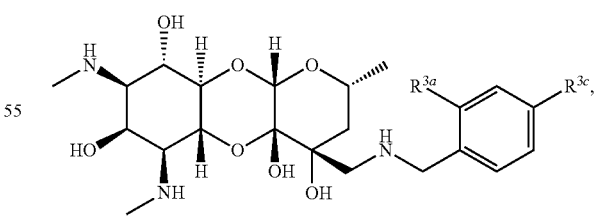

wherein each of $R^{3a}$ and $R^{3c}$ is selected from —F, —Cl, —Br, methyl, ethyl, isopropyl, —$CH_2F$, —$CHF_2$, —$CF_3$, —$CH_2CF_3$, —$OCH_3$, —$OCF_3$, —$OCH_2CF_3$, —(C=O)OH, —(C=O)$NH_2$, —$SO_2NHCH_3$, and —$SO_2NH_2$.

In various aspects, a compound can have a structure represented by a formula:

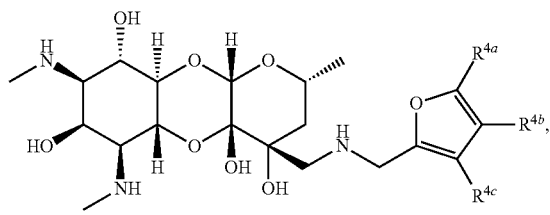

wherein each of $R^{4a}$, $R^{4b}$, and $R^{4c}$ is selected from hydrogen, halo, cyano, hydroxyl, —$NH_2$, C1-C3 alkyl, C1-C3 monoalkyl, C1-C3 polyhaloalkyl, C1-C3 alkoxy, C1-C3 monohaloalkoxy, C1-C3 polyhaloalkoxy, C1-C3 alkoxy, C1-C3 monohaloalkoxy, C1-C3 polyhaloalkoxy, —(C=O)$OR^9$, —(C=O)$NR^{10a}R^{10b}$, —$SO_2NR^{10a}R^{10b}$, —$SR^9$, and —$SO_2R^9$.

In various aspects, a compound can have a structure represented by a formula:

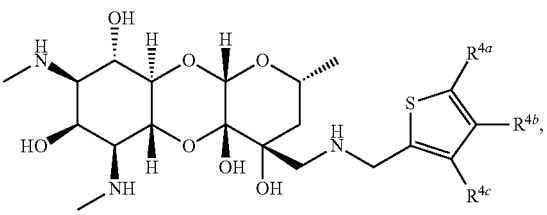

wherein each of $R^{4a}$, $R^{4b}$, and $R^{4c}$ is selected from hydrogen, halo, cyano, hydroxyl, —$NH_2$, C1-C3 alkyl, C1-C3 monoalkyl, C1-C3 polyhaloalkyl, C1-C3 alkoxy, C1-C3 monohaloalkoxy, C1-C3 polyhaloalkoxy, C1-C3 alkoxy, C1-C3 monohaloalkoxy, C1-C3 polyhaloalkoxy, —(C=O)$OR^9$, —(C=O)$NR^{10a}R^{10b}$, —$SO_2NR^{10a}R^{10b}$, —$SR^9$, and —$SO_2R^9$.

In various aspects, a compound can have a structure represented by a formula:

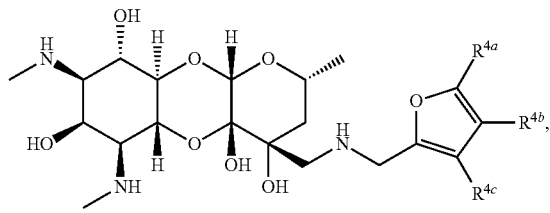

wherein each of $R^{4a}$, $R^{4b}$, and $R^{4c}$ is selected from hydrogen, —F, —Cl, —Br, cyano, hydroxyl, —$NH_2$, methyl, ethyl, propyl, isopropyl, —$CH_2F$, —$CHF_2$, —$CF_3$, —$CH_2Cl$, —$CHCl_2$, —$CCl_3$, —$CH_2CH_2F$, —$CH_2CHF_2$, —$CH_2CF_3$, —$CH_2CH_2Cl$, —$CH_2CHCl_2$, —$CH_2CCl_3$, —$OCH_3$, —$OCH_2CH_3$, —$OCH_2F$, —$OCHF_2$, —$OCF_3$, —$OCH_2Cl$, —$OCHCl_2$, —$OCCl_3$, —$OCH_2CH_2F$, —$OCH_2CHF_2$, —$OCH_2CF_3$, —$OCH_2CH_2Cl$, —$OCH_2CHCl_2$, —(C=O)$OCH_2CH_3$, —(C=O)$OCH_2CH_3$, —(C=O)$OCH_3$, —(C=O)OH, —(C=O)$NHCH_2CH_3$, —(C=O)$NHCH_3$, —(C=O)$NH_2$, —$SO_2N(CH_3)_2$, —$SO_2NHCH_2CH_3$, —$SO_2NHCH_3$, and —$SO_2NH_2$.

In various aspects, a compound can have a structure represented by a formula:

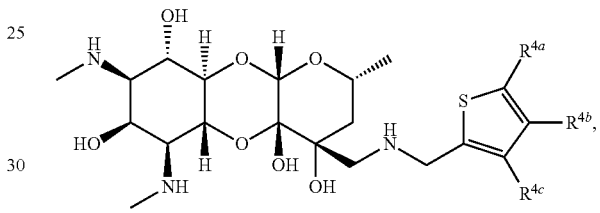

wherein each of $R^{4a}$, $R^{4b}$, and $R^{4c}$ is selected from hydrogen, —F, —Cl, —Br, cyano, hydroxyl, —$NH_2$, methyl, ethyl, propyl, isopropyl, —$CH_2F$, —$CHF_2$, —$CF_3$, —$CH_2Cl$, —$CHCl_2$, —$CCl_3$, —$CH_2CH_2F$, —$CH_2CHF_2$, —$CH_2CF_3$, —$CH_2CH_2Cl$, —$CH_2CHCl_2$, —$CH_2CCl_3$, —$OCH_3$, —$OCH_2CH_3$, —$OCH_2F$, —$OCHF_2$, —$OCF_3$, —$OCH_2Cl$, —$OCHCl_2$, —$OCCl_3$, —$OCH_2CH_2F$, —$OCH_2CHF_2$, —$OCH_2CF_3$, —$OCH_2CH_2Cl$, —$OCH_2CHCl_2$, —(C=O)$OCH_2CH_3$, —(C=O)$OCH_2CH_3$, —(C=O)$OCH_3$, —(C=O)OH, —(C=O)$NHCH_2CH_3$, —(C=O)$NHCH_3$, —(C=O)$NH_2$, —$SO_2N(CH_3)_2$, —$SO_2NHCH_2CH_3$, —$SO_2NHCH_3$, and —$SO_2NH_2$.

In various aspects, a compound can have a structure represented by a formula:

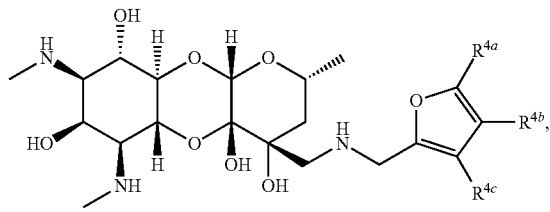

wherein each of $R^{4a}$, $R^{4b}$, and $R^{4c}$ is selected from hydrogen, —F, —Cl, —Br, methyl, ethyl, isopropyl, —$CH_2F$, —$CHF_2$, —$CF_3$, —$CH_2CF_3$, —$OCH_3$, —$OCF_3$, —$OCH_2CF_3$, —(C=O)OH, —(C=O)$NH_2$, —$SO_2NHCH_3$, and —$SO_2NH_2$.

In various aspects, a compound can have a structure represented by a formula:

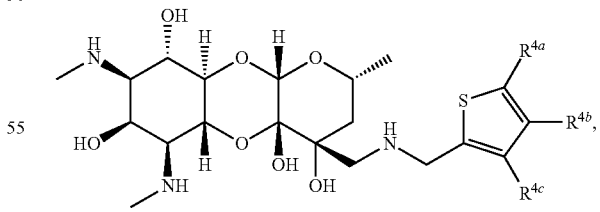

wherein each of $R^{4a}$, $R^{4b}$, and $R^{4c}$ is selected from hydrogen, —F, —Cl, —Br, methyl, ethyl, isopropyl, —$CH_2F$, —$CHF_2$, —$CF_3$, —$CH_2CF_3$, —$OCH_3$, —$OCF_3$, —$OCH_2CF_3$, —(C=O)OH, —(C=O)$NH_2$, —$SO_2NHCH_3$, and —$SO_2NH_2$.

In various aspects, a compound can have a structure represented by a formula:

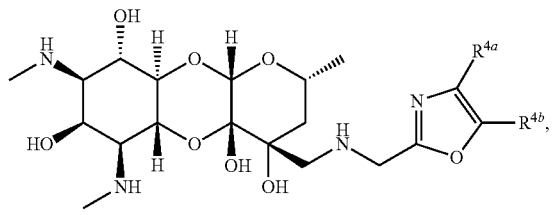

wherein each of $R^{4a}$ and $R^{4b}$ is selected from hydrogen, halo, cyano, hydroxyl, —$NH_2$, C1-C3 alkyl, C1-C3 monoalkyl, C1-C3 polyhaloalkyl, C1-C3 alkoxy, C1-C3 monohaloalkoxy, C1-C3 polyhaloalkyl, C1-C3 alkoxy, C1-C3 monohaloalkoxy, C1-C3 polyhaloalkoxy, —(C=O)$OR^9$, —(C=O)$NR^{10a}R^{10b}$, —$SO_2NR^{10a}R^{10b}$, —$SR^9$, and —$SO_2R^9$.

In various aspects, a compound can have a structure represented by a formula:

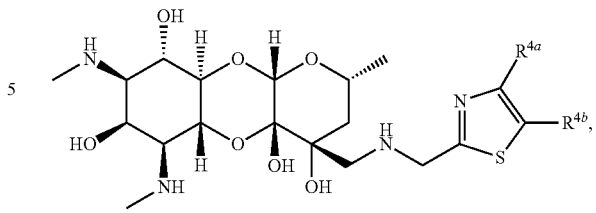

wherein each of $R^{4a}$ and $R^{4b}$ is selected from hydrogen, halo, cyano, hydroxyl, —$NH_2$, C1-C3 alkyl, C1-C3 monoalkyl, C1-C3 polyhaloalkyl, C1-C3 alkoxy, C1-C3 monohaloalkoxy, C1-C3 polyhaloalkyl, C1-C3 alkoxy, C1-C3 monohaloalkoxy, C1-C3 polyhaloalkoxy, —(C=O)$OR^9$, —(C=O)$NR^{10a}R^{10b}$, —$SO_2NR^{10a}R^{10b}$, —$SR^9$, and —$SO_2R^9$.

In various aspects, a compound can have a structure represented by a formula:

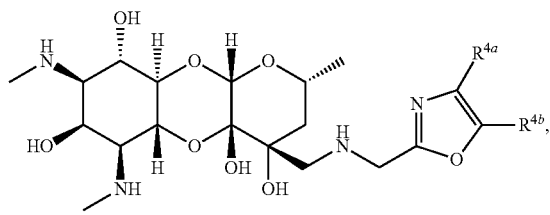

wherein each of $R^{4a}$ and $R^{4b}$ is selected from hydrogen, —F, —Cl, —Br, cyano, hydroxyl, —$NH_2$, methyl, ethyl, propyl, isopropyl, —$CH_2F$, —$CHF_2$, —$CF_3$, —$CH_2Cl$, —$CHCl_2$, —$CCl_3$, —$CH_2CH_2F$, —$CH_2CHF_2$, —$CH_2CF_3$, —$CH_2CH_2Cl$, —$CH_2CHCl_2$, —$CH_2CCl_3$, —$OCH_3$, —$OCH_2CH_3$, —$OCH_2F$, —$OCHF_2$, —$OCF_3$, —$OCH_2Cl$, —$OCHCl_2$, —$OCCl_3$, —$OCH_2CH_2F$, —$OCH_2CHF_2$, —$OCH_2CF_3$, —$OCH_2CH_2Cl$, —$OCH_2CHCl_2$, —(C=O)$OCH_2CH_3$, —(C=O)$OCH_2CH_3$, —(C=O)$OCH_3$, —(C=O)OH, —(C=O)$NHCH_2CH_3$, —(C=O)$NHCH_3$, —(C=O)$NH_2$, —$SO_2N(CH_3)_2$, —$SO_2NHCH_2CH_3$, —$SO_2NHCH_3$, and —$SO_2NH_2$.

In various aspects, a compound can have a structure represented by a formula:

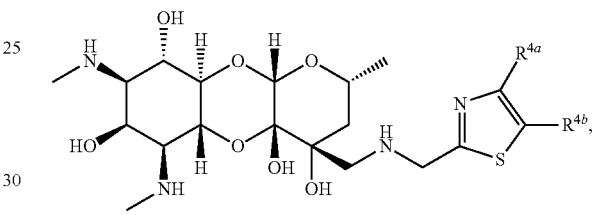

wherein each of $R^{4a}$ and $R^{4b}$ is selected from hydrogen, —F, —Cl, —Br, cyano, hydroxyl, —$NH_2$, methyl, ethyl, propyl, isopropyl, —$CH_2F$, —$CHF_2$, —$CF_3$, —$CH_2Cl$, —$CHCl_2$, —$CCl_3$, —$CH_2CH_2F$, —$CH_2CHF_2$, —$CH_2CF_3$, —$CH_2CH_2Cl$, —$CH_2CHCl_2$, —$CH_2CCl_3$, —$OCH_3$, —$OCH_2CH_3$, —$OCH_2F$, —$OCHF_2$, —$OCF_3$, —$OCH_2Cl$, —$OCHCl_2$, —$OCCl_3$, —$OCH_2CH_2F$, —$OCH_2CHF_2$, —$OCH_2CF_3$, —$OCH_2CH_2Cl$, —$OCH_2CHCl_2$, —(C=O)$OCH_2CH_3$, —(C=O)$OCH_2CH_3$, —(C=O)$OCH_3$, —(C=O)OH, —(C=O)$NHCH_2CH_3$, —(C=O)$NHCH_3$, —(C=O)$NH_2$, —$SO_2N(CH_3)_2$, —$SO_2NHCH_2CH_3$, —$SO_2NHCH_3$, and —$SO_2NH_2$.

In various aspects, a compound can have a structure represented by a formula:

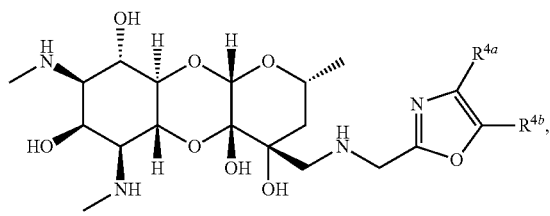

wherein each of $R^{4a}$ and $R^{4b}$ is selected from hydrogen, —F, —Cl, —Br, methyl, ethyl, isopropyl, —$CH_2F$, —$CHF_2$, —$CF_3$, —$CH_2CF_3$, —$OCH_3$, —$OCF_3$, —$OCH_2CF_3$, —(C=O)OH, —(C=O)$NH_2$, —$SO_2NHCH_3$, and —$SO_2NH_2$.

In various aspects, a compound can have a structure represented by a formula:

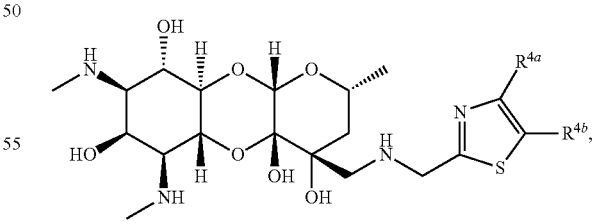

wherein each of $R^{4a}$ and $R^{4b}$ is selected from hydrogen, —F, —Cl, —Br, methyl, ethyl, isopropyl, —$CH_2F$, —$CHF_2$, —$CF_3$, —$CH_2CF_3$, —$OCH_3$, —$OCF_3$, —$OCH_2CF_3$, —(C=O)OH, —(C=O)$NH_2$, —$SO_2NHCH_3$, and —$SO_2NH_2$.

In various aspects, a compound can have a structure represented by a formula:

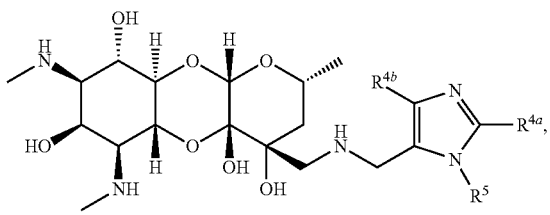

wherein each of $R^{4a}$ and $R^{4b}$ is selected from hydrogen, halo, cyano, hydroxyl, —$NH_2$, C1-C3 alkyl, C1-C3 monoalkyl, C1-C3 polyhaloalkyl, C1-C3 alkoxy, C1-C3 monohaloalkoxy C1-C3 polyhaloalkoxy, C1-C3 alkoxy, C1-C3 monohaloalkoxy, C1-C3 polyhaloalkoxy, —(C=O)$OR^9$, —(C=O)$NR^{10a}R^{10b}$, —$SO_2NR^{10a}R^{10b}$, —$SR^9$, and —$SO_2R^9$; and wherein $R^5$ is selected from hydrogen and C1-C3 alkyl.

In various aspects, a compound can have a structure represented by a formula:

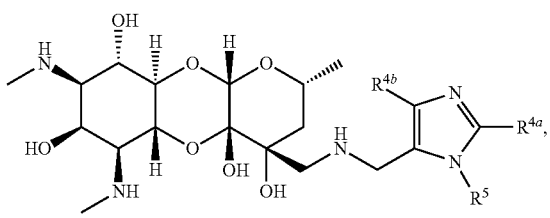

wherein each of $R^{4a}$ and $R^{4b}$ is selected from hydrogen, —F, —Cl, —Br, cyano, hydroxyl, —$NH_2$, methyl, ethyl, propyl, isopropyl, —$CH_2F$, —$CHF_2$, —$CF_3$, —$CH_2Cl$, —$CHCl_2$, —$CCl_3$, —$CH_2CH_2F$, —$CH_2CHF_2$, —$CH_2CF_3$, —$CH_2CH_2Cl$, —$CH_2CHCl_2$, —$CH_2CCl_3$, —$OCH_3$, —$OCH_2CH_3$, —$OCH_2F$, —$OCHF_2$, —$OCF_3$, —$OCH_2Cl$, —$OCHCl_2$, —$OCCl_3$, —$OCH_2CH_2F$, —$OCH_2CHF_2$, —$OCH_2CF_3$, —$OCH_2CH_2Cl$, —$OCH_2CHCl_2$, —(C=O)$OCH_2CH_3$, —(C=O)$OCH_2CH_3$, —(C=O)$OCH_3$, —(C=O)OH, —(C=O)$NHCH_2CH_3$, —(C=O)$NHCH_3$, —(C=O)$NH_2$, —$SO_2N(CH_3)_2$, —$SO_2NHCH_2CH_3$, —$SO_2NHCH_3$, and —$SO_2NH_2$; and wherein $R^5$ is selected from hydrogen and methyl.

In various aspects, a compound can have a structure represented by a formula:

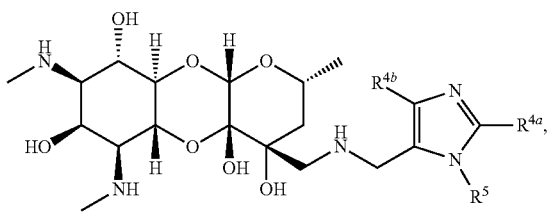

wherein each of $R^{4a}$ and $R^{4b}$ is selected from hydrogen, —F, —Cl, —Br, methyl, ethyl, isopropyl, —$CH_2F$, —$CHF_2$, —$CF_3$, —$CH_2CF_3$, —$OCH_3$, —$OCF_3$, —$OCH_2CF_3$, —(C=O)OH, —(C=O)$NH_2$, —$SO_2NHCH_3$, and —$SO_2NH_2$; and wherein $R^5$ is selected from hydrogen and methyl.

In a further aspect, a compound can have a structure listed herein. In a further aspect, the compounds can be selected from two or more of the structures listed herein.

Suitable substituents are described below.

a. $R^1$ Groups

In one aspect, $R^1$ is selected hydrogen and C1-C4 alkyl. In a further aspect, $R^1$ is selected from hydrogen and methyl. In a still further aspect, $R^1$ is selected from hydrogen, ethyl, and methyl. In a yet further aspect, $R^1$ is methyl. In an even further aspect, $R^1$ is hydrogen.

b. $R^{2a}$ and $R^{2b}$ Groups

In one aspect, each occurrence of $R^{2a}$ and $R^{2b}$ is independently selected from hydrogen and C1-C3 alkyl. In a further aspect, each occurrence of $R^{2a}$ and $R^{2b}$ is hydrogen.

In a further aspect, n is 0 and $R^{2a}$ and $R^{2b}$ are not present. In a still further aspect, n is 1 and each occurrence of $R^{2a}$ and $R^{2b}$ is hydrogen. In a yet further aspect, n is 2 and each occurrence of $R^{2a}$ and $R^{2b}$ is hydrogen. In an even further aspect, n is 3 and each occurrence of $R^{2a}$ and $R^{2b}$ is hydrogen.

In various further aspects, it is understood that multiple uses of the substituents labeled as $R^{2a}$ and $R^{2b}$ can involve multiple occurrences of the various selected substituents, each such substituent independently selected. For example, in such instances, the invention relates to a structure represented by a formula:

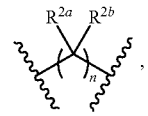

wherein n is 0-3 (i.e., n=0, n=1, n=2, or n=3); wherein each $R^{2a}$, when present, is selected from hydrogen, methyl, and ethyl; and wherein each $R^{2b}$, when present, is selected from hydrogen, methyl, and ethyl. This is understood to include and disclose a moiety wherein, e.g., for moiety n=1, substituted with $R^{2a1}$ and $R^{2b1}$, each such substituent is independently hydrogen, methyl, or ethyl. This also includes and discloses a moiety wherein, for moiety n=2, substituted with $R^{2a2}$ and $R^{2b2}$, each such substituent is independently hydrogen, methyl, or ethyl, irrespective of the selection for $R^{2a1}$ and $R^{2b1}$.

Such structures (e.g., wherein n=2) are also understood to refer to a moiety having a structure alternatively represented by a formula:

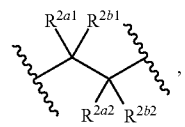

wherein each of $R^{2a1}$, $R^{2b1}$, $R^{2a2}$, and $R^{2b2}$ is independently selected from hydrogen, methyl, and ethyl (again, irrespective of the other selections).

c. $R^{3a}$, $R^{3b}$, $R^{3c}$, $R^{3d}$, and $R^{3e}$ Groups

In one aspect, each of $R^{3a}$, $R^{3b}$, $R^{3c}$, $R^{3d}$, and $R^{3e}$ is independently selected from halo, cyano, hydroxyl, —$NH_2$, C1-C3 alkyl, C1-C3 monoalkyl, C1-C3 polyhaloalkyl, C1-C3 alkoxy, C1-C3 monohaloalkoxy, C1-C3 polyhaloalkyl, C1-C3 alkoxy, C1-C3 monohaloalkoxy, C1-C3 polyhaloalkoxy, —(C=O)$OR^9$, —(C=O)$NR^{10a}R^{10b}$, —$SO_2NR^{10a}R^{10b}$, —$SR^9$, and —$SO_2R^9$, provided that at least two of $R^{3a}$, $R^{3b}$, $R^{3c}$, $R^{3d}$, and $R^{3e}$ are hydrogen. In a further aspect, each of $R^{3a}$, $R^{3b}$, $R^{3c}$, $R^{3d}$, and $R^{3e}$ is hydrogen.

In various further aspects, each of $R^{3a}$, $R^{3b}$, $R^{3c}$, $R^{3d}$, and $R^{3e}$ is independently selected from hydrogen, —F, —Cl, —Br, cyano, hydroxyl, —NH$_2$, methyl, ethyl, propyl, isopropyl, —CH$_2$F, —CHF$_2$, —CF$_3$, —CH$_2$Cl, —CHCl$_2$, —CCl$_3$, —CH$_2$CH$_2$F, —CH$_2$CHF$_2$, —CH$_2$CF$_3$, —CH$_2$CH$_2$Cl, —CH$_2$CHCl$_2$, —CH$_2$CCl$_3$, —OCH$_3$, —OCH$_2$CH$_3$, —OCH$_2$F, —OCHF$_2$, —OCF$_3$, —OCH$_2$Cl, —OCHCl$_2$, —OCCl$_3$, —OCH$_2$CH$_2$F, —OCH$_2$CHF$_2$, —OCH$_2$CF$_3$, —OCH$_2$CH$_2$Cl, —OCH$_2$CHCl$_2$, —(C=O)OCH$_2$CH$_3$, —(C=O)OCH$_2$CH$_3$, —(C=O)OCH$_3$, —(C=O)OH, —(C=O)NHCH$_2$CH$_3$, —(C=O)NHCH$_3$, —(C=O)NH$_2$, —SO$_2$N(CH$_3$)$_2$, —SO$_2$NHCH$_2$CH$_3$, —SO$_2$NHCH$_3$, and —SO$_2$NH$_2$, provided that at least two of $R^{3a}$, $R^{3b}$, $R^{3c}$, $R^{3d}$, and $R^{3e}$ are hydrogen. In a further aspect, each of $R^{3a}$, $R^{3b}$, $R^{3c}$, $R^{3d}$, and $R^{3e}$ are independently selected from hydrogen, —F, —Cl, —Br, methyl, ethyl, isopropyl, —CH$_2$F, —CHF$_2$, —CF$_3$, —CH$_2$CF$_3$, —OCH$_3$, —OCF$_3$, —OCH$_2$CF$_3$, —(C=O)OH, —(C=O)NH$_2$, —SO$_2$NHCH$_3$, and —SO$_2$NH$_2$, provided that at least two of $R^{3a}$, $R^{3b}$, $R^{3c}$, $R^{3d}$, and $R^{3e}$ are hydrogen.

In various aspects, each of $R^{3b}$, $R^{3c}$, $R^{3d}$, and $R^{3e}$ is hydrogen; and $R^{3a}$ is selected from halo, cyano, hydroxyl, —NH$_2$, C1-C3 alkyl, C1-C3 monoalkyl, C1-C3 polyhaloalkyl, C1-C3 alkoxy, C1-C3 monohaloalkoxy, C1-C3 polyhaloalkoxy. In a further aspect, each of $R^{3b}$ $R^{3c}$, $R^{3d}$, and $R^{3e}$ is hydrogen; and $R^{3a}$ is selected from —F, —Cl, —Br, cyano, hydroxyl, —NH$_2$, methyl, ethyl, propyl, isopropyl, —CH$_2$F, —CHF$_2$, —CF$_3$, —CH$_2$Cl, —CHCl$_2$, —CCl$_3$, —CH$_2$CH$_2$F, —CH$_2$CHF$_2$, —CH$_2$CF$_3$, —CH$_2$CH$_2$Cl, —CH$_2$CHCl$_2$, —CH$_2$CCl$_3$, —OCH$_3$, —OCH$_2$CH$_3$, —OCH$_2$F, —OCHF$_2$, —OCF$_3$, —OCH$_2$Cl, —OCHCl$_2$, —OCCl$_3$, —OCH$_2$CH$_2$F, —OCH$_2$CHF$_2$, —OCH$_2$CF$_3$, —OCH$_2$CH$_2$Cl, —OCH$_2$CHCl$_2$, —(C=O)OCH$_2$CH$_3$, —(C=O)OCH$_2$CH$_3$, —(C=O)OCH$_3$, —(C=O)OH, —(C=O)NHCH$_2$CH$_3$, —(C=O)NHCH$_3$, —(C=O)NH$_2$, —SO$_2$N(CH$_3$)$_2$, —SO$_2$NHCH$_2$CH$_3$, —SO$_2$NHCH$_3$, and —SO$_2$NH$_2$. In a still further aspect, each of $R^{3b}$, $R^{3c}$, $R^{3d}$, and $R^{3e}$ is hydrogen; and $R^{3a}$ is selected from —F, —Cl, —Br, methyl, ethyl, isopropyl, —CH$_2$F, —CHF$_2$, —CF$_3$, —CH$_2$CF$_3$, —OCH$_3$, —OCF$_3$, —OCH$_2$CF$_3$, —(C=O)OH, —(C=O)NH$_2$, —SO$_2$NHCH$_3$, and —SO$_2$NH$_2$.

In various aspects, each of $R^{3a}$, $R^{3c}$, $R^{3d}$, and $R^{3e}$ is hydrogen; and $R^{3b}$ is selected from halo, cyano, hydroxyl, —NH$_2$, C1-C3 alkyl, C1-C3 monoalkyl, C1-C3 polyhaloalkyl, C1-C3 alkoxy, C1-C3 monohaloalkoxy, C1-C3 polyhaloalkyl, C1-C3 alkoxy, C1-C3 monohaloalkoxy, C1-C3 polyhaloalkoxy, —(C=O)OR$^9$, —(C=O)NR$^{10a}$R$^{10b}$, —SO$_2$NR$^{10a}$R$^{10b}$, —SR$^9$, and —SO$_2$R$^9$. In a further aspect, each of $R^{3a}$, $R^{3c}$, $R^{3d}$, and $R^{3e}$ is hydrogen; and $R^{3b}$ is selected from —F, —Cl, —Br, cyano, hydroxyl, —NH$_2$, methyl, ethyl, propyl, isopropyl, —CH$_2$F, —CHF$_2$, —CF$_3$, —CH$_2$Cl, —CHCl$_2$, —CCl$_3$, —CH$_2$CH$_2$F, —CH$_2$CHF$_2$, —CH$_2$CF$_3$, —CH$_2$CH$_2$Cl, —CH$_2$CHCl$_2$, —CH$_2$CCl$_3$, —OCH$_3$, —OCH$_2$CH$_3$, —OCH$_2$F, —OCHF$_2$, —OCF$_3$, —OCH$_2$Cl, —OCHCl$_2$, —OCCl$_3$, —OCH$_2$CH$_2$F, —OCH$_2$CHF$_2$, —OCH$_2$CF$_3$, —OCH$_2$CH$_2$Cl, —OCH$_2$CHCl$_2$, —(C=O)OCH$_2$CH$_3$, —(C=O)OCH$_2$CH$_3$, —(C=O)OCH$_3$, —(C=O)OH, —(C=O)NHCH$_2$CH$_3$, —(C=O)NHCH$_3$, —(C=O)NH$_2$, —SO$_2$N(CH$_3$)$_2$, —SO$_2$NHCH$_2$CH$_3$, —SO$_2$NHCH$_3$, and —SO$_2$NH$_2$. In a still further aspect, each of $R^{3a}$, $R^{3c}$, $R^{3d}$, and $R^{3e}$ is hydrogen; and $R^{3b}$ is selected from —F, —Cl, —Br, methyl, ethyl, isopropyl, —CH$_2$F, —CHF$_2$, —CF$_3$, —CH$_2$CF$_3$, —OCH$_3$, —OCF$_3$, —OCH$_2$CF$_3$, —(C=O)OH, —(C=O)NH$_2$, —SO$_2$NHCH$_3$, and —SO$_2$NH$_2$.

In various aspects, each of $R^{3a}$, $R^{3b}$, $R^{3d}$, and $R^{3e}$ is hydrogen; and $R^{3c}$ is selected from halo, cyano, hydroxyl, —NH$_2$, C1-C3 alkyl, C1-C3 monoalkyl, C1-C3 polyhaloalkyl, C1-C3 alkoxy, C1-C3 monohaloalkoxy, C1-C3 polyhaloalkyl, C1-C3 alkoxy, C1-C3 monohaloalkoxy, C1-C3 polyhaloalkoxy, —(C=O)OR$^9$, —(C=O)NR$^{10a}$R$^{10b}$, and, —SO2NR10aR10b, —SR$^9$, and —SO$_2$R$^9$. In a further aspect, each of $R^{3a}$, $R^{3b}$, $R^{3d}$, and $R^{3e}$ is hydrogen; and $R^{3c}$ is selected from —F, —Cl, —Br, cyano, hydroxyl, —NH$_2$, methyl, ethyl, propyl, isopropyl, —CH$_2$F, —CHF$_2$, —CF$_3$, —CH$_2$Cl, —CHCl$_2$, —CCl$_3$, —CH$_2$CH$_2$F, —CH$_2$CHF$_2$, —CH$_2$CF$_3$, —CH$_2$CH$_2$Cl, —CH$_2$CHCl$_2$, —CH$_2$CCl$_3$, —OCH$_3$, —OCH$_2$CH$_3$, —OCH$_2$F, —OCHF$_2$, —OCF$_3$, —OCH$_2$Cl, —OCHCl$_2$, —OCCl$_3$, —OCH$_2$CH$_2$F, —OCH$_2$CHF$_2$, —OCH$_2$CF$_3$, —OCH$_2$CH$_2$Cl, —OCH$_2$CHCl$_2$, —(C=O)OCH$_2$CH$_3$, —(C=O)OCH$_2$CH$_3$, —(C=O)OCH$_3$, —(C=O)OH, —(C=O)NHCH$_2$CH$_3$, —(C=O)NHCH$_3$, —(C=O)NH$_2$, —SO$_2$N(CH$_3$)$_2$, —SO$_2$NHCH$_2$CH$_3$, —SO$_2$NHCH$_3$, and —SO$_2$NH$_2$. In a still further aspect, each of $R^{3a}$, $R^{3b}$, $R^{3d}$, and $R^{3e}$ is hydrogen; and $R^{3c}$ is selected from —F, —Cl, —Br, methyl, ethyl, isopropyl, —CH$_2$F, —CHF$_2$, —CF$_3$, —CH$_2$CF$_3$, —OCH$_3$, —OCF$_3$, —OCH$_2$CF$_3$, —(C=O)OH, —(C=O)NH$_2$, —SO$_2$NHCH$_3$, and —SO$_2$NH$_2$.

In various aspects, each of $R^{3a}$, $R^{3d}$, and $R^{3e}$ is hydrogen; and each of $R^{3b}$ and $R^{3c}$ is selected from halo, cyano, hydroxyl, —NH$_2$, C1-C3 alkyl, C1-C3 monoalkyl, C1-C3 polyhaloalkyl, C1-C3 alkoxy, C1-C3 monohaloalkoxy, C1-C3 polyhaloalkyl, C1-C3 alkoxy, C1-C3 monohaloalkoxy, C1-C3 polyhaloalkoxy, —(C=O)OR$^9$, —(C=O)NR$^{10a}$R$^{10b}$, and —SO$_2$NR$^{10a}$R$^{10b}$, —SR$^9$, and —SO$_2$R$^9$. In a further aspect, each of $R^{3a}$, $R^{3d}$, and $R^{3e}$ is hydrogen; and each of $R^{3b}$ and $R^{3c}$ is selected from —F, —Cl, —Br, cyano, hydroxyl, —NH$_2$, methyl, ethyl, propyl, isopropyl, —CH$_2$F, —CHF$_2$, —CF$_3$, —CH$_2$Cl, —CHCl$_2$, —CCl$_3$, —CH$_2$CH$_2$F, —CH$_2$CHF$_2$, —CH$_2$CF$_3$, —CH$_2$CH$_2$Cl, —CH$_2$CHCl$_2$, —CH$_2$CCl$_3$, —OCH$_3$, —OCH$_2$CH$_3$, —OCH$_2$F, —OCHF$_2$, —OCF$_3$, —OCH$_2$Cl, —OCHCl$_2$, —OCCl$_3$, —OCH$_2$CH$_2$F, —OCH$_2$CHF$_2$, —OCH$_2$CF$_3$, —OCH$_2$CH$_2$Cl, —OCH$_2$CHCl$_2$, —(C=O)OCH$_2$CH$_3$, —(C=O)OCH$_2$CH$_3$, —(C=O)OCH$_3$, —(C=O)OH, —(C=O)NHCH$_2$CH$_3$, —(C=O)NHCH$_3$, —(C=O)NH$_2$, —SO$_2$N(CH$_3$)$_2$, —SO$_2$NHCH$_2$CH$_3$, —SO$_2$NHCH$_3$, and —SO$_2$NH$_2$. In a still further aspect, each of $R^{3a}$, $R^{3d}$, and $R^{3e}$ is hydrogen; and each of $R^{3b}$ and $R^{3c}$ is selected from —F, —Cl, —Br, methyl, ethyl, isopropyl, —CH$_2$F, —CHF$_2$, —CF$_3$, —CH$_2$CF$_3$, —OCH$_3$, —OCF$_3$, —OCH$_2$CF$_3$, —(C=O)OH, —(C=O)NH$_2$, —SO$_2$NHCH$_3$, and —SO$_2$NH$_2$.

In various aspects, each of $R^{3b}$, $R^{3d}$, and $R^{3e}$ is hydrogen; and each of $R^{3a}$ and $R^{3c}$ is selected from halo, cyano, hydroxyl, —NH$_2$, C1-C3 alkyl, C1-C3 monoalkyl, C1-C3 polyhaloalkyl, C1-C3 alkoxy, C1-C3 monohaloalkoxy, C1-C3 polyhaloalkyl, C1-C3 alkoxy, C1-C3 monohaloalkoxy, C1-C3 polyhaloalkoxy, —(C=O)OR$^9$, —(C=O)NR$^{10a}$R$^{10b}$, —SO$_2$NR$^{10a}$R$^{10b}$, —SR$^9$, and —SO$_2$R$^9$. In a further aspect, each of $R^{3b}$, $R^{3d}$, and $R^{3e}$ is hydrogen; and each of $R^{3a}$ and $R^{3c}$ is selected from —F, —Cl, —Br, cyano, hydroxyl, —NH$_2$, methyl, ethyl, propyl, isopropyl, —CH$_2$F, —CHF$_2$, —CF$_3$, —CH$_2$Cl, —CHCl$_2$, —CCl$_3$, —CH$_2$CH$_2$F, —CH$_2$CHF$_2$, —CH$_2$CF$_3$, —CH$_2$CH$_2$Cl, —CH$_2$CHCl$_2$, —CH$_2$CCl$_3$, —OCH$_3$, —OCH$_2$CH$_3$, —OCH$_2$F, —OCHF$_2$, —OCF$_3$, —OCH$_2$Cl, —OCHCl$_2$, —OCCl$_3$, —OCH$_2$CH$_2$F, —OCH$_2$CHF$_2$, —OCH$_2$CF$_3$, —OCH$_2$CH$_2$Cl, —OCH$_2$CHCl$_2$, —(C=O)OCH$_2$CH$_3$, —(C=O)OCH$_2$CH$_3$, —(C=O)OCH$_3$, —(C=O)OH, —(C=O)NHCH$_2$CH$_3$, —(C=O)NHCH$_3$, —(C=O)NH$_2$, —SO$_2$N(CH$_3$)$_2$, —SO$_2$NHCH$_2$CH$_3$, —SO$_2$NHCH$_3$, and —SO$_2$NH$_2$. In a still further aspect, each of $R^{3b}$, $R^{3d}$, and $R^{3e}$ is hydrogen; and each of $R^{3a}$ and $R^{3c}$ is selected from —F, —Cl, —Br, methyl, ethyl, isopropyl, —CH$_2$F, —CHF$_2$, —CF$_3$, —CH$_2$CF$_3$, —OCH$_3$, —OCF$_3$, —OCH$_2$CF$_3$, —(C=O)OH, —(C=O)NH$_2$, —SO$_2$NHCH$_3$, and —SO$_2$NH$_2$.

In one aspect, each of $R^{3a}$, $R^{3b}$, $R^{3c}$, $R^{3d}$, $R^{3e}$, and $R^{3f}$ is independently selected from halo, cyano, hydroxyl, —NH$_2$, C1-C3 alkyl, C1-C3 monoalkyl, C1-C3 polyhaloalkyl, C1-C3 alkoxy, C1-C3 monohaloalkoxy, C1-C3 polyhaloalkyl, C1-C3 alkoxy, C1-C3 monohaloalkoxy, C1-C3 polyhaloalkoxy, —(C=O)OR$^9$, —(C=O)NR$^{10a}$R$^{10b}$, —SO$_2$NR$^{10a}$R$^{10b}$, —SR$^9$, and —SO$_2$R$^9$, provided that at least three of $R^{3a}$, $R^{3b}$, $R^{3c}$, $R^{3d}$, $R^{3e}$, and $R^{3f}$ are hydrogen. In a further aspect, each of $R^{3a}$, $R^{3b}$, $R^{3c}$, $R^{3d}$, $R^{3e}$, and $R^{3f}$ is hydrogen.

In various further aspects, each of $R^{3a}$, $R^{3b}$, $R^{3c}$, $R^{3d}$, $R^{3e}$, and $R^{3f}$ is independently selected from hydrogen, —F, —Cl, —Br, cyano, hydroxyl, —NH$_2$, methyl, ethyl, propyl, isopropyl, —CH$_2$F, —CHF$_2$, —CF$_3$, —CH$_2$Cl, —CHCl$_2$, —CCl$_3$, —CH$_2$CH$_2$F, —CH$_2$CHF$_2$, —CH$_2$CF$_3$, —CH$_2$CH$_2$Cl, —CH$_2$CHCl$_2$, —CH$_2$CCl$_3$, —OCH$_3$, —OCH$_2$CH$_3$, —OCH$_2$F, —OCHF$_2$, —OCF$_3$, —OCH$_2$Cl, —OCHCl$_2$, —OCCl$_3$, —OCH$_2$CH$_2$F, —OCH$_2$CHF$_2$, —OCH$_2$CF$_3$, —OCH$_2$CH$_2$Cl, —OCH$_2$CHCl$_2$, —(C=O)OCH$_2$CH$_3$, —(C=O)OCH$_2$CH$_3$, —(C=O)OCH$_3$, —(C=O)OH, —(C=O)NHCH$_2$CH$_3$, —(C=O)NHCH$_3$, —(C=O)NH$_2$, —SO$_2$N(CH$_3$)$_2$, —SO$_2$NHCH$_2$CH$_3$, —SO$_2$NHCH$_3$, and —SO$_2$NH$_2$, provided that at least three of $R^{3a}$, $R^{3b}$, $R^3R^{3d}$, $R^{3e}$, and $R^{3f}$ are hydrogen. In a further aspect, each of $R^{3a}$, $R^{3b}$, $R^{3c}$, $R^{3d}$, $R^{3e}$, and $R^{3f}$ are independently selected from hydrogen, —F, —Cl, —Br, methyl, ethyl, isopropyl, —CH$_2$F, —CHF$_2$, —CF$_3$, —CH$_2$CF$_3$, —OCH$_3$, —OCF$_3$, —OCH$_2$CF$_3$, —(C=O)OH, —(C=O)NH$_2$, —SO$_2$NHCH$_3$, and —SO$_2$NH$_2$, provided that at least three of $R^{3a}$, $R^{3b}$, $R^{3c}$, $R^{3d}$, $R^{3e}$, and $R^{3f}$ are hydrogen.

In various aspects, each of $R^{3b}$, $R^{3c}$, $R^{3d}$, $R^{3e}$, and $R^{3f}$ is hydrogen; and $R^{3a}$ is selected from halo, cyano, hydroxyl, —NH$_2$, C1-C3 alkyl, C1-C3 monoalkyl, C1-C3 polyhaloalkyl, C1-C3 alkoxy, C1-C3 monohaloalkoxy, C1-C3 polyhaloalkyl, C1-C3 alkoxy, C1-C3 monohaloalkoxy, C1-C3 polyhaloalkoxy, —(C=O)OR$^9$, —(C=O)NR$^{10a}$R$^{10b}$, and —SO$_2$NR$^{10a}$R$^{10b}$, —SR$^9$, and —SO$_2$R$^9$. In a further aspect, each of $R^{3b}$, $R^{3c}$, $R^{3d}$, $R^{3e}$, and $R^{3f}$ is hydrogen; and $R^{3a}$ is selected from —F, —Cl, —Br, cyano, hydroxyl, —NH$_2$, methyl, ethyl, propyl, isopropyl, —CH$_2$F, —CHF$_2$, —CF$_3$, —CH$_2$Cl, —CHCl$_2$, —CCl$_3$, —CH$_2$CH$_2$F, —CH$_2$CHF$_2$, —CH$_2$CF$_3$, —CH$_2$CH$_2$Cl, —CH$_2$CHCl$_2$, —CH$_2$CCl$_3$, —OCH$_3$, —OCH$_2$CH$_3$, —OCH$_2$F, —OCHF$_2$, —OCF$_3$, —OCH$_2$Cl, —OCHCl$_2$, —OCCl$_3$, —OCH$_2$CH$_2$F, —OCH$_2$CHF$_2$, —OCH$_2$CF$_3$, —OCH$_2$CH$_2$Cl, —OCH$_2$CHCl$_2$, —(C=O)OCH$_2$CH$_3$, —(C=O)OCH$_2$CH$_3$, —(C=O)OCH$_3$, —(C=O)OH, —(C=O)NHCH$_2$CH$_3$, —(C=O)NHCH$_3$, —(C=O)NH$_2$, —SO$_2$N(CH$_3$)$_2$, —SO$_2$NHCH$_2$CH$_3$, —SO$_2$NHCH$_3$, and —SO$_2$NH$_2$. In a still further aspect, each of $R^{3b}$, $R^{3c}$, $R^{3d}$, $R^{3e}$, and $R^{3f}$ is hydrogen; and $R^{3a}$ is selected from —F, —Cl, —Br, methyl, ethyl, isopropyl, —CH$_2$F, —CHF$_2$, —CF$_3$, —CH$_2$CF$_3$, —OCH$_3$, —OCF$_3$, —OCH$_2$CF$_3$, —(C=O)OH, —(C=O)NH$_2$, —SO$_2$NHCH$_3$, and —SO$_2$NH$_2$.

In various aspects, each of $R^{3a}$, $R^{3c}$, $R^{3d}$, $R^{3e}$, and $R^{3f}$ is hydrogen; and $R^{3b}$ is selected from halo, cyano, hydroxyl, —NH$_2$, C1-C3 alkyl, C1-C3 monoalkyl, C1-C3 polyhaloalkyl, C1-C3 alkoxy, C1-C3 monohaloalkoxy, C1-C3 polyhaloalkyl, C1-C3 alkoxy, C1-C3 monohaloalkoxy, C1-C3 polyhaloalkoxy, —(C=O)OR$^9$, —(C=O)NR$^{10a}$R$^{10b}$, and —SO$_2$NR$^{10a}$R$^{10b}$, —SR$^9$, and —SO$_2$R$^9$. In a further aspect, each of $R^{3a}$, $R^{3c}$, $R^{3d}$, $R^{3e}$, and $R^{3f}$ is hydrogen; and $R^{3b}$ is selected from —F, —Cl, —Br, cyano, hydroxyl, —NH$_2$, methyl, ethyl, propyl, isopropyl, —CH$_2$F, —CHF$_2$, —CF$_3$, —CH$_2$Cl, —CHCl$_2$, —CCl$_3$, —CH$_2$CH$_2$F, —CH$_2$CHF$_2$, —CH$_2$CF$_3$, —CH$_2$CH$_2$Cl, —CH$_2$CHCl$_2$, —CH$_2$CCl$_3$, —OCH$_3$, —OCH$_2$CH$_3$, —OCH$_2$F, —OCHF$_2$, —OCF$_3$, —OCH$_2$Cl, —OCHCl$_2$, —OCCl$_3$, —OCH$_2$CH$_2$F, —OCH$_2$CHF$_2$, —OCH$_2$CF$_3$, —OCH$_2$CH$_2$Cl, —OCH$_2$CHCl$_2$, —(C=O)OCH$_2$CH$_3$, —(C=O)OCH$_2$CH$_3$, —(C=O)OCH$_3$, —(C=O)OH, —(C=O)NHCH$_2$CH$_3$, —(C=O)NHCH$_3$, —(C=O)NH$_2$, —SO$_2$N(CH$_3$)$_2$, —SO$_2$NHCH$_2$CH$_3$, —SO$_2$NHCH$_3$, and —SO$_2$NH$_2$. In a still further aspect, each of $R^{3a}$, $R^{3c}$, $R^{3d}$, $R^{3e}$, and $R^{3f}$ is hydrogen; and $R^{3b}$ is selected from —F, —Cl, —Br, methyl, ethyl, isopropyl, —CH$_2$F, —CHF$_2$, —CF$_3$, —CH$_2$CF$_3$, —OCH$_3$, —OCF$_3$, —OCH$_2$CF$_3$, —(C=O)OH, —(C=O)NH$_2$, —SO$_2$NHCH$_3$, and —SO$_2$NH$_2$.

In various aspects, each of $R^{3a}$, $R^{3b}$, $R^{3d}$, $R^{3e}$, and $R^{3f}$ is hydrogen; and $R^{3c}$ is selected from halo, cyano, hydroxyl, —NH$_2$, C1-C3 alkyl, C1-C3 monoalkyl, C1-C3 polyhaloalkyl, C1-C3 alkoxy, C1-C3 monohaloalkoxy, C1-C3 polyhaloalkyl, C1-C3 alkoxy, C1-C3 monohaloalkoxy, C1-C3 polyhaloalkoxy, —(C=O)OR$^9$, —(C=O)NR$^{10a}$R$^{10b}$, and —SO$_2$NR$^{10a}$R$^{10b}$, —SR$^9$, and —SO$_2$R$^9$. In a further aspect, each of $R^{3a}$, $R^{3b}$, $R^{3d}$, $R^{3e}$, and $R^{3f}$ is hydrogen; and $R^{3c}$ is selected from —F, —Cl, —Br, cyano, hydroxyl, —NH$_2$, methyl, ethyl, propyl, isopropyl, —CH$_2$F, —CHF$_2$, —CF$_3$, —CH$_2$Cl, —CHCl$_2$, —CCl$_3$, —CH$_2$CH$_2$F, —CH$_2$CHF$_2$, —CH$_2$CF$_3$, —CH$_2$CH$_2$Cl, —CH$_2$CHCl$_2$, —CH$_2$CCl$_3$, —OCH$_3$, —OCH$_2$CH$_3$, —OCH$_2$F, —OCHF$_2$, —OCF$_3$, —OCH$_2$Cl, —OCHCl$_2$, —OCCl$_3$, —OCH$_2$CH$_2$F, —OCH$_2$CHF$_2$, —OCH$_2$CF$_3$, —OCH$_2$CH$_2$Cl, —OCH$_2$CHCl$_2$, —(C=O)OCH$_2$CH$_3$, —(C=O)OCH$_2$CH$_3$, —(C=O)OCH$_3$, —(C=O)OH, —(C=O)NHCH$_2$CH$_3$, —(C=O)NHCH$_3$, —(C=O)NH$_2$, —SO$_2$N(CH$_3$)$_2$, —SO$_2$NHCH$_2$CH$_3$, —SO$_2$NHCH$_3$, and —SO$_2$NH$_2$. In a still further aspect, each of $R^{3a}$, $R^{3b}$, $R^{3d}$, $R^{3e}$, and $R^{3f}$ is hydrogen; and $R^{3c}$ is selected from —F, —Cl, —Br, methyl, ethyl, isopropyl, —CH$_2$F, —CHF$_2$, —CF$_3$, —CH$_2$CF$_3$, —OCH$_3$, —OCF$_3$, —OCH$_2$CF$_3$, —(C=O)OH, —(C=O)NH$_2$, —SO$_2$NHCH$_3$, and —SO$_2$NH$_2$.

In various aspects, each of $R^{3a}$, $R^{3d}$, $R^{3e}$, and $R^{3f}$ is hydrogen; and each of $R^{3b}$ and $R^{3c}$ is selected from halo, cyano, hydroxyl, —NH$_2$, C1-C3 alkyl, C1-C3 monoalkyl, C1-C3 polyhaloalkyl, C1-C3 alkoxy, C1-C3 monohaloalkoxy, C1-C3 polyhaloalkyl, C1-C3 alkoxy, C1-C3 monohaloalkoxy, C1-C3 polyhaloalkoxy, —(C=O)OR$^9$, —(C=O)NR$^{10a}$R$^{10b}$, and —SO$_2$NR$^{10a}$R$^{10b}$, —SR$^9$, and —SO$_2$R$^9$. In a further aspect, each of $R^{3a}$, $R^{3d}$, $R^{3e}$, and $R^{3f}$ is hydrogen; and each of $R^{3b}$ and $R^{3c}$ is selected from —F, —Cl, —Br, cyano, hydroxyl, —NH$_2$, methyl, ethyl, propyl, isopropyl, —CH$_2$F, —CHF$_2$, —CF$_3$, —CH$_2$Cl, —CHCl$_2$, —CCl$_3$, —CH$_2$CH$_2$F, —CH$_2$CHF$_2$, —CH$_2$CF$_3$, —CH$_2$CH$_2$Cl, —CH$_2$CHCl$_2$, —CH$_2$CCl$_3$, —OCH$_3$, —OCH$_2$CH$_3$, —OCH$_2$F, —OCHF$_2$, —OCF$_3$, —OCH$_2$Cl, —OCHCl$_2$, —OCCl$_3$, —OCH$_2$CH$_2$F, —OCH$_2$CHF$_2$, —OCH$_2$CF$_3$, —OCH$_2$CH$_2$Cl, —OCH$_2$CHCl$_2$, —(C=O)OCH$_2$CH$_3$, —(C=O)OCH$_3$, —(C=O)OH, —(C=O)NHCH$_2$CH$_3$, —(C=O)NHCH$_3$, —(C=O)NH$_2$, —SO$_2$N(CH$_3$)$_2$, —SO$_2$NHCH$_2$CH$_3$, —SO$_2$NHCH$_3$, and —SO$_2$NH$_2$. In a still further aspect, each of $R^{3a}$, $R^{3d}$, $R^{3e}$, and $R^{3f}$ is hydrogen; and each of $R^{3b}$ and $R^{3c}$ is selected from —F, —Cl, —Br, methyl, ethyl, isopropyl, —CH$_2$F, —CHF$_2$, —CF$_3$, —CH$_2$CF$_3$, —OCH$_3$, —OCF$_3$, —OCH$_2$CF$_3$, —(C=O)OH, —(C=O)NH$_2$, —SO$_2$NHCH$_3$, and —SO$_2$NH$_2$.

In various aspects, each of $R^{3b}$, $R^{3d}$, $R^{3e}$, and $R^{3f}$ is hydrogen; and each of $R^{3a}$ and $R^{3c}$ is selected from halo, cyano, hydroxyl, —NH$_2$, C1-C3 alkyl, C1-C3 monoalkyl, C1-C3 polyhaloalkyl, C1-C3 alkoxy, C1-C3 monohaloalkoxy, C1-C3 polyhaloalkoxy, C1-C3 alkoxy, C1-C3 monohaloalkoxy, C1-C3 polyhaloalkoxy, —(C═O)OR$^9$, —(C═O)NR$^{10a}$R$^{10b}$, and —SO$_2$NR$^{10a}$R$^{10b}$, —SR$^9$, and —SO$_2$R$^9$. In a further aspect, each of R$^{3b}$, R$^{3d}$, R$^{3e}$, and R$^{3f}$ is hydrogen; and each of R$^{3a}$ and R$^{3c}$ is selected from —F, —Cl, —Br, cyano, hydroxyl, —NH$_2$, methyl, ethyl, propyl, isopropyl, —CH$_2$F, —CHF$_2$, —CF$_3$, —CH$_2$Cl, —CHCl$_2$, —CCl$_3$, —CH$_2$CH$_2$F, —CH$_2$CHF$_2$, —CH$_2$CF$_3$, —CH$_2$CH$_2$Cl, —CH$_2$CHCl$_2$, —CH$_2$CCl$_3$, —OCH$_3$, —OCH$_2$CH$_3$, —OCH$_2$F, —OCHF$_2$, —OCF$_3$, —OCH$_2$Cl, —OCHCl$_2$, —OCCl$_3$, —OCH$_2$CH$_2$F, —OCH$_2$CHF$_2$, —OCH$_2$CF$_3$, —OCH$_2$CH$_2$Cl, —OCH$_2$CHCl$_2$, —(C═O)OCH$_2$CH$_3$, —(C═O)OCH$_2$CH$_3$, —(C═O)OCH$_3$, —(C═O)OH, —(C═O)NHCH$_2$CH$_3$, —(C═O)NHCH$_3$, —(C═O)NH$_2$, —SO$_2$N(CH$_3$)$_2$, —SO$_2$NHCH$_2$CH$_3$, —SO$_2$NHCH$_3$, and —SO$_2$NH$_2$. In a still further aspect, each of R$^{3b}$, R$^{3d}$, R$^{3e}$, and R$^{3f}$ is hydrogen; and each of R$^{3a}$ and R$^{3c}$ is selected from —F, —Cl, —Br, methyl, ethyl, isopropyl, —CH$_2$F, —CHF$_2$, —CF$_3$, —CH$_2$CF$_3$, —OCH$_3$, —OCF$_3$, —OCH$_2$CF$_3$, —(C═O)OH, —(C═O)NH$_2$, —SO$_2$NHCH$_3$, and —SO$_2$NH$_2$.

d. R$^{4a}$, R$^{4b}$, and R$^{4c}$ Groups

In one aspect, each of R$^{4a}$, R$^{4b}$, and R$^{4c}$ is selected from hydrogen, halo, cyano, hydroxyl, —NH$_2$, C1-C3 alkyl, C1-C3 monoalkyl, C1-C3 polyhaloalkyl, C1-C3 alkoxy, C1-C3 monohaloalkoxy, C1-C3 polyhaloalkyl, C1-C3 alkoxy, C1-C3 monohaloalkoxy, C1-C3 polyhaloalkoxy, —(C═O)OR$^9$, —(C═O)NR$^{10a}$R$^{10b}$, and —SO$_2$NR$^{10a}$R$^{10b}$, —SR$^9$, and —SO$_2$R$^9$. In a further aspect, each of R$^{4a}$, R$^{4b}$, and R$^{4c}$ is hydrogen.

In various aspects, each of R$^{4a}$, R$^{4b}$, and R$^{4c}$ is selected from hydrogen, —F, —Cl, —Br, cyano, hydroxyl, —NH$_2$, methyl, ethyl, propyl, isopropyl, —CH$_2$F, —CHF$_2$, —CF$_3$, —CH$_2$Cl, —CHCl$_2$, —CCl$_3$, —CH$_2$CH$_2$F, —CH$_2$CHF$_2$, —CH$_2$CF$_3$, —CH$_2$CH$_2$Cl, —CH$_2$CHCl$_2$, —CH$_2$CCl$_3$, —OCH$_3$, —OCH$_2$CH$_3$, —OCH$_2$F, —OCHF$_2$, —OCF$_3$, —OCH$_2$Cl, —OCHCl$_2$, —OCCl$_3$, —OCH$_2$CH$_2$F, —OCH$_2$CHF$_2$, —OCH$_2$CF$_3$, —OCH$_2$CH$_2$Cl, —OCH$_2$CHCl$_2$, —(C═O)OCH$_2$CH$_3$, —(C═O)OCH$_2$CH$_3$, —(C═O)OCH$_3$, —(C═O)OH, —(C═O)NHCH$_2$CH$_3$, —(C═O)NHCH$_3$, —(C═O)NH$_2$, —SO$_2$N(CH$_3$)$_2$, —SO$_2$NHCH$_2$CH$_3$, —SO$_2$NHCH$_3$, and —SO$_2$NH$_2$. In a further aspect, each of R$^{4a}$, R$^{4b}$, and R$^{4c}$ is selected from hydrogen, —F, —Cl, —Br, methyl, ethyl, isopropyl, —CH$_2$F, —CHF$_2$, —CF$_3$, —CH$_2$CF$_3$, —OCH$_3$, —OCF$_3$, —OCH$_2$CF$_3$, —(C═O)OH, —(C═O)NH$_2$, —SO$_2$NHCH$_3$, and —SO$_2$NH$_2$.

In various aspects, each of R$^{4a}$ and R$^{4b}$ is selected from hydrogen, halo, cyano, hydroxyl, —NH$_2$, C1-C3 alkyl, C1-C3 monoalkyl, C1-C3 polyhaloalkyl, C1-C3 alkoxy, C1-C3 monohaloalkoxy, C1-C3 polyhaloalkyl, C1-C3 alkoxy, C1-C3 monohaloalkoxy, C1-C3 polyhaloalkoxy, —(C═O)OR$^9$, —(C═O)NR$^{10a}$R$^{10b}$, and —SO$_2$NR$^{10a}$R$^{10b}$, —SR$^9$, and —SO$_2$R$^9$. In a further aspect, each of R$^{4a}$ and R$^{4b}$ is selected from hydrogen, —F, —Cl, —Br, cyano, hydroxyl, —NH$_2$, methyl, ethyl, propyl, isopropyl, —CH$_2$F, —CHF$_2$, —CF$_3$, —CH$_2$Cl, —CHCl$_2$, —CCl$_3$, —CH$_2$CH$_2$F, —CH$_2$CHF$_2$, —CH$_2$CF$_3$, —CH$_2$CH$_2$Cl, —CH$_2$CHCl$_2$, —CH$_2$CCl$_3$, —OCH$_3$, —OCH$_2$CH$_3$, —OCH$_2$F, —OCHF$_2$, —OCF$_3$, —OCH$_2$Cl, —OCHCl$_2$, —OCCl$_3$, —OCH$_2$CH$_2$F, —OCH$_2$CHF$_2$, —OCH$_2$CF$_3$, —OCH$_2$CH$_2$Cl, —OCH$_2$CHCl$_2$, —(C═O)OCH$_2$CH$_3$, —(C═O)OCH$_2$CH$_3$, —(C═O)OCH$_3$, —(C═O)OH, —(C═O)NHCH$_2$CH$_3$, —(C═O)NHCH$_3$, —(C═O)NH$_2$, —SO$_2$N(CH$_3$)$_2$, —SO$_2$NHCH$_2$CH$_3$, —SO$_2$NHCH$_3$, and —SO$_2$NH$_2$. In a still further aspect, each of R$^{4a}$ and R$^{4b}$ is selected from hydrogen, —F, —Cl, —Br, methyl, ethyl, isopropyl, —CH$_2$F, —CHF$_2$, —CF$_3$, —CH$_2$CF$_3$, —OCH$_3$, —OCF$_3$, —OCH$_2$CF$_3$, —(C═O)OH, —(C═O)NH$_2$, —SO$_2$NHCH$_3$, and —SO$_2$NH$_2$.

e. R$^5$ Groups

In one aspect, R$^5$ is selected from hydrogen and C1-C3 alkyl. In a further aspect, R$^5$ is selected from hydrogen, methyl, and ethyl. In a still further aspect, R$^5$ is selected from hydrogen and methyl. In a yet further aspect, R$^5$ is methyl. In an even further aspect, R$^5$ is hydrogen.

f. R$^9$ Groups

In one aspect, each occurrence of R$^9$, when present, is selected from hydrogen and C1-C3 alkyl. In a further aspect, each occurrence of R$^9$, when present, is hydrogen.

In various aspects, each occurrence of R$^9$, when present, is selected from hydrogen, ethyl, and methyl. In a further aspect, each occurrence of R$^9$, when present, is selected from hydrogen and methyl. In a still further aspect, each occurrence of R$^9$, when present, is methyl.

g. R$^{10a}$ and R$^{10b}$ Groups

In one aspect, each occurrence of R$^{10a}$ and R$^{10b}$, when present, is independently selected from hydrogen and C1-C3 alkyl. In a further aspect, each occurrence of R$^{10a}$ and R$^{10b}$, when present, is hydrogen.

In various aspects, each occurrence of R$^{10a}$ and R$^{10b}$, when present, is independently selected from hydrogen, ethyl, and methyl. In a further aspect, each occurrence of R$^{10a}$ and R$^{10b}$, when present, is independently selected from hydrogen and methyl. In a still further aspect, each occurrence of R$^{10a}$ and R$^{10b}$, when present, is methyl.

In a further aspect, each occurrence of R$^{10a}$, when present, is hydrogen; and wherein each occurrence of R$^{10b}$, when present, is selected from hydrogen and C1-C3 alkyl. In a still further aspect, each occurrence of R$^{10a}$, when present, is hydrogen; and wherein each occurrence of R$^{10b}$, when present, is selected from hydrogen, ethyl, and methyl. In a yet further aspect, each occurrence of R$^{10a}$, when present, is hydrogen; and wherein each occurrence of R$^{10b}$, when present, is selected from hydrogen and methyl.

h. Ar Groups

In one aspect, Ar is aryl or heteroaryl substituted with 0 to 3 groups independently selected from halo, cyano, hydroxyl, —NH$_2$, C1-C3 alkyl, C1-C3 monoalkyl, C1-C3 polyhaloalkyl, C1-C3 alkoxy, C1-C3 monohaloalkoxy, C1-C3 polyhaloalkyl, C1-C3 alkoxy, C1-C3 monohaloalkoxy, C1-C3 polyhaloalkoxy, —(C═O)OR$^9$, —(C═O)NR$^{10a}$R$^{10b}$, and —SO$_2$NR$^{10a}$R$^{10b}$, —SR$^9$, and —SO$_2$R$^9$. In a further aspect, Ar is aryl or heteroaryl and is unsubstituted.

In a further aspect, Ar is aryl substituted with 0 to 3 groups independently selected from halo, cyano, hydroxyl, —NH$_2$, C1-C3 alkyl, C1-C3 monoalkyl, C1-C3 polyhaloalkyl, C1-C3 alkoxy, C1-C3 monohaloalkoxy, C1-C3 polyhaloalkyl, C1-C3 alkoxy, C1-C3 monohaloalkoxy, C1-C3 polyhaloalkoxy, —(C═O)OR$^9$, —(C═O)NR$^{10a}$R$^{10b}$, and —SO$_2$NR$^{10a}$R$^{10b}$, —SR$^9$, and —SO$_2$R$^9$. In a still further aspect, Ar is aryl substituted with 0 to 3 groups independently selected from —F, —Cl, —Br, cyano, hydroxyl, —NH$_2$, methyl, ethyl, propyl, isopropyl, —CH$_2$F, —CHF$_2$, —CF$_3$, —CH$_2$Cl, —CHCl$_2$, —CCl$_3$, —CH$_2$CH$_2$F, —CH$_2$CHF$_2$, —CH$_2$CF$_3$, —CH$_2$CH$_2$Cl, —CH$_2$CHCl$_2$, —CH$_2$CCl$_3$, —OCH$_3$, —OCH$_2$CH$_3$, —OCH$_2$F, —OCHF$_2$, —OCF$_3$, —OCH$_2$Cl, —OCHCl$_2$, —OCCl$_3$, —OCH$_2$CH$_2$F, —OCH$_2$CHF$_2$, —OCH$_2$CF$_3$, —OCH$_2$CH$_2$Cl, —OCH$_2$CHCl$_2$, —(C═O)OCH$_2$CH$_3$, —(C═O)OCH$_2$CH$_3$, —(C═O)OCH$_3$, —(C═O)OH, —(C═O)NHCH$_2$CH$_3$, —(C═O)NHCH$_3$, —(C═O)NH$_2$, —SO$_2$N (CH$_3$)$_2$, —SO$_2$NHCH$_2$CH$_3$, —SO$_2$NHCH$_3$, and —SO$_2$NH$_2$. In yet a further aspect, Ar is aryl substituted with 0 to 3 groups independently selected from —F, —Cl, —Br, methyl, ethyl, isopropyl, —CH$_2$F, —CHF$_2$, —CF$_3$, —CH$_2$CF$_3$, —OCH$_3$, —OCF$_3$, —OCH$_2$CF$_3$, —(C=O)OH, —(C=O)NH$_2$, —SO$_2$NHCH$_3$, and —SO$_2$NH$_2$.

In a further aspect, Ar is aryl monosubstituted with a group selected from halo, cyano, hydroxyl, —NH$_2$, C1-C3 alkyl, C1-C3 monoalkyl, C1-C3 polyhaloalkyl, C1-C3 alkoxy, C1-C3 monohaloalkoxy, C1-C3 polyhaloalkyl, C1-C3 alkoxy, C1-C3 monohaloalkoxy, C1-C3 polyhaloalkoxy, —(C=O)OR$^9$, —(C=O)NR$^{10a}$R$^{10b}$, and —SO$_2$NR$^{10a}$R$^{10b}$, —SR$^9$, and —SO$_2$R$^9$.

In a still further aspect, Ar is aryl monosubstituted with a group selected from —F, —Cl, —Br, cyano, hydroxyl, —NH$_2$, methyl, ethyl, propyl, isopropyl, —CH$_2$F, —CHF$_2$, —CF$_3$, —CH$_2$Cl, —CHCl$_2$, —CCl$_3$, —CH$_2$CH$_2$F, —CH$_2$CHF$_2$, —CH$_2$CF$_3$, —CH$_2$CH$_2$Cl, —CH$_2$CHCl$_2$, —CH$_2$CCl$_3$, —OCH$_3$, —OCH$_2$CH$_3$, —OCH$_2$F, —OCHF$_2$, —OCF$_3$, —OCH$_2$Cl, —OCHCl$_2$, —OCCl$_3$, —OCH$_2$CH$_2$F, —OCH$_2$CHF$_2$, —OCH$_2$CF$_3$, —OCH$_2$CH$_2$Cl, —OCH$_2$CHCl$_2$, —(C=O)OCH$_2$CH$_3$, —(C=O)OCH$_2$CH$_3$, —(C=O)OCH$_3$, —(C=O)OH, —(C=O)NHCH$_2$CH$_3$, —(C=O)NHCH$_3$, —(C=O)NH$_2$, —SO$_2$N(CH$_3$)$_2$, —SO$_2$NHCH$_2$CH$_3$, —SO$_2$NHCH$_3$, and —SO$_2$NH$_2$. In yet a further aspect, Ar is aryl monosubstituted with a group selected from —F, —Cl, —Br, methyl, ethyl, isopropyl, —CH$_2$F, —CHF$_2$, —CF$_3$, —CH$_2$CF$_3$, —OCH$_3$, —OCF$_3$, —OCH$_2$CF$_3$, —(C=O)OH, —(C=O)NH$_2$, —SO$_2$NHCH$_3$, and —SO$_2$NH$_2$.

In a further aspect, Ar is aryl substituted with 2 groups independently selected from halo, cyano, hydroxyl, —NH$_2$, C1-C3 alkyl, C1-C3 monoalkyl, C1-C3 polyhaloalkyl, C1-C3 alkoxy, C1-C3 monohaloalkoxy, C1-C3 polyhaloalkyl, C1-C3 alkoxy, C1-C3 monohaloalkoxy, C1-C3 polyhaloalkoxy, —(C=O)OR$^9$, —(C=O)NR$^{10a}$R$^{10b}$, and —SO$_2$NR$^{10a}$R$^{10b}$, —SR$^9$, and —SO$_2$R$^9$. In a still further aspect, Ar is aryl substituted with 2 groups independently selected from —F, —Cl, —Br, cyano, hydroxyl, —NH$_2$, methyl, ethyl, propyl, isopropyl, —CH$_2$F, —CHF$_2$, —CF$_3$, —CH$_2$Cl, —CHCl$_2$, —CCl$_3$, —CH$_2$CH$_2$F, —CH$_2$CHF$_2$, —CH$_2$CF$_3$, —CH$_2$CH$_2$Cl, —CH$_2$CHCl$_2$, —CH$_2$CCl$_3$, —OCH$_3$, —OCH$_2$CH$_3$, —OCH$_2$F, —OCHF$_2$, —OCF$_3$, —OCH$_2$Cl, —OCHCl$_2$, —OCCl$_3$, —OCH$_2$CH$_2$F, —OCH$_2$CHF$_2$, —OCH$_2$CF$_3$, —OCH$_2$CH$_2$Cl, —OCH$_2$CHCl$_2$, —(C=O)OCH$_2$CH$_3$, —(C=O)OCH$_2$CH$_3$, —(C=O)OCH$_3$, —(C=O)OH, —(C=O)NHCH$_2$CH$_3$, —(C=O)NHCH$_3$, —(C=O)NH$_2$, —SO$_2$N(CH$_3$)$_2$, —SO$_2$NHCH$_2$CH$_3$, —SO$_2$NHCH$_3$, and —SO$_2$NH$_2$. In yet a further aspect, Ar is aryl substituted with 2 groups independently selected from —F, —Cl, —Br, methyl, ethyl, isopropyl, —CH$_2$F, —CHF$_2$, —CF$_3$, —CH$_2$CF$_3$, —OCH$_3$, —OCF$_3$, —OCH$_2$CF$_3$, —(C=O)OH, —(C=O)NH$_2$, —SO$_2$NHCH$_3$, and —SO$_2$NH$_2$.

In a further aspect, Ar is phenyl substituted with 0 to 3 groups independently selected from halo, cyano, hydroxyl, —NH$_2$, C1-C3 alkyl, C1-C3 monoalkyl, C1-C3 polyhaloalkyl, C1-C3 alkoxy, C1-C3 monohaloalkoxy, C1-C3 polyhaloalkyl, C1-C3 alkoxy, C1-C3 monohaloalkoxy, C1-C3 polyhaloalkoxy, —(C=O)OR$^9$, —(C=O)NR$^{10a}$R$^{10b}$, and —SO$_2$NR$^{10a}$R$^{10b}$, —SR$^9$, and —SO$_2$R$^9$. In a still further aspect, Ar is phenyl substituted with 0 to 3 groups independently selected from —F, —Cl, —Br, cyano, hydroxyl, —NH$_2$, methyl, ethyl, propyl, isopropyl, —CH$_2$F, —CHF$_2$, —CF$_3$, —CH$_2$Cl, —CHCl$_2$, —CCl$_3$, —CH$_2$CH$_2$F, —CH$_2$CHF$_2$, —CH$_2$CF$_3$, —CH$_2$CH$_2$Cl, —CH$_2$CHCl$_2$, —CH$_2$CCl$_3$, —OCH$_3$, —OCH$_2$CH$_3$, —OCH$_2$F, —OCHF$_2$, —OCF$_3$, —OCH$_2$Cl, —OCHCl$_2$, —OCCl$_3$, —OCH$_2$CH$_2$F, —OCH$_2$CHF$_2$, —OCH$_2$CF$_3$, —OCH$_2$CH$_2$Cl, —OCH$_2$CHCl$_2$, —(C=O)OCH$_2$CH$_3$, —(C=O)OCH$_2$CH$_3$, —(C=O)OCH$_3$, —(C=O)OH, —(C=O)NHCH$_2$CH$_3$, —(C=O)NHCH$_3$, —(C=O)NH$_2$, —SO$_2$N(CH$_3$)$_2$, —SO$_2$NHCH$_2$CH$_3$, —SO$_2$NHCH$_3$, and —SO$_2$NH$_2$. In yet a further aspect, Ar is phenyl substituted with 0 to 3 groups independently selected from —F, —Cl, —Br, methyl, ethyl, isopropyl, —CH$_2$F, —CHF$_2$, —CF$_3$, —CH$_2$CF$_3$, —OCH$_3$, —OCF$_3$, —OCH$_2$CF$_3$, —(C=O)OH, —(C=O)NH$_2$, —SO$_2$NHCH$_3$, and —SO$_2$NH$_2$.

In a further aspect, Ar is phenyl monosubstituted with a group selected from halo, cyano, hydroxyl, —NH$_2$, C1-C3 alkyl, C1-C3 monoalkyl, C1-C3 polyhaloalkyl, C1-C3 alkoxy, C1-C3 monohaloalkoxy, C1-C3 polyhaloalkyl, C1-C3 alkoxy, C1-C3 monohaloalkoxy, C1-C3 polyhaloalkoxy, —(C=O)OR$^9$, —(C=O)NR$^{10a}$R$^{10b}$, and —SO$_2$NR$^{10a}$R$^{10b}$, —SR$^9$, and —SO$_2$R$^9$. In a still further aspect, Ar is phenyl monosubstituted with a group selected from —F, —Cl, —Br, cyano, hydroxyl, —NH$_2$, methyl, ethyl, propyl, isopropyl, —CH$_2$F, —CHF$_2$, —CF$_3$, —CH$_2$Cl, —CHCl$_2$, —CCl$_3$, —CH$_2$CH$_2$F, —CH$_2$CHF$_2$, —CH$_2$CF$_3$, —CH$_2$CH$_2$Cl, —CH$_2$CHCl$_2$, —CH$_2$CCl$_3$, —OCH$_3$, —OCH$_2$CH$_3$, —OCH$_2$F, —OCHF$_2$, —OCF$_3$, —OCH$_2$Cl, —OCHCl$_2$, —OCCl$_3$, —OCH$_2$CH$_2$F, —OCH$_2$CHF$_2$, —OCH$_2$CF$_3$, —OCH$_2$CH$_2$Cl, —OCH$_2$CHCl$_2$, —(C=O)OCH$_2$CH$_3$, —(C=O)OCH$_2$CH$_3$, —(C=O)OCH$_3$, —(C=O)OH, —(C=O)NHCH$_2$CH$_3$, —(C=O)NHCH$_3$, —(C=O)NH$_2$, —SO$_2$N(CH$_3$)$_2$, —SO$_2$NHCH$_2$CH$_3$, —SO$_2$NHCH$_3$, and —SO$_2$NH$_2$. In yet a further aspect, Ar is phenyl monosubstituted with a group selected from —F, —Cl, —Br, methyl, ethyl, isopropyl, —CH$_2$F, —CHF$_2$, —CF$_3$, —CH$_2$CF$_3$, —OCH$_3$, —OCF$_3$, —OCH$_2$CF$_3$, —(C=O)OH, —(C=O)NH$_2$, —SO$_2$NHCH$_3$, and —SO$_2$NH$_2$.

In a further aspect, Ar is phenyl substituted with 2 groups independently selected from halo, cyano, hydroxyl, —NH$_2$, C1-C3 alkyl, C1-C3 monoalkyl, C1-C3 polyhaloalkyl, C1-C3 alkoxy, C1-C3 monohaloalkoxy, C1-C3 polyhaloalkyl, C1-C3 alkoxy, C1-C3 monohaloalkoxy, C1-C3 polyhaloalkoxy, —(C=O)OR$^9$, —(C=O)NR$^{10a}$R$^{10b}$, and —SO$_2$NR$^{10a}$R$^{10b}$, —SR$^9$, and —SO$_2$R$^9$. In a still further aspect, Ar is phenyl substituted with 2 groups independently selected from —F, —Cl, —Br, cyano, hydroxyl, —NH$_2$, methyl, ethyl, propyl, isopropyl, —CH$_2$F, —CHF$_2$, —CF$_3$, —CH$_2$Cl, —CHCl$_2$, —CCl$_3$, —CH$_2$CH$_2$F, —CH$_2$CHF$_2$, —CH$_2$CF$_3$, —CH$_2$CH$_2$Cl, —CH$_2$CHCl$_2$, —CH$_2$CCl$_3$, —OCH$_3$, —OCH$_2$CH$_3$, —OCH$_2$F, —OCHF$_2$, —OCF$_3$, —OCH$_2$Cl, —OCHCl$_2$, —OCCl$_3$, —OCH$_2$CH$_2$F, —OCH$_2$CHF$_2$, —OCH$_2$CF$_3$, —OCH$_2$CH$_2$Cl, —OCH$_2$CHCl$_2$, —(C=O)OCH$_2$CH$_3$, —(C=O)OCH$_2$CH$_3$, —(C=O)OCH$_3$, —(C=O)OH, —(C=O)NHCH$_2$CH$_3$, —(C=O)NHCH$_3$, —(C=O)NH$_2$, —SO$_2$N(CH$_3$)$_2$, —SO$_2$NHCH$_2$CH$_3$, —SO$_2$NHCH$_3$, and —SO$_2$NH$_2$. In yet a further aspect, Ar is phenyl substituted with 2 groups independently selected from —F, —Cl, —Br, methyl, ethyl, isopropyl, —CH$_2$F, —CHF$_2$, —CF$_3$, —CH$_2$CF$_3$, —OCH$_3$, —OCF$_3$, —OCH$_2$CF$_3$, —(C=O)OH, —(C=O)NH$_2$, —SO$_2$NHCH$_3$, and —SO$_2$NH$_2$.

In a further aspect, Ar is heteroaryl substituted with 0 to 3 groups independently selected from halo, cyano, hydroxyl, —NH$_2$, C1-C3 alkyl, C1-C3 monoalkyl, C1-C3 polyhaloalkyl, C1-C3 alkoxy, C1-C3 monohaloalkoxy, C1-C3 polyhaloalkyl, C1-C3 alkoxy, C1-C3 monohaloalkoxy, C1-C3 polyhaloalkoxy, —(C=O)OR$^9$, —(C=O)NR$^{10a}$R$^{10b}$, and —SO$_2$NR$^{10a}$R$^{10b}$, —SR$^9$, and —SO$_2$R$^9$. In a still further aspect, Ar is heteroaryl substituted with 0 to 3 groups independently selected from —F, —Cl, —Br, cyano, hydroxyl, —NH$_2$, methyl, ethyl, propyl, isopropyl, —CH$_2$F, —CHF$_2$, —CF$_3$, —CH$_2$Cl, —CHCl$_2$, —CCl$_3$, —CH$_2$CH$_2$F, —CH$_2$CHF$_2$, —CH$_2$CF$_3$, —CH$_2$CH$_2$Cl, —CH$_2$CHCl$_2$, —CH$_2$CCl$_3$, —OCH$_3$, —OCH$_2$CH$_3$, —OCH$_2$F, —OCHF$_2$, —OCF$_3$, —OCH$_2$Cl, —OCHCl$_2$, —OCCl$_3$, —OCH$_2$CH$_2$F, —OCH$_2$CHF$_2$, —OCH$_2$CF$_3$, —OCH$_2$CH$_2$Cl, —OCH$_2$CHCl$_2$, —(C=O)OCH$_2$CH$_3$, —(C=O)OCH$_2$CH$_3$, —(C=O)OCH$_3$, —(C=O)OH, —(C=O)NHCH$_2$CH$_3$, —(C=O)NHCH$_3$, —(C=O)NH$_2$, —SO$_2$N(CH$_3$)$_2$, —SO$_2$NHCH$_2$CH$_3$, —SO$_2$NHCH$_3$, and —SO$_2$NH$_2$. In yet a further aspect, Ar is heteroaryl substituted with 0 to 3 groups independently selected from —F, —Cl, —Br, methyl, ethyl, isopropyl, —CH$_2$F, —CHF$_2$, —CF$_3$, —CH$_2$CF$_3$, —OCH$_3$, —OCF$_3$, —OCH$_2$CF$_3$, —(C=O)OH, —(C=O)NH$_2$, —SO$_2$NHCH$_3$, and —SO$_2$NH$_2$.

In a further aspect, Ar is heteroaryl monosubstituted with a group selected from halo, cyano, hydroxyl, —NH$_2$, C1-C3 alkyl, C1-C3 monoalkyl, C1-C3 polyhaloalkyl, C1-C3 alkoxy, C1-C3 monohaloalkoxy, C1-C3 polyhaloalkyl, C1-C3 alkoxy, C1-C3 monohaloalkoxy, C1-C3 polyhaloalkoxy, —(C=O)OR$^9$, —(C=O)NR$^{10a}$R$^{10b}$, and —SO$_2$NR$^{10a}$R$^{10b}$, —SR$^9$, and —SO$_2$R$^9$. In a still further aspect, Ar is heteroaryl monosubstituted with a group selected from —F, —Cl, —Br, cyano, hydroxyl, —NH$_2$, methyl, ethyl, propyl, isopropyl, —CH$_2$F, —CHF$_2$, —CF$_3$, —CH$_2$Cl, —CHCl$_2$, —CCl$_3$, —CH$_2$CH$_2$F, —CH$_2$CHF$_2$, —CH$_2$CF$_3$, —CH$_2$CH$_2$Cl, —CH$_2$CHCl$_2$, —CH$_2$CCl$_3$, —OCH$_3$, —OCH$_2$CH$_3$, —OCH$_2$F, —OCHF$_2$, —OCF$_3$, —OCH$_2$Cl, —OCHCl$_2$, —OCCl$_3$, —OCH$_2$CH$_2$F, —OCH$_2$CHF$_2$, —OCH$_2$CF$_3$, —OCH$_2$CH$_2$Cl, —OCH$_2$CHCl$_2$, —(C=O)OCH$_2$CH$_3$, —(C=O)OCH$_2$CH$_3$, —(C=O)OCH$_3$, —(C=O)OH, —(C=O)NHCH$_2$CH$_3$, —(C=O)NHCH$_3$, —(C=O)NH$_2$, —SO$_2$N(CH$_3$)$_2$, —SO$_2$NHCH$_2$CH$_3$, —SO$_2$NHCH$_3$, and —SO$_2$NH$_2$. In yet a further aspect, Ar is heteroaryl monosubstituted with a group selected from —F, —Cl, —Br, methyl, ethyl, isopropyl, —CH$_2$F, —CHF$_2$, —CF$_3$, —CH$_2$CF$_3$, —OCH$_3$, —OCF$_3$, —OCH$_2$CF$_3$, —(C=O)OH, —(C=O)NH$_2$, —SO$_2$NHCH$_3$, and —SO$_2$NH$_2$.

In a further aspect, Ar is heteroaryl substituted with 2 groups independently selected from halo, cyano, hydroxyl, —NH$_2$, C1-C3 alkyl, C1-C3 monoalkyl, C1-C3 polyhaloalkyl, C1-C3 alkoxy, C1-C3 monohaloalkoxy, C1-C3 polyhaloalkyl, C1-C3 alkoxy, C1-C3 monohaloalkoxy, C1-C3 polyhaloalkoxy, —(C=O)OR$^9$, —(C=O)NR$^{10a}$R$^{10b}$, and —SO$_2$NR$^{10a}$R$^{10b}$, —SR$^9$, and —SO$_2$R$^9$. In a still further aspect, Ar is heteroaryl substituted with 2 groups independently selected from —F, —Cl, —Br, cyano, hydroxyl, —NH$_2$, methyl, ethyl, propyl, isopropyl, —CH$_2$F, —CHF$_2$, —CF$_3$, —CH$_2$Cl, —CHCl$_2$, —CCl$_3$, —CH$_2$CH$_2$F, —CH$_2$CHF$_2$, —CH$_2$CF$_3$, —CH$_2$CH$_2$Cl, —CH$_2$CHCl$_2$, —CH$_2$CCl$_3$, —OCH$_3$, —OCH$_2$CH$_3$, —OCH$_2$F, —OCHF$_2$, —OCF$_3$, —OCH$_2$Cl, —OCHCl$_2$, —OCCl$_3$, —OCH$_2$CH$_2$F, —OCH$_2$CHF$_2$, —OCH$_2$CF$_3$, —OCH$_2$CH$_2$Cl, —OCH$_2$CHCl$_2$, —(C=O)OCH$_2$CH$_3$, —(C=O)OCH$_2$CH$_3$, —(C=O)OCH$_3$, —(C=O)OH, —(C=O)NHCH$_2$CH$_3$, —(C=O)NHCH$_3$, —(C=O)NH$_2$, —SO$_2$N(CH$_3$)$_2$, —SO$_2$NHCH$_2$CH$_3$, —SO$_2$NHCH$_3$, and —SO$_2$NH$_2$. In yet a further aspect, Ar is heteroaryl substituted with 2 groups independently selected from —F, —Cl, —Br, methyl, ethyl, isopropyl, —CH$_2$F, —CHF$_2$, —CF$_3$, —CH$_2$CF$_3$, —OCH$_3$, —OCF$_3$, —OCH$_2$CF$_3$, —(C=O)OH, —(C=O)NH$_2$, —SO$_2$NHCH$_3$, and —SO$_2$NH$_2$.

In a further aspect, Ar is selected from phenyl, pyridinyl, pyridazinyl, furanyl, thiophenyl, oxazolyl, thiazolyl, imidazolyl, pyrrolyl, benzo[d]thiazolyl, benzo[d]oxazolyl, oxazolo[4,5-c]pyridinyl, quinolinyl, and 1H-benzo[d]imidazolyl; and wherein Ar is substituted with 0 to 3 groups independently selected from halo, cyano, hydroxyl, —NH$_2$, C1-C3 alkyl, C1-C3 monoalkyl, C1-C3 polyhaloalkyl, C1-C3 alkoxy, C1-C3 monohaloalkoxy, C1-C3 polyhaloalkyl, C1-C3 alkoxy, C1-C3 monohaloalkoxy, C1-C3 polyhaloalkoxy, —(C=O)OR$^9$, —(C=O)NR$^{10a}$R$^{10b}$, and —SO$_2$NR$^{10a}$R$^{10b}$, —SR$^9$, and —SO$_2$R$^9$. In a still further aspect, Ar is selected from phenyl, pyridinyl, pyridazinyl, furanyl, thiophenyl, oxazolyl, thiazolyl, imidazolyl, pyrrolyl, benzo[d]thiazolyl, benzo[d]oxazolyl, oxazolo[4,5-c]pyridinyl, quinolinyl, and 1H-benzo[d]imidazolyl; and wherein Ar is substituted with 0 to 3 groups independently selected from —F, —Cl, —Br, cyano, hydroxyl, —NH$_2$, methyl, ethyl, propyl, isopropyl, —CH$_2$F, —CHF$_2$, —CF$_3$, —CH$_2$Cl, —CHCl$_2$, —CCl$_3$, —CH$_2$CH$_2$F, —CH$_2$CHF$_2$, —CH$_2$CF$_3$, —CH$_2$CH$_2$Cl, —CH$_2$CHCl$_2$, —CH$_2$CCl$_3$, —OCH$_3$, —OCH$_2$CH$_3$, —OCH$_2$F, —OCHF$_2$, —OCF$_3$, —OCH$_2$Cl, —OCHCl$_2$, —OCCl$_3$, —OCH$_2$CH$_2$F, —OCH$_2$CHF$_2$, —OCH$_2$CF$_3$, —OCH$_2$CH$_2$Cl, —OCH$_2$CHCl$_2$, —(C=O)OCH$_2$CH$_3$, —(C=O)OCH$_2$CH$_3$, —(C=O)OCH$_3$, —(C=O)OH, —(C=O)NHCH$_2$CH$_3$, —(C=O)NHCH$_3$, —(C=O)NH$_2$, —SO$_2$N(CH$_3$)$_2$, —SO$_2$NHCH$_2$CH$_3$, —SO$_2$NHCH$_3$, and —SO$_2$NH$_2$. In yet a further aspect, Ar is selected from phenyl, pyridinyl, pyridazinyl, furanyl, thiophenyl, oxazolyl, thiazolyl, imidazolyl, pyrrolyl, benzo[d]thiazolyl, benzo[d]oxazolyl, oxazolo[4,5-c]pyridinyl, quinolinyl, and 1H-benzo[d]imidazolyl; and wherein Ar is substituted with 0 to 3 groups independently selected from —F, —Cl, —Br, methyl, ethyl, isopropyl, —CH$_2$F, —CHF$_2$, —CF$_3$, —CH$_2$CF$_3$, —OCH$_3$, —OCF$_3$, —OCH$_2$CF$_3$, —(C=O)OH, —(C=O)NH$_2$, —SO$_2$NHCH$_3$, and —SO$_2$NH$_2$.

In a further aspect, Ar is selected from phenyl, pyridinyl, pyridazinyl, furanyl, thiophenyl, oxazolyl, thiazolyl, imidazolyl, pyrrolyl, benzo[d]thiazolyl, benzo[d]oxazolyl, oxazolo[4,5-c]pyridinyl, quinolinyl, and 1H-benzo[d]imidazolyl; and wherein Ar is monosubstituted with a group selected from halo, cyano, hydroxyl, —NH$_2$, C1-C3 alkyl, C1-C3 monoalkyl, C1-C3 polyhaloalkyl, C1-C3 alkoxy, C1-C3 monohaloalkoxy, C1-C3 polyhaloalkyl, C1-C3 alkoxy, C1-C3 monohaloalkoxy, C1-C3 polyhaloalkoxy, —(C=O)OR$^9$, —(C=O)NR$^{10a}$R$^{10b}$, and —SO$_2$NR$^{10a}$R$^{10b}$, —SR$^9$, and —SO$_2$R$^9$. In a still further aspect, Ar is selected from phenyl, pyridinyl, pyridazinyl, furanyl, thiophenyl, oxazolyl, thiazolyl, imidazolyl, pyrrolyl, benzo[d]thiazolyl, benzo[d]oxazolyl, oxazolo[4,5-c]pyridinyl, quinolinyl, and 1H-benzo[d]imidazolyl; and wherein Ar is monosubstituted with a group selected from —F, —Cl, —Br, cyano, hydroxyl, —NH$_2$, methyl, ethyl, propyl, isopropyl, —CH$_2$F, —CHF$_2$, —CF$_3$, —CH$_2$Cl, —CHCl$_2$, —CCl$_3$, —CH$_2$CH$_2$F, —CH$_2$CHF$_2$, —CH$_2$CF$_3$, —CH$_2$CH$_2$Cl, —CH$_2$CHCl$_2$, —CH$_2$CCl$_3$, —OCH$_3$, —OCH$_2$CH$_3$, —OCH$_2$F, —OCHF$_2$, —OCF$_3$, —OCH$_2$Cl, —OCHCl$_2$, —OCCl$_3$, —OCH$_2$CH$_2$F, —OCH$_2$CHF$_2$, —OCH$_2$CF$_3$, —OCH$_2$CH$_2$Cl, —OCH$_2$CHCl$_2$, —(C=O)OCH$_2$CH$_3$, —(C=O)OCH$_2$CH$_3$, —(C=O)OCH$_3$, —(C=O)OH, —(C=O)NHCH$_2$CH$_3$, —(C=O)NHCH$_3$, —(C=O)NH$_2$, —SO$_2$N(CH$_3$)$_2$, —SO$_2$NHCH$_2$CH$_3$, —SO$_2$NHCH$_3$, and —SO$_2$NH$_2$. In yet a further aspect, Ar is selected from phenyl, pyridinyl, pyridazinyl, furanyl, thiophenyl, oxazolyl, thiazolyl, imidazolyl, pyrrolyl, benzo[d]thiazolyl, benzo[d]oxazolyl, oxazolo[4,5-c]pyridinyl, quinolinyl, and 1H-benzo[d]imidazolyl; and wherein Ar is monosubstituted with a group selected from —F, —Cl, —Br, methyl, ethyl, isopropyl, —CH$_2$F, —CHF$_2$, —CF$_3$, —CH$_2$CF$_3$, —OCH$_3$, —OCF$_3$, —OCH$_2$CF$_3$, —(C=O)OH, —(C=O)NH$_2$, —SO$_2$NHCH$_3$, and —SO$_2$NH$_2$.

In a further aspect, Ar is selected from phenyl, pyridinyl, pyridazinyl, furanyl, thiophenyl, oxazolyl, thiazolyl, imidazolyl, pyrrolyl, benzo[d]thiazolyl, benzo[d]oxazolyl, oxazolo[4,5-c]pyridinyl, quinolinyl, and 1H-benzo[d]imidazolyl; and wherein Ar is substituted with 2 groups independently selected from halo, cyano, hydroxyl, —NH$_2$, C1-C3 alkyl, C1-C3 monoalkyl, C1-C3 polyhaloalkyl, C1-C3 alkoxy, C1-C3 monohaloalkoxy, C1-C3 polyhaloalkyl, C1-C3 alkoxy, C1-C3 monohaloalkoxy, C1-C3 polyhaloalkoxy, —(C=O)OR$^9$, —(C=O)NR$^{10a}$R$^{10b}$, and —SO$_2$NR$^{10a}$R$^{10b}$, —SR$^9$, and —SO$_2$R$^9$. In a still further aspect, Ar is selected from phenyl, pyridinyl, pyridazinyl, furanyl, thiophenyl, oxazolyl, thiazolyl, imidazolyl, pyrrolyl, benzo[d]thiazolyl, benzo[d]oxazolyl, oxazolo[4,5-c]pyridinyl, quinolinyl, and 1H-benzo[d]imidazolyl; and wherein Ar is substituted with 2 groups independently selected from —F, —Cl, —Br, cyano, hydroxyl, —NH$_2$, methyl, ethyl, propyl, isopropyl, —CH$_2$F, —CHF$_2$, —CF$_3$, —CH$_2$Cl, —CHCl$_2$, —CCl$_3$, —CH$_2$CH$_2$F, —CH$_2$CHF$_2$, —CH$_2$CF$_3$, —CH$_2$CH$_2$Cl, —CH$_2$CHCl$_2$, —CH$_2$CCl$_3$, —OCH$_3$, —OCH$_2$CH$_3$, —OCH$_2$F, —OCHF$_2$, —OCF$_3$, —OCH$_2$Cl, —OCHCl$_2$, —OCCl$_3$, —OCH$_2$CH$_2$F, —OCH$_2$CHF$_2$, —OCH$_2$CF$_3$, —OCH$_2$CH$_2$Cl, —OCH$_2$CHCl$_2$, —(C=O)OCH$_2$CH$_3$, —(C=O)OCH$_2$CH$_3$, —(C=O)OCH$_3$, —(C=O)OH, —(C=O)NHCH$_2$CH$_3$, —(C=O)NHCH$_3$, —(C=O)NH$_2$, —SO$_2$N(CH$_3$)$_2$, —SO$_2$NHCH$_2$CH$_3$, —SO$_2$NHCH$_3$, and —SO$_2$NH$_2$. In yet a further aspect, Ar is selected from phenyl, pyridinyl, pyridazinyl, furanyl, thiophenyl, oxazolyl, thiazolyl, imidazolyl, pyrrolyl, benzo[d]thiazolyl, benzo[d]oxazolyl, oxazolo[4,5-c]pyridinyl, quinolinyl, and 1H-benzo[d]imidazolyl; and wherein Ar is substituted with 2 groups independently selected from —F, —Cl, —Br, methyl, ethyl, isopropyl, —CH$_2$F, —CHF$_2$, —CF$_3$, —CH$_2$CF$_3$, —OCH$_3$, —OCF$_3$, —OCH$_2$CF$_3$, —(C=O)OH, —(C=O)NH$_2$, —SO$_2$NHCH$_3$, and —SO$_2$NH$_2$.

In a further aspect, Ar is pyridinyl substituted with 0 to 3 groups independently selected from halo, cyano, hydroxyl, —NH$_2$, C1-C3 alkyl, C1-C3 monoalkyl, C1-C3 polyhaloalkyl, C1-C3 alkoxy, C1-C3 monohaloalkoxy, C1-C3 polyhaloalkyl, C1-C3 alkoxy, C1-C3 monohaloalkoxy, C1-C3 polyhaloalkoxy, —(C=O)OR$^9$, —(C=O)NR$^{10a}$R$^{10b}$, and —SO$_2$NR$^{10a}$R$^{10b}$, —SR$^9$, and —SO$_2$R$^9$. In a still further aspect, Ar is pyridinyl substituted with 0 to 3 groups independently selected from —F, —Cl, —Br, cyano, hydroxyl, —NH$_2$, methyl, ethyl, propyl, isopropyl, —CH$_2$F, —CHF$_2$, —CF$_3$, —CH$_2$Cl, —CHCl$_2$, —CCl$_3$, —CH$_2$CH$_2$F, —CH$_2$CHF$_2$, —CH$_2$CF$_3$, —CH$_2$CH$_2$Cl, —CH$_2$CHCl$_2$, —CH$_2$CCl$_3$, —OCH$_3$, —OCH$_2$CH$_3$, —OCH$_2$F, —OCHF$_2$, —OCF$_3$, —OCH$_2$Cl, —OCHCl$_2$, —OCCl$_3$, —OCH$_2$CH$_2$F, —OCH$_2$CHF$_2$, —OCH$_2$CF$_3$, —OCH$_2$CH$_2$Cl, —OCH$_2$CHCl$_2$, —(C=O)OCH$_2$CH$_3$, —(C=O)OCH$_2$CH$_3$, —(C=O)OCH$_3$, —(C=O)OH, —(C=O)NHCH$_2$CH$_3$, —(C=O)NHCH$_3$, —(C=O)NH$_2$, —SO$_2$N(CH$_3$)$_2$, —SO$_2$NHCH$_2$CH$_3$, —SO$_2$NHCH$_3$, and —SO$_2$NH$_2$. In yet a further aspect, Ar is pyridinyl substituted with 0 to 3 groups independently selected from —F, —Cl, —Br, methyl, ethyl, isopropyl, —CH$_2$F, —CHF$_2$, —CF$_3$, —CH$_2$CF$_3$, —OCH$_3$, —OCF$_3$, —OCH$_2$CF$_3$, —(C=O)OH, —(C=O)NH$_2$, —SO$_2$NHCH$_3$, and —SO$_2$NH$_2$.

In a further aspect, Ar is pyridinyl monosubstituted with a group selected from halo, cyano, hydroxyl, —NH$_2$, C1-C3 alkyl, C1-C3 monoalkyl, C1-C3 polyhaloalkyl, C1-C3 alkoxy, C1-C3 monohaloalkoxy, C1-C3 polyhaloalkyl, C1-C3 alkoxy, C1-C3 monohaloalkoxy, C1-C3 polyhaloalkoxy, —(C=O)OR$^9$, —(C=O)NR$^{10a}$R$^{10b}$, and —SO$_2$NR$^{10a}$R$^{10b}$, —SR$^9$, and —SO$_2$R$^9$. In a still further aspect, Ar is pyridinyl monosubstituted with a group selected from —F, —Cl, —Br, cyano, hydroxyl, —NH$_2$, methyl, ethyl, propyl, isopropyl, —CH$_2$F, —CHF$_2$, —CF$_3$, —CH$_2$Cl, —CHCl$_2$, —CCl$_3$, —CH$_2$CH$_2$F, —CH$_2$CHF$_2$, —CH$_2$CF$_3$, —CH$_2$CH$_2$Cl, —CH$_2$CHCl$_2$, —CH$_2$CCl$_3$, —OCH$_3$, —OCH$_2$CH$_3$, —OCH$_2$F, —OCHF$_2$, —OCF$_3$, —OCH$_2$Cl, —OCHCl$_2$, —OCCl$_3$, —OCH$_2$CH$_2$F, —OCH$_2$CHF$_2$, —OCH$_2$CF$_3$, —OCH$_2$CH$_2$Cl, —OCH$_2$CHCl$_2$, —(C=O)OCH$_2$CH$_3$, —(C=O)OCH$_2$CH$_3$, —(C=O)OCH$_3$, —(C=O)OH, —(C=O)NHCH$_2$CH$_3$, —(C=O)NHCH$_3$, —(C=O)NH$_2$, —SO$_2$N(CH$_3$)$_2$, —SO$_2$NHCH$_2$CH$_3$, —SO$_2$NHCH$_3$, and —SO$_2$NH$_2$. In yet a further aspect, Ar is pyridinyl monosubstituted with a group selected from —F, —Cl, —Br, methyl, ethyl, isopropyl, —CH$_2$F, —CHF$_2$, —CF$_3$, —CH$_2$CF$_3$, —OCH$_3$, —OCF$_3$, —OCH$_2$CF$_3$, —(C=O)OH, —(C=O)NH$_2$, —SO$_2$NHCH$_3$, and —SO$_2$NH$_2$.

In a further aspect, Ar is pyridinyl substituted with 2 groups independently selected from halo, cyano, hydroxyl, —NH$_2$, C1-C3 alkyl, C1-C3 monoalkyl, C1-C3 polyhaloalkyl, C1-C3 alkoxy, C1-C3 monohaloalkoxy, C1-C3 polyhaloalkyl, C1-C3 alkoxy, C1-C3 monohaloalkoxy, C1-C3 polyhaloalkoxy, —(C=O)OR$^9$, —(C=O)NR$^{10a}$R$^{10b}$, and —SO$_2$NR$^{10a}$R$^{10b}$, —SR$^9$, and —SO$_2$R$^9$. In a still further aspect, Ar is pyridinyl substituted with 2 groups independently selected from —F, —Cl, —Br, cyano, hydroxyl, —NH$_2$, methyl, ethyl, propyl, isopropyl, —CH$_2$F, —CHF$_2$, —CF$_3$, —CH$_2$Cl, —CHCl$_2$, —CCl$_3$, —CH$_2$CH$_2$F, —CH$_2$CHF$_2$, —CH$_2$CF$_3$, —CH$_2$CH$_2$Cl, —CH$_2$CHCl$_2$, —CH$_2$CCl$_3$, —OCH$_3$, —OCH$_2$CH$_3$, —OCH$_2$F, —OCHF$_2$, —OCF$_3$, —OCH$_2$Cl, —OCHCl$_2$, —OCCl$_3$, —OCH$_2$CH$_2$F, —OCH$_2$CHF$_2$, —OCH$_2$CF$_3$, —OCH$_2$CH$_2$Cl, —OCH$_2$CHCl$_2$, —(C=O)OCH$_2$CH$_3$, —(C=O)OCH$_2$CH$_3$, —(C=O)OCH$_3$, —(C=O)OH, —(C=O)NHCH$_2$CH$_3$, —(C=O)NHCH$_3$, —(C=O)NH$_2$, —SO$_2$N(CH$_3$)$_2$, —SO$_2$NHCH$_2$CH$_3$, —SO$_2$NHCH$_3$, and —SO$_2$NH$_2$. In yet a further aspect, Ar is pyridinyl substituted with 2 groups independently selected from —F, —Cl, —Br, methyl, ethyl, isopropyl, —CH$_2$F, —CHF$_2$, —CF$_3$, —CH$_2$CF$_3$, —OCH$_3$, —OCF$_3$, —OCH$_2$CF$_3$, —(C=O)OH, —(C=O)NH$_2$, —SO$_2$NHCH$_3$, and —SO$_2$NH$_2$.

In a further aspect, Ar is pyridazinyl substituted with 0 to 3 groups independently selected from halo, cyano, hydroxyl, —NH$_2$, C1-C3 alkyl, C1-C3 monoalkyl, C1-C3 polyhaloalkyl, C1-C3 alkoxy, C1-C3 monohaloalkoxy, C1-C3 polyhaloalkyl, C1-C3 alkoxy, C1-C3 monohaloalkoxy, C1-C3 polyhaloalkoxy, —(C=O)OR$^9$, —(C=O)NR$^{10a}$R$^{10b}$, and —SO$_2$NR$^{10a}$R$^{10b}$, —SR$^9$, and —SO$_2$R$^9$. In a still further aspect, Ar is pyridazinyl substituted with 0 to 3 groups independently selected from —F, —Cl, —Br, cyano, hydroxyl, —NH$_2$, methyl, ethyl, propyl, isopropyl, —CH$_2$F, —CHF$_2$, —CF$_3$, —CH$_2$Cl, —CHCl$_2$, —CCl$_3$, —CH$_2$CH$_2$F, —CH$_2$CHF$_2$, —CH$_2$CF$_3$, —CH$_2$CH$_2$Cl, —CH$_2$CHCl$_2$, —CH$_2$CCl$_3$, —OCH$_3$, —OCH$_2$CH$_3$, —OCH$_2$F, —OCHF$_2$, —OCF$_3$, —OCH$_2$Cl, —OCHCl$_2$, —OCCl$_3$, —OCH$_2$CH$_2$F, —OCH$_2$CHF$_2$, —OCH$_2$CF$_3$, —OCH$_2$CH$_2$Cl, —OCH$_2$CHCl$_2$, —(C=O)OCH$_2$CH$_3$, —(C=O)OCH$_2$CH$_3$, —(C=O)OCH$_3$, —(C=O)OH, —(C=O)NHCH$_2$CH$_3$, —(C=O)NHCH$_3$, —(C=O)NH$_2$, —SO$_2$N(CH$_3$)$_2$, —SO$_2$NHCH$_2$CH$_3$, —SO$_2$NHCH$_3$, and —SO$_2$NH$_2$. In yet a further aspect, Ar is pyridazinyl substituted with 0 to 3 groups independently selected from —F, —Cl, —Br, methyl, ethyl, isopropyl, —CH$_2$F, —CHF$_2$, —CF₃, —CH₂CF₃, —OCH₃, —OCF₃, —OCH₂CF₃, —(C═O)OH, —(C═O)NH₂, —SO₂NHCH₃, and —SO₂NH₂.

In a further aspect, Ar is pyridazinyl monosubstituted with a group selected from halo, cyano, hydroxyl, —NH₂, C1-C3 alkyl, C1-C3 monoalkyl, C1-C3 polyhaloalkyl, C1-C3 alkoxy, C1-C3 monohaloalkoxy, C1-C3 polyhaloalkyl, C1-C3 alkoxy, C1-C3 monohaloalkoxy, C1-C3 polyhaloalkoxy, —(C═O)OR⁹, —(C═O)NR¹⁰ᵃR¹⁰ᵇ, and —SO₂NR¹⁰ᵃR¹⁰ᵇ, —SR⁹, and —SO₂R⁹. In a still further aspect, Ar is pyridazinyl monosubstituted with a group selected from —F, —Cl, —Br, cyano, hydroxyl, —NH₂, methyl, ethyl, propyl, isopropyl, —CH₂F, —CHF₂, —CF₃, —CH₂Cl, —CHCl₂, —CCl₃, —CH₂CH₂F, —CH₂CHF₂, —CH₂CF₃, —CH₂CH₂Cl, —CH₂CHCl₂, —CH₂CCl₃, —OCH₃, —OCH₂CH₃, —OCH₂F, —OCHF₂, —OCF₃, —OCH₂Cl, —OCHCl₂, —OCCl₃, —OCH₂CH₂F, —OCH₂CHF₂, —OCH₂CF₃, —OCH₂CH₂Cl, —OCH₂CHCl₂, —(C═O)OCH₂CH₃, —(C═O)OCH₂CH₃, —(C═O)OCH₃, —(C═O)OH, —(C═O)NHCH₂CH₃, —(C═O)NHCH₃, —(C═O)NH₂, —SO₂N(CH₃)₂, —SO₂NHCH₂CH₃, —SO₂NHCH₃, and —SO₂NH₂. In yet a further aspect, Ar is pyridazinyl monosubstituted with a group selected from —F, —Cl, —Br, methyl, ethyl, isopropyl, —CH₂F, —CHF₂, —CF₃, —CH₂CF₃, —OCH₃, —OCF₃, —OCH₂CF₃, —(C═O)OH, —(C═O)NH₂, —SO₂NHCH₃, and —SO₂NH₂.

In a further aspect, Ar is pyridazinyl substituted with 2 groups independently selected from halo, cyano, hydroxyl, —NH₂, C1-C3 alkyl, C1-C3 monoalkyl, C1-C3 polyhaloalkyl, C1-C3 alkoxy, C1-C3 monohaloalkoxy, C1-C3 polyhaloalkyl, C1-C3 alkoxy, C1-C3 monohaloalkoxy, C1-C3 polyhaloalkoxy, —(C═O)OR⁹, —(C═O)NR¹⁰ᵃR¹⁰ᵇ, and —SO₂NR¹⁰ᵃR¹⁰ᵇ, —SR⁹, and —SO₂R⁹. In a still further aspect, Ar is pyridazinyl substituted with 2 groups independently selected from —F, —Cl, —Br, cyano, hydroxyl, —NH₂, methyl, ethyl, propyl, isopropyl, —CH₂F, —CHF₂, —CF₃, —CH₂Cl, —CHCl₂, —CCl₃, —CH₂CH₂F, —CH₂CHF₂, —CH₂CF₃, —CH₂CH₂Cl, —CH₂CHCl₂, —CH₂CCl₃, —OCH₃, —OCH₂CH₃, —OCH₂F, —OCHF₂, —OCF₃, —OCH₂Cl, —OCHCl₂, —OCCl₃, —OCH₂CH₂F, —OCH₂CHF₂, —OCH₂CF₃, —OCH₂CH₂Cl, —OCH₂CHCl₂, —(C═O)OCH₂CH₃, —(C═O)OCH₂CH₃, —(C═O)OCH₃, —(C═O)OH, —(C═O)NHCH₂CH₃, —(C═O)NHCH₃, —(C═O)NH₂, —SO₂N(CH₃)₂, —SO₂NHCH₂CH₃, —SO₂NHCH₃, and —SO₂NH₂. In yet a further aspect, Ar is pyridazinyl substituted with 2 groups independently selected from —F, —Cl, —Br, methyl, ethyl, isopropyl, —CH₂F, —CHF₂, —CF₃, —CH₂CF₃, —OCH₃, —OCF₃, —OCH₂CF₃, —(C═O)OH, —(C═O)NH₂, —SO₂NHCH₃, and —SO₂NH₂.

In a further aspect, Ar is furanyl substituted with 0 to 3 groups independently selected from halo, cyano, hydroxyl, —NH₂, C1-C3 alkyl, C1-C3 monoalkyl, C1-C3 polyhaloalkyl, C1-C3 alkoxy, C1-C3 monohaloalkoxy, C1-C3 polyhaloalkyl, C1-C3 alkoxy, C1-C3 monohaloalkoxy, C1-C3 polyhaloalkoxy, —(C═O)OR⁹, —(C═O)NR¹⁰ᵃR¹⁰ᵇ, and —SO₂NR¹⁰ᵃR¹⁰ᵇ, —SR⁹, and —SO₂R⁹. In a still further aspect, Ar is furanyl substituted with 0 to 3 groups independently selected from —F, —Cl, —Br, cyano, hydroxyl, —NH₂, methyl, ethyl, propyl, isopropyl, —CH₂F, —CHF₂, —CF₃, —CH₂Cl, —CHCl₂, —CCl₃, —CH₂CH₂F, —CH₂CHF₂, —CH₂CF₃, —CH₂CH₂Cl, —CH₂CHCl₂, —CH₂CCl₃, —OCH₃, —OCH₂CH₃, —OCH₂F, —OCHF₂, —OCF₃, —OCH₂Cl, —OCHCl₂, —OCCl₃, —OCH₂CH₂F, —OCH₂CHF₂, —OCH₂CF₃, —OCH₂CH₂Cl, —OCH₂CHCl₂, —(C═O)OCH₂CH₃, —(C═O)OCH₂CH₃, —(C═O)OCH₃, —(C═O)OH, —(C═O)NHCH₂CH₃, —(C═O)NHCH₃, —(C═O)NH₂, —SO₂N(CH₃)₂, —SO₂NHCH₂CH₃, —SO₂NHCH₃, and —SO₂NH₂. In yet a further aspect, Ar is furanyl substituted with 0 to 3 groups independently selected from —F, —Cl, —Br, methyl, ethyl, isopropyl, —CH₂F, —CHF₂, —CF₃, —CH₂CF₃, —OCH₃, —OCF₃, —OCH₂CF₃, —(C═O)OH, —(C═O)NH₂, —SO₂NHCH₃, and —SO₂NH₂.

In a further aspect, Ar is furanyl monosubstituted with a group selected from halo, cyano, hydroxyl, —NH₂, C1-C3 alkyl, C1-C3 monoalkyl, C1-C3 polyhaloalkyl, C1-C3 alkoxy, C1-C3 monohaloalkoxy, C1-C3 polyhaloalkyl, C1-C3 alkoxy, C1-C3 monohaloalkoxy, C1-C3 polyhaloalkoxy, —(C═O)OR⁹, —(C═O)NR¹⁰ᵃR¹⁰ᵇ, and —SO₂NR¹⁰ᵃR¹⁰ᵇ, —SR⁹, and —SO₂R⁹. In a still further aspect, Ar is furanyl monosubstituted with a group selected from —F, —Cl, —Br, cyano, hydroxyl, —NH₂, methyl, ethyl, propyl, isopropyl, —CH₂F, —CHF₂, —CF₃, —CH₂Cl, —CHCl₂, —CCl₃, —CH₂CH₂F, —CH₂CHF₂, —CH₂CF₃, —CH₂CH₂Cl, —CH₂CHCl₂, —CH₂CCl₃, —OCH₃, —OCH₂CH₃, —OCH₂F, —OCHF₂, —OCF₃, —OCH₂Cl, —OCHCl₂, —OCCl₃, —OCH₂CH₂F, —OCH₂CHF₂, —OCH₂CF₃, —OCH₂CH₂Cl, —OCH₂CHCl₂, —(C═O)OCH₂CH₃, —(C═O)OCH₂CH₃, —(C═O)OCH₃, —(C═O)OH, —(C═O)NHCH₂CH₃, —(C═O)NHCH₃, —(C═O)NH₂, —SO₂N(CH₃)₂, —SO₂NHCH₂CH₃, —SO₂NHCH₃, and —SO₂NH₂. In yet a further aspect, Ar is furanyl monosubstituted with a group selected from —F, —Cl, —Br, methyl, ethyl, isopropyl, —CH₂F, —CHF₂, —CF₃, —CH₂CF₃, —OCH₃, —OCF₃, —OCH₂CF₃, —(C═O)OH, —(C═O)NH₂, —SO₂NHCH₃, and —SO₂NH₂.

In a further aspect, Ar is furanyl substituted with 2 groups independently selected from halo, cyano, hydroxyl, —NH₂, C1-C3 alkyl, C1-C3 monoalkyl, C1-C3 polyhaloalkyl, C1-C3 alkoxy, C1-C3 monohaloalkoxy, C1-C3 polyhaloalkyl, C1-C3 alkoxy, C1-C3 monohaloalkoxy, C1-C3 polyhaloalkoxy, —(C═O)OR⁹, —(C═O)NR¹⁰ᵃR¹⁰ᵇ, and —SO₂NR¹⁰ᵃR¹⁰ᵇ, —SR⁹, and —SO₂R⁹. In a still further aspect, Ar is furanyl substituted with 2 groups independently selected from —F, —Cl, —Br, cyano, hydroxyl, —NH₂, methyl, ethyl, propyl, isopropyl, —CH₂F, —CHF₂, —CF₃, —CH₂Cl, —CHCl₂, —CCl₃, —CH₂CH₂F, —CH₂CHF₂, —CH₂CF₃, —CH₂CH₂Cl, —CH₂CHCl₂, —CH₂CCl₃, —OCH₃, —OCH₂CH₃, —OCH₂F, —OCHF₂, —OCF₃, —OCH₂Cl, —OCHCl₂, —OCCl₃, —OCH₂CH₂F, —OCH₂CHF₂, —OCH₂CF₃, —OCH₂CH₂Cl, —OCH₂CHCl₂, —(C═O)OCH₂CH₃, —(C═O)OCH₂CH₃, —(C═O)OCH₃, —(C═O)OH, —(C═O)NHCH₂CH₃, —(C═O)NHCH₃, —(C═O)NH₂, —SO₂N(CH₃)₂, —SO₂NHCH₂CH₃, —SO₂NHCH₃, and —SO₂NH₂. In yet a further aspect, Ar is furanyl substituted with 2 groups independently selected from —F, —Cl, —Br, methyl, ethyl, isopropyl, —CH₂F, —CHF₂, —CF₃, —CH₂CF₃, —OCH₃, —OCF₃, —OCH₂CF₃, —(C═O)OH, —(C═O)NH₂, —SO₂NHCH₃, and —SO₂NH₂.

In a further aspect, Ar is thiophenyl substituted with 0 to 3 groups independently selected from halo, cyano, hydroxyl, —NH₂, C1-C3 alkyl, C1-C3 monoalkyl, C1-C3 polyhaloalkyl, C1-C3 alkoxy, C1-C3 monohaloalkoxy, C1-C3 polyhaloalkyl, C1-C3 alkoxy, C1-C3 monohaloalkoxy, C1-C3 polyhaloalkoxy, —(C═O)OR⁹, —(C═O)NR¹⁰ᵃR¹⁰ᵇ, and —SO₂NR¹⁰ᵃR¹⁰ᵇ, —SR⁹, and —SO₂R⁹. In a still further aspect, Ar is thiophenyl substituted with 0 to 3 groups independently selected from —F, —Cl, —Br, cyano, hydroxyl, —NH₂, methyl, ethyl, propyl, isopropyl, —CH₂F, —CHF₂, —CF₃, —CH₂Cl, —CHCl₂, —CCl₃, —CH₂CH₂F, —CH₂CHF₂, —CH₂CF₃, —CH₂CH₂Cl, —CH₂CHCl₂, —CH₂CCl₃, —OCH₃, —OCH₂CH₃, —OCH₂F, —OCHF₂, —OCF₃, —OCH₂Cl, —OCHCl₂, —OCCl₃, —OCH₂CH₂F, —OCH₂CHF₂, —OCH₂CF₃, —OCH₂CH₂Cl, —OCH₂CHCl₂, —(C=O)OCH₂CH₃, —(C=O)OCH₂CH₃, —(C=O)OCH₃, —(C=O)OH, —(C=O)NHCH₂CH₃, —(C=O)NHCH₃, —(C=O)NH₂, —SO₂N(CH₃)₂, —SO₂NHCH₂CH₃, —SO₂NHCH₃, and —SO₂NH₂. In yet a further aspect, Ar is thiophenyl substituted with 0 to 3 groups independently selected from —F, —Cl, —Br, methyl, ethyl, isopropyl, —CH₂F, —CHF₂, —CF₃, —CH₂CF₃, —OCH₃, —OCF₃, —OCH₂CF₃, —(C=O)OH, —(C=O)NH₂, —SO₂NHCH₃, and —SO₂NH₂.

In a further aspect, Ar is thiophenyl monosubstituted with a group selected from halo, cyano, hydroxyl, —NH₂, C1-C3 alkyl, C1-C3 monoalkyl, C1-C3 polyhaloalkyl, C1-C3 alkoxy, C1-C3 monohaloalkoxy, C1-C3 polyhaloalkyl, C1-C3 alkoxy, C1-C3 monohaloalkoxy, C1-C3 polyhaloalkoxy, —(C=O)OR⁹, —(C=O)NR¹⁰ᵃR¹⁰ᵇ, and —SO₂NR¹⁰ᵃR¹⁰ᵇ, —SR⁹, and —SO₂R⁹. In a still further aspect, Ar is thiophenyl monosubstituted with a group selected from —F, —Cl, —Br, cyano, hydroxyl, —NH₂, methyl, ethyl, propyl, isopropyl, —CH₂F, —CHF₂, —CF₃, —CH₂Cl, —CHCl₂, —CCl₃, —CH₂CH₂F, —CH₂CHF₂, —CH₂CF₃, —CH₂CH₂Cl, —CH₂CHCl₂, —CH₂CCl₃, —OCH₃, —OCH₂CH₃, —OCH₂F, —OCHF₂, —OCF₃, —OCH₂Cl, —OCHCl₂, —OCCl₃, —OCH₂CH₂F, —OCH₂CHF₂, —OCH₂CF₃, —OCH₂CH₂Cl, —OCH₂CHCl₂, —(C=O)OCH₂CH₃, —(C=O)OCH₂CH₃, —(C=O)OCH₃, —(C=O)OH, —(C=O)NHCH₂CH₃, —(C=O)NHCH₃, —(C=O)NH₂, —SO₂N(CH₃)₂, —SO₂NHCH₂CH₃, —SO₂NHCH₃, and —SO₂NH₂. In yet a further aspect, Ar is thiophenyl monosubstituted with a group selected from —F, —Cl, —Br, methyl, ethyl, isopropyl, —CH₂F, —CHF₂, —CF₃, —CH₂CF₃, —OCH₃, —OCF₃, —OCH₂CF₃, —(C=O)OH, —(C=O)NH₂, —SO₂NHCH₃, and —SO₂NH₂.

In a further aspect, Ar is thiophenyl substituted with 2 groups independently selected from halo, cyano, hydroxyl, —NH₂, C1-C3 alkyl, C1-C3 monoalkyl, C1-C3 polyhaloalkyl, C1-C3 alkoxy, C1-C3 monohaloalkoxy, C1-C3 polyhaloalkyl, C1-C3 alkoxy, C1-C3 monohaloalkoxy, C1-C3 polyhaloalkoxy, —(C=O)OR⁹, —(C=O)NR¹⁰ᵃR¹⁰ᵇ, and —SO₂NR¹⁰ᵃR¹⁰ᵇ, —SR⁹, and —SO₂R⁹. In a still further aspect, Ar is thiophenyl substituted with 2 groups independently selected from —F, —Cl, —Br, cyano, hydroxyl, —NH₂, methyl, ethyl, propyl, isopropyl, —CH₂F, —CHF₂, —CF₃, —CH₂Cl, —CHCl₂, —CCl₃, —CH₂CH₂F, —CH₂CHF₂, —CH₂CF₃, —CH₂CH₂Cl, —CH₂CHCl₂, —CH₂CCl₃, —OCH₃, —OCH₂CH₃, —OCH₂F, —OCHF₂, —OCF₃, —OCH₂Cl, —OCHCl₂, —OCCl₃, —OCH₂CH₂F, —OCH₂CHF₂, —OCH₂CF₃, —OCH₂CH₂Cl, —OCH₂CHCl₂, —(C=O)OCH₂CH₃, —(C=O)OCH₂CH₃, —(C=O)OCH₃, —(C=O)OH, —(C=O)NHCH₂CH₃, —(C=O)NHCH₃, —(C=O)NH₂, —SO₂N(CH₃)₂, —SO₂NHCH₂CH₃, —SO₂NHCH₃, and —SO₂NH₂. In yet a further aspect, Ar is thiophenyl substituted with 2 groups independently selected from —F, —Cl, —Br, methyl, ethyl, isopropyl, —CH₂F, —CHF₂, —CF₃, —CH₂CF₃, —OCH₃, —OCF₃, —OCH₂CF₃, —(C=O)OH, —(C=O)NH₂, —SO₂NHCH₃, and —SO₂NH₂.

In a further aspect, Ar is oxazolyl substituted with 0 to 3 groups independently selected from halo, cyano, hydroxyl, —NH₂, C1-C3 alkyl, C1-C3 monoalkyl, C1-C3 polyhaloalkyl, C1-C3 alkoxy, C1-C3 monohaloalkoxy, C1-C3 polyhaloalkyl, C1-C3 alkoxy, C1-C3 monohaloalkoxy, C1-C3 polyhaloalkoxy, —(C=O)OR⁹, —(C=O)NR¹⁰ᵃR¹⁰ᵇ, and —SO₂NR¹⁰ᵃR¹⁰ᵇ, —SR⁹, and —SO₂R⁹. In a still further aspect, Ar is oxazolyl substituted with 0 to 3 groups independently selected from —F, —Cl, —Br, cyano, hydroxyl, —NH₂, methyl, ethyl, propyl, isopropyl, —CH₂F, —CHF₂, —CF₃, —CH₂Cl, —CHCl₂, —CCl₃, —CH₂CH₂F, —CH₂CHF₂, —CH₂CF₃, —CH₂CH₂Cl, —CH₂CHCl₂, —CH₂CCl₃, —OCH₃, —OCH₂CH₃, —OCH₂F, —OCHF₂, —OCF₃, —OCH₂Cl, —OCHCl₂, —OCCl₃, —OCH₂CH₂F, —OCH₂CHF₂, —OCH₂CF₃, —OCH₂CH₂Cl, —OCH₂CHCl₂, —(C=O)OCH₂CH₃, —(C=O)OCH₂CH₃, —(C=O)OCH₃, —(C=O)OH, —(C=O)NHCH₂CH₃, —(C=O)NHCH₃, —(C=O)NH₂, —SO₂N(CH₃)₂, —SO₂NHCH₂CH₃, —SO₂NHCH₃, and —SO₂NH₂. In yet a further aspect, Ar is oxazolyl substituted with 0 to 3 groups independently selected from —F, —Cl, —Br, methyl, ethyl, isopropyl, —CH₂F, —CHF₂, —CF₃, —CH₂CF₃, —OCH₃, —OCF₃, —OCH₂CF₃, —(C=O)OH, —(C=O)NH₂, —SO₂NHCH₃, and —SO₂NH₂.

In a further aspect, Ar is oxazolyl monosubstituted with a group selected from halo, cyano, hydroxyl, —NH₂, C1-C3 alkyl, C1-C3 monoalkyl, C1-C3 polyhaloalkyl, C1-C3 alkoxy, C1-C3 monohaloalkoxy, C1-C3 polyhaloalkyl, C1-C3 alkoxy, C1-C3 monohaloalkoxy, C1-C3 polyhaloalkoxy, —(C=O)OR⁹, —(C=O)NR¹⁰ᵃR¹⁰ᵇ, and —SO₂NR¹⁰ᵃR¹⁰ᵇ, —SR⁹, and —SO₂R⁹. In a still further aspect, Ar is oxazolyl monosubstituted with a group selected from —F, —Cl, —Br, cyano, hydroxyl, —NH₂, methyl, ethyl, propyl, isopropyl, —CH₂F, —CHF₂, —CF₃, —CH₂Cl, —CHCl₂, —CCl₃, —CH₂CH₂F, —CH₂CHF₂, —CH₂CF₃, —CH₂CH₂Cl, —CH₂CHCl₂, —CH₂CCl₃, —OCH₃, —OCH₂CH₃, —OCH₂F, —OCHF₂, —OCF₃, —OCH₂Cl, —OCHCl₂, —OCCl₃, —OCH₂CH₂F, —OCH₂CHF₂, —OCH₂CF₃, —OCH₂CH₂Cl, —OCH₂CHCl₂, —(C=O)OCH₂CH₃, —(C=O)OCH₂CH₃, —(C=O)OCH₃, —(C=O)OH, —(C=O)NHCH₂CH₃, —(C=O)NHCH₃, —(C=O)NH₂, —SO₂N(CH₃)₂, —SO₂NHCH₂CH₃, —SO₂NHCH₃, and —SO₂NH₂. In yet a further aspect, Ar is oxazolyl monosubstituted with a group selected from —F, —Cl, —Br, methyl, ethyl, isopropyl, —CH₂F, —CHF₂, —CF₃, —CH₂CF₃, —OCH₃, —OCF₃, —OCH₂CF₃, —(C=O)OH, —(C=O)NH₂, —SO₂NHCH₃, and —SO₂NH₂.

In a further aspect, Ar is oxazolyl substituted with 2 groups independently selected from halo, cyano, hydroxyl, —NH₂, C1-C3 alkyl, C1-C3 monoalkyl, C1-C3 polyhaloalkyl, C1-C3 alkoxy, C1-C3 monohaloalkoxy, C1-C3 polyhaloalkyl, C1-C3 alkoxy, C1-C3 monohaloalkoxy, C1-C3 polyhaloalkoxy, —(C=O)OR⁹, —(C=O)NR¹⁰ᵃR¹⁰ᵇ, and —SO₂NR¹⁰ᵃR¹⁰ᵇ, —SR⁹, and —SO₂R⁹. In a still further aspect, Ar is oxazolyl substituted with 2 groups independently selected from —F, —Cl, —Br, cyano, hydroxyl, —NH₂, methyl, ethyl, propyl, isopropyl, —CH₂F, —CHF₂, —CF₃, —CH₂Cl, —CHCl₂, —CCl₃, —CH₂CH₂F, —CH₂CHF₂, —CH₂CF₃, —CH₂CH₂Cl, —CH₂CHCl₂, —CH₂CCl₃, —OCH₃, —OCH₂CH₃, —OCH₂F, —OCHF₂, —OCF₃, —OCH₂Cl, —OCHCl₂, —OCCl₃, —OCH₂CH₂F, —OCH₂CHF₂, —OCH₂CF₃, —OCH₂CH₂Cl, —OCH₂CHCl₂, —(C=O)OCH₂CH₃, —(C=O)OCH₂CH₃, —(C=O)OCH₃, —(C=O)OH, —(C=O)NHCH₂CH₃, —(C=O)NHCH₃, —(C=O)NH₂, —SO₂N(CH₃)₂, —SO₂NHCH₂CH₃, —SO₂NHCH₃, and —SO₂NH₂. In yet a further aspect, Ar is oxazolyl substituted with 2 groups independently selected from —F, —Cl, —Br, methyl, ethyl, isopropyl, —CH₂F, —CHF₂, —CF₃, —CH$_2$CF$_3$, —OCH$_3$, —OCF$_3$, —OCH$_2$CF$_3$, —(C=O)OH, —(C=O)NH$_2$, —SO$_2$NHCH$_3$, and —SO$_2$NH$_2$.

In a further aspect, Ar is thiazolyl substituted with 0 to 3 groups independently selected from halo, cyano, hydroxyl, —NH$_2$, C1-C3 alkyl, C1-C3 monoalkyl, C1-C3 polyhaloalkyl, C1-C3 alkoxy, C1-C3 monohaloalkoxy, C1-C3 polyhaloalkyl, C1-C3 alkoxy, C1-C3 monohaloalkoxy, C1-C3 polyhaloalkoxy, —(C=O)OR$^9$, —(C=O)NR$^{10a}$R$^{10b}$, and —SO$_2$NR$^{10a}$R$^{10b}$, —SR$^9$, and —SO$_2$R$^9$. In a still further aspect, Ar is thiazolyl substituted with 0 to 3 groups independently selected from —F, —Cl, —Br, cyano, hydroxyl, —NH$_2$, methyl, ethyl, propyl, isopropyl, —CH$_2$F, —CHF$_2$, —CF$_3$, —CH$_2$Cl, —CHCl$_2$, —CCl$_3$, —CH$_2$CH$_2$F, —CH$_2$CHF$_2$, —CH$_2$CF$_3$, —CH$_2$CH$_2$Cl, —CH$_2$CHCl$_2$, —CH$_2$CCl$_3$, —OCH$_3$, —OCH$_2$CH$_3$, —OCH$_2$F, —OCHF$_2$, —OCF$_3$, —OCH$_2$Cl, —OCHCl$_2$, —OCCl$_3$, —OCH$_2$CH$_2$F, —OCH$_2$CHF$_2$, —OCH$_2$CF$_3$, —OCH$_2$CH$_2$Cl, —OCH$_2$CHCl$_2$, —(C=O)OCH$_2$CH$_3$, —(C=O)OCH$_2$CH$_3$, —(C=O)OCH$_3$, —(C=O)OH, —(C=O)NHCH$_2$CH$_3$, —(C=O)NHCH$_3$, —(C=O)NH$_2$, —SO$_2$N(CH$_3$)$_2$, —SO$_2$NHCH$_2$CH$_3$, —SO$_2$NHCH$_3$, and —SO$_2$NH$_2$. In yet a further aspect, Ar is thiazolyl substituted with 0 to 3 groups independently selected from —F, —Cl, —Br, methyl, ethyl, isopropyl, —CH$_2$F, —CHF$_2$, —CF$_3$, —CH$_2$CF$_3$, —OCH$_3$, —OCF$_3$, —OCH$_2$CF$_3$, —(C=O)OH, —(C=O)NH$_2$, —SO$_2$NHCH$_3$, and —SO$_2$NH$_2$.

In a further aspect, Ar is thiazolyl monosubstituted with a group selected from halo, cyano, hydroxyl, —NH$_2$, C1-C3 alkyl, C1-C3 monoalkyl, C1-C3 polyhaloalkyl, C1-C3 alkoxy, C1-C3 monohaloalkoxy, C1-C3 polyhaloalkyl, C1-C3 alkoxy, C1-C3 monohaloalkoxy, C1-C3 polyhaloalkoxy, —(C=O)OR$^9$, —(C=O)NR$^{10a}$R$^{10b}$, and —SO$_2$NR$^{10a}$R$^{10b}$, —SR$^9$, and —SO$_2$R$^9$. In a still further aspect, Ar is thiazolyl monosubstituted with a group selected from —F, —Cl, —Br, cyano, hydroxyl, —NH$_2$, methyl, ethyl, propyl, isopropyl, —CH$_2$F, —CHF$_2$, —CF$_3$, —CH$_2$Cl, —CHCl$_2$, —CCl$_3$, —CH$_2$CH$_2$F, —CH$_2$CHF$_2$, —CH$_2$CF$_3$, —CH$_2$CH$_2$Cl, —CH$_2$CHCl$_2$, —CH$_2$CCl$_3$, —OCH$_3$, —OCH$_2$CH$_3$, —OCH$_2$F, —OCHF$_2$, —OCF$_3$, —OCH$_2$Cl, —OCHCl$_2$, —OCCl$_3$, —OCH$_2$CH$_2$F, —OCH$_2$CHF$_2$, —OCH$_2$CF$_3$, —OCH$_2$CH$_2$Cl, —OCH$_2$CHCl$_2$, —(C=O)OCH$_2$CH$_3$, —(C=O)OCH$_2$CH$_3$, —(C=O)OCH$_3$, —(C=O)OH, —(C=O)NHCH$_2$CH$_3$, —(C=O)NHCH$_3$, —(C=O)NH$_2$, —SO$_2$N(CH$_3$)$_2$, —SO$_2$NHCH$_2$CH$_3$, —SO$_2$NHCH$_3$, and —SO$_2$NH$_2$. In yet a further aspect, Ar is thiazolyl monosubstituted with a group selected from —F, —Cl, —Br, methyl, ethyl, isopropyl, —CH$_2$F, —CHF$_2$, —CF$_3$, —CH$_2$CF$_3$, —OCH$_3$, —OCF$_3$, —OCH$_2$CF$_3$, —(C=O)OH, —(C=O)NH$_2$, —SO$_2$NHCH$_3$, and —SO$_2$NH$_2$.

In a further aspect, Ar is thiazolyl substituted with 2 groups independently selected from halo, cyano, hydroxyl, —NH$_2$, C1-C3 alkyl, C1-C3 monoalkyl, C1-C3 polyhaloalkyl, C1-C3 alkoxy, C1-C3 monohaloalkoxy, C1-C3 polyhaloalkyl, C1-C3 alkoxy, C1-C3 monohaloalkoxy, C1-C3 polyhaloalkoxy, —(C=O)OR$^9$, —(C=O)NR$^{10a}$R$^{10b}$, and —SO$_2$NR$^{10a}$R$^{10b}$, —SR$^9$, and —SO$_2$R$^9$. In a still further aspect, Ar is thiazolyl substituted with 2 groups independently selected from —F, —Cl, —Br, cyano, hydroxyl, —NH$_2$, methyl, ethyl, propyl, isopropyl, —CH$_2$F, —CHF$_2$, —CF$_3$, —CH$_2$Cl, —CHCl$_2$, —CCl$_3$, —CH$_2$CH$_2$F, —CH$_2$CHF$_2$, —CH$_2$CF$_3$, —CH$_2$CH$_2$Cl, —CH$_2$CHCl$_2$, —CH$_2$CCl$_3$, —OCH$_3$, —OCH$_2$CH$_3$, —OCH$_2$F, —OCHF$_2$, —OCF$_3$, —OCH$_2$Cl, —OCHCl$_2$, —OCCl$_3$, —OCH$_2$CH$_2$F, —OCH$_2$CHF$_2$, —OCH$_2$CF$_3$, —OCH$_2$CH$_2$Cl, —OCH$_2$CHCl$_2$, —(C=O)OCH$_2$CH$_3$, —(C=O)OCH$_2$CH$_3$, —(C=O)OCH$_3$, —(C=O)OH, —(C=O)NHCH$_2$CH$_3$, —(C=O)NHCH$_3$, —(C=O)NH$_2$, —SO$_2$N(CH$_3$)$_2$, —SO$_2$NHCH$_2$CH$_3$, —SO$_2$NHCH$_3$, and —SO$_2$NH$_2$. In yet a further aspect, Ar is thiazolyl substituted with 2 groups independently selected from —F, —Cl, —Br, methyl, ethyl, isopropyl, —CH$_2$F, —CHF$_2$, —CF$_3$, —CH$_2$CF$_3$, —OCH$_3$, —OCF$_3$, —OCH$_2$CF$_3$, —(C=O)OH, —(C=O)NH$_2$, —SO$_2$NHCH$_3$, and —SO$_2$NH$_2$.

In a further aspect, Ar is imidazolyl substituted with 0 to 3 groups independently selected from halo, cyano, hydroxyl, —NH$_2$, C1-C3 alkyl, C1-C3 monoalkyl, C1-C3 polyhaloalkyl, C1-C3 alkoxy, C1-C3 monohaloalkoxy, C1-C3 polyhaloalkyl, C1-C3 alkoxy, C1-C3 monohaloalkoxy, C1-C3 polyhaloalkoxy, —(C=O)OR$^9$, —(C=O)NR$^{10a}$R$^{10b}$, and —SO$_2$NR$^{10a}$R$^{10b}$, —SR$^9$, and —SO$_2$R$^9$. In a still further aspect, Ar is imidazolyl substituted with 0 to 3 groups independently selected from —F, —Cl, —Br, cyano, hydroxyl, —NH$_2$, methyl, ethyl, propyl, isopropyl, —CH$_2$F, —CHF$_2$, —CF$_3$, —CH$_2$Cl, —CHCl$_2$, —CCl$_3$, —CH$_2$CH$_2$F, —CH$_2$CHF$_2$, —CH$_2$CF$_3$, —CH$_2$CH$_2$Cl, —CH$_2$CHCl$_2$, —CH$_2$CCl$_3$, —OCH$_3$, —OCH$_2$CH$_3$, —OCH$_2$F, —OCHF$_2$, —OCF$_3$, —OCH$_2$Cl, —OCHCl$_2$, —OCCl$_3$, —OCH$_2$CH$_2$F, —OCH$_2$CHF$_2$, —OCH$_2$CF$_3$, —OCH$_2$CH$_2$Cl, —OCH$_2$CHCl$_2$, —(C=O)OCH$_2$CH$_3$, —(C=O)OCH$_2$CH$_3$, —(C=O)OCH$_3$, —(C=O)OH, —(C=O)NHCH$_2$CH$_3$, —(C=O)NHCH$_3$, —(C=O)NH$_2$, —SO$_2$N(CH$_3$)$_2$, —SO$_2$NHCH$_2$CH$_3$, —SO$_2$NHCH$_3$, and —SO$_2$NH$_2$. In yet a further aspect, Ar is imidazolyl substituted with 0 to 3 groups independently selected from —F, —Cl, —Br, methyl, ethyl, isopropyl, —CH$_2$F, —CHF$_2$, —CF$_3$, —CH$_2$CF$_3$, —OCH$_3$, —OCF$_3$, —OCH$_2$CF$_3$, —(C=O)OH, —(C=O)NH$_2$, —SO$_2$NHCH$_3$, and —SO$_2$NH$_2$.

In a further aspect, Ar is imidazolyl monosubstituted with a group selected from halo, cyano, hydroxyl, —NH$_2$, C1-C3 alkyl, C1-C3 monoalkyl, C1-C3 polyhaloalkyl, C1-C3 alkoxy, C1-C3 monohaloalkoxy, C1-C3 polyhaloalkyl, C1-C3 alkoxy, C1-C3 monohaloalkoxy, C1-C3 polyhaloalkoxy, —(C=O)OR$^9$, —(C=O)NR$^{10a}$R$^{10b}$, and —SO$_2$NR$^{10a}$R$^{10b}$, —SR$^9$, and —SO$_2$R$^9$. In a still further aspect, Ar is imidazolyl monosubstituted with a group selected from —F, —Cl, —Br, cyano, hydroxyl, —NH$_2$, methyl, ethyl, propyl, isopropyl, —CH$_2$F, —CHF$_2$, —CF$_3$, —CH$_2$Cl, —CHCl$_2$, —CCl$_3$, —CH$_2$CH$_2$F, —CH$_2$CHF$_2$, —CH$_2$CF$_3$, —CH$_2$CH$_2$Cl, —CH$_2$CHCl$_2$, —CH$_2$CCl$_3$, —OCH$_3$, —OCH$_2$CH$_3$, —OCH$_2$F, —OCHF$_2$, —OCF$_3$, —OCH$_2$Cl, —OCHCl$_2$, —OCCl$_3$, —OCH$_2$CH$_2$F, —OCH$_2$CHF$_2$, —OCH$_2$CF$_3$, —OCH$_2$CH$_2$Cl, —OCH$_2$CHCl$_2$, —(C=O)OCH$_2$CH$_3$, —(C=O)OCH$_2$CH$_3$, —(C=O)OCH$_3$, —(C=O)OH, —(C=O)NHCH$_2$CH$_3$, —(C=O)NHCH$_3$, —(C=O)NH$_2$, —SO$_2$N(CH$_3$)$_2$, —SO$_2$NHCH$_2$CH$_3$, —SO$_2$NHCH$_3$, and —SO$_2$NH$_2$. In yet a further aspect, Ar is imidazolyl monosubstituted with a group selected from —F, —Cl, —Br, methyl, ethyl, isopropyl, —CH$_2$F, —CHF$_2$, —CF$_3$, —CH$_2$CF$_3$, —OCH$_3$, —OCF$_3$, —OCH$_2$CF$_3$, —(C=O)OH, —(C=O)NH$_2$, —SO$_2$NHCH$_3$, and —SO$_2$NH$_2$.

In a further aspect, Ar is imidazolyl substituted with 2 groups independently selected from halo, cyano, hydroxyl, —NH$_2$, C1-C3 alkyl, C1-C3 monoalkyl, C1-C3 polyhaloalkyl, C1-C3 alkoxy, C1-C3 monohaloalkoxy, C1-C3 polyhaloalkyl, C1-C3 alkoxy, C1-C3 monohaloalkoxy, C1-C3 polyhaloalkoxy, —(C=O)OR$^9$, —(C=O)NR$^{10a}$R$^{10b}$, and —SO$_2$NR$^{10a}$R$^{10b}$, —SR$^9$, and —SO$_2$R$^9$. In a still further aspect, Ar is imidazolyl substituted with 2 groups independently selected from —F, —Cl, —Br, cyano, hydroxyl, —NH$_2$, methyl, ethyl, propyl, isopropyl, —CH$_2$F, —CHF$_2$, —CF$_3$, —CH$_2$Cl, —CHCl$_2$, —CCl$_3$, —CH$_2$CH$_2$F, —CH$_2$CHF$_2$, —CH$_2$CF$_3$, —CH$_2$CH$_2$Cl, —CH$_2$CHCl$_2$, —CH$_2$CCl$_3$, —OCH$_3$, —OCH$_2$CH$_3$, —OCH$_2$F, —OCHF$_2$, —OCF$_3$, —OCH$_2$Cl, —OCHCl$_2$, —OCCl$_3$, —OCH$_2$CH$_2$F, —OCH$_2$CHF$_2$, —OCH$_2$CF$_3$, —OCH$_2$CH$_2$Cl, —OCH$_2$CHCl$_2$, —(C=O)OCH$_2$CH$_3$, —(C=O)OCH$_2$CH$_3$, —(C=O)OCH$_3$, —(C=O)OH, —(C=O)NHCH$_2$CH$_3$, —(C=O)NHCH$_3$, —(C=O)NH$_2$, —SO$_2$N(CH$_3$)$_2$, —SO$_2$NHCH$_2$CH$_3$, —SO$_2$NHCH$_3$, and —SO$_2$NH$_2$. In yet a further aspect, Ar is imidazolyl substituted with 2 groups independently selected from —F, —Cl, —Br, methyl, ethyl, isopropyl, —CH$_2$F, —CHF$_2$, —CF$_3$, —CH$_2$CF$_3$, —OCH$_3$, —OCF$_3$, —OCH$_2$CF$_3$, —(C=O)OH, —(C=O)NH$_2$, —SO$_2$NHCH$_3$, and —SO$_2$NH$_2$.

In a further aspect, Ar is pyrrolyl substituted with 0 to 3 groups independently selected from halo, cyano, hydroxyl, —NH$_2$, C1-C3 alkyl, C1-C3 monoalkyl, C1-C3 polyhaloalkyl, C1-C3 alkoxy, C1-C3 monohaloalkoxy, C1-C3 polyhaloalkyl, C1-C3 alkoxy, C1-C3 monohaloalkoxy, C1-C3 polyhaloalkoxy, —(C=O)OR$^9$, —(C=O)NR$^{10a}$R$^{10b}$, and —SO$_2$NR$^{10a}$R$^{10b}$, —SR$^9$, and —SO$_2$R$^9$. In a still further aspect, Ar is pyrrolyl substituted with 0 to 3 groups independently selected from —F, —Cl, —Br, cyano, hydroxyl, —NH$_2$, methyl, ethyl, propyl, isopropyl, —CH$_2$F, —CHF$_2$, —CF$_3$, —CH$_2$Cl, —CHCl$_2$, —CCl$_3$, —CH$_2$CH$_2$F, —CH$_2$CHF$_2$, —CH$_2$CF$_3$, —CH$_2$CH$_2$Cl, —CH$_2$CHCl$_2$, —CH$_2$CCl$_3$, —OCH$_3$, —OCH$_2$CH$_3$, —OCH$_2$F, —OCHF$_2$, —OCF$_3$, —OCH$_2$Cl, —OCHCl$_2$, —OCCl$_3$, —OCH$_2$CH$_2$F, —OCH$_2$CHF$_2$, —OCH$_2$CF$_3$, —OCH$_2$CH$_2$Cl, —OCH$_2$CHCl$_2$, —(C=O)OCH$_2$CH$_3$, —(C=O)OCH$_2$CH$_3$, —(C=O)OCH$_3$, —(C=O)OH, —(C=O)NHCH$_2$CH$_3$, —(C=O)NHCH$_3$, —(C=O)NH$_2$, —SO$_2$N(CH$_3$)$_2$, —SO$_2$NHCH$_2$CH$_3$, —SO$_2$NHCH$_3$, and —SO$_2$NH$_2$. In yet a further aspect, Ar is pyrrolyl substituted with 0 to 3 groups independently selected from —F, —Cl, —Br, methyl, ethyl, isopropyl, —CH$_2$F, —CHF$_2$, —CF$_3$, —CH$_2$CF$_3$, —OCH$_3$, —OCF$_3$, —OCH$_2$CF$_3$, —(C=O)OH, —(C=O)NH$_2$, —SO$_2$NHCH$_3$, and —SO$_2$NH$_2$.

In a further aspect, Ar is pyrrolyl monosubstituted with a group selected from halo, cyano, hydroxyl, —NH$_2$, C1-C3 alkyl, C1-C3 monoalkyl, C1-C3 polyhaloalkyl, C1-C3 alkoxy, C1-C3 monohaloalkoxy, C1-C3 polyhaloalkyl, C1-C3 alkoxy, C1-C3 monohaloalkoxy, C1-C3 polyhaloalkoxy, —(C=O)OR$^9$, —(C=O)NR$^{10a}$R$^{10b}$, and —SO$_2$NR$^{10a}$R$^{10b}$, —SR$^9$, and —SO$_2$R$^9$. In a still further aspect, Ar is pyrrolyl monosubstituted with a group selected from —F, —Cl, —Br, cyano, hydroxyl, —NH$_2$, methyl, ethyl, propyl, isopropyl, —CH$_2$F, —CHF$_2$, —CF$_3$, —CH$_2$Cl, —CHCl$_2$, —CCl$_3$, —CH$_2$CH$_2$F, —CH$_2$CHF$_2$, —CH$_2$CF$_3$, —CH$_2$CH$_2$Cl, —CH$_2$CHCl$_2$, —CH$_2$CCl$_3$, —OCH$_3$, —OCH$_2$CH$_3$, —OCH$_2$F, —OCHF$_2$, —OCF$_3$, —OCH$_2$Cl, —OCHCl$_2$, —OCCl$_3$, —OCH$_2$CH$_2$F, —OCH$_2$CHF$_2$, —OCH$_2$CF$_3$, —OCH$_2$CH$_2$Cl, —OCH$_2$CHCl$_2$, —(C=O)OCH$_2$CH$_3$, —(C=O)OCH$_2$CH$_3$, —(C=O)OCH$_3$, —(C=O)OH, —(C=O)NHCH$_2$CH$_3$, —(C=O)NHCH$_3$, —(C=O)NH$_2$, —SO$_2$N(CH$_3$)$_2$, —SO$_2$NHCH$_2$CH$_3$, —SO$_2$NHCH$_3$, and —SO$_2$NH$_2$. In yet a further aspect, Ar is pyrrolyl monosubstituted with a group selected from —F, —Cl, —Br, methyl, ethyl, isopropyl, —CH$_2$F, —CHF$_2$, —CF$_3$, —CH$_2$CF$_3$, —OCH$_3$, —OCF$_3$, —OCH$_2$CF$_3$, —(C=O)OH, —(C=O)NH$_2$, —SO$_2$NHCH$_3$, and —SO$_2$NH$_2$.

In a further aspect, Ar is pyrrolyl substituted with 2 groups independently selected from halo, cyano, hydroxyl, —NH$_2$, C1-C3 alkyl, C1-C3 monoalkyl, C1-C3 polyhaloalkyl, C1-C3 alkoxy, C1-C3 monohaloalkoxy, C1-C3 polyhaloalkyl, C1-C3 alkoxy, C1-C3 monohaloalkoxy, C1-C3 polyhaloalkoxy, —(C=O)OR$^9$, —(C=O)NR$^{10a}$R$^{10b}$, and —SO$_2$NR$^{10a}$R$^{10b}$, —SR$^9$, and —SO$_2$R$^9$. In a still further aspect, Ar is pyrrolyl substituted with 2 groups independently selected from —F, —Cl, —Br, cyano, hydroxyl, —NH$_2$, methyl, ethyl, propyl, isopropyl, —CH$_2$F, —CHF$_2$, —CF$_3$, —CH$_2$Cl, —CHCl$_2$, —CCl$_3$, —CH$_2$CH$_2$F, —CH$_2$CHF$_2$, —CH$_2$CF$_3$, —CH$_2$CH$_2$Cl, —CH$_2$CHCl$_2$, —CH$_2$CCl$_3$, —OCH$_3$, —OCH$_2$CH$_3$, —OCH$_2$F, —OCHF$_2$, —OCF$_3$, —OCH$_2$Cl, —OCHCl$_2$, —OCCl$_3$, —OCH$_2$CH$_2$F, —OCH$_2$CHF$_2$, —OCH$_2$CF$_3$, —OCH$_2$CH$_2$Cl, —OCH$_2$CHCl$_2$, —(C=O)OCH$_2$CH$_3$, —(C=O)OCH$_2$CH$_3$, —(C=O)OCH$_3$, —(C=O)OH, —(C=O)NHCH$_2$CH$_3$, —(C=O)NHCH$_3$, —(C=O)NH$_2$, —SO$_2$N(CH$_3$)$_2$, —SO$_2$NHCH$_2$CH$_3$, —SO$_2$NHCH$_3$, and —SO$_2$NH$_2$. In yet a further aspect, Ar is pyrrolyl substituted with 2 groups independently selected from —F, —Cl, —Br, methyl, ethyl, isopropyl, —CH$_2$F, —CHF$_2$, —CF$_3$, —CH$_2$CF$_3$, —OCH$_3$, —OCF$_3$, —OCH$_2$CF$_3$, —(C=O)OH, —(C=O)NH$_2$, —SO$_2$NHCH$_3$, and —SO$_2$NH$_2$.

In a further aspect, Ar is benzo[d]thiazolyl substituted with 0 to 3 groups independently selected from halo, cyano, hydroxyl, —NH$_2$, C1-C3 alkyl, C1-C3 monoalkyl, C1-C3 polyhaloalkyl, C1-C3 alkoxy, C1-C3 monohaloalkoxy, C1-C3 polyhaloalkyl, C1-C3 alkoxy, C1-C3 monohaloalkoxy, C1-C3 polyhaloalkoxy, —(C=O)OR$^9$, —(C=O)NR$^{10a}$R$^{10b}$ and —SO$_2$NR$^{10a}$R$^{10b}$, —SR$^9$, and —SO$_2$R$^9$. In a still further aspect, Ar is benzo[d]thiazolyl substituted with 0 to 3 groups independently selected from —F, —Cl, —Br, cyano, hydroxyl, —NH$_2$, methyl, ethyl, propyl, isopropyl, —CH$_2$F, —CHF$_2$, —CF$_3$, —CH$_2$Cl, —CHCl$_2$, —CCl$_3$, —CH$_2$CH$_2$F, —CH$_2$CHF$_2$, —CH$_2$CF$_3$, —CH$_2$CH$_2$Cl, —CH$_2$CHCl$_2$, —CH$_2$CCl$_3$, —OCH$_3$, —OCH$_2$CH$_3$, —OCH$_2$F, —OCHF$_2$, —OCF$_3$, —OCH$_2$Cl, —OCHCl$_2$, —OCCl$_3$, —OCH$_2$CH$_2$F, —OCH$_2$CHF$_2$, —OCH$_2$CF$_3$, —OCH$_2$CH$_2$Cl, —OCH$_2$CHCl$_2$, —(C=O)OCH$_2$CH$_3$, —(C=O)OCH$_2$CH$_3$, —(C=O)OCH$_3$, —(C=O)OH, —(C=O)NHCH$_2$CH$_3$, —(C=O)NHCH$_3$, —(C=O)NH$_2$, —SO$_2$N(CH$_3$)$_2$, —SO$_2$NHCH$_2$CH$_3$, —SO$_2$NHCH$_3$, and —SO$_2$NH$_2$. In yet a further aspect, Ar is benzo[d]thiazolyl substituted with 0 to 3 groups independently selected from —F, —Cl, —Br, methyl, ethyl, isopropyl, —CH$_2$F, —CHF$_2$, —CF$_3$, —CH$_2$CF$_3$, —OCH$_3$, —OCF$_3$, —OCH$_2$CF$_3$, —(C=O)OH, —(C=O)NH$_2$, —SO$_2$NHCH$_3$, and —SO$_2$NH$_2$.

In a further aspect, Ar is benzo[d]thiazolyl monosubstituted with a group selected from halo, cyano, hydroxyl, —NH$_2$, C1-C3 alkyl, C1-C3 monoalkyl, C1-C3 polyhaloalkyl, C1-C3 alkoxy, C1-C3 monohaloalkoxy C1-C3 polyhaloalkyl, C1-C3 alkoxy, C1-C3 monohaloalkoxy, C1-C3 polyhaloalkoxy, —(C=O)OR$^9$, —(C=O)NR$^{10a}$R$^{10b}$, and —SO$_2$NR$^{10a}$R$^{10b}$, —SR$^9$, and —SO$_2$R$^9$. In a still further aspect, Ar benzo[d]thiazolyl monosubstituted with a group selected from —F, —Cl, —Br, cyano, hydroxyl, —NH$_2$, methyl, ethyl, propyl, isopropyl, —CH$_2$F, —CHF$_2$, —CF$_3$, —CH$_2$Cl, —CHCl$_2$, —CCl$_3$, —CH$_2$CH$_2$F, —CH$_2$CHF$_2$, —CH$_2$CF$_3$, —CH$_2$CH$_2$Cl, —CH$_2$CHCl$_2$, —CH$_2$CCl$_3$, —OCH$_3$, —OCH$_2$CH$_3$, —OCH$_2$F, —OCHF$_2$, —OCF$_3$, —OCH$_2$Cl, —OCHCl$_2$, —OCCl$_3$, —OCH$_2$CH$_2$F, —OCH$_2$CHF$_2$, —OCH$_2$CF$_3$, —OCH$_2$CH$_2$Cl, —OCH$_2$CHCl$_2$, —(C=O)OCH$_2$CH$_3$, —(C=O)OCH$_2$CH$_3$, —(C=O)OCH$_3$, —(C=O)OH, —(C=O)NHCH$_2$CH$_3$, —(C=O)NHCH$_3$, —(C=O)NH$_2$, —SO$_2$N(CH$_3$)$_2$, —SO$_2$NHCH$_2$CH$_3$, —SO$_2$NHCH$_3$, and —SO$_2$NH$_2$. In yet a further aspect, Ar is benzo[d]thiazolyl monosubstituted with a group selected from —F, —Cl, —Br, methyl, ethyl, isopropyl, —CH$_2$F, —CHF$_2$, —CF$_3$, —CH₂CF₃, —OCH₃, —OCF₃, —OCH₂CF₃, —(C=O)OH, —(C=O)NH₂, —SO₂NHCH₃, and —SO₂NH₂.

In a further aspect, Ar is benzo[d]thiazolyl substituted with 2 groups independently selected from halo, cyano, hydroxyl, —NH₂, C1-C3 alkyl, C1-C3 monoalkyl, C1-C3 polyhaloalkyl, C1-C3 alkoxy, C1-C3 monohaloalkoxy, C1-C3 polyhaloalkyl, C1-C3 alkoxy, C1-C3 monohaloalkoxy, C1-C3 polyhaloalkoxy, —(C=O)OR⁹, —(C=O)NR¹⁰ᵃR¹⁰ᵇ, and —SO₂NR¹⁰ᵃR¹⁰ᵇ, —SR⁹, and —SO₂R⁹. In a still further aspect, Ar is benzo[d]thiazolyl substituted with 2 groups independently selected from —F, —Cl, —Br, cyano, hydroxyl, —NH₂, methyl, ethyl, propyl, isopropyl, —CH₂F, —CHF₂, —CF₃, —CH₂Cl, —CHCl₂, —CCl₃, —CH₂CH₂F, —CH₂CHF₂, —CH₂CF₃, —CH₂CH₂Cl, —CH₂CHCl₂, —CH₂CCl₃, —OCH₃, —OCH₂CH₃, —OCH₂F, —OCHF₂, —OCF₃, —OCH₂Cl, —OCHCl₂, —OCCl₃, —OCH₂CH₂F, —OCH₂CHF₂, —OCH₂CF₃, —OCH₂CH₂Cl, —OCH₂CHCl₂, —(C=O)OCH₂CH₃, —(C=O)OCH₂CH₃, —(C=O)OCH₃, —(C=O)OH, —(C=O)NHCH₂CH₃, —(C=O)NHCH₃, —(C=O)NH₂, —SO₂N(CH₃)₂, —SO₂NHCH₂CH₃, —SO₂NHCH₃, and —SO₂NH₂. In yet a further aspect, Ar is benzo[d]thiazolyl substituted with 2 groups independently selected from —F, —Cl, —Br, methyl, ethyl, isopropyl, —CH₂F, —CHF₂, —CF₃, —CH₂CF₃, —OCH₃, —OCF₃, —OCH₂CF₃, —(C=O)OH, —(C=O)NH₂, —SO₂NHCH₃, and —SO₂NH₂.

In a further aspect, Ar is benzo[d]oxazolyl substituted with 0 to 3 groups independently selected from halo, cyano, hydroxyl, —NH₂, C1-C3 alkyl, C1-C3 monoalkyl, C1-C3 polyhaloalkyl, C1-C3 alkoxy, C1-C3 monohaloalkoxy, C1-C3 polyhaloalkyl, C1-C3 alkoxy, C1-C3 monohaloalkoxy, C1-C3 polyhaloalkoxy, —(C=O)OR⁹, —(C=O)NR¹⁰ᵃR¹⁰ᵇ, and —SO₂NR¹⁰ᵃR¹⁰ᵇ, —SR⁹, and —SO₂R⁹. In a still further aspect, Ar is benzo[d]oxazolyl substituted with 0 to 3 groups independently selected from —F, —Cl, —Br, cyano, hydroxyl, —NH₂, methyl, ethyl, propyl, isopropyl, —CH₂F, —CHF₂, —CF₃, —CH₂Cl, —CHCl₂, —CCl₃, —CH₂CH₂F, —CH₂CHF₂, —CH₂CF₃, —CH₂CH₂Cl, —CH₂CHCl₂, —CH₂CCl₃, —OCH₃, —OCH₂CH₃, —OCH₂F, —OCHF₂, —OCF₃, —OCH₂Cl, —OCHCl₂, —OCCl₃, —OCH₂CH₂F, —OCH₂CHF₂, —OCH₂CF₃, —OCH₂CH₂Cl, —OCH₂CHCl₂, —(C=O)OCH₂CH₃, —(C=O)OCH₂CH₃, —(C=O)OCH₃, —(C=O)OH, —(C=O)NHCH₂CH₃, —(C=O)NHCH₃, —(C=O)NH₂, —SO₂N(CH₃)₂, —SO₂NHCH₂CH₃, —SO₂NHCH₃, and —SO₂NH₂. In yet a further aspect, Ar is benzo[d]oxazolyl substituted with 0 to 3 groups independently selected from —F, —Cl, —Br, methyl, ethyl, isopropyl, —CH₂F, —CHF₂, —CF₃, —CH₂CF₃, —OCH₃, —OCF₃, —OCH₂CF₃, —(C=O)OH, —(C=O)NH₂, —SO₂NHCH₃, and —SO₂NH₂.

In a further aspect, Ar is benzo[d]oxazolyl monosubstituted with a group selected from halo, cyano, hydroxyl, —NH₂, C1-C3 alkyl, C1-C3 monoalkyl, C1-C3 polyhaloalkyl, C1-C3 alkoxy, C1-C3 monohaloalkoxy, C1-C3 polyhaloalkyl, C1-C3 alkoxy, C1-C3 monohaloalkoxy, C1-C3 polyhaloalkoxy, —(C=O)OR⁹, —(C=O)NR¹⁰ᵃR¹⁰ᵇ, and —SO₂NR¹⁰ᵃR¹⁰ᵇ, —SR⁹, and —SO₂R⁹. In a still further aspect, Ar is benzo[d]oxazolyl monosubstituted with a group selected from —F, —Cl, —Br, cyano, hydroxyl, —NH₂, methyl, ethyl, propyl, isopropyl, —CH₂F, —CHF₂, —CF₃, —CH₂Cl, —CHCl₂, —CCl₃, —CH₂CH₂F, —CH₂CHF₂, —CH₂CF₃, —CH₂CH₂Cl, —CH₂CHCl₂, —CH₂CCl₃, —OCH₃, —OCH₂CH₃, —OCH₂F, —OCHF₂, —OCF₃, —OCH₂Cl, —OCHCl₂, —OCCl₃, —OCH₂CH₂F, —OCH₂CHF₂, —OCH₂CF₃, —OCH₂CH₂Cl, —OCH₂CHCl₂, —(C=O)OCH₂CH₃, —(C=O)OCH₂CH₃, —(C=O)OCH₃, —(C=O)OH, —(C=O)NHCH₂CH₃, —(C=O)NHCH₃, —(C=O)NH₂, —SO₂N(CH₃)₂, —SO₂NHCH₂CH₃, —SO₂NHCH₃, and —SO₂NH₂. In yet a further aspect, Ar is benzo[d]oxazolyl monosubstituted with a group selected from —F, —Cl, —Br, methyl, ethyl, isopropyl, —CH₂F, —CHF₂, —CF₃, —CH₂CF₃, —OCH₃, —OCF₃, —OCH₂CF₃, —(C=O)OH, —(C=O)NH₂, —SO₂NHCH₃, and —SO₂NH₂.

In a further aspect, Ar is benzo[d]oxazolyl substituted with 2 groups independently selected from halo, cyano, hydroxyl, —NH₂, C1-C3 alkyl, C1-C3 monoalkyl, C1-C3 polyhaloalkyl, C1-C3 alkoxy, C1-C3 monohaloalkoxy, C1-C3 polyhaloalkyl, C1-C3 alkoxy, C1-C3 monohaloalkoxy, C1-C3 polyhaloalkoxy, —(C=O)OR⁹, —(C=O)NR¹⁰ᵃR¹⁰ᵇ, and —SO₂NR¹⁰ᵃR¹⁰ᵇ, —SR⁹, and —SO₂R⁹. In a still further aspect, Ar is benzo[d]oxazolyl substituted with 2 groups independently selected from —F, —Cl, —Br, cyano, hydroxyl, —NH₂, methyl, ethyl, propyl, isopropyl, —CH₂F, —CHF₂, —CF₃, —CH₂Cl, —CHCl₂, —CCl₃, —CH₂CH₂F, —CH₂CHF₂, —CH₂CF₃, —CH₂CH₂Cl, —CH₂CHCl₂, —CH₂CCl₃, —OCH₃, —OCH₂CH₃, —OCH₂F, —OCHF₂, —OCF₃, —OCH₂Cl, —OCHCl₂, —OCCl₃, —OCH₂CH₂F, —OCH₂CHF₂, —OCH₂CF₃, —OCH₂CH₂Cl, —OCH₂CHCl₂, —(C=O)OCH₂CH₃, —(C=O)OCH₂CH₃, —(C=O)OCH₃, —(C=O)OH, —(C=O)NHCH₂CH₃, —(C=O)NHCH₃, —(C=O)NH₂, —SO₂N(CH₃)₂, —SO₂NHCH₂CH₃, —SO₂NHCH₃, and —SO₂NH₂. In yet a further aspect, Ar is benzo[d]oxazolyl substituted with 2 groups independently selected from —F, —Cl, —Br, methyl, ethyl, isopropyl, —CH₂F, —CHF₂, —CF₃, —CH₂CF₃, —OCH₃, —OCF₃, —OCH₂CF₃, —(C=O)OH, —(C=O)NH₂, —SO₂NHCH₃, and —SO₂NH₂.

In a further aspect, Ar is oxazolo[4,5-c]pyridinyl substituted with 0 to 3 groups independently selected from halo, cyano, hydroxyl, —NH₂, C1-C3 alkyl, C1-C3 monoalkyl, C1-C3 polyhaloalkyl, C1-C3 alkoxy, C1-C3 monohaloalkoxy, C1-C3 polyhaloalkyl, C1-C3 alkoxy, C1-C3 monohaloalkoxy, C1-C3 polyhaloalkoxy, —(C=O)OR⁹, —(C=O)NR¹⁰ᵃR¹⁰ᵇ, and —SO₂NR¹⁰ᵃR¹⁰ᵇ, —SR⁹, and —SO₂R⁹. In a still further aspect, Ar is oxazolo[4,5-c]pyridinyl substituted with 0 to 3 groups independently selected from —F, —Cl, —Br, cyano, hydroxyl, —NH₂, methyl, ethyl, propyl, isopropyl, —CH₂F, —CHF₂, —CF₃, —CH₂Cl, —CHCl₂, —CCl₃, —CH₂CH₂F, —CH₂CHF₂, —CH₂CF₃, —CH₂CH₂Cl, —CH₂CHCl₂, —CH₂CCl₃, —OCH₃, —OCH₂CH₃, —OCH₂F, —OCHF₂, —OCF₃, —OCH₂Cl, —OCHCl₂, —OCCl₃, —OCH₂CH₂F, —OCH₂CHF₂, —OCH₂CF₃, —OCH₂CH₂Cl, —OCH₂CHCl₂, —(C=O)OCH₂CH₃, —(C=O)OCH₂CH₃, —(C=O)OCH₃, —(C=O)OH, —(C=O)NHCH₂CH₃, —(C=O)NHCH₃, —(C=O)NH₂, —SO₂N(CH₃)₂, —SO₂NHCH₂CH₃, —SO₂NHCH₃, and —SO₂NH₂. In yet a further aspect, Ar is oxazolo[4,5-c]pyridinyl substituted with 0 to 3 groups independently selected from —F, —Cl, —Br, methyl, ethyl, isopropyl, —CH₂F, —CHF₂, —CF₃, —CH₂CF₃, —OCH₃, —OCF₃, —OCH₂CF₃, —(C=O)OH, —(C=O)NH₂, —SO₂NHCH₃, and —SO₂NH₂.

In a further aspect, Ar is oxazolo[4,5-c]pyridinyl monosubstituted with a group selected from halo, cyano, hydroxyl, —NH₂, C1-C3 alkyl, C1-C3 monoalkyl, C1-C3 polyhaloalkyl, C1-C3 alkoxy, C1-C3 monohaloalkoxy, C1-C3 polyhaloalkyl, C1-C3 alkoxy, C1-C3 monohaloalkoxy, C1-C3 polyhaloalkoxy, —(C=O)OR⁹, —(C=O)NR¹⁰ᵃR¹⁰ᵇ, and —SO₂NR¹⁰ᵃR¹⁰ᵇ, —SR⁹, and —SO₂R⁹. In a still further aspect, Ar is oxazolo[4,5-c]pyridinyl monosubstituted with a group selected from —F, —Cl, —Br, cyano, hydroxyl, —NH$_2$, methyl, ethyl, propyl, isopropyl, —CH$_2$F, —CHF$_2$, —CF$_3$, —CH$_2$Cl, —CHCl$_2$, —CCl$_3$, —CH$_2$CH$_2$F, —CH$_2$CHF$_2$, —CH$_2$CF$_3$, —CH$_2$CH$_2$Cl, —CH$_2$CHCl$_2$, —CH$_2$CCl$_3$, —OCH$_3$, —OCH$_2$CH$_3$, —OCH$_2$F, —OCHF$_2$, —OCF$_3$, —OCH$_2$Cl, —OCHCl$_2$, —OCCl$_3$, —OCH$_2$CH$_2$F, —OCH$_2$CHF$_2$, —OCH$_2$CF$_3$, —OCH$_2$CH$_2$Cl, —OCH$_2$CHCl$_2$, —(C=O)OCH$_2$CH$_3$, —(C=O)OCH$_2$CH$_3$, —(C=O)OCH$_3$, —(C=O)OH, —(C=O)NHCH$_2$CH$_3$, —(C=O)NHCH$_3$, —(C=O)NH$_2$, —SO$_2$N(CH$_3$)$_2$, —SO$_2$NHCH$_2$CH$_3$, —SO$_2$NHCH$_3$, and —SO$_2$NH$_2$. In yet a further aspect, Ar is oxazolo[4,5-c]pyridinyl monosubstituted with a group selected from —F, —Cl, —Br, methyl, ethyl, isopropyl, —CH$_2$F, —CHF$_2$, —CF$_3$, —CH$_2$CF$_3$, —OCH$_3$, —OCF$_3$, —OCH$_2$CF$_3$, —(C=O)OH, —(C=O)NH$_2$, —SO$_2$NHCH$_3$, and —SO$_2$NH$_2$.

In a further aspect, Ar is oxazolo[4,5-c]pyridinyl substituted with 2 groups independently selected from halo, cyano, hydroxyl, —NH$_2$, C1-C3 alkyl, C1-C3 monoalkyl, C1-C3 polyhaloalkyl, C1-C3 alkoxy, C1-C3 monohaloalkoxy, C1-C3 polyhaloalkyl, C1-C3 alkoxy, C1-C3 monohaloalkoxy, C1-C3 polyhaloalkoxy, —(C=O)OR$^9$, —(C=O)NR$^{10a}$R$^{10b}$, and —SO$_2$NR$^{10a}$R$^{10b}$, —SR$^9$, and —SO$_2$R$^9$. In a still further aspect, Ar is oxazolo[4,5-c]pyridinyl substituted with 2 groups independently selected from —F, —Cl, —Br, cyano, hydroxyl, —NH$_2$, methyl, ethyl, propyl, isopropyl, —CH$_2$F, —CHF$_2$, —CF$_3$, —CH$_2$Cl, —CHCl$_2$, —CCl$_3$, —CH$_2$CH$_2$F, —CH$_2$CHF$_2$, —CH$_2$CF$_3$, —CH$_2$CH$_2$Cl, —CH$_2$CHCl$_2$, —CH$_2$CCl$_3$, —OCH$_3$, —OCH$_2$CH$_3$, —OCH$_2$F, —OCHF$_2$, —OCF$_3$, —OCH$_2$Cl, —OCHCl$_2$, —OCCl$_3$, —OCH$_2$CH$_2$F, —OCH$_2$CHF$_2$, —OCH$_2$CF$_3$, —OCH$_2$CH$_2$Cl, —OCH$_2$CHCl$_2$, —(C=O)OCH$_2$CH$_3$, —(C=O)OCH$_2$CH$_3$, —(C=O)OCH$_3$, —(C=O)OH, —(C=O)NHCH$_2$CH$_3$, —(C=O)NHCH$_3$, —(C=O)NH$_2$, —SO$_2$N(CH$_3$)$_2$, —SO$_2$NHCH$_2$CH$_3$, —SO$_2$NHCH$_3$, and —SO$_2$NH$_2$. In yet a further aspect, Ar is oxazolo[4,5-c]pyridinyl substituted with 2 groups independently selected from —F, —Cl, —Br, methyl, ethyl, isopropyl, —CH$_2$F, —CHF$_2$, —CF$_3$, —CH$_2$CF$_3$, —OCH$_3$, —OCF$_3$, —OCH$_2$CF$_3$, —(C=O)OH, —(C=O)NH$_2$, —SO$_2$NHCH$_3$, and —SO$_2$NH$_2$.

In a further aspect, Ar is quinolinyl substituted with 0 to 3 groups independently selected from halo, cyano, hydroxyl, —NH$_2$, C1-C3 alkyl, C1-C3 monoalkyl, C1-C3 polyhaloalkyl, C1-C3 alkoxy, C1-C3 monohaloalkoxy, C1-C3 polyhaloalkyl, C1-C3 alkoxy, C1-C3 monohaloalkoxy, C1-C3 polyhaloalkoxy, —(C=O)OR$^9$, —(C=O)NR$^{10a}$R$^{10b}$, and —SO$_2$NR$^{10a}$R$^{10b}$, —SR$^9$, and —SO$_2$R$^9$. In a still further aspect, Ar is quinolinyl substituted with 0 to 3 groups independently selected from —F, —Cl, —Br, cyano, hydroxyl, —NH$_2$, methyl, ethyl, propyl, isopropyl, —CH$_2$F, —CHF$_2$, —CF$_3$, —CH$_2$Cl, —CHCl$_2$, —CCl$_3$, —CH$_2$CH$_2$F, —CH$_2$CHF$_2$, —CH$_2$CF$_3$, —CH$_2$CH$_2$Cl, —CH$_2$CHCl$_2$, —CH$_2$CCl$_3$, —OCH$_3$, —OCH$_2$CH$_3$, —OCH$_2$F, —OCHF$_2$, —OCF$_3$, —OCH$_2$Cl, —OCHCl$_2$, —OCCl$_3$, —OCH$_2$CH$_2$F, —OCH$_2$CHF$_2$, —OCH$_2$CF$_3$, —OCH$_2$CH$_2$Cl, —OCH$_2$CHCl$_2$, —(C=O)OCH$_2$CH$_3$, —(C=O)OCH$_2$CH$_3$, —(C=O)OCH$_3$, —(C=O)OH, —(C=O)NHCH$_2$CH$_3$, —(C=O)NHCH$_3$, —(C=O)NH$_2$, —SO$_2$N(CH$_3$)$_2$, —SO$_2$NHCH$_2$CH$_3$, —SO$_2$NHCH$_3$, and —SO$_2$NH$_2$. In yet a further aspect, Ar is quinolinyl substituted with 0 to 3 groups independently selected from —F, —Cl, —Br, methyl, ethyl, isopropyl, —CH$_2$F, —CHF$_2$, —CF$_3$, —CH$_2$CF$_3$, —OCH$_3$, —OCF$_3$, —OCH$_2$CF$_3$, —(C=O)OH, —(C=O)NH$_2$, —SO$_2$NHCH$_3$, and —SO$_2$NH$_2$.

In a further aspect, Ar is quinolinyl monosubstituted with a group selected from halo, cyano, hydroxyl, —NH$_2$, C1-C3 alkyl, C1-C3 monoalkyl, C1-C3 polyhaloalkyl, C1-C3 alkoxy, C1-C3 monohaloalkoxy, C1-C3 polyhaloalkyl, C1-C3 alkoxy, C1-C3 monohaloalkoxy, C1-C3 polyhaloalkoxy, —(C=O)OR$^9$, —(C=O)NR$^{10a}$R$^{10b}$, and —SO$_2$NR$^{10a}$R$^{10b}$, —SR$^9$, and —SO$_2$R$^9$. In a still further aspect, Ar is quinolinyl monosubstituted with a group selected from —F, —Cl, —Br, cyano, hydroxyl, —NH$_2$, methyl, ethyl, propyl, isopropyl, —CH$_2$F, —CHF$_2$, —CF$_3$, —CH$_2$Cl, —CHCl$_2$, —CCl$_3$, —CH$_2$CH$_2$F, —CH$_2$CHF$_2$, —CH$_2$CF$_3$, —CH$_2$CH$_2$Cl, —CH$_2$CHCl$_2$, —CH$_2$CCl$_3$, —OCH$_3$, —OCH$_2$CH$_3$, —OCH$_2$F, —OCHF$_2$, —OCF$_3$, —OCH$_2$Cl, —OCHCl$_2$, —OCCl$_3$, —OCH$_2$CH$_2$F, —OCH$_2$CHF$_2$, —OCH$_2$CF$_3$, —OCH$_2$CH$_2$Cl, —OCH$_2$CHCl$_2$, —(C=O)OCH$_2$CH$_3$, —(C=O)OCH$_2$CH$_3$, —(C=O)OCH$_3$, —(C=O)OH, —(C=O)NHCH$_2$CH$_3$, —(C=O)NHCH$_3$, —(C=O)NH$_2$, —SO$_2$N(CH$_3$)$_2$, —SO$_2$NHCH$_2$CH$_3$, —SO$_2$NHCH$_3$, and —SO$_2$NH$_2$. In yet a further aspect, Ar is quinolinyl monosubstituted with a group selected from —F, —Cl, —Br, methyl, ethyl, isopropyl, —CH$_2$F, —CHF$_2$, —CF$_3$, —CH$_2$CF$_3$, —OCH$_3$, —OCF$_3$, —OCH$_2$CF$_3$, —(C=O)OH, —(C=O)NH$_2$, —SO$_2$NHCH$_3$, and —SO$_2$NH$_2$.

In a further aspect, Ar is quinolinyl substituted with 2 groups independently selected from halo, cyano, hydroxyl, —NH$_2$, C1-C3 alkyl, C1-C3 monoalkyl, C1-C3 polyhaloalkyl, C1-C3 alkoxy, C1-C3 monohaloalkoxy, C1-C3 polyhaloalkyl, C1-C3 alkoxy, C1-C3 monohaloalkoxy, C1-C3 polyhaloalkoxy, —(C=O)OR$^9$, —(C=O)NR$^{10a}$R$^{10b}$, —SO$_2$NR$^{10a}$R$^{10b}$, —SR$^9$, and —SO$_2$R$^9$. In a still further aspect, Ar is quinolinyl substituted with 2 groups independently selected from —F, —Cl, —Br, cyano, hydroxyl, —NH$_2$, methyl, ethyl, propyl, isopropyl, —CH$_2$F, —CHF$_2$, —CF$_3$, —CH$_2$Cl, —CHCl$_2$, —CCl$_3$, —CH$_2$CH$_2$F, —CH$_2$CHF$_2$, —CH$_2$CF$_3$, —CH$_2$CH$_2$Cl, —CH$_2$CHCl$_2$, —CH$_2$CCl$_3$, —OCH$_3$, —OCH$_2$CH$_3$, —OCH$_2$F, —OCHF$_2$, —OCF$_3$, —OCH$_2$Cl, —OCHCl$_2$, —OCCl$_3$, —OCH$_2$CH$_2$F, —OCH$_2$CHF$_2$, —OCH$_2$CF$_3$, —OCH$_2$CH$_2$Cl, —OCH$_2$CHCl$_2$, —(C=O)OCH$_2$CH$_3$, —(C=O)OCH$_2$CH$_3$, —(C=O)OCH$_3$, —(C=O)OH, —(C=O)NHCH$_2$CH$_3$, —(C=O)NHCH$_3$, —(C=O)NH$_2$, —SO$_2$N(CH$_3$)$_2$, —SO$_2$NHCH$_2$CH$_3$, —SO$_2$NHCH$_3$, and —SO$_2$NH$_2$. In yet a further aspect, Ar is quinolinyl substituted with 2 groups independently selected from —F, —Cl, —Br, methyl, ethyl, isopropyl, —CH$_2$F, —CHF$_2$, —CF$_3$, —CH$_2$CF$_3$, —OCH$_3$, —OCF$_3$, —OCH$_2$CF$_3$, —(C=O)OH, —(C=O)NH$_2$, —SO$_2$NHCH$_3$, and —SO$_2$NH$_2$.

In a further aspect, Ar is 1H-benzo[d]imidazolyl substituted with 0 to 3 groups independently selected from halo, cyano, hydroxyl, —NH$_2$, C1-C3 alkyl, C1-C3 monoalkyl, C1-C3 polyhaloalkyl, C1-C3 alkoxy, C1-C3 monohaloalkoxy, C1-C3 polyhaloalkyl, C1-C3 alkoxy, C1-C3 monohaloalkoxy, C1-C3 polyhaloalkoxy, —(C=O)OR$^9$, —(C=O)NR$^{10a}$R$^{10b}$, —SO$_2$NR$^{10a}$R$^{10b}$, —SR$^9$, and —SO$_2$R$^9$. In a still further aspect, Ar is 1H-benzo[d]imidazolyl substituted with 0 to 3 groups independently selected from —F, —Cl, —Br, cyano, hydroxyl, —NH$_2$, methyl, ethyl, propyl, isopropyl, —CH$_2$F, —CHF$_2$, —CF$_3$, —CH$_2$Cl, —CHCl$_2$, —CCl$_3$, —CH$_2$CH$_2$F, —CH$_2$CHF$_2$, —CH$_2$CF$_3$, —CH$_2$CH$_2$Cl, —CH$_2$CHCl$_2$, —CH$_2$CCl$_3$, —OCH$_3$, —OCH$_2$CH$_3$, —OCH$_2$F, —OCHF$_2$, —OCF$_3$, —OCH$_2$Cl, —OCHCl$_2$, —OCCl$_3$, —OCH$_2$CH$_2$F, —OCH$_2$CHF$_2$, —OCH$_2$CF$_3$, —OCH$_2$CH$_2$Cl, —OCH₂CHCl₂, —(C=O)OCH₂CH₃, —(C=O)OCH₂CH₃, —(C=O)OCH₃, —(C=O)OH, —(C=O)NHCH₂CH₃, —(C=O)NHCH₃, —(C=O)NH₂, —SO₂N(CH₃)₂, —SO₂NHCH₂CH₃, —SO₂NHCH₃, and —SO₂NH₂. In yet a further aspect, Ar is 1H-benzo[d]imidazolyl substituted with 0 to 3 groups independently selected from —F, —Cl, —Br, methyl, ethyl, isopropyl, —CH₂F, —CHF₂, —CF₃, —CH₂CF₃, —OCH₃, —OCF₃, —OCH₂CF₃, —(C=O)OH, —(C=O)NH₂, —SO₂NHCH₃, and —SO₂NH₂.

In a further aspect, Ar is 1H-benzo[d]imidazolyl monosubstituted with a group selected from halo, cyano, hydroxyl, —NH₂, C1-C3 alkyl, C1-C3 monoalkyl, C1-C3 polyhaloalkyl, C1-C3 alkoxy, C1-C3 monohaloalkoxy, C1-C3 polyhaloalkyl, C1-C3 alkoxy, C1-C3 monohaloalkoxy, C1-C3 polyhaloalkoxy, —(C=O)OR⁹, —(C=O)NR¹⁰ᵃR¹⁰ᵇ, —SO₂NR¹⁰ᵃR¹⁰ᵇ, —SR⁹, and —SO₂R⁹. In a still further aspect, Ar is 1H-benzo[d]imidazolyl monosubstituted with a group selected from —F, —Cl, —Br, cyano, hydroxyl, —NH₂, methyl, ethyl, propyl, isopropyl, —CH₂F, —CHF₂, —CF₃, —CH₂Cl, —CHCl₂, —CCl₃, —CH₂CH₂F, —CH₂CHF₂, —CH₂CF₃, —CH₂CH₂Cl, —CH₂CHCl₂, —CH₂CCl₃, —OCH₃, —OCH₂CH₃, —OCH₂F, —OCHF₂, —OCF₃, —OCH₂Cl, —OCHCl₂, —OCCl₃, —OCH₂CH₂F, —OCH₂CHF₂, —OCH₂CF₃, —OCH₂CH₂Cl, —OCH₂CHCl₂, —(C=O)OCH₂CH₃, —(C=O)OCH₂CH₃, —(C=O)OCH₃, —(C=O)OH, —(C=O)NHCH₂CH₃, —(C=O)NHCH₃, —(C=O)NH₂, —SO₂N(CH₃)₂, —SO₂NHCH₂CH₃, —SO₂NHCH₃, and —SO₂NH₂. In yet a further aspect, Ar is 1H-benzo[d]imidazolyl monosubstituted with a group selected from —F, —Cl, —Br, methyl, ethyl, isopropyl, —CH₂F, —CHF₂, —CF₃, —CH₂CF₃, —OCH₃, —OCF₃, —OCH₂CF₃, —(C=O)OH, —(C=O)NH₂, —SO₂NHCH₃, and —SO₂NH₂.

In a further aspect, Ar is 1H-benzo[d]imidazolyl substituted with 2 groups independently selected from halo, cyano, hydroxyl, —NH₂, C1-C3 alkyl, C1-C3 monoalkyl, C1-C3 polyhaloalkyl, C1-C3 alkoxy, C1-C3 monohaloalkoxy, C1-C3 polyhaloalkyl, C1-C3 alkoxy, C1-C3 monohaloalkoxy, C1-C3 polyhaloalkoxy, —(C=O)OR⁹, —(C=O)NR¹⁰ᵃR¹⁰ᵇ, —SO₂NR¹⁰ᵃR¹⁰ᵇ, —SR⁹, and —SO₂R⁹. In a still further aspect, Ar is 1H-benzo[d]imidazolyl substituted with 2 groups independently selected from —F, —Cl, —Br, cyano, hydroxyl, —NH₂, methyl, ethyl, propyl, isopropyl, —CH₂F, —CHF₂, —CF₃, —CH₂Cl, —CHCl₂, —CCl₃, —CH₂CH₂F, —CH₂CHF₂, —CH₂CF₃, —CH₂CH₂Cl, —CH₂CHCl₂, —CH₂CCl₃, —OCH₃, —OCH₂CH₃, —OCH₂F, —OCHF₂, —OCF₃, —OCH₂Cl, —OCHCl₂, —OCCl₃, —OCH₂CH₂F, —OCH₂CHF₂, —OCH₂CF₃, —OCH₂CH₂Cl, —OCH₂CHCl₂, —(C=O)OCH₂CH₃, —(C=O)OCH₂CH₃, —(C=O)OCH₃, —(C=O)OH, —(C=O)NHCH₂CH₃, —(C=O)NHCH₃, —(C=O)NH₂, —SO₂N(CH₃)₂, —SO₂NHCH₂CH₃, —SO₂NHCH₃, and —SO₂NH₂. In yet a further aspect, Ar is 1H-benzo[d]imidazolyl substituted with 2 groups independently selected from —F, —Cl, —Br, methyl, ethyl, isopropyl, —CH₂F, —CHF₂, —CF₃, —CH₂CF₃, —OCH₃, —OCF₃, —OCH₂CF₃, —(C=O)OH, —(C=O)NH₂, —SO₂NHCH₃, and —SO₂NH₂.

In a further aspect, Ar is a moiety having a structure represented by a formula:

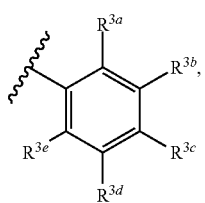

wherein each of $R^{3a}$, $R^{3b}$, $R^{3c}$, $R^{3d}$, and $R^{3e}$ is independently selected from hydrogen, halo, cyano, hydroxyl, —NH₂, C1-C3 alkyl, C1-C3 monoalkyl, C1-C3 polyhaloalkyl, C1-C3 alkoxy, C1-C3 monohaloalkoxy, C1-C3 polyhaloalkyl, C1-C3 alkoxy, C1-C3 monohaloalkoxy, C1-C3 polyhaloalkoxy, —(C=O)OR⁹, —(C=O)NR¹⁰ᵃR¹⁰ᵇ, —SO₂NR¹⁰ᵃR¹⁰ᵇ, —SR⁹, and —SO₂R⁹, provided that at least two of $R^{3a}$, $R^{3b}$, $R^{3c}$, $R^{3d}$, and $R^{3e}$ are hydrogen.

In a further aspect, Ar is a moiety having a structure represented by a formula:

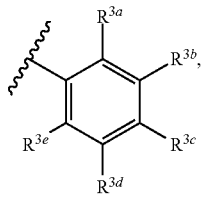

wherein each of $R^{3a}$, $R^{3b}$, $R^{3c}$, $R^{3d}$, and $R^{3e}$ is independently selected from hydrogen, —F, —Cl, —Br, cyano, hydroxyl, —NH₂, methyl, ethyl, propyl, isopropyl, —CH₂F, —CHF₂, —CF₃, —CH₂Cl, —CHCl₂, —CCl₃, —CH₂CH₂F, —CH₂CHF₂, —CH₂CF₃, —CH₂CH₂Cl, —CH₂CHCl₂, —CH₂CCl₃, —OCH₃, —OCH₂CH₃, —OCH₂F, —OCHF₂, —OCF₃, —OCH₂Cl, —OCHCl₂, —OCCl₃, —OCH₂CH₂F, —OCH₂CHF₂, —OCH₂CF₃, —OCH₂CH₂Cl, —OCH₂CHCl₂, —(C=O)OCH₂CH₃, —(C=O)OCH₂CH₃, —(C=O)OCH₃, —(C=O)OH, —(C=O)NHCH₂CH₃, —(C=O)NHCH₃, —(C=O)NH₂, —SO₂N(CH₃)₂, —SO₂NHCH₂CH₃, —SO₂NHCH₃, and —SO₂NH₂, provided that at least two of $R^{3a}$, $R^{3b}$, $R^{3c}$, $R^{3d}$, and $R^{3e}$ are hydrogen.

In a further aspect, Ar is a moiety having a structure represented by a formula:

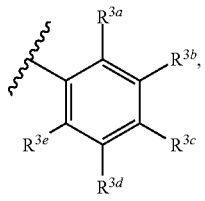

wherein each of $R^{3a}$, $R^{3b}$, $R^{3c}$, $R^{3d}$, and $R^{3e}$ are independently selected from hydrogen, —F, —Cl, —Br, methyl, ethyl, isopropyl, —CH₂F, —CHF₂, —CF₃, —CH₂CF₃, —OCH₃, —OCF₃, —OCH₂CF₃, —(C=O)OH, —(C=O)NH₂, —SO₂NHCH₃, and —SO₂NH₂, provided that at least two of $R^{3a}$, $R^{3b}$, $R^{3c}$, $R^{3d}$, and $R^{3e}$ are hydrogen.

In a further aspect, Ar is a moiety having a structure represented by a formula:

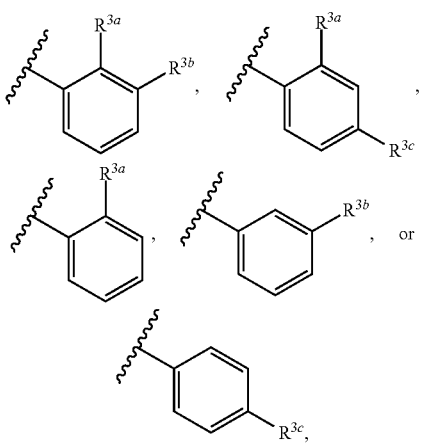

wherein each of $R^{3a}$, $R^{3b}$, and $R^{3c}$, when present, is independently selected from halo, cyano, hydroxyl, —NH$_2$, C1-C3 alkyl, C1-C3 monoalkyl, C1-C3 polyhaloalkyl, C1-C3 alkoxy, C1-C3 monohaloalkoxy, C1-C3 polyhaloalkyl, C1-C3 alkoxy, C1-C3 monohaloalkoxy, C1-C3 polyhaloalkoxy, —(C=O)OR$^9$, —(C=O)NR$^{10a}$R$^{10b}$, —SO$_2$NR$^{10a}$R$^{10b}$, —SR$^9$, and —SO$_2$R$^9$.

In a further aspect, Ar is a moiety having a structure represented by a formula:

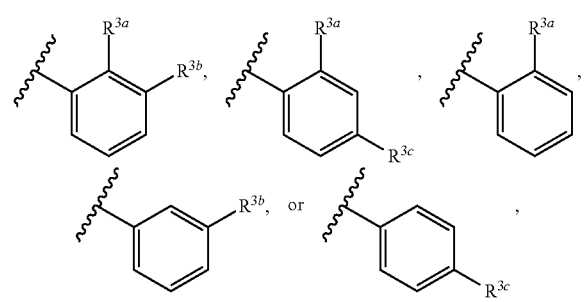

wherein each of $R^{3a}$, $R^{3b}$, and $R^{3c}$, when present, is independently selected from —F, —Cl, —Br, cyano, hydroxyl, —NH$_2$, methyl, ethyl, propyl, isopropyl, —CH$_2$F, —CHF$_2$, —CF$_3$, —CH$_2$Cl, —CHCl$_2$, —CCl$_3$, —CH$_2$CH$_2$F, —CH$_2$CHF$_2$, —CH$_2$CF$_3$, —CH$_2$CH$_2$Cl, —CH$_2$CHCl$_2$, —CH$_2$CCl$_3$, —OCH$_3$, —OCH$_2$CH$_3$, —OCH$_2$F, —OCHF$_2$, —OCF$_3$, —OCH$_2$Cl, —OCHCl$_2$, —OCCl$_3$, —OCH$_2$CH$_2$F, —OCH$_2$CHF$_2$, —OCH$_2$CF$_3$, —OCH$_2$CH$_2$Cl, —OCH$_2$CHCl$_2$, —(C=O)OCH$_2$CH$_3$, —(C=O)OCH$_2$CH$_3$, —(C=O)OCH$_3$, —(C=O)OH, —(C=O)NHCH$_2$CH$_3$, —(C=O)NHCH$_3$, —(C=O)NH$_2$, —SO$_2$N(CH$_3$)$_2$, —SO$_2$NHCH$_2$CH$_3$, —SO$_2$NHCH$_3$, and —SO$_2$NH$_2$, provided that at least two of $R^{3a}$, $R^{3b}$, $R^{3c}$, $R^{3d}$, and $R^{3e}$ are hydrogen.

In a further aspect, Ar is a moiety having a structure represented by a formula:

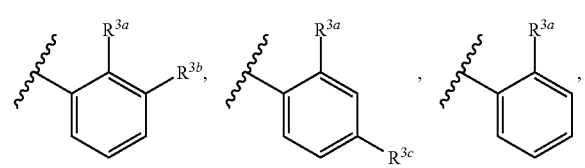

wherein each of $R^{3a}$, $R^{3b}$, and $R^{3c}$, when present, is independently selected from —F, —Cl, —Br, methyl, ethyl, isopropyl, —CH$_2$F, —CHF$_2$, —CF$_3$, —CH$_2$CF$_3$, —OCH$_3$, —OCF$_3$, —OCH$_2$CF$_3$, —(C=O)OH, —(C=O)NH$_2$, —SO$_2$NHCH$_3$, and —SO$_2$NH$_2$, provided that at least two of $R^{3a}$, $R^{3b}$, $R^{3c}$, $R^{3d}$, and $R^{3e}$ are hydrogen.

In a further aspect, Ar is a moiety having a structure represented by a formula:

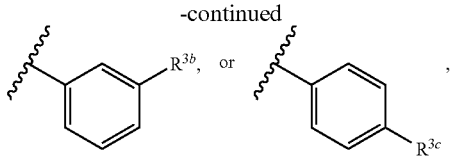

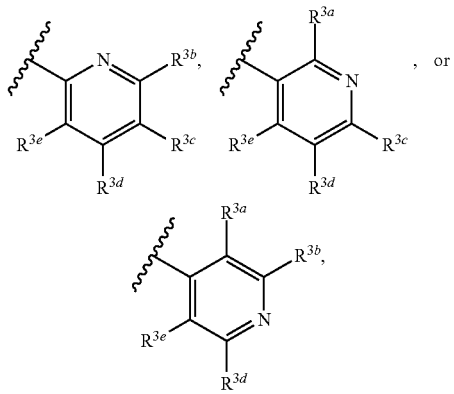

wherein each of $R^{3a}$, $R^{3b}$, $R^{3c}$, $R^{3d}$, and $R^{3e}$ is independently selected from hydrogen, halo, cyano, hydroxyl, —NH$_2$, C1-C3 alkyl, C1-C3 monoalkyl, C1-C3 polyhaloalkyl, C1-C3 alkoxy, C1-C3 monohaloalkoxy, C1-C3 polyhaloalkyl, C1-C3 alkoxy, C1-C3 monohaloalkoxy, C1-C3 polyhaloalkoxy, —(C=O)OR$^9$, —(C=O)NR$^{10a}$R$^{10b}$, —SO$_2$NR$^{10a}$R$^{10b}$, —SR$^9$, and —SO$_2$R$^9$, provided that at least one of $R^{3a}$, $R^{3b}$, $R^{3c}$, $R^{3d}$, and $R^{3e}$ are hydrogen.

In a further aspect, Ar is a moiety having a structure represented by a formula:

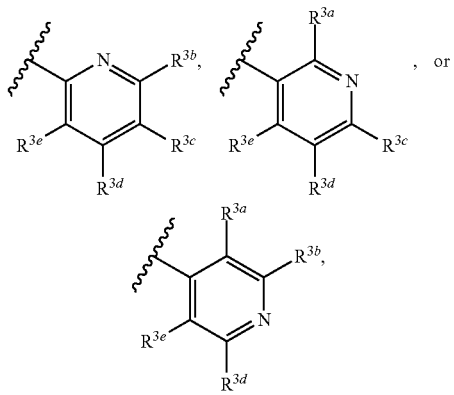

wherein each of $R^{3a}$, $R^{3b}$, $R^{3c}$, $R^{3d}$, and $R^{3e}$ is independently selected from hydrogen, —F, —Cl, —Br, cyano, hydroxyl, —NH$_2$, methyl, ethyl, propyl, isopropyl, —CH$_2$F, —CHF$_2$, —CF$_3$, —CH$_2$Cl, —CHCl$_2$, —CCl$_3$, —CH$_2$CH$_2$F, —CH$_2$CHF$_2$, —CH$_2$CF$_3$, —CH$_2$CH$_2$Cl, —CH$_2$CHCl$_2$, —CH₂CCl₃, —OCH₃, —OCH₂CH₃, —OCH₂F, —OCHF₂, —OCF₃, —OCH₂Cl, —OCHCl₂, —OCCl₃, —OCH₂CH₂F, —OCH₂CHF₂, —OCH₂CF₃, —OCH₂CH₂Cl, —OCH₂CHCl₂, —(C=O)OCH₂CH₃, —(C=O)OCH₂CH₃, —(C=O)OCH₃, —(C=O)OH, —(C=O)NHCH₂CH₃, —(C=O)NHCH₃, —(C=O)NH₂, —SO₂N(CH₃)₂, —SO₂NHCH₂CH₃, —SO₂NHCH₃, and —SO₂NH₂, provided that at least one of R$^{3a}$, R$^{3b}$, R$^{3c}$, R$^{3d}$, and R$^{3e}$ are hydrogen.

In a further aspect, Ar is a moiety having a structure represented by a formula:

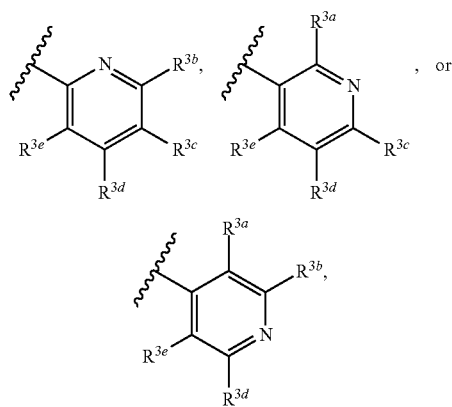

wherein each of R$^{3a}$, R$^{3b}$, R$^{3c}$, R$^{3d}$, and R$^{3e}$ are independently selected from hydrogen, —F, —Cl, —Br, methyl, ethyl, isopropyl, —CH₂F, —CHF₂, —CF₃, —CH₂CF₃, —OCH₃, —OCF₃, —OCH₂CF₃, —(C=O)OH, —(C=O)NH₂, —SO₂NHCH₃, and —SO₂NH₂, provided that at least one of R$^{3a}$, R$^{3b}$, R$^{3c}$, R$^{3d}$, and R$^{3e}$ are hydrogen.

In a further aspect, Ar is a moiety having a structure represented by a formula:

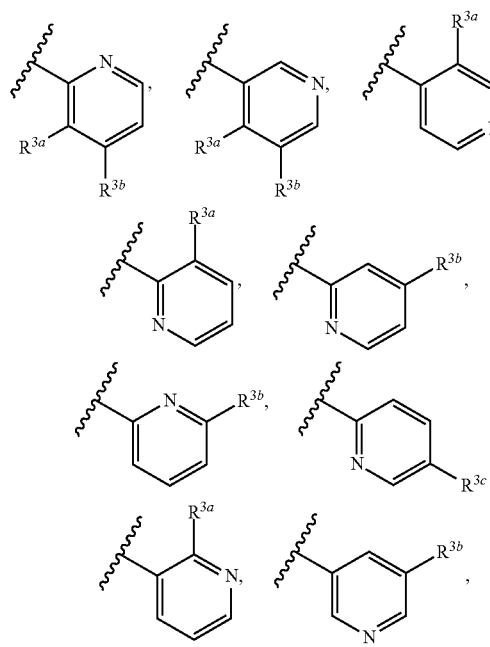

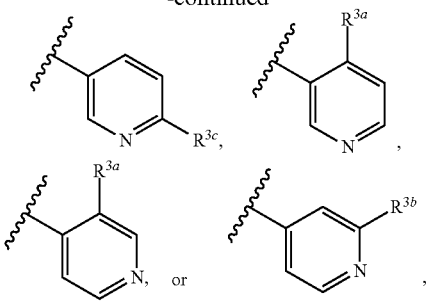

wherein each of R$^{3a}$, R$^{3b}$, and R$^{3c}$, when present, is independently selected from halo, cyano, hydroxyl, —NH₂, C1-C3 alkyl, C1-C3 monoalkyl, C1-C3 polyhaloalkyl, C1-C3 alkoxy, C1-C3 monohaloalkoxy, C1-C3 polyhaloalkyl, C1-C3 alkoxy, C1-C3 monohaloalkoxy, C1-C3 polyhaloalkoxy, —(C=O)OR⁹, —(C=O)NR$^{10a}$R$^{10b}$, —SO₂NR$^{10a}$R$^{10b}$, —SR⁹, and —SO₂R⁹.

In a further aspect, Ar is a moiety having a structure represented by a formula:

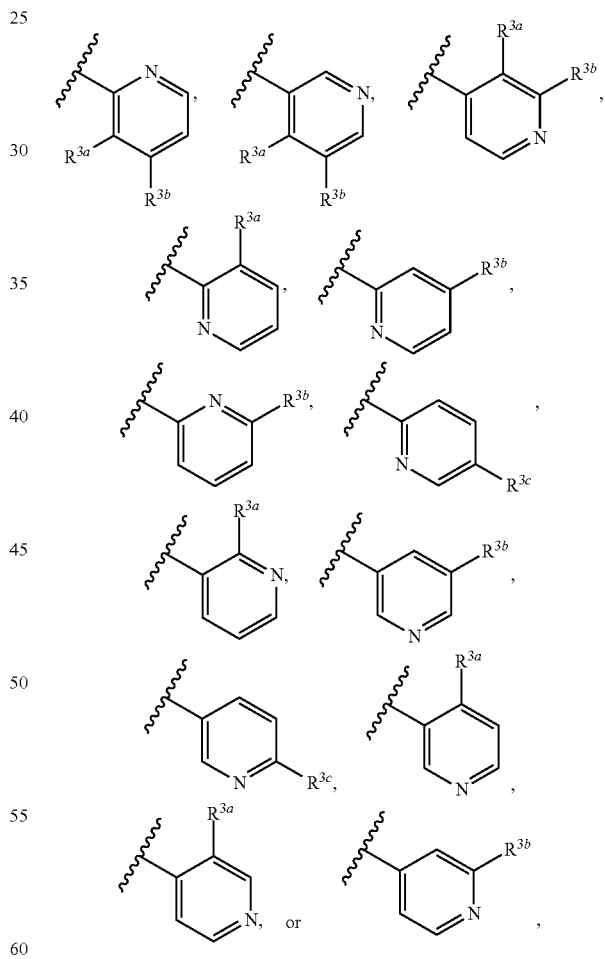

wherein each of R$^{3a}$, R$^{3b}$, and R$^{3c}$, when present, is independently selected from —F, —Cl, —Br, cyano, hydroxyl, —NH₂, methyl, ethyl, propyl, isopropyl, —CH₂F, —CHF₂, —CF₃, —CH₂Cl, —CHCl₂, —CCl₃, —CH₂CH₂F, —CH₂CHF₂, —CH₂CF₃, —CH₂CH₂Cl, —CH₂CHCl₂, —CH₂CCl₃, —OCH₃, —OCH₂CH₃, —OCH₂F, —OCHF₂, —OCF₃, —OCH₂Cl, —OCHCl₂, —OCCl₃, —OCH₂CH₂F, —OCH₂CHF₂, —OCH₂CF₃, —OCH₂CH₂Cl, —OCH₂CHCl₂, —(C=O)OCH₂CH₃, —(C=O)OCH₂CH₃, —(C=O)OCH₃, —(C=O)OH, —(C=O)NHCH₂CH₃, —(C=O)NHCH₃, —(C=O)NH₂, —SO₂N(CH₃)₂, —SO₂NHCH₂CH₃, —SO₂NHCH₃, and —SO₂NH₂, provided that at least two of R$^{3a}$, R$^{3b}$, R$^{3c}$, R$^{3d}$, and R$^{3e}$ are hydrogen.

In a further aspect, Ar is a moiety having a structure represented by a formula:

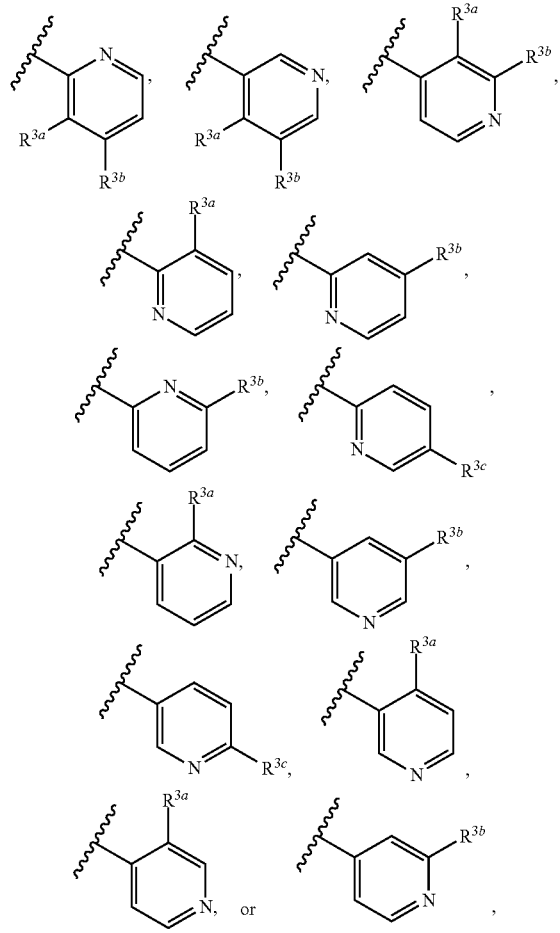

wherein each of R$^{3a}$, R$^{3b}$, and R$^{3c}$, when present, is independently selected from —F, —Cl, —Br, methyl, ethyl, isopropyl, —CH₂F, —CHF₂, —CF₃, —CH₂CF₃, —OCH₃, —OCF₃, —OCH₂CF₃, —(C=O)OH, —(C=O)NH₂, —SO₂NHCH₃, and —SO₂NH₂, provided that at least two of R$^{3a}$, R$^{3b}$, R$^{3c}$, R$^{3d}$, and R$^{3e}$ are hydrogen.

In a further aspect, Ar is a moiety having a structure represented by a formula:

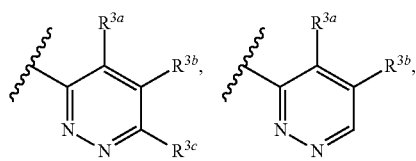

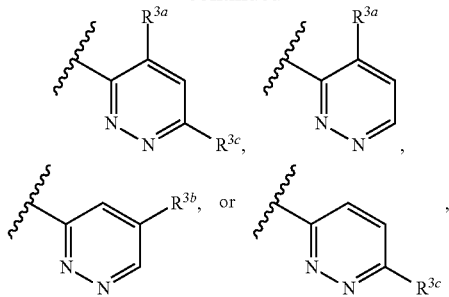

wherein each of R$^{3a}$, R$^{3b}$, and R$^{3c}$, when present, is independently selected from halo, cyano, hydroxyl, —NH₂, C1-C3 alkyl, C1-C3 monoalkyl, C1-C3 polyhaloalkyl, C1-C3 alkoxy, C1-C3 monohaloalkoxy, C1-C3 polyhaloalkyl, C1-C3 alkoxy, C1-C3 monohaloalkoxy, C1-C3 polyhaloalkoxy, —(C=O)OR$^{9}$, —(C=O)NR$^{10a}$R$^{10b}$, —SO₂NR$^{10a}$R$^{10b}$, —SR$^{9}$, and —SO₂R$^{9}$.

In a further aspect, Ar is a moiety having a structure represented by a formula:

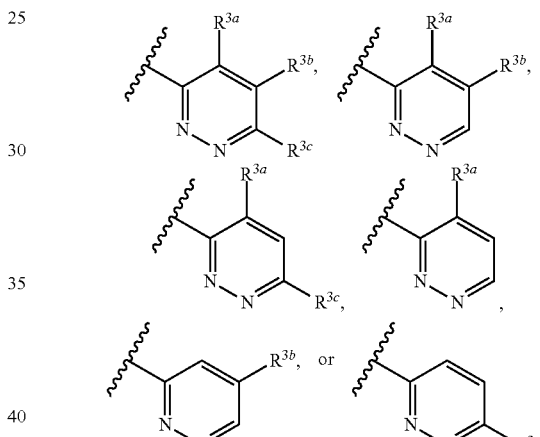

wherein each of R$^{3a}$, R$^{3b}$, and R$^{3c}$, when present, is independently selected from —F, —Cl, —Br, cyano, hydroxyl, —NH₂, methyl, ethyl, propyl, isopropyl, —CH₂F, —CHF₂, —CF₃, —CH₂Cl, —CHCl₂, —CCl₃, —CH₂CH₂F, —CH₂CHF₂, —CH₂CF₃, —CH₂CH₂Cl, —CH₂CHCl₂, —CH₂CCl₃, —OCH₃, —OCH₂CH₃, —OCH₂F, —OCHF₂, —OCF₃, —OCH₂Cl, —OCHCl₂, —OCCl₃, —OCH₂CH₂F, —OCH₂CHF₂, —OCH₂CF₃, —OCH₂CH₂Cl, —OCH₂CHCl₂, —(C=O)OCH₂CH₃, —(C=O)OCH₂CH₃, —(C=O)OCH₃, —(C=O)OH, —(C=O)NHCH₂CH₃, —(C=O)NHCH₃, —(C=O)NH₂, —SO₂N(CH₃)₂, —SO₂NHCH₂CH₃, —SO₂NHCH₃, and —SO₂NH₂, provided that at least two of R$^{3a}$, R$^{3b}$, R$^{3c}$, R$^{3d}$, and R$^{3e}$ are hydrogen.

In a further aspect, Ar is a moiety having a structure represented by a formula:

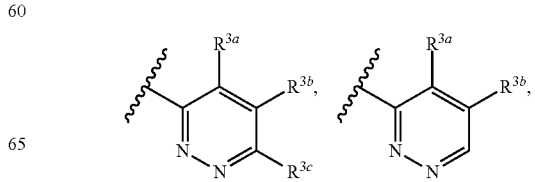

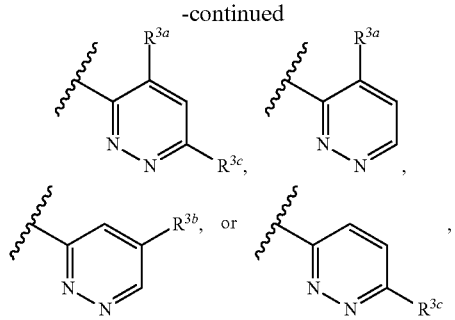

wherein each of $R^{3a}$, $R^{3b}$, and $R^{3c}$, when present, is independently selected from —F, —Cl, —Br, methyl, ethyl, isopropyl, —CH$_2$F, —CHF$_2$, —CF$_3$, —CH$_2$CF$_3$, —OCH$_3$, —OCF$_3$, —OCH$_2$CF$_3$, —(C=O)OH, —(C=O)NH$_2$, —SO$_2$NHCH$_3$, and —SO$_2$NH$_2$, provided that at least two of $R^{3a}$, $R^{3b}$, $R^{3c}$, $R^{3d}$, and $R^{3e}$ are hydrogen.

In a further aspect, Ar is a moiety having a structure represented by a formula:

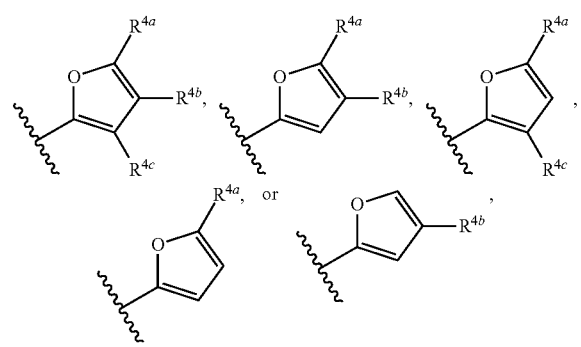

wherein each of $R^{4a}$, $R^{4b}$, and $R^{4c}$, when present, is independently selected from hydrogen, halo, cyano, hydroxyl, —NH$_2$, C1-C3 alkyl, C1-C3 monoalkyl, C1-C3 polyhaloalkyl, C1-C3 alkoxy, C1-C3 monohaloalkoxy, C1-C3 polyhaloalkyl, C1-C3 alkoxy, C1-C3 monohaloalkoxy, C1-C3 polyhaloalkoxy, —(C=O)OR$^9$, —(C=O)NR$^{10a}$R$^{10b}$, —SO$_2$NR$^{10a}$R$^{10b}$, —SR$^9$, and —SO$_2$R$^9$.

In a further aspect, Ar is a moiety structure represented by a formula:

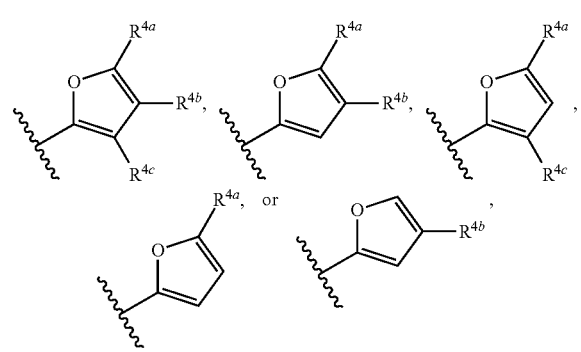

wherein each of $R^{4a}$, $R^{4b}$, and $R^{4c}$, when present, is independently selected from hydrogen, —F, —Cl, —Br, cyano, hydroxyl, —NH$_2$, methyl, ethyl, propyl, isopropyl, —CH$_2$F, —CHF$_2$, —CF$_3$, —CH$_2$Cl, —CHCl$_2$, —CCl$_3$, —CH$_2$CH$_2$F, —CH$_2$CHF$_2$, —CH$_2$CF$_3$, —CH$_2$CH$_2$Cl, —CH$_2$CHCl$_2$, —CH$_2$CCl$_3$, —OCH$_3$, —OCH$_2$CH$_3$, —OCH$_2$F, —OCHF$_2$, —OCF$_3$, —OCH$_2$Cl, —OCHCl$_2$, —OCCl$_3$, —OCH$_2$CH$_2$F, —OCH$_2$CHF$_2$, —OCH$_2$CF$_3$, —OCH$_2$CH$_2$Cl, —OCH$_2$CHCl$_2$, —(C=O)OCH$_2$CH$_3$, —(C=O)OCH$_2$CH$_3$, —(C=O)OCH$_3$, —(C=O)OH, —(C=O)NHCH$_2$CH$_3$, —(C=O)NHCH$_3$, —(C=O)NH$_2$, —SO$_2$N(CH$_3$)$_2$, —SO$_2$NHCH$_2$CH$_3$, —SO$_2$NHCH$_3$, and —SO$_2$NH$_2$.

In a further aspect, Ar is a moiety having a structure represented by a formula:

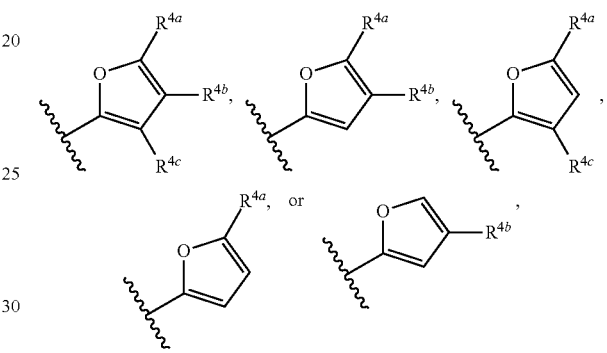

wherein each of $R^{4a}$, $R^{4b}$, and $R^{4c}$, when present, is independently selected from hydrogen, —F, —Cl, —Br, methyl, ethyl, isopropyl, —CH$_2$F, —CHF$_2$, —CF$_3$, —CH$_2$CF$_3$, —OCH$_3$, —OCF$_3$, —OCH$_2$CF$_3$, —(C=O)OH, —(C=O)NH$_2$, —SO$_2$NHCH$_3$, and —SO$_2$NH$_2$.

In a further aspect, Ar is a moiety having a structure represented by a formula:

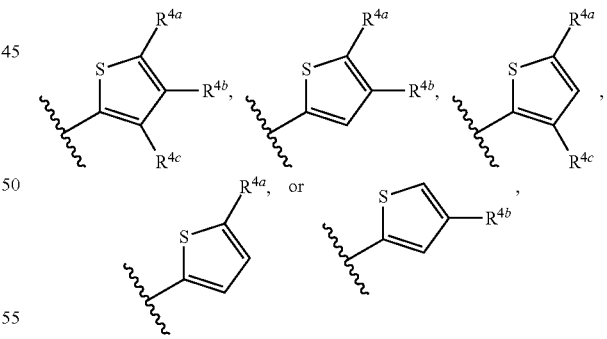

wherein each of $R^{4a}$, $R^{4b}$, and $R^{4c}$, when present, is independently selected from hydrogen, halo, cyano, hydroxyl, —NH$_2$, C1-C3 alkyl, C1-C3 monoalkyl, C1-C3 polyhaloalkyl, C1-C3 alkoxy, C1-C3 monohaloalkoxy, C1-C3 polyhaloalkyl, C1-C3 alkoxy, C1-C3 monohaloalkoxy, C1-C3 polyhaloalkoxy, —(C=O)OR$^9$, —(C=O)NR$^{10a}$R$^{10b}$, —SO$_2$NR$^{10a}$R$^{10b}$, —SR$^9$, and —SO$_2$R$^9$.

In a further aspect, Ar is a moiety having a structure represented by a formula:

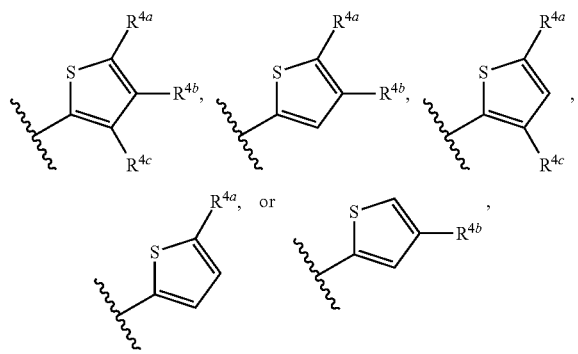

wherein each of $R^{4a}$, $R^{4b}$, and $R^{4c}$, when present, is independently selected from hydrogen, —F, —Cl, —Br, cyano, hydroxyl, —NH$_2$, methyl, ethyl, propyl, isopropyl, —CH$_2$F, —CHF$_2$, —CF$_3$, —CH$_2$Cl, —CHCl$_2$, —CCl$_3$, —CH$_2$CH$_2$F, —CH$_2$CHF$_2$, —CH$_2$CF$_3$, —CH$_2$CH$_2$Cl, —CH$_2$CHCl$_2$, —CH$_2$CCl$_3$, —OCH$_3$, —OCH$_2$CH$_3$, —OCH$_2$F, —OCHF$_2$, —OCF$_3$, —OCH$_2$Cl, —OCHCl$_2$, —OCCl$_3$, —OCH$_2$CH$_2$F, —OCH$_2$CHF$_2$, —OCH$_2$CF$_3$, —OCH$_2$CH$_2$Cl, —OCH$_2$CHCl$_2$, —(C=O)OCH$_2$CH$_3$, —(C=O)OCH$_2$CH$_3$, —(C=O)OCH$_3$, —(C=O)OH, —(C=O)NHCH$_2$CH$_3$, —(C=O)NHCH$_3$, —(C=O)NH$_2$, —SO$_2$N(CH$_3$)$_2$, —SO$_2$NHCH$_2$CH$_3$, —SO$_2$NHCH$_3$, and —SO$_2$NH$_2$.

In a further aspect, Ar is a moiety having a structure represented by a formula:

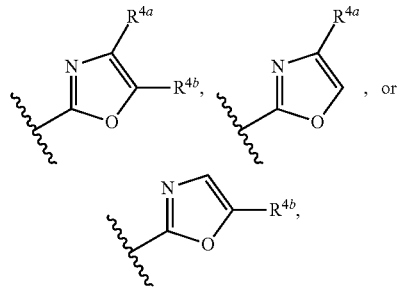

wherein each of $R^{4a}$, $R^{4b}$, and $R^{4c}$, when present, is independently selected from hydrogen, —F, —Cl, —Br, methyl, ethyl, isopropyl, —CH$_2$F, —CHF$_2$, —CF$_3$, —CH$_2$CF$_3$, —OCH$_3$, —OCF$_3$, —OCH$_2$CF$_3$, —(C=O)OH, —(C=O)NH$_2$, —SO$_2$NHCH$_3$, and —SO$_2$NH$_2$.

In a further aspect, Ar is a moiety having a structure represented by a formula:

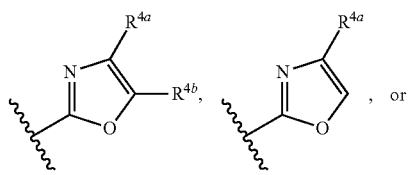

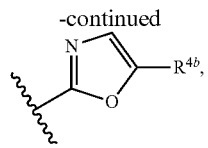

wherein each of $R^{4a}$ and $R^{4b}$, when present, is independently selected from hydrogen, halo, cyano, hydroxyl, —NH$_2$, C1-C3 alkyl, C1-C3 monoalkyl, C1-C3 polyhaloalkyl, C1-C3 alkoxy, C1-C3 monohaloalkoxy, C1-C3 polyhaloalkyl, C1-C3 alkoxy, C1-C3 monohaloalkoxy, C1-C3 polyhaloalkoxy, —(C=O)OR$^9$, —(C=O)NR$^{10a}$R$^{10b}$, —SO$_2$NR$^{10a}$R$^{10b}$, —SR$^9$, and —SO$_2$R$^9$.

In a further aspect, Ar is a moiety having a structure represented by a formula:

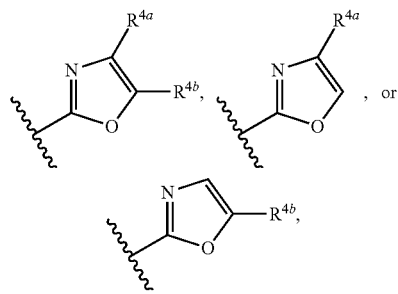

wherein each of $R^{4a}$ and $R^{4b}$, when present, is independently from hydrogen, —F, —Cl, —Br, cyano, hydroxyl, —NH$_2$, methyl, ethyl, propyl, isopropyl, —CH$_2$F, —CHF$_2$, —CF$_3$, —CH$_2$Cl, —CHCl$_2$, —CCl$_3$, —CH$_2$CH$_2$F, —CH$_2$CHF$_2$, —CH$_2$CF$_3$, —CH$_2$CH$_2$Cl, —CH$_2$CHCl$_2$, —CH$_2$CCl$_3$, —OCH$_3$, —OCH$_2$CH$_3$, —OCH$_2$F, —OCHF$_2$, —OCF$_3$, —OCH$_2$Cl, —OCHCl$_2$, —OCCl$_3$, —OCH$_2$CH$_2$F, —OCH$_2$CHF$_2$, —OCH$_2$CF$_3$, —OCH$_2$CH$_2$Cl, —OCH$_2$CHCl$_2$, —(C=O)OCH$_2$CH$_3$, —(C=O)OCH$_2$CH$_3$, —(C=O)OCH$_3$, —(C=O)OH, —(C=O)NHCH$_2$CH$_3$, —(C=O)NHCH$_3$, —(C=O)NH$_2$, —SO$_2$N(CH$_3$)$_2$, —SO$_2$NHCH$_2$CH$_3$, —SO$_2$NHCH$_3$, and —SO$_2$NH$_2$.

In a further aspect, Ar is a moiety having a structure represented by a formula:

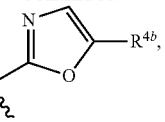

wherein each of $R^{4a}$ and $R^{4b}$, when present, is independently from hydrogen, —F, —Cl, —Br, methyl, ethyl, isopropyl, —CH$_2$F, —CHF$_2$, —CF$_3$, —CH$_2$CF$_3$, —OCH$_3$, —OCF$_3$, —OCH$_2$CF$_3$, —(C=O)OH, —(C=O)NH$_2$, —SO$_2$NHCH$_3$, and —SO$_2$NH$_2$.

In a further aspect, Ar is a moiety having a structure represented by a formula:

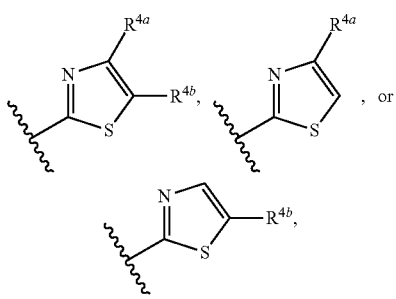

wherein each of $R^{4a}$ and $R^{4b}$, when present, is independently selected from hydrogen, halo, cyano, hydroxyl, —NH$_2$, C1-C3 alkyl, C1-C3 monoalkyl, C1-C3 polyhaloalkyl, C1-C3 alkoxy, C1-C3 monohaloalkoxy, C1-C3 polyhaloalkyl, C1-C3 alkoxy, C1-C3 monohaloalkoxy, C1-C3 polyhaloalkoxy, —(C=O)OR$^9$, —(C=O)NR$^{10a}$R$^{10b}$, —SO$_2$NR$^{10a}$R$^{10b}$, —SR$^9$, and —SO$_2$R$^9$.

In a further aspect, Ar is a moiety having a structure represented by a formula:

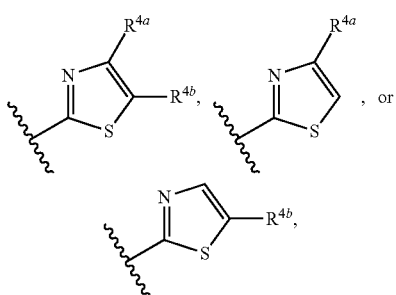

wherein each of $R^{4a}$ and $R^{4b}$, when present, is independently from hydrogen, —F, —Cl, —Br, cyano, hydroxyl, —NH$_2$, methyl, ethyl, propyl, isopropyl, —CH$_2$F, —CHF$_2$, —CF$_3$, —CH$_2$Cl, —CHCl$_2$, —CCl$_3$, —CH$_2$CH$_2$F, —CH$_2$CHF$_2$, —CH$_2$CF$_3$, —CH$_2$CH$_2$Cl, —CH$_2$CHCl$_2$, —CH$_2$CCl$_3$, —OCH$_3$, —OCH$_2$CH$_3$, —OCH$_2$F, —OCHF$_2$, —OCF$_3$, —OCH$_2$Cl, —OCHCl$_2$, —OCCl$_3$, —OCH$_2$CH$_2$F, —OCH$_2$CHF$_2$, —OCH$_2$CF$_3$, —OCH$_2$CH$_2$Cl, —OCH$_2$CHCl$_2$, —(C=O)OCH$_2$CH$_3$, —(C=O)OCH$_2$CH$_3$, —(C=O)OCH$_3$, —(C=O)OH, —(C=O)NHCH$_2$CH$_3$, —(C=O)NHCH$_3$, —(C=O)NH$_2$, —SO$_2$N(CH$_3$)$_2$, —SO$_2$NHCH$_2$CH$_3$, —SO$_2$NHCH$_3$, and —SO$_2$NH$_2$.

In a further aspect, Ar is a moiety having a structure represented by a formula:

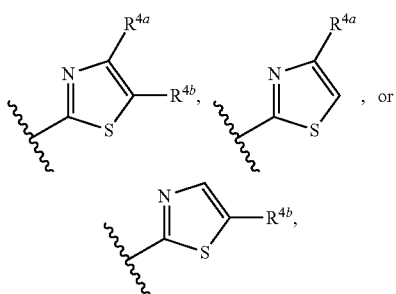

wherein each of $R^{4a}$ and $R^{4b}$, when present, is independently from hydrogen, —F, —Cl, —Br, methyl, ethyl, isopropyl, —CH$_2$F, —CHF$_2$, —CF$_3$, —CH$_2$CF$_3$, —OCH$_3$, —OCF$_3$, —OCH$_2$CF$_3$, —(C=O)OH, —(C=O)NH$_2$, —SO$_2$NHCH$_3$, and —SO$_2$NH$_2$.

In a further aspect, Ar is a moiety having a structure represented by a formula:

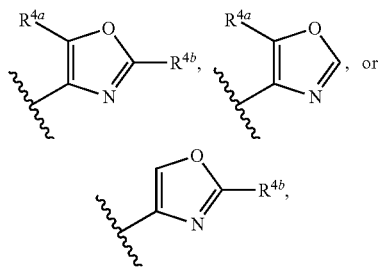

wherein each of $R^{4a}$ and $R^{4b}$, when present, is independently selected from hydrogen, halo, cyano, hydroxyl, —NH$_2$, C1-C3 alkyl, C1-C3 monoalkyl, C1-C3 polyhaloalkyl, C1-C3 alkoxy, C1-C3 monohaloalkoxy, C1-C3 polyhaloalkyl, C1-C3 alkoxy, C1-C3 monohaloalkoxy, C1-C3 polyhaloalkoxy, —(C=O)OR$^9$, —(C=O)NR$^{10a}$R$^{10b}$, —SO$_2$NR$^{10a}$R$^{10b}$, —SR$^9$, and —SO$_2$R$^9$.

In a further aspect, Ar is a moiety having a structure represented by a formula:

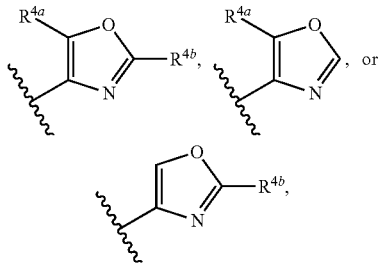

wherein each of $R^{4a}$ and $R^{4b}$, when present, is independently from hydrogen, —F, —Cl, —Br, cyano, hydroxyl, —NH$_2$, methyl, ethyl, propyl, isopropyl, —CH$_2$F, —CHF$_2$, —CF$_3$, —CH$_2$Cl, —CHCl$_2$, —CCl$_3$, —CH$_2$CH$_2$F, —CH$_2$CHF$_2$, —CH$_2$CF$_3$, —CH$_2$CH$_2$Cl, —CH$_2$CHCl$_2$, —CH$_2$CCl$_3$, —OCH$_3$, —OCH$_2$CH$_3$, —OCH$_2$F, —OCHF$_2$, —OCF$_3$, —OCH$_2$Cl, —OCHCl$_2$, —OCCl$_3$, —OCH$_2$CH$_2$F, —OCH$_2$CHF$_2$, —OCH$_2$CF$_3$, —OCH$_2$CH$_2$Cl, —OCH$_2$CHCl$_2$, —(C=O)OCH$_2$CH$_3$, —(C=O)OCH$_2$CH$_3$, —(C=O)OCH$_3$, —(C=O)OH, —(C=O)NHCH$_2$CH$_3$, —(C=O)NHCH$_3$, —(C=O)NH$_2$, —SO$_2$N(CH$_3$)$_2$, —SO$_2$NHCH$_2$CH$_3$, —SO$_2$NHCH$_3$, and —SO$_2$NH$_2$.

In a further aspect, Ar is a moiety having a structure represented by a formula:

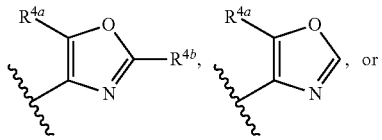

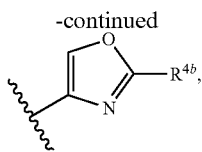

wherein each of $R^{4a}$ and $R^{4b}$, when present, is independently from hydrogen, —F, —Cl, —Br, methyl, ethyl, isopropyl, —CH$_2$F, —CHF$_2$, —CF$_3$, —CH$_2$CF$_3$, —OCH$_3$, —OCF$_3$, —OCH$_2$CF$_3$, —(C=O)OH, —(C=O)NH$_2$, —SO$_2$NHCH$_3$, and —SO$_2$NH$_2$.

In a further aspect, Ar is a moiety having a structure represented by a formula:

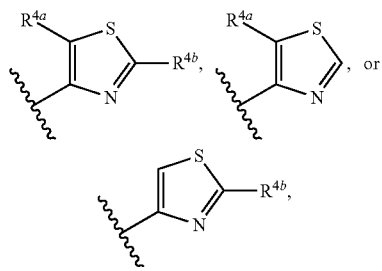

wherein each of $R^{4a}$ and $R^{4b}$, when present, is independently selected from hydrogen, halo, cyano, hydroxyl, —NH$_2$, C1-C3 alkyl, C1-C3 monoalkyl, C1-C3 polyhaloalkyl, C1-C3 alkoxy, C1-C3 monohaloalkoxy, C1-C3 polyhaloalkyl, C1-C3 alkoxy, C1-C3 monohaloalkoxy, C1-C3 polyhaloalkoxy, —(C=O)OR$^9$, —(C=O)NR$^{10a}$R$^{10b}$, —SO$_2$NR$^{10a}$R$^{10b}$, —SR$^9$, and —SO$_2$R$^9$.

In a further aspect, Ar is a moiety having a structure represented by a formula:

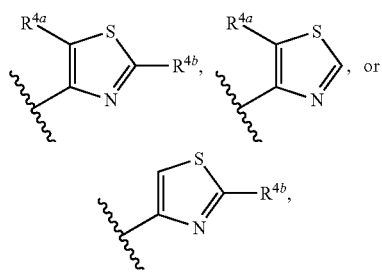

wherein each of $R^{4a}$ and $R^{4b}$, when present, is independently from hydrogen, —F, —Cl, —Br, cyano, hydroxyl, —NH$_2$, methyl, ethyl, propyl, isopropyl, —CH$_2$F, —CHF$_2$, —CF$_3$, —CH$_2$Cl, —CHCl$_2$, —CCl$_3$, —CH$_2$CH$_2$F, —CH$_2$CHF$_2$, —CH$_2$CF$_3$, —CH$_2$CH$_2$Cl, —CH$_2$CHCl$_2$, —CH$_2$CCl$_3$, —OCH$_3$, —OCH$_2$CH$_3$, —OCH$_2$F, —OCHF$_2$, —OCF$_3$, —OCH$_2$Cl, —OCHCl$_2$, —OCCl$_3$, —OCH$_2$CH$_2$F, —OCH$_2$CHF$_2$, —OCH$_2$CF$_3$, —OCH$_2$CH$_2$Cl, —OCH$_2$CHCl$_2$, —(C=O)OCH$_2$CH$_3$, —(C=O)OCH$_2$CH$_3$, —(C=O)OCH$_3$, —(C=O)OH, —(C=O)NHCH$_2$CH$_3$, —(C=O)NHCH$_3$, —(C=O)NH$_2$, —SO$_2$N(CH$_3$)$_2$, —SO$_2$NHCH$_2$CH$_3$, —SO$_2$NHCH$_3$, and —SO$_2$NH$_2$.

In a further aspect, Ar is a moiety having a structure represented by a formula:

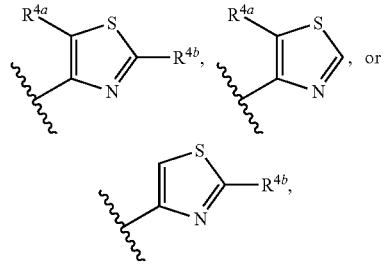

wherein each of $R^{4a}$ and $R^{4b}$, when present, is independently from hydrogen, —F, —Cl, —Br, methyl, ethyl, isopropyl, —CH$_2$F, —CHF$_2$, —CF$_3$, —CH$_2$CF$_3$, —OCH$_3$, —OCF$_3$, —OCH$_2$CF$_3$, —(C=O)OH, —(C=O)NH$_2$, —SO$_2$NHCH$_3$, and —SO$_2$NH$_2$.

In a further aspect, Ar is a moiety having a structure represented by a formula:

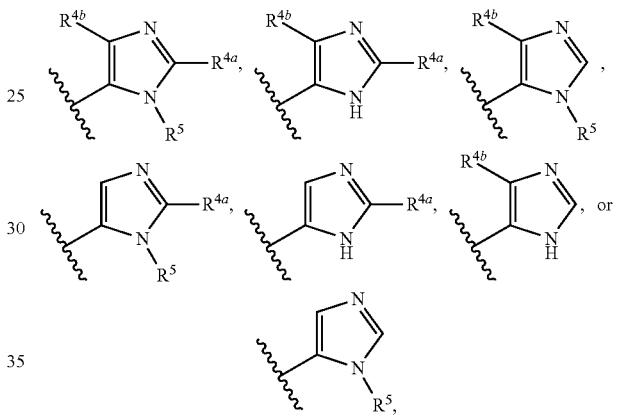

wherein each of $R^{4a}$ and $R^{4b}$, when present, is independently selected from hydrogen, halo, cyano, hydroxyl, —NH$_2$, C1-C3 alkyl, C1-C3 monoalkyl, C1-C3 polyhaloalkyl, C1-C3 alkoxy, C1-C3 monohaloalkoxy, C1-C3 polyhaloalkyl, C1-C3 alkoxy, C1-C3 monohaloalkoxy, C1-C3 polyhaloalkoxy, —(C=O)OR$^9$, —(C=O)NR$^{10a}$R$^{10b}$, —SO$_2$NR$^{10a}$R$^{10b}$, —SR$^9$, and —SO$_2$R$^9$; and wherein $R^5$, when present, is selected from hydrogen and C1-C3 alkyl.

In a further aspect, Ar is a moiety having a structure represented by a formula:

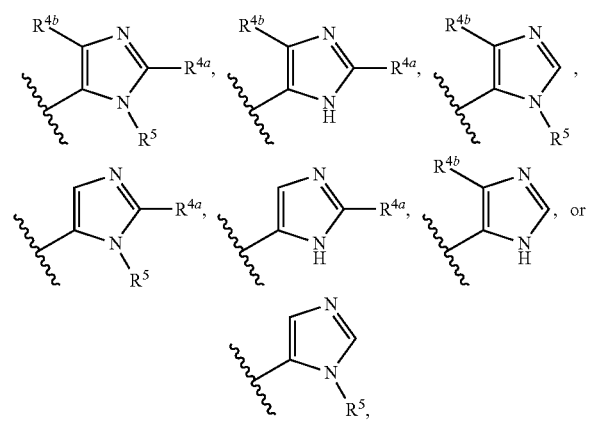

wherein each of R⁴ᵃ and R⁴ᵇ, when present, is independently from hydrogen, —F, —Cl, —Br, cyano, hydroxyl, —NH₂, methyl, ethyl, propyl, isopropyl, —CH₂F, —CHF₂, —CF₃, —CH₂Cl, —CHCl₂, —CCl₃, —CH₂CH₂F, —CH₂CHF₂, —CH₂CF₃, —CH₂CH₂Cl, —CH₂CHCl₂, —CH₂CCl₃, —OCH₃, —OCH₂CH₃, —OCH₂F, —OCHF₂, —OCF₃, —OCH₂Cl, —OCHCl₂, —OCCl₃, —OCH₂CH₂F, —OCH₂CHF₂, —OCH₂CF₃, —OCH₂CH₂Cl, —OCH₂CHCl₂, —(C=O)OCH₂CH₃, —(C=O)OCH₂CH₃, —(C=O)OCH₃, —(C=O)OH, —(C=O)NHCH₂CH₃, —(C=O)NHCH₃, —(C=O)NH₂, —SO₂N(CH₃)₂, —SO₂NHCH₂CH₃, —SO₂NHCH₃, and —SO₂NH₂; and wherein R⁵, when present, is selected from hydrogen and methyl.

In a further aspect, Ar is a moiety having a structure represented by a formula:

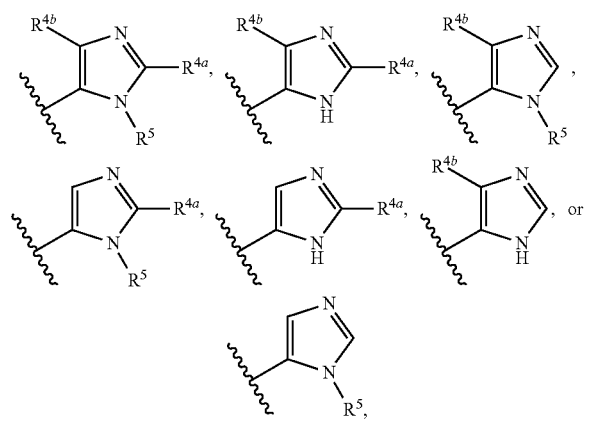

wherein each of R⁴ᵃ and R⁴ᵇ, when present, is independently from hydrogen, —F, —Cl, —Br, methyl, ethyl, isopropyl, —CH₂F, —CHF₂, —CF₃, —CH₂CF₃, —OCH₃, —OCF₃, —OCH₂CF₃, —(C=O)OH, —(C=O)NH₂, —SO₂NHCH₃, and —SO₂NH₂; and wherein R⁵, when present, is selected from hydrogen and methyl.

In a further aspect, Ar is a moiety having a structure represented by a formula:

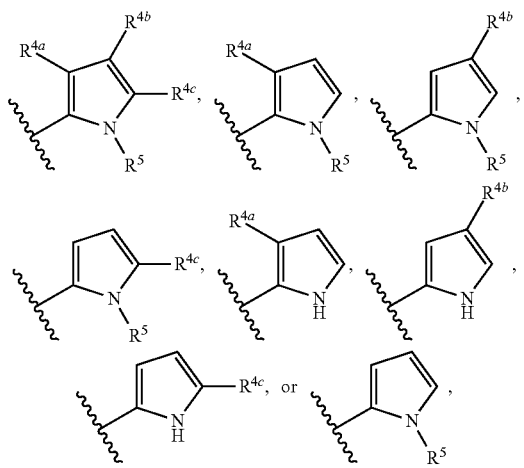

wherein each of R⁴ᵃ, R⁴ᵇ, and R⁴ᶜ, when present, is independently selected from hydrogen, halo, cyano, hydroxyl, —NH₂, C1-C3 alkyl, C1-C3 monoalkyl, C1-C3 polyhaloalkyl, C1-C3 alkoxy, C1-C3 monohaloalkoxy, C1-C3 polyhaloalkyl, C1-C3 alkoxy, C1-C3 monohaloalkoxy, C1-C3 polyhaloalkoxy, —(C=O)OR⁹, —(C=O)NR¹⁰ᵃR¹⁰ᵇ, —SO₂NR¹⁰ᵃR¹⁰ᵇ, —SR⁹, and —SO₂R⁹; and wherein R⁵, when present, is selected from hydrogen and C1-C3 alkyl.

In a further aspect, Ar is a moiety having a structure represented by a formula:

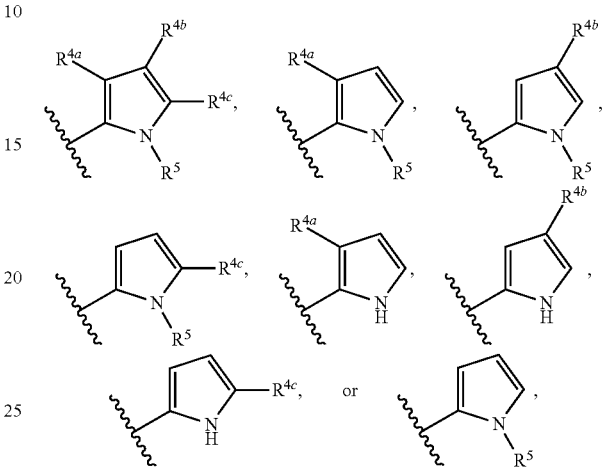

wherein each of R⁴ᵃ, R⁴ᵇ, and R⁴ᶜ, when present, is independently from hydrogen, —F, —Cl, —Br, cyano, hydroxyl, —NH₂, methyl, ethyl, propyl, isopropyl, —CH₂F, —CHF₂, —CF₃, —CH₂Cl, —CHCl₂, —CCl₃, —CH₂CH₂F, —CH₂CHF₂, —CH₂CF₃, —CH₂CH₂Cl, —CH₂CHCl₂, —CH₂CCl₃, —OCH₃, —OCH₂CH₃, —OCH₂F, —OCHF₂, —OCF₃, —OCH₂Cl, —OCHCl₂, —OCCl₃, —OCH₂CH₂F, —OCH₂CHF₂, —OCH₂CF₃, —OCH₂CH₂Cl, —OCH₂CHCl₂, —(C=O)OCH₂CH₃, —(C=O)OCH₂CH₃, —(C=O)OCH₃, —(C=O)OH, —(C=O)NHCH₂CH₃, —(C=O)NHCH₃, —(C=O)NH₂, —SO₂N(CH₃)₂, —SO₂NHCH₂CH₃, —SO₂NHCH₃, and —SO₂NH₂; and wherein R⁵, when present, is selected from hydrogen and methyl.

In a further aspect, Ar is a moiety having a structure represented by a formula:

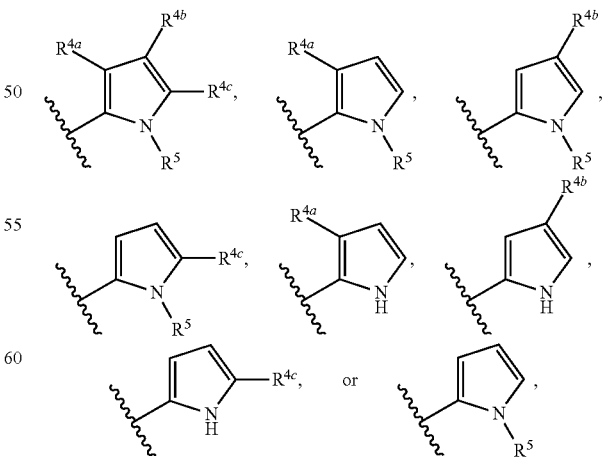

wherein each of R⁴ᵃ, R⁴ᵇ, and R⁴ᶜ, when present, is independently from hydrogen, —F, —Cl, —Br, methyl, ethyl, isopropyl, —CH$_2$F, —CHF$_2$, —CF$_3$, —CH$_2$CF$_3$, —OCH$_3$, —OCF$_3$, —OCH$_2$CF$_3$, —(C=O)OH, —(C=O)NH$_2$, —SO$_2$NHCH$_3$, and —SO$_2$NH$_2$; and wherein R$^5$, when present, is selected from hydrogen and methyl.

In a further aspect, Ar is a moiety having a structure represented by a formula:

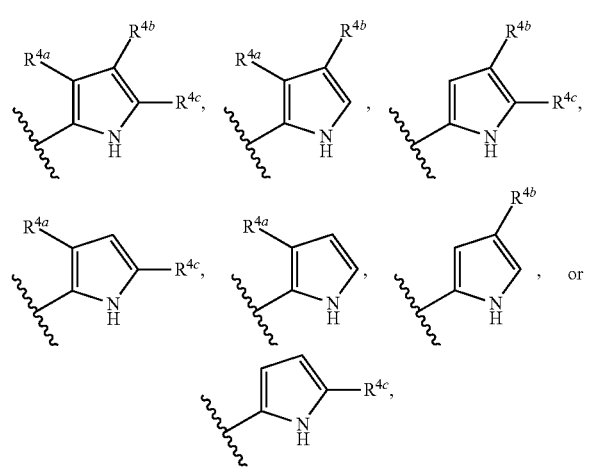

wherein each of R$^{4a}$, R$^{4b}$, and R$^{4c}$, when present, is independently selected from hydrogen, halo, cyano, hydroxyl, —NH$_2$, C1-C3 alkyl, C1-C3 monoalkyl, C1-C3 polyhaloalkyl, C1-C3 alkoxy, C1-C3 monohaloalkoxy, C1-C3 polyhaloalkyl, C1-C3 alkoxy, C1-C3 monohaloalkoxy, C1-C3 polyhaloalkoxy, —(C=O)OR$^9$, —(C=O)NR$^{10a}$R$^{10b}$, —SO$_2$NR$^{10a}$R$^{10b}$, —SR$^9$, and —SO$_2$R$^9$.

In a further aspect, Ar is a moiety having a structure represented by a formula:

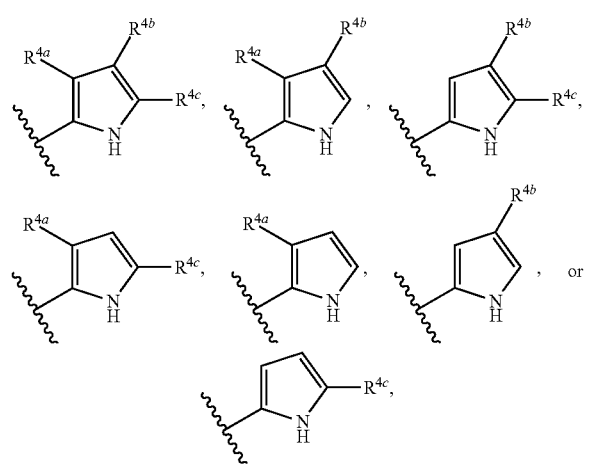

wherein each of R$^{4a}$, R$^{4b}$, and R$^{4c}$, when present, is independently from hydrogen, —F, —Cl, —Br, cyano, hydroxyl, —NH$_2$, methyl, ethyl, propyl, isopropyl, —CH$_2$F, —CHF$_2$, —CF$_3$, —CH$_2$Cl, —CHCl$_2$, —CCl$_3$, —CH$_2$CH$_2$F, —CH$_2$CHF$_2$, —CH$_2$CF$_3$, —CH$_2$CH$_2$Cl, —CH$_2$CHCl$_2$, —CH$_2$CCl$_3$, —OCH$_3$, —OCH$_2$CH$_3$, —OCH$_2$F, —OCHF$_2$, —OCF$_3$, —OCH$_2$Cl, —OCHCl$_2$, —OCCl$_3$, —OCH$_2$CH$_2$F, —OCH$_2$CHF$_2$, —OCH$_2$CF$_3$, —OCH$_2$CH$_2$Cl, —OCH$_2$CHCl$_2$, —(C=O)OCH$_2$CH$_3$, —(C=O)OCH$_2$CH$_3$, —(C=O)OCH$_3$, —(C=O)OH, —(C=O)NHCH$_2$CH$_3$, —(C=O)NHCH$_3$, —(C=O)NH$_2$, —SO$_2$N(CH$_3$)$_2$, —SO$_2$NHCH$_2$CH$_3$, —SO$_2$NHCH$_3$, and —SO$_2$NH$_2$.

In a further aspect, Ar is a moiety having a structure represented by a formula:

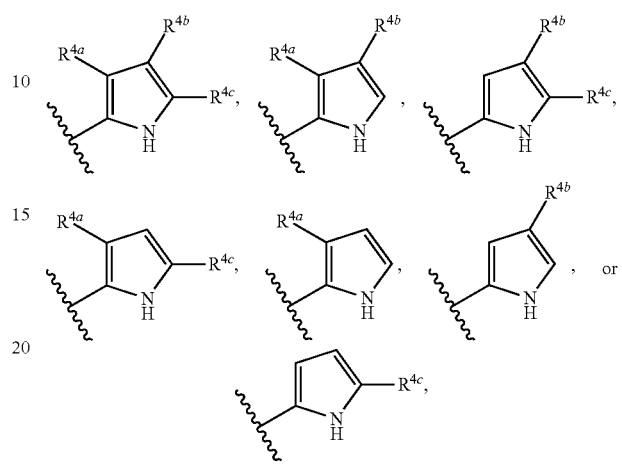

wherein each of R$^{4a}$, R$^{4b}$, and R$^{4c}$, when present, is independently from hydrogen, —F, —Cl, —Br, methyl, ethyl, isopropyl, —CH$_2$F, —CHF$_2$, —CF$_3$, —CH$_2$CF$_3$, —OCH$_3$, —OCF$_3$, —OCH$_2$CF$_3$, —(C=O)OH, —(C=O)NH$_2$, —SO$_2$NHCH$_3$, and —SO$_2$NH$_2$.

In a further aspect, Ar is a moiety having a structure represented by a formula:

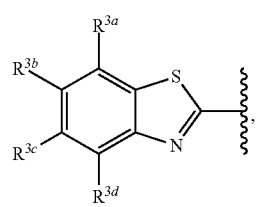

wherein each of R$^{3a}$, R$^{3b}$, R$^{3c}$, and R$^{3d}$, when present, is independently selected from hydrogen, halo, cyano, hydroxyl, —NH$_2$, C1-C3 alkyl, C1-C3 monoalkyl, C1-C3 polyhaloalkyl, C1-C3 alkoxy, C1-C3 monohaloalkoxy, C1-C3 polyhaloalkyl, C1-C3 alkoxy, C1-C3 monohaloalkoxy, C1-C3 polyhaloalkoxy, —(C=O)OR$^9$, —(C=O)NR$^{10a}$R$^{10b}$, —SO$_2$NR$^{10a}$R$^{10b}$, —SR$^9$, and —SO$_2$R$^9$, provided that at least one of R$^{3a}$, R$^{3b}$, R$^{3c}$, and R$^{3d}$ is hydrogen.

In a further aspect, Ar is a moiety having a structure represented by a formula:

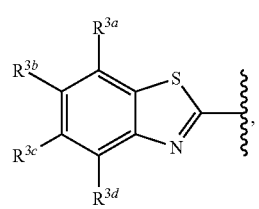

wherein each of R$^{3a}$, R$^{3b}$, R$^{3c}$, and R$^{3d}$, when present, is independently selected from hydrogen, —F, —Cl, —Br, cyano, hydroxyl, —NH$_2$, methyl, ethyl, propyl, isopropyl, —CH$_2$F, —CHF$_2$, —CF$_3$, —CH$_2$Cl, —CHCl$_2$, —CCl$_3$, —CH$_2$CH$_2$F, —CH$_2$CHF$_2$, —CH$_2$CF$_3$, —CH$_2$CH$_2$Cl, —CH$_2$CHCl$_2$, —CH$_2$CCl$_3$, —OCH$_3$, —OCH$_2$CH$_3$, —OCH$_2$F, —OCHF$_2$, —OCF$_3$, —OCH$_2$Cl, —OCHCl$_2$, —OCCl$_3$, —OCH$_2$CH$_2$F, —OCH$_2$CHF$_2$, —OCH$_2$CF$_3$, —OCH$_2$CH$_2$Cl, —OCH$_2$CHCl$_2$, —(C=O)OCH$_2$CH$_3$, —(C=O)OCH$_2$CH$_3$, —(C=O)OCH$_3$, —(C=O)OH, —(C=O)NHCH$_2$CH$_3$, —(C=O)NHCH$_3$, —(C=O)NH$_2$, —SO$_2$N(CH$_3$)$_2$, —SO$_2$NHCH$_2$CH$_3$, —SO$_2$NHCH$_3$, and —SO$_2$NH$_2$, provided that at least one of R$^{3a}$, R$^{3b}$, R$^{3c}$, and R$^{3d}$ are hydrogen.

In a further aspect, Ar is a moiety having a structure represented by a formula:

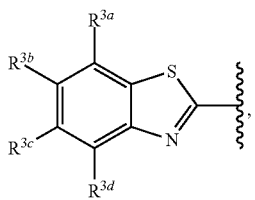

wherein each of R$^{3a}$, R$^{3b}$, R$^{3c}$, and R$^{3d}$, when present, is independently selected from hydrogen, —F, —Cl, —Br, methyl, ethyl, isopropyl, —CH$_2$F, —CHF$_2$, —CF$_3$, —CH$_2$CF$_3$, —OCH$_3$, —OCF$_3$, —OCH$_2$CF$_3$, —(C=O)OH, —(C=O)NH$_2$, —SO$_2$NHCH$_3$, and —SO$_2$NH$_2$, provided that at least one of R$^{3a}$, R$^{3b}$, R$^{3c}$, and R$^{3d}$ are hydrogen.

In a further aspect, Ar is a moiety having a structure represented by a formula:

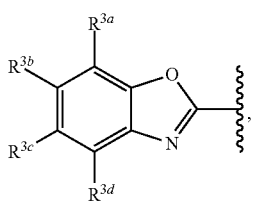

wherein each of R$^{3a}$, R$^{3b}$, R$^{3c}$, and R$^{3d}$, when present, is independently selected from hydrogen, halo, cyano, hydroxyl, —NH$_2$, C1-C3 alkyl, C1-C3 monoalkyl, C1-C3 polyhaloalkyl, C1-C3 alkoxy, C1-C3 monohaloalkoxy, C1-C3 polyhaloalkyl, C1-C3 alkoxy, C1-C3 monohaloalkoxy, C1-C3 polyhaloalkyl, —(C=O)OR$^9$, —(C=O)NR$^{10a}$R$^{10b}$, —SO$_2$NR$^{10a}$R$^{10b}$, —SR$^9$, and —SO$_2$R$^9$, provided that at least one of R$^{3a}$, R$^{3b}$, R$^{3c}$, and R$^{3d}$ are hydrogen.

In a further aspect, Ar is a moiety having a structure represented by a formula:

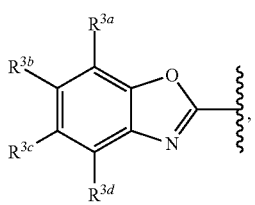

wherein each of R$^{3a}$, R$^{3b}$, R$^{3c}$, and R$^{3d}$, when present, is independently selected from hydrogen, —F, —Cl, —Br, cyano, hydroxyl, —NH$_2$, methyl, ethyl, propyl, isopropyl, —CH$_2$F, —CHF$_2$, —CF$_3$, —CH$_2$Cl, —CHCl$_2$, —CCl$_3$, —CH$_2$CH$_2$F, —CH$_2$CHF$_2$, —CH$_2$CF$_3$, —CH$_2$CH$_2$Cl, —CH$_2$CHCl$_2$, —CH$_2$CCl$_3$, —OCH$_3$, —OCH$_2$CH$_3$, —OCH$_2$F, —OCHF$_2$, —OCF$_3$, —OCH$_2$Cl, —OCHCl$_2$, —OCCl$_3$, —OCH$_2$CH$_2$F, —OCH$_2$CHF$_2$, —OCH$_2$CF$_3$, —OCH$_2$CH$_2$Cl, —OCH$_2$CHCl$_2$, —(C=O)OCH$_2$CH$_3$, —(C=O)OCH$_2$CH$_3$, —(C=O)OCH$_3$, —(C=O)OH, —(C=O)NHCH$_2$CH$_3$, —(C=O)NHCH$_3$, —(C=O)NH$_2$, —SO$_2$N(CH$_3$)$_2$, —SO$_2$NHCH$_2$CH$_3$, —SO$_2$NHCH$_3$, and —SO$_2$NH$_2$, provided that at least one of R$^{3a}$, R$^{3b}$, R$^{3c}$, and R$^{3d}$ are hydrogen.

In a further aspect, Ar is a moiety having a structure represented by a formula:

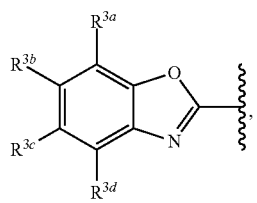

wherein each of R$^{3a}$, R$^{3b}$, R$^{3c}$, and R$^{3d}$, when present, is independently selected from hydrogen, —F, —Cl, —Br, methyl, ethyl, isopropyl, —CH$_2$F, —CHF$_2$, —CF$_3$, —CH$_2$CF$_3$, —OCH$_3$, —OCF$_3$, —OCH$_2$CF$_3$, —(C=O)OH, —(C=O)NH$_2$, —SO$_2$NHCH$_3$, and —SO$_2$NH$_2$, provided that at least one of R$^{3a}$, R$^{3b}$, R$^{3c}$, and R$^{3d}$ are hydrogen.

In a further aspect, Ar is a moiety having a structure represented by a formula:

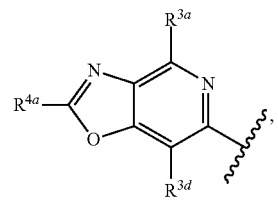

wherein each of R$^{3a}$, R$^{3b}$, R$^{3c}$, and R$^{3d}$, when present, is independently selected from hydrogen, halo, cyano, hydroxyl, —NH$_2$, C1-C3 alkyl, C1-C3 monoalkyl, C1-C3 polyhaloalkyl, C1-C3 alkoxy, C1-C3 monohaloalkoxy, C1-C3 polyhaloalkoxy, —(C=O)OR$^9$, —(C=O)NR$^{10a}$R$^{10b}$, —SO$_2$NR$^{10a}$R$^{10b}$, —SR$^9$, and —SO$_2$R$^9$; and wherein R$^{4a}$, when present, is selected from hydrogen, halo, cyano, hydroxyl, —NH$_2$, C1-C3 alkyl, C1-C3 monoalkyl, C1-C3 polyhaloalkyl, C1-C3 alkoxy, C1-C3 monohaloalkoxy, C1-C3 polyhaloalkyl, C1-C3 alkoxy, C1-C3 monohaloalkoxy, C1-C3 polyhaloalkoxy, —(C=O)OR$^9$, —(C=O)NR$^{10a}$R$^{10b}$, —SO$_2$NR$^{10a}$R$^{10b}$, —SR$^9$, and —SO$_2$R$^9$.

In a further aspect, Ar is a moiety having a structure represented by a formula:

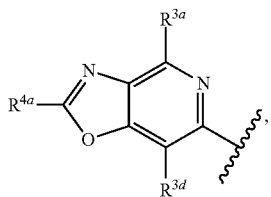

wherein each of $R^{3a}$, $R^{3b}$, $R^{3c}$, and $R^{3d}$, when present, is independently selected from hydrogen, —F, —Cl, —Br, cyano, hydroxyl, —NH$_2$, methyl, ethyl, propyl, isopropyl, —CH$_2$F, —CHF$_2$, —CF$_3$, —CH$_2$Cl, —CHCl$_2$, —CCl$_3$, —CH$_2$CH$_2$F, —CH$_2$CHF$_2$, —CH$_2$CF$_3$, —CH$_2$CH$_2$Cl, —CH$_2$CHCl$_2$, —CH$_2$CCl$_3$, —OCH$_3$, —OCH$_2$CH$_3$, —OCH$_2$F, —OCHF$_2$, —OCF$_3$, —OCH$_2$Cl, —OCHCl$_2$, —OCCl$_3$, —OCH$_2$CH$_2$F, —OCH$_2$CHF$_2$, —OCH$_2$CF$_3$, —OCH$_2$CH$_2$Cl, —OCH$_2$CHCl$_2$, —(C=O)OCH$_2$CH$_3$, —(C=O)OCH$_2$CH$_3$, —(C=O)OCH$_3$, —(C=O)OH, —(C=O)NHCH$_2$CH$_3$, —(C=O)NHCH$_3$, —(C=O)NH$_2$, —SO$_2$N(CH$_3$)$_2$, —SO$_2$NHCH$_2$CH$_3$, —SO$_2$NHCH$_3$, and —SO$_2$NH$_2$; and wherein $R^{4a}$, when present, is selected from hydrogen, —F, —Cl, —Br, cyano, hydroxyl, —NH$_2$, methyl, ethyl, propyl, isopropyl, —CH$_2$F, —CHF$_2$, —CF$_3$, —CH$_2$Cl, —CHCl$_2$, —CCl$_3$, —CH$_2$CH$_2$F, —CH$_2$CHF$_2$, —CH$_2$CF$_3$, —CH$_2$CH$_2$Cl, —CH$_2$CHCl$_2$, —CH$_2$CCl$_3$, —OCH$_3$, —OCH$_2$CH$_3$, —OCH$_2$F, —OCHF$_2$, —OCF$_3$, —OCH$_2$Cl, —OCHCl$_2$, —OCCl$_3$, —OCH$_2$CH$_2$F, —OCH$_2$CHF$_2$, —OCH$_2$CF$_3$, —OCH$_2$CH$_2$Cl, —OCH$_2$CHCl$_2$, —(C=O)OCH$_2$CH$_3$, —(C=O)OCH$_2$CH$_3$, —(C=O)OCH$_3$, —(C=O)OH, —(C=O)NHCH$_2$CH$_3$, —(C=O)NHCH$_3$, —(C=O)NH$_2$, —SO$_2$N(CH$_3$)$_2$, —SO$_2$NHCH$_2$CH$_3$, —SO$_2$NHCH$_3$, and —SO$_2$NH$_2$.

In a further aspect, Ar is a moiety having a structure represented by a formula:

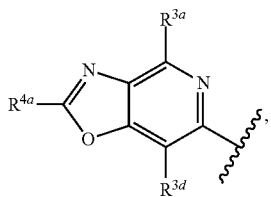

wherein each of $R^{3a}$, $R^{3b}$, $R^{3c}$, and $R^{3d}$, when present, is independently selected from hydrogen, —F, —Cl, —Br, methyl, ethyl, isopropyl, —CH$_2$F, —CHF$_2$, —CF$_3$, —CH$_2$CF$_3$, —OCH$_3$, —OCF$_3$, —OCH$_2$CF$_3$, —(C=O)OH, —(C=O)NH$_2$, —SO$_2$NHCH$_3$, and —SO$_2$NH$_2$; and wherein $R^{4a}$, when present, is selected from hydrogen, —F, —Cl, —Br, methyl, ethyl, isopropyl, —CH$_2$F, —CHF$_2$, —CF$_3$, —CH$_2$CF$_3$, —OCH$_3$, —OCF$_3$, —OCH$_2$CF$_3$, —(C=O)OH, —(C=O)NH$_2$, —SO$_2$NHCH$_3$, and —SO$_2$NH$_2$.

In a further aspect, Ar is a moiety having a structure represented by a formula:

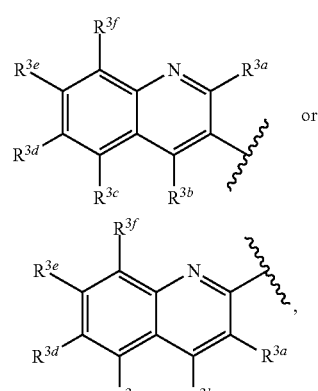

wherein each of $R^{3a}$, $R^{3b}$, $R^{3c}$, $R^{3d}$, $R^{3e}$, and $R^{3f}$, when present, is independently selected from hydrogen, halo, cyano, hydroxyl, —NH$_2$, C1-C3 alkyl, C1-C3 monoalkyl, C1-C3 polyhaloalkyl, C1-C3 alkoxy, C1-C3 monohaloalkoxy, C1-C3 polyhaloalkyl, C1-C3 alkoxy, C1-C3 monohaloalkoxy, C1-C3 polyhaloalkoxy, —(C=O)OR$^9$, —(C=O)NR$^{10a}$R$^{10b}$, —SO$_2$NR$^{10a}$R$^{10b}$, —SR$^9$, and —SO$_2$R$^9$, provided that at least three of $R^{3a}$, $R^{3b}$, $R^{3c}$, $R^{3d}$, $R^{3e}$, and $R^{3f}$ are hydrogen.

In a further aspect, Ar is a moiety having a structure represented by a formula:

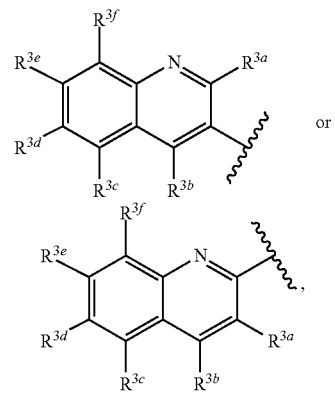

wherein each of $R^{3a}$, $R^{3b}$, $R^{3c}$, $R^{3d}$, $R^{3e}$, and $R^{3f}$, when present, is independently selected from hydrogen, —F, —Cl, —Br, cyano, hydroxyl, —NH$_2$, methyl, ethyl, propyl, isopropyl, —CH$_2$F, —CHF$_2$, —CF$_3$, —CH$_2$Cl, —CHCl$_2$, —CCl$_3$, —CH$_2$CH$_2$F, —CH$_2$CHF$_2$, —CH$_2$CF$_3$, —CH$_2$CH$_2$Cl, —CH$_2$CHCl$_2$, —CH$_2$CCl$_3$, —OCH$_3$, —OCH$_2$CH$_3$, —OCH$_2$F, —OCHF$_2$, —OCF$_3$, —OCH$_2$Cl, —OCHCl$_2$, —OCCl$_3$, —OCH$_2$CH$_2$F, —OCH$_2$CHF$_2$, —OCH$_2$CF$_3$, —OCH$_2$CH$_2$Cl, —OCH$_2$CHCl$_2$, —(C=O)OCH$_2$CH$_3$, —(C=O)OCH$_2$CH$_3$, —(C=O)OCH$_3$, —(C=O)OH, —(C=O)NHCH$_2$CH$_3$, —(C=O)NHCH$_3$, —(C=O)NH$_2$, —SO$_2$N(CH$_3$)$_2$, —SO$_2$NHCH$_2$CH$_3$, —SO$_2$NHCH$_3$, and —SO$_2$NH$_2$, provided that at least three of $R^{3a}$, $R^{3b}$, $R^{3c}$, $R^{3d}$, $R^{3e}$, and $R^{3f}$ are hydrogen.

In a further aspect, Ar is a moiety having a structure represented by a formula:

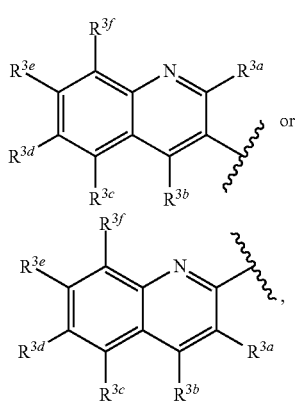

wherein each of $R^{3a}$, $R^{3b}$, $R^{3c}$, $R^{3d}$, $R^{3e}$, and $R^{3f}$, when present, is independently selected from hydrogen, —F, —Cl, —Br, methyl, ethyl, isopropyl, —CH$_2$F, —CHF$_2$, —CF$_3$, —CH$_2$CF$_3$, —OCH$_3$, —OCF$_3$, —OCH$_2$CF$_3$, —(C═O)OH, —(C═O)NH$_2$, —SO$_2$NHCH$_3$, and —SO$_2$NH$_2$, provided that at least three of $R^{3a}$, $R^{3b}$, $R^{3c}$, $R^{3d}$, $R^{3e}$, and $R^{3f}$ are hydrogen.

In a further aspect, Ar is a moiety having a structure represented by a formula:

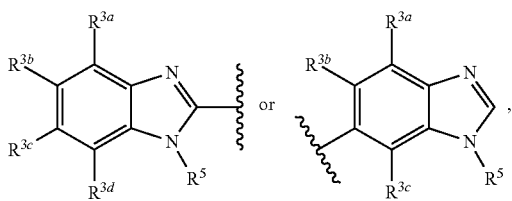

wherein each of $R^{3a}$, $R^{3b}$, $R^{3c}$, and $R^{3d}$, when present, is independently selected from hydrogen, halo, cyano, hydroxyl, —NH$_2$, C1-C3 alkyl, C1-C3 monoalkyl, C1-C3 polyhaloalkyl, C1-C3 alkoxy, C1-C3 monohaloalkoxy, C1-C3 polyhaloalkyl, C1-C3 alkoxy, C1-C3 monohaloalkoxy, C1-C3 polyhaloalkoxy, —(C═O)OR$^9$, —(C═O)NR$^{10a}$R$^{10b}$, —SO$_2$NR$^{10a}$R$^{10b}$, —SR$^9$, and —SO$_2$R$^9$; wherein R$^5$, when present, is selected from hydrogen and C1-C3 alkyl; and wherein at least one $R^{3a}$, $R^{3b}$, $R^{3c}$, and R$^5$ is hydrogen.

In a further aspect, Ar is a moiety having a structure represented by a formula:

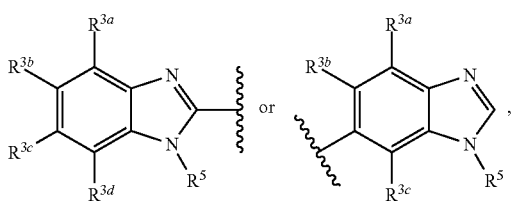

wherein each of $R^{3a}$, $R^{3b}$, $R^{3c}$, and $R^{3d}$, when present, is independently selected from hydrogen, —F, —Cl, —Br, cyano, hydroxyl, —NH$_2$, methyl, ethyl, propyl, isopropyl, —CH$_2$F, —CHF$_2$, —CF$_3$, —CH$_2$Cl, —CHCl$_2$, —CCl$_3$, —CH$_2$CH$_2$F, —CH$_2$CHF$_2$, —CH$_2$CF$_3$, —CH$_2$CH$_2$Cl, —CH$_2$CHCl$_2$, —CH$_2$CCl$_3$, —OCH$_3$, —OCH$_2$CH$_3$, —OCH$_2$F, —OCHF$_2$, —OCF$_3$, —OCH$_2$Cl, —OCHCl$_2$, —OCCl$_3$, —OCH$_2$CH$_2$F, —OCH$_2$CHF$_2$, —OCH$_2$CF$_3$, —OCH$_2$CH$_2$Cl, —OCH$_2$CHCl$_2$, —(C═O)OCH$_2$CH$_3$, —(C═O)OCH$_2$CH$_3$, —(C═O)OCH$_3$, —(C═O)OH, —(C═O)NHCH$_2$CH$_3$, —(C═O)NHCH$_3$, —(C═O)NH$_2$, —SO$_2$N(CH$_3$)$_2$, —SO$_2$NHCH$_2$CH$_3$, —SO$_2$NHCH$_3$, and —SO$_2$NH$_2$; wherein R$^5$, when present, is selected from hydrogen and methyl; and wherein at least one $R^{3a}$, $R^{3b}$, $R^{3c}$, and R$^5$ is hydrogen.

In a further aspect, Ar is a moiety having a structure represented by a formula:

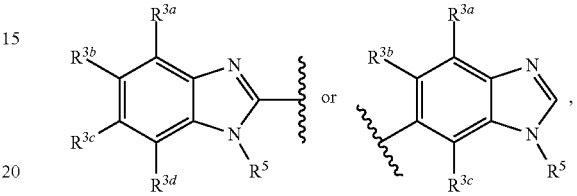

wherein each of $R^{3a}$, $R^{3b}$, $R^{3c}$, and $R^{3d}$, when present, is independently selected from hydrogen, —F, —Cl, —Br, methyl, ethyl, isopropyl, —CH$_2$F, —CHF$_2$, —CF$_3$, —CH$_2$CF$_3$, —OCH$_3$, —OCF$_3$, —OCH$_2$CF$_3$, —(C═O)OH, —(C═O)NH$_2$, —SO$_2$NHCH$_3$, and —SO$_2$NH$_2$; wherein R$^5$, when present, is selected from hydrogen and methyl; and wherein at least one $R^{3a}$, $R^{3b}$, $R^{3c}$, and R$^5$ is hydrogen.

2. Exemplary Compounds

In one aspect, a compound is selected from:

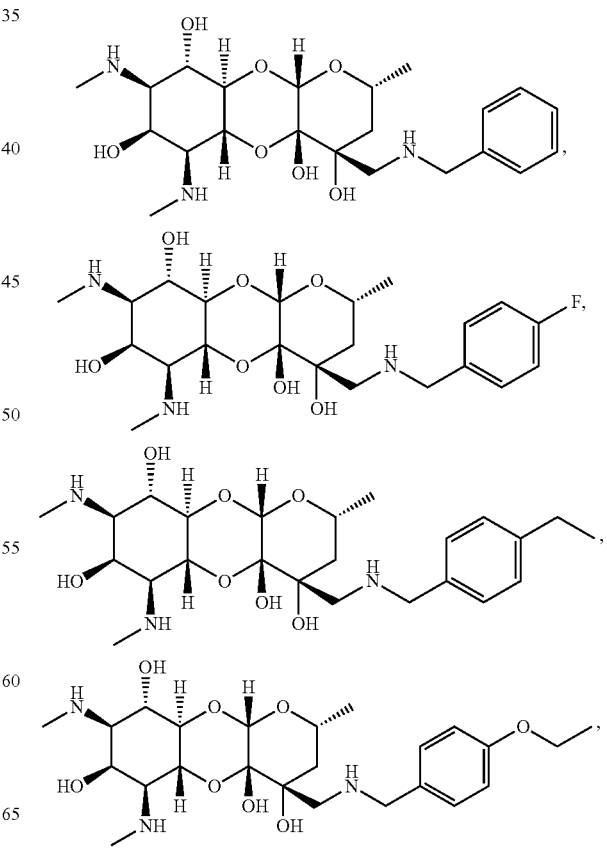

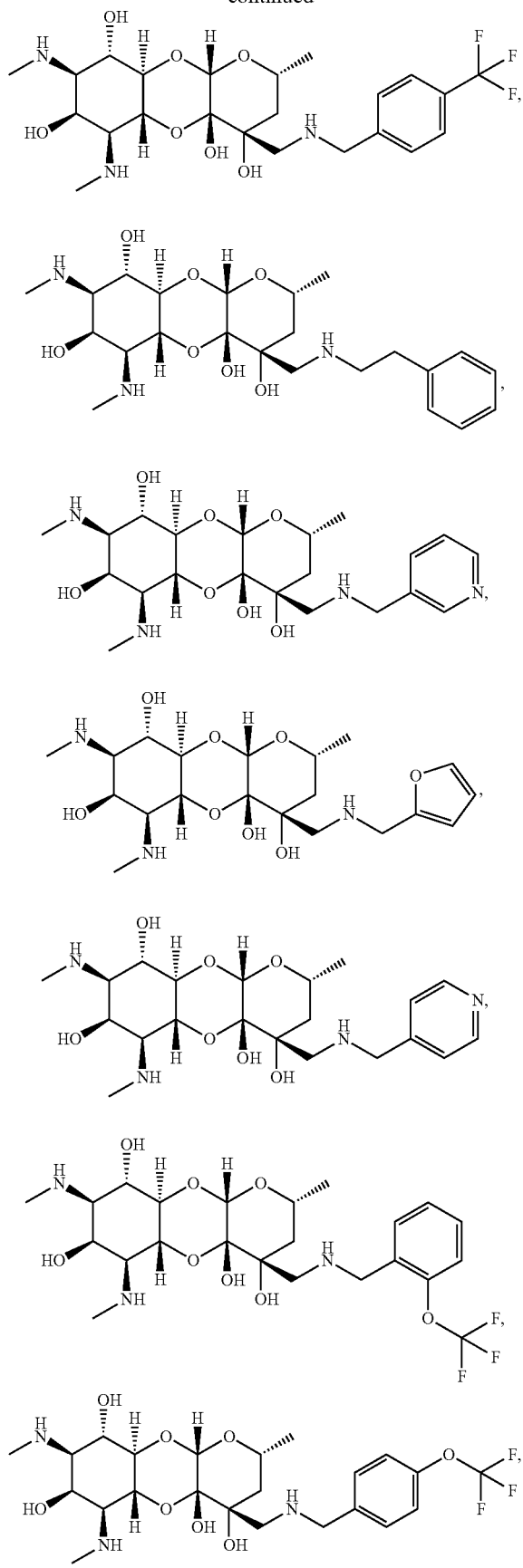
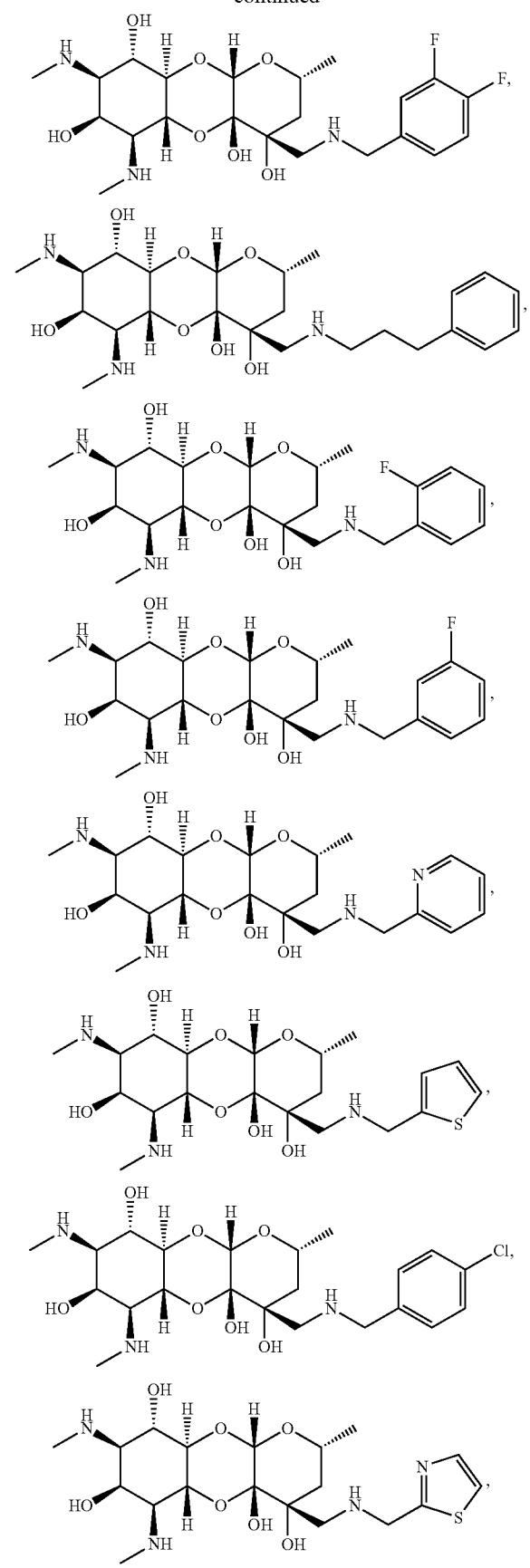

97
-continued
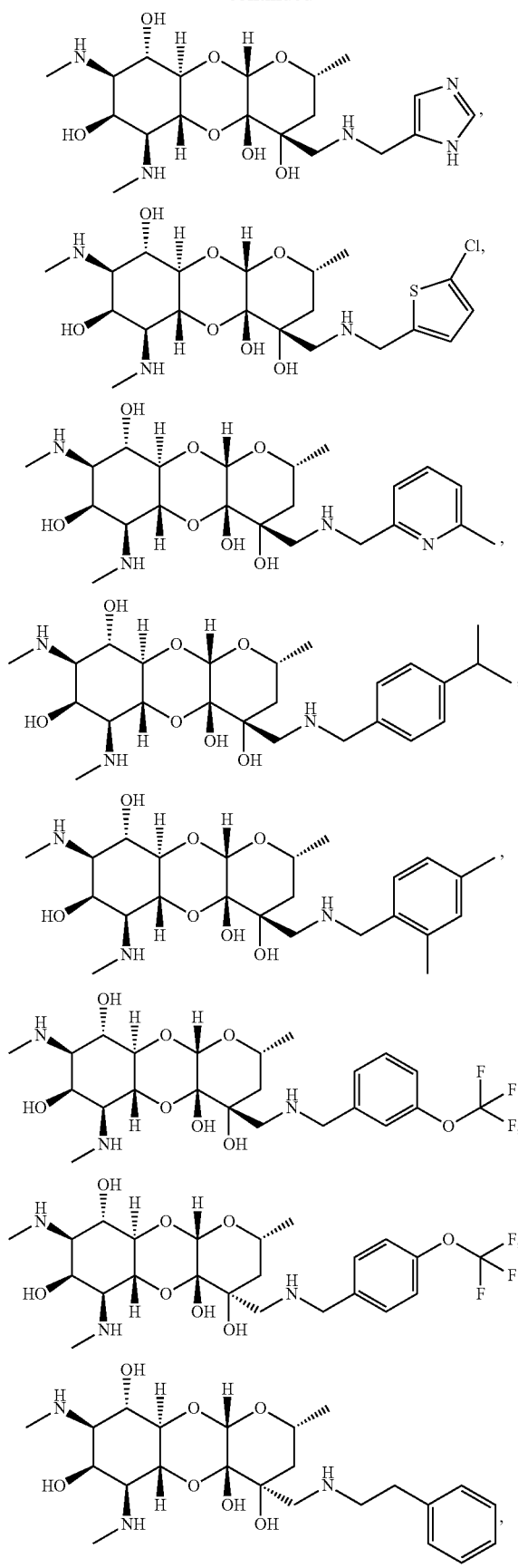
98
-continued
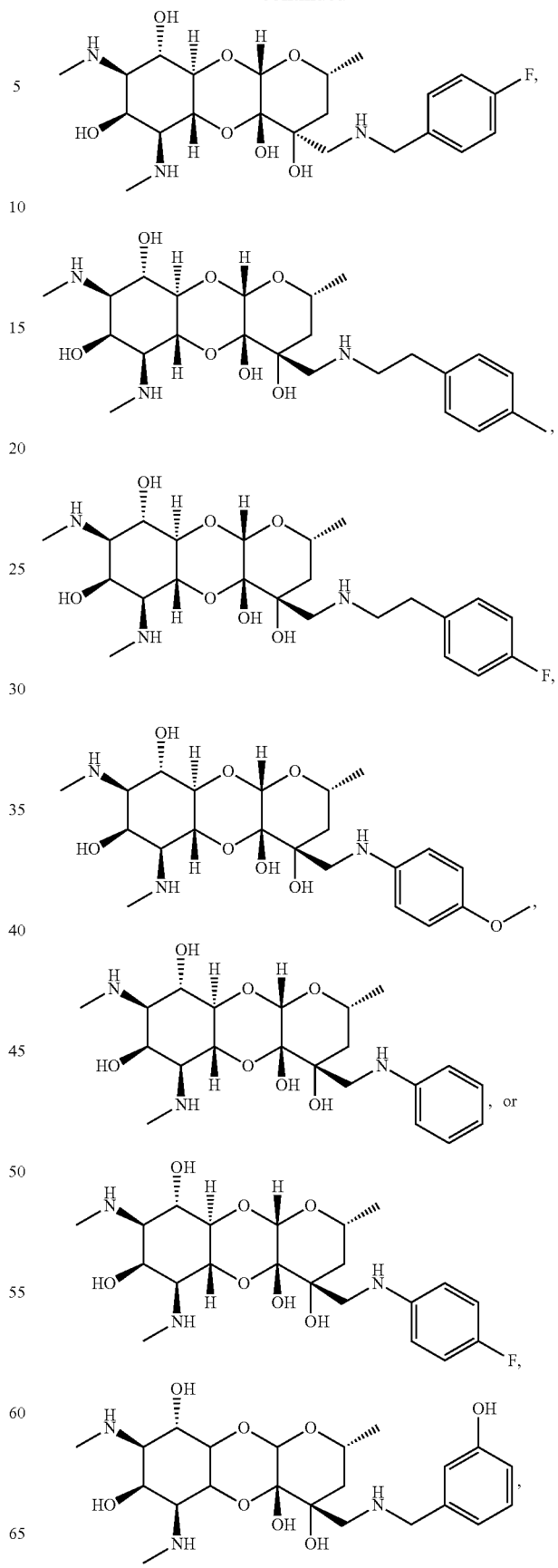

99
-continued
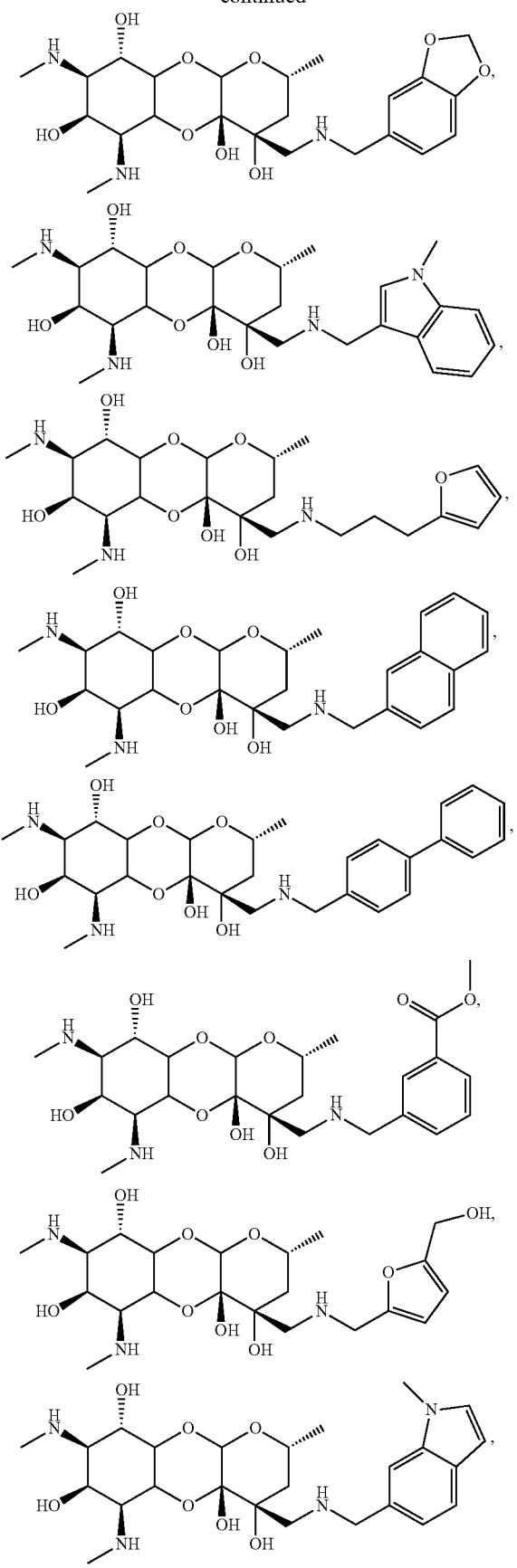
100
-continued
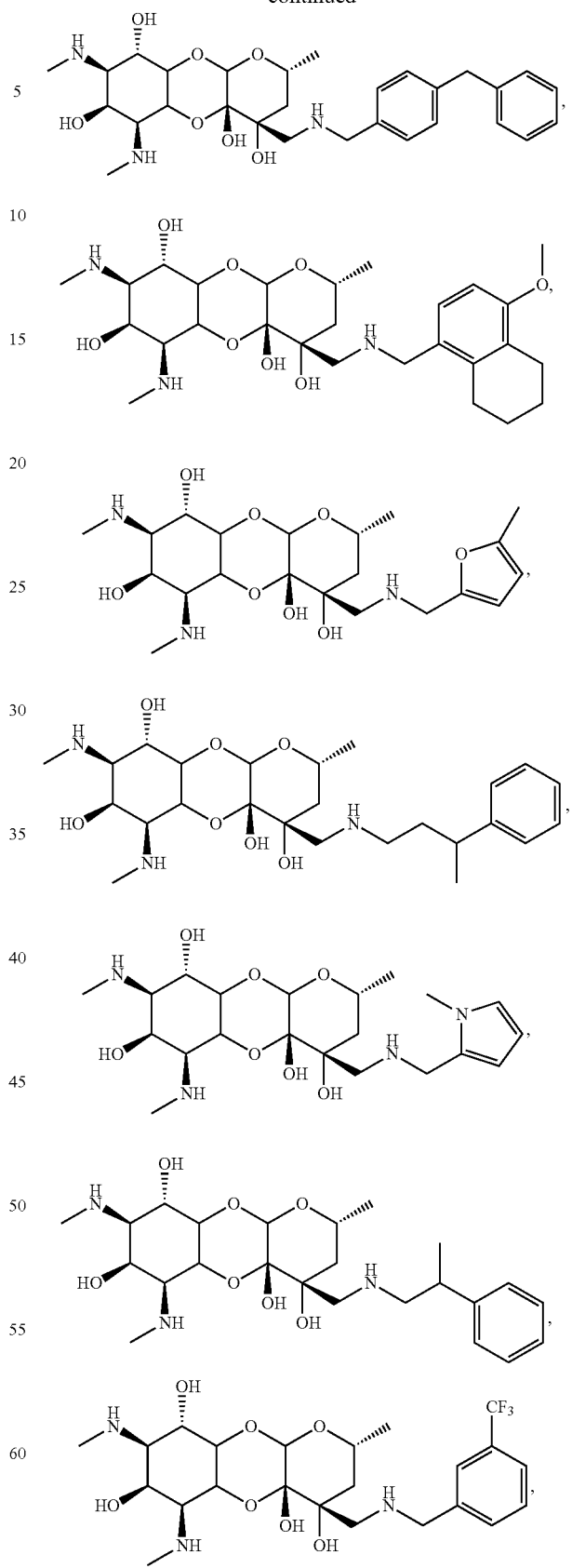
or a subgroup thereof.

In one aspect, a compound is selected from:
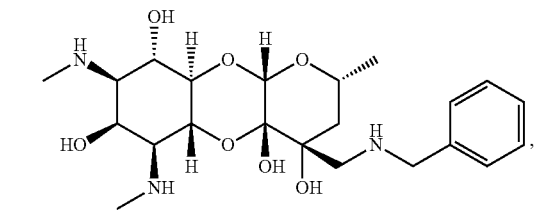,
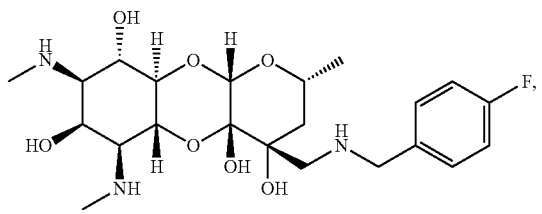,
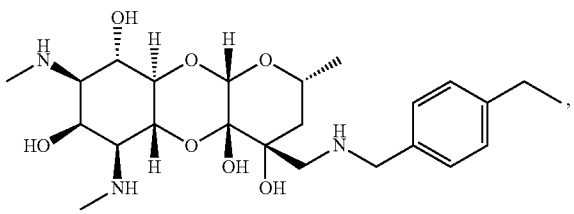,
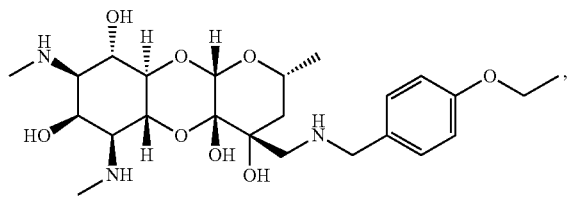,
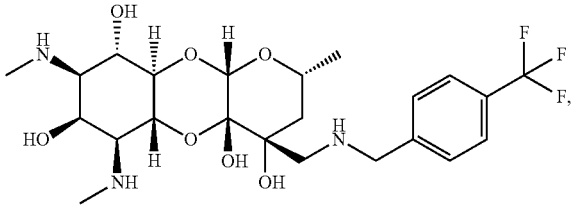,
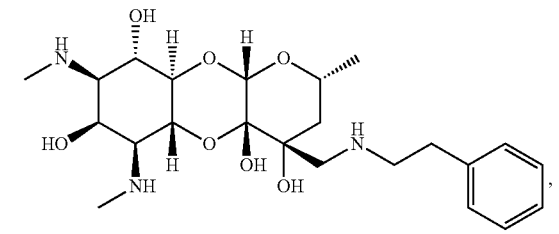,
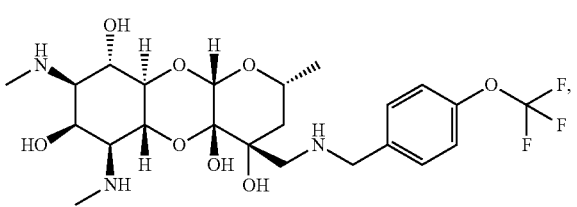,
-continued
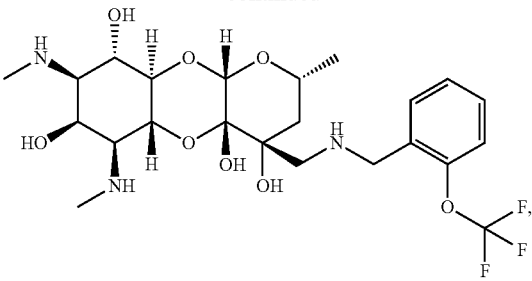,
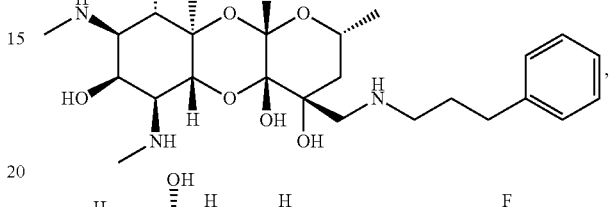,
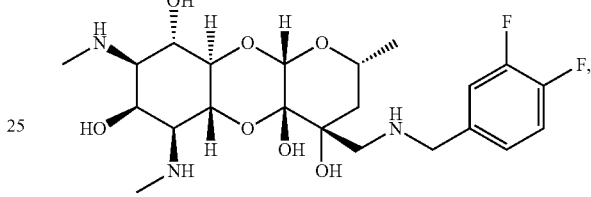,
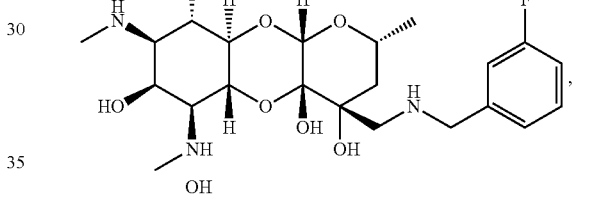,
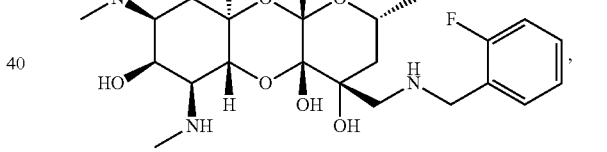,
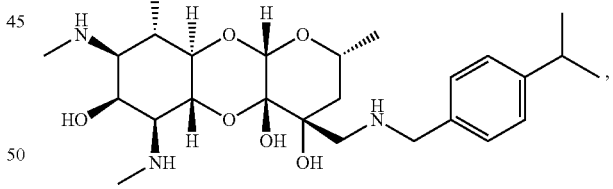,
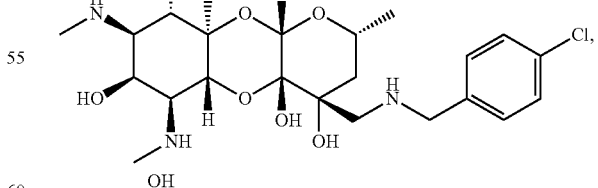,
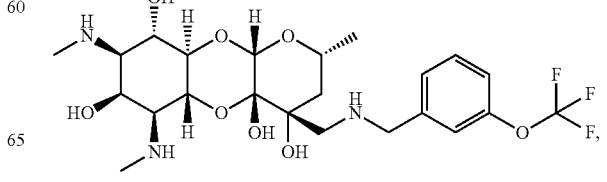, 103
-continued
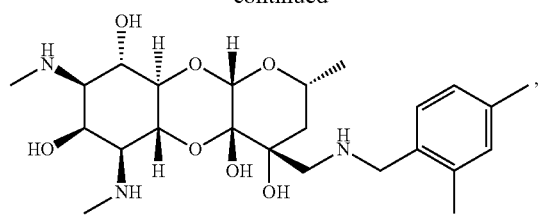
,
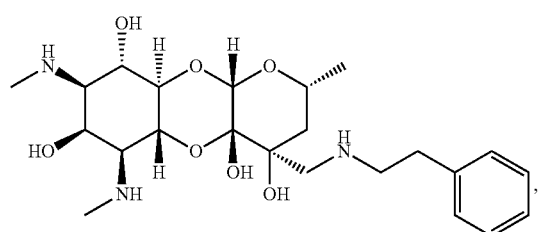
,
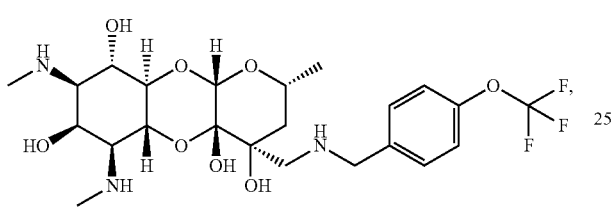
,
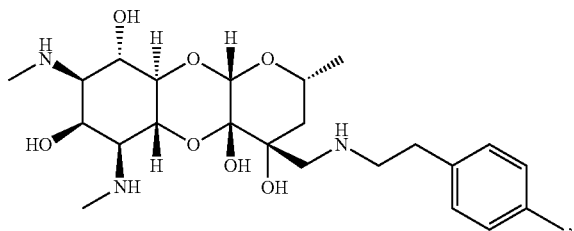
,
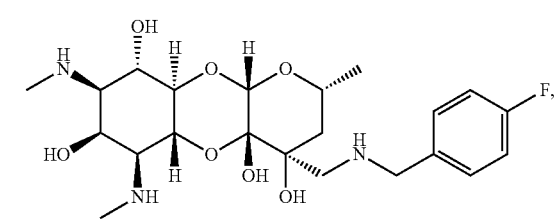
,
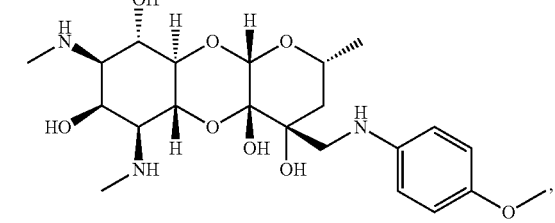
,
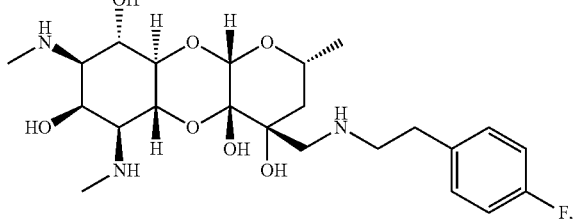
,
104
-continued
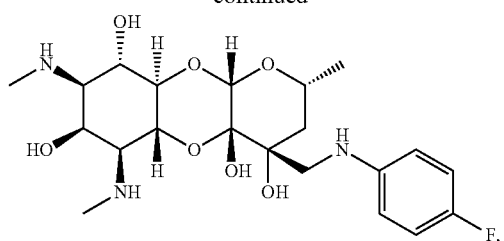
,
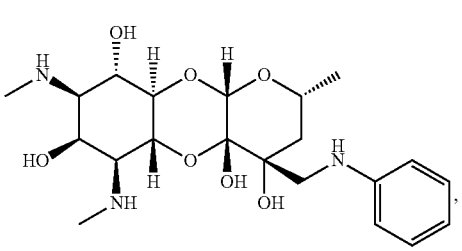
,
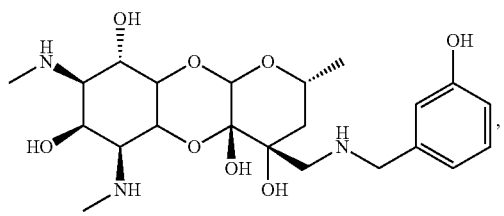
,
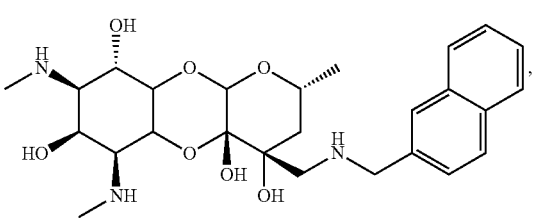
,
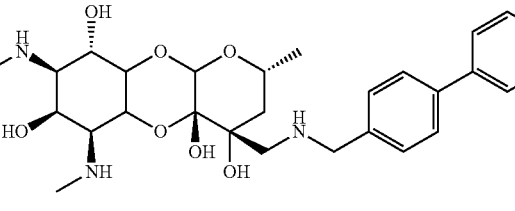
,
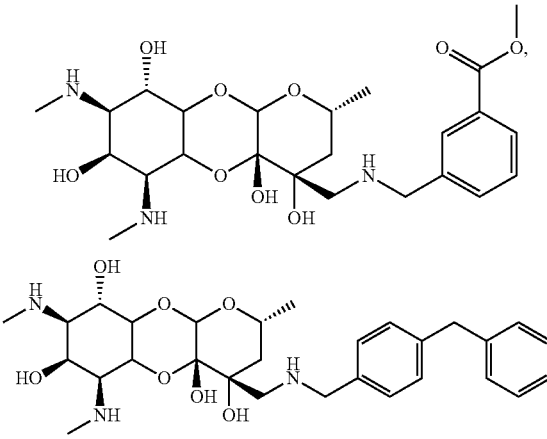
,

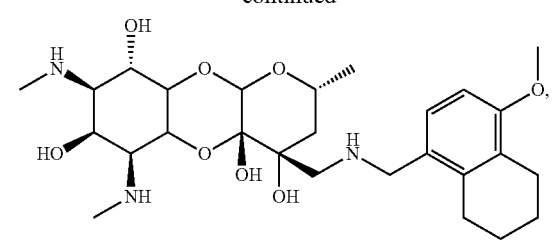
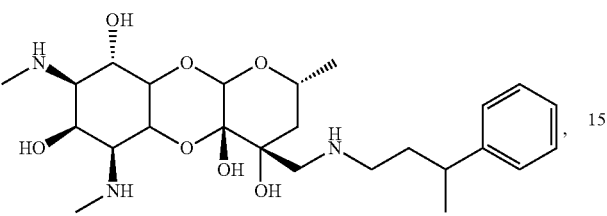
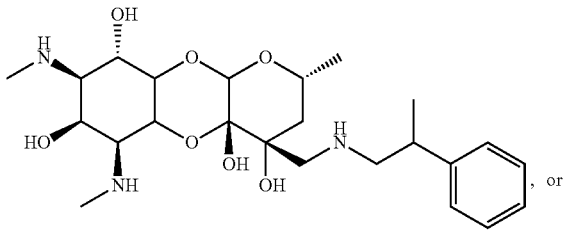,or
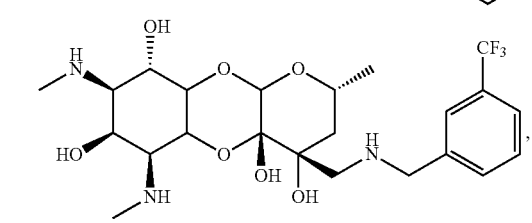
or a subgroup thereof.
In one aspect, a compound is selected from:
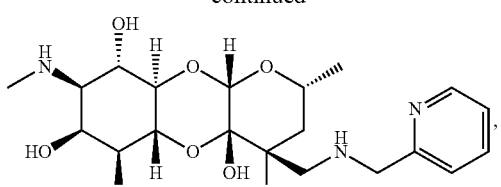
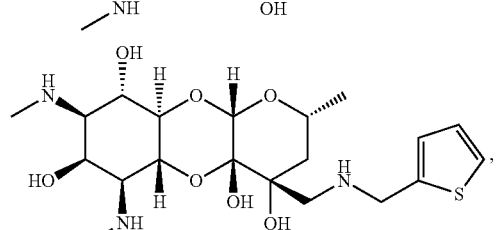
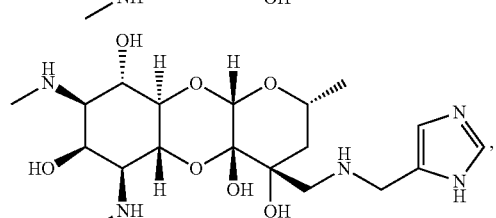
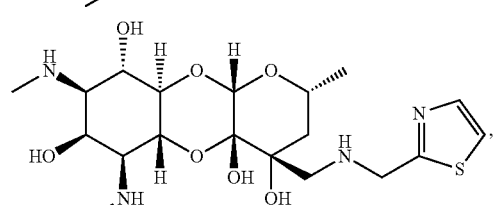
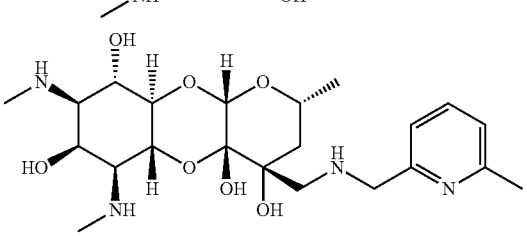
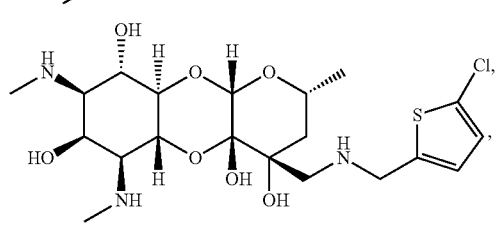
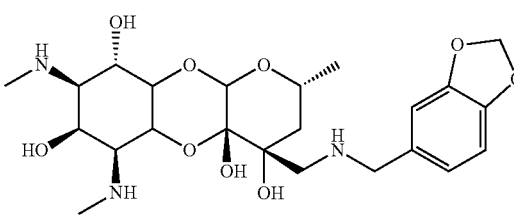
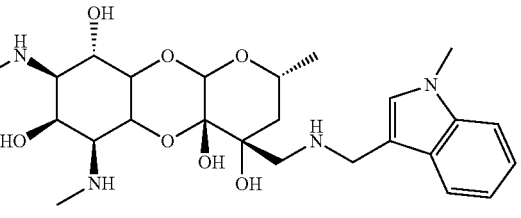
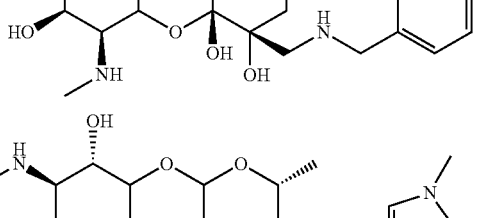
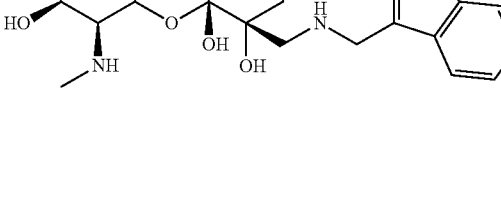
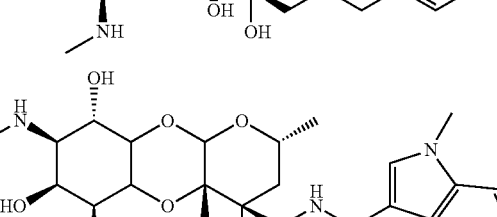

107
-continued
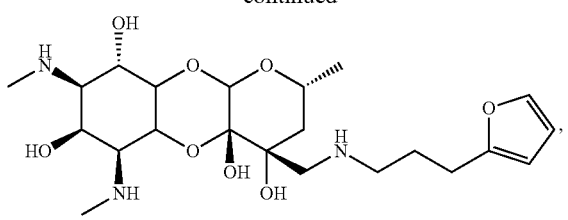
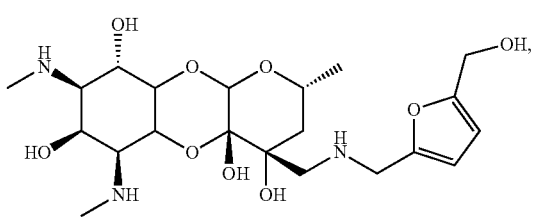
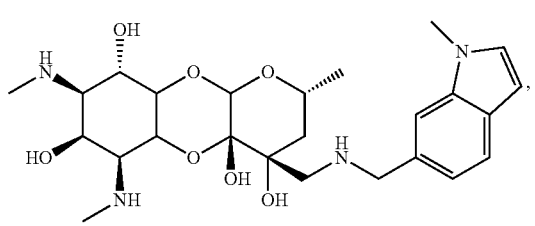
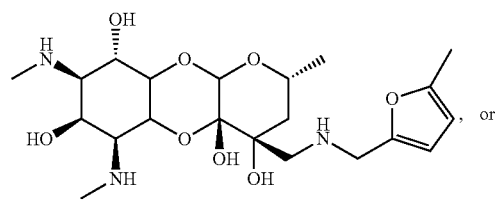,  or
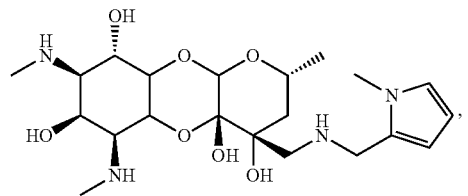,
or a subgroup thereof.
In one aspect, a compound is selected from:
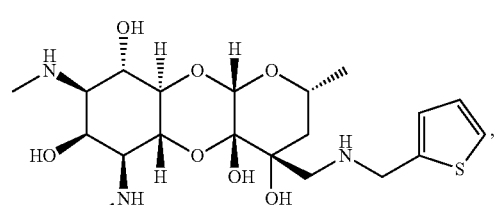,
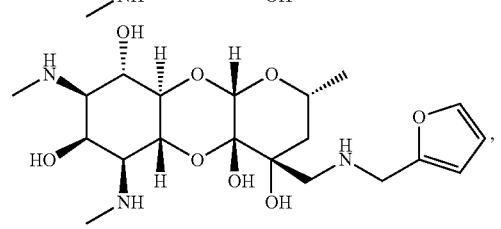,
108
-continued
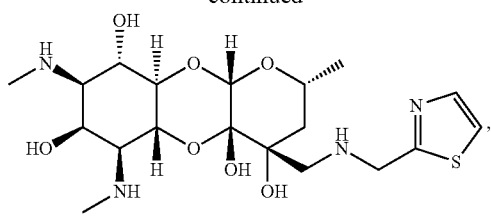,
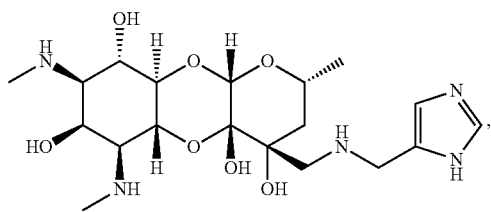,
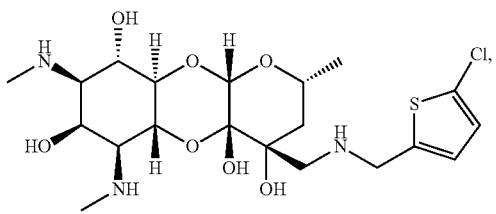,
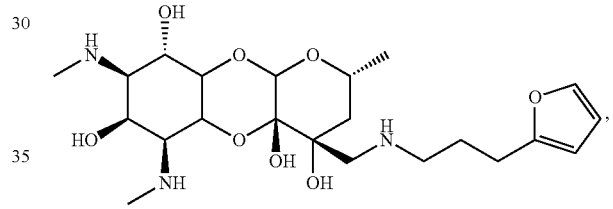,
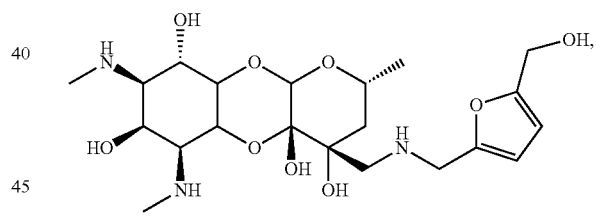,
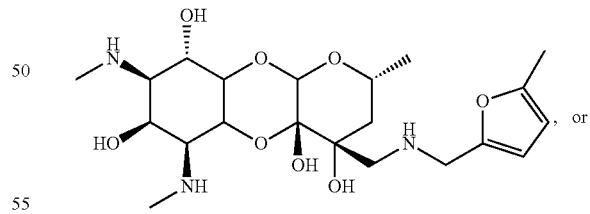,  or
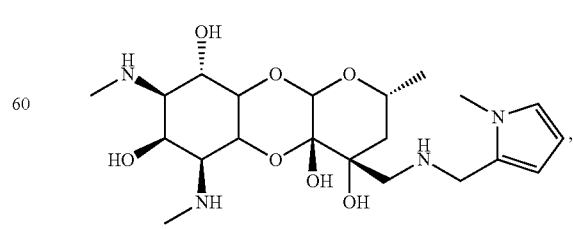,
or a subgroup thereof.

109
In one aspect, a compound is selected from:
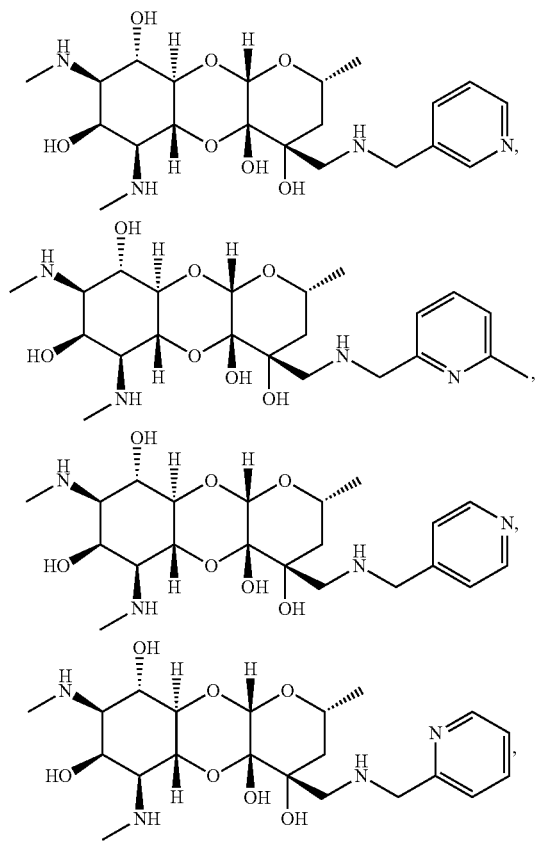
or a subgroup thereof.
In one aspect, a compound is selected from:
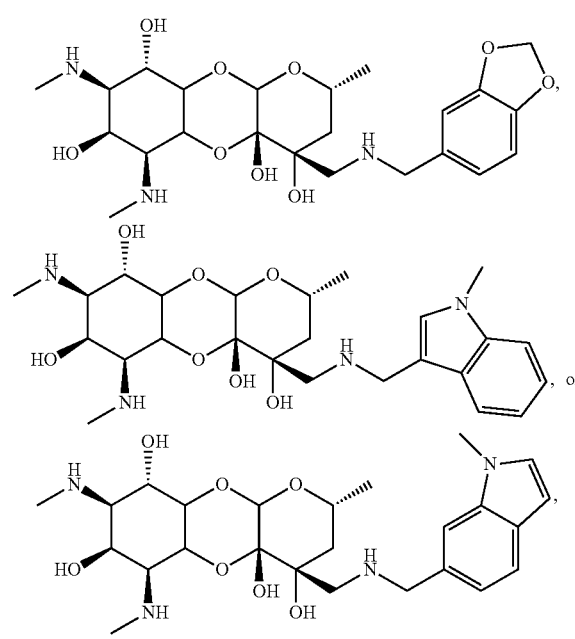
or a subgroup thereof.
110
In one aspect, a compound is selected from:
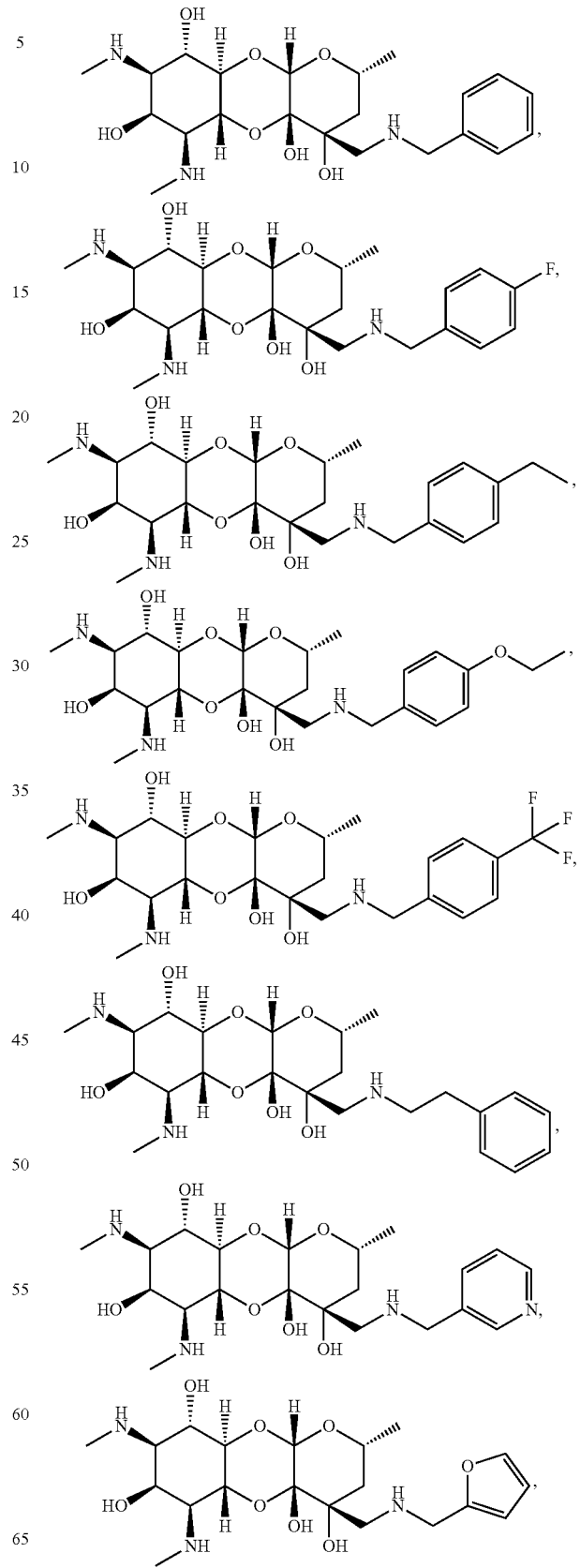

111
-continued
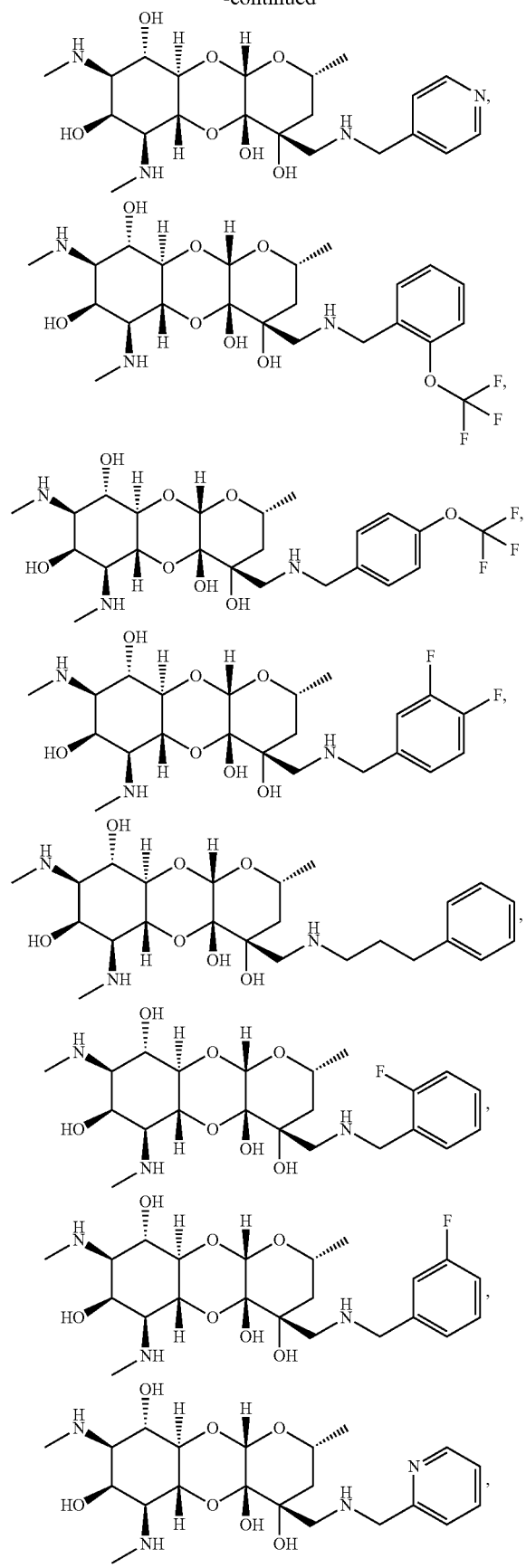
112
-continued
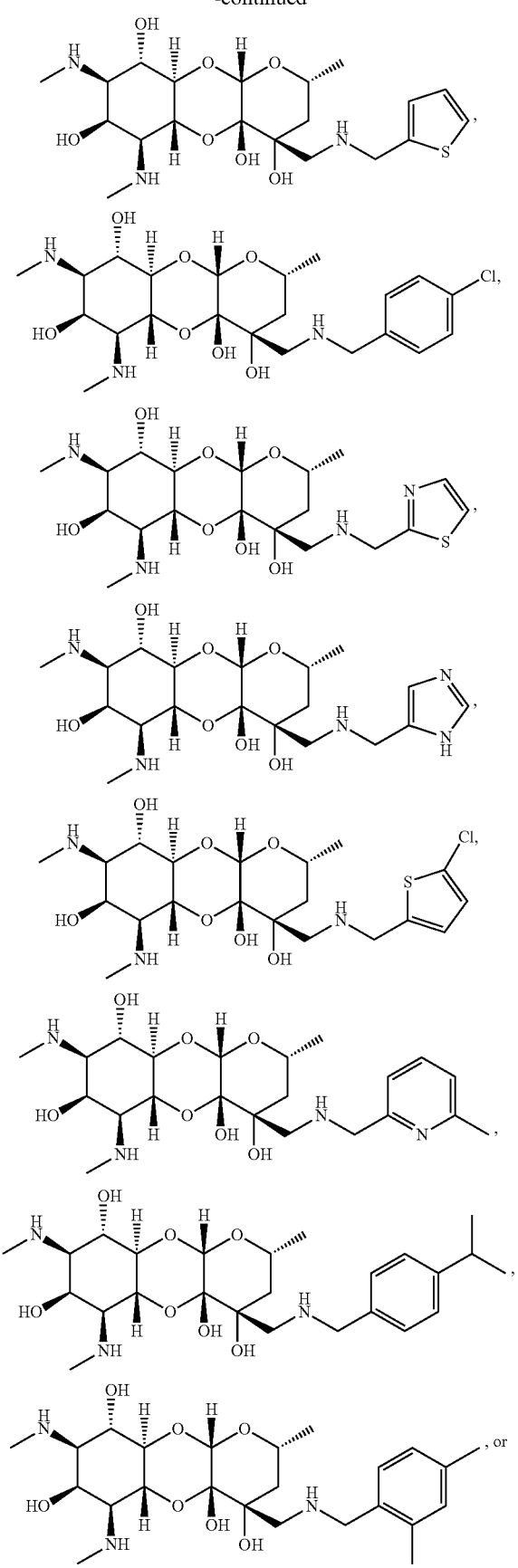

113
-continued
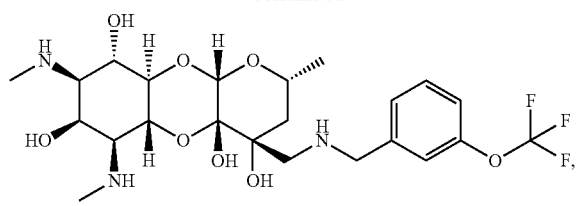
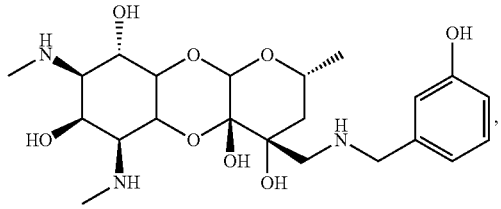 [SMILES: CN[C@@H]1[C@H](O)[C@H](NC)C2O[C@]3(O)C(OC2[C@H]1O)O[C@H](C)C[C@@]3(O)CNCc1cccc(C(F)(F)F)c1]
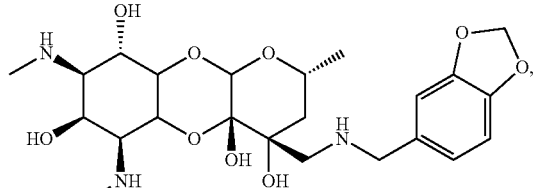
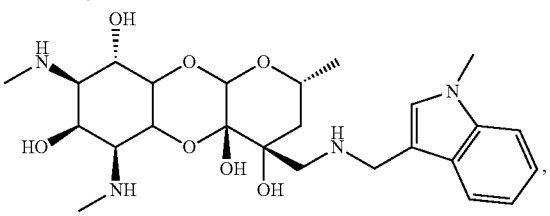
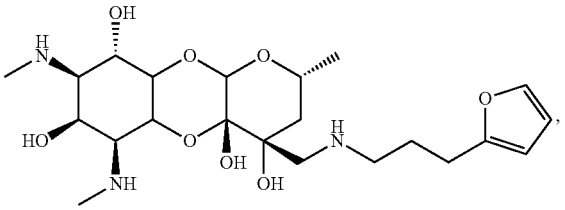
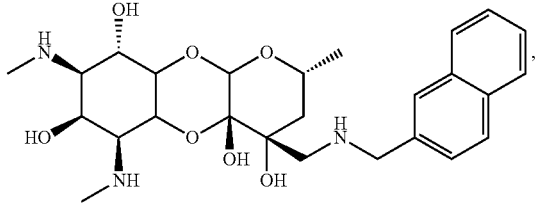
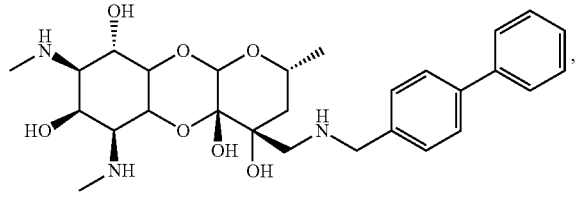
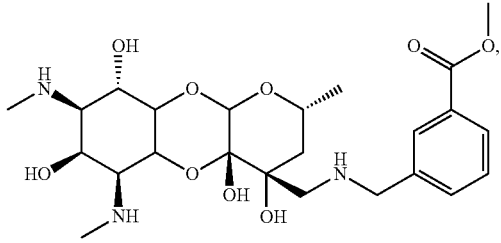
114
-continued
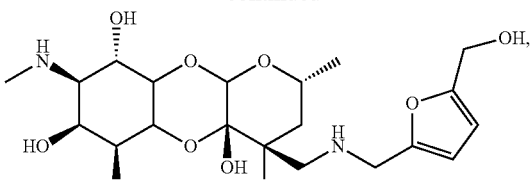
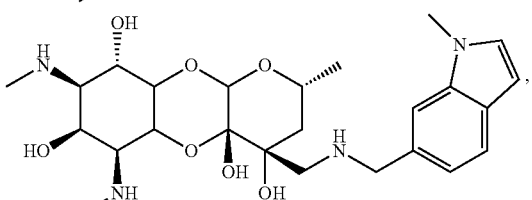
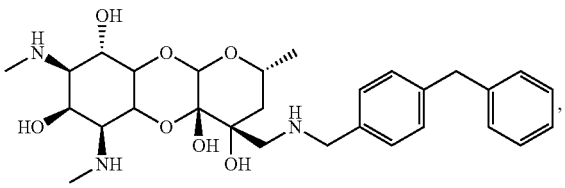
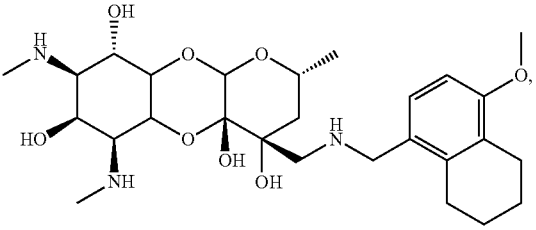
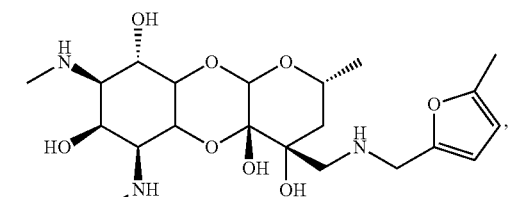
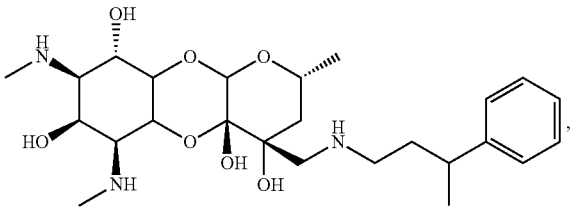
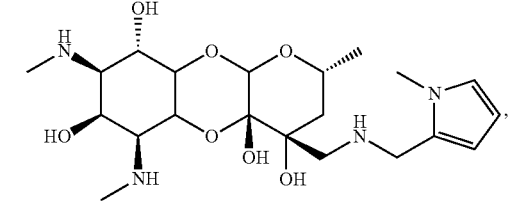 [SMILES: CN[C@@H]1[C@H](O)[C@H](NC)C2O[C@]3(O)C(OC2[C@H]1O)O[C@H](C)C[C@@]3(O)CNCc1cccn1C]
, or -continued
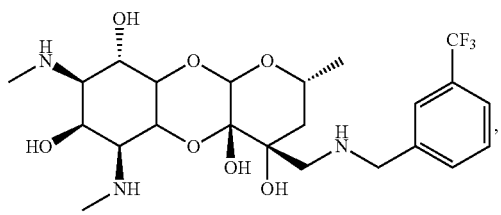 [SMILES: CN[C@@H]1[C@H](O)[C@H](NC)C2O[C@]3(O)C(OC2[C@H]1O)O[C@H](C)C[C@@]3(O)CNCc1cccc(C(F)(F)F)c1]
or subgroup thereof.
In one aspect, a compound is selected from:
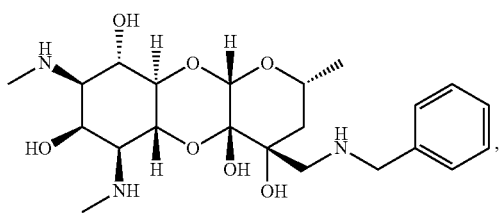
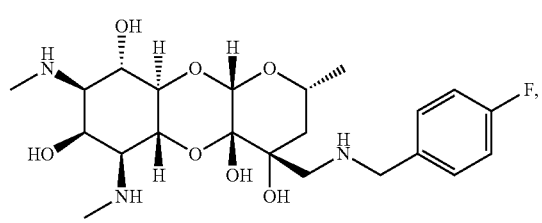
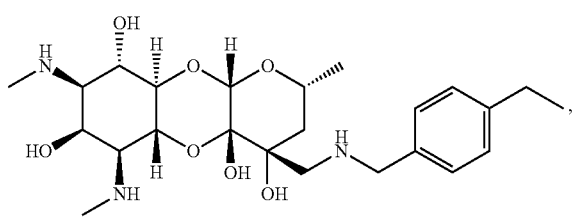
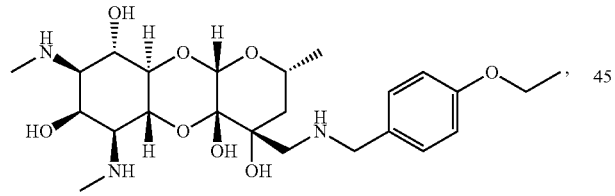
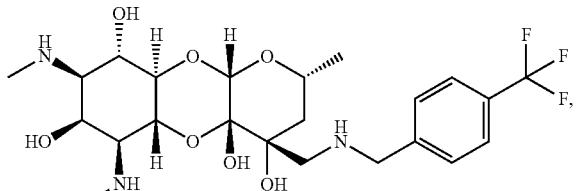
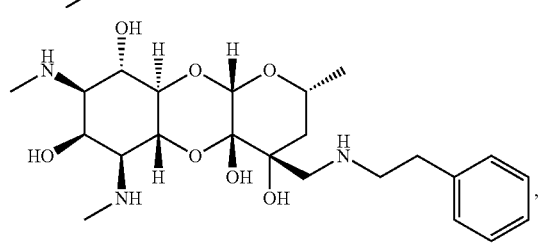
-continued
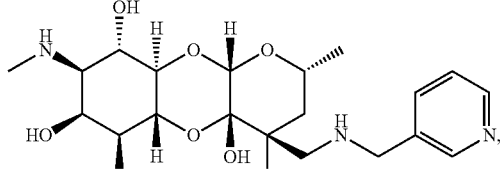
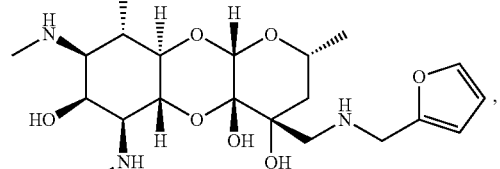
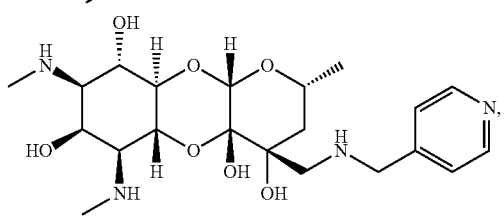
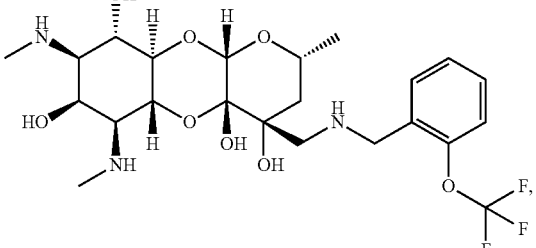
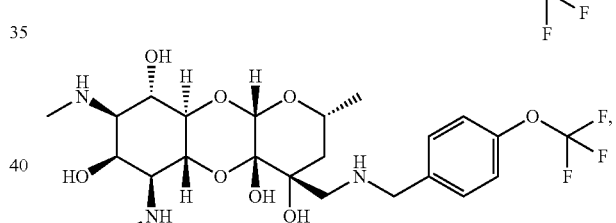
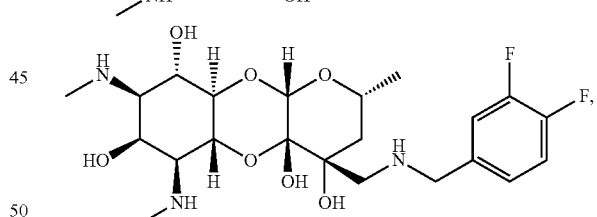
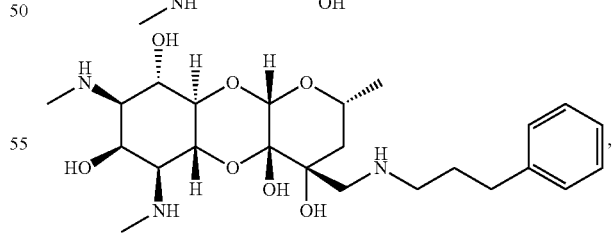
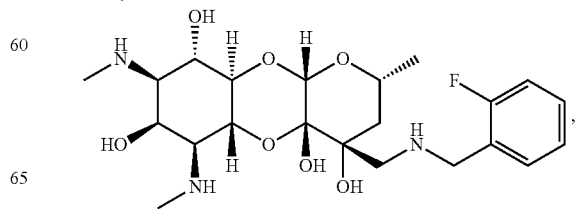

117
-continued
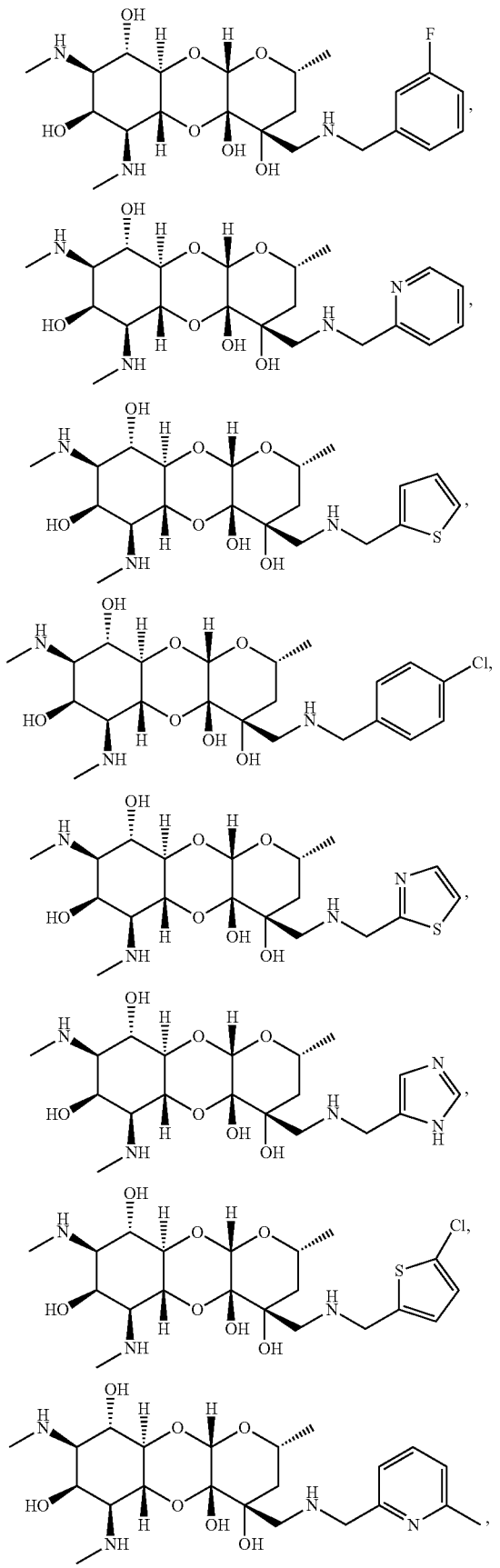
118
-continued
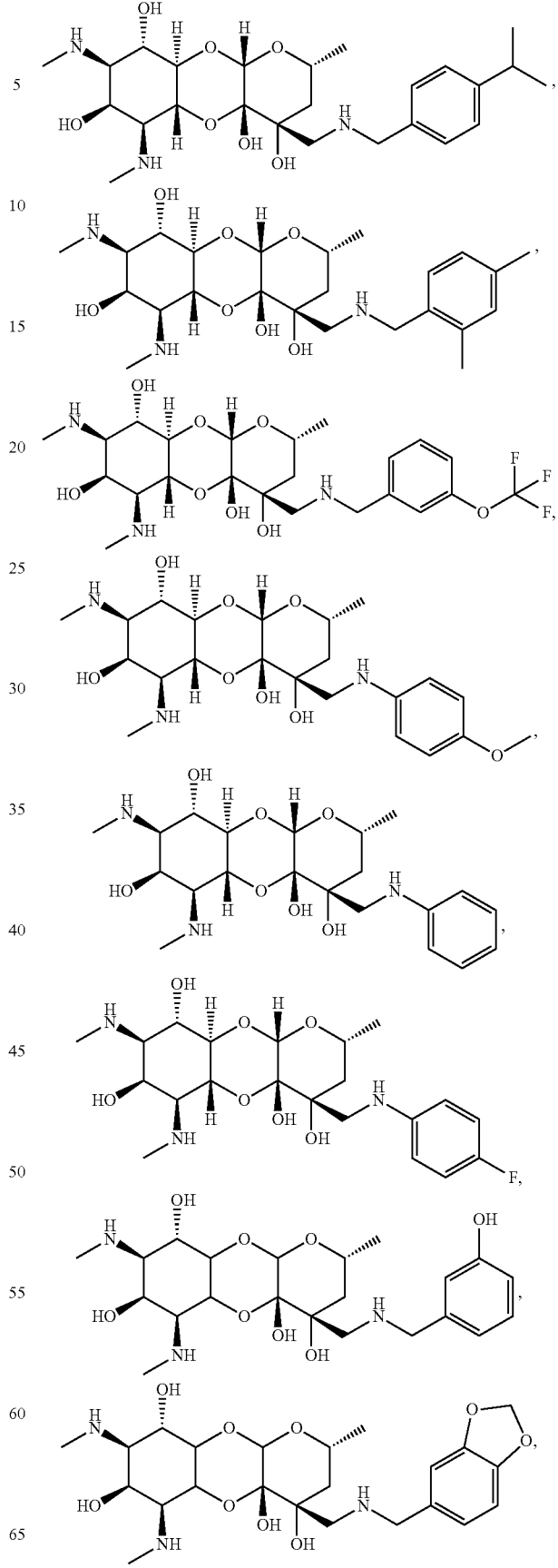

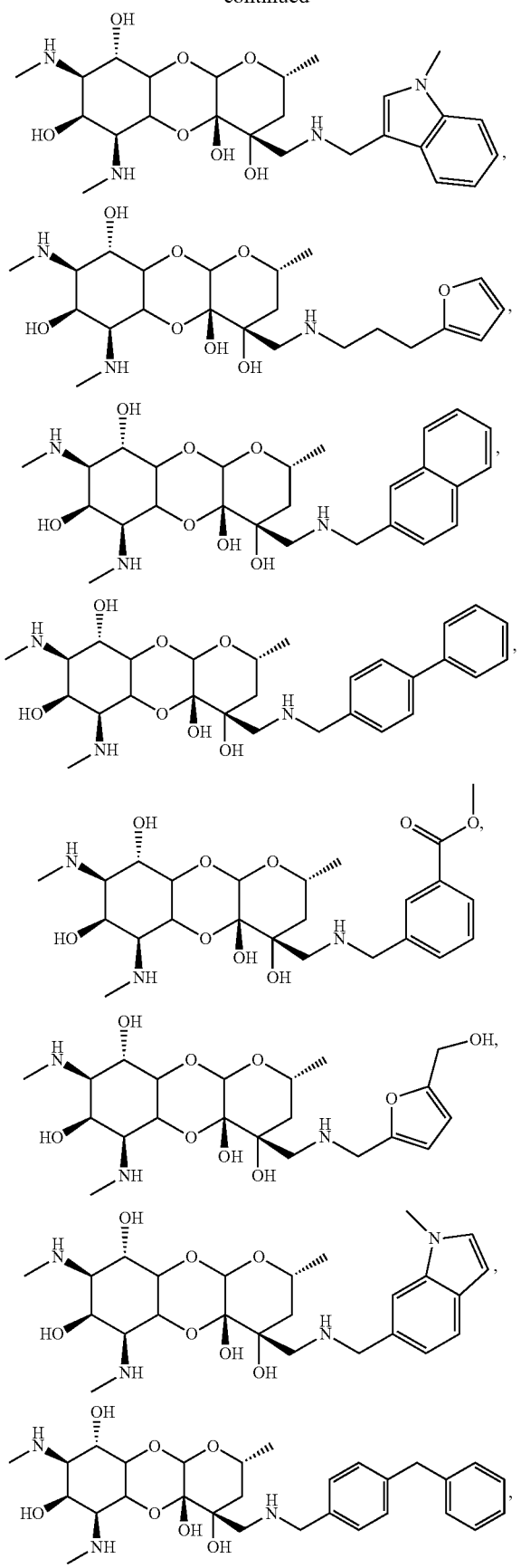
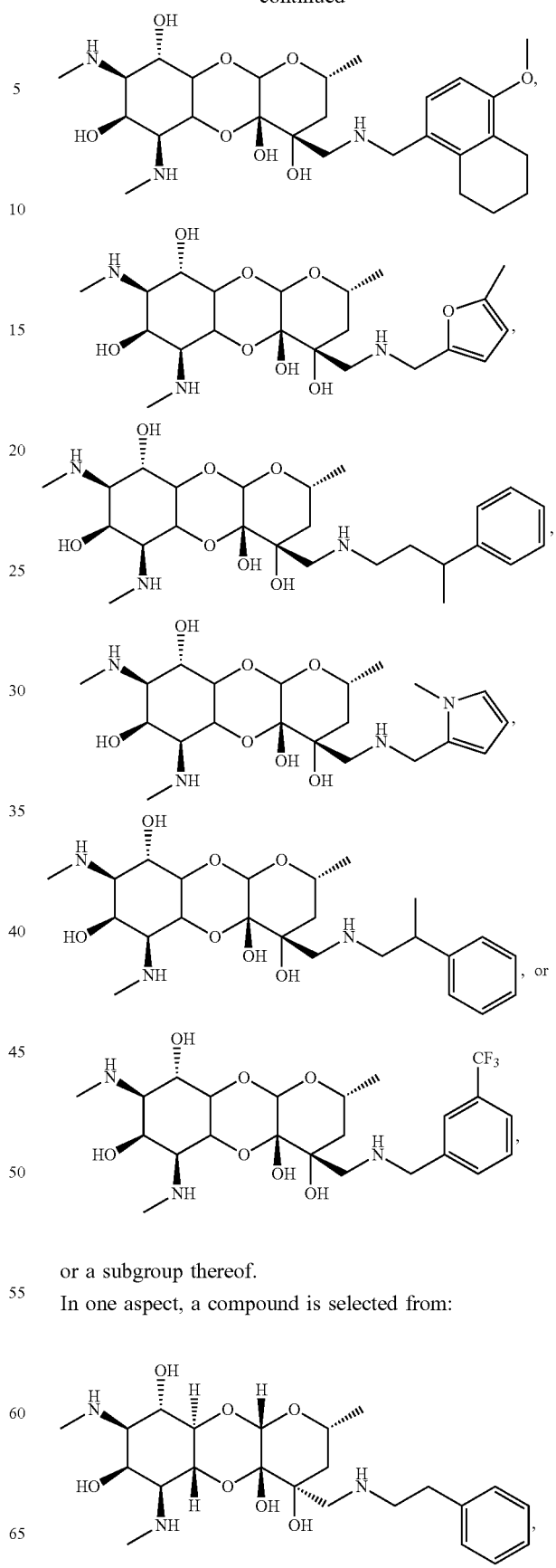
or a subgroup thereof.
In one aspect, a compound is selected from:
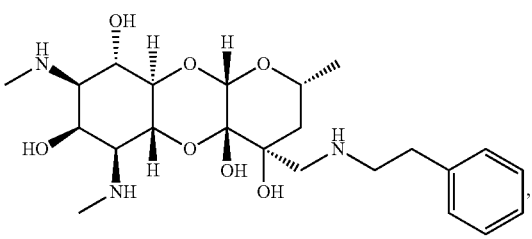

-continued
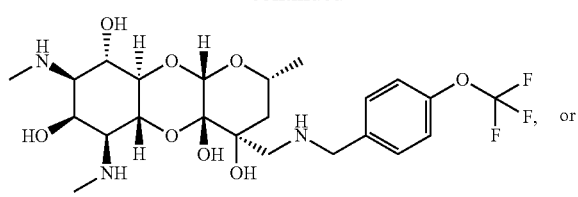
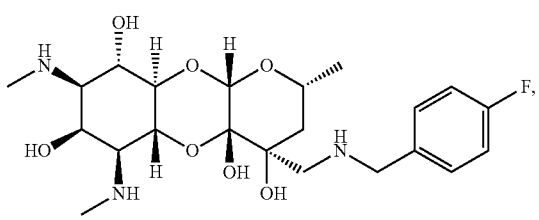
or a subgroup thereof.
In another aspect, a compound is selected from:
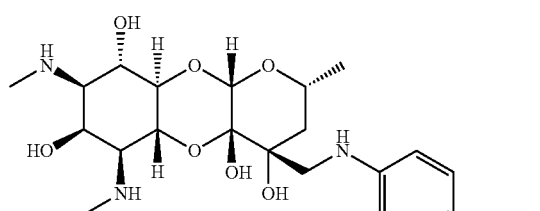
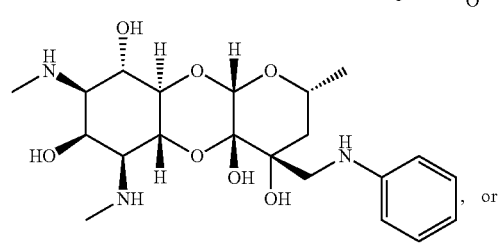
, or
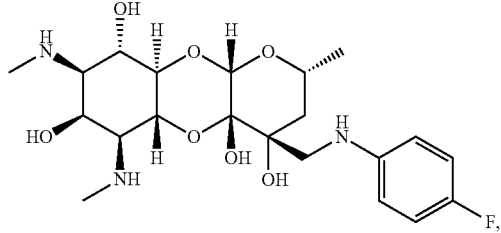
or a subgroup thereof.
In another aspect, a compound is selected from
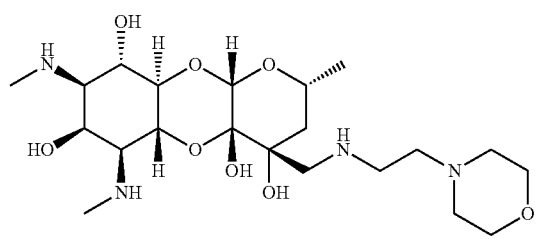
-continued
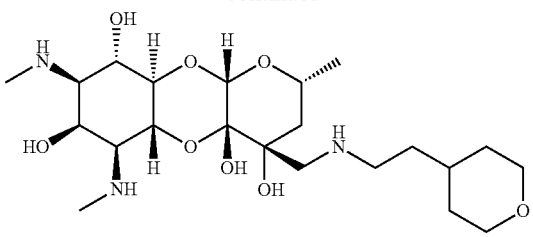
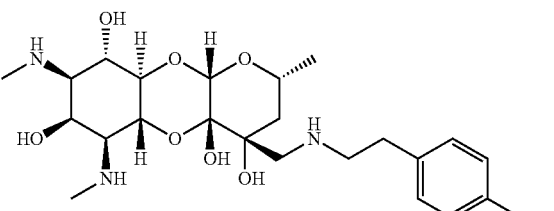
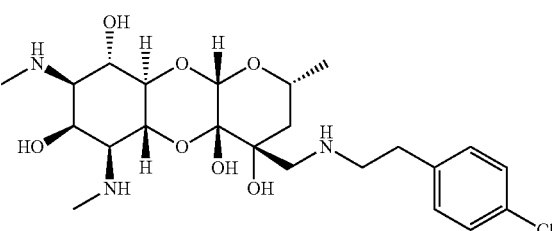
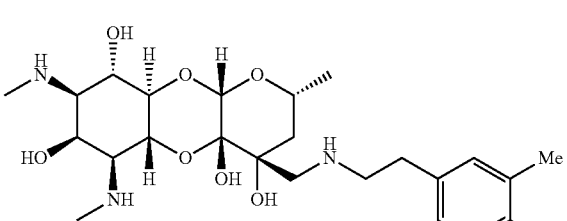
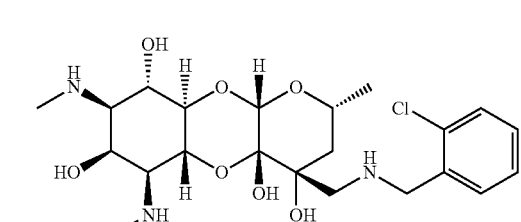
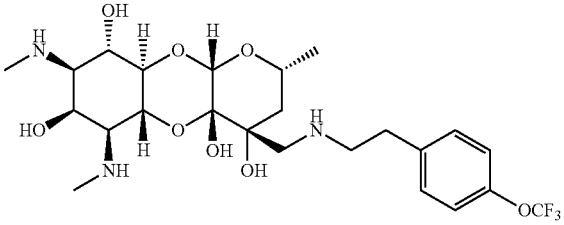
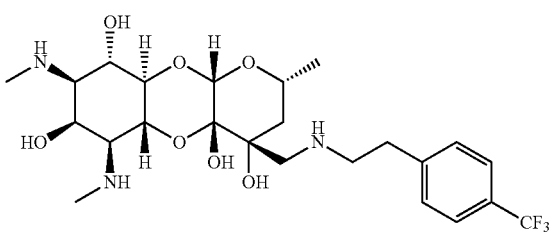

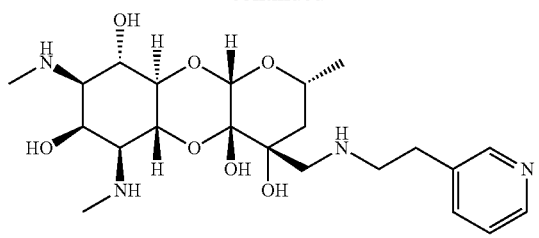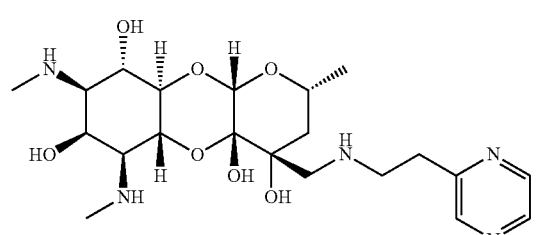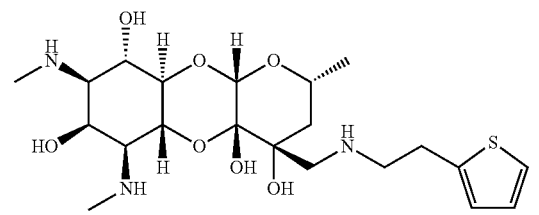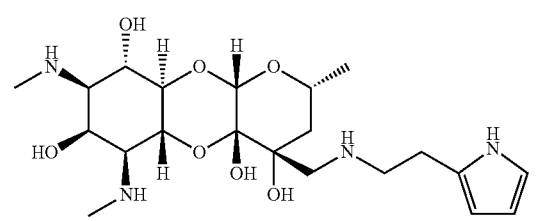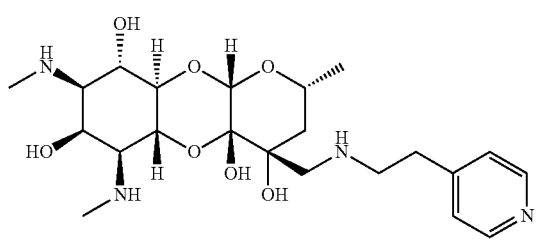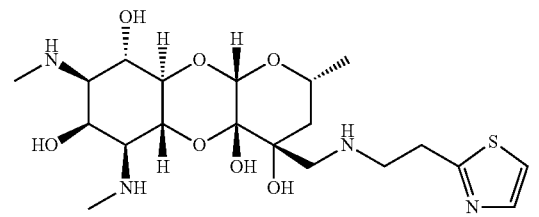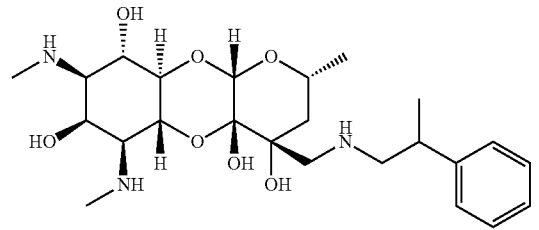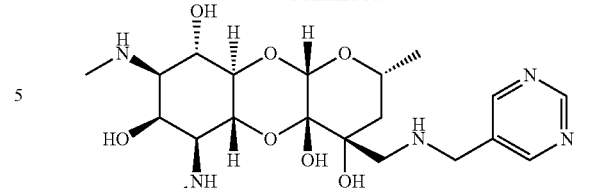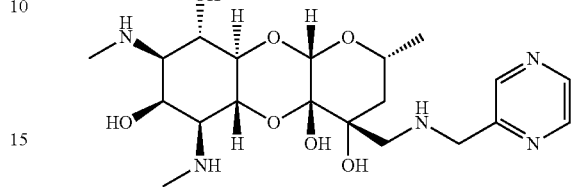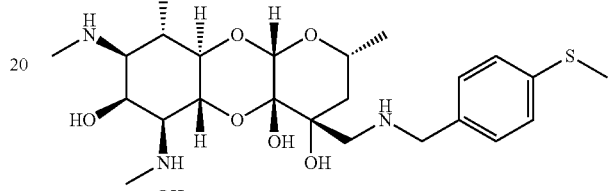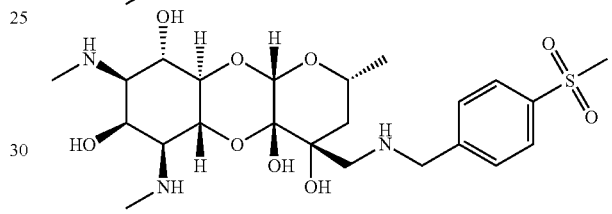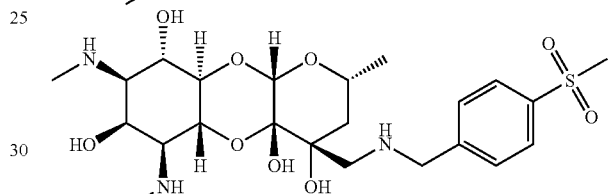

or a subgroup thereof.

It is contemplated that one or more compounds can optionally be omitted from the disclosed invention.

It is understood that the disclosed compounds of the present invention can be used in connection with the disclosed methods, compositions, kits, and uses.

It is understood that pharmaceutically acceptable derivatives of the disclosed compounds of Formula I can be used also in connection with the disclosed methods, compositions, kits, and uses. The pharmaceutical acceptable derivatives of the compounds can include any suitable derivative, such as pharmaceutically acceptable salts as discussed below, isomers, radiolabeled analogs, tautomers, and the like.

3. Spectinomycin

Numerically, the most successful strategy in antibacterial drug discovery has been the synthetic modification of natural products to produce new semisynthetic antibiotics (Fischbach et al. *Science* 2009, 325 (5944), 1089-1093; Wright et al. *Trends Mol. Med.* 2007, 13 (6), 260-270; Nakasako et al. *J. Mol. Biol.* 1999, 291 (1), 117-134). However, this approach has only been successfully applied to a few select scaffolds. Revisiting this approach, the low molecular weight antibiotic spectinomycin (see FIG. 1, panel (A)) was examined, which appears to have been neglected in spite of its safe pharmacological profile (Carter et al. *Nature* 1988, 332 (6164), 564-568; Wilcox et al. *Br. J. Clin. Pract.* 1975, 29 (2), 34-36; Sykes et al. *Nature* 1981, 291 (5815), 489-491). Spectinomycin is an aminocyclitol antibiotic that specifically inhibits bacterial protein synthesis by binding to 30S ribosome at a unique site that is highly conserved across bacterial pathogens (Carter et al. *Nature* 2000, 407(6802), 340-348; Borovinskaya et al. *ACS Chem. Biol.* 2007, 2 (8), 545-552; Wirmer et al. *Methods in enzymology* 2006, 415, 180-202). Although spectinomycin is potent in cell free assays its clinical use is restricted to second line treatment for *Neisseria gonorrhoeae* infections (McCormack et al. *Annals of internal medicine* 1976, 84 (6), 712-716; Reyn et al. *Br. J. Vener. Dis.* 1973, 49 (1), 54-59; Zenilman et al. *J. Infect. Dis.* 1987, 156 (6), 1002-1004. Previous attempts to develop spectinomycin analogs in the 1980's led to the discovery of trospectinomycin (see FIG. 1, panel (B)), which showed improved activity against different bacterial pathogens and progressed into late stage clinical trials before being withdrawn for commercial reasons. This evidence validated that modifications to the core of spectinomycin could potentially generate more potent generations of drug (Montiel et al. *Diagn. Microbiol. Infect. Dis.* 1991, 14 (3), 259-164; Barry et al. *Antimicrob. Agents Chemother.* 1989, 33 (4), 569-572; Zurenko et al. *Antimicrob. Agents Chemother.* 1988, 32 (2), 216-223; Zurenko et al. *Drugs Exp. Clin. Res.* 1988, 14 (6), 403-409).

More recently, a highly specific set of 3'-dihydro-3'-deoxy-(R)-acylamino spectinomycins, or alternatively referred to as spectinamides (see FIG. 1, panel (C)) demonstrated excellent efficacy in acute and chronic models of tuberculosis infection (see US 2011/0118272). This class of compounds, which has a tight structure activity relationship as demonstrated by the synthesis over 140 analogs, is highly selective for *M. tuberculosis*.

Surprisingly, the disclosed compounds of the present invention, i.e., aryl substituted 3'-aminomethyl-3'-hydroxy spectinomycins, were found to provide broad spectrum anti-bacterial activity against a variety of gram negative and gram positive pathogens, including drug resistant pathogens and biodefense pathogens, a result in strong contrast to the results obtained with the spectinamides previously described in US 2011/0118272.

Figure 2:
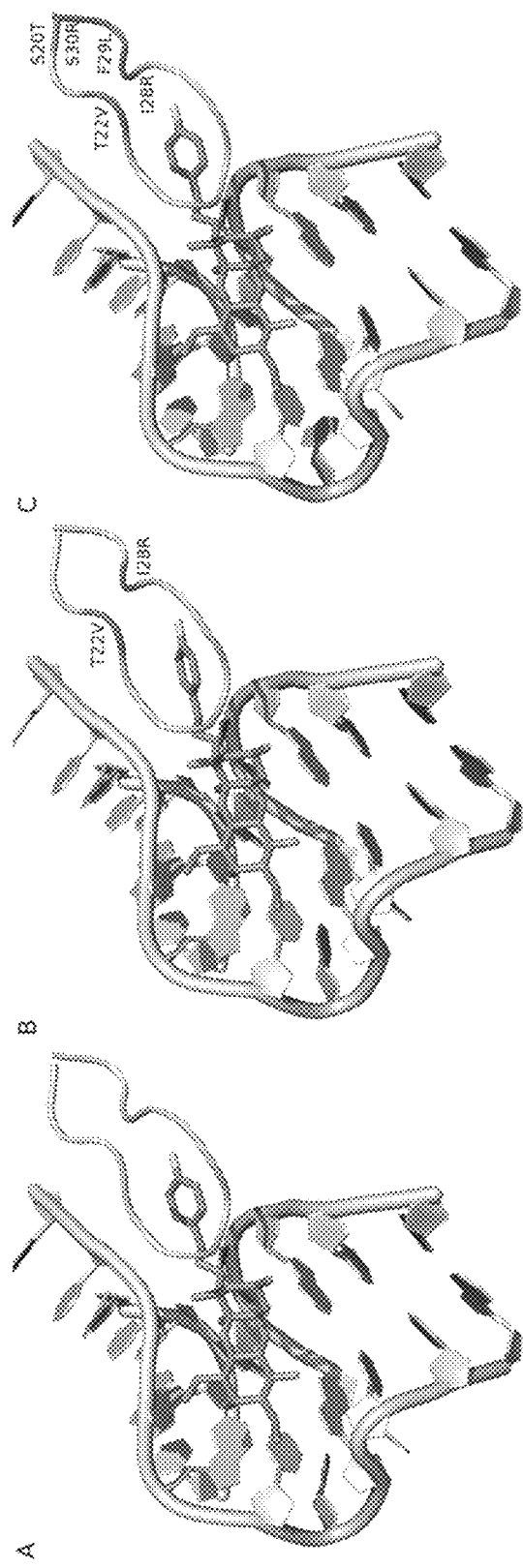
FIG. 2 is a computer generated model depicting the interaction of a compound of the invention with bacterial RNA and ribosomal protein. Each of panels A, B, and C shows compound 2 docked into bacterial ribosome at RNA helix 34 of the 30S ribosomal subunit, and the loop of interacting ribosomal protein RspE, which is a binding site for the aryl side chain of compound 2. The figure shows the amino acid differences and docking results for compound 2 to ribosomes of different bacterial species, namely (A) *E. coli*, (B) *M. tuberculosis*, or (C) *S. pneumonia*. The homologous *E. coli* RpsE positions are given in parentheses for panels B and C.

The crystal structure of SPC bound to the bacterial ribosome from *E. coli* is available and was used for the structure-based design of the disclosed compounds of the present invention. The binding site of SPC is situated near the RNA helix34 and a small loop from RspE protein. SPC forms an intricate hydrogen bonding network with ribosome that contributes significantly to its excellent ribosomal inhibition. A homology model of both *M. tuberculosis* and *S. pneumoniae* ribosomes was built for a 15 Å sphere centered at the SPC binding site which is highly conserved among these species with only a single RNA residue variance (A1081G) observed. More structural differences were observed for the RspE protein loop (see FIG. 2 and the amino acid variances noted therein). Protein variations at this site are particularly important for the disclosed compounds of the present invention as the RspE loop makes close contacts with the 3' side chain (e.g. the methylene linker of compound 2). Docking and short molecular dynamics simulations were performed on *E coli*, *M. tuberculosis* and *S. pneumoniae* ribosomes to investigate the binding of the disclosed compounds of the present invention. Compound 2 will be used as an example. Docking study shows this representative compound retains the active conformation of SPC and the modified 3' side chain fits well into an extended binding pocket sandwiched by both nucleic acids and protein. In addition a well-defined binding mode was seen between different species suggesting excellent ribosome inhibition against all three ribosomes.

4. Inhibition of Bacterial Protein Synthesis

In various aspects, the disclosed compounds according to Formula I may have a known mechanism of antimicrobial action and/or may bind to and/or inhibit one or more bacterial target molecules or macromolecular complexes containing a bacterial target molecule. Mechanisms of action may include inhibiting or interfering with a biological or biochemical pathway of the bacterium. Exemplary pathways include, but are not limited to, protein synthesis, cell wall synthesis, DNA replication, transcription, and cell division. It will be appreciated that biological and biochemical pathways are not mutually exclusive and that some biological or biochemical pathways may be considered to be subsets or sub-pathways of other biological or biochemical pathways. Mechanisms of action include, but are not limited to, inhibiting protein synthesis (e.g., by binding ribosomal RNA or proteins, blocking tRNA binding to the ribosome-mRNA complex, inhibiting peptidyl transferase), inhibiting or interfering with synthesis of a cell wall component (e.g., inhibition of peptidoglycan synthesis, disruption of peptidoglycan cross-linkage, disruption of movement of peptidoglycan precursors, disruption of mycolic acid or arabinoglycan synthesis), cell membrane disruption, inhibiting or interfering with nucleic acid synthesis of processing, acting as "antimetabolites" and either inhibiting an essential bacterial enzyme or competing with a substrate of an essential bacterial enzyme, inhibiting or interfering with cell division.

Molecules, or macromolecular complexes containing them, that may be targets for antibiotics include, but are not limited to, peptidoglycans, penicillin binding proteins, lipopolysaccharides, ribosomes or ribosomal subunits or RNA or protein components thereof (23S rRNA, 16S rRNA, proteins of the 30S or 50S subunit), DNA-dependent DNA polymerase, DNA-dependent RNA polymerase, microbial type I topoisomerase, microbial type II topoisomerase (e.g., topoisomerase IV or gyrase), enzymes involved in cell division such as FtsZ, etc.

In various aspects, the disclosed compounds of the present invention inhibit bacterial protein synthesis. The bacterial species may be of any one or more types, e.g., gram-negative bacteria, gram-positive bacteria, atypical bacteria, and/or acid fast bacteria. Suitable organisms can include, but are not limited to members of the following genera: *Actinomyces, Staphylococcus, Streptococcus, Enterococcus, Erysipelothrix, Neisseria, Branhamella, Listeria, Bacillus, Corynbacterium, Erysipelothrix, Gardnerella, Mycobacterium, Nocardia, Enterobacteriaceae, Escherichia, Salmonella, Shigella, Yersinia, Enterobacter, Klebsiella, Citrobacter, Serratia, Providencia, Proteus, Morganella, Edwardsiella, Erwinia, Vibrio, Aeromonas, Helicobacter, Campylobacter, Eikenella, Pasteurella, Pseudomonas, Burkholderia, Stenotrophomonas, Acinetobacter, Ralstonia, Alcaligenes, Moraxella, Mycoplasma, Legionella, Francisella, Brucella, Haemophilus, Bordetella, Clostridium, Bacteroides, Porphyromonas, Prevotella, Fusobacterium, Borrelia, Chlamydia, Rickettsia, Ehrlichia, Bartonella, Trichomonas*, and *Treponema*.

In various aspects of the invention the bacteria are species that are causative agents of disease in humans and/or animals. Examples include, but are not limited to, *Acinetobacter baumannii, Aeromonas hydrophila, Bacillus anthracis, Bacillus anthracis sterne, Bacillus subtilis, Burkholderia cepacia, Escherichia coli, Enterobacter cloacae, Enterococcus faecalis, Francisella tularensis, Campylobacter jejuni, Haemophilus influenzae, Klebsiella pneumoniae, Klebsiella oxytoca, Legionella pneumophila, Pasteurella multocida, Proteus mirabilis, Proteus vulgaris, Mycobacterium tuberculosis, Morganella morganii, Helicobacter pylori, Neisseria meningitides, Neisseria gonorrhoeae, Chlamydia trachomatis, Pseudomonas aeruginosa, Salmonella enterica, Salmonella typhimurium, Staphylococ-* cus aureus, Staphylococcus epidermidis, Streptococcus pneumoniae, Streptococcus pyogenes, Strenotrophomonas maltophilia, Streptococcus agalactiae, and Yersinia pestis.

In one aspect, the disclosed compounds of the present invention inhibit bacterial protein synthesis. The inhibition of bacterial protein synthesis can be demonstrated by methodology known in the art. For example, inhibition of bacterial protein synthesis can be determined by measurement of cell proliferation in response to antagonist. In a further aspect, the cell proliferation was analyzed as a concentration-dependent decrease in the $IC_{50}$ antagonist response (i.e. the ribosomal response at a concentration of antagonist that yields 50% of the maximal response).

In one aspect, the disclosed compounds of the present invention exhibit inhibition of bacterial protein synthesis. For example, a compound can exhibit inhibition of bacterial protein synthesis with an $IC_{50}$ of less than about 10 µg/mL, less than about 5 µg/mL, less than about 1 µg/mL, less than about 0.5 µg/mL, or less than about 0.25 µg/mL.

5. Methods of Making the Compounds

In one aspect, the invention relates to methods of making compounds according to Formula I that are useful as antibacterial agents, which can be useful in the treatment of bacterial infections. In one aspect, the invention relates to the disclosed synthetic manipulations. In a further aspect, the disclosed compounds of the present invention comprise the products of the synthetic methods described herein.

In a further aspect, the disclosed compounds of the present invention comprise a compound produced by a synthetic method described herein. In a still further aspect, the invention comprises a pharmaceutical composition comprising the product of the disclosed methods and a pharmaceutically acceptable carrier. In a still further aspect, the invention comprises a method for manufacturing a medicament comprising combining at least one product of the disclosed methods with a pharmaceutically acceptable carrier or diluent. In a still further aspect, the invention comprises a pharmaceutical composition comprising a therapeutically effective amount of the product of the disclosed methods and a pharmaceutically acceptable carrier The compounds of this invention can be prepared by employing reactions as shown in the disclosed schemes, in addition to other standard manipulations that are known in the literature, exemplified in the experimental sections or clear to one skilled in the art. For clarity, examples having a fewer substituent can be shown where multiple substituents are allowed under the definitions disclosed herein. Thus, the following examples are provided so that the invention might be more fully understood, are illustrative only, and should not be construed as limiting.

It is contemplated that each disclosed method can further comprise additional steps, manipulations, and/or components. It is also contemplated that any one or more step, manipulation, and/or component can be optionally omitted from the invention. It is understood that a disclosed method can be used to provide the disclosed compounds of the present invention. It is also understood that the products of the disclosed methods can be employed in the disclosed compositions, kits, and uses.

A. Synthesis Route 1

In one aspect, a useful intermediate for the preparation of aryl substituted aminomethyl spectinomycin analogues of the present invention can be prepared generically by the synthesis scheme as shown below. All positions are defined herein.

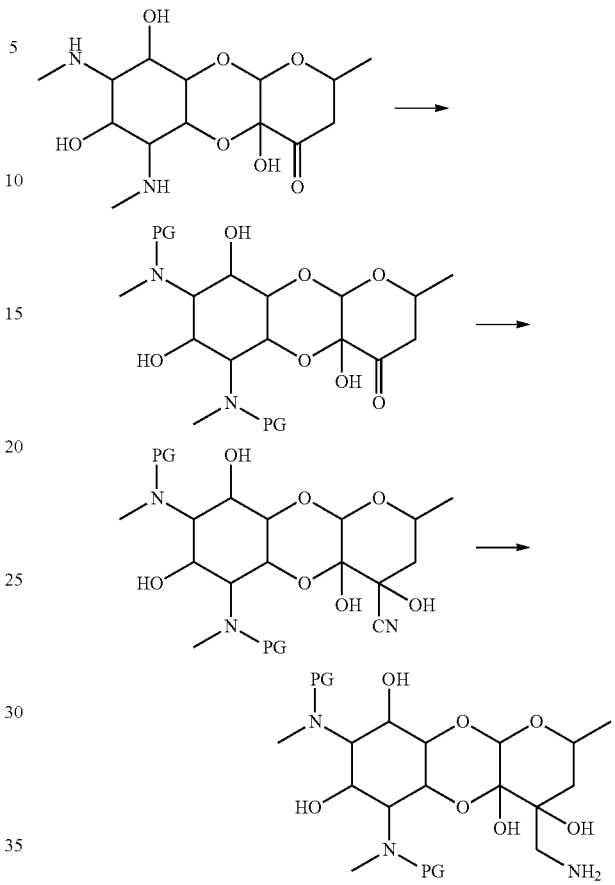

PG: Protecting Group

Compounds are represented in generic form, with substituents as noted in compound descriptions elsewhere herein. A more specific example is set forth below.

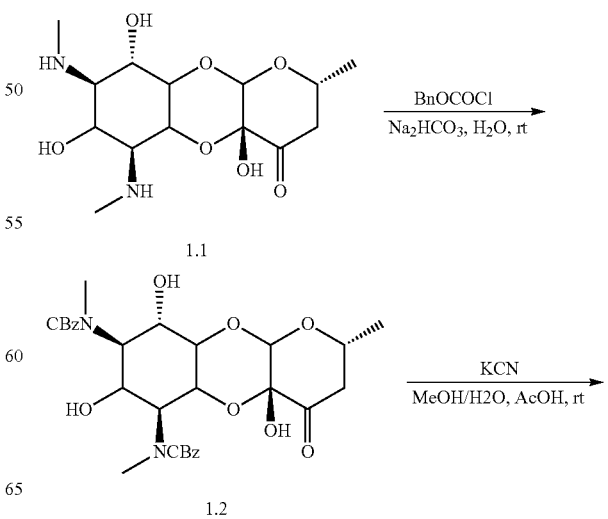

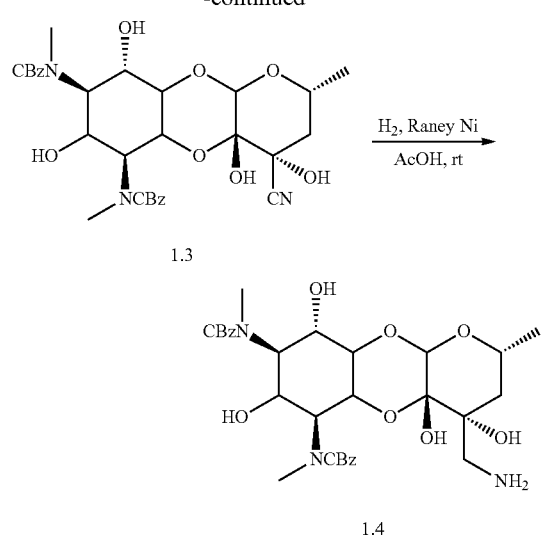

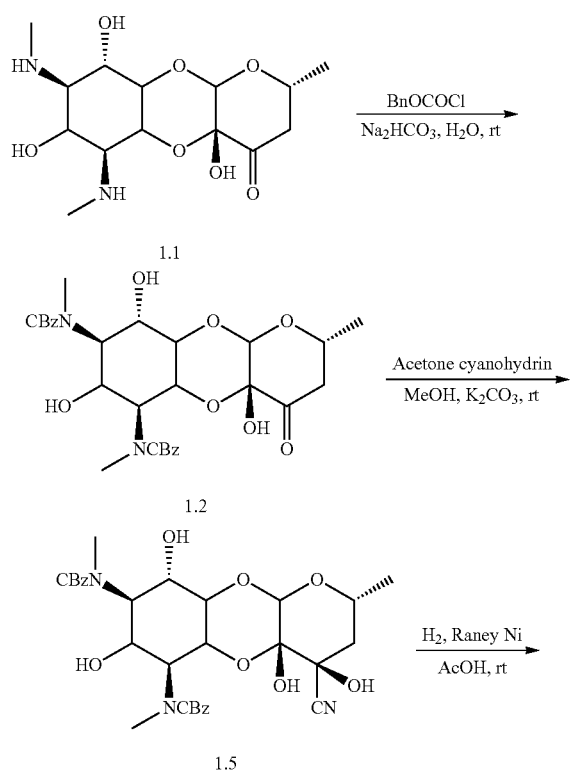

The 3'hydroxy-3'-methylamino derivative, i.e. compound 1.4 in reaction Scheme 1B above, and related compounds, can be prepared beginning with spectinomycin, 1.1. In the initial step, the 1- and 3-aminomethyl groups are protected. The specific reaction shown above yields the CBz protected, 1.2, following reaction with benzyl chloroformate, with the reaction carried out in the presence of a suitable base, e.g., Na$_2$HCO$_3$, in a suitable solvent, e.g., water, and the reaction carried out a suitable temperature, e.g. about 20-30° C., for a suitable period of time, e.g., 10-18 hr, to complete the reaction. The cyanohydrin, 1.3, is prepared by reaction of 1.2 with a suitable cyano nucleophile, e.g. KCN, in the presence of a suitable acid, e.g., acetic acid, in a suitable solvent system, e.g. methanol/water, at a suitable temperature, e.g., about 20-30° C., for a suitable period of time sufficient to complete the reaction, e.g., 15-60 minutes. The last step is reduction of the nitrile to yield the corresponding amine. The reaction can be carried out in the presence of a suitable hydrogen source, e.g., hydrogen gas, a suitable reducing agent, e.g., Raney Ni, and a suitable acid, e.g., acetic acid, at a suitable temperature, e.g., about 20-30° C., for a suitable period of time sufficient to complete the reaction, e.g., about 4-12 hr. As can be appreciated by one skilled in the art, alternative conditions can be used for reduction of the nitrile to yield the desired amine.

The (S)-3'hydroxy-3'-methylamino derivative, i.e. compound 1.6 in reaction Scheme 1C above, and related compounds, can be prepared beginning with spectinomycin, 1.1. In the initial step, the 1- and 3-aminomethyl groups are protected. The specific reaction shown above yields the CBz protected, 1.2, following reaction with benzyl chloroformate, with the reaction carried out in the presence of a suitable base, e.g., NaHCO3, in a suitable solvent, e.g., water, and the reaction carried out a suitable temperature, e.g., about 20-30° C., for a suitable period of time, e.g., 10-18 hr, to complete the reaction. The cyanohydrin, 1.5, is prepared by reaction of 1.2 with suitable cyano nucleophile, e.g., acetone cyanohydrin, in the presence of a suitable base, e.g., K$_2$CO$_3$, in a suitable solvent system, e.g., methanol, at a suitable temperature, e.g., about 20-30° C., for a suitable period of time sufficient to complete the reaction, e.g., 4-5 hrs. The last step is reduction of the nitrile to yield the corresponding amine. The reaction can be carried out in the presence of a suitable hydrogen source, e.g., hydrogen gas, a suitable reducing agent, e.g., Raney Ni, and a suitable acid, e.g., acetic acid, at a suitable temperature, e.g., about 20-30° C., for a suitable period of time sufficient to complete the reaction, e.g., about 4-12 hr. As can be appreciated by one skilled in the art, alternative conditions can be used for reduction of the nitrile to yield the desired amine.

B. Synthesis Route 2

In one aspect, aryl substituted aminomethyl spectinomycin analogues of the present invention can be prepared generically by the synthesis scheme as shown below. All positions are defined herein.

SCHEME 2A

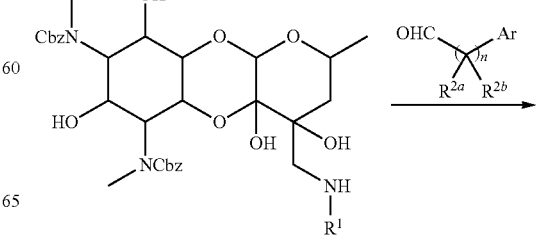

-continued

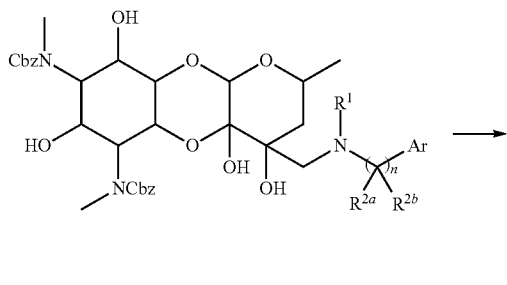

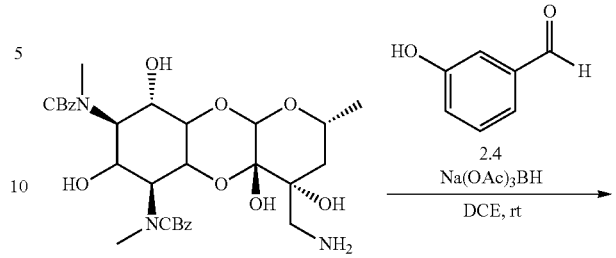

Scheme 2C

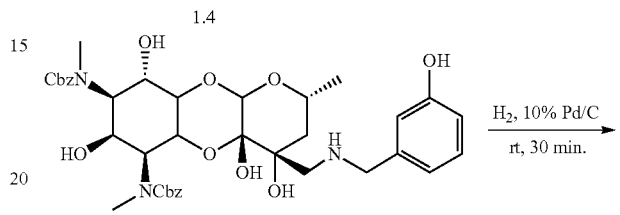

Compounds are represented in generic form, with substituents as noted in compound descriptions elsewhere herein. A more specific example is set forth below.

Scheme 2B

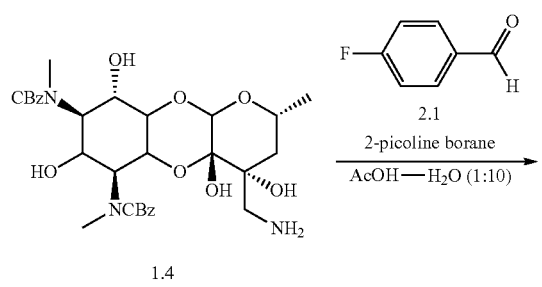

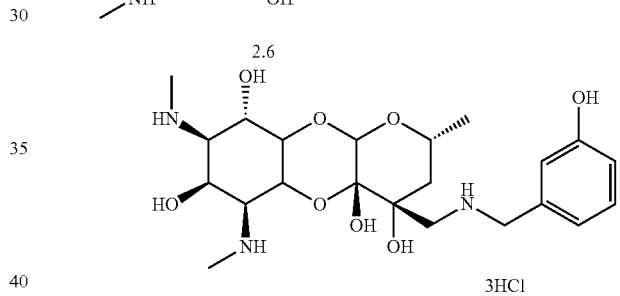

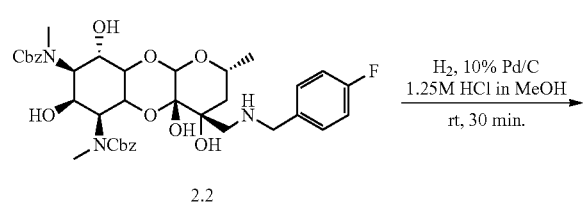

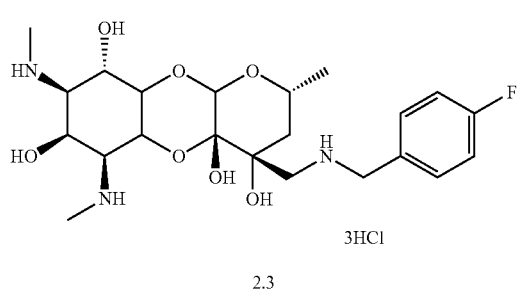

In one aspect, compounds of type 2.2, and similar compounds, can be prepared according to reaction Scheme 2B above. Thus, compounds of type 2.2 can be prepared by reductive amination of an appropriate amine, e.g., dibenzyl ((2R,4R,4aS,6S,7S,8R,9S)-4-(aminomethyl)-4,4a,7,9-tetrahydroxy-2-methyldecahydro-2H-benzo[b]pyrano[2,3-e][1,4]dioxine-6,8-diyl)bis(methylcarbamate) (1.4) as shown above, which can be prepared by methods similar to those discussed for Route 1 above. The reaction can be carried out using an appropriate solvent system, e.g., acetic acid and methanol, in the presence of a suitable borane reagent, e.g., 2-picoline borane as shown above, and a suitable aldehyde, e.g., 4-fluorbenzaldehyde (compound 2.1), as shown above. Suitable aldehydes that can be used in the reaction are commercially available or can be prepared by methods known to one skilled in the art. A compound of type 2.3 can be prepared by deprotection of a compound of type 2.3 via a hydrogenation reaction. For example, as shown above, such a hydrogenation reaction can be accomplished using a suitable hydrogen source, e.g., hydrogen gas, with a suitable catalyst, e.g., 10% Pd/C, in a suitable protic solvent, e.g., methanol, in the presence of an acid, e.g., 1.25 M HCl, at a suitable temperature, e.g., about 20-30° C., for a suitable period of time, e.g., about 15 to about 120 min. As can be appreciated by one skilled in the art, the above reaction provides an example of a generalized approach wherein compounds similar in structure to the specific reactants above (compounds similar to compounds of type 1.4, 2.1 and 2.2), can be substituted in the reaction to provide aryl substituted aminomethyl spectinomycin analogues similar to Formula 2.3.

In one aspect, compounds of type 2.7, and similar compounds, can be prepared according to reaction Scheme 2C above. Thus, compounds of type 2.5 can be prepared by reductive amination of an appropriate amine, e.g., dibenzyl ((2R,4R,4aS,6S,7S,8R,9S)-4-(aminomethyl)-4,4a,7,9-tetrahydroxy-2-methyldecahydro-2H-benzo[b]pyrano[2,3-e][1,4]dioxine-6,8-diyl)bis(methylcarbamate) (1.4) as shown above, which can be prepared by methods similar to those discussed for Route 1 above. The reaction can be carried out in the presence of a suitable reducing agent, e.g., sodium triacetoxyborohydride, in a suitable solvent, e.g., dichloroethane, at a suitable temperature, e.g., about 20-30° C., for a suitable period of time, e.g., about 1-3 hr, with a suitable aldehyde, e.g., 3-hydroxybenzaldehyde (compound 2.4) as shown above. Aldehydes useful in this reaction are commercially available or can be prepared by methods known to one skilled in the art. A compound of type 2.7 can be prepared by deprotection of a compound of type 2.5 via a hydrogenation reaction followed by treating with methanolic HCl. For example, as shown above, such a hydrogenation reaction can be accomplished using a suitable hydrogen source, e.g., hydrogen gas, with a suitable catalyst, e.g., 10% Pd/C, in a suitable protic solvent, e.g., methanol, at a suitable temperature, e.g., about 20-30° C., for a suitable period of time, e.g., about 15 to about 120 min followed by addition of anhydrous acid, e.g., methanolic HCl. As can be appreciated by one skilled in the art, the above reaction provides an example of a generalized approach wherein compounds similar in structure to the specific reactants above (compounds similar to compounds of type 1.4, 2.4 and 2.5), can be substituted in the reaction to provide aryl substituted aminomethyl spectinomycin analogues similar to Formula 2.7.

As can be appreciated, depending upon the specific nature of the aldehyde used in the reductive amination step, alternative conditions can be used for the reductive amination step. For example, the reductive amination reaction step can be carried out in the presence of a suitable reducing agent, e.g., sodium cyanoborohydride, in a suitable solvent, e.g., methanol, at a suitable pH, e.g., about pH 4, at a suitable temperature, e.g., about 20-30° C., for a suitable period of time, e.g., about 1-3 hr, with a suitable aldehyde. Aldehydes useful in this reaction are commercially available or can be prepared by methods known to one skilled in the art.

In various aspects, deprotection of a compound similar to a compound of type 2.1 can be accomplished by a variety of alternative approaches. For example, deprotection can be accomplished using a suitable acid, e.g., 48% aq. HBr, with the reaction carried out at a suitable temperature, e.g., about 20-30° C., for a suitable period of time to complete the reaction, e.g., about 15-120 min, to provide the desired a product, a compound similar to a 2.2.

c. Synthesis Route 3

In one aspect, aryl substituted aminomethyl spectinomycin analogues of the present invention can be prepared generically by the synthesis scheme as shown below. All positions are defined herein.

SCHEME 3A

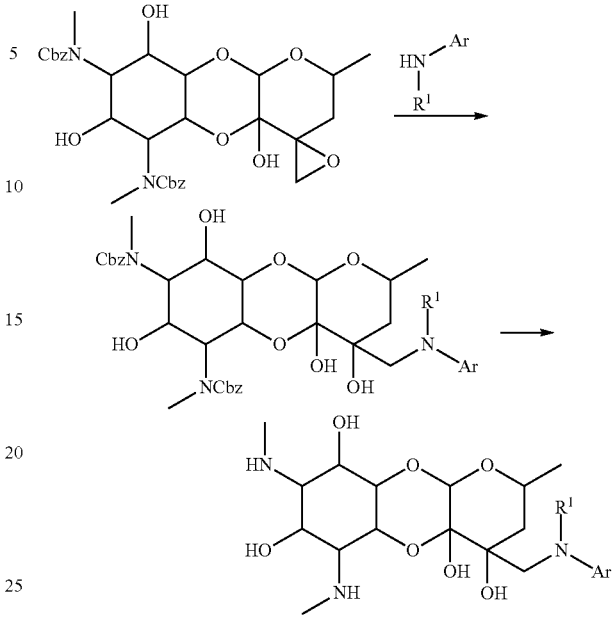

Compounds are represented in generic form, with substituents as noted in compound descriptions elsewhere herein. A more specific example is set forth below.

SCHEME 3B

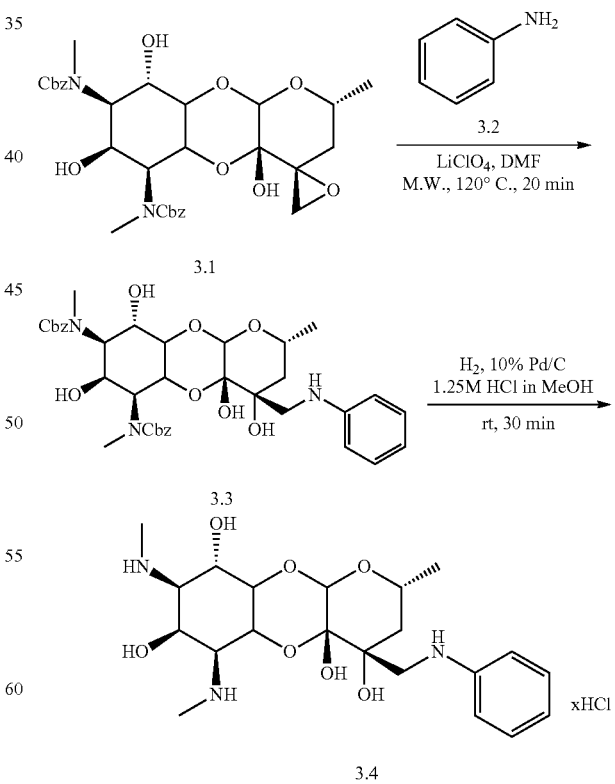

In one aspect, compounds of type 3.4 and similar compounds, can be prepared according to reaction Scheme 3b above. Thus, compounds of type 3.3 can be prepared by base-promoted epoxide opening of an appropriate epoxide derivative, e.g., dibenzyl ((2R,2'R,4aS,6S,7S,8R,9S)-4a,7,9-trihydroxy-2-methyldecahydrospiro[benzo[b]pyrano[2,3-e][1,4]dioxine-4,2'-oxirane]-6,8-diyl)bis(methylcarbamate) (3.1) as shown above. The epoxide derivative, i.e. 3.1, and related compounds can be generally prepared by methods previously described by Thomas and Fritzen (J. Antibiot. (Tokyo) 41:1445-1451, (1988)). Appropriate amine derivatives are commercially available or can be prepared by methods known to one skilled in the art. The reaction is carried out in the presence of a suitable base, e.g., lithium perchlorate, in a suitable solvent, e.g., dimethylformamide, at a suitable temperature, e.g., about 100° C. to about 150° C., for a suitable period of time, e.g., about 10 to about 30 minutes, with a suitable aryl amine, e.g., aniline as shown in Scheme 3B. Suitable aryl amines, including substituted anilines, useful in the reaction shown above are commercially available or can be prepared by methods known to one skilled in the art. A compound of type 3.3 can be prepared by deprotection of a compound of type 3.2. For example, as shown above, such a deprotection reaction can be accomplished by hydrogenation using a suitable hydrogen source, e.g., hydrogen gas, with a suitable catalyst, e.g., 10% Pd/C, in a suitable protic solvent, e.g., methanol, in the presence of an acid, e.g., about 1.25 M HCl, at a suitable temperature, e.g., about 20° C. to about 30° C., for a suitable period of time, e.g., about 15 to about 60 minutes. As can be appreciated by one skilled in the art, the above reaction provides an example of a generalized approach wherein compounds similar in structure to the specific reactants above (compounds similar to compounds of type 3.1, 3.2 and 3.3), can be substituted in the reaction to provide aryl substituted aminomethyl spectinomycin analogues similar to Formula 3.4.

In various aspects, deprotection of a compound similar to a compound of type 3.3 can be accomplished by a variety of alternative approaches. For example, deprotection can be accomplished using a suitable acid, e.g., 48% aq. HBr, with the reaction carried out at a suitable temperature, e.g., about 20-30° C., for a suitable period of time to complete the reaction, e.g., about 15-120 min, to provide the desired a product, a compound similar to a 3.4. In addition, as can be appreciated, the base-promoted epoxide opening of the epoxide, i.e. a compound similar to 3.1, by an aryl amine can be accomplished using other reaction conditions as appropriate for the aryl amine and requirements of the specific reaction.

It is contemplated that each disclosed method can further comprise additional steps, manipulations, and/or components. It is also contemplated that any one or more step, manipulation, and/or component can be optionally omitted from the invention. It is understood that a disclosed method can be used to provide the disclosed compounds of the present invention. It is also understood that the products of the disclosed methods can be employed in the disclosed methods of using.

C. Pharmaceutical Compositions

In one aspect, the invention relates to pharmaceutical compositions comprising one or more compounds according to Formula I or a pharmaceutically acceptable salt, solvate, hydrate, or polymorph thereof, and a pharmaceutically acceptable carrier. That is, a pharmaceutical composition can be provided comprising at least one disclosed compound of the present invention, at least one product of a disclosed method, or a pharmaceutically acceptable salt, solvate, hydrate, or polymorph thereof, and a pharmaceutically acceptable carrier. In one aspect, the invention relates to pharmaceutical compositions comprising a pharmaceutically acceptable carrier and at least one compound according to Formula I or a pharmaceutically acceptable salt, hydrate, solvate, or polymorph thereof.

In one aspect of the invention, a pharmaceutical composition will comprise an effective amount of at least one compound according to Formula I or a pharmaceutically acceptable salt, solvate, hydrate, or polymorph thereof, and a pharmaceutically acceptable carrier. In a further aspect, the effective amount is a therapeutically effective amount. In a still further aspect, the effective amount is a prophylactically effective amount. In a still further aspect, the pharmaceutical composition comprises a compound that is a product of a disclosed method of making.

In a further aspect, the pharmaceutical composition is used to treat a mammal. In a yet further aspect, the mammal is a human. In a further aspect, the mammal has been diagnosed with a bacterial infection. In a still further aspect, the mammal has been diagnosed with a need for treatment of a bacterial infection. In an even further aspect, the mammal is a human.

In a further aspect, the pharmaceutical composition is a solid dosage form selected from a capsule, a tablet, a pill, a powder, a granule, an effervescing granule, a gel, a paste, a troche, and a pastille. In a still further aspect, the pharmaceutical composition is a liquid dosage form selected from an emulsion, a solution, a suspension, a syrup, and an elixir.

In various aspects, the pharmaceutical composition of the present invention comprises a pharmaceutically acceptable carrier; an effective amount of at least one disclosed compound of the present invention; or a pharmaceutically acceptable salt, solvate, or polymorph thereof; and an antibacterial agent, and further comprises a second active agent. In a further aspect, the second active agent is an antibacterial agent. In a still further aspect, the antibacterial agent comprises a compound selected from amoxicillin, ampicillin, azithromycin, aztreonam, azlocillin, bacitracin, carbenicillin, cefaclor, cefadroxil, cefamandole, cefazolin, cephalexin, cefdinir, cefditoren, cefepime, cefixime, cefoperazone, cefotaxime, cefoxitin, cefpodoxime, cefprozil, ceftazidime, ceftibuten, ceftizoxime, ceftriaxone, cefuroxime, chloramphenicol, cilastin, ciprofloxacin, clarithromycin, clavulanic acid, clinafloxacin, clindamycin, clofazimine, cloxacillin, colistin, cycloserin, dalbavancin, dalfopristin, demeclocycline, dicloxacillin, dirithromycin, doxycycline, erythromycin, enrofloxacin, enoxacin, enviomycin, ertepenem, ethambutol, ethionmide, flucloxacillin, fosfomycin, furazolidone, gatifloxacin, gentamicin, imipenem, isoniazid, kanamycin, levofloxacin, linezolid, lomefloxacin, loracarbef, mafenide, moxifloxacin, meropenem, metronidazole, mezlocillin, minocycline, mupirocin, nafcillin, nalidixic acid, neomycin, netilmicin, nitrofurantoin, norfloxacin, ofloxacin, oritavancin, oxytetracycline, penicillin, piperacillin, platensimycin, polymixin B, pyrazinamide, quinupristin, retapamulin, rifabutin, rifampin, rifapentine, roxithromycin, sparfloxacin, spectinomycin, sulbactam, sulfacetamide, sulfamethizole, sulfamethoxazole, teicoplanin, telithromycin, telavancin, temafloxacin, tetracycline, thioacetazone, thioridazine, ticarcillin, tinidazole, tobramycin, torezolid, tosufloxacin, trimethoprim, troleandomycin, trovafloxacin, and vancomycin, or combinations thereof.

In certain aspects, the disclosed pharmaceutical compositions comprise the disclosed compounds according to Formula I (including pharmaceutically acceptable salt(s)

thereof) as an active ingredient, a pharmaceutically acceptable carrier, and, optionally, other therapeutic ingredients or adjuvants. The instant compositions include those suitable for oral, rectal, topical, and parenteral (including subcutaneous, intramuscular, and intravenous) administration, although the most suitable route in any given case will depend on the particular host, and nature and severity of the conditions for which the active ingredient is being administered. The pharmaceutical compositions can be conveniently presented in unit dosage form and prepared by any of the methods well known in the art of pharmacy.

As used herein, the term "pharmaceutically acceptable salts" refers to salts prepared from pharmaceutically acceptable non-toxic bases or acids. When the compound of the present invention is acidic, its corresponding salt can be conveniently prepared from pharmaceutically acceptable non-toxic bases, including inorganic bases and organic bases. Salts derived from such inorganic bases include aluminum, ammonium, calcium, copper (-ic and -ous), ferric, ferrous, lithium, magnesium, manganese (-ic and -ous), potassium, sodium, zinc and the like salts. Particularly preferred are the ammonium, calcium, magnesium, potassium and sodium salts. Salts derived from pharmaceutically acceptable organic non-toxic bases include salts of primary, secondary, and tertiary amines, as well as cyclic amines and substituted amines such as naturally occurring and synthesized substituted amines. Other pharmaceutically acceptable organic non-toxic bases from which salts can be formed include ion exchange resins such as, for example, arginine, betaine, caffeine, choline, N,N-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine and the like.

As used herein, the term "pharmaceutically acceptable non-toxic acids", includes inorganic acids, organic acids, and salts prepared therefrom, for example, acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid and the like. Preferred are citric, hydrobromic, hydrochloric, maleic, phosphoric, sulfuric, and tartaric acids.

In practice, the compounds of the invention, or pharmaceutically acceptable salts thereof, of this invention can be combined as the active ingredient in intimate admixture with a pharmaceutical carrier according to conventional pharmaceutical compounding techniques. The carrier can take a wide variety of forms depending on the form of preparation desired for administration, e.g., oral or parenteral (including intravenous). Thus, the pharmaceutical compositions of the present invention can be presented as discrete units suitable for oral administration such as capsules, cachets or tablets each containing a predetermined amount of the active ingredient. Further, the compositions can be presented as a powder, as granules, as a solution, as a suspension in an aqueous liquid, as a non-aqueous liquid, as an oil-in-water emulsion or as a water-in-oil liquid emulsion. In addition to the common dosage forms set out above, the compounds of the invention, and/or pharmaceutically acceptable salt(s) thereof, can also be administered by controlled release means and/or delivery devices. The compositions can be prepared by any of the methods of pharmacy. In general, such methods include a step of bringing into association the active ingredient with the carrier that constitutes one or more necessary ingredients. In general, the compositions are prepared by uniformly and intimately admixing the active ingredient with liquid carriers or finely divided solid carriers or both. The product can then be conveniently shaped into the desired presentation.

Thus, the pharmaceutical compositions of this invention can include a pharmaceutically acceptable carrier and a compound or a pharmaceutically acceptable salt of the compounds of the invention. The compounds of the invention, or pharmaceutically acceptable salts thereof, can also be included in pharmaceutical compositions in combination with one or more other therapeutically active compounds.

The pharmaceutical carrier employed can be, for example, a solid, liquid, or gas. Examples of solid carriers include lactose, terra alba, sucrose, talc, gelatin, agar, pectin, acacia, magnesium stearate, and stearic acid. Examples of liquid carriers are sugar syrup, peanut oil, olive oil, and water. Examples of gaseous carriers include carbon dioxide and nitrogen.

In preparing the compositions for oral dosage form, any convenient pharmaceutical media can be employed. For example, water, glycols, oils, alcohols, flavoring agents, preservatives, coloring agents and the like can be used to form oral liquid preparations such as suspensions, elixirs and solutions; while carriers such as starches, sugars, microcrystalline cellulose, diluents, granulating agents, lubricants, binders, disintegrating agents, and the like can be used to form oral solid preparations such as powders, capsules and tablets. Because of their ease of administration, tablets and capsules are the preferred oral dosage units whereby solid pharmaceutical carriers are employed. Optionally, tablets can be coated by standard aqueous or nonaqueous techniques A tablet containing the composition of this invention can be prepared by compression or molding, optionally with one or more accessory ingredients or adjuvants. Compressed tablets can be prepared by compressing, in a suitable machine, the active ingredient in a free-flowing form such as powder or granules, optionally mixed with a binder, lubricant, inert diluent, surface active or dispersing agent. Molded tablets can be made by molding in a suitable machine, a mixture of the powdered compound moistened with an inert liquid diluent.

The pharmaceutical compositions of the present invention comprise a compound of the invention (or pharmaceutically acceptable salts thereof) as an active ingredient, a pharmaceutically acceptable carrier, and optionally one or more additional therapeutic agents or adjuvants. The instant compositions include compositions suitable for oral, rectal, topical, and parenteral (including subcutaneous, intramuscular, and intravenous) administration, although the most suitable route in any given case will depend on the particular host, and nature and severity of the conditions for which the active ingredient is being administered. The pharmaceutical compositions can be conveniently presented in unit dosage form and prepared by any of the methods well known in the art of pharmacy.

Pharmaceutical compositions of the present invention suitable for parenteral administration can be prepared as solutions or suspensions of the active compounds in water. A suitable surfactant can be included such as, for example, hydroxypropylcellulose. Dispersions can also be prepared in glycerol, liquid polyethylene glycols, and mixtures thereof in oils. Further, a preservative can be included to prevent the detrimental growth of microorganisms.

Pharmaceutical compositions of the present invention suitable for injectable use include sterile aqueous solutions or dispersions. Furthermore, the compositions can be in the form of sterile powders for the extemporaneous preparation of such sterile injectable solutions or dispersions. In all cases, the final injectable form must be sterile and must be effectively fluid for easy syringability. The pharmaceutical compositions must be stable under the conditions of manufacture and storage; thus, preferably should be preserved against the contaminating action of microorganisms such as bacteria and fungi. The carrier can be a solvent or dispersion medium containing, for example, water, ethanol, polyol (e.g., glycerol, propylene glycol and liquid polyethylene glycol), vegetable oils, and suitable mixtures thereof.

Pharmaceutical compositions of the present invention can be in a form suitable for topical use such as, for example, an aerosol, cream, ointment, lotion, dusting powder, mouth washes, gargles, and the like. Further, the compositions can be in a form suitable for use in transdermal devices. These formulations can be prepared, utilizing a compound of the invention, or pharmaceutically acceptable salts thereof, via conventional processing methods. As an example, a cream or ointment is prepared by mixing hydrophilic material and water, together with about 5 wt % to about 10 wt % of the compound, to produce a cream or ointment having a desired consistency.

Pharmaceutical compositions of this invention can be in a form suitable for rectal administration wherein the carrier is a solid. It is preferable that the mixture forms unit dose suppositories. Suitable carriers include cocoa butter and other materials commonly used in the art. The suppositories can be conveniently formed by first admixing the composition with the softened or melted carrier(s) followed by chilling and shaping in molds.

In addition to the aforementioned carrier ingredients, the pharmaceutical formulations described above can include, as appropriate, one or more additional carrier ingredients such as diluents, buffers, flavoring agents, binders, surface-active agents, thickeners, lubricants, preservatives (including anti-oxidants) and the like. Furthermore, other adjuvants can be included to render the formulation isotonic with the blood of the intended recipient. Compositions containing a compound of the invention, and/or pharmaceutically acceptable salts thereof, can also be prepared in powder or liquid concentrate form.

The present invention is further directed to a method for the manufacture of a medicament for bacterial infection in mammals (e.g., humans) comprising combining one or more disclosed compounds of the present invention, products, or compositions with a pharmaceutically acceptable carrier or diluent. Thus, in one aspect, the invention relates to a method for manufacturing a medicament comprising combining at least one disclosed compound according to the present invention or at least one disclosed product with a pharmaceutically acceptable carrier or diluent.

The disclosed pharmaceutical compositions can further comprise other active compounds, which are usually applied in the treatment of the above mentioned conditions. In another embodiment, the disclosed pharmaceutical compositions can further comprise other therapeutically active compounds, which are usually applied in the treatment of the above mentioned conditions.

It is understood that the disclosed compositions can be prepared from the disclosed compounds of the present invention. It is also understood that the disclosed compositions can be employed in the disclosed methods of using.

D. Methods of Using the Compounds and Compositions

Also provided is a method of use of a disclosed compound according to Formula I, composition, or medicament. In one aspect, the method of use is directed to the treatment of a disorder. In a further aspect, the disclosed compounds of the present invention can be used as single agents or in combination with one or more other drugs in the treatment, prevention, control, amelioration or reduction of risk of the aforementioned diseases, disorders and conditions for which the compound or the other drugs have utility, where the combination of drugs together are safer or more effective than either drug alone. The other drug(s) can be administered by a route and in an amount commonly used therefore, contemporaneously or sequentially with a disclosed compound of the present invention. When a disclosed compound of the present invention is used contemporaneously with one or more other drugs, a pharmaceutical composition in unit dosage form containing such drugs and the disclosed compound of the present invention is preferred. However, the combination therapy can also be administered on overlapping schedules. It is also envisioned that the combination of one or more active ingredients and a disclosed compound of the present invention can be more efficacious than either as a single agent.

The pharmaceutical compositions and methods of the present invention can further comprise other therapeutically active compounds as noted herein which are usually applied in the treatment of the above mentioned pathological conditions.

1. Treatment Methods

The compounds according to Formula I disclosed herein are useful for treating, preventing, ameliorating, controlling or reducing the risk of a variety of bacterial infections, including infection associated with gram positive or gram negative bacteria, wherein the patient or subject would benefit from an antibacterial agent. For example, a treatment can include inhibiting protein synthesis activity in bacteria by binding to bacterial ribosomes. In one aspect, provided is a method of treating or preventing a bacterial infection in a subject comprising the step of administering to the subject at least one disclosed compound of the present invention; at least one disclosed pharmaceutical composition; and/or at least one disclosed product in a dosage and amount effective to treat the disorder in the subject.

Also provided is a method for the treatment of one or more disorders associated with infection by a pathogenic bacteria wherein inhibiting bacterial protein synthesis can sterilize or decrease the presence of the pathogenic bacteria in a subject comprising the step of administering to the subject at least one disclosed compound of the present invention; at least one disclosed pharmaceutical composition; and/or at least one disclosed product in a dosage and amount effective to treat the disorder in the subject.

Also provided is a method for the treatment of one or more bacterial infections in a subject comprising the step of administering to the subject at least one disclosed compound of the present invention; at least one disclosed pharmaceutical composition; and/or at least one disclosed product in a dosage and amount effective to treat the disorder in the subject.

Also provided is a method for the treatment of a bacterial infection in a mammal comprising the step of administering to the mammal at least one disclosed compound of the present invention, composition, or medicament.

The compounds are further useful in a method for the prevention, treatment, control, amelioration, or reduction of risk of the bacterial infections noted herein. The compounds are further useful in a method for the prevention, treatment, control, amelioration, or reduction of risk of the aforementioned bacterial infections in combination with other agents.

In one aspect, the compounds according to Formula I can be used in combination with one or more other drugs in the treatment, prevention, control, amelioration, or reduction of risk of bacterial infections for which disclosed compounds of the present invention or the other drugs can have utility, where the combination of the drugs together are safer or more effective than either drug alone. Such other drug(s) can be administered, by a route and in an amount commonly used therefor, contemporaneously or sequentially with a compound of the present invention. When a compound of the present invention is used contemporaneously with one or more other drugs, a pharmaceutical composition in unit dosage form containing such other drugs and a disclosed compound of the present invention is preferred. However, the combination therapy can also include therapies in which a disclosed compound of the present invention and one or more other drugs are administered on different overlapping schedules. It is also contemplated that when used in combination with one or more other active ingredients, the disclosed compounds of the present invention and the other active ingredients can be used in lower doses than when each is used singly.

Accordingly, the pharmaceutical compositions include those that contain one or more other active ingredients, in addition to a compound of the present invention.

The above combinations include combinations of a disclosed compound of the present invention not only with one other active compound, but also with two or more other active compounds. Likewise, disclosed compounds of the present invention can be used in combination with other drugs that are used in the prevention, treatment, control, amelioration, or reduction of risk of the bacterial infections for which disclosed compounds of the present invention are useful. Such other drugs can be administered, by a route and in an amount commonly used therefor, contemporaneously or sequentially with a compound of the present invention. When a compound of the present invention is used contemporaneously with one or more other drugs, a pharmaceutical composition containing such other drugs in addition to a disclosed compound of the present invention is preferred. Accordingly, the pharmaceutical compositions include those that also contain one or more other active ingredients, in addition to a compound of the present invention.

The weight ratio of a disclosed compound of the present invention to the second active ingredient can be varied and will depend upon the effective dose of each ingredient. Generally, an effective dose of each will be used. Thus, for example, when a compound of the present invention is combined with another agent, the weight ratio of a disclosed compound of the present invention to the other agent will generally range from about 1000:1 to about 1:1000, preferably about 200:1 to about 1:200. Combinations of a compound of the present invention and other active ingredients will generally also be within the aforementioned range, but in each case, an effective dose of each active ingredient should be used.

In such combinations a disclosed compound of the present invention and other active agents can be administered separately or in conjunction. In addition, the administration of one element can be prior to, concurrent to, or subsequent to the administration of other agent(s).

Accordingly, the subject compounds can be used alone or in combination with other agents which are known to be beneficial in the subject indications or other drugs that affect receptors or enzymes that either increase the efficacy, safety, convenience, or reduce unwanted side effects or toxicity of the disclosed compounds of the present invention. The subject compound and the other agent can be coadministered, either in concomitant therapy or in a fixed combination.

In one aspect, the compound can be employed in combination with antibacterial or antimicrobial agents, and combinations thereof, and the like, or the subject compound can be administered in conjunction with the use of physical methods such as with debridement of a wound or infected tissue.

In the treatment of an infectious disease condition, an appropriate dosage level will generally be about 0.01 to 500 mg per kg patient body weight per day which can be administered in single or multiple doses. Preferably, the dosage level will be about 0.1 to about 250 mg/kg per day; more preferably about 0.5 to about 100 mg/kg per day. A suitable dosage level can be about 0.01 to 250 mg/kg per day, about 0.05 to 100 mg/kg per day, or about 0.1 to 50 mg/kg per day. Within this range the dosage can be 0.05 to 0.5, 0.5 to 5 or 5 to 50 mg/kg per day. For oral administration, the compositions are preferably provided in the form of tablets containing 1.0 to 1000 milligrams of the active ingredient, particularly 1.0, 5.0, 10, 15. 20, 25, 50, 75, 100, 150, 200, 250, 300, 400, 500, 600, 750, 800, 900, and 1000 milligrams of the active ingredient for the symptomatic adjustment of the dosage to the patient to be treated. The compounds can be administered on a regimen of 1 to 4 times per day, preferably once or twice per day. This dosage regimen can be adjusted to provide the optimal therapeutic response. It will be understood, however, that the specific dose level and frequency of dosage for any particular patient can be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy.

Thus, in one aspect, the invention relates to methods for treating a bacterial infection in at least one cell, comprising the step of contacting the at least one cell with at least one compound of the invention, in an amount effective to alter the response in the at least one cell. In a further aspect, the cell is mammalian, for example human. In a further aspect, the cell has been isolated from a subject prior to the contacting step. In a further aspect, contacting is via administration to a subject.

a. Treatment of an Infectious Disease in a Human Subject

In one aspect, the invention relates to a method for the treatment of an infectious disease, particularly a bacterial infection, in a human subject comprising the step of administering to the human subject a therapeutically effective amount of at least one compound according to Formula I or a pharmaceutically acceptable salt, hydrate, solvate, or polymorph thereof. In a further aspect, the human subject has been diagnosed with a need for treatment of the infectious disease prior to the administering step.

In a further aspect, the invention relates to a method for the treatment of an infectious disease in a human subject comprising the step of administering to the human subject a therapeutically effective amount of at least one compound that is a product of a disclosed method of making a compound; or a pharmaceutically acceptable salt, hydrate, solvate, or polymorph thereof.

In a further aspect, the invention relates to a method for the treatment of an infectious disease in a human subject, further comprising the step of identifying a human subject in need of treatment of the infectious disease.

In a further aspect, the invention relates to a method for the treatment of an infectious disease in a human subject comprising the step of administering to the human subject a therapeutically effective amount of at least one compound according to Formula I or a pharmaceutically acceptable salt, hydrate, solvate, or polymorph thereof; wherein the compound is formulated as a lotion, a cream, an ointment, a spray, or a soap.

In a further aspect, the compound is formulated as a solid dosage form. In a still further aspect, the solid dosage form is selected from a capsule, a tablet, a pill, a powder, a granule, an effervescing granule, a gel, a paste, a troche, and a pastille. In yet a further aspect, the solid dosage form is formulated for oral administration.

In a further aspect, the compound is formulated as a liquid dosage form. In a still further aspect, the liquid dosage form is selected from an emulsion, a solution, a suspension, a syrup, and an elixir. In yet a further aspect, the liquid dosage form is formulated for intravenous administration.

In a further aspect, the infectious disease is associated with a *Mycobacterium tuberculosis* infection. In a still further aspect, the *Mycobacterium tuberculosis* infection is associated with infection by an MDR strain of *Mycobacterium tuberculosis*. In a yet further aspect, the *Mycobacterium tuberculosis* infection is associated with infection by an XDR strain of *Mycobacterium tuberculosis*.

In a further aspect, the infectious disease is associated with a gram positive bacterial infection. In a still further aspect, the gram positive bacteria is selected from *Bacillus* sp. *Clostridium* sp., *Corynebacterium* sp., *Enterococcus* sp., *Mycoplasma* sp., *Staphylococcus* sp., and *Streptococcus* sp. In yet a further aspect, the gram positive bacteria is vancomycin resistant *Enterococcus* sp. (VRE). In an even further aspect, the gram positive bacteria is methicillin resistant *Staphylococcus* sp. (MRS). In a still further aspect, the gram positive bacteria is selected from *Bacillus anthracis, Bacillus cereus, Bacillus subtilis, Clostridium difficile, Clostridium tetani, Clostridium botulinum, Clostridium perfringens, Corynebacterium diphtheria, Enterococcus faecalis, Enterococcus faecium, Listeria monocytogenes, Listeria ivanovii, Micrococcus luteus, Mycoplasma genitalium, Mycoplasma pneumoniae, Staphylococcus aureus, Staphylococcus epidermidis, Staphylococcus saprophyticus, Staphylococcus hyicus, Staphylococcus intermedius, Streptococcus pneumoniae,* and *Streptococcus pyogenes*. In yet a further aspect, the gram positive bacteria is selected from *Bacillus anthracis, Bacillus subtilis, Enterococcus faecalis, Staphylococcus aureus, Streptococcus pneumoniae,* and *Streptococcus pyogenes*. In an even further aspect, the gram positive bacteria is selected from vancomycin resistant *Enterococcus faecalis*, vancomycin resistant methicillin resistant *Enterococcus faecium, Staphylococcus aureus* (MRSA), methicillin resistant *Staphylococcus epidermidis* (MRSE), macrolide resistant *Streptococcus pneumoniae* (Mac-R SPN) and penicillin resistant *Streptococcus pneumonia* (PRSP).

In a further aspect, the infectious disease is associated with a gram negative bacterial infection. In a still further aspect, the gram negative bacteria is selected from *Acinetobacter* sp., *Aeromonas* sp., *Burkholderia* sp., *Bordatella* sp., *Citrobacter* sp., *Chlamydia* sp., *Enterobacter* sp., *Escherichia* sp., *Francisella* sp., *Haemophilus* sp., *Klebsiella* sp., *Legionella* sp., *Moraxella* sp., *Neisseria* sp., *Proteus* sp., *Pseudomonas* sp., *Rickettsia* sp., *Salmonella* sp., *Shigella* sp., *Stenotrophomonas* sp., *Vibrio* sp., and *Yersinia* sp. In yet a further aspect, the gram negative bacteria is selected from *Acinetobacter baumannii, Aeromonas hydrophila, Bordetella pertussis, Bordetella parapertussis, Bordetella bronchiseptica, Burkholderia cepacia, Citrobacter freundii, Chlamydia pneumoniae, Chlamydia trachomatis, Chlamydia psittaci, Enterobacter aerogenes, Enterobacter cloacae, Enterobacter sakazakii, Escherichia coli, Francisella tularensis, Haemophilus influenzae, Haemophilus aegypticus, Haemophilus ducreyi, Klebsiella edwardsii, Klebsiella pneumoniae, Legionella pneumophilia, Moraxella catarrhalis, Neisseria meningitidis, Neisseria gonorrhoeae, Proteus mirabilis, Proteus vulgaris, Pseudomonas aeruginosa, Rickettsia rickettsii, Rickettsia akari, Rickettsia conorrii, Rickettsia sibirica, Rickettsia australis, Rickettsia felis, Rickettsia japonica, Rickettsia africae, Rickettsia prowazekii, Rickettsia typhi, Salmonella enterica, Shigella boydii, Shigella dysenteriae, Shigella flexneri, Shigella sonnei, Stenotrophomonas maltophilia, Vibrio cholerae, Vibrio parahaemolyticus, Vibrio vulnificus, Vibriofluvialis, Yersinia pestis, Yersina enterocolitica,* and *Yersina pseudotuberculosis*.

In a further aspect, the gram negative bacteria is a multi-drug resistant gram negative bacteria strain (MDR-GNB). In a still further aspect, the multi-drug resistant gram negative bacteria strain (MDR-GNB) is resistant to at least one anti-microbial agent selected from amikacin, tobramycin, cefepime, ceftazidime, imipenem, meropenem, piperacillin-tazobactam, ciprofloxacin, levofloxacin, tigecycline, and polymyxin B. In yet a further aspect, the multi-drug resistant gram negative bacteria strain (MDR-GNB) is selected from *Acinetobacter* sp., *Enterobacter* sp., *Klebsiella* sp., and *Pseuodomonas* sp. In an even further aspect, the multi-drug resistant gram negative bacteria strain (MDR-GNB) is selected from *Acinetobacter baumannii, Enterobacter aerogenes, Klebsiella pneumoniae,* and *Pseudomonas aeruginosa*. In a still further aspect, the multi-drug resistant gram negative bacteria strain (MDR-GNB) is *Enterobacter* sp.

In a further aspect, the infectious disease is selected from atypical pneumonia, bacterial meningitis, bronchitis, cholera, dental infection, dermatitis, diarrhea, diphtheria, dysentery, ear infection, endocarditis, gastritis, gastroenteritis, genital infection, genitourinary infection, infection associated with an indwelling device, intestinal infection, leprosy, listeriosis, lung infection, nocosomial infection, ocular infection, oral infection, otitis, osteo-articular infection, osteomyelitis, pharyngitis, papules, pharyngitis, pneumonia, pneumonia conjunctivitis, pruritius, pustules, pyoderma, pyothorax, respiratory infection, salmonellosis, septicemia, sexually transmitted disease, sinusitis, skin infection, skin and soft tissue infection ("SSTI"), soft tissue infection, tetanus, tuberculosis, typhus, ulcer, urinary tract infection, and wound infection. In a still further aspect, the infectious disease is selected from endocarditis, osteomyelitis, skin and soft tissue infection ("SSTI"), and infection associated with an indwelling device. In yet a further aspect, the infectious disease is endocarditis. In an even further aspect, the infectious disease is osteomyelitis. In a still further aspect, the infectious disease is an SSTI. In yet a further aspect, the SSTI is a complicated SSTI (cSSTI). In an even further aspect, the infectious disease is associated with an indwelling device.

In a further aspect, the invention relates to a method for the treatment of an infectious disease in a human subject, further comprising administering to the human subject a therapeutically effective amount of a second active agent. In a still further aspect, the second active agent comprises at least one antibacterial agent. In yet a further aspect, the antibacterial agent comprises a compound selected from amoxicillin, ampicillin, azithromycin, aztreonam, azlocillin, bacitracin, carbenicillin, cefaclor, cefadroxil, cefamandole, cefazolin, cephalexin, cefdinir, cefditorin, cefepime, cefixime, cefoperazone, cefotaxime, cefoxitin, cefpodoxime, cefprozil, ceftazidime, ceftibuten, ceftizoxime, ceftriaxone, cefuroxime, chloramphenicol, cilastin, ciprofloxacin, clarithromycin, clavulanic acid, clinafloxacin, clindamycin, clofazimine, cloxacillin, colistin, cycloserin, dalbavancin, dalfopristin, demeclocycline, dicloxacillin, dirithromycin, doxycycline, erythromycin, enrofloxacin, enoxacin, enviomycin, ertepenem, ethambutol, ethionmide, flucloxacillin, fosfomycin, furazolidone, gatifloxacin, gentamicin, imipenem, isoniazid, kanamycin, levofloxacin, linezolid, lomefloxacin, loracarbef, mafenide, moxifloxacin, meropenem, metronidazole, mezlocillin, minocycline, mupirocin, nafcillin, nalidixic acid, neomycin, netilmicin, nitrofurantoin, norfloxacin, ofloxacin, oritavancin, oxytetracycline, penicillin, piperacillin, platensimycin, polymixin B, pyrazinamide, quinupristin, retapamulin, rifabutin, rifampin, rifapentine, roxithromycin, sparfloxacin, spectinomycin, sulbactam, sulfacetamide, sulfamethizole, sulfamethoxazole, teicoplanin, telithromycin, telavancin, temafloxacin, tetracycline, thioacetazone, thioridazine, ticarcillin, tinidazole, tobramycin, torezolid, tosufloxacin, trimethoprim, troleandomycin, trovafloxacin, and vancomycin, or combinations thereof.

In a further aspect, the administering is co-administering of the compound and the antibacterial agent. In a still further aspect, the co-administration is administration in a substantially simultaneous manner. In yet a further aspect, the co-administration is administration in a substantially sequential manner.

In a further aspect, the administration in a substantially simultaneous manner comprises a single dose form containing a fixed ratio of the compound and the antibacterial agent. In a still further aspect, the single dose form is a capsule or a tablet. In yet a further aspect, the single dose form is an ampule for a single intravenous administration.

b. Treatment of an Infectious Disease in a Vertebrate Animal

In one aspect, the invention relates to a method for treatment of an infectious disease, particularly a bacterial infection, in a vertebrate animal comprising the step of administering to the vertebrate animal a therapeutically effective amount of at least one compound according to Formula I, or a pharmaceutically acceptable salt, solvate, or polymorph thereof.

In a further aspect, the invention relates to a method for treatment of an infectious disease in a vertebrate animal comprising the step of administering to the vertebrate animal a therapeutically effective amount of at least one compound that is a product of a disclosed method of making a compound; or a pharmaceutically acceptable salt, hydrate, solvate, or polymorph thereof.

In a further aspect, the vertebrate animal is a fish, a bird, or a mammal. In a still further aspect, the vertebrate animal is a livestock animal. In yet a further aspect, the vertebrate animal is a companion animal. In an even further aspect, the vertebrate animal is a farm animal. In a still further aspect, the vertebrate animal is a zoo animal. In yet a further aspect, the vertebrate animal is a laboratory animal. In an even further aspect, the vertebrate animal is an aquaculture fish. In a still further aspect, the vertebrate animal is selected from *Bison* sp., *Bos* sp., *Canis* sp., *Capra* sp., *Equus* sp., *Felis* sp., *Gallus* sp., *Lama* sp., *Meleagris* sp., *Oryctolagus* sp., *Ovis* sp., and *Sus* sp.

In a further aspect, the vertebrate animal has been diagnosed with a need for treatment of the infectious disease prior to the administering step.

In a further aspect, the invention relates to a method for the treatment of an infectious disease in a vertebrate animal, further comprising the step of identifying a vertebrate animal in need of treatment of the infectious disease.

In a further aspect, administering comprises mixing an effective amount of the compound with the food of the vertebrate animal. In a still further aspect, administering comprises administering enterally an effective amount of the compound with the food of the vertebrate animal. In yet a further aspect, administering comprises administering an oral bolus of an effective amount of the compound with the food of the vertebrate animal.

In a further aspect, the infectious disease is associated with a gram positive bacterial infection. In a still further aspect, the gram positive bacteria is selected from *Bacillus* sp. *Clostridium* sp., *Enterococcus* sp., *Corynebacterium* sp., and *Staphylococcus* sp., *Streptococcus* sp. In yet a further aspect, the gram positive bacteria is selected from *Mycoplasma gallisepticum, Mycoplasma meleagridis*, and *Mycoplasma synoviae.*

In a further aspect, the infectious disease is associated with a gram negative bacterial infection. In a still further aspect, the gram negative bacteria is selected from *Acinetobacter* sp., *Bacteroides* sp., *Brucella* sp., *Citrobacter* sp., *Escherichia* sp., *Enterobacter* sp., *Haemophilus* sp., *Klebsiella* sp., *Mannheimia* sp., *Neisseria* sp., *Pasteurella* sp., *Proteus* sp., *Pseudomonas* sp., *Salmonella* sp., *Shigella* sp., and *Serratia* sp. In yet a further aspect, the gram negative bacteria is selected from *Escherichia coli, Haemophilus somnus, Mannheimia haemolytica, Pasteurella multocida, Salmonella infantis*, and *Salmonella typhimurium.*

In a further aspect, the infectious disease is selected from dental infection, dermatitis, diarrhea, ear infection, gastritis, gastroenteritis, genitourinary infection, intestinal infection, lung infection, ocular infection, oral infection, otitis, osteoarticular infection, pharyngitis, papules, pneumonia conjunctivitis, pruritius, pustules, pyoderma, pyothorax, respiratory infection, salmonellosis, septicemia, skin infection, soft tissue infection, ulcer, urinary tract infection, and wound infection.

In a further aspect, the invention relates to a method for the treatment of an infectious disease in a vertebrate animal, further comprising administering to the vertebrate animal a therapeutically effective amount of second active agent. In a still further aspect, the second active agent is an antibacterial agent. In yet a further aspect, the antibacterial agent is a penicillin, a cephalosporin, a sulfonamide, a tetracycline, a lincosamide, an aminoglycoside, or a fluoroquinolone, or combinations thereof. In an even further aspect, the antibacterial agent comprises a compound selected from amoxicillin, ampicillin, azithromycin, cefovecin, cephalexin, chloramphenicol, ciprofloxacin, clavulanic acid, cloxacillin, clindamycin, doxycycline, enrofloxacin, erythromycin, gentamicin, ibafloxacin, kanamycin, lincomycin, marbofloxacin, metronidazole, minocycline, neomycin, novobiocin, ofloxacin, orbifloxacin, oxytetracycline, penicillin G, rifampin, sulfadimethoxine, sulfadiazine, tetracycline, tiamulin, ticarcillin, trimethoprim, and tylosin, or combinations thereof.

In a further aspect, the administering of a second active agent is co-administering of the compound and the antibacterial agent. In a still further aspect, the co-administration is administration in a substantially simultaneous manner. In yet a further aspect, the co-administration is administration in a substantially sequential manner.

In a further aspect, the administration in a substantially simultaneous manner comprises a single dose form containing a fixed ratio of the compound and the antibacterial agent. In a still further aspect, the single dose form is a capsule or a tablet. In yet a further aspect, the single dose form is an ampule for a single intravenous administration.

c. Treatment in a Human Subject of a Disorder Associated with Exposure to a Biodefense Pathogen In one aspect, the invention relates to a method for treatment in a human subject of a disorder associated with exposure to a biodefense pathogen comprising the step of administering to the human subject a therapeutically effective amount of at least one compound according to Formula I, or a pharmaceutically acceptable salt, hydrate, solvate, or polymorph thereof.

In a further aspect, the invention relates to a method for treatment in a human subject of a disorder associated with exposure to a biodefense pathogen comprising the step of administering to the human subject a therapeutically effective amount of at least one compound that is a product of a disclosed method of making a compound; or a pharmaceutically acceptable salt, hydrate, solvate, or polymorph thereof.

In a further aspect, the human subject has been diagnosed with a need for treatment of the disorder associated with exposure to the biodefense pathogen prior to the administering step.

In a further aspect, the invention relates to a method for the treatment in a human subject of a disorder associated with exposure to a biodefense pathogen, further comprising the step of identifying a human subject in need of treatment of the disorder associated with exposure to the biodefense pathogen.

In a further aspect, the compound is formulated as a solid dosage form. In a still further aspect, the solid dosage form is selected from a capsule, a tablet, a pill, a powder, a granule, an effervescing granule, a gel, a paste, a troche, and a pastille. In yet a further aspect, the solid dosage form is formulated for oral administration.

In a further aspect, the compound is formulated as a liquid dosage form. In a still further aspect, the liquid dosage form is selected from an emulsion, a solution, a suspension, a syrup, and an elixir. In yet a further aspect, the liquid dosage form is formulated for intravenous administration.

In a further aspect, the infectious disease is associated with a Category A biodefense pathogen. In a still further aspect, the Category A biodefense pathogen is selected from *Bacillus anthracis*, *Clostridium botulinum*, *Yersinia pestis*, and *Francisella tularensis*.

In a further aspect, the infectious disease is associated with a Category B biodefense pathogen. In a still further aspect, the Category B biodefense pathogen is selected from *Burkholderia cepacia*, *Burkholderia mallei*, *Burkholderia pseudomallei*, *Chlamydia psittaci*, *Coxiella burnetii*, *Rickettsia prowazekii*, *Brucella* sp., *Escherichia coli*, *Shigella* sp., *Salmonella* sp., *Vibrio cholera*, *Listeria monocytogenes*, *Campylobacter jejuni*, and *Yersinia enterocolitica*. In yet a further aspect, the *Escherichia coli* is a diarrheagenic strain, a enterotoxigenic strain (ETEC), or a enteropathogenic strain (EPEC). In an even further aspect, the *Escherichia coli* is selected from serotype O157:H7, serotype O26:H11, serotype O111:H8, and serotype STEC 0104:H4. In a still further aspect, the *Shigella* sp. is selected from *Shigella sonnei*, *Shigella dysenteriae*, *Shigella flexneri*, and *Shigella boydii*. In yet a further aspect, the *Salmonella* sp. is selected from *Salmonella typhimurium* and *Salmonella enteritidis*.

In a further aspect, the disorder is selected from anthrax, botulism, plague, tularemia, glanders, meliodosis, respiratory psittacosis, Q fever, typhus fever, bucellosis, shigellosis, salmonellosis, cholera, listeriosis, gastroenteritis, and yersinoiosis.

d. Inhibition of Protein Synthesis in at Least One Bacterial Cell

In one aspect, the invention relates to a method for the inhibition of protein synthesis in at least one bacterial cell, comprising the step of contacting the at least one bacterial cell with an effective amount of at least one compound according to Formula I or a pharmaceutically acceptable salt, hydrate, solvate, or polymorph thereof.

In a further aspect, the invention relates to a method for the inhibition of protein synthesis in at least one bacterial cell, comprising the step of contacting the at least one bacterial cell with an effective amount of at least one disclosed compound according to the present invention that is a product of a disclosed method of making a compound; or a pharmaceutically acceptable salt, hydrate, solvate, or polymorph thereof.

In a further aspect, the bacterial cell is a gram positive bacterial cell. In a still further aspect, the bacterial cell is a gram negative bacterial cell.

In a further aspect, contacting is via administration to a mammal.

In a further aspect, the mammal has been diagnosed with a need for treatment of an infectious disease prior to the administering step. In a still further aspect, the mammal has been diagnosed with a need for inhibiting protein synthesis in the bacterial cell prior to the administering step.

In a further aspect, the compound exhibits a minimal inhibitory concentration (MIC) of less than about 100 µg/mL. In a still further aspect, the compound exhibits a minimal inhibitory concentration (MIC) of less than about 50 µg/mL. In yet a further aspect, the compound exhibits a minimal inhibitory concentration (MIC) of less than about 25 µg/mL. In an even further aspect, the compound exhibits a minimal inhibitory concentration (MIC) of less than about 12.5 µg/mL. In a still further aspect, the compound exhibits a minimal inhibitory concentration (MIC) of less than about 6.2 µg/mL. In yet a further aspect, the compound exhibits a minimal inhibitory concentration (MIC) of less than about 3.2 µg/mL. In an even further aspect, the compound exhibits a minimal inhibitory concentration (MIC) of less than about 1.6 µg/mL.

In a further aspect, the MIC is determined by a microbroth dilution method in accordance with Clinical Laboratory Standards Institute approved standard methods M7-A7. In a still further aspect, the MIC is determined using *Bacillus anthracis*, Sterne 34F$_2$ strain. In yet a further aspect, the MIC is determined using *Bacillus subtilis*, ATCC 23857. In an even further aspect, the MIC is determined using *Enterococcus faecalis*, ATCC 33186. In a still further aspect, the MIC is determined using *Staphylococcus aureus*, NRS70. In yet a further aspect, the MIC is determined using *Streptococcus pneumoniae*, R6. In an even further aspect, the MIC is determined using *Streptococcus pyogenes*, ATCC 700294. In a still further aspect, the MIC is determined using Acinetobacter baumannii, ATCC 19606. In yet a further aspect, the MIC is determined using Burkholderia cepacia, ATCC 25416. In an even further aspect, the MIC is determined using Escherichia coli, ATCC 700926. In a still further aspect, the MIC is determined using Klebsiella pneumonia, ATCC 33495. In yet a further aspect, the MIC is determined using Pseudomonas aeruginosa, PA01. In an even further aspect, the MIC is determined using Proteus mirabilis, ATCC 25933. In a still further aspect, the MIC is determined using Proteus vulgaris, ATCC 33420. In yet a further aspect, the MIC is determined using Stenotrophomonas maltophilia, ATCC 13637.

In a further aspect, the compound exhibits an $IC_{50}$ for inhibition of protein synthesis of less than or equal to about 5.0 µg/mL. In a still further aspect, the compound exhibits an $IC_{50}$ for inhibition of protein synthesis of less than or equal to about 2.5 µg/mL. In yet a further aspect, the compound exhibits an $IC_{50}$ for inhibition of protein synthesis of less than or equal to about 1.0 µg/mL. In an even further aspect, the compound exhibits an $IC_{50}$ for inhibition of protein synthesis of less than or equal to about 0.50 µg/mL. In a still further aspect, the compound exhibits an $IC_{50}$ for inhibition of protein synthesis of less than or equal to about 0.25 µg/mL.

2. Manufacture of a Medicament

In one aspect, the invention relates to a medicament comprising one or more compounds according to Formula I or a pharmaceutically acceptable salt, hydrate, solvate, or polymorph thereof. In a further aspect, the one or more compounds are a product of a disclosed method of making.

In various aspect, the invention relates methods for the manufacture of a medicament for inhibition of bacterial protein synthesis (e.g., treatment of one or more bacterial infections) in mammals (e.g., humans) comprising combining one or more disclosed compounds of the present invention, products, or compositions or a pharmaceutically acceptable salt, solvate, hydrate, or polymorph thereof, with a pharmaceutically acceptable carrier. It is understood that the disclosed methods can be performed with the disclosed compounds of the present invention, products, and pharmaceutical compositions. It is also understood that the disclosed methods can be employed in connection with the disclosed methods of using.

3. Use of Compounds

Also provided are the uses of the compounds according to Formula I and products. In one aspect, the invention relates to use of at least one compound of Formula I or a pharmaceutically acceptable salt, hydrate, solvate, or polymorph thereof. In a further aspect, the compound used is a product of a disclosed method of making.

In one aspect, the invention relates to the use of a compound in the manufacture of a medicament for the treatment of infectious diseases, wherein the compound is a compound of Formula I or a pharmaceutically acceptable salt, hydrate, solvate, or polymorph thereof.

In a further aspect, the invention relates to the use of a compound in the manufacture of a medicament for the treatment of infectious diseases, wherein the compound is a product of a disclosed method of making; or a pharmaceutically acceptable salt, hydrate, solvate, or polymorph thereof.

In a further aspect, the use relates to a process for preparing a pharmaceutical composition comprising a compound of Formula I or a product of a disclosed method of making, or a pharmaceutically acceptable salt, solvate, or polymorph thereof, for use as a medicament. In another aspect, the use relates to a process for preparing a pharmaceutical composition comprising a therapeutically effective amount of a compound of Formula I or a product of a disclosed method of making, or a pharmaceutically acceptable salt, solvate, or polymorph thereof, for use as a medicament.

In a further aspect, the use relates to a process for preparing a pharmaceutical composition comprising a compound of Formula I or a product of a disclosed method of making, or a pharmaceutically acceptable salt, solvate, or polymorph thereof, wherein a pharmaceutically acceptable carrier is intimately mixed with the compound or the product of a disclosed method of making. In another aspect, the use relates to a process for preparing a pharmaceutical composition comprising a therapeutically effective amount of a compound of Formula I or a product of a disclosed method of making, or a pharmaceutically acceptable salt, solvate, or polymorph thereof, wherein a pharmaceutically acceptable carrier is intimately mixed with a therapeutically effective amount of the compound or the product of a disclosed method of making.

In various aspects, the use relates to the treatment of an infectious diseases in a vertebrate animal. In a further aspect, the use relates to the treatment of an infectious disease in a human subject.

In a further aspect, the use is the treatment of an infectious disease. In a still further aspect, the infectious disease is associated with a gram positive bacterial infection. In yet a further aspect, the infectious disease is associated with a gram negative bacterial infection.

It is understood that the disclosed uses can be employed in connection with the compounds of Formula I, methods, compositions, and kits. In a further aspect, the invention relates to the use of a disclosed compound of the present invention or a disclosed product in the manufacture of a medicament for the treatment of a bacterial infection in a mammal.

In a further aspect, the invention relates to the use of a compound according to Formula I or a disclosed product in the manufacture of a medicament for the treatment of an infectious disease selected from atypical pneumonia, bacterial meningitis, bronchitis, cholera, dental infection, dermatitis, diarrhea, diphtheria, dysentery, ear infection, endocarditis, gastritis, gastroenteritis, genital infection, genitourinary infection, infection associated with an indwelling device, intestinal infection, leprosy, listeriosis, lung infection, nocosomial infection, ocular infection, oral infection, otitis, osteo-articular infection, osteomyelitis, pharyngitis, papules, pharyngitis, pneumonia, pneumonia conjunctivitis, pruritius, pustules, pyoderma, pyothorax, respiratory infection, salmonellosis, septicemia, sexually transmitted disease, sinusitis, skin infection, skin and soft tissue infection ("SSTI"), soft tissue infection, tetanus, tuberculosis, typhus, ulcer, urinary tract infection, and wound infection.

In a further aspect, the invention relates to the use of a disclosed compound of the present invention or a disclosed product in the manufacture of a medicament for the treatment of tuberculosis.

In a further aspect, the invention relates to the use of a disclosed compound of the present invention or a disclosed product in the manufacture of a medicament for the treatment of a bacterial infection associated with infection by with a bacterial species selected from Bacillus sp. Clostridium sp., Corynebacterium sp., Enterococcus sp., Mycoplasma sp., Staphylococcus sp., and Streptococcus sp.

In a further aspect, the invention relates to the use of a disclosed compound of the present invention or a disclosed product in the manufacture of a medicament for the treatment of a bacterial infection associated with infection by with a bacterial species selected from *Bacillus anthracis, Bacillus cereus, Bacillus subtilis, Clostridium difficile, Clostridium tetani, Clostridium botulinum, Clostridium perfringens, Corynebacterium diphtheria, Enterococcus faecalis, Enterococcus faecium, Listeria monocytogenes, Listeria ivanovii, Micrococcus luteus, Mycoplasma genitalium, Mycoplasma pneumoniae, Staphylococcus aureus, Staphylococcus epidermidis, Staphylococcus saprophyticus, Staphylococcus hyicus, Staphylococcus intermedius, Streptococcus pneumoniae*, and *Streptococcus pyogenes*.

In a further aspect, the invention relates to the use of a disclosed compound of the present invention or a disclosed product in the manufacture of a medicament for the treatment of a bacterial infection associated with infection by with a bacterial species selected from *Acinetobacter* sp., *Aeromonas* sp., *Burkholderia* sp., *Bordatella* sp., *Citrobacter* sp., *Chlamydia* sp., *Enterobacter* sp., *Escherichia* sp., *Francisella* sp., *Haemophilus* sp., *Klebsiella* sp., *Legionella* sp., *Moraxella* sp., *Neisseria* sp., *Proteus* sp., *Pseudomonas* sp., *Rickettsia* sp., *Salmonella* sp., *Shigella* sp., *Stenotrophomonas* sp., *Vibrio* sp., and *Yersinia* sp.

In a further aspect, the invention relates to the use of a disclosed compound of the present invention or a disclosed product in the manufacture of a medicament for the treatment of a bacterial infection associated with infection by with a bacterial species selected from *Acinetobacter baumannii, Aeromonas hydrophila, Bordetella pertussis, Bordetella parapertussis, Bordetella bronchiseptica, Burkholderia cepacia, Citrobacter freundii, Chlamydia pneumoniae, Chlamydia trachomatis, Chlamydia psittaci, Enterobacter aerogenes, Enterobacter cloacae, Enterobacter sakazakii, Escherichia coli, Francisella tularensis, Haemophilus influenzae, Haemophilus aegypticus, Haemophilus ducreyi, Klebsiella edwardsii, Klebsiella pneumoniae, Legionella pneumophilia, Moraxella catarrhalis, Neisseria meningitidis, Neisseria gonorrhoeae, Proteus mirabilis, Proteus vulgaris, Pseudomonas aeruginosa, Rickettsia rickettsii, Rickettsia akari, Rickettsia conorrii, Rickettsia sibirica, Rickettsia australis, Rickettsia felis, Rickettsia japonica, Rickettsia africae, Rickettsia prowazekii, Rickettsia typhi, Salmonella enterica, Shigella boydii, Shigella dysenteriae, Shigella flexneri, Shigella sonnei, Stenotrophomonas maltophilia, Vibrio cholerae, Vibrio parahaemolyticus, Vibrio vulnificus, Vibrio fluvialis, Yersinia pestis, Yersina enterocolitica*, and *Yersina pseudotuberculosis*.

4. Kits

In one aspect, the invention relates to a kit comprising at least one compound according to Formula I, or a pharmaceutically acceptable salt, solvate, or polymorph thereof; and one or more of:

a) at least one agent known to inhibit microbial ribosomal activity;
b) at least one agent known to have antimicrobial activity;
c) at least one agent known to treat an infectious disease;
d) instructions for treating an infectious disease;
e) instructions for administering the compound in connection with treating a microbial infection; or
f) instructions for administering the compound with at least one agent known to treat an infectious disease.

In various further aspects, the invention relates to kits comprising at least one product of a disclosed method of making and at least one agent known to treat an infectious disease. In a further aspect, the kit comprises a disclosed compound of the present invention or a product of a disclosed method.

In a further aspect, the at least one compound and the at least one agent are co-formulated. In a still further aspect, the at least one compound and the at least one agent are co-packaged.

The kits can also comprise compounds and/or products co-packaged, co-formulated, and/or co-delivered with other components. For example, a drug manufacturer, a drug reseller, a physician, a compounding shop, or a pharmacist can provide a kit comprising a disclosed compound of the present invention and/or product and another component for delivery to a patient.

In a further aspect, the kit further comprises a plurality of dosage forms, the plurality comprising one or more doses; wherein each dose comprises an amount of the compound and the agent known to have antimicrobial activity. In another aspect, the kit further comprises a plurality of dosage forms, the plurality comprising one or more doses; wherein each dose comprises an effective amount of the compound and the agent known to have antimicrobial activity.

In a further aspect, an effective amount is a therapeutically effective amount. In a still further aspect, an effective amount is a prophylactically effective amount.

In a further aspect, each dose of the compound and the agent known to have antimicrobial activity are co-formulated. In a still further aspect, each dose of the compound and the agent known to have antimicrobial activity are co-packaged.

In a further aspect, the dosage forms are formulated for oral administration and/or intravenous administration. In a still further aspect, the dosage forms are formulated for oral administration. In yet a further aspect, the dosage forms are formulated for intravenous administration. In an even further aspect, the dosage form for the compound is formulated for oral administration and the dosage form for the agent known to have antimicrobial activity is formulated for intravenous administration. In a still further aspect, the dosage form for the compound is formulated for intravenous administration and the dosage form for the agent known to have antimicrobial activity is formulated for oral administration.

In a further aspect, the agent known to have antimicrobial activity is selected from amoxicillin, ampicillin, azithromycin, aztreonam, azlocillin, bacitracin, carbenicillin, cefaclor, cefadroxil, cefamandole, cefazolin, cephalexin, cefdinir, cefditorin, cefepime, cefixime, cefoperazone, cefotaxime, cefoxitin, cefpodoxime, cefprozil, ceftazidime, ceftibuten, ceftizoxime, ceftriaxone, cefuroxime, chloramphenicol, cilastin, ciprofloxacin, clarithromycin, clavulanic acid, clinafloxacin, clindamycin, clofazimine, cloxacillin, colistin, cycloserin, dalbavancin, dalfopristin, demeclocycline, dicloxacillin, dirithromycin, doxycycline, erythromycin, enrofloxacin, enoxacin, enviomycin, ertepenem, ethambutol, ethionmide, flucloxacillin, fosfomycin, furazolidone, gatifloxacin, gentamicin, imipenem, isoniazid, kanamycin, levofloxacin, linezolid, lomefloxacin, loracarbef, mafenide, moxifloxacin, meropenem, metronidazole, mezlocillin, minocycline, mupirocin, nafcillin, nalidixic acid, neomycin, netilmicin, nitrofurantoin, norfloxacin, ofloxacin, oritavancin, oxytetracycline, penicillin, piperacillin, platensimycin, polymixin B, pyrazinamide, quinupristin, retapamulin, rifabutin, rifampin, rifapentine, roxithromycin, sparfloxacin, spectinomycin, sulbactam, sulfacetamide, sulfamethizole, sulfamethoxazole, teicoplanin, telithromycin, telavancin, temafloxacin, tetracycline, thioacetazone, thioridazine, ticarcillin, tinidazole, tobramycin, torezolid, tosufloxacin, trimethoprim, troleandomycin, trovafloxacin, and vancomycin, or combinations.

In a further aspect, the instructions for treating an infectious disease provide for treatment of a gram positive bacterial infection. In a still further aspect, the instructions for treating an infectious disease provide for treatment of a gram negative bacterial infection.

In a further aspect, the instructions for treating an infectious disease provide for treatment of an infectious disease selected from bacterial meningitis, cholera, dental infection, dermatitis, diarrhea, diphtheria, dysentery, ear infection, endocarditis, gastritis, gastroenteritis, genital infection, genitourinary infection, infection associated with an indwelling device, intestinal infection, leprosy, listeriosis, lung infection, nocosomial infection, ocular infection, oral infection, otitis, osteo-articular infection, osteomyelitis, pharyngitis, papules, pharyngitis, pneumonia conjunctivitis, pruritius, pustules, pyoderma, pyothorax, respiratory infection, salmonellosis, septicemia, sexually transmitted disease, sinusitis, skin infection, skin and soft tissue infection ("SSTI"), soft tissue infection, tetanus, tuberculosis, ulcer, urinary tract infection, and wound infection. In a still further aspect, the instructions for treating an infectious disease provide for treatment of an infectious disease selected endocarditis, osteomyelitis, skin and soft tissue infection (SSTI), and infection associated with an indwelling device.

In a further aspect, the infectious disease is endocarditis. In a still further aspect, the infectious disease is osteomyelitis. In yet a further aspect, the infectious disease is an SSTI. In an even further aspect, the SSTI is a complicated SSTI (cSSTI). In a still further aspect, the infectious disease is associated with an indwelling device.

In a further aspect, the instructions for administering the compound with at least one agent known to treat an infectious disease provide for co-administering of the compound and the agent. In a still further aspect, the co-administration is administration in a substantially simultaneous manner. In yet a further aspect, the co-administration is administration in a substantially sequential manner.

In a further aspect, the administration in a substantially simultaneous manner comprises a single dose form containing a fixed ratio of the compound and the antibacterial agent. In a still further aspect, the single dose form is a capsule or a tablet. In a still further aspect, the single dose form is an ampule for a single intravenous administration.

It is understood that the disclosed kits can be prepared from the disclosed compounds of the present invention, products, and pharmaceutical compositions. It is also understood that the disclosed kits can be employed in connection with the disclosed methods of using.

5. Subjects

The subject of the herein disclosed methods can be a vertebrate, such as a mammal, a fish, a bird, a reptile, or an amphibian. Thus, the subject of the herein disclosed methods can be a human, non-human primate, horse, pig, rabbit, dog, sheep, goat, cow, cat, guinea pig or rodent. The term does not denote a particular age or sex. Thus, adult and juvenile subjects, whether male or female, are intended to be covered. It is further contemplated that prenatal or neonatal treatments can be performed using the compounds of the present invention, and in the case of prenatal treatment, the treatment is typically accomplished by administration of a compound according to the invention to the mother. A patient refers to a subject afflicted with a disease or disorder. The term "patient" includes human and veterinary subjects.

In some aspects of the disclosed methods, the subject has been diagnosed with a need for treatment prior to the administering step. In some aspects of the disclosed method, the subject has been diagnosed with a disorder treatable by inhibiting the activity of a bacterial protein synthesis prior to the administering step. In some aspects of the disclosed method, the subject has been diagnosed with an infectious disease prior to the administering step. In some aspects of the disclosed methods, the subject has been identified with a need for treatment prior to the administering step. In one aspect, a subject can be treated prophylactically with a compound or composition disclosed herein, as discussed herein elsewhere.

E. Examples

The following examples are put forth so as to provide those of ordinary skill in the art with a complete disclosure and description of how the compounds, compositions, articles, devices and/or methods claimed herein are made and evaluated, and are intended to be purely exemplary and are not intended to limit the disclosure. Efforts have been made to ensure accuracy with respect to numbers (e.g., amounts, temperature, etc.), but some errors and deviations should be accounted for. Unless indicated otherwise, parts are parts by weight, temperature is in ° C. or is at ambient temperature, and pressure is at or near atmospheric.

1. General Methods

All materials and reagents were used as is unless otherwise indicated. Air- or moisture-sensitive reactions were carried out under a nitrogen atmosphere. THF, toluene, acetonitrile, N,N-dimethyl formamide and $CH_2Cl_2$ were distilled before use. All compounds were purified on Biotage® pre-packed silica gel columns. TLC analysis was performed using glass TLC plates (0.25 mm, 60 F-254 silica gel). Visualization of the developed plates was accomplished by staining with ethanolic phosphomolybdic acid, ceric ammonium molybdate, or ethanolic ninhydrin followed by heating on a hot plate (120° C.). All tested compounds possessed a purity of >95% as determined by ultra-high pressure liquid chromatography on a Waters Acquity UPLC/PDA/ELSD/MS system carried out with a BEH C18 2.1×50 mm column using gradient elution with stationary phase: BEH C18, 1.7 mm, solvents: A: 0.1% formic acid in water, B: 0.1% formic acid in acetonitrile. NMR spectra were obtained on Bruker Avance II 400 MHz. The values $d_H$ 7.26 and $d_C$ 77.0 ppm were used as references for NMR spectroscopy in $CDCl_3$. The coupling constants deduced in $^1H$ NMR data cases were obtained by first-order coupling analysis. Analytical and preparative SFC (Supercritical Fluid Chromatography) systems (AD-H) were used for analysis and purification. IR spectra were collected using a Nicolet IR 100 (FT IR). FT IR analyses were prepared as neat and neat films on KBr plates, and the data are reported in wave-numbers ($cm^{-1}$) unless specified otherwise. Melting points (mp) were obtained on a Buchi apparatus and are uncorrected. The University of Illinois Mass Spectroscopy Laboratories and High Throughput Analytical Center at St. Jude Children's Research Hospital collected the high resolution mass spectral data.

2. Analog Route I

To a stirred solution of di-benzyloxy carbonyl-3'-(R)-methylene mSPC (0.475 mmol) in MeOH:$CH_3COOH$ (10:

1) (4.0 mL) and the selected aldehyde (0.475 mmol) was added 2-picoline borane (0.475 mmol) and stirred at room temperature overnight. The methanol was removed and the residue partitioned between EtOAc and water and the 2-phase mixture was extracted with EtOAc (2×5 mL). The combined organic layers were dried with $Na_2SO_4$ and concentrated under reduced pressure and purified by column chromatography to afford the corresponding protected amine using $CH_3CN$/MeOH gradient eluent system. Deprotection of the amino protecting groups was achieved by dissolution of the protected amine in MeOH and 1.25 M HCl in MeOH with 10% Pd/C. The mixture was hydrogenated under 1 atm at room temperature for 1 hr, filtered, concentrated and dried in vacuo to give the target 3'-methylene mSPC.

3. Analog Route II

To a stirred solution of di-benzyloxy carbonyl-3'-(R)-mSPC (0.475 mmol) in MeOH:$CH_3COOH$ (10:1) (4.0 mL) and the selected aldehyde (0.475 mmol) was added 2-picoline borane (0.475 mmol) and stirred at room temperature overnight. The methanol was removed and the residue partitioned between EtOAc and water and the 2-phase mixture was extracted with EtOAc (2×5 mL). The combined organic layers were dried with $Na_2SO_4$ and concentrated under reduced pressure and purified by column chromatography to afford the corresponding protected amine using $CH_3CN$/MeOH gradient eluent system. Deprotection of the amino protecting groups was achieved by dissolving the protected amine in 48% HBr (in water). The mixture was stirred at room temperature for 2 hr, and then the solution was poured into 300 mL of acetone while stirring gently with a glass rod. Decanted the acetone and the resultant solid was washed with acetone (4×50 mL). The residue was dissolved by methanol and concentrated under reduced pressure, dried in vacuo to give the target 3'-methylene mSPC.

4. Analog Route III

To a stirred solution of di-benzyloxy carbonyl-3'-(R)-mSPC (0.317 mmol) and the selected aldehyde (0.380 mmol) in MeOH (5.0 mL) was added $NaCNBH_3$ (0.108 mmol). Then the pH of the solution was adjusted to pH 4 using 1.25 M HCl in methanol and stirred at room temperature for 2 hr maintaining the pH. The methanol was removed and the residue partitioned between EtOAc and water and the 2-phase mixture was extracted with EtOAc (2×5 mL). The combined organic layers were dried with $Na_2SO_4$ and concentrated under reduced pressure and purified by column chromatography to afford the corresponding protected amine using $CH_3CN$/MeOH gradient eluent system. Deprotection of the amino protecting groups was achieved by dissolution of the protected amine in Methanol and 1.25 M HCl in MeOH with 10% Pd—C. The mixture was hydrogenated under 1 atm at room temperature for 1 hr, filtered, concentrated and dried in vacuo to give the target 3'-methylene mSPC.

5. Analog Route IV

To a stirred solution of di-benzyloxy carbonyl-3'-(R)-mSPC (0.317 mmol) and the selected aldehyde (0.380 mmol) in MeOH (5.0 mL) was added $NaCNBH_3$ (0.108 mmol). Then the pH of the solution was adjusted to pH 4 using 1.25 M HCl in methanol and stirred at room temperature for 2 hr maintaining the pH. The methanol was removed and the residue partitioned between EtOAc and water and the 2-phase mixture was extracted with EtOAc (2×5 mL). The combined organic layers were dried with $Na_2SO_4$ and concentrated under reduced pressure and purified by column chromatography to afford the corresponding protected amine using $CH_3CN$/MeOH gradient eluent system. Deprotection of the amino protecting groups was achieved by dissolving the protected amine in 48% HBr (in water). The mixture was stirred at room temperature for 2 hr, and then the solution was poured into 300 mL of acetone while stirring gently with a glass rod. Decanted the acetone and the resultant solid was washed with acetone (3×50). The residue was dissolved by methanol and concentrated under reduced pressure, dried in vacuo to give the target 3'-methylene mSPC.

6. Analog Route V

A mixture of di-benzyloxy carbonyl-3'-deoxo-3'-(R)-mSPC oxide (0.488 mmol), $LiClO_4$ (0.976 mmol), and the selected aniline (0.586 mmol) in DMF (10.0 mL) was irradiated with microwave for 20 min at 120° C. The DMF was removed and the residue partitioned between EtOAc and water and the 2-phase mixture was extracted with EtOAc (2×10 mL). The combined organic layers were dried with $Na_2SO_4$ and concentrated under reduced pressure and purified by column chromatography to afford the corresponding protected amine using EtOAc/Hexanes gradient eluent system. Deprotection of the amino protecting groups was achieved by dissolution of the protected amine in Methanol and 1.25 M HCl in MeOH with 10% Pd—C. The mixture was hydrogenated under 1 atm at room temperature for 1 hr, filtered, concentrated and dried in vacuo to give the target 3'-methylene mSPC.

7. Analog Route VI

To a stirred solution of di-benzyloxy carbonyl-3'-(S)-methylene mSPC (0.475 mmol) in MeOH:$CH_3COOH$ (10:1) (4.0 mL) and the selected aldehyde (0.475 mmol) was added 2-picoline borane (0.475 mmol) and stirred at room temperature overnight. The methanol was removed and the residue partitioned between EtOAc and water and the 2-phase mixture was extracted with EtOAc (2×5 mL). The combined organic layers were dried with $Na_2SO_4$ and concentrated under reduced pressure and purified by column chromatography to afford the corresponding protected amine using $CH_3CN$/MeOH gradient eluent system. Deprotection of the amino protecting groups was achieved by dissolution of the protected amine in MeOH and 1.25 M HCl in MeOH with 10% Pd/C. The mixture was hydrogenated under 1 atm at room temperature for 1 hr, filtered, concentrated and dried in vacuo to give the target 3'-methylene mSPC.

8. Analog Route VII

To a stirred solution of di-benzyloxy carbonyl-3'-(R)-methylene mSPC (0.158 mmol) in dichloroethane (4.0 mL) and the selected aldehyde (0.317 mmol) was added sodium triacetoxyborohydride (0.237 mmol) and stirred at room temperature for about 1-3 hr. The methanol was removed and the residue partitioned between EtOAc and water and the 2-phase mixture was extracted with EtOAc (2×5 mL). The combined organic layers were dried with Na2SO4 and concentrated under reduced pressure and purified by column chromatography to afford the corresponding protected amine using CH$_3$CN/MeOH gradient eluent system. Deprotection of the amino protecting groups was achieved by dissolution of the protected amine in MeOH with 10% Pd/C. The mixture was hydrogenated under 1 atm at room temperature for 1 hr, filtered, concentrated and dried in vacuo. The resulting compound was dissolved in methanol (2.0 mL) and treated with 1.25 M methanolic solution (0.190 mL) to give the target 3'-methylene mSPC hydrochloride salt.

9. Analog Route VIII

A mixture of di-benzyloxy carbonyl-3'-deoxo-3'-(R)-mSPC oxide (0.325 mmol), LiClO$_4$ (0.976 mmol), and the selected amine (1.627 mmol) in MeOH (10.0 mL) was heated for 24 h at 40° C. The MeOH was removed and the residue partitioned between CHCl$_3$ and water and the 2-phase mixture was extracted with CHCl$_3$ (2×10 mL). The combined organic layers were dried with Na$_2$SO$_4$ and concentrated under reduced pressure and purified by column chromatography to afford the corresponding protected amine using CHCl$_3$/MeOH gradient eluent system. Deprotection of the amino protecting groups was achieved by dissolving the protected amine in 48% HBr (in water). The mixture was stirred at room temperature for 2 hr, and then the solution was poured into 300 mL of acetone while stirring gently with a glass rod. Decanted the acetone and the resultant solid was washed with acetone (3×50). The residue was dissolved by methanol and concentrated under reduced pressure, dried in vacuo to give the target 3'-methylene mSPC.

10. Analog Route IX

A mixture of di-benzyloxy carbonyl-3'-deoxo-3'-(R)-mSPC oxide (0.325 mmol), LiClO$_4$ (0.976 mmol), and the selected amine (1.627 mmol) in MeOH (10.0 mL) was heated for 24 h at 40° C. The MeOH was removed and the residue partitioned between CHCl$_3$ and water and the 2-phase mixture was extracted with CHCl$_3$ (2×10 mL). The combined organic layers were dried with Na$_2$SO$_4$ and concentrated under reduced pressure and purified by column chromatography to afford the corresponding protected amine using CHCl$_3$/MeOH gradient eluent system. Deprotection of the amino protecting groups was achieved by dissolution of the protected amine in Methanol and 1.25 M HCl in MeOH with 10% Pd—C. The mixture was hydrogenated under 1 atm at room temperature for 1 hr, filtered, concentrated and dried in vacuo to give the target 3'-methylene mSPC.

11. Preparation of 3'-(R)-3'-(benzylaminomethyl) dihydrospectinomycin Trihydrochloride (1)

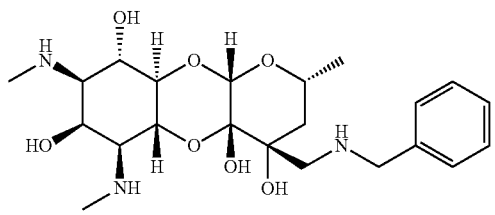 [SMILES: CN[C@@H]1[C@H](O)[C@H](NC)[C@H]2O[C@]3(O)[C@H](O[C@@H]2[C@H]1O)O[C@H](C)C[C@@]3(O)CNCc1ccccc1]

Compound 1 was prepared via Analog Route I (as described herein above) to afford the title compound (97 mg, 52%) as the trihydrochloride salt. $^1$H NMR (D$_2$O, 400 MHz) δ 7.53 (s, 5H), 4.72 (t, J=2.9 Hz, 1H), 4.40-4.24 (m, 3H), 4.05 (t, J=9.9 Hz, 1H), 3.97 (t, J=10.1 Hz, 1H), 3.79 (dd, J=10.9, 9.4 Hz, 1H), 3.62-3.56 (m, 1H), 3.46-3.38 (m, 1H), 3.31-3.20 (m, 3H), 2.85-2.83 (m, 6H), 1.92-1.76 (m, 2H), 1.23 (d, J=5.9 Hz, 3H); MS-ESI m/z=454.29 [M+H]+.

12. Preparation of 3'-(R)-3'-[(4-fluoro)benzylaminomethyl)]dihydrospectinomycin Trihydrochloride (2)

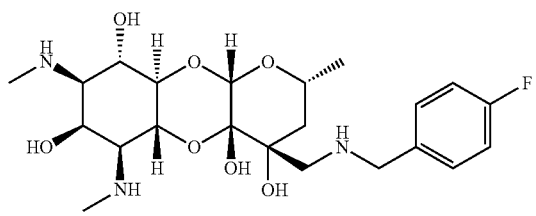 [SMILES: CN[C@@H]1[C@H](O)[C@H](NC)[C@H]2O[C@]3(O)[C@H](O[C@@H]2[C@H]1O)O[C@H](C)C[C@@]3(O)CNCc1ccc(F)cc1]

Compound 2 was prepared via Analog Route I (as described herein above) to afford the title compound (361 mg, 64%) as the trihydrochloride salt. $^1$H NMR (D$_2$O, 400 MHz) δ 7.34 (dd, J=10.3, 3.6 Hz, 2H), 7.12-7.07 (m, 2H), 4.51 (s, 1H), 4.48 (s, 1H), 3.98 (t, J=10.5 Hz, 1H), 3.90 (d, J=13.4 Hz, 1H), 3.86-3.76 (m, 2H), 3.73-3.63 (m, 2H), 2.99 (d, J=13.5 Hz, 1H), 2.88-2.79 (m, 3H), 2.57 (s, 3H), 2.42 (s, 3H), 1.75-1.60 (m, 2H), 1.13 (d, J=6.0 Hz, 3H); MS-ESI m/z=472.32 [M+H]$^+$.

13. Preparation of 3'-(R)-3'-[(4-ethyl)benzylaminomethyl)]dihydrospectinomycin Trihydrochloride (3)

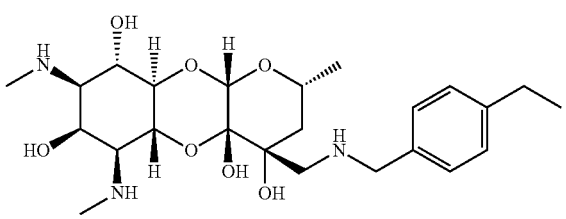 [SMILES: CCc1ccc(CNC[C@]2(O)C[C@@H](C)O[C@H]3O[C@@H]4[C@@H](O)[C@H](NC)[C@H](O)[C@H](NC)[C@H]4O[C@]32O)cc1]

Compound 3 was prepared via Analog Route III (as described herein above) to afford the title compound (89 mg, 59%) as the trihydrochloride salt. $^1$H NMR (D$_2$O, 400 MHz) δ 7.26 (q, J=8.4 Hz, 4H), 4.58 (s, 2H), 4.17-4.04 (m, 3H), 3.85 (t, J=9.9 Hz, 1H), 3.77 (t, J=10.0 Hz, 1H), 3.57-3.50 (m, 1H), 3.28-3.19 (m, 2H), 3.07-2.98 (m, 2H), 2.62 (d, J=22.1 Hz, 6H), 2.55-2.49 (m, 2H), 1.72-1.58 (m, 2H), 1.08-1.03 (m, 6H); MS-ESI m/z=482.30 [M+H]$^+$.

14. Preparation of 3'-(R)-3'-[(4-ethoxyl)benzylaminomethyl)]dihydrospectinomycin Trihydrochloride (4)

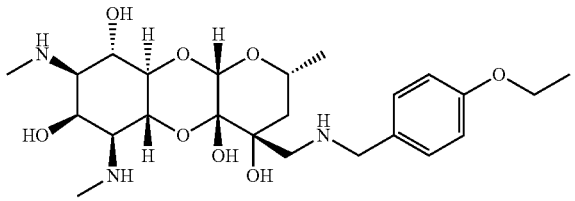 [SMILES: CCOc1ccc(CNC[C@]2(O)C[C@@H](C)O[C@H]3O[C@@H]4[C@@H](O)[C@H](NC)[C@H](O)[C@H](NC)[C@H]4O[C@]32O)cc1]

Compound 4 was prepared via Analog Route III (as described herein above) to afford the title compound (59 mg, 38%) as the trihydrochloride salt. $^1$H NMR (D$_2$O, 400 MHz) δ 7.47 (d, J=8.7 Hz, 2H), 7.09 (d, J=8.8 Hz, 2H), 4.77 (m, 1H), 4.33-4.23 (m, 3H), 4.17 (q, J=7.0 Hz, 2H), 4.05 (t, J=9.7 Hz, 1H), 3.97 (t, J=10.1 Hz, 1H), 3.73 (dq, J=12.5, 6.0 Hz, 1H), 3.56 (d, J=11.4 Hz, 1H), 3.40 (d, J=14.3 Hz, 1H), 3.35 (d, J=1.5 Hz, 1H), 3.27 (dd, J=9.6, 2.2 Hz, 1H), 3.20 (d, J=13.7 Hz, 1H), 2.83 (dd, J=3.0, 1.5 Hz, 6H), 1.81 (dd, J=27.6, 12.2 Hz, 2H), 1.40 (t, J=7.0 Hz, 3H), 1.22 (d, J=6.1 Hz, 3H); MS-ESI m/z=498.45[M+H]$^+$.

15. Preparation of 3'-(R)-3'-[(4-trifluoromethyl)benzylaminomethyl)]dihydrospectinomycin Trihydrochloride (5)

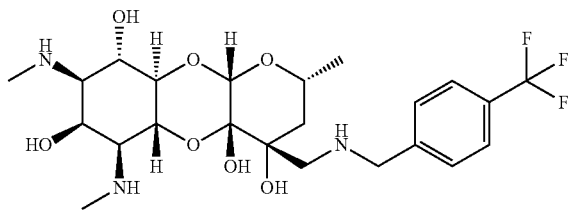 [SMILES: CN[C@@H]1[C@H](O)[C@H](NC)[C@H]2O[C@]3(O)[C@H](O[C@@H]2[C@H]1O)O[C@H](C)C[C@@]3(O)CNCc1ccc(C(F)(F)F)cc1]

Compound 5 was prepared via Analog Route III (as described herein above) to afford the title compound (166 mg, 46%) as the trihydrochloride salt. $^1$H NMR (D$_2$O, 400 MHz) δ 7.84 (d, J=8.2 Hz, 2H), 7.70 (d, J=8.0 Hz, 2H), 4.82 (s, 1H), 4.72 (q, J=3.3, 2.9 Hz, 1H), 4.43 (q, J=13.6 Hz, 2H), 4.32-4.25 (m, 1H), 4.07 (t, J=9.9 Hz, 1H), 3.97 (t, J=10.1 Hz, 1H), 3.82-3.75 (m, 2H), 3.63-3.57 (m, 1H), 3.46-3.42 (m, 1H), 3.30-3.24 (m, 1H), 2.84 (d, J=2.0 Hz, 6H), 1.93-1.77 (m, 2H), 1.24 (d, J=6.1 Hz, 3H); MS-ESI m/z=522.30 [M+H]$^+$.

16. Preparation of 3'-(R)-3'-(phenethylaminomethyl)dihydrospectinomycin Trihydrochloride (6)

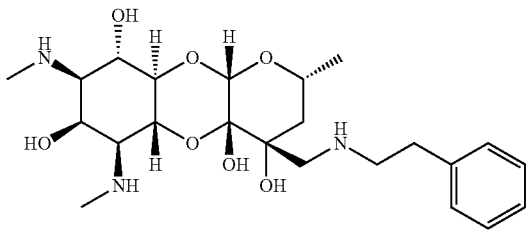

Compound 6 was prepared via Analog Route I (as described herein above) to afford the title compound (520 mg, 57%) as the trihydrochloride salt. $^1$H NMR (D$_2$O, 400 MHz) δ 7.36 (d, J=7.2 Hz, 2H), 7.29 (d, J=8.1 Hz, 3H), 4.82 (s, 1H), 4.21 (t, J=10.4 Hz, 1H), 3.99 (t, J=9.9 Hz, 1H), 3.90 (t, J=10.0 Hz, 1H), 3.76 (q, J=5.1, 4.2 Hz, 1H), 3.52-3.41 (m, 2H), 3.40-3.31 (m, 2H), 3.28 (s, 1H), 3.26-3.16 (m, 2H), 3.03 (td, J=7.9, 7.5, 3.7 Hz, 2H), 2.77 (s, 6H), 1.82-1.73 (m, 2H), 1.19 (d, J=5.9 Hz, 3H); MS-ESI m/z=468.42 [M+H]$^+$.

17. Preparation of 3'-(R)-3'-(3-pyridinylmethylaminomethyl)dihydrospectinomycin Tetrahydrobromide (7)

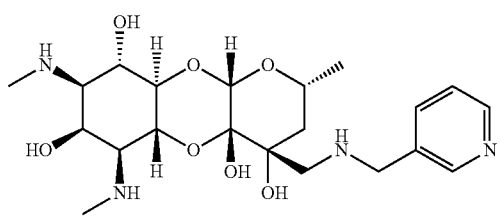 [SMILES: CN[C@@H]1[C@H](O)[C@H](NC)[C@H]2O[C@]3(O)[C@H](O[C@@H]2[C@H]1O)O[C@H](C)C[C@@]3(O)CNCc1cccnc1]

Compound 7 was prepared via Analog Route II (as described herein above) to afford the title compound (49 mg, 31%) as the tetrahydrobromide salt. $^1$H NMR (D$_2$O, 400 MHz) δ 9.07 (d, J=2.1 Hz, 1H), 8.93 (d, J=5.9 Hz, 1H), 8.83 (dt, J=8.3, 1.8 Hz, 1H), 8.20 (dd, J=8.2, 5.8 Hz, 1H), 4.97 (s, 1H), 4.82 (d, J=3.0 Hz, 1H), 4.67 (s, 2H), 4.35-4.28 (m, 1H), 4.10 (t, J=9.9 Hz, 1H), 3.99 (t, J=10.1 Hz, 1H), 3.96-3.87 (m, 1H), 3.66-3.59 (m, 2H), 3.49 (d, J=13.4 Hz, 1H), 3.32 (dd, J=10.3, 3.0 Hz, 1H), 2.87-2.85 (m, 6H), 1.98-1.86 (m, 2H), 1.27 (d, J=6.0 Hz, 3H); MS-ESI m/z=455.39 [M+H]$^+$.

18. Preparation of 3'-(R)-3'-(2-furanylmethylaminomethyl)dihydrospectinomycin Trihydrochloride (8)

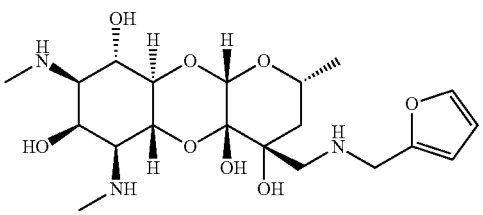 [SMILES: CN[C@@H]1[C@H](O)[C@H](NC)[C@H]2O[C@]3(O)[C@H](O[C@@H]2[C@H]1O)O[C@H](C)C[C@@]3(O)CNCc1ccco1]

Compound 8 was prepared via Analog Route I (as described herein above) to afford the title compound (45 mg, 21%) as the trihydrochloride salt. $^1$H NMR (D$_2$O, 400 MHz) δ 7.65 (dd, J=1.9, 0.9 Hz, 1H), 6.71 (d, J=3.4 Hz, 1H), 6.55 (dd, J=3.3, 1.9 Hz, 1H), 4.88 (s, 1H), 4.81 (s, 1H), 4.40 (d, J=2.3 Hz, 2H), 4.36-4.28 (m, 1H), 4.03 (dt, J=32.9, 10.0 Hz, 2H), 3.82 (ddd, J=11.4, 6.1, 2.4 Hz, 1H), 3.57 (dd, J=11.0, 2.8 Hz, 1H), 3.48 (d, J=13.6 Hz, 1H), 3.30-3.23 (m, 2H), 2.85 (d, J=1.4 Hz, 6H), 1.97-1.79 (m, 2H), 1.26 (d, J=5.9 Hz, 3H); MS-ESI m/z=444.41 [M+H]$^+$.

19. Preparation of 3'-(R)-3'-(4-pyridinylmethylaminomethyl)dihydrospectinomycin Tetrahydrobromide (9)

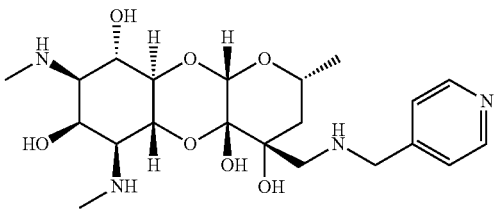 [SMILES: CN[C@@H]1[C@H](O)[C@H](NC)[C@H]2O[C@]3(O)[C@H](O[C@@H]2[C@H]1O)O[C@H](C)C[C@@]3(O)CNCc1ccncc1]

Compound 9 was prepared via Analog Route II (as described herein above) to afford the title compound (113 mg, 39%) as the tetrahydrobromide salt. $^1$H NMR (D$_2$O, 400 MHz) δ 8.93-8.86 (m, 2H), 8.18 (d, J=5.4 Hz, 2H), 4.94 (s, 1H), 4.70 (s, 2H), 4.34-4.27 (m, 1H), 4.07 (t, J=10.0 Hz, 1H), 4.00-3.93 (m, 1H), 3.91 (s, 1H), 3.69 (s, 1H), 3.63-3.57 (m, 2H), 3.45 (d, J=13.5 Hz, 1H), 3.28 (dd, J=10.3, 2.8 Hz, 1H), 2.83 (d, J=2.6 Hz, 6H), 1.90 (d, J=10.4 Hz, 2H), 1.25 (d, J=6.0 Hz, 3H); MS-ESI m/z=455.31 [M+H]$^+$.

20. Preparation of 3'-(R)-3'-[(4-trifluoromethoxyl)benzylaminomethyl)]dihydrospectinomycin Trihydrochloride (10)

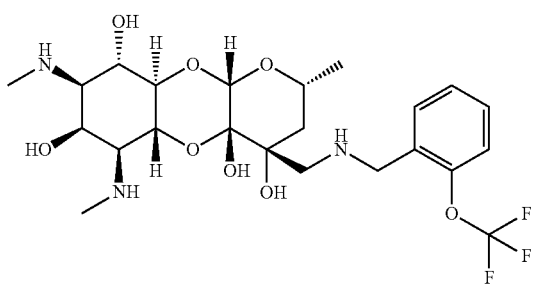 [SMILES: CN[C@@H]1[C@H](O)[C@H](NC)[C@H]2O[C@]3(O)[C@H](O[C@@H]2[C@H]1O)O[C@H](C)C[C@@]3(O)CNCc1ccccc1OC(F)(F)F]

Compound 10 was prepared via Analog Route III (as described herein above) to afford the title compound (140 mg, 51%) as the trihydrochloride salt. $^1$H NMR (D$_2$O, 400 MHz) δ 7.39 (d, J=7.3 Hz, 1H), 7.35-7.28 (m, 3H), 4.53 (s, 1H), 4.46-4.42 (m, 1H), 3.96-3.88 (m, 2H), 3.83-3.78 (m, 2H), 3.69-3.63 (m, 2H), 2.92 (d, J=13.5 Hz, 1H), 2.81 (dtd, J=21.8, 11.3, 5.6 Hz, 3H), 2.53 (s, 3H), 2.39 (s, 3H), 1.70-1.57 (m, 2H), 1.10 (t, J=6.3 Hz, 3H); MS-ESI m/z=538.34 [M+H]$^+$.

21. Preparation of 3'-(R)-3'-[(4-trifluoromethoxyl)benzylaminomethyl)]dihydrospectinomycin Trihydrochloride (11)

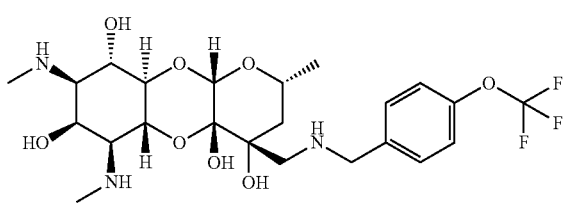 [SMILES: CN[C@@H]1[C@H](O)[C@H](NC)[C@H]2O[C@]3(O)[C@H](O[C@@H]2[C@H]1O)O[C@H](C)C[C@@]3(O)CNCc1ccc(OC(F)(F)F)cc1]

Compound 11 was prepared via Analog Route I (as described herein above) to afford the title compound (522 mg, 50%) as the trihydrochloride salt. $^1$H NMR (D$_2$O, 400 MHz): δ 7.47 (d, J=8.6 Hz, 2H), 7.37 (d, J=8.0 Hz, 2H), 4.59 (s, 1H), 4.54 (s, 1H), 4.05 (t, J=10.4 Hz, 1H), 3.97-3.90 (m, 2H), 3.88-3.81 (m, 1H), 3.74 (t, J=10.0 Hz, 2H), 3.01 (d, J=13.4 Hz, 1H), 2.89 (d, J=13.1 Hz, 2H), 2.80 (d, J=12.8 Hz, 1H), 2.61 (d, J=2.5 Hz, 3H), 2.47 (s, 3H), 1.81-1.69 (m, 2H), 1.21 (d, J=6.0 Hz, 3H). MS-ESI m/z=538.34 [M+H]$^+$.

22. Preparation of 3'-(R)-3'-[(3,4-difluoro)benzylaminomethyl)]dihydrospectinomycin Trihydrochloride (12)

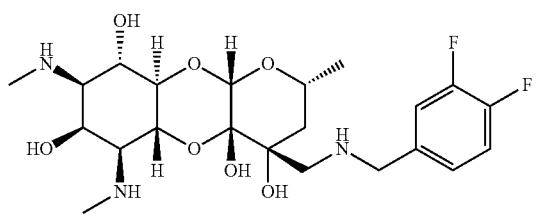 [SMILES: CN[C@@H]1[C@H](O)[C@H](NC)[C@H]2O[C@]3(O)[C@H](O[C@@H]2[C@H]1O)O[C@H](C)C[C@@]3(O)CNCc1ccc(F)c(F)c1]

Compound 12 was prepared via Analog Route III (as described herein above) to afford the title compound (51 mg, 42%) as the trihydrochloride salt. $^1$H NMR (400 MHz, D$_2$O) δ 7.23 (ddd, J=13.1, 9.8, 7.1 Hz, 2H), 7.13-7.09 (m, 1H), 4.60 (s, 1H), 4.55 (t, J=2.7 Hz, 1H), 4.07-3.91 (m, 3H), 3.85 (t, J=9.9 Hz, 1H), 3.75 (d, J=10.0 Hz, 1H), 3.64 (ddd, J=11.4, 6.0, 2.2 Hz, 1H), 3.14-3.08 (m, 2H), 3.02-2.92 (m, 2H), 2.64 (s, 3H), 2.52 (s, 3H), 1.74-1.60 (m, 2H), 1.09 (d, J=6.0 Hz, 3H); MS-ESI m/z=490.30 [M+H]$^+$.

23. Preparation of 3'-(R)-3'-(phenylpropylaminomethyl)dihydrospectinomycin Trihydrochloride (13)

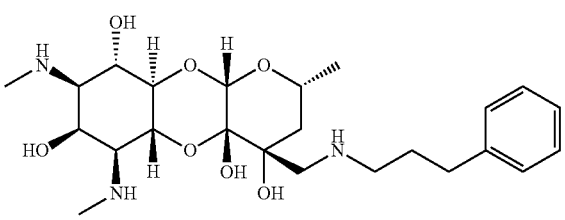 [SMILES: CN[C@@H]1[C@H](O)[C@H](NC)[C@H]2O[C@]3(O)[C@H](O[C@@H]2[C@H]1O)O[C@H](C)C[C@@]3(O)CNCCCc1ccccc1]

Compound 13 was prepared via Analog Route I (as described herein above) to afford the title compound (30 mg, 41%) as the trihydrochloride salt. $^1$H NMR (D$_2$O, 400 MHz) δ 7.34-7.29 (m, 2H), 7.23 (d, J=7.4 Hz, 3H), 4.80 (s, 1H), 4.59 (t, J=2.8 Hz, 1H), 4.07 (t, J=10.5 Hz, 1H), 3.92 (t, J=9.9 Hz, 1H), 3.81 (m, 2H), 3.73 (s, 1H), 3.34 (d, J=13.6 Hz, 1H), 3.14 (d, J=13.6 Hz, 1H), 3.07-2.98 (m, 3H), 2.67 (d, J=11.7 Hz, 6H), 2.54 (s, 2H), 1.97 (dq, J=12.9, 7.6 Hz, 2H), 1.78 (d, J=11.5 Hz, 1H), 1.73-1.67 (m, 1H), 1.17 (d, J=5.9 Hz, 3H); MS-ESI m/z=482.32 [M+H]$^+$.

24. Preparation of 3'-(R)-3'-[(2-fluoro)benzylaminomethyl)]dihydrospectinomycin Trihydrochloride (14)

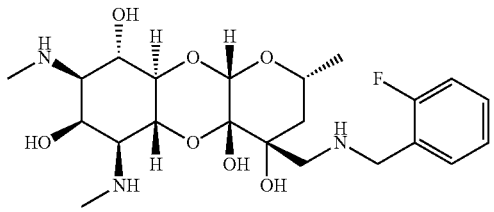

Compound 14 was prepared via Analog Route I (as described herein above) to afford the title compound (47 mg, 31%) as the trihydrochloride salt. $^1$H NMR (D$_2$O, 400 MHz) δ 7.46-7.39 (m, 2H), 7.27-7.14 (m, 2H), 4.68 (s, 1H), 4.63 (t, J=3.0 Hz, 1H), 4.22 (q, J=13.4 Hz, 2H), 4.11 (t, J=10.4 Hz, 1H), 3.92 (t, J=9.9 Hz, 1H), 3.83 (t, J=10.1 Hz, 1H), 3.69 (ddd, J=12.4, 8.7, 4.6 Hz, 1H), 3.33-3.22 (m, 2H), 3.15-3.07 (m, 2H), 2.71 (s, 3H), 2.62 (s, 3H), 1.69 (d, J=13.6 Hz, 2H), 1.14 (d, J=6.0 Hz, 3H); MS-ESI m/z=472.32 [M+H]$^+$.

25. Preparation of 3'-(R)-3'-[(3-fluoro)benzylaminomethyl)]dihydrospectinomycin Trihydrochloride (15)

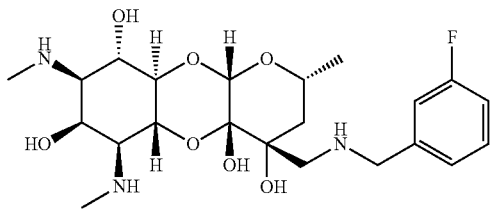

Compound 15 was prepared via Analog Route I (as described herein above) to afford the title compound (63 mg, 42%) as the trihydrochloride salt. $^1$H NMR (D$_2$O, 400 MHz) δ 7.46-7.41 (m, 1H), 7.26-7.14 (m, 3H), 4.78 (s, 1H), 4.30-4.13 (m, 3H), 3.98-3.83 (m, 2H), 3.68 (dt, J=11.7, 4.5 Hz, 1H), 3.39 (dq, J=10.2, 2.9 Hz, 1H), 3.31 (dd, J=13.8, 5.9 Hz, 1H), 3.18-3.09 (m, 2H), 2.72 (dd, J=13.5, 6.5 Hz, 7H), 1.74 (ddd, J=23.7, 12.8, 7.7 Hz, 2H), 1.14 (t, J=6.3 Hz, 3H); MS-ESI m/z=472.32 [M+H]$^+$.

26. Preparation of 3'-(R)-3'-(2-pyridinylmethylaminomethyl)dihydrospectinomycin Tetrahydrobromide (16)

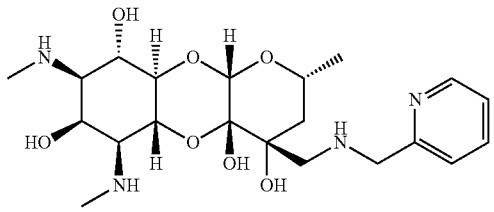

Compound 16 was prepared via Analog Route II (as described herein above) to afford the title compound (80 mg, 34%) as the tetrahydrobromide salt. $^1$H NMR (D$_2$O, 400 MHz) δ 8.81-8.71 (m, 1H), 8.24 (d, J=21.8 Hz, 1H), 7.82 (d, J=29.0 Hz, 2H), 4.93 (s, 1H), 4.62 (s, 2H), 4.35-4.27 (m, 1H), 4.08 (t, J=9.9 Hz, 1H), 4.02-3.94 (m, 1H), 3.87 (td, J=6.8, 6.3, 3.0 Hz, 1H), 3.67-3.56 (m, 2H), 3.47-3.39 (m, 1H), 3.36-3.22 (m, 2H), 2.85 (t, J=1.6 Hz, 6H), 1.91 (dd, J=10.4, 3.0 Hz, 2H), 1.27 (d, J=6.1 Hz, 3H); MS-ESI m/z=455.31 [M+H]$^+$.

27. Preparation of 3'-(R)-3'-(2-thiophenylmethylaminomethyl)dihydrospectinomycin Trihydrochloride (17)

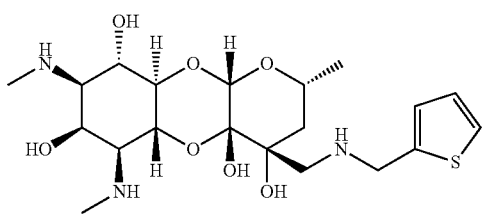

Compound 17 was prepared via Analog Route IV (as described herein above) to afford the title compound (73 mg, 40%) as the trihydrochloride salt. $^1$H NMR (D$_2$O, 400 MHz): δ 7.57 (dd, J=3.0, 1.4 Hz, 1H), 7.50 (dd, J=5.0, 2.9 Hz, 1H), 7.16 (dd, J=5.0, 1.4 Hz, 1H), 4.33-4.26 (m, 2H), 4.24-4.17 (m, 1H), 3.97 (t, J=9.9 Hz, 1H), 3.88 (t, J=10.0 Hz, 1H), 3.70 (dd, J=10.8, 9.4 Hz, 2H), 3.52-3.47 (m, 1H), 3.37-3.30 (m, 1H), 3.22-3.11 (m, 3H), 2.76-2.74 (m, 6H), 1.85-1.68 (m, 2H), 1.15 (d, J=6.0 Hz, 3H). MS-ESI m/z=460.24 [M+H]$^+$.

28. Preparation of 3'-(R)-3'-(4-Chlorobenzylaminomethyl)dihydrospectinomycin Trihydrobromide (18)

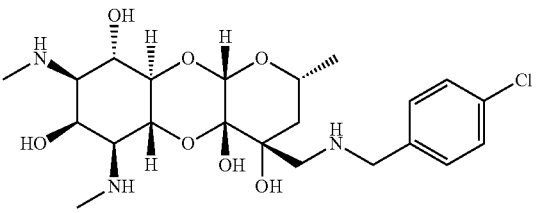 [SMILES: CN[C@@H]1[C@H](O)[C@H](NC)[C@H]2O[C@]3(O)[C@H](O[C@@H]2[C@H]1O)O[C@H](C)C[C@@]3(O)CNCc1ccc(Cl)cc1]

Compound 18 was prepared via Analog Route IV (as described herein above) to afford the title compound (111 mg, 34%) as the trihydrochloride salt. $^1$H NMR (D$_2$O, 400 MHz) δ 7.48-7.37 (m, 4H), 4.30-4.16 (m, 3H), 3.97 (t, J=9.9 Hz, 1H), 3.88 (t, J=10.0 Hz, 1H), 3.73-3.62 (m, 1H), 3.50-3.45 (m, 1H), 3.33 (d, J=13.6 Hz, 1H), 3.26 (s, 2H), 3.21-3.12 (m, 2H), 2.75 (s, 6H), 1.83-1.67 (m, 2H), 1.15 (d, J=6.0 Hz, 3H); MS-ESI m/z=488.20 [M+H]$^+$.

29. Preparation of 3'-(R)-3'-(2-thiazolylmethyl)aminomethyldihydrospectinomycin Tetrahydrobromide (19)

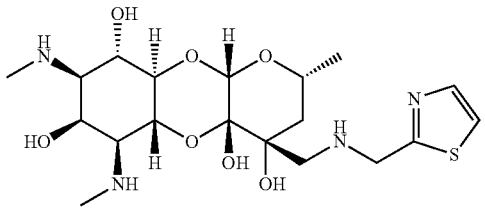

Compound 19 was prepared via Analog Route II (as described herein above) to afford the title compound (54 mg, 29%) as the tetrahydrobromide salt. $^1$H NMR (D$_2$O, 400 MHz) δ 7.84 (dd, J=3.4, 0.8 Hz, 1H), 7.67 (dd, J=3.3, 0.9 Hz, 1H), 4.81 (s, 1H), 4.71 (s, 1H), 4.65 (t, J=5.6 Hz, 2H), 4.24-4.17 (m, 1H), 3.99 (t, J=10.0 Hz, 1H), 3.89 (t, J=10.1 Hz, 1H), 3.76 (ddd, J=11.4, 6.0, 2.6 Hz, 1H), 3.57-3.48 (m, 2H), 3.31 (d, J=13.6 Hz, 1H), 3.20 (dd, J=10.2, 2.9 Hz, 1H), 2.75 (s, 6H), 1.89-1.72 (m, 2H), 1.17 (d, J=5.9 Hz, 3H); MS-ESI m/z=461.29 [M+H]$^+$.

30. Preparation of 3'-(R)-3'-(2-imidazolylmethyl)aminomethyldihydrospectinomycin Tetrahydrobromide (20)

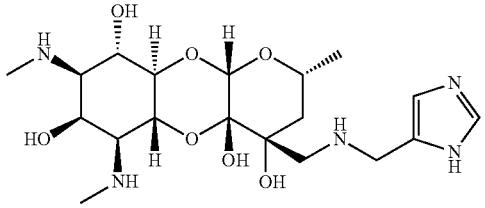 [SMILES: CN[C@@H]1[C@H](O)[C@H](NC)[C@H]2O[C@]3(O)[C@H](O[C@@H]2[C@H]1O)O[C@H](C)C[C@@]3(O)CNCc1cnc[nH]1]

Compound 20 was prepared via Analog Route I (as described herein above) to afford the title compound (21 mg, 29%) as the tetrahydrobromide salt. $^1$H NMR (D$_2$O, 400 MHz) δ 7.71 (d, J=1.2 Hz, 1H), 7.21 (d, J=1.2 Hz, 1H), 4.66 (s, 1H), 4.56-4.53 (m, 1H), 4.14-4.06 (m, 2H), 4.05-3.97 (m, 1H), 3.86 (d, J=9.9 Hz, 1H), 3.79-3.74 (m, 2H), 3.67 (dd, J=11.1, 5.0 Hz, 1H), 3.31 (d, J=13.4 Hz, 1H), 3.08-2.97 (m, 2H), 2.64 (q, J=1.5 Hz, 6H), 1.78-1.62 (m, 2H), 1.12 (d, J=6.0 Hz, 3H); MS-ESI m/z=444.29 [M+H]$^+$.

31. Preparation of 3'-(A')-3'-[(5-Chloro)-2-thiophenylmethylaminomethyl)dihydrospectinomycin Trihydrobromide (21)

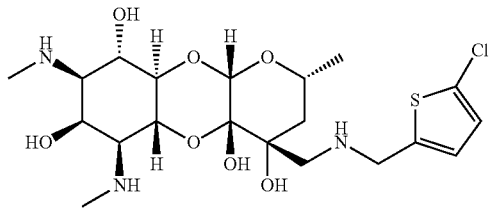 [SMILES: CN[C@@H]1[C@H](O)[C@H](NC)[C@H]2O[C@]3(O)[C@H](O[C@@H]2[C@H]1O)O[C@H](C)C[C@@]3(O)CNCc1ccc(Cl)s1]

Compound 21 was prepared via Analog Route II (as described herein above) to afford the title compound (78 mg, 33%) as the trihydrochloride salt. $^1$H NMR (D$_2$O, 400 MHz) δ 7.16 (d, J=3.9 Hz, 1H), 7.04 (d, J=3.8 Hz, 1H), 4.85 (s, 1H), 4.71 (t, J=2.8 Hz, 1H), 4.48 (d, J=7.1 Hz, 1H), 4.32-4.26 (m, 1H), 4.06 (t, J=9.9 Hz, 1H), 3.98 (t, J=10.1 Hz, 1H), 3.79 (dd, J=10.9, 9.4 Hz, 2H), 3.57 (dd, J=11.0, 2.8 Hz, 1H), 3.29-3.22 (m, 3H), 2.86-2.81 (m, 6H), 1.93-1.79 (m, 2H), 1.25 (d, J=5.9 Hz, 3H); MS-ESI m/z=494.20 [M+H]$^+$.

32. Preparation of 3'-(A)-3'-[(6-Methyl)-2-pyridinylmethylamino)dihydrospectinomycin Tetrahydrobromide (22)

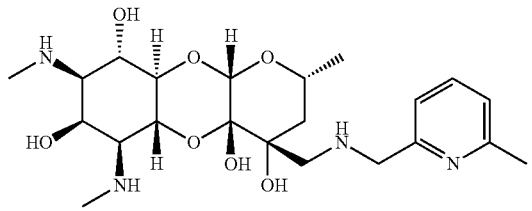

Compound 22 was prepared via Analog Route II (as described herein above) to afford the title compound (63 mg, 28%) as the tetrahydrobromide salt. $^1$H NMR (D$_2$O, 400 MHz) δ 8.25 (t, J=8.0 Hz, 1H), 7.74 (dd, J=19.8, 7.8 Hz, 2H), 4.87 (s, 1H), 4.57 (s, 2H), 4.30-4.20 (m, 2H), 4.01 (t, J=10.0 Hz, 1H), 3.90 (t, J=10.2 Hz, 1H), 3.81 (tt, J=9.7, 6.1 Hz, 1H), 3.58 (d, J=13.5 Hz, 1H), 3.52 (dd, J=11.0, 2.7 Hz, 1H), 3.39 (d, J=13.5 Hz, 1H), 3.21 (dd, J=10.3, 2.9 Hz, 1H), 2.77 (d, J=1.6 Hz, 6H), 2.68 (s, 3H), 1.89-1.78 (m, 2H), 1.19 (d, J=5.9 Hz, 3H); MS-ESI m/z=469.30 [M+H]$^+$.

33. Preparation of 3'-(R)-3'-[(4-isopropyl)benzylaminomethyl)]dihydrospectinomycin Trihydrochloride (23)

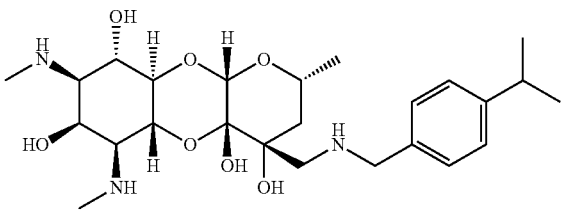

Compound 23 was prepared via Analog Route I (as described herein above) to afford the title compound (67 mg, 34%) as the trihydrochloride salt. $^1$H NMR (D$_2$O, 400 MHz) δ$^1$ δ 7.36 (s, 4H), 4.67 (d, J=1.1 Hz, 1H), 4.25-4.15 (m, 3H), 3.94 (t, J=10.0 Hz, 1H), 3.87 (dd, J=10.6, 9.3 Hz, 1H), 3.44 (dd, J=11.0, 2.7 Hz, 1H), 3.31 (d, J=13.6 Hz, 1H), 3.16 (dd, J=10.1, 2.9 Hz, 1H), 3.10 (d, J=13.8 Hz, 1H), 2.91-2.86 (m, 2H), 2.74 (d, J=5.1 Hz, 6H), 2.69-2.64 (m, 1H), 1.79-1.63 (m, 2H), 1.14 (dd, J=14.3, 6.6 Hz, 9H); MS-ESI m/z=496.40 [M+H]$^+$.

34. Preparation of 3'-(R)-3'-[(2,4-dimethyl)benzylaminomethyl)]dihydrospectinomycin Trihydrochloride (24)

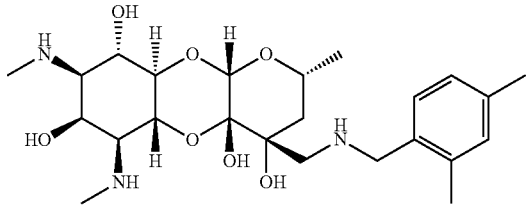

Compound 24 was prepared via Analog Route I (as described herein above) to afford the title compound (29 mg, 58%) as the trihydrochloride salt. $^1$H NMR (D$_2$O, 400 MHz) δ 7.32 (d, J=7.8 Hz, 1H), 7.23 (s, 1H), 7.18 (d, J=7.8 Hz, 1H), 4.78 (s, 1H), 4.76 (d, J=3.0 Hz, 1H), 4.39-4.31 (m, 2H), 4.30-4.22 (m, 1H), 4.03 (t, J=9.9 Hz, 1H), 3.96 (t, J=10.0 Hz, 1H), 3.79-3.71 (m, 1H), 3.51 (dd, J=11.0, 2.7 Hz, 1H), 3.43 (d, J=13.6 Hz, 1H), 3.30-3.21 (m, 2H), 2.82 (d, J=7.9 Hz, 6H), 2.37 (s, 3H), 2.33 (s, 3H), 1.91-1.76 (m, 2H), 1.23 (d, J=6.0 Hz, 3H); MS-ESI m/z=482.40 [M+H]$^+$.

35. Preparation of 3'-(R)-3'-[(3-trifluoromethoxyl)benzylaminomethyl)]dihydrospectinomycin Trihydrochloride (25)

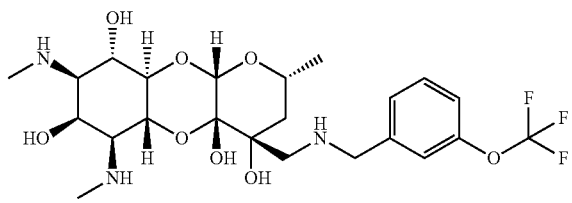 [SMILES: CN[C@@H]1[C@H](O)[C@H](NC)[C@H]2O[C@]3(O)[C@H](O[C@@H]2[C@H]1O)O[C@H](C)C[C@@]3(O)CNCc1cccc(OC(F)(F)F)c1]

Compound 25 was prepared via Analog Route I (as described herein above) to afford the title compound (81 mg, 38%) as the trihydrochloride salt. $^1$H NMR (D$_2$O, 400 MHz) δ 7.58 (t, J=7.8 Hz, 1H), 7.50-7.40 (m, 3H), 4.73 (d, J=3.4 Hz, 2H), 4.32-4.18 (m, 3H), 4.00 (t, J=9.9 Hz, 1H), 3.92 (t, J=10.0 Hz, 1H), 3.77-3.68 (m, 1H), 3.35 (dd, J=14.4, 10.5 Hz, 2H), 3.22-3.13 (m, 2H), 2.80 (s, 3H), 2.73 (s, 3H), 1.88-1.73 (m, 2H), 1.22 (d, J=6.0 Hz, 3H); MS-ESI m/z=538.31 [M+H]$^+$.

36. Preparation of 3'-(S)-3'-[(4-trifluoromethoxyl)benzylaminomethyl)]dihydrospectinomycin Trihydrochloride (26)

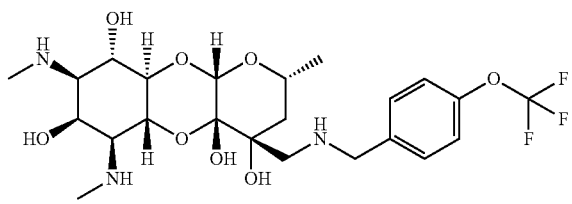 [SMILES: CN[C@@H]1[C@H](O)[C@H](NC)[C@H]2O[C@]3(O)[C@H](O[C@@H]2[C@H]1O)O[C@H](C)C[C@@]3(O)CNCc1ccc(OC(F)(F)F)cc1]

Compound 26 was prepared via Analog Route VI (as described herein above) to afford the title compound (26 mg, 22%) as the trihydrochloride salt. $^1$H NMR (D$_2$O, 400 MHz) δ 7.60 (d, J=8.7 Hz, 2H), 7.43 (d, J=7.3 Hz, 2H), 4.99 (s, 1H), 4.73 (t, J=2.8 Hz, 1H), 4.38-4.30 (m, 3H), 4.20-4.14 (m, 1H), 4.04 (t, J=9.8 Hz, 1H), 3.97 (d, J=10.1 Hz, 1H), 3.53 (d, J=13.3 Hz, 1H), 3.46 (dd, J=11.0, 2.7 Hz, 1H), 3.24 (dd, J=10.2, 2.9 Hz, 1H), 3.10 (d, J=13.3 Hz, 1H), 2.83 (d, J=2.1 Hz, 4H), 2.74 (s, 2H), 1.77-1.64 (m, 2H), 1.25 (d, J=6.2 Hz, 3H); MS-ESI m/z=538.34 [M+H]$^+$.

37. Preparation of 3'-(S)-3'-(phenethylaminomethyl)dihydrospectinomycin Trihydrochloride (27)

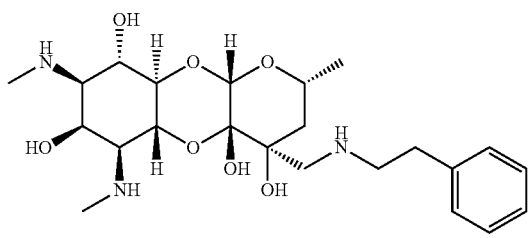 [SMILES: CN[C@@H]1[C@H](O)[C@H](NC)[C@H]2O[C@]3(O)[C@H](O[C@@H]2[C@H]1O)O[C@H](C)C[C@]3(O)CNCCc1ccccc1]

Compound 27 was prepared via Analog Route VI (as described herein above) to afford the title compound (80 mg, 48%) as the trihydrochloride salt. $^1$H NMR (D$_2$O, 400 MHz) δ 7.42 (t, J=7.2 Hz, 2H), 7.34 (t, J=7.6 Hz, 3H), 4.92 (s, 1H), 4.57 (s, 1H), 4.19-4.09 (m, 1H), 4.06 (t, J=10.3 Hz, 1H), 3.95 (t, J=9.8 Hz, 1H), 3.84 (t, J=10.0 Hz, 1H), 3.54 (d, J=13.3 Hz, 1H), 3.32 (td, J=12.2, 5.0 Hz, 2H), 3.16-2.97 (m, 5H), 2.74 (s, 3H), 2.54 (s, 3H), 1.75-1.60 (m, 2H), 1.23 (d, J=6.0 Hz, 3H); MS-ESI m/z=468.30 [M+H]$^+$.

38. Preparation of 3'-(S)-3'-[(4-fluoro)benzylaminomethyl)]dihydrospectinomycin Trihydrochloride (28)

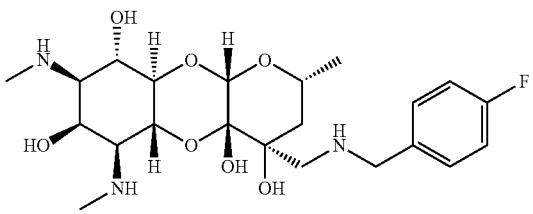 [SMILES: CN[C@@H]1[C@H](O)[C@H](NC)[C@H]2O[C@]3(O)[C@H](O[C@@H]2[C@H]1O)O[C@H](C)C[C@]3(O)CNCc1ccc(F)cc1]

Compound 28 was prepared via Analog Route VI (as described herein above) to afford the title compound (61 mg, 60%) as the trihydrochloride salt. $^1$H NMR (D$_2$O, 400 MHz) δ 7.51 (dt, J=8.3, 4.4 Hz, 2H), 7.23 (td, J=8.8, 3.4 Hz, 2H), 4.96 (d, J=3.4 Hz, 1H), 4.63 (q, J=2.9 Hz, 1H), 4.33-4.13 (m, 4H), 3.99 (dt, J=10.0, 5.2 Hz, 1H), 3.96-3.83 (m, 1H), 3.47 (dd, J=13.3, 3.3 Hz, 1H), 3.26-3.12 (m, 2H), 3.08-3.01 (m, 1H), 2.78 (d, J=3.3 Hz, 3H), 2.61 (d, J=3.0 Hz, 3H), 1.68 (tt, J=13.0, 6.5 Hz, 2H), 1.23 (dd, J=6.1, 3.4 Hz, 3H); MS-ESI m/z=472.32 [M+H]$^+$.

39. Preparation of 3'-(R)-3'-[(4-methoxy)phenylaminomethyl)]dihydrospectinomycin Trihydrochloride (29)

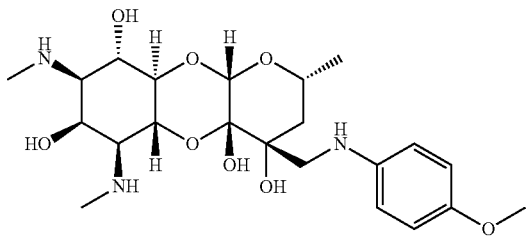

Compound 29 was prepared via Analog Route V (as described herein above) to afford the title compound (18 mg, 51%) as the trihydrochloride salt. ¹H NMR (D₂O, 400 MHz) δ 6.95-6.88 (m, 4H), 4.96 (s, 1H), 4.54 (t, J=2.6 Hz, 1H), 4.23 (s, 1H), 4.19-4.14 (m, 1H), 3.99 (s, 1H), 3.85 (t, J=10.1 Hz, 2H), 3.79 (s, 3H), 3.47 (d, J=13.4 Hz, 1H), 3.25 (d, J=13.4 Hz, 1H), 3.04 (d, J=2.8 Hz, 1H), 2.71 (s, 3H), 2.58 (s, 3H), 1.77-1.69 (m, 2H), 1.25 (d, J=6.3 Hz, 3H); MS-ESI m/z=470.40 [M+H]⁺.

40. Preparation of 3'-(R)-3'-(phenylaminomethyl)dihydrospectinomycin Trihydrochloride (30)

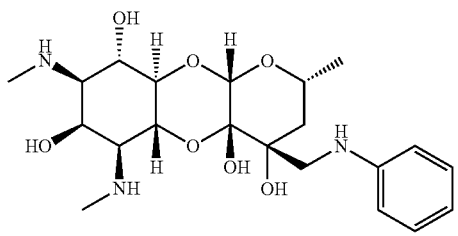 [SMILES: CN[C@@H]1[C@H](O)[C@H](NC)[C@H]2O[C@]3(O)[C@H](O[C@@H]2[C@H]1O)O[C@H](C)C[C@@]3(O)CNc1ccccc1]

Compound 30 was prepared via Analog Route V (as described herein above) to afford the title compound (29 mg, 44%) as the trihydrochloride salt. ¹H NMR (D₂O, 400 MHz) δ 7.23-7.17 (m, 2H), 6.80 (dd, J=12.4, 8.0 Hz, 3H), 4.88 (s, 1H), 4.48 (s, 1H), 4.17 (t, J=10.5 Hz, 1H), 4.11-4.06 (m, 1H), 3.92 (t, J=9.9 Hz, 1H), 3.78 (t, J=10.1 Hz, 1H), 3.43 (d, J=13.7 Hz, 1H), 3.00 (dd, J=24.4, 10.8 Hz, 3H), 2.64 (s, 3H), 2.54 (s, 3H), 1.68 (t, J=13.2 Hz, 2H), 1.15 (s, 3H); MS-ESI m/z=440.39 [M+H]⁺.

41. Preparation of 3'-(R)-3'-[(4-fluoro)phenylaminomethyl)]dihydrospectinomycin Trihydrochloride (31)

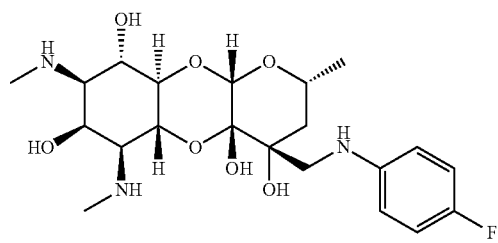 [SMILES: CN[C@@H]1[C@H](O)[C@H](NC)[C@H]2O[C@]3(O)[C@H](O[C@@H]2[C@H]1O)O[C@H](C)C[C@@]3(O)CNc1ccc(F)cc1]

Compound 31 was prepared via Analog Route V (as described herein above) to afford the title compound (24 mg, 36%) as the trihydrochloride salt. ¹H NMR (D₂O, 400 MHz) δ 6.97-6.90 (m, 2H), 6.82-6.76 (m, 2H), 4.87 (d, J=1.5 Hz, 1H), 4.47 (t, J=2.8 Hz, 1H), 4.16 (t, J=10.5 Hz, 1H), 4.12-4.03 (m, 1H), 3.91 (t, J=9.9 Hz, 1H), 3.77 (t, J=10.1 Hz, 1H), 3.39 (d, J=13.5 Hz, 1H), 3.19 (d, J=13.5 Hz, 1H), 3.03-2.95 (m, 2H), 2.63 (s, 3H), 2.52 (s, 3H), 1.75-1.59 (m, 2H), 1.16 (d, J=6.1 Hz, 3H); MS-ESI m/z=458.59 [M+H]⁺.

42. Preparation of 3'-(R)-3'-[(4-Methyl)]Phenethylaminomethyl)]Dihydrospectinomycin Trihydrochloride (32)

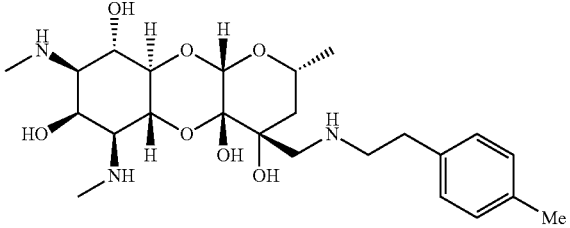 [SMILES: CN[C@@H]1[C@H](O)[C@H](NC)[C@H]2O[C@]3(O)[C@H](O[C@@H]2[C@H]1O)O[C@H](C)C[C@@]3(O)CNCCc1ccc(C)cc1]

Compound 32 was prepared via Analog Route I (as described herein above) to afford the title compound (12.6 mg 46%) as the trihydrochloride salt. ¹H NMR (D2O, 500 MHz) δ 7.27-7.09 (m, 4H), 4.79 (s, 1H), 4.20 (t, J=9.9 Hz, 1H), 4.12 (d, J=9.6 Hz, 1H), 4.00-3.85 (m, 2H), 3.73 (t, J=7.4 Hz, 1H), 3.64-3.54 (m, 1H), 3.50-3.33 (m, 2H), 3.33-3.24 (m, 2H), 3.23-3.13 (m, 2H), 2.96 (dq, J=12.1, 7.1, 6.1 Hz, 1H), 2.75 (d, J=3.4 Hz, 6H), 2.24 (S, 3H), 1.77 (dt, J=22.5, 12.9 Hz, 2H), 1.17 (s, 3H). MS-ESI m/z=482.40 [M+H]⁺.

43. Preparation of 3'-(R)-3'-(4-FLUOROphenethylaminomethyl)dihydrospectinomycin Trihydrochloride (33)

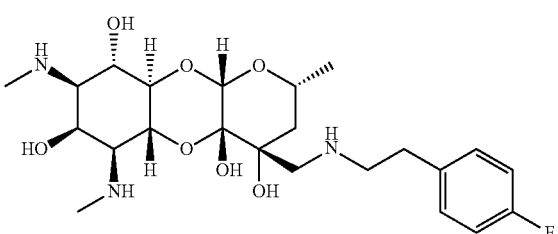

Compound 33 was prepared via Analog Route I (as described herein above) to afford the title compound (32 mg, 34%) as the trihydrochloride salt. ¹H NMR (D₂O, 400 MHz) δ 7.28-7.21 (m, 2H), 7.09-7.02 (m, 2H), 4.76 (s, 1H), 4.54 (p, J=3.8, 3.3 Hz, 1H), 4.00 (t, J=10.4 Hz, 1H), 3.89 (t, J=9.9 Hz, 1H), 3.81-3.70 (m, 2H), 3.34 (d, J=13.5 Hz, 1H), 3.21 (td, J=7.6, 7.2, 5.8 Hz, 2H), 3.13 (d, J=13.5 Hz, 1H), 2.97 (dddd, J=18.6, 9.7, 4.6, 2.2 Hz, 4H), 2.65 (s, 3H), 2.47 (s, 3H), 1.79-1.63 (m, 2H), 1.16 (d, J=6.1 Hz, 3H); MS-ESI m/z=486.20 [M+H]⁺.

44. Preparation of 3'-(A')-3'-(benzo[d]thiazolylmethyl)aminomethyl dihydrospectinomycin Trihydrobromide (34)

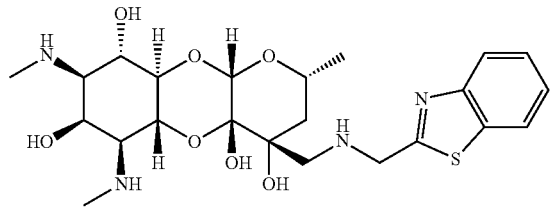 [SMILES: CN[C@@H]1[C@H](O)[C@H](NC)[C@H]2O[C@]3(O)[C@H](O[C@@H]2[C@H]1O)O[C@H](C)C[C@@]3(O)CNCc1nc2ccccc2s1]

Compound 34 was prepared via Analog Route II (as described herein above) to afford the title compound (37 mg, 29%) as the trihydrobromide salt. $^1$H NMR (D$_2$O, 400 MHz) δ 8.02 (ddd, J=7.6, 4.0, 1.1 Hz, 2H), 7.56 (ddd, J=8.2, 7.3, 1.3 Hz, 1H), 7.49 (ddd, J=8.4, 7.3, 1.2 Hz, 1H), 4.86 (s, 1H), 4.77 (d, J=4.1 Hz, 2H), 4.77 (s, 1H), 4.26-4.19 (m, 1H), 4.00 (t, J=9.9 Hz, 1H), 3.90 (t, J=10.1 Hz, 1H), 3.79 (tt, J=9.5, 6.0 Hz, 1H), 3.67 (d, J=13.5 Hz, 1H), 3.52 (dd, J=11.0, 2.7 Hz, 1H), 3.42 (d, J=13.5 Hz, 1H), 3.21 (dd, J=10.3, 2.9 Hz, 1H), 2.76 (d, J=2.5 Hz, 6H), 1.89-1.79 (m, 2H), 1.18 (d, J=6.0 Hz, 3H); MS-ESI m/z=511.30 [M+H]$^+$.

45. Preparation of 3'-(R)-3'-[(2-morpholinoethyl)aminomethyl]dihydrospectinomycin tetrahydrochloride (51)

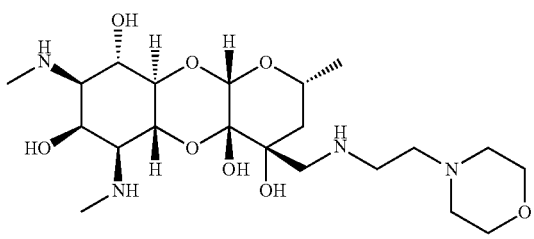

Compound 51 was prepared via Analog Route I (as described herein above) to afford the title compound (68 mg, 23%) as the tetrahydrochloride salt. $^1$H NMR (D2O, 400 MHz) δ 4.88 (s, 1H), 4.77 (m, 4H), 4.21 (t, J=10.4 Hz, 1H), 3.98 (td, J=9.8, 3.4 Hz, 1H), 3.94-3.73 (m, 4H), 3.69 (dt, J=13.5, 5.0 Hz, 1H), 3.65-3.56 (m, 1H), 3.50-3.37 (m, 3H), 3.23-3.09 (m, 3H), 2.79-2.56 (m, 9H), 1.84-1.72 (m, 2H), 1.18 (d, J=6.2 Hz, 3H). MS-ESI m/z=477.28 [M+H]$^+$

46. Preparation of 3'-(R)-3'-[(2-(tetrahydro-2H-pyran-4-yl)ethyl)aminomethyl]dihydrospectinomycin Trihydrochloride (52)

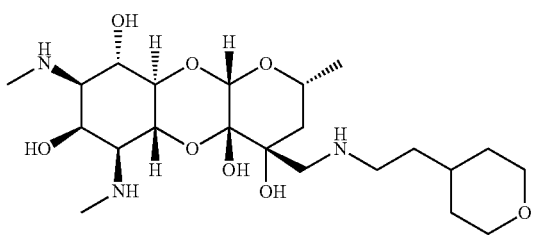 [SMILES: CN[C@@H]1[C@H](O)[C@H](NC)[C@H]2O[C@]3(O)[C@H](O[C@@H]2[C@H]1O)O[C@H](C)C[C@@]3(O)CNCCN1CCOCC1]

Compound 52 was prepared via Analog Route I (as described herein above) to afford the title compound (70 mg, 31%) as the trihydrochloride salt. $^1$H NMR (D2O, 400 MHz) δ 4.87 (s, 1H), 4.26-4.21 (m, 1H), 3.98 (t, J=9.9 Hz, 1H), 3.92-3.86 (m, 3H), 3.81 (ddd, J=10.0, 6.1, 3.6 Hz, 1H), 3.48 (dd, J=11.0, 2.8 Hz, 1H), 3.42-3.35 (m, 3H), 3.25-3.17 (m, 2H), 3.10-3.05 (m, 2H), 2.75 (s, 6H), 1.84-1.75 (m, 2H), 1.60 (t, J=11.2 Hz, 5H), 1.28-1.20 (m, 3H), 1.19 (d, J=6.0 Hz, 3H). MS-ESI m/z=476.28 [M+H]$^+$

47. Preparation of 3'-(R)-3'-[(4-methoxy)phenethylaminomethyl]dihydrospectinomycin Trihydrochloride (53)

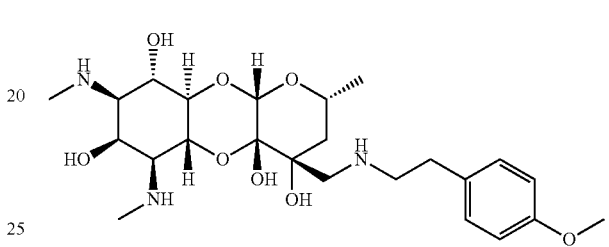

Compound 53 was prepared via Analog Route I (as described herein above) to afford the title compound (72 mg, 25%) as the trihydrochloride salt. $^1$H NMR (D2O, 500 MHz) δ 7.21 (d, J=8.7 Hz, 2H), 6.93 (d, J=8.6 Hz, 2H), 4.78 (s, 1H), 4.13 (t, J=10.4 Hz, 1H), 3.94 (t, J=10.0 Hz, 1H), 3.85 (t, J=10.1 Hz, 2H), 3.77 (s, 1H), 3.75 (s, 3H), 3.72 (dd, J=7.0, 3.3 Hz, 2H), 3.38 (d, J=13.6 Hz, 1H), 3.29-3.27 (m, 1H), 3.18 (d, J=13.6 Hz, 1H), 3.12 (dd, J=10.3, 3.0 Hz, 1H), 2.94 (q, J=6.7 Hz, 2H), 2.73 (d, J=3.9 Hz, 6H), 1.74 (dd, J=28.6, 11.6 Hz, 2H), 1.16 (d, J=6.0 Hz, 3H). MS-ESI m/z=498.28 [M+H]$^+$

48. Preparation of 3'-(R)-3'-[(4-chloro)phenethylaminomethyl]dihydrospectinomycin Trihydrobromide (54)

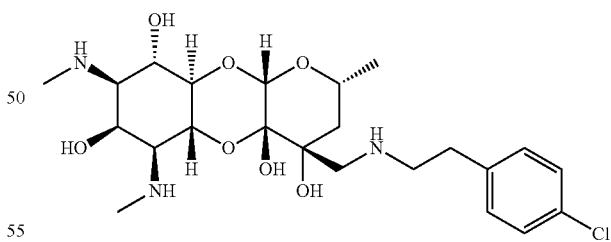

Compound 54 was prepared via Analog Route VIII (as described herein above) to afford the title compound (30 mg, 26%) as the trihydrobromide salt. $^1$H NMR (D2O, 500 MHz) δ 7.34 (d, J=8.4 Hz, 2H), 7.22 (d, J=8.4 Hz, 2H), 4.91 (s, 1H), 4.28-4.21 (m, 1H), 4.11 (ddd, J=10.8, 6.3, 2.9 Hz, 1H), 3.99-3.94 (m, 1H), 3.88 (td, J=10.1, 4.2 Hz, 1H), 3.53 (d, J=13.3 Hz, 1H), 3.50-3.42 (m, 2H), 3.31-3.26 (m, 2H), 3.20-3.14 (m, 2H), 2.98 (dd, J=9.3, 6.6 Hz, 2H), 2.75 (d, J=2.2 Hz, 6H), 1.69-1.62 (m, 2H), 1.18 (d, J=6.0 Hz, 3H). MS-ESI m/z=502.40 [M+H]$^+$

49. Preparation of 3'-(R)-3'-[(3,4-dimethyl)phenethylaminomethyl]dihydrospectinomycin Trihydrochloride (55)

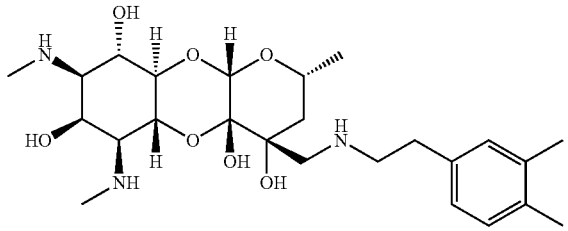

Compound 55 was prepared via Analog Route IX (as described herein above) to afford the title compound (38 mg, 37%) as the trihydrochloride salt. $^1$H NMR (D2O, 500 MHz) δ 7.13 (d, J=7.6 Hz, 1H), 7.07-7.04 (m, 1H), 6.99 (dd, J=7.7, 2.1 Hz, 1H), 4.92 (s, 1H), 4.25 (q, J=10.6 Hz, 1H), 4.10 (ddd, J=10.1, 6.3, 3.2 Hz, 1H), 3.97 (td, J=10.1, 3.9 Hz, 1H), 3.91-3.85 (m, 2H), 3.83-3.78 (m, 1H), 3.52 (d, J=13.2 Hz, 1H), 3.44 (td, J=10.4, 9.7, 2.6 Hz, 1H), 3.26-3.14 (m, 4H), 2.92 (dd, J=9.3, 6.6 Hz, 1H), 2.76-2.73 (m, 6H), 2.17 (d, J=6.6 Hz, 6H), 1.68-1.61 (m, 2H), 1.18 (t, J=6.3 Hz, 3H). MS-ESI m/z=496.40 [M+H]$^+$

50. Preparation of 3'-(R)-3'-[(2-chloro)benzylaminomethyl]dihydrospectinomycin Trihydrobromide (56)

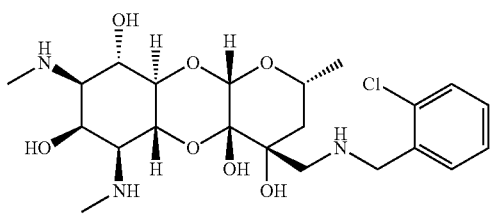

Compound 56 was prepared via Analog Route II (as described herein above) to afford the title compound (123 mg, 26%) as the trihydrobromide salt. $^1$H NMR (D2O, 500 MHz) δ 7.53-7.46 (m, 2H), 7.45-7.34 (m, 2H), 4.92 (s, 1H), 4.41 (h, J=10.8 Hz, 2H), 4.29-4.22 (m, 1H), 4.09 (d, J=7.5 Hz, 1H), 3.96 (d, J=9.6 Hz, 1H), 3.92-3.84 (m, 1H), 3.58 (d, J=13.1 Hz, 1H), 3.43 (d, J=11.4 Hz, 1H), 3.26 (d, J=2.5 Hz, 1H), 3.19-3.08 (m, 2H), 2.72 (dd, J=21.0, 3.3 Hz, 6H), 1.69-1.59 (m, 2H), 1.17 (d, J=5.1 Hz, 3H). MS-ESI m/z=488.20 [M+H]$^+$

51. Preparation of 3'-(R)-3'-[(4-trifluoromethoxy)phenethylaminomethyl]dihydrospectinomycin Trihydrochloride (57)

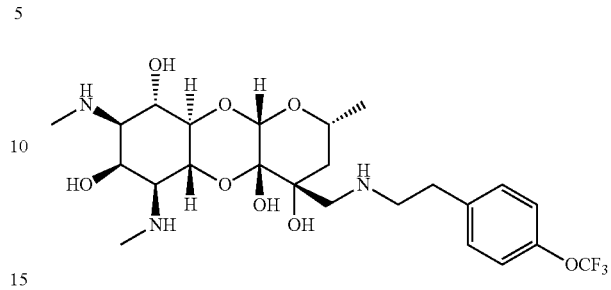

Compound 56 was prepared via Analog Route IX (as described herein above) to afford the title compound (39 mg, 19%) as the trihydrochloride salt. $^1$H NMR (D2O, 500 MHz) δ 7.27 (d, J=8.6 Hz, 2H), 7.19 (d, J=8.1 Hz, 2H), 4.48-4.43 (m, 2H), 4.06-4.00 (m, 1H), 3.97-3.90 (m, 2H), 3.85-3.80 (m, 1H), 3.72-3.67 (m, 2H), 2.97-2.90 (m, 2H), 2.85-2.78 (m, 4H), 2.55 (d, J=6.2 Hz, 6H), 1.65 (m, 2H), 1.22 (d, J=5.7 Hz, 3H). MS-ESI m/z=552.51 [M+H]$^+$

52. Preparation of 3'-(R)-3'-[(4-trifluoromethyl)phenethylaminomethyl]dihydrospectinomycin Trihydrochloride (58)

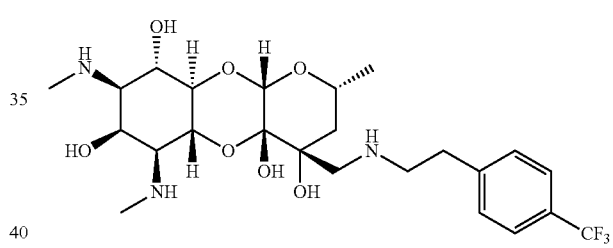

Compound 58 was prepared via Analog Route IX (as described herein above) to afford the title compound (80 mg, 36%) as the trihydrochloride salt. $^1$H NMR (D2O, 500 MHz) δ 7.62 (d, J=7.9 Hz, 2H), 7.39 (d, J=8.0 Hz, 2H), 4.50 (m, 2H), 3.97 (t, J=10.4 Hz, 1H), 3.86 (t, J=10.0 Hz, 1H), 3.79-3.66 (m, 2H), 3.26-2.88 (m, 8H), 2.52 (d, J=93.6 Hz, 6H), 1.69 (dd, J=42.6, 13.0 Hz, 2H), 1.14 (d, J=6.2 Hz, 3H). MS-ESI m/z=536.51 [M+H]$^+$

53. Preparation of 3'-(R)-3'-[((2-(pyridin-3-yl)ethyl)aminomethyl]dihydrospectinomycin tetrahydrobromide (59)

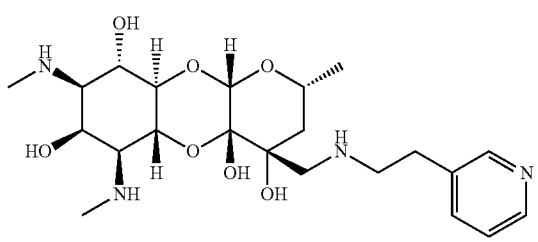

Compound 59 was prepared via Analog Route VIII (as described herein above) to afford the title compound (53 mg, 26%) as the tetrahydrobromide salt. ¹H NMR (D2O, 500 MHz) δ 8.64 (d, J=2.0 Hz, 1H), 8.60 (dd, J=5.6, 1.4 Hz, 1H), 8.35 (d, J=8.2 Hz, 1H), 7.87 (dd, J=8.1, 5.7 Hz, 1H), 4.89 (s, 1H), 4.25-4.21 (m, 1H), 4.00 (t, J=10.0 Hz, 1H), 3.90 (t, J=10.1 Hz, 1H), 3.86-3.81 (m, 1H), 3.53-3.48 (m, 2H), 3.42-3.31 (m, 3H), 3.27-3.17 (m, 3H), 2.76 (d, J=1.8 Hz, 6H), 1.85-1.78 (m, 2H), 1.20 (d, J=6.0 Hz, 3H). MS-ESI m/z=469.30 [M+H]⁺

54. Preparation of 3'-(R)-3'-[((2-(pyrazin-2-yl)ethyl)aminomethyl]dihydrospectinomycin tetrahydrobromide (60)

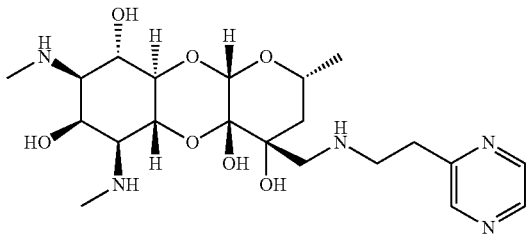 [SMILES: CN[C@@H]1[C@H](O)[C@H](NC)[C@H]2O[C@]3(O)[C@H](O[C@@H]2[C@H]1O)O[C@H](C)C[C@@]3(O)CNCCc1cnccn1]

Compound 60 was prepared via Analog Route VIII (as described herein above) to afford the title compound (91 mg, 28%) as the tetrahydrobromide salt. ¹H NMR (D2O, 500 MHz) δ 8.64 (s, 1H), 7.87 (d, J=4.8 Hz, 2H), 4.94 (t, J=2.7 Hz, 1H), 4.28 (td, J=11.4, 10.6, 2.8 Hz, 1H), 4.15-4.09 (m, 1H), 4.01-3.96 (m, 1H), 3.92-3.86 (m, 1H), 3.60-3.56 (m, 1H), 3.52-3.41 (m, 3H), 3.34 (d, J=9.2 Hz, 2H), 3.26 (t, J=2.7 Hz, 2H), 3.18 (d, J=11.0 Hz, 1H), 2.75 (d, J=3.0 Hz, 6H), 1.71 (d, J=11.0 Hz, 2H), 1.19 (d, J=5.2 Hz, 3H). MS-ESI m/z=470.30 [M+H]⁺

55. Preparation of 3'-(R)-3'-[((2-(thiophen-2-yl)ethyl)aminomethyl]dihydrospectinomycin trihydrobromide (61)

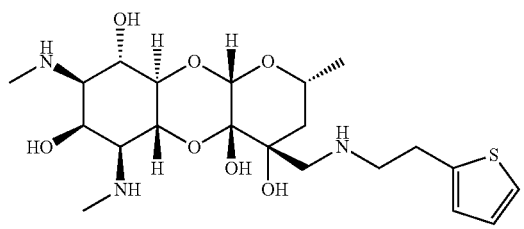

Compound 61 was prepared via Analog Route VIII (as described herein above) to afford the title compound (29 mg, 24%) as the trihydrobromide salt. ¹H NMR (D₂O, 500 MHz) δ 7.31 (dd, J=4.9, 1.4 Hz, 1H), 7.02-6.94 (m, 2H), 4.83 (s, 1H), 4.19 (t, J=10.5 Hz, 1H), 3.98 (t, J=9.9 Hz, 1H), 3.89 (t, J=10.1 Hz, 1H), 3.77 (ddd, J=11.4, 6.1, 2.3 Hz, 1H), 3.71-3.66 (m, 1H), 3.51-3.42 (m, 2H), 3.39-3.33 (m, 2H), 3.27-3.13 (m, 4H), 2.75 (q, J=3.8, 3.2 Hz, 6H), 1.83-1.71 (m, 2H), 1.18 (d, J=6.1 Hz, 3H). MS-ESI m/z=474.40 [M+H]⁺

56. Preparation of 3'-(R)-3'-[((2-(1H-pyrrol-2-yl)ethyl)aminomethyl]dihydrospectinomycin tetrahydrobromide (62)

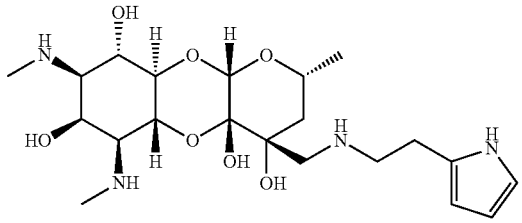

Compound 62 was prepared via Analog Route VIII (as described herein above) to afford the title compound (33 mg, 21%) as the tetrahydrobromide salt. ¹H NMR (D2O, 500 MHz) δ 7.31 (dd, J=4.9, 1.4 Hz, 1H), 7.02-6.95 (m, 2H), 4.83 (s, 1H), 4.18 (d, J=10.5 Hz, 1H), 3.98 (t, J=9.9 Hz, 1H), 3.89 (t, J=10.0 Hz, 1H), 3.77 (ddt, J=11.4, 6.3, 3.1 Hz, 1H), 3.69 (dd, J=10.8, 9.4 Hz, 1H), 3.48 (dd, J=11.0, 2.8 Hz, 1H), 3.44 (d, J=13.6 Hz, 1H), 3.39-3.33 (m, 2H), 3.27-3.14 (m, 4H), 2.75 (q, J=3.8, 3.2 Hz, 6H), 1.83-1.71 (m, 2H), 1.18 (d, J=6.1 Hz, 3H). MS-ESI m/z=457.30 [M+H]⁺

57. Preparation of 3'-(R)-3'-[((2-(pyridin-4-yl)ethyl)aminomethyl]dihydrospectinomycin tetrahydrobromide (63)

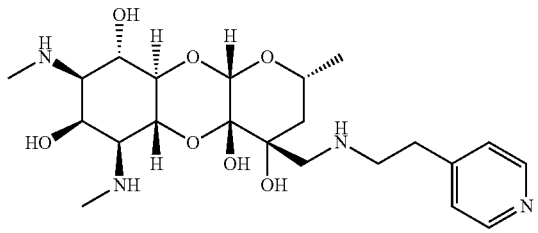 [SMILES: CN[C@@H]1[C@H](O)[C@H](NC)[C@H]2O[C@]3(O)[C@H](O[C@@H]2[C@H]1O)O[C@H](C)C[C@@]3(O)CNCCc1ccncc1]

Compound 63 was prepared via Analog Route VIII (as described herein above) to afford the title compound (32 mg, 25%) as the tetrahydrobromide salt. ¹H NMR (D2O, 500 MHz) δ 8.64 (s, 2H), 7.87 (s, 2H), 4.94 (s, 1H), 4.28 (td, J=11.4, 10.6, 2.8 Hz, 1H), 4.16-4.10 (m, 1H), 4.02-3.96 (m, 1H), 3.93-3.85 (m, 1H), 3.61-3.56 (m, 1H), 3.51-3.40 (m, 3H), 3.34 (d, J=9.2 Hz, 2H), 3.26 (t, J=2.7 Hz, 2H), 3.18 (d, J=11.0 Hz, 1H), 2.75 (d, J=2.9 Hz, 6H), 1.74-1.62 (m, 2H), 1.19 (d, J=5.2 Hz, 3H). MS-ESI m/z=469.30 [M+H]⁺

58. Preparation of 3'-(R)-3'-[((2-(thiazol-2-yl)ethyl)aminomethyl]dihydrospectinomycin tetrahydrobromide (64)

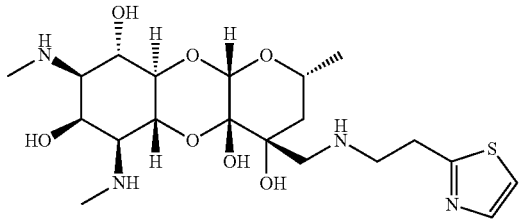

Compound 64 was prepared via Analog Route VIII (as described herein above) to afford the title compound (77 mg, 30%) as the tetrahydrobromide salt. $^1$H NMR (D2O, 500 MHz) δ 7.78 (d, J=3.5 Hz, 1H), 7.58 (d, J=3.5 Hz, 1H), 4.89 (s, 1H), 4.22 (dd, J=11.0, 10.1 Hz, 1H), 3.99 (t, J=10.0 Hz, 1H), 3.89 (d, J=10.2 Hz, 1H), 3.81 (ddt, J=12.0, 6.0, 3.0 Hz, 1H), 3.56-3.49 (m, 6H), 3.42 (d, J=7.2 Hz, 1H), 3.30 (d, J=13.5 Hz, 1H), 3.20 (dd, J=10.4, 3.0 Hz, 1H), 2.76 (d, J=1.8 Hz, 6H), 1.85-1.76 (m, 2H), 1.19 (d, J=6.1 Hz, 3H). MS-ESI m/z=475.40 [M+H]$^+$

59. Preparation of 3'-(R)-3'-[(pyrimidin-5-ylmethyl) aminomethyl]dihydrospectinomycin tetrahydrobromide (66)

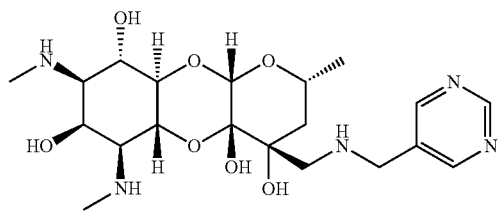 [SMILES: CN[C@@H]1[C@H](O)[C@H](NC)[C@H]2O[C@]3(O)[C@H](O[C@@H]2[C@H]1O)O[C@H](C)C[C@@]3(O)CNCc1cncnc1]

Compound 66 was prepared via Analog Route II (as described herein above) to afford the title compound (52 mg 37%) 51% as the tetrahydrobromide salt. $^1$H NMR (D20, 500 MHz) δ 9.14 (d, J=5.0 Hz, 1H), 8.91 (t, J=2.9 Hz, 2H), 4.83 (s, 1H), 4.39 (d, J=3.8 Hz, 2H), 4.22 (t, J=11.3 Hz, 1H), 3.98 (t, J=9.2 Hz, 1H), 3.89 (td, J=10.0, 4.8 Hz, 1H), 3.79 (q, J=7.9, 6.9 Hz, 1H), 3.52-3.44 (m, 2H), 3.33 (dt, J=13.6, 2.9 Hz, 1H), 3.27-3.24 (m, 1H), 3.19 (d, J=10.6 Hz, 1H), 2.75 (d, J=3.1 Hz, 6H), 1.79 (m, 2H), 1.18 (d, J=5.2 Hz, 3H). MS-ESI m/z=456.54 [M+H]$^+$

60. Preparation of 3'-(R)-3'-[(pyrazin-2-ylmethyl) aminomethyl]dihydrospectinomycin tetrahydrobromide (67)

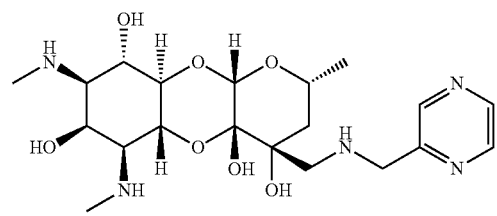

Compound 67 was prepared via Analog Route II (as described herein above) to afford the title compound (48 mg 39%) as the tetrahydrobromide salt. $^1$H NMR (D2O, 500 MHz) δ 9.14 (d, J=5.2 Hz, 1H), 8.95-8.86 (m, 2H), 4.83 (s, 1H), 4.39 (d, J=4.0 Hz, 1H), 4.22 (td, J=10.6, 5.1 Hz, 1H), 4.01-3.95 (m, 1H), 3.89 (dt, J=13.3, 6.0 Hz, 1H), 3.82-3.76 (m, 1H), 3.72-3.65 (m, 1H), 3.47 (td, J=13.2, 12.1, 5.6 Hz, 2H), 3.36-3.27 (m, 1H), 3.26 (d, J=3.3 Hz, 1H), 3.19 (d, J=10.4 Hz, 1H), 2.75 (d, J=3.4 Hz, 6H), 1.79 (m, 2H), 1.18 (d, J=5.8 Hz, 3H). MS-ESI m/z=456.44 [M+H]$^+$

61. Preparation of 3'-(R)-3'-[(4-(methylthio)benzylaminomethyl)]dihydrospectinomycin trihydrobromide (68)

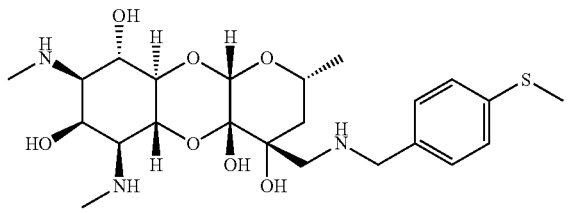

Compound 68 was prepared via Analog Route II (as described herein above) to afford the title compound (69 mg 51%) as the trihydrobromide salt. $^1$H NMR (D2O, 500 MHz) δ 7.34 (qd, J=10.2, 6.7 Hz, 4H), 4.26-4.15 (m, 3H), 3.98-3.92 (m, 1H), 3.87 (td, J=10.2, 5.0 Hz, 1H), 3.64 (dt, J=11.4, 6.1 Hz, 1H), 3.45 (d, J=12.1 Hz, 1H), 3.31 (dd, J=13.7, 3.5 Hz, 1H), 3.26 (t, J=3.0 Hz, 1H), 3.15 (ddd, J=25.0, 15.4, 8.7 Hz, 3H), 2.74 (s, 6H), 2.44 (s, 3H), 1.78-1.66 (m, 2H), 1.14 (d, J=5.7 Hz, 3H). MS-ESI m/z=500.24 [M+H]$^+$

62. Preparation of 3'-(R)-3'-[(4-(methylsulfonyl) benzylaminomethyl)]dihydrospectino-mycin trihydrobromide (69)

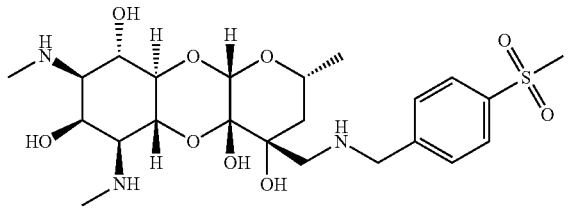

Compound 69 was prepared via Analog Route II (as described herein above) to afford the title compound (86 mg 52%) as the trihydrobromide salt. $^1$H NMR (D2O, 500 MHz) δ 8.01-7.97 (m, 2H), 7.74-7.69 (m, 2H), 4.74 (s, 1H), 4.44-4.33 (m, 2H), 4.20 (td, J=10.7, 5.8 Hz, 1H), 3.96 (td, J=9.7, 5.2 Hz, 1H), 3.88 (td, J=10.3, 5.2 Hz, 1H), 3.71 (dt, J=10.5, 4.7 Hz, 1H), 3.48 (dd, J=11.0, 3.5 Hz, 1H), 3.40-3.34 (m, 1H), 3.27-3.25 (m, 1H), 3.25-3.13 (m, 5H), 2.75 (s, 6H), 1.75 (dd, J=22.9, 13.3 Hz, 2H), 1.15 (s, 3H). MS-ESI m/z=532.44 [M+H]$^+$

45. Characterization of Exemplary Compounds

The compounds in Table 1 were synthesized with methods identical or analogous to those described herein, e.g., the column denoted as "Synthesis Route" refers to the designated synthesis route described herein above. For example, "I" refers to "Route I" described herein above. The other methods identified in Table 1 are similarly associated with the appropriate method as described herein above. The requisite starting materials were commercially available, described in the literature, or readily synthesized by one skilled in the art of organic synthesis.

TABLE 1

| No. | Structure | [M + H]+ | Synthesis Route |
|---|---|---|---|
| 1 | 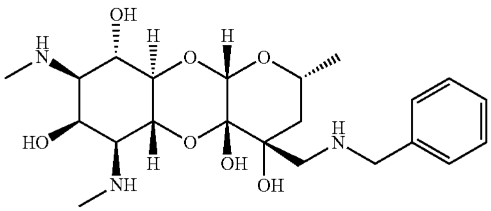 [SMILES: CN[C@@H]1[C@H](O)[C@H](NC)[C@H]2O[C@]3(O)[C@H](O[C@@H]2[C@H]1O)O[C@H](C)C[C@@]3(O)CNCc1ccccc1] | 454.29 | I |
| 2 | 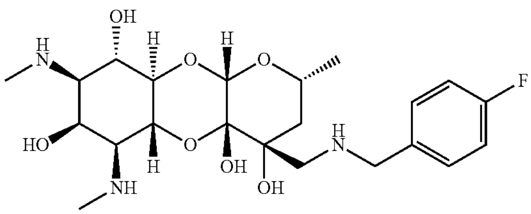 [SMILES: CN[C@@H]1[C@H](O)[C@H](NC)[C@H]2O[C@]3(O)[C@H](O[C@@H]2[C@H]1O)O[C@H](C)C[C@@]3(O)CNCc1ccc(F)cc1] | 472.32 | I |
| 3 | 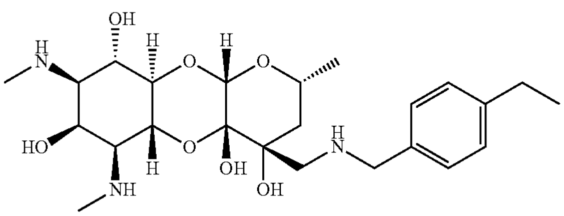 | 482.30 | III |
| 4 | 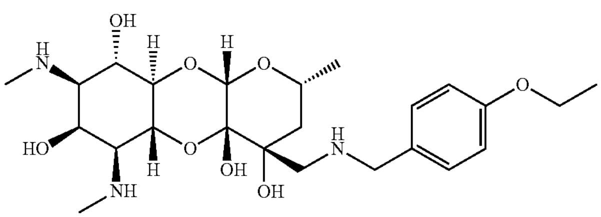 [SMILES: CCOc1ccc(CNC[C@]2(O)C[C@@H](C)O[C@H]3O[C@@H]4[C@@H](O)[C@H](NC)[C@H](O)[C@H](NC)[C@H]4O[C@]32O)cc1] | 498.45 | III |
| 5 | 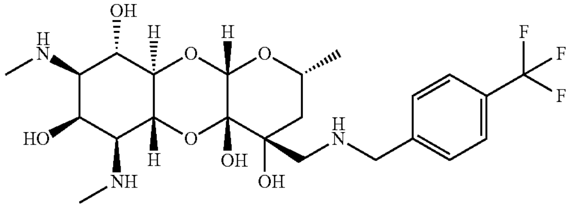 [SMILES: CN[C@@H]1[C@H](O)[C@H](NC)[C@H]2O[C@]3(O)[C@H](O[C@@H]2[C@H]1O)O[C@H](C)C[C@@]3(O)CNCc1ccc(C(F)(F)F)cc1] | 522.30 | III |
| 6 | 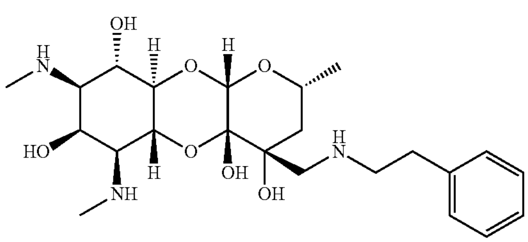 | 468.42 | I |
| 7 | 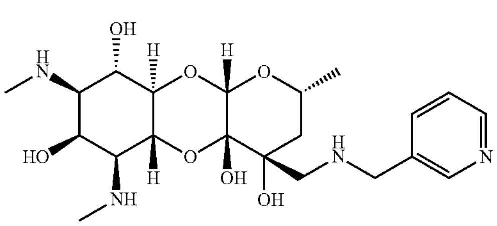 | 455.39 | II |

TABLE 1-continued
| No. | Structure | [M + H]+ | Synthesis Route |
|-----|-----------|----------|-----------------|
| 8 | 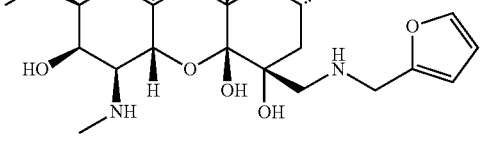 | 444.41 | I |
| 9 | 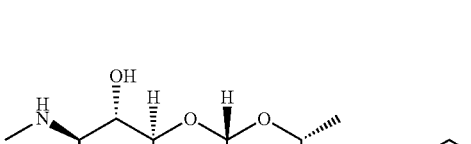 | 455.31 | II |
| 10 | 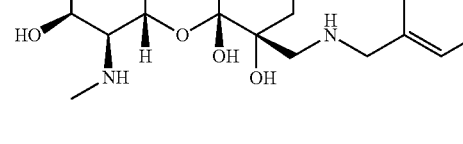 | 538.34 | III |
| 11 | 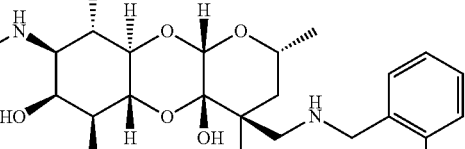 | 538.34 | I |
| 12 | 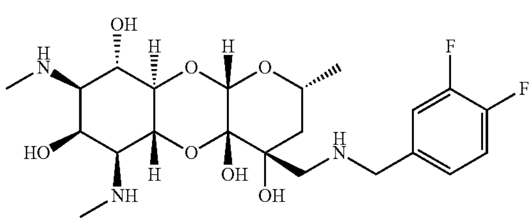 [SMILES: CN[C@@H]1[C@H](O)[C@H](NC)[C@H]2O[C@]3(O)[C@H](O[C@@H]2[C@H]1O)O[C@H](C)C[C@@]3(O)CNCc1ccc(F)c(F)c1] | 490.30 | III |
| 13 | 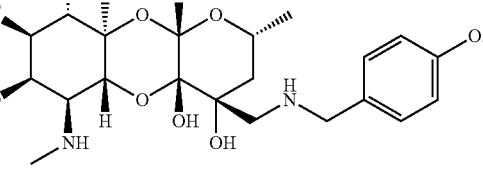 | 482.32 | I |

US 10,266,544 B2
183 184
TABLE 1-continued
| No. | Structure | [M + H]+ | Synthesis Route |
|---|---|---|---|
| 14 | 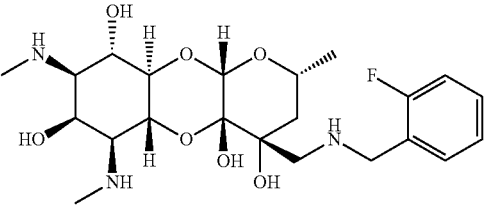 [SMILES: CN[C@@H]1[C@H](O)[C@H](NC)[C@H]2O[C@]3(O)[C@H](O[C@@H]2[C@H]1O)O[C@H](C)C[C@@]3(O)CNCc1ccccc1F] | 472.32 | I |
| 15 | 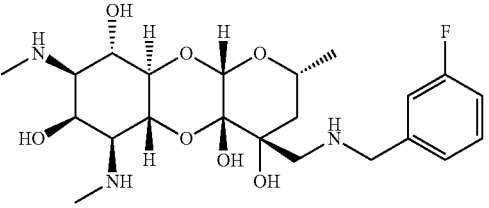 [SMILES: CN[C@@H]1[C@H](O)[C@H](NC)[C@H]2O[C@]3(O)[C@H](O[C@@H]2[C@H]1O)O[C@H](C)C[C@@]3(O)CNCc1cccc(F)c1] | 472.32 | I |
| 16 | 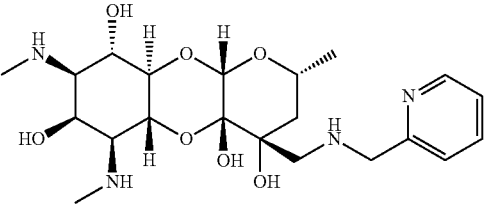 | 455.31 | II |
| 17 | 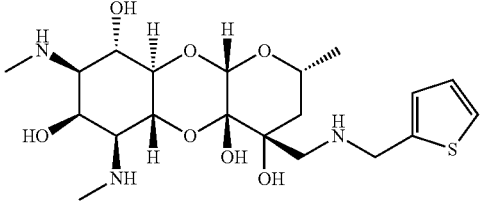 [SMILES: CN[C@@H]1[C@H](O)[C@H](NC)[C@H]2O[C@]3(O)[C@H](O[C@@H]2[C@H]1O)O[C@H](C)C[C@@]3(O)CNCc1cccs1] | 460.24 | IV |
| 18 | 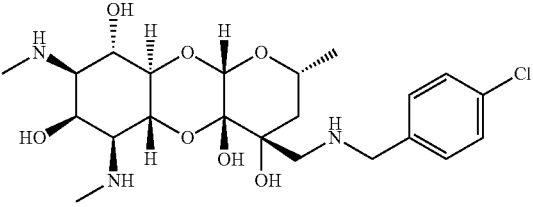 [SMILES: CN[C@@H]1[C@H](O)[C@H](NC)[C@H]2O[C@]3(O)[C@H](O[C@@H]2[C@H]1O)O[C@H](C)C[C@@]3(O)CNCc1ccc(Cl)cc1] | 488.20 | IV |
| 19 | 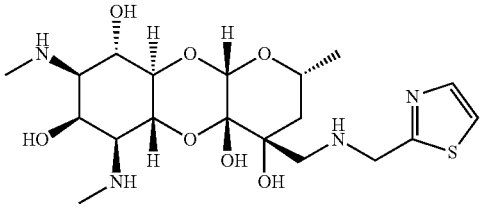 [SMILES: CN[C@@H]1[C@H](O)[C@H](NC)[C@H]2O[C@]3(O)[C@H](O[C@@H]2[C@H]1O)O[C@H](C)C[C@@]3(O)CNCc1nccs1] | 461.29 | II |
| 20 | 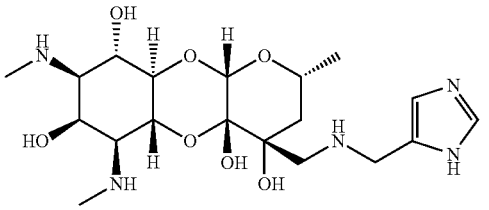 [SMILES: CN[C@@H]1[C@H](O)[C@H](NC)[C@H]2O[C@]3(O)[C@H](O[C@@H]2[C@H]1O)O[C@H](C)C[C@@]3(O)CNCc1cnc[nH]1] | 444.29 | I |

TABLE 1-continued
| No. | Structure | [M + H]+ | Synthesis Route |
|---|---|---|---|
| 21 | 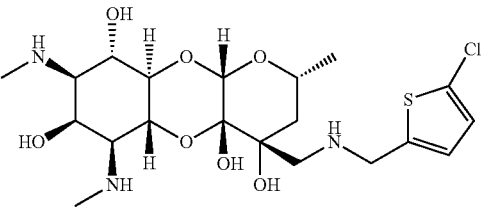 [SMILES: CN[C@@H]1[C@H](O)[C@H](NC)[C@H]2O[C@]3(O)[C@H](O[C@@H]2[C@H]1O)O[C@H](C)C[C@@]3(O)CNCc1ccc(Cl)s1] | 494.20 | II |
| 22 | 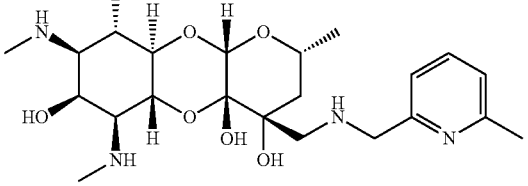 | 469.30 | II |
| 23 | 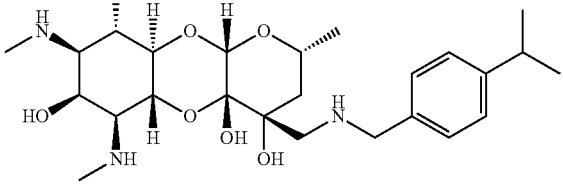 | 496.40 | I |
| 24 | 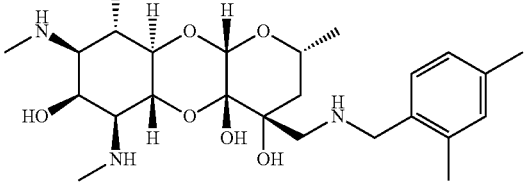 | 482.40 | I |
| 25 | 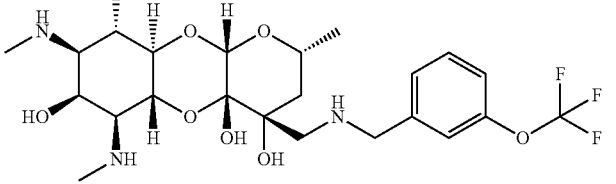 | 538.31 | I |
| 26 | 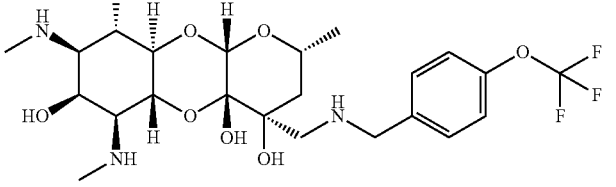 | 538.34 | I |
| 27 | 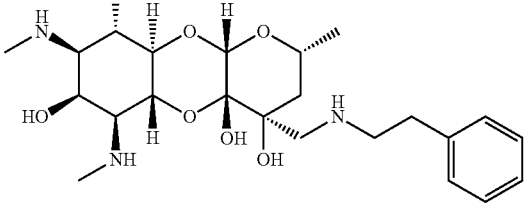 | 468.30 | I |

TABLE 1-continued
| No. | Structure | [M + H]+ | Synthesis Route |
|---|---|---|---|
| 28 | 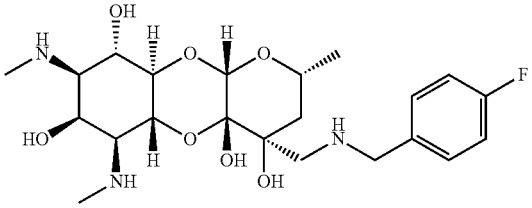 [SMILES: CN[C@@H]1[C@H](O)[C@H](NC)[C@H]2O[C@]3(O)[C@H](O[C@@H]2[C@H]1O)O[C@H](C)C[C@]3(O)CNCc1ccc(F)cc1] | 472.32 | I |
| 29 | 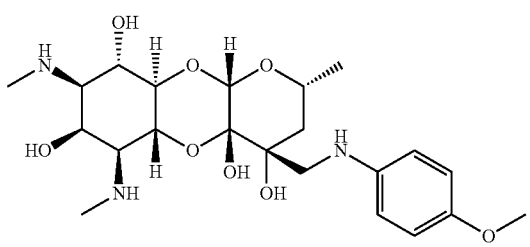 | 470.40 | V |
| 30 | 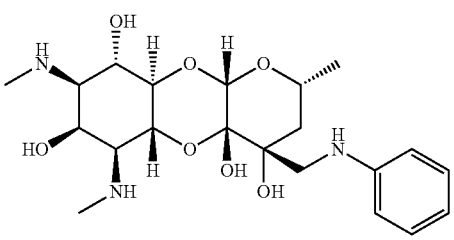 [SMILES: CN[C@@H]1[C@H](O)[C@H](NC)[C@H]2O[C@]3(O)[C@H](O[C@@H]2[C@H]1O)O[C@H](C)C[C@@]3(O)CNc1ccccc1] | 440.39 | V |
| 31 | 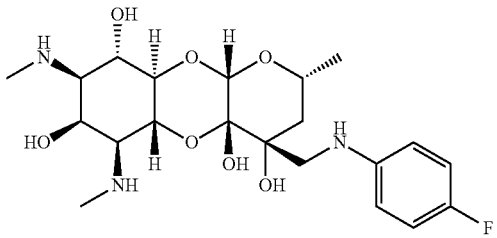 [SMILES: CN[C@@H]1[C@H](O)[C@H](NC)[C@H]2O[C@]3(O)[C@H](O[C@@H]2[C@H]1O)O[C@H](C)C[C@@]3(O)CNc1ccc(F)cc1] | 458.59 | V |
| 32 | 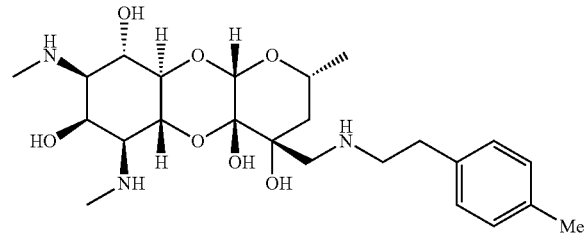 [SMILES: CN[C@@H]1[C@H](O)[C@H](NC)[C@H]2O[C@]3(O)[C@H](O[C@@H]2[C@H]1O)O[C@H](C)C[C@@]3(O)CNCCc1ccc(C)cc1] | 482.40 | I |
| 33 | 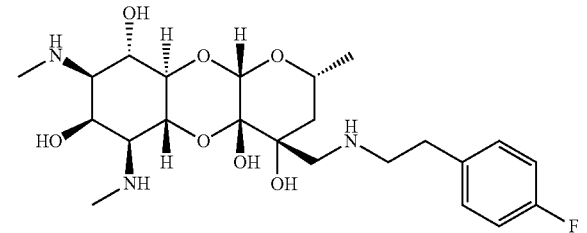 [SMILES: CN[C@@H]1[C@H](O)[C@H](NC)[C@H]2O[C@]3(O)[C@H](O[C@@H]2[C@H]1O)O[C@H](C)C[C@@]3(O)CNCCc1ccc(F)cc1] | 486.20 | I |

TABLE 1-continued
| No. | Structure | [M + H]+ | Synthesis Route |
|---|---|---|---|
| 34 | 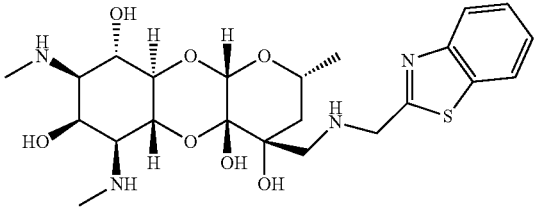 [SMILES: CN[C@@H]1[C@H](O)[C@H](NC)[C@H]2O[C@]3(O)[C@H](O[C@@H]2[C@H]1O)O[C@H](C)C[C@@]3(O)CNCc1nc2ccccc2s1] | 511.30 | II |
| 35 | 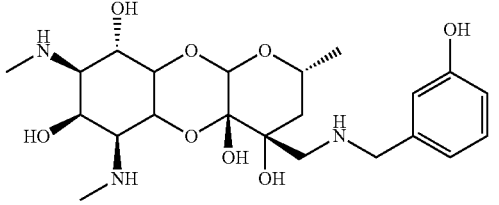 | 470.3 | VII |
| 36 | 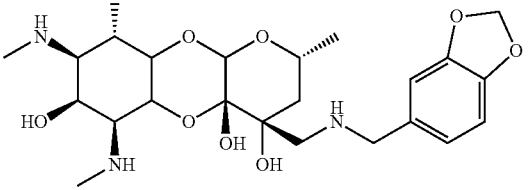 | 498.6 | VII |
| 37 | 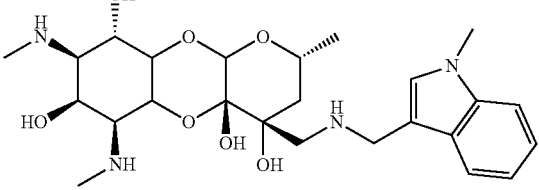 | 507.6 | VII |
| 38 | 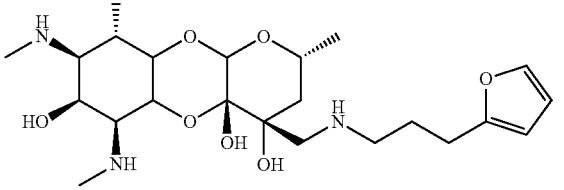 | 472.3 | VII |
| 39 | 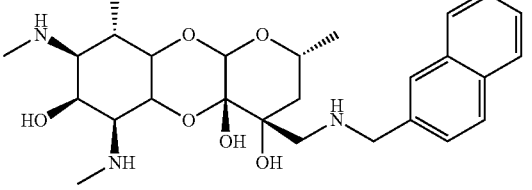 | 504.5 | VII |
| 40 | 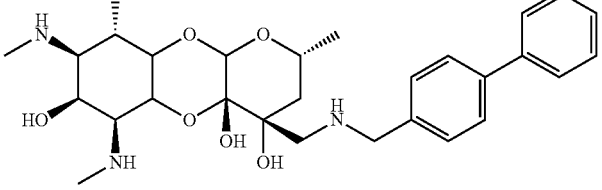 | 530.4 | VII |

TABLE 1-continued

| No. | Structure | [M + H]+ | Synthesis Route |
|-----|-----------|----------|-----------------|
| 41  | 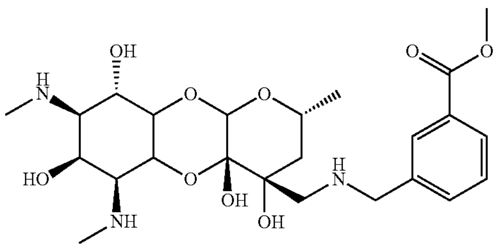          | 512.5    | VII             |
| 42  | 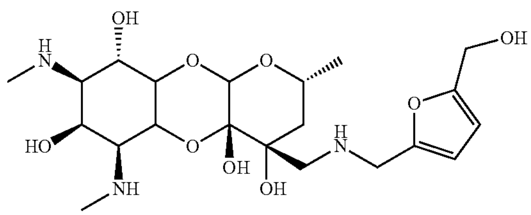 [SMILES: CN[C@@H]1[C@H](O)[C@H](NC)C2O[C@]3(O)C(OC2[C@H]1O)O[C@H](C)C[C@@]3(O)CNCc1ccc(CO)o1]          | 474.6    | VII             |
| 43  | 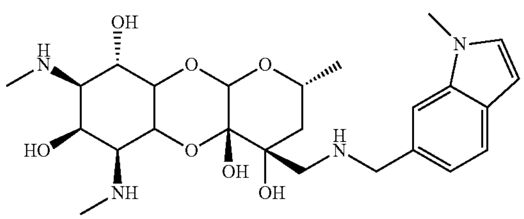 [SMILES: CN[C@@H]1[C@H](O)[C@H](NC)C2O[C@]3(O)C(OC2[C@H]1O)O[C@H](C)C[C@@]3(O)CNCc1ccc2ccn(C)c2c1]          | 507.5    | VII             |
| 44  | 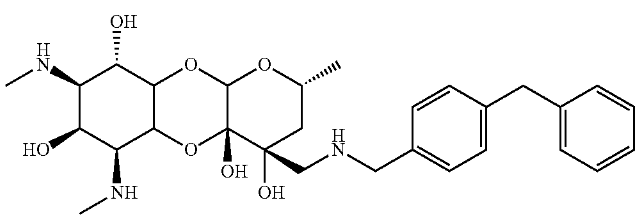 [SMILES: CN[C@@H]1[C@H](O)[C@H](NC)C2O[C@]3(O)C(OC2[C@H]1O)O[C@H](C)C[C@@]3(O)CNCc1ccc(Cc2ccccc2)cc1]          | 544.5    | VII             |
| 45  | 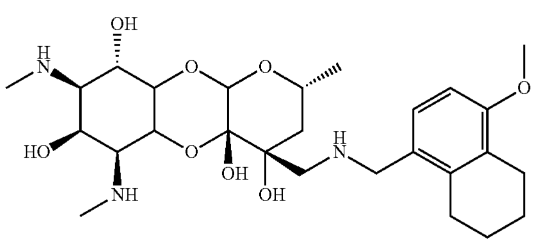          | 538.7    | VII             |
| 46  | 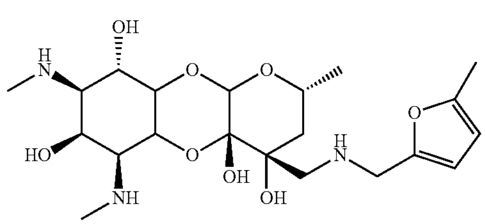 [SMILES: CN[C@@H]1[C@H](O)[C@H](NC)C2O[C@]3(O)C(OC2[C@H]1O)O[C@H](C)C[C@@]3(O)CNCc1ccc(C)o1]          | 458.3    | VII             |
| 47  | 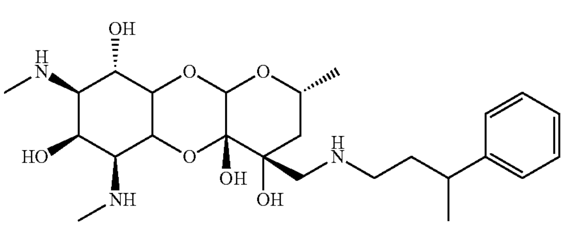 [SMILES: CN[C@@H]1[C@H](O)[C@H](NC)C2O[C@]3(O)C(OC2[C@H]1O)O[C@H](C)C[C@@]3(O)CNCCC(C)c1ccccc1]          | 496.3    | VII             |

TABLE 1-continued

| No. | Structure | [M + H]⁺ | Synthesis Route |
|-----|-----------|----------|-----------------|
| 48 | 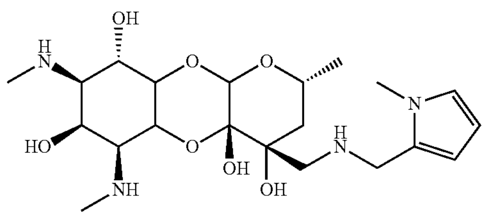 [SMILES: CN[C@@H]1[C@H](O)[C@H](NC)C2O[C@]3(O)C(OC2[C@H]1O)O[C@H](C)C[C@@]3(O)CNCc1cccn1C] | 457.4 | VII |
| 49 | 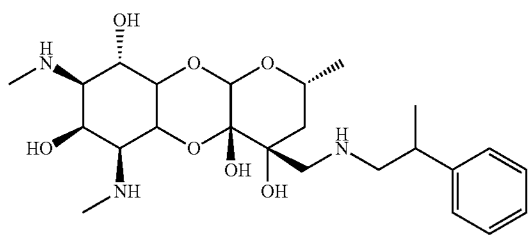 [SMILES: CN[C@@H]1[C@H](O)[C@H](NC)C2O[C@]3(O)C(OC2[C@H]1O)O[C@H](C)C[C@@]3(O)CNCC(C)c1ccccc1] | 482.6 | VII |
| 50 | 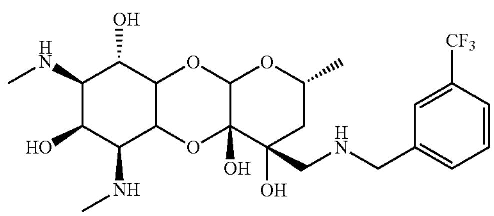 | 522.3 | VII |
| 51 | 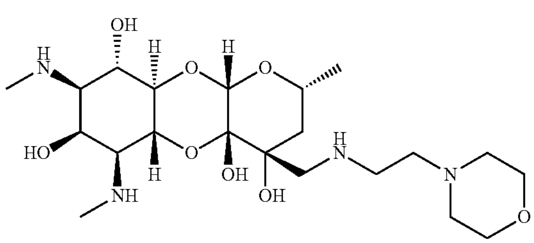 [SMILES: CN[C@@H]1[C@H](O)[C@H](NC)[C@H]2O[C@]3(O)[C@H](O[C@@H]2[C@H]1O)O[C@H](C)C[C@@]3(O)CNCCN1CCOCC1] | 477.28 | I |
| 52 | 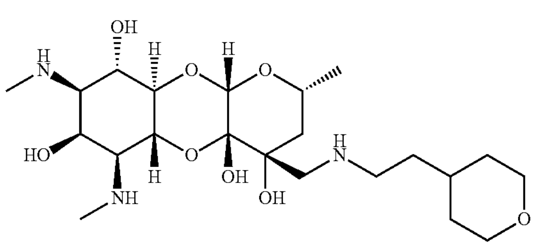 [SMILES: CN[C@@H]1[C@H](O)[C@H](NC)[C@H]2O[C@]3(O)[C@H](O[C@@H]2[C@H]1O)O[C@H](C)C[C@@]3(O)CNCCC1CCOCC1] | 476.28 | I |
| 53 | 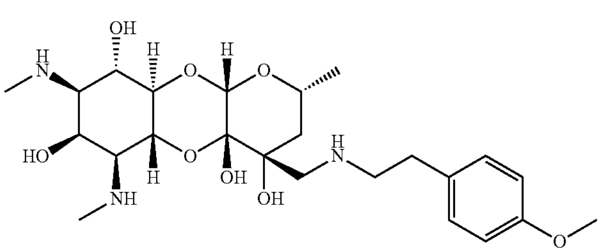 | 498.28 | I |

TABLE 1-continued
| No. | Structure | [M + H]+ | Synthesis Route |
|---|---|---|---|
| 54 | 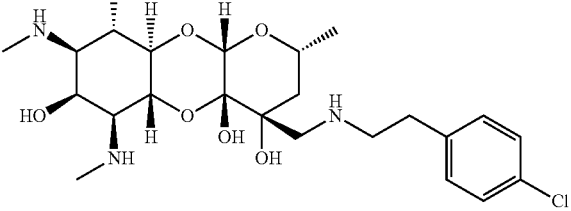 | 502.40 | VIII |
| 55 | 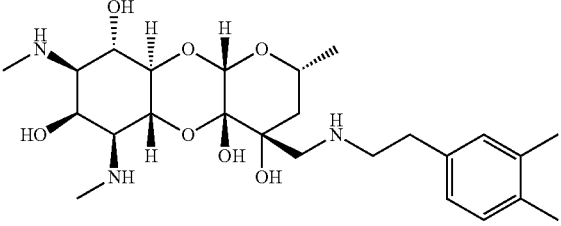 | 496.40 | IX |
| 56 | 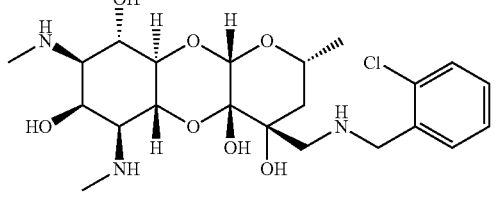 | 488.20 | II |
| 57 | 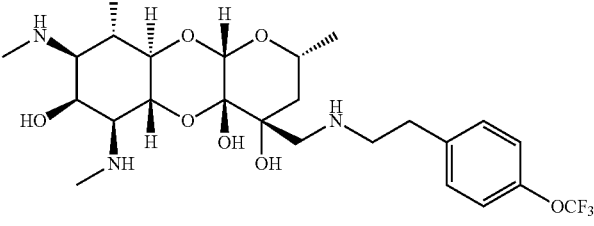 | 552.51 | IX |
| 58 | 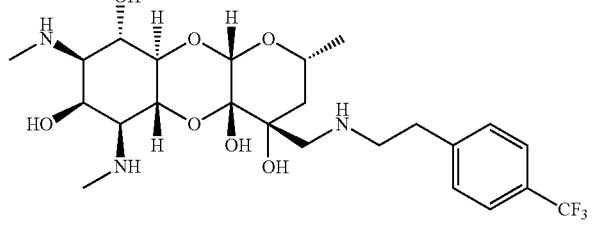 | 536.51 | IX |
| 59 | 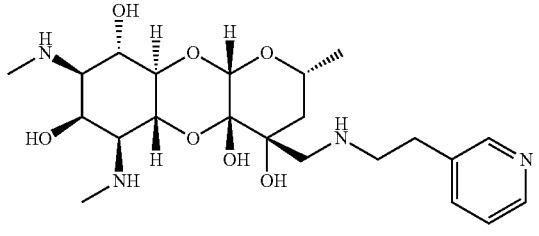 [SMILES: CN[C@@H]1[C@H](O)[C@H](NC)[C@H]2O[C@]3(O)[C@H](O[C@@H]2[C@H]1O)O[C@H](C)C[C@@]3(O)CNCCc1cccnc1] | 469.30 | VIII |

TABLE 1-continued

| No. | Structure | [M + H]+ | Synthesis Route |
|-----|-----------|----------|-----------------|
| 60  | 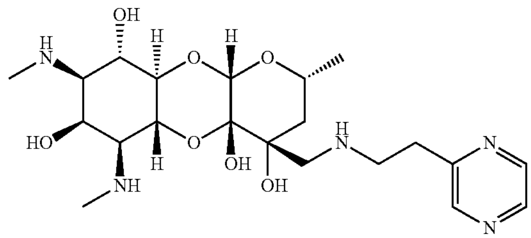 [SMILES: CN[C@@H]1[C@H](O)[C@H](NC)[C@H]2O[C@]3(O)[C@H](O[C@@H]2[C@H]1O)O[C@H](C)C[C@@]3(O)CNCCc1cnccn1]          | 470.30   | VIII            |
| 61  | 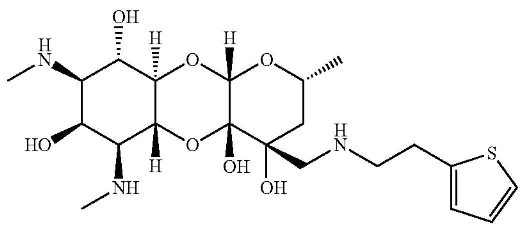 [SMILES: CN[C@@H]1[C@H](O)[C@H](NC)[C@H]2O[C@]3(O)[C@H](O[C@@H]2[C@H]1O)O[C@H](C)C[C@@]3(O)CNCCc1cccs1]          | 474.40   | VIII            |
| 62  | 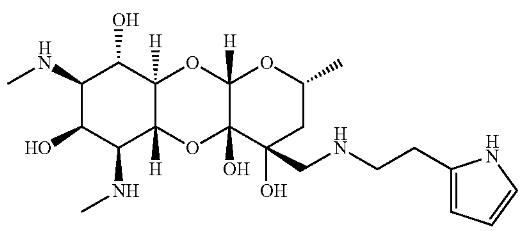 [SMILES: CN[C@@H]1[C@H](O)[C@H](NC)[C@H]2O[C@]3(O)[C@H](O[C@@H]2[C@H]1O)O[C@H](C)C[C@@]3(O)CNCCc1ccc[nH]1]          | 457.30   | VIII            |
| 63  | 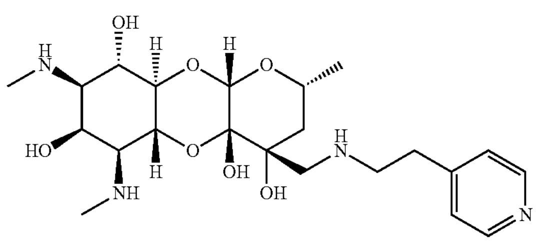 [SMILES: CN[C@@H]1[C@H](O)[C@H](NC)[C@H]2O[C@]3(O)[C@H](O[C@@H]2[C@H]1O)O[C@H](C)C[C@@]3(O)CNCCc1ccncc1]          | 469.30   | VIII            |
| 64  | 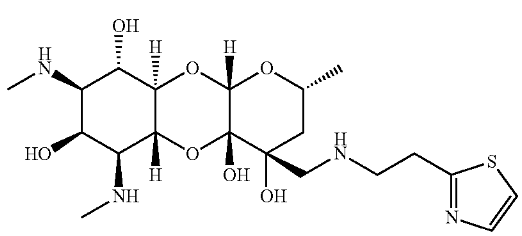          | 475.40   | VIII            |
| 66  | 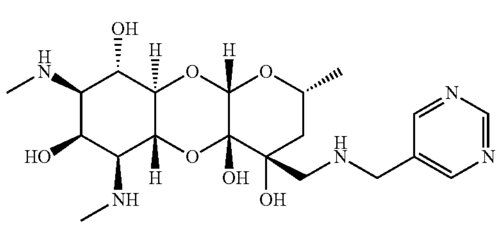          | 456.54   | II              |

TABLE 1-continued

| No. | Structure | [M + H]+ | Synthesis Route |
|---|---|---|---|
| 67 | 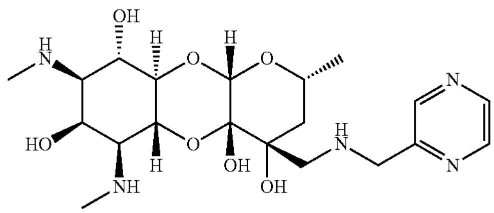 [SMILES: CN[C@@H]1[C@H](O)[C@H](NC)[C@H]2O[C@]3(O)[C@H](O[C@@H]2[C@H]1O)O[C@H](C)C[C@@]3(O)CNCc1cnccn1] | 456.44 | II |
| 68 | 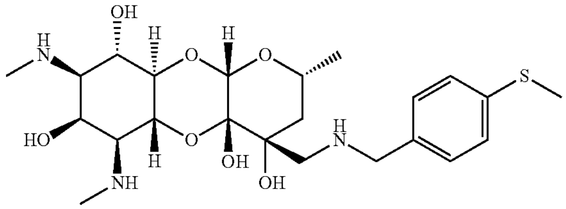 | 500.24 | II |
| 69 | 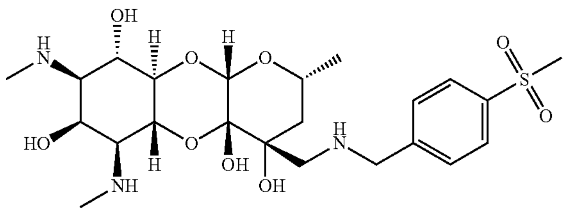 | 532.44 | II |

9. Ribosomal Inhibition Assays

Luciferase-based protein synthesis inhibition assays were performed as described previously (Salian, et al. *Antimicrob Agents Chemother.* 2011 56(12), 6104-6108) using purified *Mycobacterium smegmatis* 70S bacterial ribosomes, the Dual-Luciferase Reporter Assay System (Promega Corporation, Madison, Wis.), T7 RNA polymerase (Thermo Fisher Scientific Biosciences Inc., formerly Fermentas, Pittsburgh, Pa.), plasmids pGL4.12 and pGL4.75 (Promega Corporation), RiboLock (Thermo Fisher Scientific Biosciences Inc.), and S30 Premix without amino acids (Promega Corporation).

10. Minimum Inhibitory Concentration (MIC) Determination

MICs were determined using the microbroth dilution method according to Clinical Laboratory Standards Institute (CLSI; National, C. F. C. L. S., *Methods for Dilution Antimicrobial Susceptibility Tests for Bacteria Grow aerobically-Seventh Edition: Approved Standard M7-A7*, CLSI, Wayne, Pa., USA, 2008) and were read by visual inspection. Two fold serial dilutions of antibiotic in 100 µL of the appropriate broth media were first prepared in 96-well round bottom microtiter plates (Nalge Nunc International, Rochester, N.Y., USA). An equivalent volume (100 µL) of bacterial broth inocula containing approximately $10^5$ bacterial cfu/mL was added to each well to give final concentrations of drug starting at 200 µg/mL and the plates were incubated aerobically at 37° C. *M. tuberculosis* microtiter plates were incubated for 7 days and all other strains were incubated overnight. After incubations, in all cases the MIC was recorded as the lowest concentration of drug that prevented bacterial growth.

11. Disc Diffusion Assays

Fastidious bacteria were grown on appropriate solid media and incubated at 37° C., 5% $CO_2$ in sealed, $CO_2$ permeable bags (Garner US Enterprises). *Neisseria gonorrhoeae* (ATCC 49226), *Neisseria meningitides* (ATCC 13077), and *Haemophilus influenza* (ATCC 49247) were grown on GC agar supplemented with hemoglobin and IsovitalX while *Legionella pneumophila* (ATCC 33153) was grown on buffered CYE agar. For susceptibility testing, a direct colony suspension was prepared in Brain Heart Infusion broth (BHI), optical density adjusted to a 0.5 McFarland Standard equivalent, and used to evenly coat 100 mm agar plates. Whatman discs (5 mm diameter) were placed firmly against bacteria coated agar and to the center of each disc 4 µg of appropriate test compound or control dissolved in 100% DSMO at a concentration of 10 mg/mL delivered. Plates were placed in sealed, gas permeable bags and incubated either overnight (*N. gonorrhoeae, N. meningitides,* and *H. influenza*) or 3 days (*L. pneumophilia*). Zones of inhibition were measured using calipers with 1 mm markings. Results presented are the range of at least two biologically independent experiments.

12. Agar MIC Determination

*Neisseria gonorrhoeae* (ATCC 49226) was cultured and incubated as described for disc diffusion assays. Two-fold serial dilutions of test and control compounds were prepared across a 96-well plates and 2 µl of diluted compounds were transferred to the corresponding wells of a 96-well polystyrene plate containing 100 µl of solid growth medium. A direct colony suspension prepared in BHI was adjusted to an OD625 of 0.01 and 10 µl transferred to each well. After overnight incubation, 100 µl of a 30% Alamar Blue (in 50 mM Tris-HCl, pH 7.5) was added. Plates were incubated an additional 2 hours, to permit reduction of resazurin and corresponding change in color from blue to red/pink by viable bacteria. The MIC was recorded as the lowest concentration preventing growth, as inferred by resazurin reduction.

13. Cytotoxicity

Vero cells (kidney epithelial cells; ATCC CCL-81) were cultured in Dulbecco's Modified Eagle's Medium (DMEM) supplemented with 10% fetal bovine serum (FBS) and maintained in a humidified incubator (37° C., 5% $CO_2$). Monolayers were trypsinized, seeded at ~10% confluency in white-wall, clear-bottom 96-well microtiter plates, and allowed to adhere overnight. The next day, media was removed and replaced with fresh DMEM/FBS containing two-fold serial dilutions of test compounds. Following additional 72 hours of incubation, cell viability was evaluated using MTT (CellTiter96®, Promega) according to the manufacturer's instructions, with overnight solubilization. Absorbance at 570 nm was recorded and $IC_{50}$ values calculated from corresponding dose response curves. Results reported are the average of at least 2 independent experiments.

14. Resistance Frequency Determination

Resistance frequencies were determined by plating bacteria on 100 mm agar pads containing 4-32-fold MIC concentrations of selecting agent. The titer of bacteria in inoculum was determined by enumeration of colony forming units and resistance frequencies determined by dividing the number of resistant colonies per plate by the number of bacteria in the inoculum.

15. In Vitro Microsomal Metabolic Stability

Human and/or mouse liver microsomal degradation is determined using multiple time points to monitor the rate of disappearance of the parent compound during incubation. NADPH regenerating agent solutions A and B and mouse liver microsomes (CD-1) were obtained from BD Gentest (Woburn, Mass.). Pooled human liver microsomes were purchased from XenoTech (Lenexa, Kans.). Ninety-six deep well plates were obtained from Midsci (St. Louis, Mo.). Ninety-six analytical plates were obtained from Corning Incorporated (Acton, Mass.). Sample preparation for microsomal stability was modified from Di's publications (Di et al. *Int. J. Pharm.* 317(1), 54-60 (2006); Di et. al. *Comb. Chem. High Throughput Screen* 11(6) 469-476 (2008). A set of incubation times of 0, 15, 30, 60, 120, and 240 min were used. DMSO stock solutions of test compounds were prepared at 10 mM concentration. Human or mouse liver microsomal solution was prepared by adding 0.058 mL of concentrated human or mouse liver microsomes (20 mg/mL protein concentration) to 1.756 mL of 0.1 M potassium phosphate buffer (pH 7.4) and 5 µL of 0.5 M EDTA to make a 0.6381 mg/mL (protein) microsomal solution. NADPH regenerating agent contained 0.113 mL of NADPH A, 0.023 mL of NADPH B, and 0.315 mL of 0.1 M potassium phosphate buffer (pH 7.4). 2.2 µL of each test compound diluted solution was each added directly to 1.79 mL of liver microsomal solution. This solution was mixed and 90 µL was transferred to 6 time points plates (each in triplicate wells). For the Time 0 plate, 225 µL of cold acetonitrile with internal standard (4 µg/ml warfarin) was added to each well, followed by addition of NADPH regenerating agent (22.5 µL) and no incubation. For other five time points' plate, NADPH regenerating agent (22.5 µL) was added to each well to initiate the reaction, the plate was incubated at 37° C. for required time, followed by quenching of the reaction by adding 225 µL of cold acetonitrile with internal standard (4 D g/ml warfarin) to each well. All of the plates were sealed and mixed well at 600 rpm for 10 min and were centrifuged at 4000 rpm for 20 min. The supernatants (120 µL) were transferred to analytical plates for analysis by LC-MS. The metabolic stability is evaluated via the half-life from least-squares fit of the multiple time points based on first-order kinetics.

16. Plasma Protein Binding

Plasma protein binding was determined by equilibrium dialysis. The red device inserts are supplied ready to use (Thermo Scientific, Rockford, USA) containing plasma and buffer chambers for dialysis. The inserts were placed in base plate. Two different concentrations (0.5 and 5 µg/mL) of test compounds (Lee 1946, 1950, 1980 and 2106) were prepared in rat plasma and an aliquot of 300 µL was added in the plasma chamber in triplicate. A 500 µL aliquot of phosphate buffer solution (PBS) was added in the buffer chamber for dialysis. Base plate was covered with sealing tape and incubated at 37° C. at 100 rpm on an orbital shaker for 4 hr to achieve equilibrium. After incubation 50 µL of each post-dialysis sample was pipetted from the plasma and buffer chambers into separate micro-centrifuge tubes. 50 µL of plasma was added to the buffer samples and an equal volume of PBS to the collected plasma samples and vortex. Pipette out 50 µL and analyzed for bound and unbound drug concentrations using LC-MS/MS assay.

17. Mouse Challenge

All experimental animal protocols were approved by the St. Jude Children's Research Hospital Institutional Animal Care and Use Committee. Seven week old, female BalbC/J mice (Jackson Labs, Bar Harbor, Me.) we utilized in these studies. All mice were maintained in BSL2 facilities and all experiments were done under inhaled isoflurane (2.5%). Bacteria (strain D39x) were introduced by intranasal administration of $2 \times 10^7$ CFU in 25 µL PBS. Mice received no treatment, plasmalyte A (vehicle control), ampicillin (100 mg/kg), spectinomycin (50, 25, 5 mg/kg) or the respective compounds (50, 25, 5 mg/kg) at dosages indicated. Antibiotics were administered in a volume of 100 µL by subcutaneous infection starting at 18 hours post challenge, a time point when the mice have developed pneumonia and bacteria have translocated into the bloodstream. Mice were subsequently dosed every 12 hours until 96 hours post challenge. Mice were monitored daily for signs of infection and weight loss. Differences in time to death were compared via Kaplan-Meier survival estimates. Bacterial density in blood was quantified at 24, 48, 72, and 96 hours post infection via blood collection, serial dilution, and plating. Groups were then compared by Mann-Whitney to determine statistical significance. At 8 days following challenge, surviving mice were euthanized and bacterial loads in lungs determined by homogenization followed by serial dilution and plating. In all instances, surviving mice had completely cleared bacteria from both the lungs and the bloodstream by this time point.

18. Activity of Aryl Substituted Aminomethyl Spectinomycin Analogs in a Ribosomal Inhibition Assay Aryl substituted aminomethyl spectinomycin analogs were synthesized as described above. Ribosomal inhibition ($IC_{50}$) was determined in the ribosomal inhibition assay as described above and the data are shown in Table 2. The compound number corresponds to the compound numbers used in Table 1.

TABLE 2

| No.* | $IC_{50}$ (µg/mL)** |
|---|---|
| SPC | 0.39 |
| 1 | 0.87 |
| 2 | 0.74 |
| 3 | 0.24 |
| 4 | 0.72 |
| 5 | 0.87 |

TABLE 2-continued

| No.* | IC$_{50}$ (µg/mL)** |
|---|---|
| 6 | 0.23 |
| 7 | 0.41 |
| 8 | 0.40 |
| 9 | 0.72 |
| 10 | 9.58 |
| 11 | 1.15 |
| 12 | 2.09 |
| 13 | 0.25 |
| 14 | 0.71 |
| 15 | 1.04 |
| 16 | 0.44 |
| 17 | 0.39 |
| 18 | 0.34 |
| 19 | 0.54 |
| 20 | 0.25 |
| 21 | 0.40 |
| 22 | 0.43 |
| 23 | n.d. |
| 24 | n.d. |
| 25 | n.d. |
| 26 | 20.14 |
| 27 | n.d. |
| 28 | 16.59 |
| 29 | n.d. |
| 30 | n.d. |
| 31 | n.d. |
| 32 | n.d. |
| 33 | n.d. |
| 34 | n.d. |
| 51 | 0.38 |
| 52 | 0.34 |
| 53 | 0.80 |
| 54 | 2.98 |
| 55 | 2.16 |
| 56 | 21.35 |

*Compound number corresponds to the compound number and associated structure given in Table 1; and "SPC" indicates spectinomycin.
**IC$_{50}$ determined using the luciferase-based protein synthesis inhibition assay using purified *Mycobacterium smegmatis* ribosomes; "n.d." indicates the IC$_{50}$ was not determined for the indicated compound.

3'-Methylene aryl substituted aminomethyl spectinomycin analogs were evaluated for potency as ribosomal inhibitors using purified mycobacterial ribosomes, as described previously (Salian, et al. *Antimicrob Agents Chemother.* 2011 56(12), 6104-6108). The data suggest that the introduction of amino methyl linkage to the 3' position of spectinomycin C-ring was well tolerated. The resulting compound, 1, maintained a low ribosomal IC$_{50}$ of 0.87 µg/mL. Without wishing to be bound by a particular theory, the meta position appeared to be less preferred for substitution than para position. Adding a trifluoromethoxy (10) decreased binding by 10-fold. Without wishing to be bound by a particular theory, linker length appeared to be an important parameter for inhibitory activity, as extending the linker to an ethyl (6) or propyl (13) increased potencies to 0.23 and 0.25 µg/mL, respectively. Without wishing to be bound by a particular theory, introduction of a nitrogen to the ortho (16) and meta (7) position of non-substituted aryl analog 1 was favorable, decreasing IC$_{50}$'s to 0.4 µg/mL in each case. Fluorination of the ortho (14), meta (15), or para (2) positions of the aryl ring resulted in a slight loss of potency.

19. Antibacterial Activity of Aryl Substituted Aminomethyl Spectinomycin Analogs The MIC determination of aryl substituted aminomethyl spectinomycin analogs against gram-positive and gram-negative bacteria was performed as described above and the data are shown in Tables 3 and 4. The compound number corresponds to the compound numbers used in Table 1.

* Organisms abbreviated above are as follows: B.a., *Bacillus anthracis*, Sterne 34F$_2$; B.s., *Bacillus subtilis* (ATCC 23857); E.f., *Enterococcus faecalis* (ATCC 33186); S.a., *Staphylococcus aureus* (ATCC 29213); MRSA, *Staphylococcus aureus* (NRS70); S.pn, *Streptococcus pneumoniae* (R6); and S.py, *Streptococcus pyogenes* (ATCC 700294).

** Compound number corresponds to the compound number and associated structure given in Table 1; and "SPC" indicates spectinomycin.

TABLE 3*

| | MIC (µg/mL) | | | | | | |
|---|---|---|---|---|---|---|---|
| No.** | B.a. | B.s. | E.f. | S.a. | MRSA | S. pn. | S. py. |
| SPC | 25 | 25 | 50-100 | 100->200 | >200 | 12.5 | 25 |
| 1 | 50 | 3.1 | 25.0 | 50 | 50-100 | 6.3-12.5 | 3.1-6.3 |
| 2 | 25 | 3.1 | 12.5-25 | 25-50 | 50 | 1.6-3.1 | 1.6-3.1 |
| 3 | 12.5-25 | 3.1-6.3 | 12.5-25 | 50 | 12.5-25 | 1.6-3.1 | 1.6-3.1 |
| 4 | 100 | 12.5-25 | 12.5-25 | 25-50 | 50 | 1.6-3.1 | 1.6-3.1 |
| 5 | 25-50 | 6.3 | 12.5-25 | 50 | 25 | 1.6 | 1.6 |
| 6 | 6.3-12.5 | 1.6 | 12.5 | 6.3-12.5 | 12.5-25 | 3.1 | 3.1 |
| 7 | 100 | 100 | 200 | ≥200 | >200 | 12.5-25 | 25 |
| 8 | 50 | 12.5 | 50 | 50 | 200 | 12.5 | 12.5-25 |
| 9 | 100-200 | 200 | >200 | ≥200 | ≥200 | 25-50 | 25-50 |
| 10 | 200 | 50 | 200 | 200 | 200 | 25 | 25-50 |
| 11 | 100-200 | 100 | 25-50 | 100 | 100-200 | 3.1 | 1.6 |
| 12 | 50 | 25-50 | 50 | 100-200 | 200 | 6.3 | 3.1 |
| 13 | 3.1-6.3 | 6.3 | 6.3 | 12.5 | 12.5-25 | 3.1 | 3.1 |
| 14 | 50-100 | 6.3 | 50 | 200 | ≥200 | 3.1-6.3 | 3.1 |
| 15 | 12.5-25 | 3.1-6.3 | 12.5-25 | 100 | 50 | 3.1 | 3.1 |
| 16 | 50 | 50 | 100 | 100-200 | >200 | 12.5 | 12.5-25 |
| 17 | 50 | 25 | 50 | 50 | 100-200 | 12.5 | 6.3-12.5 |
| 18 | 25 | 3.1 | 6.3-12.5 | 25-50 | 12.5-25 | 1.6-3.1 | 0.8-1.6 |
| 19 | 100 | 100 | 50 | 100 | >200 | 12.5 | 12.5 |
| 20 | 50-100 | 25 | 100 | 200 | ≥200 | 25-50 | 50 |
| 21 | 50 | 25-50 | 12.5 | 25-50 | 200 | 3.1 | 1.6 |
| 22 | 50 | 50 | 25 | 50-100 | ≥200 | 6.3-12.5 | 6.3 |
| 23 | 12.5 | 6.3 | 12.5 | 12.5-25 | 12.5 | 1.6-3.1 | 1.6 |
| 24 | 50 | 12.5 | 12.5 | 6.3-12.5 | 50 | 3.1 | 1.6 |
| 25 | 25 | 12.5-25 | 12.5-25 | 25-50 | 50 | 1.6-3.1 | 1.6 |
| 26 | ≥200 | 100-200 | >200 | ≥200 | >200 | >200 | >200 |
| 27 | >200 | >200 | >200 | >200 | >200 | >200 | 50-100 |

TABLE 3*-continued

| No.** | B.a. | B.s. | E.f. | S.a. | MRSA | S. pn. | S. py. |
|---|---|---|---|---|---|---|---|
| | | | | MIC (μg/mL) | | | |
| 28 | >200 | ND | >200 | >200 | >200 | ≥200 | 100-200 |
| 29 | 100-200 | 200 | ND | 200 | >200 | >200 | 25 |
| 30 | 100-200 | ≥200 | ND | >200 | >200 | 12.5-25 | 12.5-25 |
| 31 | 200 | 200 | ND | >200 | >200 | 12.5-25 | 12.5-25 |
| 32 | 12.5 | 3.1-6.3 | 12.5 | 12.5 | 12.5-25 | 6.3 | 3.1-6.3 |
| 33 | 12.5 | 3.1-6.3 | 25 | 12.5-25 | 25-50 | ND | ND |
| 34 | 50 | 50-100 | 25 | 50-100 | 100-200 | 6.3 | 3.1 |
| 35 | 25 | 6.3 | 12.5 | 25-50 | 25-50 | 0.8-1.6 | 0.4-0.8 |
| 36 | >200 | 12.5 | 100 | 100 | >200 | 25 | 25 |
| 37 | >200 | 12.5 | 50 | 50 | 200 | 25 | 12.5 |
| 38 | >200 | 6.25 | 50 | 50 | 100 | 12.5 | 25 |
| 39 | >200 | 25 | 50 | 100 | 100 | 12.5 | 12.5 |
| 40 | >200 | 50 | 25 | 100 | 100 | 12.5 | 6.25 |
| 41 | >200 | 50 | 200 | 200 | 200 | 50 | 50 |
| 42 | >200 | 50 | 200 | 200 | >200 | 50 | 50 |
| 43 | >200 | 12.5 | 100 | 50 | 12.5 | 200 | 100 |
| 44 | >200 | 25 | 25 | 50 | 25 | 6.25 | 3.13 |
| 45 | >200 | 50 | 50 | 100 | 200 | 25 | 25 |
| 46 | >200 | 50 | 100 | 50 | >200 | 12.5 | 12.5 |
| 47 | >200 | 12.5 | 25 | 25 | 100 | 25 | 25 |
| 48 | >200 | 12.5 | >200 | 200 | 200 | 100 | 200 |
| 49 | >200 | 12.5 | 6.25 | 50 | 12.5 | 12.5 | 12.5 |
| 50 | >200 | 12.5 | 25 | 50 | 50 | 3.13 | 1.56 |
| 51 | 100-200 | 50-100 | ND | 100-200 | >200 | 100 | 100 |
| 52 | 50-100 | 25 | ND | 200 | >200 | 25-50 | 100 |
| 53 | 25-50 | 12.5 | ND | 25 | 100 | 12.5 | 12.5-25 |
| 54 | 200 | 25-50 | ND | 100-200 | >200 | 25 | 25 |
| 55 | 100 | 50 | ND | 100 | >200 | 12.5 | 12.5-25 |
| 56 | >200 | >200 | ND | >200 | >200 | 100 | 50 |
| 57 | 25 | 12.5 | ND | 25 | 50-100 | 3.1 | 3.1-6.3 |
| 58 | 12.5-25 | 6.3 | ND | 12.5 | 50-100 | 1.6-3.1 | 1.6-3.1 |
| 59 | 50 | 12.5-25 | ND | 100 | >200 | ND | ND |
| 60 | 100 | 50-100 | ND | 200 | >200 | 25 | 50 |
| 61 | 12.5-50 | 6.3 | ND | 12.5 | 25-50 | 6.3 | 12.5 |
| 62 | 25 | 6.3 | ND | 25 | 12.5-25 | 100 | 200 |
| 63 | >200 | ND | ND | >200 | >200 | ND | ND |
| 64 | 50 | 12.5-25 | ND | 50-100 | >200 | 12.5 | 25 |
| 65 | 12.5 | 12.5 | ND | 25 | 12.5-25 | 12.5 | 12.5 |
| 66 | 100 | 200 | ND | >200 | >200 | 0.8 | 100 |
| 67 | 200 | 100 | ND | >200 | >200 | 6.3 | 100 |
| 68 | 25 | 25 | ND | 25 | 50.0 | 1.6 | 3.1 |
| 69 | >200 | >200 | ND | >200 | >200 | 100 | 100 |

*Organisms abbreviated above are as follows: B.a., *Bacillus anthracis*, Sterne 34F2; B.s., *Bacillus subtilis* (ATCC 23857); E.f., *Enterococcus faecalis* (ATCC 33186); S.a., *Staphylococcus aureus* (ATCC 29213); MRSA, *Staphylococcus aureus* (NRS70); S. pn., *Streptococcus pneumoniae* (R6); and S. py., *Streptococcus pyogenes* (ATCC 700294).
**Compound number corresponds to the compound number and associated structure given in Table 1; and "SPC" indicates spectinomycin.

TABLE 4*

| No.** | A.b. | B.c. | E.c. | E.c. Δtolc | K.p. |
|---|---|---|---|---|---|
| | | | MIC (μg/mL) | | |
| SPC | >200 | 50-100 | 25-50 | 3.1-12.5 | >200 |
| 1 | >200 | ≥200 | 100 | 25 | >200 |
| 2 | >200 | >200 | 25 | 6.3 | 100-200 |
| 3 | 200 | >200 | 12.5-25 | 6.3 | 100-200 |
| 4 | ≥200 | >200 | 25-50 | 6.3 | 100-200 |
| 5 | ≥200 | 100 | 50 | 6.3-12.5 | 100 |
| 6 | >200 | >200 | 6.3-12.5 | 3.1-6.3 | 25-50 |
| 7 | ≥200 | ≥200 | 50 | 12.5-25 | >200 |
| 8 | ≥200 | ≥200 | 50 | 6.3-12.5 | 200 |
| 9 | ≥200 | >200 | 50 | 12.5 | >200 |
| 10 | 100-200 | >200 | 200 | 25-50 | 100-200 |
| 11 | >200 | >200 | 25 | 12.50 | >200 |
| 12 | ≥200 | ≥200 | 25-50 | 12.5-25 | >200 |
| 13 | >200 | >200 | 12.5 | 6.3 | 50 |
| 14 | >200 | 100-200 | 50 | 25 | ≥200 |
| 15 | >200 | ≥200 | 25-50 | 6.3-12.5 | >200 |
| 16 | >200 | >200 | 100-200 | 50 | 200 |
| 17 | >200 | >200 | 50 | 6.3-12.5 | 200 |
| 18 | >200 | 100-200 | 12.5-25 | 3.1-6.3 | 200 |
| 19 | >200 | >200 | 200 | 12.5-25 | >200 |
| 20 | >200 | 100-200 | 50 | 25 | 50-100 |
| 21 | >200 | 200 | 50 | 12.5 | >200 |
| 22 | >200 | >200 | 100-200 | 25 | >200 |
| 23 | 50 | >200 | 12.5 | 3.1-6.3 | 50 |
| 24 | 200 | >200 | 25 | 12.5-25 | 100-200 |
| 26 | 50-100 | >200 | 50 | 6.3 | 100 |
| 27 | ≥200 | 200 | 50-100 | 25-50 | >200 |
| 28 | >200 | >200 | >200 | ≥200 | >200 |
| 29 | ≥200 | ND | ≥200 | 50 | >200 |
| 30 | >200 | >200 | 200 | 50 | >200 |
| 31 | >200 | >200 | 100-200 | 50-100 | >200 |
| 32 | >200 | >200 | 100-200 | 50-100 | >200 |
| 33 | >200 | ≥200 | 12.5 | 6.3 | 200 |
| 34 | >200 | >200 | ND | ND | 100-200 |
| 35 | >200 | >200 | 200 | 6.3-12.5 | >200 |
| 51 | >200 | >200 | 50 | 25-50 | 100-200 |
| 52 | >200 | >200 | 50-100 | 25-50 | 100 |
| 53 | >200 | >200 | 50 | 12.5 | 100-200 |
| 54 | >200 | >200 | 50-100 | 12.5-25 | >200 |
| 55 | >200 | >200 | 100-200 | 12.5-25 | >200 |
| 56 | >200 | >200 | >200 | >200 | >200 |
| 57 | ≥200 | ≥200 | 25 | 1.3-3.1 | >200 |
| 58 | >200 | >200 | 6.3-12.5 | 1.6 | >200 |
| 59 | >200 | >200 | ND | ND | 100 |
| 60 | >200 | >200 | 100 | 50 | 100-200 |
| 61 | >200 | ≥200 | 25 | 3.1-6.3 | 50 |

TABLE 4*-continued

| 62 | >200 | >200 | 50 | 12.5 | 100-200 |
| 63 | >200 | >200 | ND | ND | >200 |
| 64 | >200 | >200 | 50-100 | 25-50 | 100-200 |
| 65 | >200 | ≥200 | 50 | 6.3-12.5 | >200 |
| 66 | >200 | >200 | 50 | 25-50 | 100-200 |
| 67 | >200 | >200 | 50-100 | 25-50 | 100 |
| 68 | >200 | >200 | 50 | 12.5 | 100-200 |
| 69 | >200 | >200 | 50-100 | 12.5-25 | >200 |

|  | MIC (μg/mL) | | | |
| --- | --- | --- | --- | --- |
| No. | P.a. | P.m. | P.v. | S.m. |
| SPC | 50-100 | >200 | 50 | 50-200 |
| 1 | >200 | >200 | 200 | 25 |
| 2 | 100-200 | >200 | ≥200 | 25 |
| 3 | 100-200 | 100-200 | 25-50 | 12.5 |
| 4 | 100-200 | >200 | >200 | 25-50 |
| 5 | 200 | >200 | >200 | 25 |
| 6 | ≥200 | >200 | 50-100 | 1.6 |
| 7 | >200 | >200 | >200 | 100 |
| 8 | 200 | >200 | >200 | 6.3-12.5 |
| 9 | ≥200 | >200 | >200 | 200 |
| 10 | 200 | >200 | >200 | 50 |
| 11 | 100-200 | >200 | >200 | 50-100 |
| 12 | ≥200 | >200 | >200 | 12.5-25 |
| 13 | 200 | >200 | ≥200 | 6.3-12.5 |
| 14 | ≥200 | >200 | 100 | 12.5-25 |
| 15 | ≥200 | >200 | 200 | 12.5 |
| 16 | >200 | >200 | >200 | 12.5-25 |
| 17 | ≥200 | >200 | 200 | 6.3 |
| 18 | 200 | 200 | 100-200 | 25 |
| 19 | >200 | >200 | >200 | 25-50 |
| 20 | 200 | 200 | 100-200 | 3.1-6.3 |
| 21 | >200 | >200 | ≥200 | 12.5 |
| 22 | >200 | >200 | >200 | 12.5 |
| 23 | 25 | >200 | >200 | 6.3 |
| 24 | 50 | >200 | 200 | 25-50 |
| 25 | 50-100 | >200 | >200 | 12.5-25 |
| 26 | >200 | >200 | >200 | 50 |
| 27 | >200 | >200 | >200 | ≥200 |
| 28 | ND | ND | ND | ND |
| 29 | >200 | >200 | >200 | 200 |
| 30 | >200 | >200 | >200 | ≥200 |
| 31 | >200 | >200 | >200 | 200 |
| 32 | ≥200 | >200 | 100 | 6.3 |
| 33 | ND | ND | ND | ND |
| 34 | >200 | >200 | >200 | 100 |
| 35 | ≥200 | >200 | ≥200 | 25 |
| 51 | ≥200 | 50-100 | ≥200 | 50 |
| 52 | >200 | 200 | >200 | 12.5-25 |
| 53 | >200 | >200 | 200 | 12.5 |
| 54 | >200 | >200 | >200 | ≥200 |
| 55 | >200 | >200 | >200 | 50 |
| 56 | >200 | >200 | >200 | >200 |
| 57 | >200 | 200 | 200 | 50-100 |
| 58 | >200 | 200 | 200 | ND |
| 59 | ND | ND | ND | ND |
| 60 | >200 | >200 | >200 | 25 |
| 61 | >200 | 200 | 100-200 | 12.5 |
| 62 | >200 | 200 | 50-100 | 6.3 |
| 63 | ND | ND | ND | ND |
| 64 | >200 | >200 | >200 | 25-50 |
| 65 | >200 | >200 | >200 | 12.5 |
| 66 | >200 | >200 | >200 | 100 |
| 67 | >200 | >200 | >200 | 100 |
| 68 | 200 | >200 | >200 | 25 |
| 69 | >200 | >200 | >200 | >200 |

*Organisms abbreviated above are as follows A.b., *acinetobacter baumannii* (ATCC 19606); B.c., *Burkholderia cepacia* (ATCC 25416); E.c., *Escherichia coli* (ATCC 700926); E.c. ΔtolC, *E. coli* K12 ΔtolC; K.n., *Klebsiella pneumoniae* (ATCC 33495); P.a., *Pseudomonas aeruginosa* (PA01); P.m., *Proteus mirabilis* (ATCC 25933); P.v., *Proteus vulgaris* (ATCC 33420); and S.m., *Stenotrophomonas maltophilia* (ATCC 13637). ND indicates values not determined.
**Compound number corresponds to the compound number and associated structure given in Table 1; and "SPC" indicates spectinomycin.

Compared to spectinomycin, many aryl substituted aminomethyl spectinomycin analogs showed superior activity against a broad spectrum of pathogens, with notably increased potency against *Bacillus subtilis*, *Enterococcus faecalis*, *Streptococcus pneumoniae* and *pyogenes*, *Escherichia coli*, and *Stenotrophomonas maltophilia*. Compound 13 showed excellent broad spectrum activity against gram positive species, where its MIC was markedly improved, typically 10% of parent SPC. All ribosomal active ($IC_{50}$<1 μg/mL) aryl substituted aminomethyl spectinomycin analogs tested showed moderate to high active against *Stenotrophomonas maltophilia*, a difficult to treat gram-negative pathogen with a mortality rate of 20-40%, and for which multidrug resistant infections have been recently reported. Most aryl substituted aminomethyl spectinomycin analogs with improved activity against efflux competent *E. coli* K12 were also more potent than SPC against efflux deficient *E. coli* K12 ΔtolC.

The inhibitory action of this series was also tested against additional fastidious pathogens (Table 5) and strains of interest for biodefense (Table 6).

TABLE 5*

| | Zone of inhibition (mm) | | | | MIC (μg/mL) |
| --- | --- | --- | --- | --- | --- |
| No.** | H.i. | L.p. | N.m. | N.g. | N.g. |
| SPC | 11-13 | 0 | 13-14 | 11-13 | 50 |
| 1 | 16 | 36-40 | 16-22 | 16 | 100 |
| 2 | 17-19 | 32-49 | 19-20 | 16-19 | 25 |
| 3 | 15-17 | 28-40 | 18 | 16 | 12.5 |
| 4 | 15-18 | 18-33 | 16-18 | 15-17 | 12.5 |
| 5 | 17-18 | 27-28 | 21 | 18 | 100 |
| 6 | 14 | 36 | 16 | 16 | ND |
| 7 | 7 | 42 | 9 | 7 | 200 |
| 8 | 9 | 41 | 10 | 8 | 50 |
| 9 | 8 | 28 | 6 | 6 | ≥200 |
| 10 | 0 | ND | 0 | 8 | 200 |
| 11 | 16 | 21 | 18-19 | 16-20 | 12.5 |
| 12 | 16-17 | ND | 17 | 15-17 | 25-50 |
| 13 | 14 | ND | 21 | 15 | 12.5-25 |
| 14 | 11-12 | 36 | 19 | 18 | 12.5-25 |
| 15 | 14 | 41 | 20 | 18 | 25-50 |
| 16 | 7 | 34 | 13 | 6 | ≥200 |
| 17 | 13 | 41 | 15 | 11 | 50 |
| 18 | 15-16 | 21 | 16-18 | ND | 25 |
| 19 | 10 | 39 | 13 | 9 | 100 |
| 20 | ND | ND | ND | ND | 100-200 |
| 21 | 13 | 22 | 19 | 20 | 12.5-25 |
| 22 | 10 | ND | 14 | 11 | 100 |
| 23 | 15 | 12 | 17 | 18 | ND |
| 24 | 14 | 18 | 17 | 18 | ND |
| 25 | 9-10 | 19 | 18 | 18 | ND |
| 26 | ND | 8 | ND | ND | 50-100 |
| 27 | 0 | 0 | 0 | 7 | ND |
| 28 | 0 | 0 | 0 | ND | 200 |
| 29 | 7 | 0 | 7 | 12 | ND |
| 30 | 6 | 0 | 6 | 7 | ND |
| 31 | 6 | 0 | | 12 | ND |
| 32 | ND | ND | ND | ND | ND |
| 33 | ND | ND | ND | ND | ND |
| 34 | 7 | ND | 12 | 8 | 100 |
| 35 | 15-16 | 30 | 18 | 16 | ND |
| 51 | 6 | 22 | 6 | 0 | — |
| 52 | 10 | 32 | 12 | 7 | — |
| 53 | 11 | 30 | 10 | 12 | — |
| 54 | 9 | 15 | 7 | 11 | — |
| 55 | 9 | 15 | 8 | 11 | — |
| 56 | 0 | 0 | 0 | 0 | — |
| 57 | 12 | 22 | 15 | 14 | — |
| 58 | 19 | 26 | 16 | 19 | — |
| 61 | 14 | 30 | 14 | 13 | — |
| 62 | 0 | 12 | 0 | 0 | — |
| 64 | 11 | 33 | 11 | 8 | — |
| 65 | 10 | 22 | 13 | 12 | — |

*Organisms abbreviated above are as follows: H.i., *Haemophilus influenza*; L.p., *Legionella pneumophila*; N.m., *Neisseria meningitides*; N.g., *Neisseria gonorrhoeae*.
**Compound number corresponds to the compound number and associated structure given in Table 1; and "SPC" indicates spectinomycin.

TABLE 6*

| | MIC (μg/mL) | | | | | |
|---|---|---|---|---|---|---|
| No.** | B.c. | B.a. | Y.p. | F.t. | L.m | M.c. |
| SPC | 50-100 | 25.0 | 12.5 | 12.5-25 | 25-50 | 3.1-6.3 |
| 1 | ≥200 | 50.0 | 100-200 | 3.1 | 25 | 6.3 |
| 2 | >200 | 25 | 100 | 1.6-3.1 | 6.3 | 3.1 |
| 3 | >200 | 12.5-25 | >200 | 1.6-3.1 | 6.3 | 3.1-6.3 |
| 4 | >200 | 100.0 | >200 | 0.8-3.1 | 6.3-12.5 | 3.1-6.3 |
| 5 | 100 | 25-50 | ND | ND | 12.5 | 3.1-6.3 |
| 6 | >200 | 6.3-12.5 | 200 | 1.6 | 3.1 | 0.4 |
| 7 | ≥200 | 100 | ND | ND | 25 | 6.3 |
| 8 | ≥200 | 100 | ND | ND | 25 | 6.3 |
| 9 | >200 | 100-200 | ND | ND | 100 | 12.5 |
| 10 | >200 | 200.0 | 200.0 | 25.0 | 100 | 50-100 |
| 11 | >200 | 100-200 | 200.0 | 1.6-3.1 | 12.5-25 | 6.3 |
| 12 | ≥200 | 50 | 200 | 3.1-6.3 | 6.3-12.5 | 6.3-12.5 |
| 13 | >200 | 3.1-6.3 | 50 | ND | 1.6-3.1 | 0.4 |
| 14 | 100-200 | 50-100 | >200 | ND | 25 | 1.6 |
| 15 | ≥200 | 12.5-25 | 100 | ND | 6.3 | 1.6 |
| 16 | >200 | 50 | 100 | ND | 25 | 12.5 |
| 17 | >200 | 50 | ND | ND | 12.5 | 3.1 |
| 18 | 100-200 | 25 | ND | ND | 6.3 | 0.8 |
| 19 | >200 | 100 | ND | ND | 25 | 12.5 |
| 20 | 100-200 | 50-100 | ND | ND | ND | ND |
| 21 | 200 | 50 | ND | ND | 6.3 | 0.8 |
| 22 | >200 | 50 | ND | ND | 12.5 | 3.1 |
| 23 | >200 | 12.5 | ND | ND | 6.3 | 3.1-6.3 |
| 24 | >200 | 50 | ND | ND | 12.5 | 1.6 |
| 25 | >200 | 25 | ND | ND | 6.3 | 6.3 |
| 27 | >200 | >200 | ND | ND | ND | ND |
| 32 | ≥200 | 12.5 | ND | ND | ND | ND |
| 33 | >200 | 12.5 | ND | ND | ND | ND |
| 51 | >200 | 100-200 | ND | ND | 25 | 3.1 |
| 52 | >200 | 50-100 | ND | ND | 12.5 | 3.1 |
| 53 | >200 | 25-50 | ND | ND | 6.3 | 3.1 |
| 54 | >200 | 200 | ND | ND | 25 | 6.3 |
| 55 | >200 | 100 | ND | ND | 25 | 3.1 |
| 56 | >200 | >200 | ND | ND | >200 | 100 |
| 57 | ≥200 | 25 | ND | ND | 6.3 | 0.8 |
| 58 | >200 | 12.5-25 | ND | ND | 3.1 | 0.4 |
| 59 | >200 | 50 | ND | ND | 12.5 | 3.1 |
| 60 | >200 | 100 | ND | ND | 25 | 6.3 |
| 61 | ≥200 | 12.5-50 | ND | ND | 6.3 | 1.6 |
| 62 | >200 | 25 | ND | ND | 25 | 12.5 |
| 63 | >200 | >200 | ND | ND | 100 | 12.5 |
| 64 | >200 | 50 | ND | ND | 12.5 | 3.1 |
| 65 | ≥200 | 12.5 | ND | ND | 12.5 | 3.1 |

*Organisms abbreviated above are as follows: Y.p., *Yersinia pestis*; M.c., *Moraxella catarrhalis*; L.m., *Listeria monocytogenes*; F.t., *Francisella tularensis*; B.c., *Burkholderia cepacia*; B.s., *Bacillus anthracis*.

**Compound number corresponds to the compound number and associated structure given in Table 1; and "SPC" indicates spectinomycin.

Aryl substituted aminomethyl spectinomycin analogs tested showed improved potency against fastidious bacteria *Neisseria meningitides* and *Haemophilus* influenza but were less effective than the parent spectinomycin in inhibiting growth of *Bacillus anthracis* and *Yersinia pestis*. Unanticipated potency was seen for testing aryl substituted aminomethyl spectinomycin analogs activity against the live vaccine strain (LVS) of *Francisella tularensis*. Introduction of the methyl-linked phenyl ring (1) was well tolerated and further substitutions, most notably to the para position, yielded aryl substituted aminomethyl spectinomycin analogs with MICs of approximately 1 μg/mL, about 10-fold lower than the parent spectinomycin. Substitution of $OCF_3$ to the para position increased potency, as in 11 (MIC 1.6 μg/mL) but deceased potency to 25 μg/mL when present in the ortho position (10), likely reflecting the loss of ribosomal inhibitory action witnessed cell-free ribosomal inhibition assays (see Table 2). The loss of activity in both whole cell and isolated ribosome assays by 10 suggests that compound 11 remains on the ribosomal target to inhibit bacterial growth.

Amongst the pathogens tested for increased susceptibility to aryl substituted aminomethyl spectinomycin analogs, *S. pneumoniae* strain R6 was particularly sensitive to ribosomal active members of the series, several of which produced MICs of 1-3 μg/mL. Since R6 is a non-encapsulated laboratory strain that may be more susceptible to aryl substituted aminomethyl spectinomycin analogs, compounds were assessed for activity against a panel of clinical isolates representing several serotypes (Table 7).

TABLE 7

| | Streptococcus pneumoniae Panel** | | | | | | |
|---|---|---|---|---|---|---|---|
| | Drug Susceptible | | | | | Macrolide Resistant | |
| No.* | R6 | T4X | D39X | BHN97x | A66.1x | OVA6 | BAA-1407 |
| SPC | 12.5 | 12.5 | 12.5 | 6.3 | 6.3 | 12.5 | 12.5 |
| mSPC | 50.0 | 50.0 | 100.0 | 50.0 | 50.0 | 50.0 | 200.0 |
| 1 | 6.3 | 6.3 | 3.1 | 3.1 | 3.1 | 6.3 | 12.5 |
| 2 | 3.1 | 3.1 | 1.6 | 1.6 | 1.6 | 3.1 | 6.3 |
| 3 | 3.1 | 3.1 | 1.6 | 3.1 | 1.6 | 6.3 | 6.3 |
| 4 | 1.6 | 1.6 | 0.8 | 1.6 | 0.8 | 3.1 | 6.3 |
| 6 | 6.3 | 3.1 | 3.1 | 3.1 | 3.1 | 3.1 | 12.5 |
| 10 | 12.5 | 3.1 | NT | NT | NT | 6.3 | 25.0 |
| 11 | 3.1 | 0.8 | NT | NT | NT | 6.3 | 6.3 |

| | Streptococcus pneumoniae Panel* PenG Resistant | | | | |
|---|---|---|---|---|---|
| No. | Daw7 | Daw8 | Daw9 | Daw62 | Daw64 |
| SPC | 25.0 | 25.0 | 12.5 | 25.0 | 25.0 |
| mSPC | 100.0 | 100.0 | 50.0 | 100.0 | 100.0 |
| 1 | 6.3 | 6.3 | 6.3 | 6.3 | 6.3 |
| 2 | 3.1 | 3.1 | 3.1 | 3.1 | 3.1 |
| 3 | 6.3 | 3.1 | 3.1 | 6.3 | 6.3 |
| 4 | 3.1 | 1.6 | 3.1 | 3.1 | 3.1 |
| 6 | 6.3 | 6.3 | 6.3 | 6.3 | 6.3 |
| 10 | 12.5 | 12.5 | 12.5 | 12.5 | 25.0 |
| 11 | 3.1 | 1.6 | 1.6 | 1.6 | 3.1 |

*Compound number corresponds to the compound number and associated structure given in Table 1; "SPC" indicates spectinomycin; and "mSPC" is methylamino spectinomycin core structure.
**MIC values were determined as described above for de-identified clinical isolates collected at St. Jude's Children's Research Hospital; MIC values given in µg/ml.

Activity was sustained against this panel of clinical isolates, which included strains resistant for macrolides, penicillin G, and streptomycin, indicating the potential of aryl substituted aminomethyl spectinomycin analogs for the development of S. pneumonia therapeutics.

20. Resistance Frequency of Aryl Substituted Aminomethyl Spectinomycin Analogs

The resistance frequency was determined as described above for analog 2. Spontaneous mutants of 2 were selected on agar containing drug at 4, 8, 16 and 32× their MICs. Mutants exhibiting resistance to 2 emerged at a frequency of $5.7 \times 10^{-11}$ to $2.9 \times 10^{-10}$ lower than that of ciprofloxacin previously determined using the same method (Mani, et al. Antimicrob Agents Chemother. 2006 50(4), 1228-1237). Fifteen stable mutants exhibiting high-level resistance (50 to ≥200 µg/mL) to 2 and cross resistance to spectinomycin remained susceptible to penicillin and erythromycin. Similarly, strains with mono-resistance to penicillin, streptomycin, and erythromycin were highly susceptible to 2. A subset of 2 mutants were tested for cross resistance to additional frontline treatments and aminoglycosides, and remained susceptible to amikacin, ampicillin, gentamycin, kanamycin, levofloxacin, linezolid, meropenem, and vancomycin. These data demonstrate that 2 shares the unique mode of action of spectinomycin, is unlikely to be affected by mechanisms that confer resistance to established S. pneumoniae antibiotics, and should therefore have activity against all MDR strains.

Figure 3:
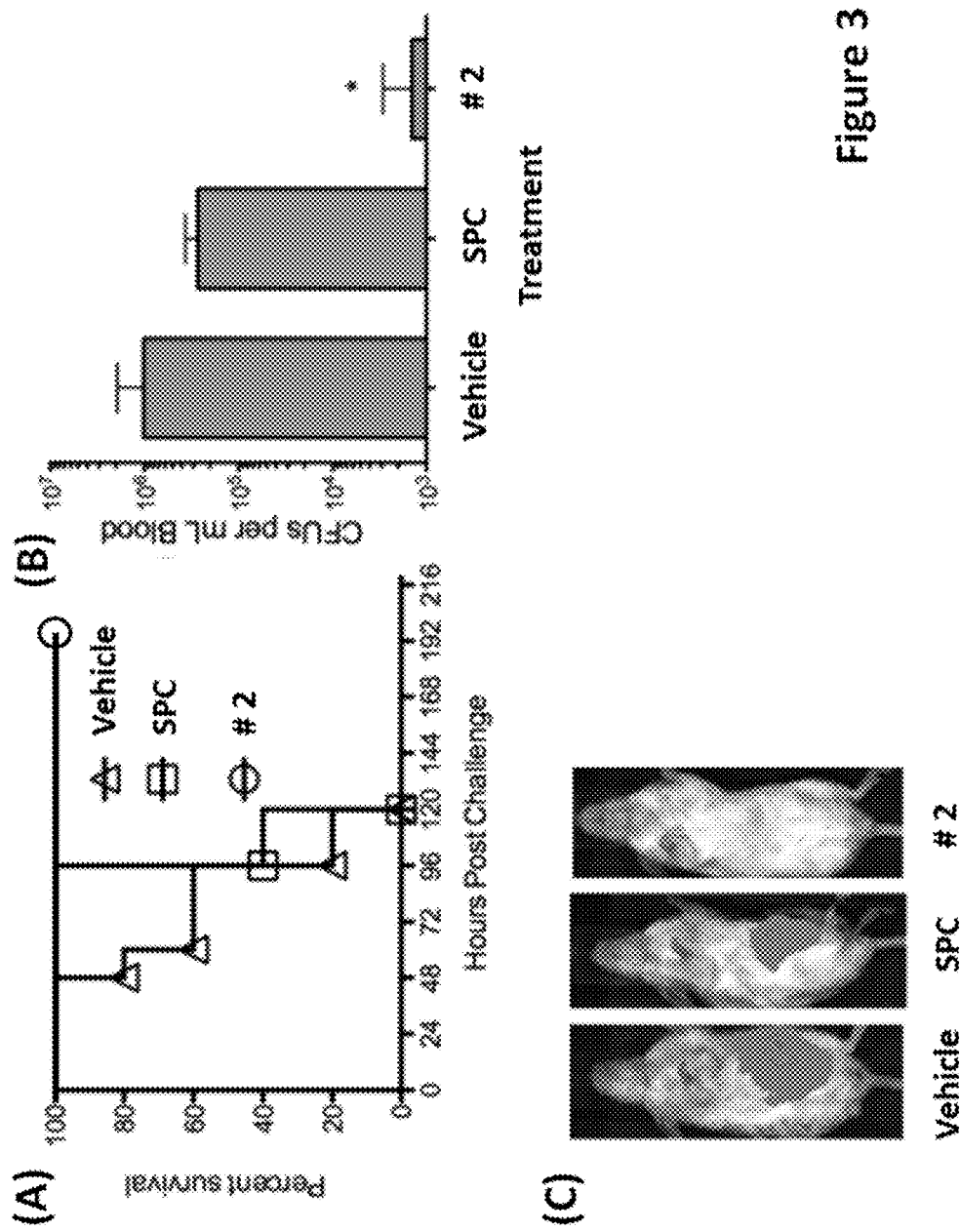
FIG. 3 shows data showing the anti-*S. pneumoniae* activity of a representative compound in a mouse model of lung infection. (Panel A) The graph shows the overall survival at various times following intranasal bacterial challenge (*S. pneumoniae* D39x). Mice were treated with a 5 mg/kg dose b.i.d. of spectinomycin (indicated as "SPC" in the figure) or compound 2 (the compound number refers to the compound number and associated structure shown in Table 1), or vehicle. (Panel B) The bacterial burden of mice at 18 hours post-challenge with *S. pneumoniae* D39x. (Panel C) Representative bioluminescent images of mice at 72 hours post challenge.

21. Anti-S. pneumoniae Activity of Aryl Substituted Aminomethyl Spectinomycin Analogs in the Mouse Model of Lung Infection Compound 2 was tested for anti-pneumococcal activity in mice as described above. All compounds and the control spectinomycin were formulated in Plasma-Lyte A (an FDA approved iv fluid) and administered subcutaneously at a dose of 50, 25 and 5 mg/kg BID to infected mice 18 hours post intranasal challenge, a time when mice have developed both pneumonia and bacteremia (Lebensberger et al., Blood 2012, 119 (8), 1915-1921). Mice receiving 2 at the lowest dose (5 mg/Kg) had significantly improved survival ($p<0.02$) compared to vehicle and spectinomycin controls (see FIG. 3A). The bacterial burden in the blood 48 hours post-challenge was reduced significantly ($p<0.02$) in groups receiving 2 compared to the spectinomycin and vehicle controls (see FIG. 3B). Clearance of the infection was also evident in the bioluminescent images of mice at 72 hours post challenge, which showed systemic bacterial infection in both the vehicle and spectinomycin groups whereas mice receiving the analogs cleared the infection below detectable limits (see FIG. 3C). At higher dosages all the analogs resulted in equivalent clearance of bacteria from the bloodstream at 48 hours compared to control groups of mice receiving high dose (100 mg/kg twice daily) ampicillin therapy. These results indicate that the reported analogs mediate significantly greater protection at lower dosage than spectinomycin, preventing the progression of fatal pneumococcal pneumonia and sepsis.

22. Antituberculosis Activity of Aryl Substituted Aminomethyl Spectinomycin Analogs The MIC determination of aryl substituted aminomethyl spectinomycin analogs against tuberculosis clinical isolates was performed as described above and the data are shown in Table 8. The compound number corresponds to the compound numbers used in Table 1.

TABLE 8

| No. | Structure | IC$_{50}$ (Sm) (μg/mL) | Clinical Isolates MIC (μg/mL) | | |
|---|---|---|---|---|---|
| | | | H37Rv | TN022 | TN026 |
| SPC | 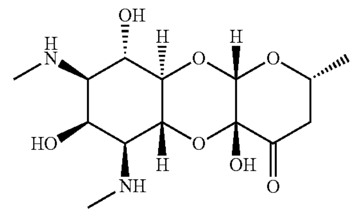 | 0.36 | 100 | 200 | 200 |
| 1 | 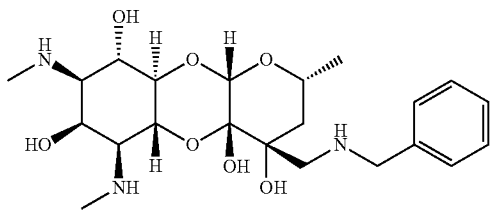 [SMILES: CN[C@@H]1[C@H](O)[C@H](NC)[C@H]2O[C@]3(O)[C@H](O[C@@H]2[C@H]1O)O[C@H](C)C[C@@]3(O)CNCc1ccccc1] | — | 25 | — | — |
| 2 | 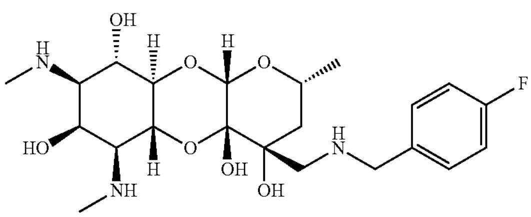 [SMILES: CN[C@@H]1[C@H](O)[C@H](NC)[C@H]2O[C@]3(O)[C@H](O[C@@H]2[C@H]1O)O[C@H](C)C[C@@]3(O)CNCc1ccc(F)cc1] | — | 25 | — | — |
| 3 | 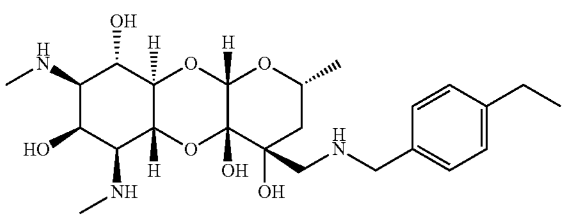 [SMILES: CCc1ccc(CNC[C@]2(O)C[C@@H](C)O[C@H]3O[C@@H]4[C@@H](O)[C@H](NC)[C@H](O)[C@H](NC)[C@H]4O[C@]32O)cc1] | — | 25 | — | — |
| 4 | 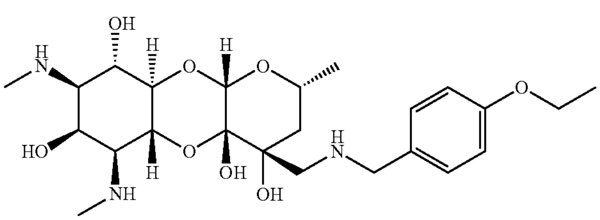 [SMILES: CCOc1ccc(CNC[C@]2(O)C[C@@H](C)O[C@H]3O[C@@H]4[C@@H](O)[C@H](NC)[C@H](O)[C@H](NC)[C@H]4O[C@]32O)cc1] | — | 25 | — | — |
| 5 | 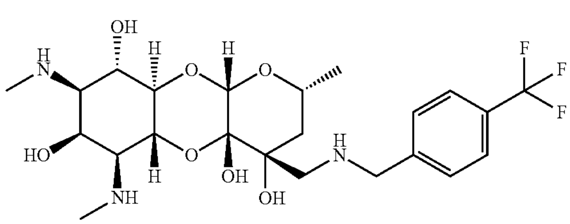 [SMILES: CN[C@@H]1[C@H](O)[C@H](NC)[C@H]2O[C@]3(O)[C@H](O[C@@H]2[C@H]1O)O[C@H](C)C[C@@]3(O)CNCc1ccc(C(F)(F)F)cc1] | — | 25 | — | — |
| 6 | 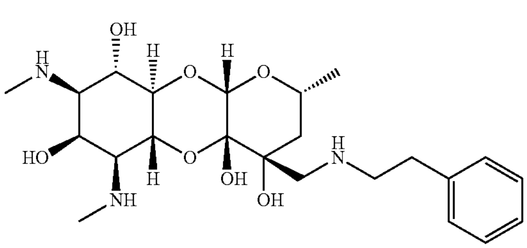 [SMILES: CN[C@@H]1[C@H](O)[C@H](NC)[C@H]2O[C@]3(O)[C@H](O[C@@H]2[C@H]1O)O[C@H](C)C[C@@]3(O)CNCCc1ccccc1] | 0.23 | 1.6 | 3.1 | 3.1 |

TABLE 8-continued

| No. | Structure | IC$_{50}$ (Sm) (μg/mL) | Clinical Isolates MIC (μg/mL) | | |
| --- | --- | --- | --- | --- | --- |
| | | | H37Rv | TN022 | TN026 |
| 7 | 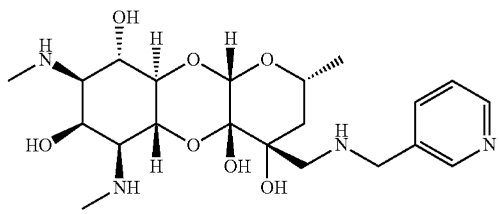 [SMILES: CN[C@@H]1[C@H](O)[C@H](NC)[C@H]2O[C@]3(O)[C@H](O[C@@H]2[C@H]1O)O[C@H](C)C[C@@]3(O)CNCc1cccnc1] | — | 50-100 | — | — |
| 8 | 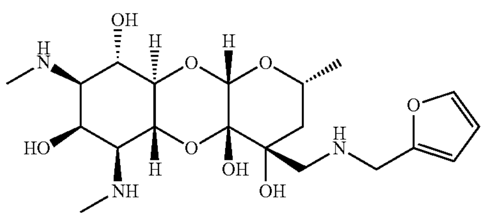 [SMILES: CN[C@@H]1[C@H](O)[C@H](NC)[C@H]2O[C@]3(O)[C@H](O[C@@H]2[C@H]1O)O[C@H](C)C[C@@]3(O)CNCc1ccco1] | — | 25 | — | — |
| 9 | 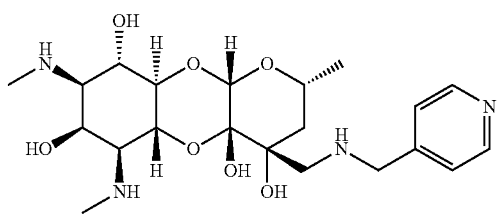 [SMILES: CN[C@@H]1[C@H](O)[C@H](NC)[C@H]2O[C@]3(O)[C@H](O[C@@H]2[C@H]1O)O[C@H](C)C[C@@]3(O)CNCc1ccncc1] | — | 200 | — | — |
| 10 | 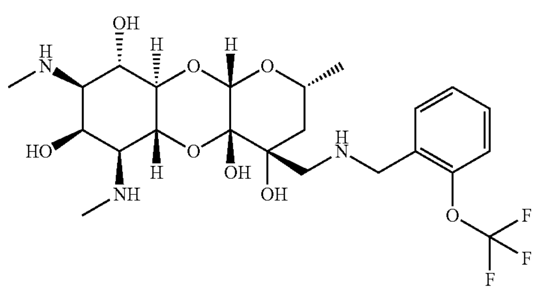 [SMILES: CN[C@@H]1[C@H](O)[C@H](NC)[C@H]2O[C@]3(O)[C@H](O[C@@H]2[C@H]1O)O[C@H](C)C[C@@]3(O)CNCc1ccccc1OC(F)(F)F] | — | 200 | — | — |
| 11 | 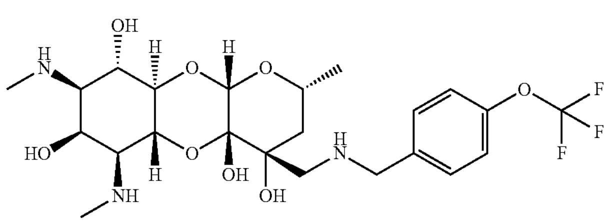 [SMILES: CN[C@@H]1[C@H](O)[C@H](NC)[C@H]2O[C@]3(O)[C@H](O[C@@H]2[C@H]1O)O[C@H](C)C[C@@]3(O)CNCc1ccc(OC(F)(F)F)cc1] | — | 50 | — | — |
| 12 | 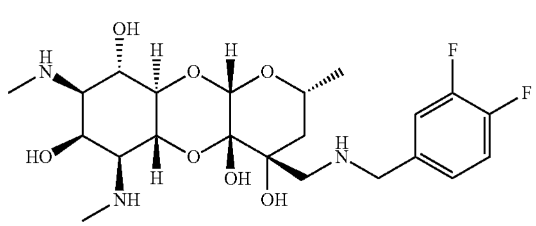 [SMILES: CN[C@@H]1[C@H](O)[C@H](NC)[C@H]2O[C@]3(O)[C@H](O[C@@H]2[C@H]1O)O[C@H](C)C[C@@]3(O)CNCc1ccc(F)c(F)c1] | — | 50 | — | — |

TABLE 8-continued
| No. | Structure | IC$_{50}$ (Sm) (μg/mL) | Clinical Isolates MIC (μg/mL) | | |
|---|---|---|---|---|---|
| | | | H37Rv | TN022 | TN026 |
| 13 | 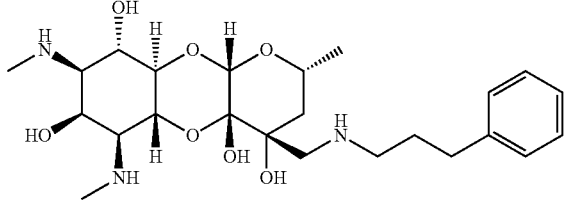 [SMILES: CN[C@@H]1[C@H](O)[C@H](NC)[C@H]2O[C@]3(O)[C@H](O[C@@H]2[C@H]1O)O[C@H](C)C[C@@]3(O)CNCCCc1ccccc1] | — | 3.1 | — | — |
| 14 | 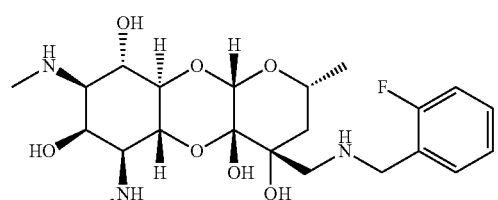 | — | 50 | — | — |
| 15 | 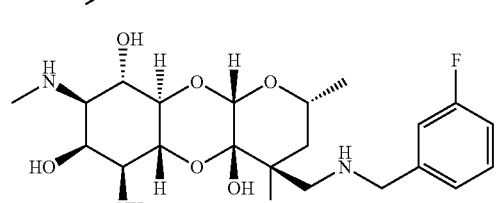 | — | 25 | — | — |
| 16 | 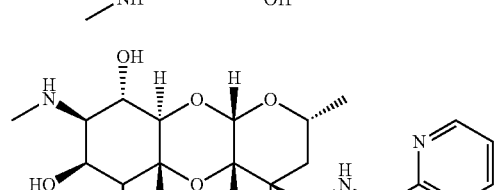 | — | 12.5 | — | — |
| 17 | 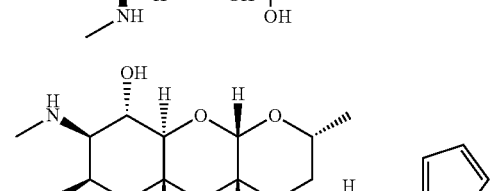 | — | 25 | — | — |
| 18 | 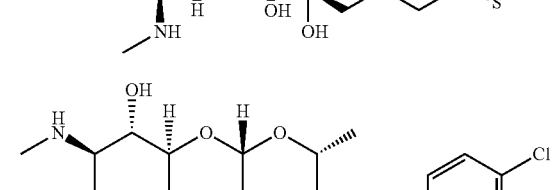 | — | 12.5 | — | — |
| 19 | 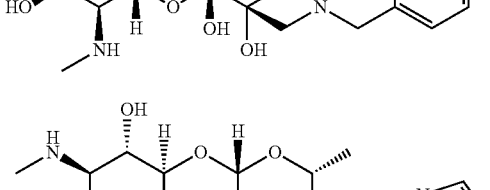 | — | 100 | — | — |

TABLE 8-continued

| No. | Structure | IC$_{50}$ (Sm) (μg/mL) | Clinical Isolates MIC (μg/mL) | | |
|---|---|---|---|---|---|
| | | | H37Rv | TN022 | TN026 |
| 20 | 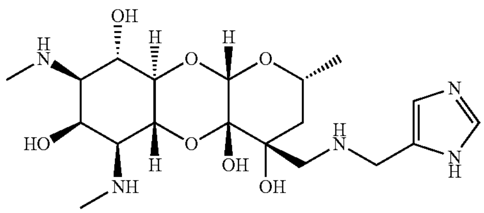 [SMILES: CN[C@@H]1[C@H](O)[C@H](NC)[C@H]2O[C@]3(O)[C@H](O[C@@H]2[C@H]1O)O[C@H](C)C[C@@]3(O)CNCc1cnc[nH]1] | — | 6.3 | — | — |
| 21 | 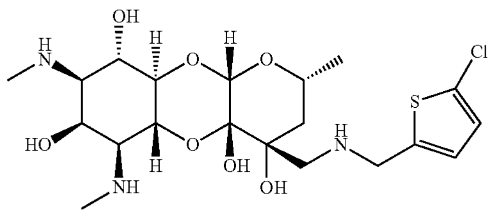 [SMILES: CN[C@@H]1[C@H](O)[C@H](NC)[C@H]2O[C@]3(O)[C@H](O[C@@H]2[C@H]1O)O[C@H](C)C[C@@]3(O)CNCc1ccc(Cl)s1] | — | 100 | — | — |
| 22 | 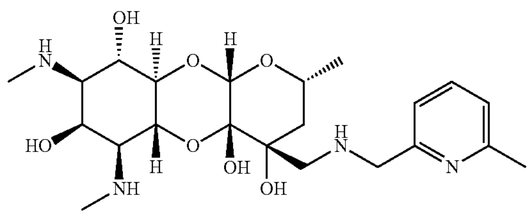 | — | 6.3 | — | — |
| 23 | 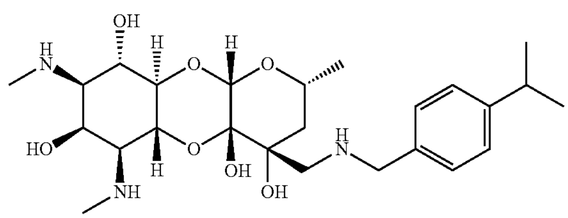 | — | 25 | — | — |
| 24 | 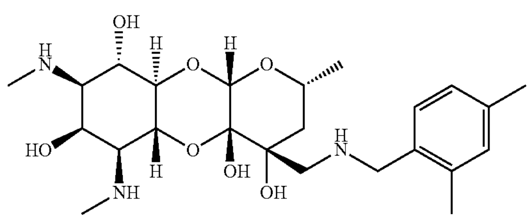 | — | 25 | — | — |
| 25 | 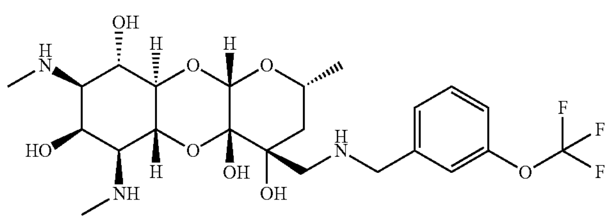 [SMILES: CN[C@@H]1[C@H](O)[C@H](NC)[C@H]2O[C@]3(O)[C@H](O[C@@H]2[C@H]1O)O[C@H](C)C[C@@]3(O)CNCc1cccc(OC(F)(F)F)c1] | — | 200 | — | — |
| 26 | 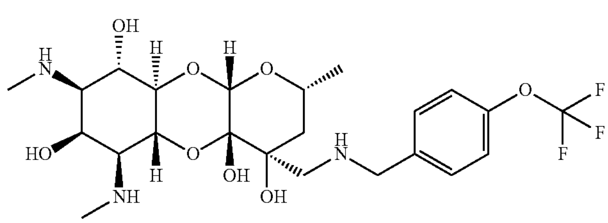 [SMILES: CN[C@@H]1[C@H](O)[C@H](NC)[C@H]2O[C@]3(O)[C@H](O[C@@H]2[C@H]1O)O[C@H](C)C[C@]3(O)CNCc1ccc(OC(F)(F)F)cc1] | — | 100 | — | — |

TABLE 8-continued

| No. | Structure | IC$_{50}$ (Sm) (μg/mL) | Clinical Isolates MIC (μg/mL) | | |
|---|---|---|---|---|---|
| | | | H37Rv | TN022 | TN026 |
| 27 | 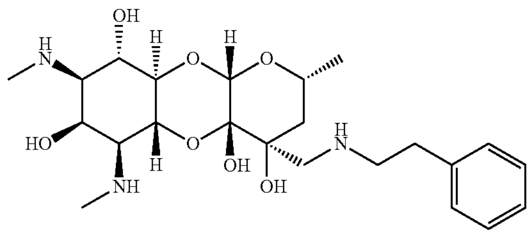 [SMILES: CN[C@@H]1[C@H](O)[C@H](NC)[C@H]2O[C@]3(O)[C@H](O[C@@H]2[C@H]1O)O[C@H](C)C[C@]3(O)CNCCc1ccccc1] | — | 200 | — | — |
| 28 | 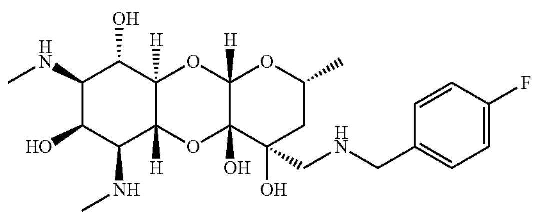 [SMILES: CN[C@@H]1[C@H](O)[C@H](NC)[C@H]2O[C@]3(O)[C@H](O[C@@H]2[C@H]1O)O[C@H](C)C[C@]3(O)CNCc1ccc(F)cc1] | — | 200 | — | — |
| 29 | 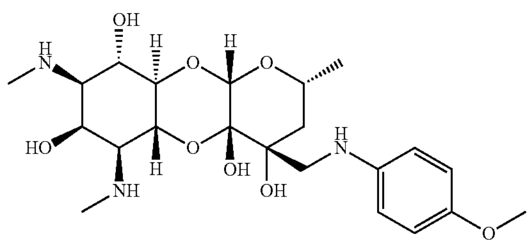 | — | >200 | — | — |
| 30 | 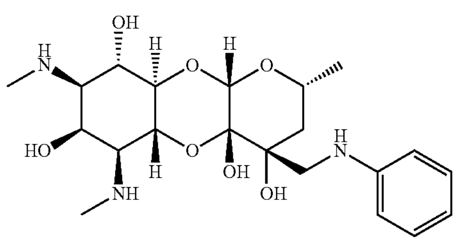 [SMILES: CN[C@@H]1[C@H](O)[C@H](NC)[C@H]2O[C@]3(O)[C@H](O[C@@H]2[C@H]1O)O[C@H](C)C[C@@]3(O)CNc1ccccc1] | — | >200 | — | — |
| 31 | 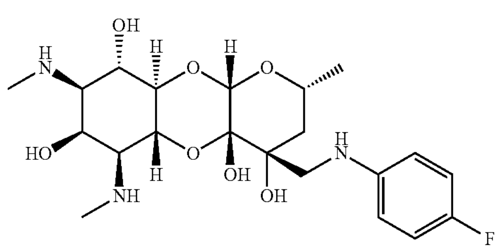 [SMILES: CN[C@@H]1[C@H](O)[C@H](NC)[C@H]2O[C@]3(O)[C@H](O[C@@H]2[C@H]1O)O[C@H](C)C[C@@]3(O)CNc1ccc(F)cc1] | — | 200 | — | — |
| 32 | 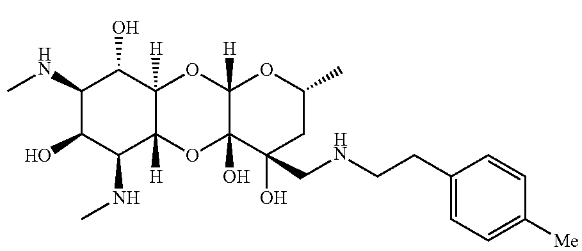 [SMILES: CN[C@@H]1[C@H](O)[C@H](NC)[C@H]2O[C@]3(O)[C@H](O[C@@H]2[C@H]1O)O[C@H](C)C[C@@]3(O)CNCCc1ccc(C)cc1] | 0.49 | 3.1 | 6.3 | 6.3 |

TABLE 8-continued

| No. | Structure | IC$_{50}$ (Sm) (μg/mL) | Clinical Isolates MIC (μg/mL) | | |
|---|---|---|---|---|---|
| | | | H37Rv | TN022 | TN026 |
| 33 | 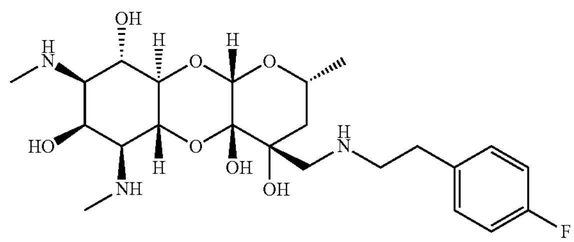 [SMILES: CN[C@@H]1[C@H](O)[C@H](NC)[C@H]2O[C@]3(O)[C@H](O[C@@H]2[C@H]1O)O[C@H](C)C[C@@]3(O)CNCCc1ccc(F)cc1] | ND | 3.1 | 6.3 | 6.3 |
| 34 | 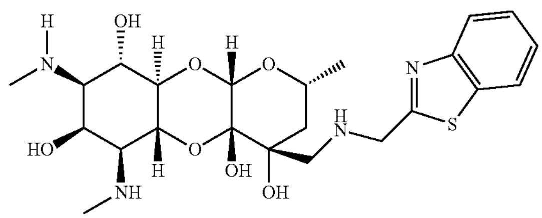 [SMILES: CN[C@@H]1[C@H](O)[C@H](NC)[C@H]2O[C@]3(O)[C@H](O[C@@H]2[C@H]1O)O[C@H](C)C[C@@]3(O)CNCc1nc2ccccc2s1] | — | 12.5 | — | — |
| 35 | 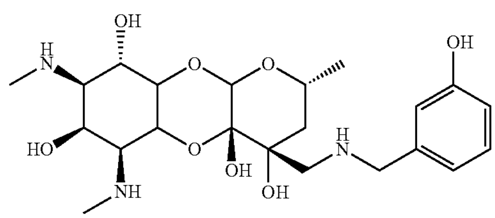 | — | 50 | — | — |
| 36 | 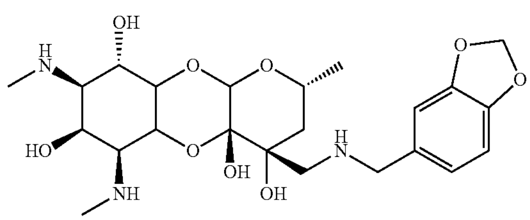 [SMILES: CN[C@@H]1[C@H](O)[C@H](NC)C2O[C@]3(O)C(OC2[C@H]1O)O[C@H](C)C[C@@]3(O)CNCc1ccc2c(c1)OCO2] | — | 50 | — | — |
| 37 | 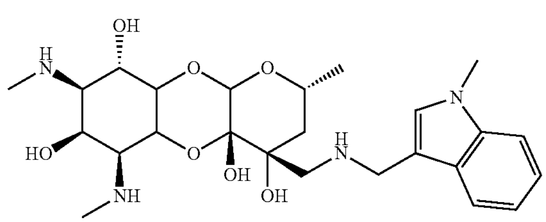 [SMILES: CN[C@@H]1[C@H](O)[C@H](NC)C2O[C@]3(O)C(OC2[C@H]1O)O[C@H](C)C[C@@]3(O)CNCc1cn(C)c2ccccc12] | — | 50 | — | — |
| 38 | 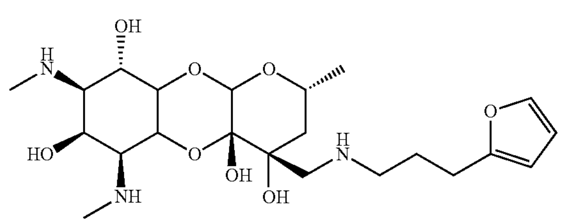 [SMILES: CN[C@@H]1[C@H](O)[C@H](NC)C2O[C@]3(O)C(OC2[C@H]1O)O[C@H](C)C[C@@]3(O)CNCCCc1ccco1] | — | 6.3 | — | — |

TABLE 8-continued
| No. | Structure | IC$_{50}$ (Sm) (µg/mL) | Clinical Isolates MIC (µg/mL) | | |
|---|---|---|---|---|---|
| | | | H37Rv | TN022 | TN026 |
| 39 | 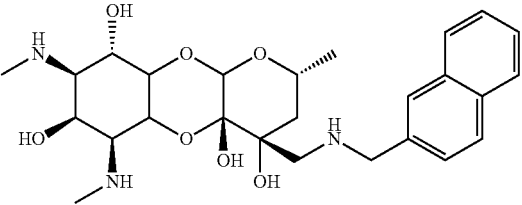 [SMILES: CN[C@@H]1[C@H](O)[C@H](NC)C2O[C@]3(O)C(OC2[C@H]1O)O[C@H](C)C[C@@]3(O)CNCc1ccc2ccccc2c1] | — | 50 | — | — |
| 40 | 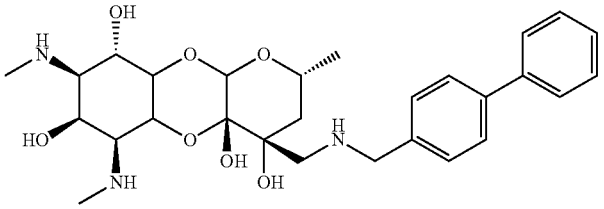 [SMILES: CN[C@@H]1[C@H](O)[C@H](NC)C2O[C@]3(O)C(OC2[C@H]1O)O[C@H](C)C[C@@]3(O)CNCc1ccc(-c2ccccc2)cc1] | — | 100 | — | — |
| 41 | 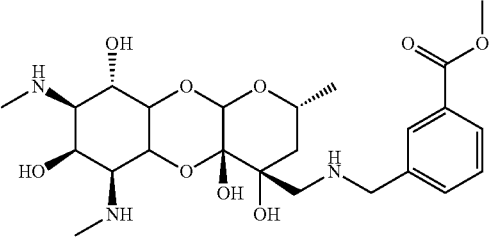 | — | 50 | — | — |
| 42 | 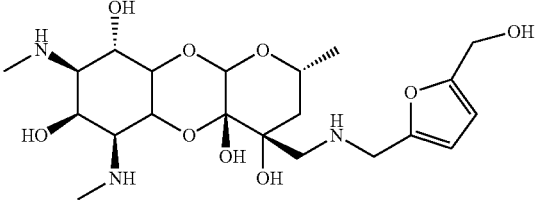 [SMILES: CN[C@@H]1[C@H](O)[C@H](NC)C2O[C@]3(O)C(OC2[C@H]1O)O[C@H](C)C[C@@]3(O)CNCc1ccc(CO)o1] | — | 25 | — | — |
| 43 | 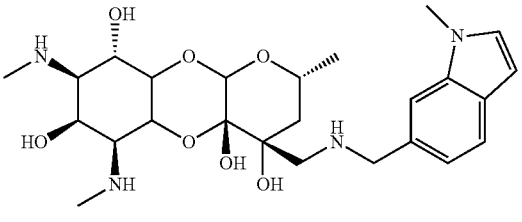 [SMILES: CN[C@@H]1[C@H](O)[C@H](NC)C2O[C@]3(O)C(OC2[C@H]1O)O[C@H](C)C[C@@]3(O)CNCc1ccc2ccn(C)c2c1] | — | 100 | — | — |
| 44 | 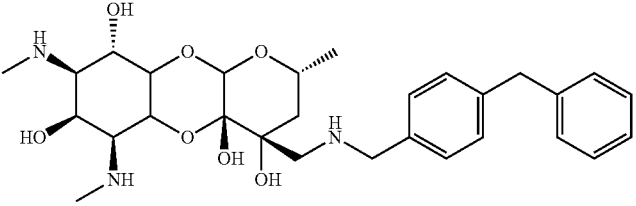 [SMILES: CN[C@@H]1[C@H](O)[C@H](NC)C2O[C@]3(O)C(OC2[C@H]1O)O[C@H](C)C[C@@]3(O)CNCc1ccc(Cc2ccccc2)cc1] | — | 100 | — | — |

TABLE 8-continued

| No. | Structure | IC$_{50}$ (Sm) (μg/mL) | Clinical Isolates MIC (μg/mL) | | |
|---|---|---|---|---|---|
| | | | H37Rv | TN022 | TN026 |
| 45 | 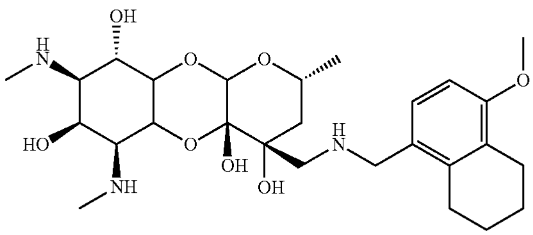 | — | 200 | — | — |
| 46 | 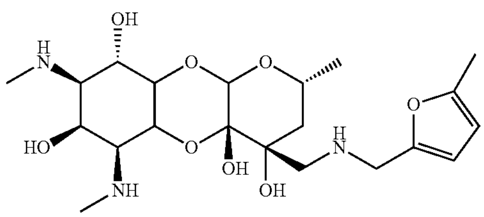 [SMILES: CN[C@@H]1[C@H](O)[C@H](NC)C2O[C@]3(O)C(OC2[C@H]1O)O[C@H](C)C[C@@]3(O)CNCc1ccc(C)o1] | — | 25 | — | — |
| 47 | 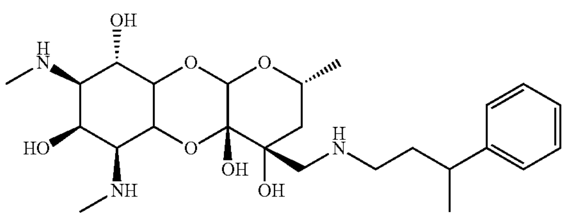 [SMILES: CN[C@@H]1[C@H](O)[C@H](NC)C2O[C@]3(O)C(OC2[C@H]1O)O[C@H](C)C[C@@]3(O)CNCCC(C)c1ccccc1] | — | 6.3 | — | — |
| 48 | 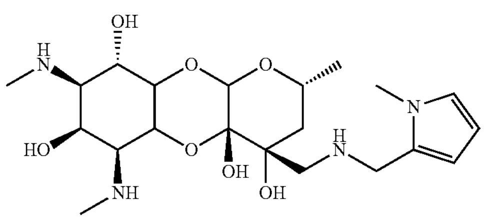 [SMILES: CN[C@@H]1[C@H](O)[C@H](NC)C2O[C@]3(O)C(OC2[C@H]1O)O[C@H](C)C[C@@]3(O)CNCc1cccn1C] | — | 200 | — | — |
| 49 | 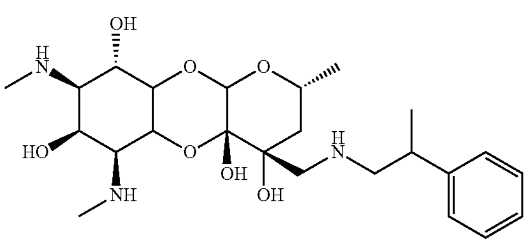 [SMILES: CN[C@@H]1[C@H](O)[C@H](NC)C2O[C@]3(O)C(OC2[C@H]1O)O[C@H](C)C[C@@]3(O)CNCC(C)c1ccccc1] | — | 100 | — | — |
| 50 | 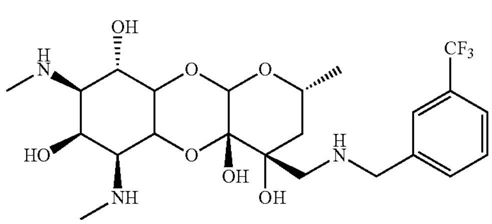 [SMILES: CN[C@@H]1[C@H](O)[C@H](NC)C2O[C@]3(O)C(OC2[C@H]1O)O[C@H](C)C[C@@]3(O)CNCc1cccc(C(F)(F)F)c1] | — | — | — | — |

TABLE 8-continued

| No. | Structure | IC$_{50}$ (Sm) (μg/mL) | Clinical Isolates MIC (μg/mL) | | |
|---|---|---|---|---|---|
| | | | H37Rv | TN022 | TN026 |
| 51 | 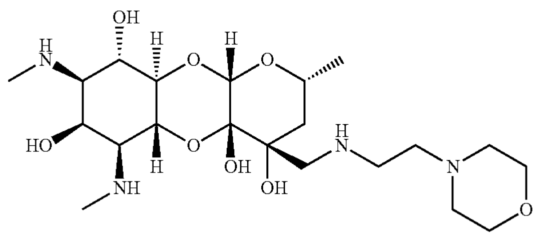 | 0.38 | 25 | 50 | 100 |
| 52 | 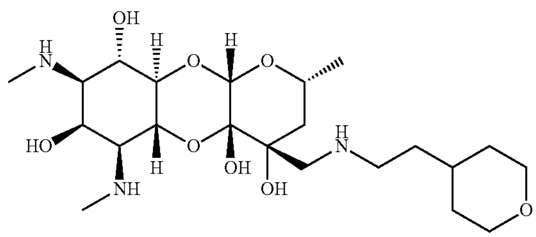 [SMILES: CN[C@@H]1[C@H](O)[C@H](NC)[C@H]2O[C@]3(O)[C@H](O[C@@H]2[C@H]1O)O[C@H](C)C[C@@]3(O)CNCCC1CCOCC1] | 0.34 | 3.1 | 6.3 | 3.1 |
| 53 | 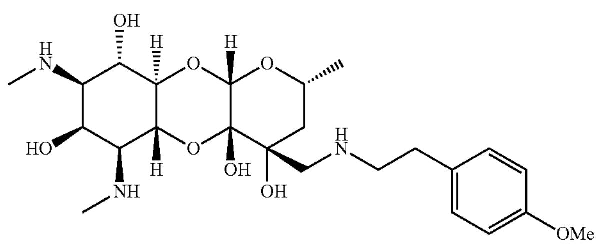 [SMILES: CN[C@@H]1[C@H](O)[C@H](NC)[C@H]2O[C@]3(O)[C@H](O[C@@H]2[C@H]1O)O[C@H](C)C[C@@]3(O)CNCCc1ccc(OC)cc1] | 0.80 | 6.3 | 12.5 | 12.5 |
| 54 | 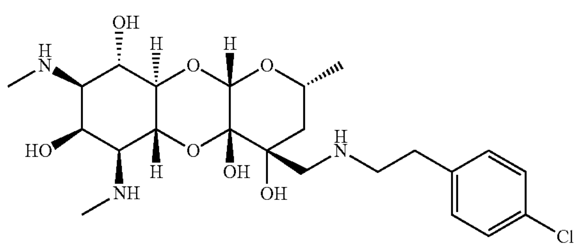 [SMILES: CN[C@@H]1[C@H](O)[C@H](NC)[C@H]2O[C@]3(O)[C@H](O[C@@H]2[C@H]1O)O[C@H](C)C[C@@]3(O)CNCCc1ccc(Cl)cc1] | 2.98 | 25 | 25 | 50 |
| 55 | 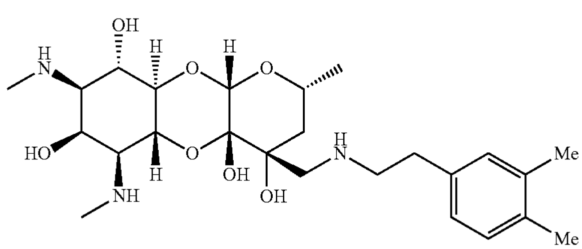 [SMILES: CN[C@@H]1[C@H](O)[C@H](NC)[C@H]2O[C@]3(O)[C@H](O[C@@H]2[C@H]1O)O[C@H](C)C[C@@]3(O)CNCCc1ccc(C)c(C)c1] | 2.16 | 25 | 50 | 50 |
| 56 | 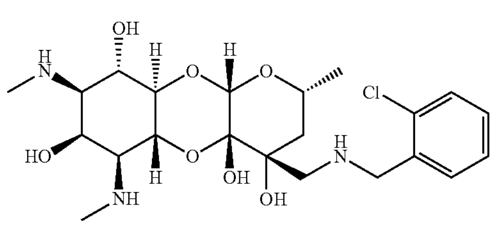 [SMILES: CN[C@@H]1[C@H](O)[C@H](NC)[C@H]2O[C@]3(O)[C@H](O[C@@H]2[C@H]1O)O[C@H](C)C[C@@]3(O)CNCc1ccccc1Cl] | 21.35 | >200 | ND | ND |

TABLE 8-continued

| No. | Structure | IC$_{50}$ (Sm) (μg/mL) | Clinical Isolates MIC (μg/mL) | | |
|-----|-----------|------------------------|-------------------------------|---|---|
| | | | H37Rv | TN022 | TN026 |
| 57 | 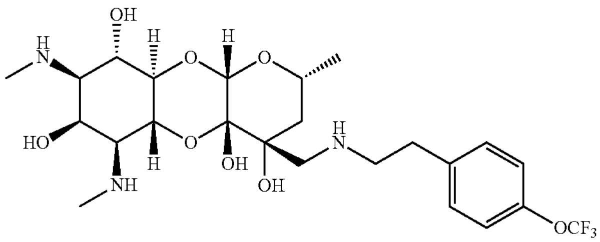 [SMILES: CN[C@@H]1[C@H](O)[C@H](NC)[C@H]2O[C@]3(O)[C@H](O[C@@H]2[C@H]1O)O[C@H](C)C[C@@]3(O)CNCCc1ccc(OC(F)(F)F)cc1] | — | 12.5 | 6.3 | 25 |
| 58 | 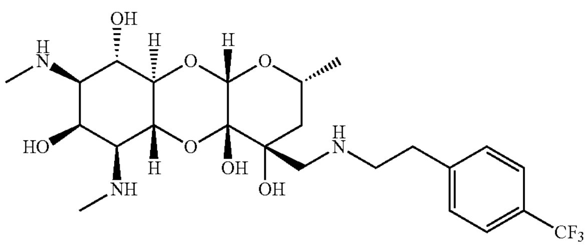 [SMILES: CN[C@@H]1[C@H](O)[C@H](NC)[C@H]2O[C@]3(O)[C@H](O[C@@H]2[C@H]1O)O[C@H](C)C[C@@]3(O)CNCCc1ccc(C(F)(F)F)cc1] | — | 3.1 | 3.1 | 6.3 |
| 59 | 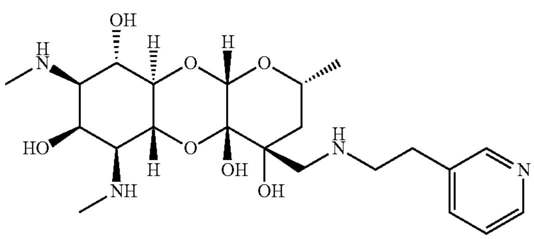 [SMILES: CN[C@@H]1[C@H](O)[C@H](NC)[C@H]2O[C@]3(O)[C@H](O[C@@H]2[C@H]1O)O[C@H](C)C[C@@]3(O)CNCCc1cccnc1] | — | 6.3 | 6.3 | 6.3 |
| 60 | 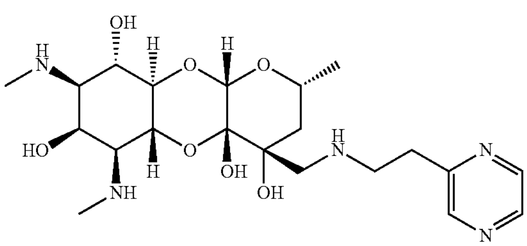 [SMILES: CN[C@@H]1[C@H](O)[C@H](NC)[C@H]2O[C@]3(O)[C@H](O[C@@H]2[C@H]1O)O[C@H](C)C[C@@]3(O)CNCCc1cnccn1] | — | 3.1 | 6.3 | 6.3 |
| 61 | 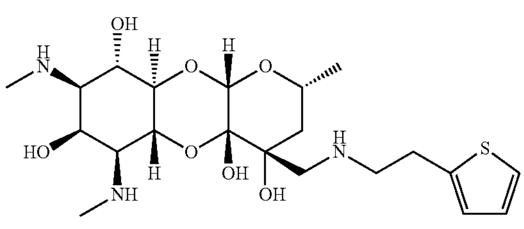 [SMILES: CN[C@@H]1[C@H](O)[C@H](NC)[C@H]2O[C@]3(O)[C@H](O[C@@H]2[C@H]1O)O[C@H](C)C[C@@]3(O)CNCCc1cccs1] | — | 6.3 | 6.3 | 6.3 |
| 62 | 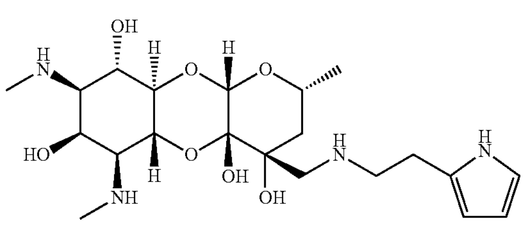 [SMILES: CN[C@@H]1[C@H](O)[C@H](NC)[C@H]2O[C@]3(O)[C@H](O[C@@H]2[C@H]1O)O[C@H](C)C[C@@]3(O)CNCCc1ccc[nH]1] | — | 50 | 25 | 100 |

TABLE 8-continued

| No. | Structure | IC$_{50}$ (Sm) (μg/mL) | Clinical Isolates MIC (μg/mL) H37Rv | TN022 | TN026 |
|---|---|---|---|---|---|
| 63 | [structure] | — | 25 | 25 | 25 |
| 64 | [structure] | — | 1.6 | 1.6 | 1.6 |
| 65 | [structure] | — | 50 | 100 | 100 |

23. Prophetic Pharmaceutical Composition Examples

"Active ingredient" as used throughout these examples relates to one or more compounds according to Formula I or products of disclosed methods of making as described hereinbefore, or a pharmaceutically acceptable salt, solvate, or polymorph thereof. The following examples of the formulation of the compounds of the present invention in tablets, suspension, injectables and ointments are prophetic. Typical examples of recipes for the formulation of the invention are as given below.

Various other dosage forms can be applied herein such as a filled gelatin capsule, liquid emulsion/suspension, ointments, suppositories or chewable tablet form employing the disclosed compounds of the present invention in desired dosage amounts in accordance with the present invention. Various conventional techniques for preparing suitable dosage forms can be used to prepare the prophetic pharmaceutical compositions, such as those disclosed herein and in standard reference texts, for example the British and US Pharmacopoeias, Remington's Pharmaceutical Sciences (Mack Publishing Co.) and Martindale The Extra Pharmacopoeia (London The Pharmaceutical Press).

The disclosure of this reference is hereby incorporated herein by reference.

a. Pharmaceutical Composition for Oral Administration

A tablet can be prepared as follows:

| Component | Amount |
|---|---|
| Active ingredient | 10 to 500 mg |
| Lactose | 100 mg |

-continued

| Component | Amount |
|---|---|
| Crystalline cellulose | 60 mg |
| Magnesium stearate | 5 |
| Starch (e.g., potato starch) | Amount necessary to yield total weight indicated below |
| Total (per capsule) | 1000 mg |

Alternatively, about 100 mg of a disclosed compound of the present invention, 50 mg of lactose (monohydrate), 50 mg of maize starch (native), 10 mg of polyvinylpyrrolidone (PVP 25) (e.g., from BASF, Ludwigshafen, Germany) and 2 mg of magnesium stearate are used per tablet. The mixture of active component, lactose and starch is granulated with a 5% solution (m/m) of the PVP in water. After drying, the granules are mixed with magnesium stearate for 5 min. This mixture is molded using a customary tablet press (e.g., tablet format: diameter 8 mm, curvature radius 12 mm). The molding force applied is typically about 15 kN.

Alternatively, a disclosed compound of the present invention can be administered in a suspension formulated for oral use. For example, about 100-5000 mg of the desired disclosed compound of the present invention, 1000 mg of ethanol (96%), 400 mg of xanthan gum, and 99 g of water are combined with stirring. A single dose of about 10-500 mg of the desired disclosed compound of the present invention according can be provided by 10 ml of oral suspension.

In these Examples, active ingredient can be replaced with the same amount of any of the compounds according to the present invention, in particular by the same amount of any of the exemplified compounds. In some circumstances it may be desirable to use a capsule, e.g., a filled gelatin capsule, instead of a tablet form. The choice of tablet or capsule will depend, in part, upon physicochemical characteristics of the particular disclosed compound of the present invention used.

Examples of alternative useful carriers for making oral preparations are lactose, sucrose, starch, talc, magnesium stearate, crystalline cellulose, methyl cellulose, hydroxypropyl cellulose, hydroxypropylmethyl cellulose, carboxymethyl cellulose, glycerin, sodium alginate, gum arabic, etc. These alternative carriers can be substituted for those given above as required for desired dissolution, absorption, and manufacturing characteristics.

The amount of a disclosed compound of the present invention per tablet for use in a pharmaceutical composition for human use is determined from both toxicological and pharmacokinetic data obtained in suitable animal models, e.g., rat and at least one non-rodent species, and adjusted based upon human clinical trial data. For example, it could be appropriate that a disclosed compound of the present invention is present at a level of about 10 to 1000 mg per tablet dosage unit.

b. Pharmaceutical Composition for Injectable Use

A parenteral composition can be prepared as follows:

| Component | Amount |
|---|---|
| Active ingredient | 10 to 500 mg |
| Sodium carbonate | 560 mg* |
| Sodium hydroxide | 80 mg* |
| Distilled, sterile water | Quantity sufficient to prepare total volume indicated below. |
| Total (per capsule) | 10 ml per ampule |

*Amount adjusted as required to maintain physiological pH in the context of the amount of active ingredient, and form of active ingredient, e.g., a particular salt form of the active ingredient.

Alternatively, a pharmaceutical composition for intravenous injection can be used, with composition comprising about 100-5000 mg of a disclosed compound of the present invention, 15 g polyethylenglycol 400 and 250 g water in saline with optionally up to about 15% Cremophor EL, and optionally up to 15% ethyl alcohol, and optionally up to 2 equivalents of a pharmaceutically suitable acid such as citric acid or hydrochloric acid are used. The preparation of such an injectable composition can be accomplished as follows: The disclosed compound of the present invention and the polyethylenglycol 400 are dissolved in the water with stirring. The solution is sterile filtered (pore size 0.22 μm) and filled into heat sterilized infusion bottles under aseptic conditions. The infusion bottles are sealed with rubber seals.

In a further example, a pharmaceutical composition for intravenous injection can be used, with composition comprising about 10-500 mg of a disclosed compound of the present invention, standard saline solution, optionally with up to 15% by weight of Cremophor EL, and optionally up to 15% by weight of ethyl alcohol, and optionally up to 2 equivalents of a pharmaceutically suitable acid such as citric acid or hydrochloric acid. Preparation can be accomplished as follows: a desired disclosed compound of the present invention is dissolved in the saline solution with stirring. Optionally Cremophor EL, ethyl alcohol or acid are added. The solution is sterile filtered (pore size 0.22 μm) and filled into heat sterilized infusion bottles under aseptic conditions. The infusion bottles are sealed with rubber seals.

In this Example, active ingredient can be replaced with the same amount of any of the compounds according to the present invention, in particular by the same amount of any of the exemplified compounds.

The amount of a disclosed compound of the present invention per ampule for use in a pharmaceutical composition for human use is determined from both toxicological and pharmacokinetic data obtained in suitable animal models, e.g., rat and at least one non-rodent species, and adjusted based upon human clinical trial data. For example, it could be appropriate that a disclosed compound of the present invention is present at a level of about 10 to 1000 mg per tablet dosage unit.

Carriers suitable for parenteral preparations are, for example, water, physiological saline solution, etc. which can be used with tris(hydroxymethyl)aminomethane, sodium carbonate, sodium hydroxide or the like serving as a solubilizer or pH adjusting agent. The parenteral preparations contain preferably 50 to 1000 mg of a disclosed compound of the present invention per dosage unit.

The publications mentioned above are incorporated herein by reference. It will be apparent to those skilled in the art that various modifications and variations can be made in the present invention without departing from the scope or spirit of the invention. Other aspects of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A compound having a structure represented by a Formula I:

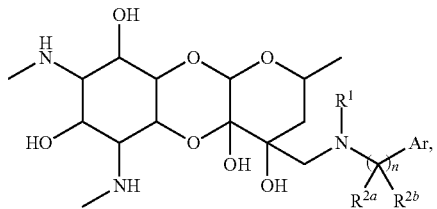

wherein n is an integer selected from 1, 2, and 3;
wherein $R^1$ is selected from hydrogen and C1-C4 alkyl;
wherein each occurrence of $R^{2a}$ and $R^{2b}$, when present, is independently selected from hydrogen and C1-C3 alkyl; and
wherein Ar is aryl or heteroaryl substituted with 0 to 3 groups independently selected from halo, cyano, hydroxyl, —NH$_2$, C1-C3 alkyl, C1-C3 monoalkyl, C1-C3 polyhaloalkyl, C1-C3 alkoxy, C1-C3 monohaloalkoxy, C1-C3 polyhaloalkoxy, —(C═O)OR$^9$, —(C═O)NR$^{10a}$R$^{10b}$, —SO$_2$NR$^{10a}$R$^{10b}$, —SR$^9$, and —SO$_2$R$^9$,
wherein each occurrence of $R^9$, when present, is selected from hydrogen and C1-C3 alkyl;
wherein each occurrence of $R^{10a}$ and $R^{10b}$, when present, is independently selected from hydrogen and C1-C3 alkyl;
or a pharmaceutically acceptable salt thereof.

2. The compound of claim 1, wherein $R^1$ is selected from hydrogen and methyl.

3. The compound of claim 1, wherein each occurrence of $R^{2a}$ and $R^{2b}$ is hydrogen.

4. The compound of claim 1, wherein Ar is phenyl substituted with 0 to 3 groups independently selected from halo, cyano, hydroxyl, —NH$_2$, C1-C3 alkyl, C1-C3 monoalkyl, C1-C3 polyhaloalkyl, C1-C3 alkoxy, C1-C3 monohaloalkoxy, C1-C3 polyhaloalkoxy, —(C=O)OR$^9$, —(C=O)NR$^{10a}$R$^{10b}$, —SO$_2$NR$^{10a}$R$^{10b}$, —SR$^9$, and —SO$_2$R$^9$.

5. The compound of claim 4, wherein Ar is phenyl substituted with 0 to 3 groups independently selected from —F, —Cl, —Br, cyano, hydroxyl, —NH$_2$, methyl, ethyl, propyl, isopropyl, —CH$_2$F, —CHF$_2$, —CF$_3$, —CH$_2$Cl, —CHCl$_2$, —CCl$_3$, —CH$_2$CH$_2$F, —CH$_2$CHF$_2$, —CH$_2$CF$_3$, —CH$_2$CH$_2$Cl, —CH$_2$CHCl$_2$, —CH$_2$CCl$_3$, —OCH$_3$, —OCH$_2$CH$_3$, —OCH$_2$F, —OCHF$_2$, —OCF$_3$, —OCH$_2$Cl, —OCHCl$_2$, —OCCl$_3$, —OCH$_2$CH$_2$F, —OCH$_2$CHF$_2$, —OCH$_2$CF$_3$, —OCH$_2$CH$_2$Cl, —OCH$_2$CHCl$_2$, —(C=O)OCH$_2$CH$_3$, —(C=O)OCH$_2$CH$_3$, —(C=O)OCH$_3$, —(C=O)OH, —(C=O)NHCH$_2$CH$_3$, —(C=O)NHCH$_3$, —(C=O)NH$_2$, —SO$_2$N(CH$_3$)$_2$, —SO$_2$NHCH$_2$CH$_3$, —SO$_2$NHCH$_3$, and —SO$_2$NH$_2$.

6. The compound of claim 1, wherein Ar is heteroaryl substituted with 0 to 3 groups independently selected from halo, cyano, hydroxyl, —NH$_2$, C1-C3 alkyl, C1-C3 monoalkyl, C1-C3 polyhaloalkyl, C1-C3 alkoxy, C1-C3 monohaloalkoxy, C1-C3 polyhaloalkoxy, —(C=O)OR$^9$, —(C=O)NR$^{10a}$R$^{10b}$, —SO$_2$NR$^{10a}$R$^{10b}$, —SR$^9$, and —SO$_2$R$^9$.

7. The compound of claim 6, wherein Ar is heteroaryl substituted with 0 to 3 groups independently selected from —F, —Cl, —Br, cyano, hydroxyl, —NH$_2$, methyl, ethyl, propyl, isopropyl, —CH$_2$F, —CHF$_2$, —CF$_3$, —CH$_2$Cl, —CHCl$_2$, —CCl$_3$, —CH$_2$CH$_2$F, —CH$_2$CHF$_2$, —CH$_2$CF$_3$, —CH$_2$CH$_2$Cl, —CH$_2$CHCl$_2$, —CH$_2$CCl$_3$, —OCH$_3$, —OCH$_2$CH$_3$, —OCH$_2$F, —OCHF$_2$, —OCF$_3$, —OCH$_2$Cl, —OCHCl$_2$, —OCCl$_3$, —OCH$_2$CH$_2$F, —OCH$_2$CHF$_2$, —OCH$_2$CF$_3$, —OCH$_2$CH$_2$Cl, —OCH$_2$CHCl$_2$, —(C=O)OCH$_2$CH$_3$, —(C=O)OCH$_2$CH$_3$, —(C=O)OCH$_3$, —(C=O)OH, —(C=O)NHCH$_2$CH$_3$, —(C=O)NHCH$_3$, —(C=O)NH$_2$, —SO$_2$N(CH$_3$)$_2$, —SO$_2$NHCH$_2$CH$_3$, —SO$_2$NHCH$_3$, and —SO$_2$NH$_2$.

8. The compound of claim 1, wherein Ar is selected from phenyl, pyridinyl, pyridazinyl, furanyl, thiophenyl, oxazolyl, thiazolyl, imidazolyl, pyrrolyl, benzo[d]thiazolyl, benzo[d]oxazolyl, oxazolo[4,5-c]pyridinyl, quinolinyl, and 1H-benzo[d]imidazolyl; and wherein Ar is substituted with 0 to 3 groups independently selected from halo, cyano, hydroxyl, —NH$_2$, C1-C3 alkyl, C1-C3 monoalkyl, C1-C3 polyhaloalkyl, C1-C3 alkoxy, C1-C3 monohaloalkoxy, C1-C3 polyhaloalkyl, C1-C3 alkoxy, C1-C3 monohaloalkoxy, C1-C3 polyhaloalkoxy, —(C=O)OR$^9$, —(C=O)NR$^{10a}$R$^{10b}$, —SO$_2$NR$^{10a}$R$^{10b}$, —SR$^9$, and —SO$_2$R$^9$.

9. The compound of claim 8, wherein Ar is selected from phenyl, pyridinyl, pyridazinyl, furanyl, thiophenyl, oxazolyl, thiazolyl, imidazolyl, pyrrolyl, benzo[d]thiazolyl, benzo[d]oxazolyl, oxazolo[4,5-c]pyridinyl, quinolinyl, and 1H-benzo[d]imidazolyl; and wherein Ar is substituted with 0 to 3 groups independently selected from —F, —Cl, —Br, cyano, hydroxyl, —NH$_2$, methyl, ethyl, propyl, isopropyl, —CH$_2$F, —CHF$_2$, —CF$_3$, —CH$_2$Cl, —CHCl$_2$, —CCl$_3$, —CH$_2$CH$_2$F, —CH$_2$CHF$_2$, —CH$_2$CF$_3$, —CH$_2$CH$_2$Cl, —CH$_2$CHCl$_2$, —CH$_2$CCl$_3$, —OCH$_3$, —OCH$_2$CH$_3$, —OCH$_2$F, —OCHF$_2$, —OCF$_3$, —OCH$_2$Cl, —OCHCl$_2$, —OCCl$_3$, —OCH$_2$CH$_2$F, —OCH$_2$CHF$_2$, —OCH$_2$CF$_3$, —OCH$_2$CH$_2$Cl, —OCH$_2$CHCl$_2$, —(C=O)OCH$_2$CH$_3$, —(C=O)OCH$_2$CH$_3$, —(C=O)OCH$_3$, —(C=O)OH, —(C=O)NHCH$_2$CH$_3$, —(C=O)NHCH$_3$, —(C=O)NH$_2$, —SO$_2$N(CH$_3$)$_2$, —SO$_2$NHCH$_2$CH$_3$, —SO$_2$NHCH$_3$, and —SO$_2$NH$_2$.

10. The compound of claim 1, having a structure represented by a formula:

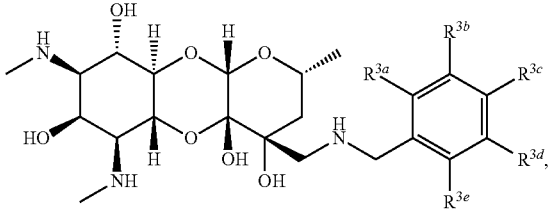

wherein each of R$^{3a}$, R$^{3b}$, R$^{3c}$, R$^{3d}$, and R$^{3e}$ are independently selected from hydrogen, halo, cyano, hydroxyl, —NH$_2$, C1-C3 alkyl, C1-C3 monoalkyl, C1-C3 polyhaloalkyl, C1-C3 alkoxy, C1-C3 monohaloalkoxy, C1-C3 polyhaloalkoxy, —(C=O)OR$^9$, —(C=O)NR$^{10a}$R$^{10b}$, —SO$_2$NR$^{10a}$R$^{10b}$, —SR$^9$, and —SO$_2$R$^9$, provided that at least two of R$^{3a}$, R$^{3b}$, R$^{3c}$, R$^{3d}$, and R$^{3e}$ are hydrogen.

11. The compound of claim 10, wherein each of R$^{3a}$, R$^{3b}$, R$^{3c}$, R$^{3d}$, and R$^{3e}$ are independently selected from hydrogen, —F, —Cl, —Br, cyano, hydroxyl, —NH$_2$, methyl, ethyl, propyl, isopropyl, —CH$_2$F, —CHF$_2$, —CF$_3$, —CH$_2$Cl, —CHCl$_2$, —CCl$_3$, —CH$_2$CH$_2$F, —CH$_2$CHF$_2$, —CH$_2$CF$_3$, —CH$_2$CH$_2$Cl, —CH$_2$CHCl$_2$, —CH$_2$CCl$_3$, —OCH$_3$, —OCH$_2$CH$_3$, —OCH$_2$F, —OCHF$_2$, —OCF$_3$, —OCH$_2$Cl, —OCHCl$_2$, —OCCl$_3$, —OCH$_2$CH$_2$F, —OCH$_2$CHF$_2$, —OCH$_2$CF$_3$, —OCH$_2$CH$_2$Cl, —OCH$_2$CHCl$_2$, —(C=O)OCH$_2$CH$_3$, —(C=O)OCH$_2$CH$_3$, —(C=O)OCH$_3$, —(C=O)OH, —(C=O)NHCH$_2$CH$_3$, —(C=O)NHCH$_3$, —(C=O)NH$_2$, —SO$_2$N(CH$_3$)$_2$, —SO$_2$NHCH$_2$CH$_3$, —SO$_2$NHCH$_3$, and —SO$_2$NH$_2$, provided that at least two of R$^{3a}$, R$^{3b}$, R$^{3c}$, R$^{3d}$, and R$^{3e}$ are hydrogen.

12. The compound of claim 1, having a structure represented by a formula:

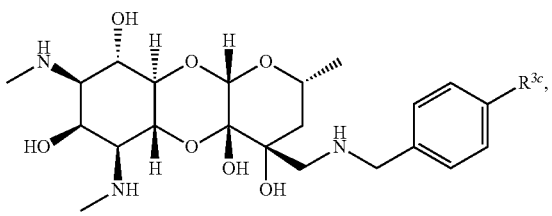

wherein R$^{3c}$ is selected from halo, cyano, hydroxyl, —NH$_2$, C1-C3 alkyl, C1-C3 monoalkyl, C1-C3 polyhaloalkyl, C1-C3 alkoxy, C1-C3 monohaloalkoxy, C1-C3 polyhaloalkoxy, —(C=O)OR$^9$, —(C=O)NR$^{10a}$R$^{10b}$, —SO$_2$NR$^{10a}$R$^{10b}$, —SR$^9$, and —SO$_2$R$^9$.

13. The compound of claim 1, selected from the group consisting of:

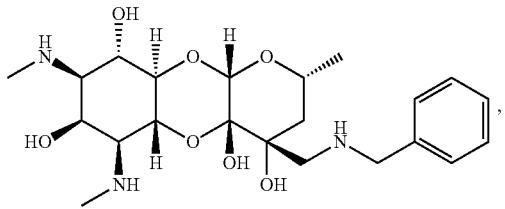

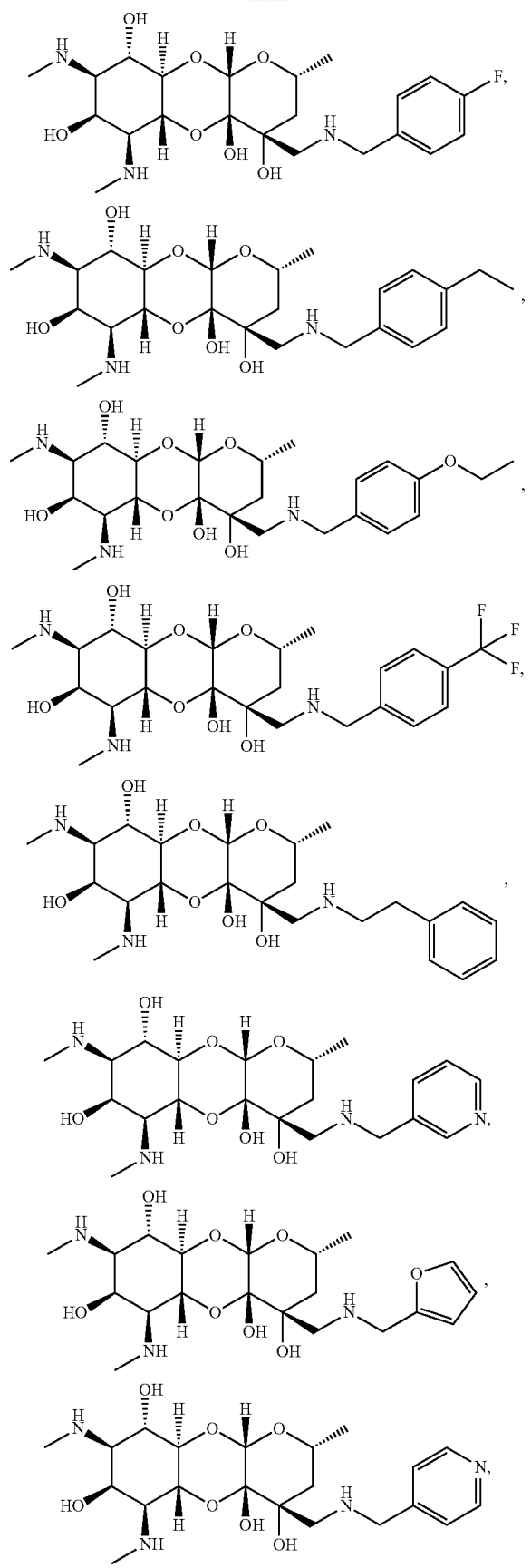
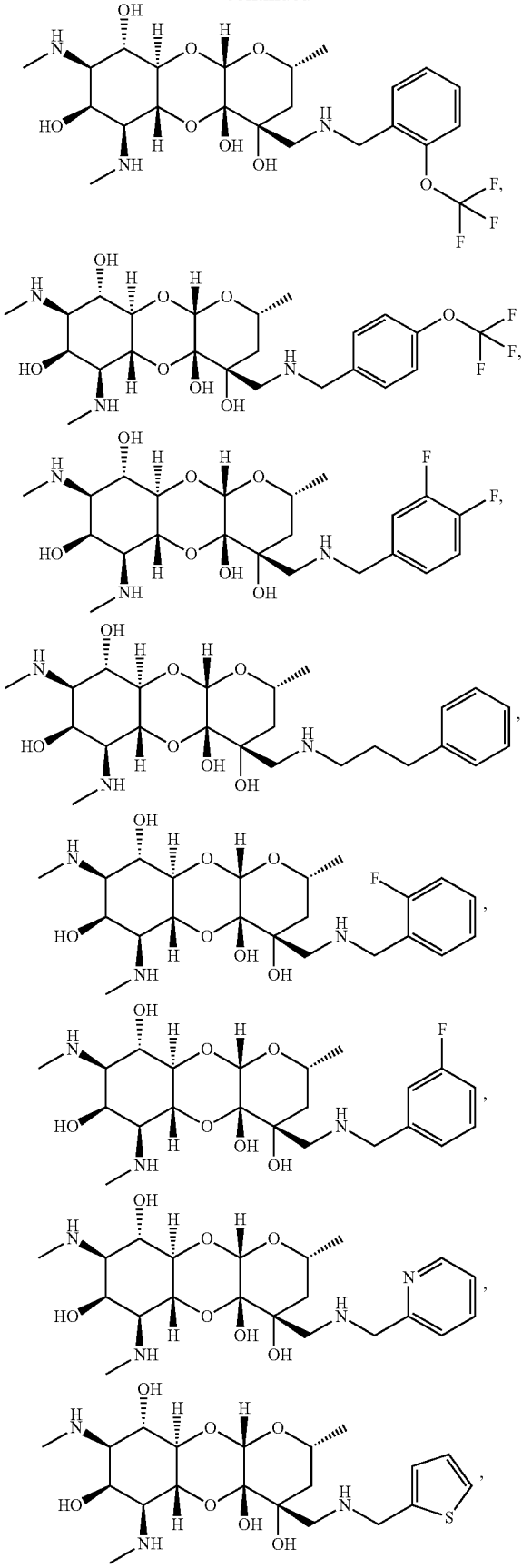

241
-continued
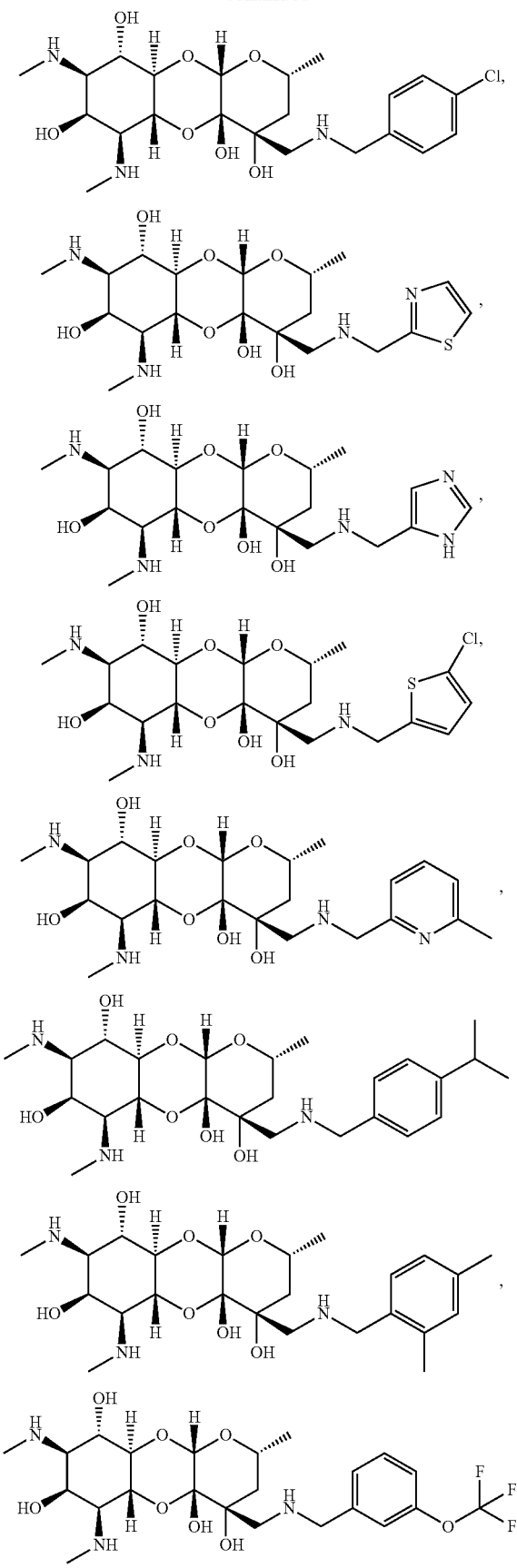
242
-continued
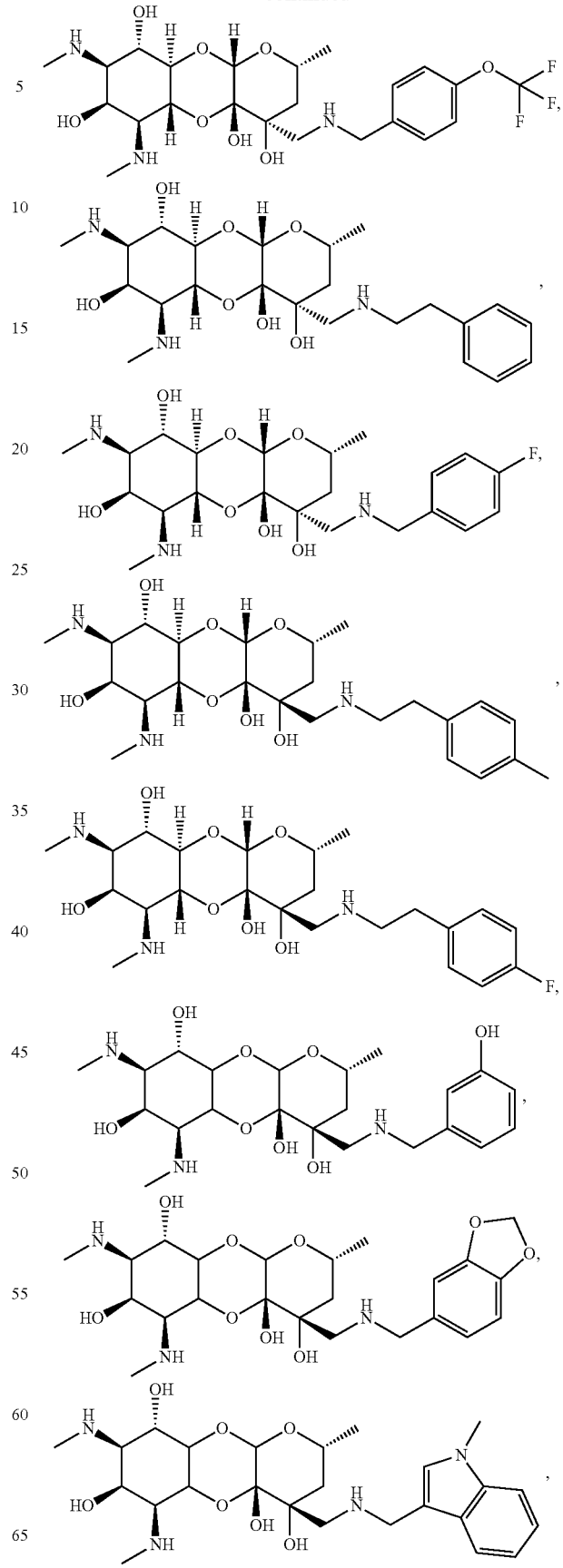

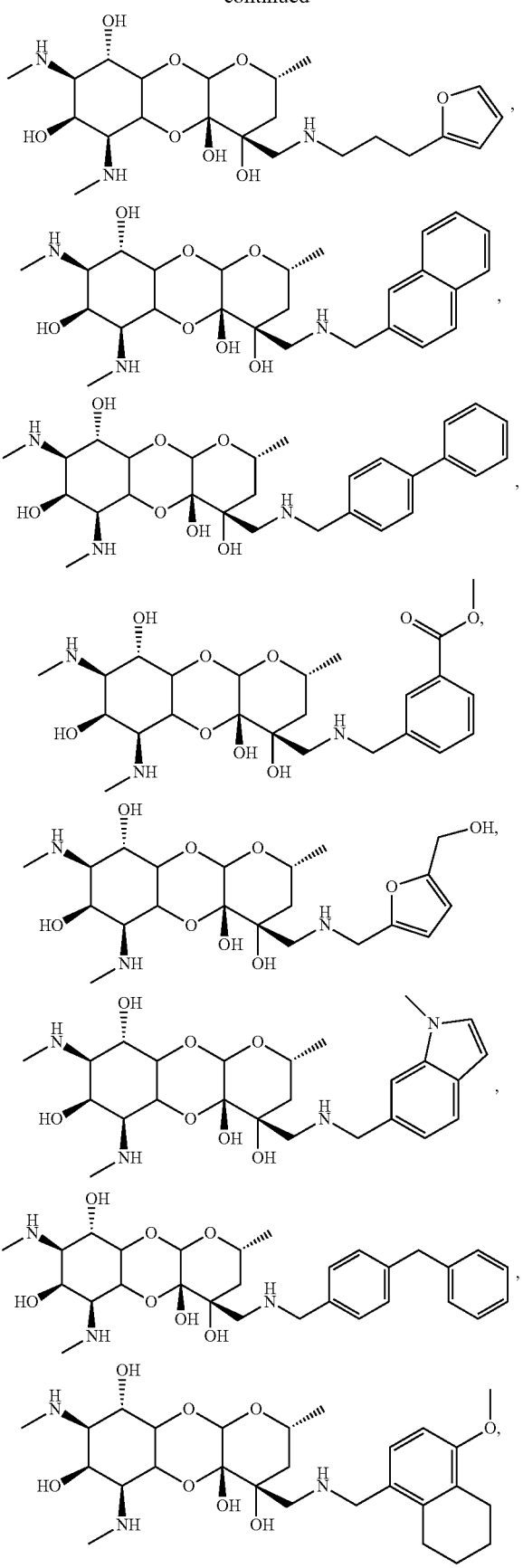
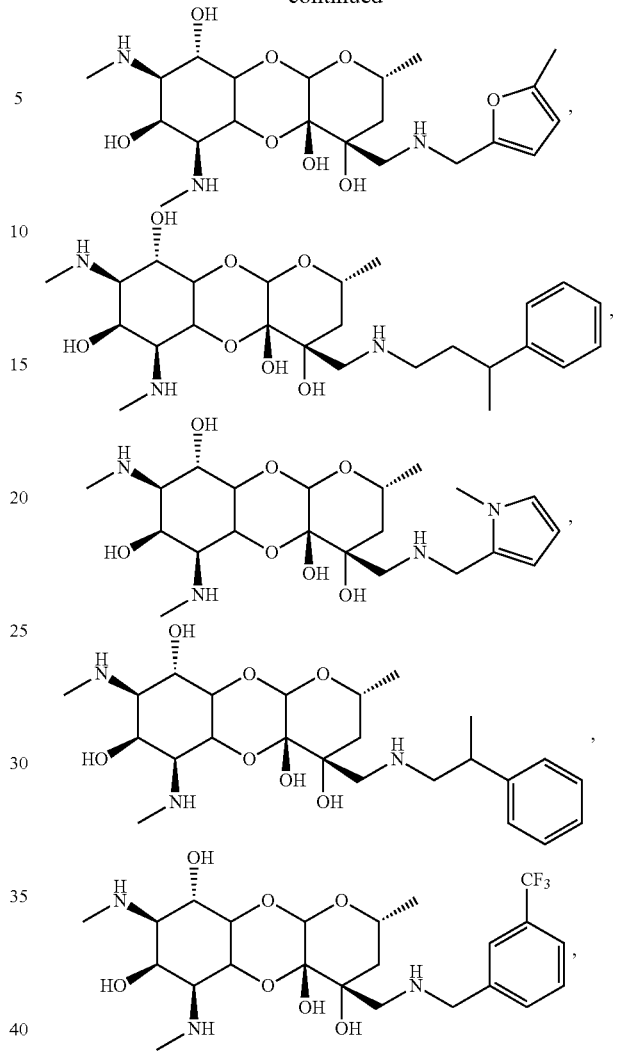

or a subgroup thereof.

14. A pharmaceutical composition comprising a compound of claim 1, or a pharmaceutically acceptable salt thereof, and a pharmaceutically acceptable carrier.

15. The pharmaceutical composition of claim 14, wherein the pharmaceutical composition is a solid dosage form selected from a capsule, a tablet, a pill, a powder, a granule, an effervescing granule, a gel, a paste, a troche, and a pastille.

16. The pharmaceutical composition of claim 14, wherein the pharmaceutical composition is a liquid dosage form selected from an emulsion, a solution, a suspension, a syrup, and an elixir.

17. The pharmaceutical composition of claim 14, further comprising a second active agent.

18. The pharmaceutical composition of claim 17, wherein the second active agent is an antibacterial agent.

19. A method for the treatment of a bacterial infection in a human subject comprising the step of administering to the human subject a therapeutically effective amount of the compound of claim 1, or a pharmaceutically acceptable salt thereof.

20. The method of claim 19, wherein the compound is formulated as a lotion, a cream, an ointment, a spray, or a soap.

21. The method of claim 19, wherein the compound is formulated as a solid dosage form.

22. The method of claim 19, wherein the compound is formulated as a liquid dosage form.

23. The method of claim 22, wherein the liquid dosage form is formulated for intravenous administration.

24. The method of claim 23, wherein the bacterial infection is associated with a gram positive bacterial infection.

25. The method of claim 24, wherein the gram positive bacteria is selected from *Bacillus* sp. *Clostridium* sp., *Enterococcus* sp., *Corynebacterium* sp., and *Staphylococcus* sp., *Streptococcus* sp.

26. The method of claim 19, wherein the bacterial infection is associated with a gram negative bacterial infection.

27. The method of claim 26, wherein the gram negative bacteria is selected from *Acinetobacter* sp., *Aeromonas* sp., *Burkholderia* sp., *Bordatella* sp., *Citrobacter* sp., *Enterobacter* sp., *Escherichia* sp., *Francisella* sp., *Haemophilus* sp., *Klebsiella* sp., *Legionella* sp., *Moraxella* sp., *Neisseria* sp., *Proteus* sp., *Pseudomonas* sp., *Salmonella* sp., *Shigella* sp., *Stenotrophomonas* sp., *Vibrio* sp., and *Yersinia* sp.

28. The method of claim 19, further comprising administering to the human subject a therapeutically effective amount of a second active agent.

29. The method of claim 28, wherein the second active agent comprises at least one antibacterial agent.

30. A method for the treatment of a bacterial infection in a vertebrate animal comprising the step of administering to the vertebrate animal a therapeutically effective amount of a compound of claim 1, or a pharmaceutically acceptable salt thereof.

31. A method for the treatment in a human subject of a disorder associated with exposure to a biodefense pathogen comprising the step of administering to the human subject an effective amount of a compound of claim 1, or a pharmaceutically acceptable salt thereof.

\* \* \* \* \*